United States Patent
Novák et al.

(10) Patent No.: US 9,828,421 B2
(45) Date of Patent: Nov. 28, 2017

(54) PROTEIN-BASED THERAPY AND DIAGNOSIS OF TAU-MEDIATED PATHOLOGY IN ALZHEIMER'S DISEASE

(71) Applicant: AXON NEUROSCIENCE SE, Larnaca (CY)

(72) Inventors: Michal Novák, Bratislava (SK); Eva Kontseková, Senec (SK); Branislav Kováceǒh, Bratislava (SK); Norbert Žilka, Senec (SK)

(73) Assignee: Axon Neuroscience SE, Larnaca (CY)

( * ) Notice: Subject to any disclaimer, the term of this patent is extended or adjusted under 35 U.S.C. 154(b) by 0 days.

(21) Appl. No.: 15/342,629

(22) Filed: Nov. 3, 2016

(65) Prior Publication Data
US 2017/0145082 A1    May 25, 2017

Related U.S. Application Data

(62) Division of application No. 14/345,561, filed as application No. PCT/IB2012/002246 on Sep. 14, 2012, now Pat. No. 9,518,101.

(60) Provisional application No. 61/536,339, filed on Sep. 19, 2011, provisional application No. 61/653,115, filed on May 30, 2012.

(51) Int. Cl.
| | |
|---|---|
| C07K 14/47 | (2006.01) |
| C07K 16/18 | (2006.01) |
| A61K 39/00 | (2006.01) |
| A61K 49/00 | (2006.01) |
| A61K 45/06 | (2006.01) |
| A61K 39/395 | (2006.01) |
| A61K 47/48 | (2006.01) |
| G01N 33/68 | (2006.01) |

(52) U.S. Cl.
CPC .......... *C07K 16/18* (2013.01); *A61K 39/3955* (2013.01); *A61K 45/06* (2013.01); *A61K 47/48538* (2013.01); *A61K 49/0004* (2013.01); *G01N 33/6896* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,589,746 B1 | 7/2003 | Zemian | |
| 6,953,794 B2 | 10/2005 | Wischik et al. | |
| 7,070,775 B2 | 5/2006 | Le et al. | |
| 7,446,180 B2 | 11/2008 | Novak | |
| 2005/0175626 A1 | 8/2005 | Delacourte | |
| 2006/0167227 A1 | 7/2006 | Kontsekova | |
| 2008/0050383 A1 | 2/2008 | Sigurdsson et al. | |
| 2009/0162336 A1 | 6/2009 | Mandelkow | |
| 2010/0316564 A1 | 12/2010 | Sigurdsson | |
| 2011/0016537 A1 | 1/2011 | Wouters et al. | |
| 2011/0059093 A1 | 3/2011 | Bohrmann et al. | |

FOREIGN PATENT DOCUMENTS

| | | |
|---|---|---|
| EP | 1214598 A2 | 6/2002 |
| EP | 2149584 | 2/2010 |
| WO | WO 96/13592 | 5/1996 |
| WO | WO 96/20218 | 7/1996 |
| WO | WO 96/30766 | 10/1996 |
| WO | WO 01/018546 A2 | 3/2001 |
| WO | WO 01/18546 A3 | 3/2001 |
| WO | WO 2004/007547 | 1/2004 |
| WO | WO 2008/084483 | 7/2008 |
| WO | WO 2009/000520 | 12/2008 |
| WO | WO 2010/144711 | 12/2010 |
| WO | WO 2011/026031 | 3/2011 |
| WO | WO 2011/053565 | 5/2011 |
| WO | WO 2011/056300 | 5/2011 |
| WO | WO 2011/083175 | 7/2011 |

OTHER PUBLICATIONS

Rafii 2009 "recent developments in Alzheimer's disease therapeutics" BMC Med 7:7.*
Kontsekova 2014 "identification of structural determinant on tau protein essential for its pathological function: novel therapeutic target for tau immunotherapy in Alzheimer's disease" Alz Research Therapy 6:45.*
Abraha, A., et al., "C-terminal inhibition of tau assembly in vitro and in Alzheimer's disease," *Journal of Cell Science* 113, 3737-3745 (2000).
Acha, A., et al., "Handgrip Strength and Cognitive Decline in Older Mexican Americans," *J Gerontol A Biol Sci Med Sci.* Aug. 2006 ; 61(8): 859-865.
Al-Lazikani, B., Lesk, A.M., and Chothia, C. (1997). Standard conformations for the canonical structures of immunoglobulins. Journal of molecular biology 273, 927-948.
Alonso, A., et al., "Hyperphosphorylation induces self-assembly of t into tangles of paired helical filaments/straight filaments," *PNAS*, vol. 98, No. 12, 6923-6928, Jun. 5, 2001.

(Continued)

*Primary Examiner* — Adam M Weidner
(74) *Attorney, Agent, or Firm* — Finnegan, Henderson, Farabow, Garrett & Dunner, L.L.P.

(57) ABSTRACT

The invention provides unique therapeutic and diagnostic antibodies, as well as their fragments, portions, derivatives, and variants thereof, that bind regions of the tau protein that contribute to the initiation and propagation of pathological tau-tau interactions, as well as methods of making them. The invention also relates to methods of using those antibodies for diagnostics, prevention, and treatment of Alzheimer's disease and related tauopathies. The present invention also provides a method for a prophylactic and therapeutic treatment of Alzheimer's disease and other neurodegenerative tauopathies. This method entails the injection of antibodies and/or peptide vaccines that elicits an immune response directed to pathological tau proteins and tau deposits in the brains of patients. Suitable vaccines represent a tau peptide carrying one or more of the tau therapeutic epitopes provided herein.

24 Claims, 115 Drawing Sheets

(56) References Cited

OTHER PUBLICATIONS

Alonso, A., et al., "Interaction of Tau Isoforms with Alzheimer's Disease Abnormally Hyperphosphorylated Tau and in Vitro Phosphorylation into the Disease-like Protein," *The Journal of Biological Chemistry*, vol. 276, No. 41, pp. 37967-37973, Oct. 12, 2001.
Alonso, A., et al., "Promotion of Hyperphosphorylation by Frontotemporal Dementia Tau Mutations," *The Journal of Biological Chemistry*, vol. 279, No. 33, Aug. 13, 2004, pp. 34873-34881.
Andreasen, N., et al., "Neuroinflammation Screening in Immunotherapy Trials against Alzheimer's Disease," *International Journal of Alzheimer's Disease*, vol. 2010, Article ID 638379, 3 pages.
Asuni, A., et al., Immunotherapy Targeting Pathological Tau Conformers in a Tangle Mouse Model Reduces Brain Pathology with Associated Functional Improvements, *The Journal of Neuroscience*, Aug. 22, 2007, 27(34):9115-9129.
Avila, J., "Intracellular and extracellular tau," *Frontiers in Neuroscience*, vol. No. 49, Jun. 2010.
Balin, B., et al., "Chlamydophila Pneumoniae and the Etiology of Late-Onset Alzheimer's Disease," *Journal of Alzheimer's Disease* 13 (2008) 371-380.
Barré, P., et al., "Folding of the Repeat Domain of Tau Upon Binding to Lipid Surfaces," *J. Mol. Biol.* (2006) 362, 312-326.
Berg, L., et al., "Clinicopathologic Studies in Cognitively Healthy Aging and Alzheimer Disease," *Arch Neurol.* Mar 1998; 55(3):326-35.
Berry, R., et al., "Inhibition of Tau Polymerization by Its Carboxy-Terminal Caspase Cleavage," *Biochemistry* 2003, 42, 8325-8331.
Bondareff, W., et al., "Molecular Analysis of Neurofibrillary Degeneration in Alzheimer's Disease," *American Journal of Pathology*, vol. 137, No. 3, Sep. 1990.
Bondareff, W., et al., "Sequestration of Tau by Granulovacuolar Degeneration in Alzheimer's Disease," *American Journal of Pathology*, vol. 139, No. 3, Sep. 1991.
Boutajangou, A., et al., "Immunotherapy Targeting Pathological Tau Prevents Cognitive Decline in a New Tangle Mouse Model," *The Journal of Neuroscience*, Dec. 8, 2010, 30(49):16559-16566.
Boyle, P., et al.,"Association of Muscle Strength With the Risk of Alzheimer Disease and the Rate of Cognitive Decline in Community-Dwelling Older Persons," *Arch Neurol*, vol. 66 (No. 11), Nov. 2009.
Braak, H., et al., "Alzheimer's disease: intraneuronal alterations precede insoluble amyloid-β formation," *Neurobiology of Aging* 25 (2004) 713-718.
Braak, H., et al., "Neuropathological stageing of Alzheimer-related changes," *Acta Neuropathol* (1991) 82:239-259.
Braak, H., et al., "Staging of Alzheimer disease-associated neurofibrillary pathology using paraffin sections and immunocytochemistry," *Acta Neuropathol* (2006) 112:389-404.
Braak, H., et al., "The pathological process underlying Alzheimer's disease in individuals under thirty," *Acta Neuropathol* (2011) 121:171-181.
Braak, H., et al., "Vulnerability of cortical neurons to Alzheimer's and Parkinson's diseases," *Journal of Alzheimer's Disease* 9 (2006) 35-44.
Brandt, R., et al., "Interaction of Tau with the Neural Plasma Membrane Mediated by Tau's Amino-terminal Projection Domain," *The Journal of Cell Biology*, vol. 131, No. 5, Dec. 1995 1327-1340.
Buchman, A., et al., "Frailty is Associated With Incident Alzheimer's Disease and Cognitive Decline in the Elderly," *Psychosomatic Medicine* 69:483-489 (2007).
Buchman, A., et al., "Grip Strength and the Risk of Incident Alzheimer's Disease," *Neuroepidemiology* 2007; 29:66-73.
Buée, L., et al., "Tau protein isoforms, phosphorylation and role in neurodegenerative disorders", *Brain Research Reviews* 33 (2000) 95-130.
Bugos, O., et al., "Beyond the Rat Models of Human Neurodegenerative Disorders," *Cell Mol Neurobiol* (2009) 29:859-869.
Burns, A., et al., "Alzheimer's disease," *The Lancet*, vol. 360, Jul. 13, 2002.
Burns, J.M., et al., "The pathology of the substantia nigra in Alzheimer disease with extrapyramidal signs," *Neurology*, Apr. 26, 2005; 64(8):1397-403.
Butner, K., et al., "Tau Protein Binds to Microtubules through a Flexible Array of Distributed Weak Sites," *The Journal of Cell Biology*, vol. 115, No. 3, Nov. 1991, 717-730.
Canu, N., et al., "Tau Cleavage and Dephosphorylation in Cerebellar Granule Neurons Undergoing Apoptosis," *The Journal of Neuroscience*, Sep. 15, 1998, 18(18):7061-7074.
Caputo, C., et al., "Immunological Characterization of the Region of Tau Protein That Is Bound to Alzheimer Paired Helical Filaments," *Neurobiology of Aging*, vol. 13, pp. 267-274, 1992.
Carter, J., et al., "β-Amyloid, Neuronal Death and Alzheimer's Disease," *Current Molecular Medicine* 2001, 1, 733-737.
Cattaneo, A., et al., "Functional Blockade of Tyrosine Kinase A in the Rat Basal Forebrain by a Novel Antagonistic Anti-Receptor Monoclonal Antibody," *The Journal of Neuroscience*, Nov. 15, 1999, 19(22):9687-9697.
Cente, M., et al., "Expression of a Truncated Human Tau Protein Induces Aqueous-Phase Free Radicals in a Rat Model of Tauopathy: Implications for Targeted Antioxidative Therapy," *Journal of Alzheimer's Disease* 17 (2009) 913-920.
Cente, M., et al., "Expression of a truncated tau protein induces oxidative stress in a rodent model of tauopathy," *European Journal of Neuroscience*, vol. 24, pp. 1085-1090, 2006.
Cente, M., et al., "Memantine Prevents Sensitivity to Excitotoxic Cell Death of Rat Cortical Neurons Expressing Human Truncated Tau Protein," *Cell Mol Neurobiol* (2009) 29:945-949.
Cevc, G., et al., "Ultraflexible vesicles, Transfersomes, have an extremely low pore penetration resistance and transport therapeutic amounts of insulin across the intact mammalian skin," *Biochimica et Biophysics Acta* 1368 (1998) 201-215.
Chang, J., et al., "Adjuvant activity of incomplete Freund's adjuvant," *Advanced Drug Delivery Reviews* 32 (1998) 173-186.
Chouard, T., "Breaking the Protein Rules," *Nature* 471, 151-153 (2011).
Chui, H., et al., "Extrapyramidal Signs and Psychiatric Symptoms Predict Faster Cognitive Decline in Alzheimer's Disease," *Arch Neurol.* Jul. 1994; 51(7):676-81.
Chung, C.W., et al., "Proapoptotic Effects of Tau Cleavage Product Generated by Caspase-3," *Neurobiology of Disease* 8, 162-172 (2001).
Citron, M., "Alzheimer's disease: strategies for disease modification," *Nature Reviews*, vol. 9, May 2010, 397.
Csóková, N., et al., "Preparation, Crystallization and Preliminary X-Ray Analysis of the Fab Fragment of Monoclonal Antibody MN423, Revealing the Structural Aspects of Alzheimer's Paired Helical Filaments," *Protein & Peptide Letters*, 2006, 13, 941-944.
Csokova, N., et al., "Rapid purification of truncated tau proteins: model approach to purification of functionally active fragments of disordered proteins, implication for neurodegenerative diseases," *Protein Expression and Purification* 35 (2004) 366-372.
Davies, P., "A long trek down the pathways of cell death in Alzheimer's disease," *Journal of Alzheimer's Disease* 9 (2006) 265-269.
de Silva, R., et al., "Pathological inclusion bodies in tauopathies contain distinct complements of tau with three or four microtubule-binding repeat domains as demonstrated by new specific monoclonal antibodies," *Neuropathology and Applied Neurobiology* (2003), 29, 288-302.
Delacourte, A., et al., "Tau aggregation in the hippocampal formation: an ageing or a pathological process?" *Experimental Gerontology* 37 (2002) 1291-1296.
Delacourte, A., et al., "The biochemical pathway of neurofibrillary degeneration in aging and Alzheimer's disease," *Neurology* 1999; 52:1158-1165.
Dickey, C., et al., "Current strategies for the treatment of Alzheimer's disease and other tauopathies," *Expert Opin. Ther. Targets* (2006) 10(5).

(56) References Cited

OTHER PUBLICATIONS

Dickey, C., et al., "Development of a High Throughput Drug Screening Assay for the Detection of Changes in Tau Levels—Proof of Concept with HSP90 inhibitors," *Current Alzheimer Research*, 2005, 2, 231-238.
Dickey, C., et al., "Pharmacologic reductions of total tau levels; implications for the role of microtubule dynamics in regulating tau expression," *Molecular Neurodegeneration* 2006, 1:6.
Dingus, J., et al., "Use of a Heat-stable Microtubule-associated Protein Class-specific Antibody to Investigate the Mechanism of Microtubule Binding," *The Journal of Biological Chemistry*, vol. 266, No. 28, pp. 18854-18860, 1991.
Duyckaerts, C., "Tau pathology in children and young adults: can you still be unconditionally baptist?" *Acta Neuropathol* (2011) 121:145-147.
Duyckaerts, C., et al., "Classification and basic pathology of Alzheimer disease," *Acta Neuropathol* (2009) 118:5-36.
Esposito, G., et al., "The Solution Structure of the C-terminal Segment of Tau Protein," *Journal of Peptide Science*, 6:550-559 (2000).
Fasulo, L., et al., "Tau truncation in Alzheimer's disease: expression of a fragment encompassing PHF core tau induces apoptosis in COS cells," *Alzheimer's Reports* 1, 25-32 (1998).
Fasulo, L., et al., "The Neuronal Microtubule-Associated Protein Tau Is a Substrate for Caspase-3 and an Effector of Apoptosis," *Journal of Neurochemistry*, vol. 75, No. 2, 624-633, 2000.
Fasulo, L., et al., Overexpression of Alzheimer's PHF Gore tau fragments: implications for the tau truncation hypothesis, *Alzheimer's Research*, 2 195-200, (1996).
Ferenčík, M., et al., "Inflammation—a Lifelong Companion," *Folia Microbiol.* 52 (2), 159-173 (2007).
Filipcik, P., et al., "Cortical and Hippocampal Neurons from Truncated Tau Transgenic Rat Express Multiple Markers of Neurodegeneration," *Cell Mol Neurobiol* (2009) 29:895-900.
Filipcik, P., et al., "First transgenic rat model developing progressive cortical neurofibrillary tangles," *Neurobiology of Aging* (2010).
Fischer, D., et al., "Structural and Microtubule Binding Properties of Tau Mutants of Frontotemporal Dementias," *Biochemistry* 2007, 46, 2574-2582.
Fodero-Tavoletti, M., et al., "[18] F-THK523: a novel in vivo tau imaging ligand for Alzheimer's disease," *Brain* 2011:134; 1089-1100.
Friedhoff, P., et al., "Structure of tau protein and assembly into paired helical filaments," *Biochimica et Biophysica Acta* 1502 (2000) 122-132.
Frost, B., et al., "Propagation of Tau Misfolding From the Outside to the Inside of a Cell," *The Journal of Biological Chemistry*, Mar. 16, 2009.
Frost, B., et al., "The expanding realm of prion phenomena in neurodegenerative disease," *Prion*, 4:2, 74-77, 2009.
Gallucci 1999 "natural adjuvants: endogenous activators of dendritic cells" nature medicine 5(11 ):1249-1255.
Gamblin, T., et al., "Caspase cleavage of tau: Linking amyloid and neurofibrillary tangles in Alzheimer's disease," *PNAS*, No. 17, vol. 100, 10032-10037, Aug. 19, 2003.
Gamblin, T., et al., "Modeling Tau Polymerization in Vitro: A Review and Synthesis," *Biochemistry*, vol. 42, No. 51, Dec. 30, 2003.
Gendron, T., et al., "The role of tau in neurodegeneration," *Molecular Neurodegeneration* 2009, 4:13.
Giannakopoulos, P., et al., "Pathologic Correlates of Apraxia in Alzheimer Disease," *Arch Neurol.* May 1998; 55(5):689-95.
Glenn, G., et al., "Skin immunization made possible by cholera toxin," *Nature*, vol. 391, Feb. 26, 1998.
Goedert, M., "Tau Protein and the Neurofibrillary Pathology of Alzheimer's Disease," *Ann NY Acad Sci.* Jan. 17, 1996; 777:121-31.
Goedert, M., et al., "Cloning of a big tau microtubule-associated protein characteristic of the peripheral nervous system," *Proc. Natl. Acad. Sci. USA*, vol. 89, pp. 1983-1987, Mar. 1992.
Golde, T., et al., "Targeting Aβ and tau in Alzheimer's disease, an early interim report," *Exp. Neurol.* (2009).
Goldman, W.P., et al., "Motor dysfunction in mildly demented AD individuals without extrapyramidal signs," *Neurology*. Sep. 22, 1999; 53(5):956-62.
Gómez-Isla, T., et al., "Neuronal Loss Correlates with but Exceeds Neurofibrillary Tangles in Alzheimer's Disease," *Annals of Neurology* vol. 41, No. 1, Jan. 1997.
Gómez-Isla, T., et al., "Profound Loss of Layer II Entorhinal Cortex Neurons Occurs in Very Mild Alzheimer's Disease," *The Journal of Neuroscience*, Jul. 15, 1996, 16(14):4491-4500.
Gómez-Ramos, A., et al., "Extracellular tau is toxic to neuronal cells," *FEBS Letters* 580 (2006) 4842-4850.
Gong, C., et al., "Targeting Tau Protein in Alzheimer's Disease," *Drugs Aging* 2010; 27 (5):351-365.
Goode, B., et al., "Functional Interactions between the Proline-rich and Repeat Regions of Tau Enhance Microtubule Binding and Assembly," *Molecular Biology of the Cell*, vol. 8, 353-365, Feb. 1997.
Goode, B., et al., "Identification of a Novel Microtubule Binding and Assembly Domain in the Developmentally Regulated Inter-repeat Region of Tau," *The Journal of Cell Biology*, vol. 124, No. 5,769-782, Mar. 1994.
Goode, B., et al., "Structural and Functional Differences between, 3-Repeat and 4-Repeat Tau Isoforms," *The Journal of Biological Chemistry*, vol. 275, No. 49, pp. 38182-38189, Dec. 8, 2000.
Götz, J., et al., "Animal models for Alzheimer's disease and frontotemporal dementia: a perspective," *ASN Neuro* 1(4), 2009.
Greenberg, S., et al., "A preparation of Alzheimer paired helical filaments that displays distinct τ proteins by polyacrylamide gel electrophoresis," *Proc. Natl. Acad. Sci. USA*, vol. 87, pp. 5827-5831, Aug. 1990.
Grudzien, A., et al., "Locus coeruleus neurofibrillary degeneration in aging, mild cognitive impairment and early Alzheimer's disease," *Neurobiology of Aging* 28 (2007) 327-335.
Gustke, N., et al., "Domains of τ Protein and Interactions with Microtubules," *Biochemistry*, vol. 33, No. 32, 1994.
Hampel, H., et al., "Total and Phosphorylated Tau Protein as Biological Markers of Alzheimer's Disease," *Experimental Gerontology*, (2009).
Hampel, H., et al., "Total and Phosphorylated Tau Protein as Biological Markers of Alzheimer's Disease," *Experimental Gerontology*, 2010, 45(1):30.
Hanes, J., et al., "New advances in microsphere-based single-dose vaccines," *Advanced Drug Delivery Reviews* 28 (1997) 97-119.
Hanes, J., et al., "Rat Tau proteome conists of six tau isoforms: implication for animal models of human tauopathies," *Journal of Neurochemistry*, (2009) 108, 1167-1176.
Hardy, J., et al., "Amyloid deposition as the central event in the aetiology of Alzheimer's disease," *TiPS*, Oct. 1991, vol. 12.
Hardy, J., et al., "Genetic dissection of Alzheimer's disease and related dementias: amyloid and its relationship to tau," *Nature Neuroscience*, vol. 1, No. 5, Sep. 1998.
Hardy, J., et al., "The Amyloid Hypothesis of Alzheimer's Disease: Progress and Problems on the Road to Therapeutics," *Science*, vol. 297, Jul. 19, 2002.
Harrington, C., et al., "Measurement of distinct immunochemical presentations of tau protein in Alzheimer disease," *Proc. Natl. Acad. Sci. USA*, vol. 88, pp. 5842-5846, Jul. 1991.
Hertz, L. "Is Alzheimer's disease an anterograde degeneration, originating in the brainstem, and disrupting metabolic and functional interactions between neurons and glial cells?" *Brain Research Reviews*, 14 (1989) 335-353.
Hrnkova, M., et al., Neurodegeneration caused by expression of human truncated tau leads to progressive neurobehavioural impairment in transgenic rats, *Brain Research*, 1130 (2007) 206-213.
Hunter, R., "Overview of vaccine adjuvants: present and future," *Vaccine* 20 (2002) S7-S12.
International Search Report issued by the European Patent Office in corresponding International Application No. PCT/182012/002246, dated Feb. 7, 2013, 6 pages.
Iqbal, K., et al., "Developing pharmacological therapies for Alzheimer disease," *Cell. Mol. Life Sci.* 64 (2007) 2234-2244.

(56) References Cited

OTHER PUBLICATIONS

Iqbal, K., et al., "Inhibition of Neurofibrillary Degeneration: A Promising Approach to Alzheimer's Disease and Other Tauopathies," *Current Drug Targets*, 2004, 5, 495-502.
Iqbal, K., et al., "Molecular Mechanism of Alzheimer's Neurofibrillary Degeneration and Therapeutic Intervention," *Ann NY Acad Sci.* Jan. 17, 1996; 777:132-8.
Irving, E., et al., "Intracortical perfusion of glutamate in vivo induces alterations of tau and microtubule-associated protein 2 immunoreactivity in the rat," *Acta Neuropathol* (1996) 92:186-196.
Ittner, L., et al., "Dendritic Function of Tau Mediates Amyloid-β Toxicity in Alzheimer's Disease Mouse Models," *Cell* 142, 1-11, Aug. 6, 2010.
Itzhaki, R., et al., "Herpes Simplex Virus Type 1 in Alzheimer's Disease: The Enemy Within," *Journal of Alzheimer's Disease* 13 (2008) 393-405.
Ivanovova, N., et al., "High-yield purification of fetal tau preserving its structure and phosphorylation pattern," *Journal of Immunological Methods* 339 (2008) 17-22.
Jakes, R., et al., "Identification of 3- and 4-repeat tau isoforms within the PHF in Alzheimer's disease," *The EMBO Journal*, vol. 10, No. 10, pp. 2725-2729, 1991.
Jansen, F., et al., "Immunotoxins: Hybrid Molecules Combining High Specificity and Potent Cytotoxicity," *Immunological Rev.* (1982), vol. 62.
Janus, C., et al., "Aβ peptide immunization reduces behavioural impairment and plaques in amodel of Alzheimer's disease," *Nature*, vol. 408, 21/28 Dec. 2000.
Jicha, G., et al., "Sequence Requirements for Formation of Conformational Variants of Tau Similar to Those Found in Alzheimer's Disease," *Journal of Neuroscience Research* 55:713-723 (1999).
Kar, S., et al., "Repeat motifs of tau bind to the insides of microtubules in the absence of taxol" *The EMBO Journal*, vol. 22 No. 1 pp. 70±77, 2003.
Kayed, R., et al., "Anti-tau oligomers passive vaccination for the treatment of Alzheimer disease," *Human Vaccines* 6:11, 931-935; Nov. 2010.
Kayed, R., et al., "Prefilament tau species as potential targets for immunotherapy for Alzheimer disease and related disorders," *Current Opinion in Immunology* 2009, 21:359-363.
Khuebachova, M., et al., "Mapping the C terminal epitope of the Alzheimer's disease specific antibody MN423," *Journal of Immunological Methods* 262 (2002) 205-215.
Koechling, T., et al., "NeuronalModels for Studying Tau Pathology," *International Journal of Alzheimer's Disease*, vol. 2010, Article ID 528474, 11 pages.
Kontsekova, E., et al., "Identification of Structural Determinant on Tau Protein Essential for its Pathological Function: Novel Therapeutic Target for Tau Immunotherapy in Alzheimer's Disease," *Alz. Res. Ther.*, 6:45, (2014).
Kontsekova, E., et al., "Chaperone-Like Antibodies in Neurodegenerative Tauopathies: Implication for Immunotherapy," *Cell Mol Neurobiol* (2009) 29:793-798.
Kontsekova, E., et al., "Quick purification of recombinant human truncated tau proteins," *Journal of Immunological Methods*, 185 (1995) 245-248.
Korenova, M., et al., "Improved Behavioral Response as a Valid Biomarker for Drug Screening Program in Transgenic Rodent Models of Tauopathies," *Cell Mol Neurobiol* (2009) 29:937-944.
Korenova, M., et al., "NeuroScale, the battery of behavioral tests with novel scoring system for phenotyping of transgenic rat model of tauopathy," *Journal of Neuroscience Methods* 177 (2009) 108-114.
Koson P, Zilka N, Kovac A, Kovacech B, Korenova M, Filipcik P, Novak M. 2008. Truncated tau expression levels determine life span of a rat model of tauopathy without causing neuronal loss or correlating with terminal neurofibrillary tangle load. Eur J Neurosci 28: 239-246.
Koson, P., et al., "Truncated tau expression levels determine life span of a rat model of tauopathy without causing neuronal loss or correlating with terminal neurofibrillary tangle load," *European Journal of Neuroscience*, vol. 28, pp. 239-246, 2008.
Kovac, A., et al., "Human Truncated Tau is Using a Different Mechanism from Amyloid-β to Damage the Blood-Brain Barrier," *Journal of Alzheimer's Disease* 18 (2009) 1-10.
Kovacec, B., et al., "Transition of Tau Protein from Disordered to Misordered in Alzheimer's Disease," *Neurodegenerative Dis* 2010; 7:24-27.
Kovacech, B., et al., "A novel monoclonal antibody DC63 reveals that inhibitor 1 of protein phosphatase 2A is preferentially nuclearly localised in human brain," *FEBS Letters* 581 (2007) 617-622.
Kovacech, B., et al., "Can We Develop an Anti-Tau Immunization Therapy?" *Neurobiology of Aging* 31S (2010) S1-S34.
Kovacech, B., et al., "New Age of Neuroproteomics in Alzheimer's Disease Research," *Cell Mol Neurobiol* (2009) 29:799-805.
Kovacech, B., et al., "Pathological Microtubule Assembly by N-Terminally Truncated Tau Could Be Abolished by Tau Mutation (T220E)," *Neurobiology of Aging* (Impact Factor: 5.01). Jul. 2004; 25.
Kovacech, B., et al., "Tau Truncation is a Productive Post-translational Modification of Neurofibrillary Degeneration in Alzheimer's Disease," *Current Alzheimer Research*, 2010, vol. 7, No. 6.
Kraemer, H., et al., "'How Far' vs 'How Fast' in Alzheimer's Disease," *Arch Neurol.* Mar. 1994; 51(3):275-9.
Krajciova, G., et al., "Preserving free thiols of intrinsically disordered tau protein without the use of a reducing agent," *Analytical Biochemistry* 383 (2008) 343-345.
Langer, R., "New Methods of Drug Delivery," *Science*, vol. 259, Sep. 28, 1990.
Larbig, G., et al., "Screening for Inhibitors of Tau Protein Aggregation into Alzheimer Paired Helical Filaments: A Ligand Based Approach Results in Successful Scaffold Hopping," *Current Alzheimer Research*, 2007, 4, 315-323.
Lasagna-Reeves, C., et al., "Preparation and Characterization of Neurotoxic Tau Oligomers," *Biochemistry*, 2010, 49, 10039-10041.
Lee, G., et al., "Tau interacts with src-family non-receptor tyrosine kinases," *Journal of Cell Science* 111, 3167-3177 (1998).
Lee, H., et al., "Tau phosphorylation in Alzheimer's disease: pathogen or protector?" *Trends in Molecular Medicine*, vol. 11, No. 4, Apr. 2005.
Livingston, B., et al., "The Hepatitis B Virus-Specific CTL Responses Induced in Humans by Lipopeptide Vaccination Are Comparable to Those Elicited by Acute Viral Infection," *The Journal of Immunology*, Aug. 1, 1997;159(3):1383-92.
Louis, E., et al., "Parkinsonian Signs in Older People in a Community-Based Study," *Arch Neurol.* Aug. 2004; 61(8)1273-6.
MacCallum, R.M., Martin, A.C., and Thornton, J.M. (1996). Antibody-antigen interactions: contact analysis and binding site topography. Journal of molecular biology 262, 732-745.
Mandelkow, E., "Structure, Microtubule Interactions, and Phosphorylation of Tau Protein," *Ann NY Acad Sci*. Jan. 17, 1996; 777:96-106.
März W., et al., "Apolipoprotein E Polymorphism Is Associated with Both Senile Plaque Load and Alzheimer-Type Neurofibrillary Tangle Formation," *Ann NY Acad Sci.*, 777:276-80, Jan. 17, 1996.
Medina, M., "Recent Developments in Tau-Based Therapeutics for Neurodegenerative Diseases," *Recent Pat CNS Drug Discov.* Jan. 2011; 6(1):20-30.
Mena, R., et al., "A Progressive Deposition of Paired Helical Filaments (PHF) in the Brain Characterizes the Evolution of Dementia in Alzheimer's Disease. An Immunocytochemical Study with a Monoclonal Antibody Against PFH Core," *Journal of Neuropathology and Experimental Neurology*, vol. 50, No. 5, pp. 474-490, Jul. 1991.
Miklossy, J., "Chronic Inflammation and Amyloidogenesis in Alzheimer's Disease —Role of Spirochetes," *Journal of Alzheimer's Disease* 13 (2008) 381-391.
Mittag, T., et al., "Structure/Function Implications in a Dynamic Complex of the Intrinsically Disordered Sic1 with the Cdc4 Subunit of an SCF Ubiquitin Ligase," *Structure* 18, 494-506, Apr. 14, 2010.

(56) References Cited

OTHER PUBLICATIONS

Morgan, D., "Immunotherapy for Alzheimer's disease," *Journal of Internal Medicine*, 269:54-63, 2010.
Morgan, D., et al., "Aβ peptide vaccination prevents memory loss in an animal model of Alzheimer's disease," *Nature*, vol. 408, 21/28 Dec. 2000.
Morris, J., et al., "Clinical and Pathological Aspects of Parkinsonism in Alzheimer's Disease," *Arch Neurol.* Jun. 1989; 46(6):651-7.
Mukrasch, M., et al., "Sites of Tau Important for Aggregation Populate β-Structure and Bind to Microtubules and Polyanions," *The Journal of Biological Chemistry*, vol. 280, No. 26, pp. 24978-24986, Jul. 1, 2005.
Mukrasch, M., et al., "Structural Polymorphism of 441-Residue Tau at Single Residue Resolution," *PLoS Biology*, vol. 7, No. 2, Feb. 2009.
Myszka, D.G. (1999) Improving biosensor analysis. J. Mol. Recognit. 12, 279-84.
Necula, M., et al., "Cyanine Dye N744 Inhibits Tau Fibrillization by Blocking Filament Extension: Implications for the Treatment of Tauopathic Neurodegenerative Diseases," *Biochemistry* 2005, 44, 10227-10237.
Nelson, P., et al., "Neuropathology and Cognitive Impairment in Alzheimer Disease: A Complex but Coherent Relationship," *J Neuropathol Exp Neurol*, Jan. 2009; 68(1):1-14.
Noble, W., et al., "Inhibition of glycogen synthase kinase-3 by lithium correlates with reduced tauopathy and degeneration in vivo," *PNAS*, vol. 102, No. 19, 6990-6995.
Nohria 1994 "cytokines as potential vaccine adjuvants" biotherapy 7:261-269.
Novak, M., "Genetic background modifies neurodegeneration and neuroinflammation driven by misfolded human tau protein in rat model of tauopathy: for immunomodulatory approach to Alzheimer's disease," 7th International Winter Conference on Alzheimer's Disease, Dec. 9-12, 2010.
Novak, M., "Immunomodulation of Memory Impairing Protein Tau in Alzheimer's disease," AD/PD 2001, Barcelona, Spain.
Novak, M., "Truncated Tau Protein As a New Marker for Alzheimer's Disease," *Acta virologica* 38: 173-189, 1994.
Novak, M., et al., "Alzheimer's disease template tau as a candidate for vaccine development," The Century of the Alzheimer Brain Interactome Smolenice Jun. 14-18, 2009.
Novak, M., et al., "Difference between the tau protein of Alzheimer paired helical filament core and normal tau revealed by epitope analysis of monoclonal antibodies 423 and 7.51," *Proc. Natl. Acad. Sci. USA*, vol. 88, pp. 5837-5841, Jul. 1991.
Novak, M., et al., "From disease pathways to biomarkers and drug targets," *Brain Club International*, Jun. 14-18, 2009, Smolenic Castle, Slovak Republic.
Novak, M., et al., "Molecular characterization of the minimal protease resistant tau unit of the Alzheimer's disease paired helical filament," *The EMBO Journal*, vol. 12, No. 1, pp. 365-370, 1993.
Novak, P., et al., "Tauons and Prions," *J. Alzheimers Dis.* 2011; 26(3):413-30.
Oddo, S., et al., "Aβ Immunotherapy Leads to Clearance of Early, but Not Late, Hyperphosphorylated Tau Aggregates via the Proteasome," *Neuron*, vol. 43, 321-332, Aug. 5, 2004.
Paul, A., et al., "Transdermal immunization with large proteins by means of ultradeformable drug carriers," *Eur. J. Immunol.* 1995.25: 3521-3524.
Perez, M., et al., "In Vitro Assembly of Tau Protein: Mapping the Regions Involved in Filament Formation," *Biochemistry*, 2001, 40:5983-5991.
Pettersson, A.F., et al., "Motor Function in Subjects with Mild Cognitive Impairment and Early Alzheimer's Disease," *Dement Geriatr Cogn Disord* 2005;19:299-304.
Pickhardt, M., et al., "Screening for Inhibitors of Tau Polymerization," *Current Alzheimer Research*, 2005, 2, 219-226.

Poland, G., et al., The Old and the New: successful vaccines of the 20th century and approaches to making vaccines for the important diseases of the 21st century, *Current Opinion in Immunology* 2009, 21:305-307.
Pooler, A., et al., "Dynamic association of tau with neuronal membranes is regulated by phosphorylation," *Neurobiology of Aging*, (2011).
Rafii "Recent Developments in Alzheimer's Disease Therapeutics", *BMC Med.*, 7:7, (2009).
Rapoport, M., et al., "Tau is essential to β-amyloid-induced neurotoxicity," *PNAS*, vol. 99, No. 9, 6364-6269.
Reichert, J., "Antibody-based therapeutics to watch in 2011," *mAbs* 3:1, 76-99, Jan./Feb. 2011.
Reitz, C., et al., "Memory performance is related to amyloid and tau pathology in the hippocampus," *J. Neurol. Neurosurg. Psychiatry* 2009, 80:715-721.
Rissman, R., et al., "Caspase-cleavage of tau is an early event in Alzheimer disease tangle pathology," *The Journal of Clinical Investigation*, vol. 114, No. 1, Jul. 2004.
Roberson, E., et al., "Reducing Endogenous Tau Ameliorates Amyloid β-Induced Deficits in an Alzheimer's Disease Mouse Model," *Science* 316, 750 (2007).
Rosenberg, K., et al., "Complementary dimerization of microtubule-associated tau protein: Implications for microtubule bundling and tau-mediated pathogenesis," *PNAS*, vol. 105, No. 21, 7445-7450, May 27, 2008.
Ruben, G., et al., "Alzheimer Paired Helical Filaments (PHFs) Studied by High-Resolution TEM: What Can Vertical Pt-C Replication Tell Us About the Organization of the Pronase-Digested PHF Core?," *Microscopy Research and Technique* 67:196-209 (2005).
Ruben, G., et al., "Alzheimer paired helical filaments, untreated and pronase digested, studied by vertical platinum-carbon replication and high resolution transmission electron microscopy," *Brain Research*, 675 (1995) 1-12.
SantaCruz, K, et al., "Tau Suppression in a Neurodegenerative Mouse Model Improves Memory Function," *Science*; Jul. 15, 2005; 309, 5733.
Saurwein-Teissl, M., et al., "Lack of Antibody Production Following Immunization in Old Age: Association with $CD8^{30}$ $CD28^{31}$ T Cell Clonal Expansions and an Imbalance in the Production of Th1 and Th2 Cytokines," *The Journal of Immunology*, 168:5893-5899, 2002.
Scarmeas, N., et al., "Motor signs during the course of Alzheimer disease," *Neurology*, Sep. 28, 2004; 63(6):975-982.
Scarmeas, N., et al., "Motor signs predict poor outcomes in Alzheimer disease," *Neurology*, May 24, 2005; 64(10):1696-1703.
Schenk, D., et al., "Immunization with amyloid-β attenuates Alzheimer-disease-like pathology in the PDAPP mouse," *Nature*, vol. 400, Jul. 8, 1999.
Schneider, A., et al., "Tau-Based Treatment Strategies in Neurodegenerative Diseases," *Neurotherapeutics*, vol. 5, 443-457, Jul. 2008.
Schönheit, B., et al., "Spatial and temporal relationships between plaques and tangles in Alzheimer-pathology," *Neurobiology of Aging* 25 (2004) 697-711.
Seabrook, G., et al., "Beyond Amyloid the Next Generation of Alzheimer's Disease Therapeutics," *Molecular Interventions*, vol. 7, Issue 5, Oct. 2007.
Sen Mun Wai, M., et al., "Co-localization of hyperphosphorylated tau and caspases in the brainstem of Alzheimer's disease patients," *Biogerontology* (2009) 10:457-469.
Sengupta, A., et al., "Phosphorylation of Tau at Both Thr 231 and Ser 262 Is Required for Maximal Inhibition of Its Binding to Microtubules," *Archives of Biochemistry and Biophysics*, vol. 357, No. 2, Sep. 15, pp. 299-309, 1998.
Sengupta, A., et al., "Regulation of phosphorylation of tau by cyclin-dependent kinase 5 and glycogen synthase kinase-3 at substrate level," *FEBS Letters* 580 (2006) 5925-5933.
Sergeant, N., et al., "Tau protein as a differential biomarker of tauopathies," *Biochimica et Biophysica Acta* 1739 (2005) 179-197.
Sevcik, J., et al., "Structure Solution of Misfolded Conformations Adopted by Intrinsically Disordered Alzheimer's Tau Protein," *Protein & Peptide Letters*, 2009, 16, 61-64.

(56) References Cited

OTHER PUBLICATIONS

Sevcik, J., et al., X-ray structure of the PHF core C-terminus: Insight into the folding of the intrinsically disordered protein tau in Alzheimer's disease, *FEBS Letters* 581 (2007) 5872-5878.

Shawkatová, I., et al., "No association between cytokine gene polymorphism and risk of Alzheimer's disease in Slovaks," *Acta Neurobiol Exp* 2010, 70: 1-5.

Shipton, O., et al., Tau Protein Is Required for Amyloid β-Induced Impairment of Hippocampal Long-Term Potentiation, *The Journal of Neuroscience*, Feb. 2, 2011, 31(5)1688-1692.

Sigurdsson, E., et al., "Immunization with a Nontoxic/Nonfibrillar Amyloid-β Homologous Peptide Reduces Alzheimer's Disease-Associated Pathology in Transgenic Mice," *American Journal of Pathology*, vol. 159, No. 2, Aug. 2001.

Simic, G., et al., "Annotation—Does Alzheimer's disease begin in the brainstem?" *Neuropathol Appl Neurobiol.* Dec. 2009; 35(6):532-554.

Singh, T., et al., "Calcium/calmodulin-dependent protein kinase II phosphorylates tau at Ser-262 but only partially inhibits its binding to microtubules," FEBS Letters, 387 (1996) 145-148.

Singh, T., et al., "Protein kinase C and calcium/calmodulin-dependent protein kinase II phosphorylate three-repeat and four-repeat tau isoforms at different rates," *Molecular and Cellular Biochemistry*, 168:141-148, 1997.

Skrabana, R., et al., "Alzheimer's-disease-associated conformation of intrinsically disordered tau protein studied by intrinsically disordered protein liquid-phase competitive enzyme-linked immunosorbent assay," *Analytical Biochemistry* 359 (2006) 230-237.

Skrabana, R., et al., "Folding of Alzheimer's core PHF subunit revealed by monoclonal antibody 423," *FEBS Letters* 568 (2004) 178-182.

Skrabana, R., et al., "Intrinsically Disordered Proteins in the Neurodegenerative Processes: Formation of Tau Protein Paired Helical Filaments and Their Analysis," *Cellular and Molecular Neurobiology*, vol. 26, Nos. 7/8, Oct./Nov. 2006.

Skrabana, R., et al., "Monoclonal antibody MN423 as a stable mold facilitates structure determination of disordered tau protein," *Journal of Structural Biology* 171 (2010) 74-81.

Sloane, P., et al., "The Public Health Impact of Alzheimer's Disease, 2000-2050: Potential Implication of Treatment Advances," *Annu. Rev. Public Health*, 2002, 23:213-31.

Soinine, H., et al., "Extrapyramidal signs in Alzheimer's disease: a 3-year follow-up study," *J Neural Transm* (1992) 4:107-119.

Soltys, K., et al., "First insert of tau protein is present in all stages of tau pathology in Alzheimer's disease," *Neuroreport*, vol. 16, No. 15, Oct. 17, 2005.

Spillantini, M., et al., "Different configurational states of β-amyloid and their distributions relative to plaques and tangles in Alzheimer disease," *Proc. Nadl. Acad. Sci. USA*, vol. 87, pp. 3947-3951, May 1990.

Spina, S., et al., "The novel Tau mutation G335S: clinical, neuropathological and molecular characterization," *Acta Neuropathol* (2007) 113:461-470.

Stozicka, Z., et al., "Genetic background modifies neurodegeneration and neuroinflammation driven by misfolded human tau protein in rat model of tauopathy: implication for immunomodulatory approach to Alzheimer's disease," *Journal of Neuroinflammation* 2010, 7:64.

Stožická, Z., et al., "Risk and Protective Factors for Sporadic Alzheimer's Disease," *Acta virologica* 51: 205-222, 2007.

Sugase, K., e al., "Mechanism of coupled folding and binding of an intrinsically disordered protein," *Nature*, vol. 447, Jun. 21, 2007.

Tabaton, M., et al., "Ultrastructural localization of β-amyloid, τ, and ubiquitin epitopes in extracellular neurofibrillary tangles," *Proc. Natl. Acad. Sci. USA*, vol. 88, pp. 2098-2102, Mar. 1991.

Takuma, H., et al., "I soforms changes of tau protein during development in various species," *Developmental Brain Research* 142 (2003) 121-127.

Taniguch, T., et al., "Effects of different anti-tau antibodies on tau fibrillogenesis: RTA-1 and RTA-2 counteract tau aggregation," *FEBS Letters* 579 (2005) 1399-1404.

Taniguchi, S., et al., "Inhibition of Heparin-induced Tau Filament Formation by Phenothiazines, Polyphenols, and Porphyrins," *The Journal of Biological Chemistry*, vol. 280, No. 9, Issue of Mar. 4, pp. 7614-7623, 2005.

Theunis, C., et al., "Protein Tau, Target for Immunotherapy: Pre-Clinical Evaluation in Transgenic Mice," *Experimental Genetics Group*—LEGTEGG, KULeuven, Leuven, Belgium, ACImmune, Lausanne, Switzerland.

Ugolini, G., et al., "Co-localization of truncated tau and DNA fragmentation in Alzheimer's disease neurones," *NeuroReport* 8, 3709- 3712 (1997).

Uneo, H., et al., "Novel conformation-sensitive antibodies specific to three- and four-repeat tau," *Biochemical and Biophysical Research Communications* 358 (2007) 602-607.

Uversky, V., et al., "Intrinsically Disordered Proteins in Human Diseases: Introducing the $D^2$ Concept," *Annu. Rev. Biophys.* 2008, 37:215-46.

Uversky, V., et al., "Understanding protein non-folding," *Biochimica et Biophysica Acta* 1804 (2010) 1231-1264.

Vechterova, L., et al., "DC11: a novel monoclonal antibody revealing Alzheimer's disease-specific tau epitope," *Neuroreport*, vol. 14, No. 1, 2003.

von Bergen, M., et al., "Assembly of τ protein into Alzheimer paired helical filaments depends on a local sequence motif ($^{306}$VQIVYK$^{311}$) forming β structure," *PNAS*, vol. 97, No. 10, 5129-5134, May 9, 2000.

Waite, L.M., et al., "Gait slowing as a predictor of incident dementia: 6-year longitudinal data from the Sydney Older Persons Study," *Journal of the Neurological Sciences* 229-230 (2005) 89-93.

Walsh, D., et al., "Deciphering the Molecular Basis of Memory Failure in Alzheimer's Disease," *Neuron*, vol. 44, 181-193, Sep. 30, 2004.

Wang, L., et al., "Performance-Based Physical Function and Future Dementia in Older People," *Arch Intern Med.* May 22, 2006;166(10):1115-20.

Wang, Y., et al., "Tau fragmentation, aggregation and clearance: the dual role of lysosomal processing," *Human Molecular Genetics*, 2009, vol. 18, No. 21, 4153-4170.

Weingarten, M. et al., A Protein Factor Essential for Microtubule Assembly, *Proc. Nat. Acad. Sci. USA*, vol. 72, No. 5, pp. 1858-1862, May 1975.

Weng, N., et al., "CD28 T cells: their role in the age-associated decline of immune function," *Trends Immunol.* Jul. 2009; 30(7):306-312.

West, M., et al., Differences in the pattern of hippocampal neuronal loss in normal ageing and Alzheimer's disease, *The Lancent*, vol. 344, Sep. 17, 1994.

Whitwell, J., et al., "MRI correlates of neurofibrillary tangle pathology at autopsy," *Neurology* 71 Sep. 2, 2008.

Wilson, R., et al., "Parkinsonianlike Signs and Risk of Incident Alzheimer Disease in Older Persons," *Arch Neurol.* Apr. 2003; 60(4):539-44.

Wischik, C., et al., "Selective inhibition of Alzheimer disease-like tau aggregation by phenothiazines," Proc. *Natl. Acad. Sci. USA*, vol. 93, pp. 11213-11218, Oct. 1996.

Wischik, C.M., et al., "Isolation of a fragment of tau derived from the core of the paired helical filament of Alzheimer disease," *Proc. Natl. Acad. Sci. USA*, vol. 85, pp. 4506-4510, Jun. 1988.

Wischik, C.M., et al., "Structural characterization of the core of the paired helical filament of Alzheimer disease," *Proc. Natl. Acad. Sci. USA*, vol. 85, pp. 4884-4888, Jul. 1988.

Wisniewski, T., et al., "Immunotherapeutic approaches for Alzheimer's disease in transgenic mouse models," *Brain Struct Funct* (2010) 214:201-218.

Wisniewski, T., et al., "Vaccination as a Therapeutic Approach to Alzheimer's Disease," *Mount Sinai Journal of Medicine*, 77:17-31, 2010.

Wszolek, Z., et al., "Frontotemporal dementia and parkinsonism linked to chromosome 17 (FTDP-17)," *Orphanet J Rare Dis.* 2006; 1:30.

(56) References Cited

OTHER PUBLICATIONS

Zarow, C., et al., "Neuronal Loss Is Greater in the Locus Coeruleus Than Nucleus Basalis and Substantia Nigra in Alzheimer and Parkinson Diseases," *Arch Neurol*, vol. 60, Mar. 2003.

Zhang, B., et al., "Microtubule-binding drugs offset tau sequestration by stabilizing microtubules and reversing fast axonal transport deficits in a tauopathy model," *PNAS*, Jan. 4, 2005, vol. 102, No. 1, 227-231.

Zilka, N., et al., "Chaperone-like Antibodies Targeting Misfolded Tau Protein: New Vistas in the Immunotherapy of Neurodegenerative Foldopathies," *Journal of Alzheimer's Disease* 15 (2008) 169-117.

Zilka, N., et al., "CSF phospho-tau correlates with behavioural decline and brain insoluble phospho-tau levels in a rat model of tauopathy," *Acta Neuropathol* (2010) 119:679-687.

Zilka, N., et al., "Human misfolded truncated tau protein promotes activation of microglia and leukocyte infiltration in the transgenic rat model of tauopathy," *Journal of Neuroimmunology* 209 (2009) 16-25.

Zilka, N., et al., "Misfolded tau protein and disease modifying pathways in transgenic rodent models of human tauopathies," *Acta Neuropathol* (2009) 118:71-86.

Zilka, N., et al., "Truncated tau from sporadic Alzheimer's disease suffices to drive neurofibrillary degeneration in vivo," *FEBS Letters* 580 (2006) 3582-3588.

Zilkova, M., et al., "Hyperphosphorylated Truncated Protein Tau Induces Caspase-3 Independent Apoptosis-Like Pathway in the Alzheimer's Disease Cellular Model," *Journal of Alzheimer's Disease* 23 (2010) 1-9.

Zilkova, M., et al., "Process of Diseased Tau Assembly Into Neurofibrillary Structures Differs Inalzheimer'sdisease and Other Tauopathies," *Neurobiology of Aging*, 25:Supplement 2, 2004.

* cited by examiner

FIG. 3A

A. Nucleotide sequence of DC8E8 variable light chain (VL):
GACATTGTGATGTCACAGTCTCCATCCCCTGCTGTGTCAGCAGAGAAGGTCACTATGAGCTGCAAATCCAGTCAGAGTCTGCTC
AACAGTAGAACCCGAAAGAACTACCTGGCTTGGTACCAGCAGAAACCAGGGCAGTCTCCTAAACTGCTGATCTACTGGGCATCCACTAGG
GAATCTGGGGTCCCTGATCGCTTCACAGGCAGTGGATCTGGGACAGATTTCACTCTCACCATCAGCAGTGTGCAGGCTGAAGACCTGGCA
GTTTATTACTGCAAGCAATCTTTTTATCTTCGGACGTTCGGTGGAGGCACCAAGCTGGACATCAAA

B. Amino acid sequence of DC8E8 variable light chain (VL):
DIVMSQSPSSLAVSAGEKVTMSCKSSQSLLNSRTRKNYLAWYQQKPGQSPKLLIYWASTRESGVPDRFTGSGSGTDFTLTISSVQAEDLA
VYYCKQSFYLRTFGGGTKLDIK

CDR1:   QSLLNSRTRKNY
CDR2:   WAS
CDR3:   KQSFYLRT

**C. Alignment of DC8E8 (VL) sequence with the closest mouse germline sequence IGKV8-21*01:**
V-gene (298/301; 99.0% sequence identity):
DC8E8 light    GACATTGTGATGTCACAGTCTCCATCCCCTGCTGTGTCAGCAGGAGA
IGKV8-21*01    GACATTGTGATGTCACAGTCTCCATCCCCTGCTGTGTCAGCAGGAGA
               ***********************************************

DC8E8 light    GAAGGTCACTATGAGCTGCAAATCCAGTCAGAGTCTGCTCAACAGTAGAA
IGKV8-21*01    GAAGGTCACTATGAGCTGCAAATCCAGTCAGAGTCTGCTCAACAGTAGAA
               **************************************************

DC8E8 light    CCCGAAAGAACTACCTGGCTTGGTACCAGCAGAAACCAGGGCAGTCTCCT
IGKV8-21*01    CCCGAAAGAACTACTTGGCTTGGTACCAGCAGAAACCAGGGCAGTCTCCT
               ************ *********************************

DC8E8 light    AAACTGCTGATCTACTGGGCATCCACTAGGGAATCTGGGGTCCCTGATCG
IGKV8-21*01    AAACTGCTGATCTACTGGGCATCCACTAGGGAATCTGGGGTCCCTGATCG
               **************************************************

FIG. 3B

```
DC8E8 light      ****************************** CTTCACAGGCAGTGGATCTGGGACAGATTTCACTCTCCACCATCAGCAGTG
IGKV8-21*01      ****************************** CTTCACAGGCAGTGGATCTGGGACAGATTTCACTCTCCACCATCAGCAGTG
                 ************************************************************

DC8E8 light      TGCAGGCTGAAGACCTGGCAGTTTATTACTGCAAGCAATCTTTTTATCTT
IGKV8-21*01      TGCAGGCTGAAGACCTGGCAGTTTATTACTGCAAGCAATCTTTATAATCTT
                 ****************************** * ******

DC8E8 light      C
IGKV8-21*01      C
                 *

J-gene (35/36; 97.2% sequence identity):

DC8E8 light      GGACGTTCGGTGGAGGCACCAAGCTGGACATCAAAC
IGKJ1*01         GGACGTTCGGTGGAGGCACCAAGCTGGAAATCAAAC
                 **************************** *******
```

D. Nucleotide sequence of DC8E8 heavy chain variable region (VH):
CAGGTCCAATTGCAGCAGTCAGCAGTCTGAGCTGGACCTGAGCTGGTGAAGCCTGGGACTTCAGTGGAAGATGCCCTGTAAGGCTTCTGGATACATATTCACT
GACTATGTCATAAGCTGGGTGAAGCAGAGAACTGGACAGGGCCCTTGAGTGGATTGGAGAGATTTTCCTAGAAGTGGTAGTACTTACTAC
AATGAGAAGTTCAAGGGCAAGGCCACACTGACTGCAGACAAATCCTCCAACACAGCCTACATGCAGCTCAGCAGCGTGACATCTGAGGAC
TCTGCGGTCTATTTCTGTGCAAGAGATTACTACGGTACTTCATTTGCTATGGACTACTGGGGTCAAGGAACCTCAGTCACCGTCTCCTCA

E. Amino acid sequence of DC8E8 heavy chain variable region (VH):
QVQLQQSGPELVKPGTSVKMPCKASGYIFTDYVISWVKQRTGQGLEWIGEIFPRSGSTYYNEKFKGKATLTADKSSNTAYMQLSSVTSED
SAVYFCARDYYGTSFAMDYWGQGTSVTVSS

CDR1:    GYIFTDYVIS
CDR2:    IFPRSGST
CDR3:    ARDYYGTSFAMDY

FIG. 3C

F. Alignment of DC8E8 (VH) sequence with the closest mouse germline sequence IGKV8-81*01:

V-gene (269/294; 91.5% sequence identity):

```
DC8E8 heavy    CAGGTCCAATTGCAGCAGTCTGGACCTGAGCTGGTGAAGCCTGGACTTC
IGHV1-81*01    CAGGTTCAGCTGCAGCAGTCTGGAGCTGAGCTGGTGGCGAGGCCTGGGCTTC
               ***** **  ************** ************  *********

DC8E8 heavy    AGTGAAGATGCCCCTGTAAGGCTTCTGGATACATATTCACTGACTATGTCA
IGHV1-81*01    AGTGAAGCTGTCCTGCAAGGCTTCTGGCTACACCTTCACAAGCTATGTA
               ******* **  ** ***********  *****  *****  ****** *

DC8E8 heavy    TAAGCTGGGTGAAGCAGAGAACTGGACAGGGCCTTGAGTGGATTGGAGAG
IGHV1-81*01    TAAGCTGGGTGAAGCAGAGAACTGGACAGGGCCTTGAGTGGATTGGAGAG
               **************************************************

DC8E8 heavy    ATTTTTCCTAGAAGTGGTAGTACTTACTACAATGAGAAGTTCAAGGGCAA
IGHV1-81*01    ATTTATCCTAGAAGTGGTAATACTTACTACAATGAGAAGTTCAAGGGCAA
               ****  ************* ******************************

DC8E8 heavy    GGCCACACTGACTGCAGACAAATCCTCCAACACAGCCTACATGCAGCTCA
IGHV1-81*01    GGCCACACTGACTGCAGACACATCCTCCAGCACAGCGTACATGGAGCTCC
               ******************** ******** ****** ****** *****

DC8E8 heavy    GCAGCCTGACATCTGAGGACTCTGCGGTCTATTTCTGTGCAAGA
IGHV1-81*01    GCAGCCTGACATCTGAGGACTCTGCGGTCTATTTCTGTGCAAGA
               ********************************************
```

FIG. 3D

D-gene (12/15; 80.0% sequence identity):

```
DC8E8 heavy      GATTACTAC-GGTAC
IGHD2-14*01      GACTACTATAGGTAC
                 ** ****** *****
```

J-gene (50/53; 94.3% sequence identity):

```
DC8E8 heavy     TTCATTTGCTATGGACTACTGGGGTCAAGGAACCTCAGTCACCGTCTCC
IGHJ4*01        TTACTATGCTATGGACTACTGGGGTCAAGGAACCTCAGTCACCGTCTCC
             ** * ********************************************

DC8E8 heavy     TCAG
IGHJ4*01        TCAG
                ****
```

G. Nucleotide sequence of the DC8E8 kappa light chain constant region:

Gggctgatgctgcaccaactgtatccatcttcccaccatccagtgagcagttaacatctggaggtgcctcagtcgtgtgcttcttgaaca
Acttctacccaaagacaccctgagcagtgacagtcaggtggaagattgatggcagtggaacgacaaaatggcgtcctgaacagttgactcaggaca
gcaaagacagcacctacagcatgagcagcaccctcacgttgaccaaggacgagtatgaacgacataacagctataacctgtgaggcca

H. Nucleotide sequence of the DC8E8 heavy chain constant region CH1:

Ccaaaacgacacccccatctgtctatccactggcccctggatctgctgcccaaactaactccatggtgaccttggatgcctggtcaagg
Gctattccctgagccagtgacagtgagctccagtgacctccatggtgcacacttccagcggtgtgcacacctccagctgtcctgcagtctgacc
Tctacactctgagcagtgagcagtcagtgactgactgtcccctcccagcaccctggcccagcgagaccgtcacctgcaacgttgccaccccggccagcagca
ccaagg

FIG. 4

V-gene (242/301; 80.4 % sequence identity):

```
DC8E8                         GACATTGTGATGTCACAGTCTCCATCCTCCCTGCTGTGTCAGCAGGAGA
IGKV4-1*01_Homo+sapiens       GACATCGTGATGACCCAGTCTCCAGACTCCCTGGCTGTGTCTCTGGGCGA
                              ******   *****   ******  * ******** ******  ** **

DC8E8                         GAAGGTCACTATGAGCTGCAAATCCAGTCAGAGTCTGCTCAACAGTAGAA
IGKV4-1*01_Homo+sapiens       GAGGGCCACCATCAACTGCAAGTCCAGCCAGAGTGTTTTATACAGCTCCA
                              **  * ***  **  ******  ****  *****  *  * *    *

DC8E8                         CCCGAAAGAACTACCTGGCTTGGTACCAGCAGAAACCAGGCAGTCTCCT
IGKV4-1*01_Homo+sapiens       ACAATAAGAACTACTTAGCTTGGTACCAGCAGAAACCAGGACAGCCTCCT
                                *  ******** *  ***********************  *** ****

DC8E8                         AAACTGCTGATCTACTGGGCATCCACTAGGGAATCTGGGGTCCCTGATCG
IGKV4-1*01_Homo+sapiens       AAGCTGCTCATTTACTGGGCATCTACCCGGGAATCCGGGGTCCCTGACCG
                              ** ***** ** *********** **  ****** ***********  *

DC8E8                         CTTCACAGGCAGTGGATCTGGGACAGATTTCACTCTCACCATCAGCAGTG
IGKV4-1*01_Homo+sapiens       ATTCAGTGGCAGCGGGTCTGGGACAGATTTCACTCTCACCATCAGCAGCC
                               *** * **** *  ************************ *******

DC8E8                         TGCAGGCTGAAGACCTGGCAGTTTATTACTGCAAGCAATCTTTTATCTT
IGKV4-1*01_Homo+sapiens       TGCAGGCTGAAGATGTGGCAGTTTATTACTGTCAGCAATATTATAGTACT
                              ************* ************** * ******  * *   * *

DC8E8                         C----
IGKV4-1*01_Homo+sapiens       CCTCC
                              *
```

J-gene (30/36; 83.3 % sequence identity):

```
DC8E8                              --GGACGTTCGGTGGAGGCACCAAGCTGGACATCAAAC
IGKV4-1*01_Homo+sapiens_J-REGION   GTGGACGTTCGGCCAAGGGACCAAGGTGGAAATCAAAC
                                     *********    ***  *******  *** *******
```

FIG. 5A

V-gene (219/294; 74.5% sequence identity):

```
DC8E8_heavy_V           CAGGTCCAATTGCAGCAGTCTGGACCTGAGCTGGTGAAGCCTGGACTTC
IGHV1-69*10_Homo+sapiens CAGGTCCAGCTGGTGCAGTCTGGGGCTGAGGTGAAGAAGCCTGGGTCCTC
                        ********** ** ******** *     ******* *** * **** **

DC8E8_heavy_V           AGTGAAGATGCCCTGTAAGGCTTCTGGATACATATTCACTGACTATGTCA
IGHV1-69*10_Homo+sapiens AGTGAAGGTCTCCTGCAAGGCTTCTGGAGGCACCTTCAGCAGCTATGCTA
                        ******* * ***** **********  * **  ***  ** ***  **

DC8E8_heavy_V           TAAGCTGGTGGGTGAAGCAGAGAACTGGACAGGGCCTTGAGTGGATTGGAGAG
IGHV1-69*10_Homo+sapiens TCAGCTGGGTGCGACAGGCCCCTGGACAAGGGCTTGAGTGGATGGGAGGG
                        * ******  *  *   ** *  ****** ****** ******* ****

DC8E8_heavy_V           ATTTTTCCTAGAAGTGGTAGTACTTACTACAATGAGAAGTTCAAGGGCAA
IGHV1-69*10_Homo+sapiens ATCATCCCTATCCTTGGTATAGCAAACTACGCACAGAAGTTCCAGGGCAG
                        ** * ****    * ****  **   *****    ******* ******

DC8E8_heavy_V           GGCCACACTGACTGCAGACAAATCCTCCAACACAGCCTACATGCAGCTCA
IGHV1-69*10_Homo+sapiens AGTCACGATTACCGCGGACACAAATCCACGAGCAGCACAGCCTACATGGAGCTGA
                        * *** * ** ** ** **  *****  *  ***** ** ******** *

DC8E8_heavy_V           GCAGCCTGACATCTGAGGACTCTGCGGTCTATTTCTGTGCAAGA--
IGHV1-69*10_Homo+sapiens GCAGCCTGAGATCTGAGGACACGGCCGTGTATTACTGTGCGAGAGA
                        ********* *********** *  ** ****  ****** ***
```

FIG. 5B

D-gene (9/14; 64.3 % sequence identity):

```
DC8E8                         -------GATTACTACGGTAC---------------------------------------
IGHD7-27*01_Homo+sapiens  CTGAGCTGAGAACCACTGTGCTAACTGGGGACACAGTGATTGGCAGCTCT
                                 **  *** ** ** *

DC8E8                     -
IGHD7-27*01_Homo+sapiens  A
```

J-gene (35/53; 66.0 % sequence identity):

```
DC8E8                     TTCATTTGCTATGGACTACTGGGGTCAAGGAACCTCAGTCACCGTCTCCT
IGHJ3*01_Homo+sapiens     ----TGATGCTTTTGATGTCTGGGGCCAAGGACAATGGTCACCGTCTCTT
                              * *  *** *      ******* ** ********* *******  *

DC8E8                     CAG
IGHJ3*01_Homo+sapiens        CAG
                             ***
```

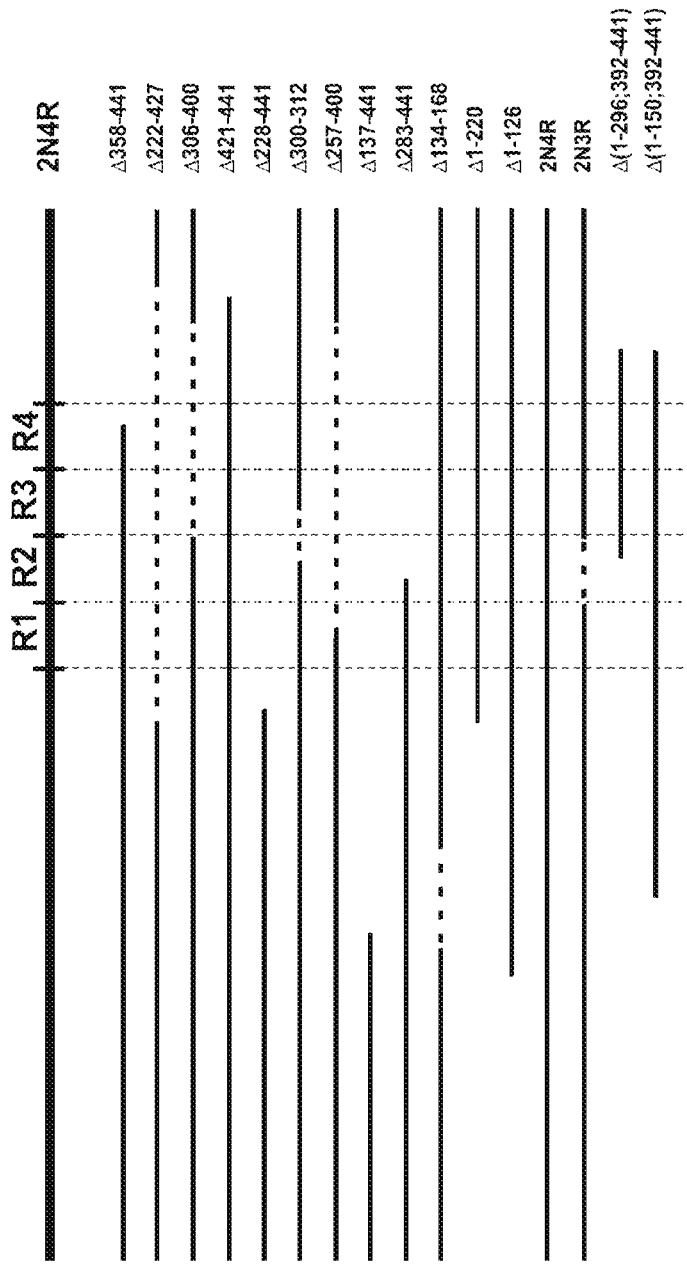

```
1    MAEPRQEFEV MEDHAGTYGL GDRKDQGGYT MHQDQEGDTD AGLKESPLQT PTEDGSEEPG
61   SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVKSKI GSTENLKHQP GGGKVQIINK KLDLSNVQSK CGSKDNIKHV
301  PGGGSVQIVY KPVDLSKVTS KCGSLGNIHH KPGGGQVEVK SEKLDFKDRV QSKIGSL
```

Δ222-427

```
1    MAEPRQEFEV MEDHAGTYGL GDRKDQGGYT MHQDQEGDTD AGLKESPLQT PTEDGSEEPG
61   SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT RLADEVSASL AKQGL
```

Δ306-400

```
1    MAEPRQEFEV MEDHAGTYGL GDRKDQGGYT MHQDQEGDTD AGLKESPLQT PTEDGSEEPG
61   SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVKSKI GSTENLKHQP GGGKVQIINK KLDLSNVQSK CGSKDNIKHV
301  PGGGSGDTSP RHLSNVSSTG SIDMVDSPQL ATLADEVSAS LAKQGL
```

Δ421-441

```
1    MAEPRQEFEV MEDHAGTYGL GDRKDQGGYT MHQDQEGDTD AGLKESPLQT PTEDGSEEPG
61   SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVKSKI GSTENLKHQP GGGKVQIINK KLDLSNVQSK CGSKDNIKHV
301  PGGGSVQIVY KPVDLSKVTS KCGSLGNIHH KPGGGQVEVK SEKLDFKDRV QSKIGSLDNI
361  THVPGGGNKK IETHKLTFRE NAKAKTDHGA EIVYKSPVVS GDTSPRHLSN VSSTGSIDMV
```

Δ228-441

```
1    MAEPRQEFEV MEDHAGTYGL GDRKDQGGYT MHQDQEGDTD AGLKESPLQT PTEDGSEEPG
61   SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVA
```

```
  1  MAEPRQEFEV MEDHAGTYGL GDRKDQGGYT MHQDQEGDTD AGLKESPLQT PTEDGSEEPG
 61  SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVKSKI GSTENLKHQP GGGKVQIINK KLDLSNVQSK CGSKDNIKHV
301  DLSKVTSKCG SLGNIHHKPG GGQVEVKSEK LDFKDRVQSK IGSLDNITHV PGGGNKKIET
361  HKLTFRENAK AKTDHGAEIV YKSPVVSGDT SPRHLSNVSS TGSIDMVDSP QLATLADEVS
421  ASLAKQGL
```

Δ257-400

```
  1  MAEPRQEFEV MEDHAGTYGL GDRKDQGGYT MHQDQEGDTD AGLKESPLQT PTEDGSEEPG
 61  SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVGDTS PRHLSNVSST GSIDMVDSPQ LATLADEVSA SLAKQGL
```

Δ137-441

```
  1  MAEPRQEFEV MEDHAGTYGL GDRKDQGGYT MHQDQEGDTD AGLKESPLQT PTEDGSEEPG
 61  SETSDAKSTP TAEDVTAPLV DEGAPGKQAA AQPHTEIPEG TTAEEAGIGD TPSLEDEAAG
121  HVTQARMVSK SKDGTG
```

Δ283-441

```
  1  MAEPRQEFEV MEDHAGTYGL GDRKDQGGYT MHQDQEGDTD AGLKESPLQT PTEDGSEEPG
 61  SETSDAKSTP TAEDVTAPLV DEGAPGKQAA AQPHTEIPEG TTAEEAGIGD TPSLEDEAAG
121  HVTQARMVSK SKDGTGSDDK KAKGADGKTK IATPRGAAPP GQKGQANATR IPAKTPPAPK
181  TPPSSGEPPK SGDRSGYSSP GSPGTPGSRS RTPSLPTPPT REPKKVAVVR TPPKSPSSAK
241  SRLQTAPVPM PDLKNVKSKI GSTENLKHQP GGGKVQIINK KL
```

Δ134-168

```
  1  MAEPRQEFEV MEDHAGTYGL GDRKDQGGYT MHQDQEGDTD AGLKESPLQT PTEDGSEEPG
 61  SETSDAKSTP TAEDVTAPLV DEGAPGKQAA AQPHTEIPEG TTAEEAGIGD TPSLEDEAAG
121  HVTQARMVSK SKDTRIPAKT PPAPKTPPSS GEPPKSGDRS GYSSPGSPGT PGSRSRTPSL
181  PTPPTREPKK VAVVRTPPKS PSSAKSRLQT APVPMPDLKN VKSKIGSTEN LKHQPGGGKV
241  QIINKKLDLS NVQSKCGSKD NIKHVPGGGS VQIVYKPVDL SKVTSKCGSL GNIHHKPGGG
301  QVEVKSEKLD FKDRVQSKIG SLDNITHVPG GGNKKIETHK LTFRENAKAK TDHGAEIVYK
361  SPVVSGDTSP RHLSNVSSTG SIDMVDSPQL ATLADEVSAS LAKQGL
```

Δ1-220

```
  1  MREPKKVAVV RTPPKSPSSA KSRLQTAPVP MPDLKNVKSK IGSTENLKHQ PGGGKVQIIN
 61  KKLDLSNVQS KCGSKDNIKH VPGGGSVQIV YKPVDLSKVT SKCGSLGNIH HKPGGGQVEV
121  KSEKLDFKDR VQSKIGSLDN ITHVPGGGNK KIETHKLTFR ENAKAKTDHG AEIVYKSPVV
181  SGDTSPRHLS NVSSTGSIDM VDSPQLATLA DEVSASLAKQ GL
```

FIG. 6D

Δ1-126
```
1   MVSKSKDGTG SDDKKAKGAD GKTKIATPRG AAPPGQKGQA NATRIPAKTP PAPKTPPSSG
61  EPPKSGDRSG YSSPGSPGTP GSRSRTPSLP TPPTREPKKV AVVRTPPKSP SSAKSRLQTA
121 PVPMPDLKNV KSKIGSTENL KHQPGGGKVQ IINKKLDLSN VQSKCGSKDN IKHVPGGGSV
181 QIVYKPVDLS KVTSKCGSLG NIHHKPGGGQ VEVKSEKLDF KDRVQSKIGS LDNITHVPGG
241 GNKKIETHKL TFRENAKAKT DHGAEIVYKS PVVSGDTSPR HLSNVSSTGS IDMVDSPQLA
301 TLADEVSASL AKQGL
```

4R2N
```
1   MAEPRQEFEV MEDHAGTYGL GDRKDQGGYT MHQDQEGDTD AGLKESPLQT PTEDGSEEPG
61  SETSDAKSTP TAEDVTAPLV DEGAPGKQAA AQPHTEIPEG TTAEEAGIGD TPSLEDEAAG
121 HVTQARMVSK SKDGTGSDDK KAKGADGKTK IATPRGAAPP GQKGQANATR IPAKTPPAPK
181 TPPSSGEPPK SGDRSGYSSP GSPGTPGSRS RTPSLPTPPT REPKKVAVVR TPPKSPSSAK
241 SRLQTAPVPM PDLKNVKSKI GSTENLKHQP GGGKVQIINK KLDLSNVQSK CGSKDNIKHV
301 PGGGSVQIVY KPVDLSKVTS KCGSLGNIHH KPGGGQVEVK SEKLDFKDRV QSKIGSLDNI
361 THVPGGGNKK IETHKLTFRE NAKAKTDHGA EIVYKSPVVS GDTSPRHLSN VSSTGSIDMV
421 DSPQLATLAD EVSASLAKQG L
```

3R2N
```
1   MAEPRQEFEV MEDHAGTYGL GDRKDQGGYT MHQDQEGDTD AGLKESPLQT PTEDGSEEPG
61  SETSDAKSTP TAEDVTAPLV DEGAPGKQAA AQPHTEIPEG TTAEEAGIGD TPSLEDEAAG
121 HVTQARMVSK SKDGTGSDDK KAKGADGKTK IATPRGAAPP GQKGQANATR IPAKTPPAPK
181 TPPSSGEPPK SGDRSGYSSP GSPGTPGSRS RTPSLPTPPT REPKKVAVVR TPPKSPSSAK
241 SRLQTAPVPM PDLKNVKSKI GSTENLKHQP GGGKVQIVYK PVDLSKVTSK CGSLGNIHHK
301 PGGGQVEVKS EKLDFKDRVQ SKIGSLDNIT HVPGGGNKKI ETHKLTFREN AKAKTDHGAE
361 IVYKSPVVSG DTSPRHLSNV SSTGSIDMVD SPQLATLADE VSASLAKQGL
```

Δ(1-296;392-441)
```
1   MIKHVPGGGS VQIVYKPVDL SKVTSKCGSL GNIHHKPGGG QVEVKSEKLD FKDRVQSKIG
61  SLDNITHVPG GGNKKIETHK LTFRENAKAK TDHGAE
```

Δ(1-150;392-441)
```
1   MIATPRGAAP PGQKGQANAT RIPAKTPPAP KTPPSSGEPP KSGDRSGYSS PGSPGTPGSR
61  SRTPSLPTPP TREPKKVAVV RTPPKSPSSA KSRLQTAPVP MPDLKNVKSK IGSTENLKHQ
121 PGGGKVQIIN KKLDLSNVQS KCGSKDNIKH VPGGGSVQIV YKPVDLSKVT SKCGSLGNIH
181 HKPGGGQVEV KSEKLDFKDR VQSKIGSLDN ITHVPGGGNK KIETHKLTFR ENAKAKTDHG
241 AE
```

Note
The Methionine (M) at the position 1 in the tau deletion constructs Δ1-220, Δ(1-296;392-441) and Δ(1-150;392-441) is not part of the natural human tau sequence. It was added in order to provide a start codon for the bacterial translational machinery.

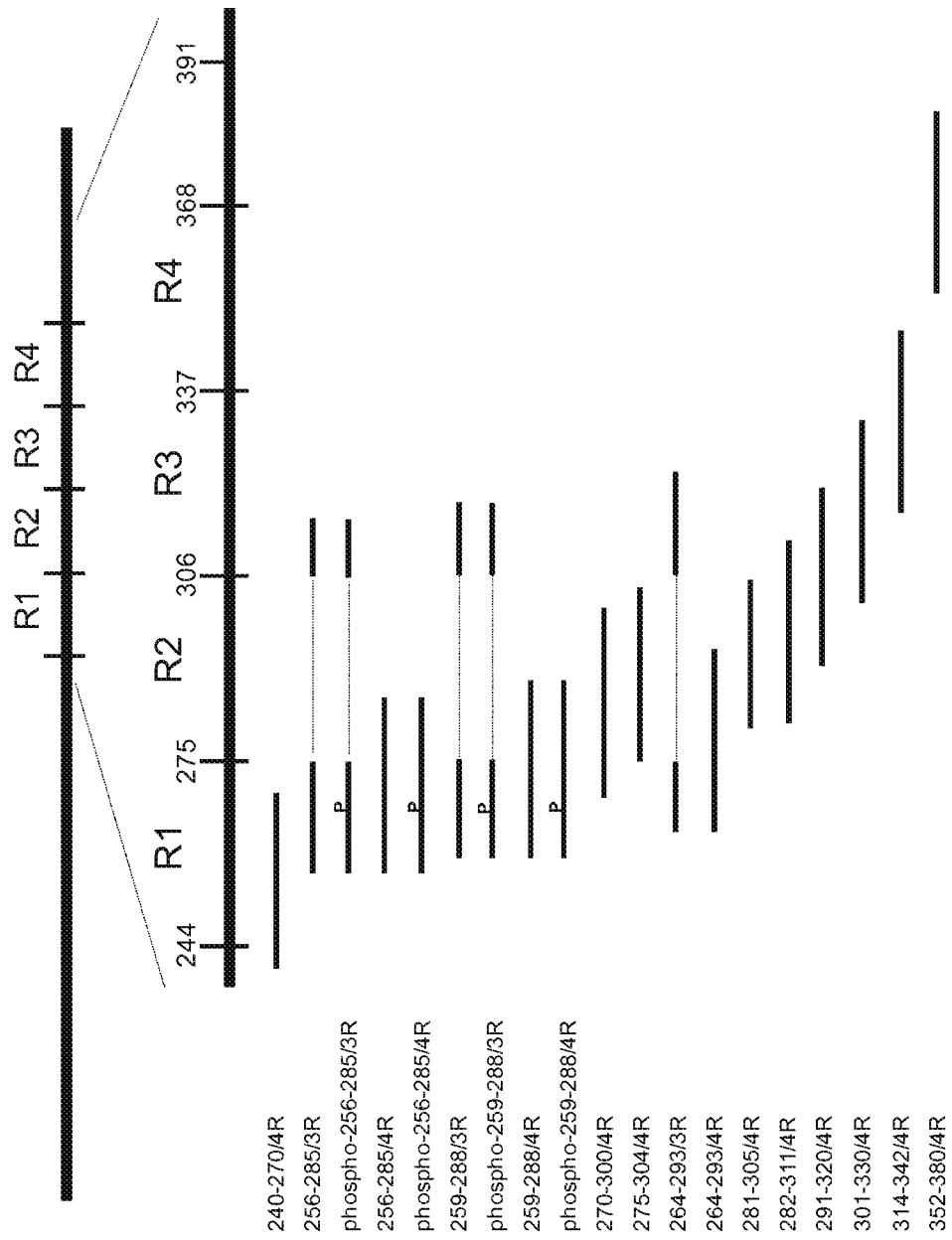

FIG. 7B

| Synthetic peptide | Sequence |
|---|---|
| 240-270/4R | KSRLQTAPVPMPDLKNVKSKIGSTENLKHQP |
| 256-285/3R | VKSKIGSTENLKHQPGGGKVQIVYKPVDLS |
| phospho 256-285/3R (pSer262) | VKSKIGpSTENLKHQPGGGKVQIVYKPVDLS |
| 256-285/4R | VKSKIGSTENLKHQPGGGKVQIINKKLDLS |
| phospho 256-285/4R (pSer262) | VKSKIGpSTENLKHQPGGGKVQIINKKLDLS |
| 259-288/3R | KIGSTENLKHQPGGGKVQIVYKPVDLSKVT |
| phospho 259-288/3R (pSer262) | KIGpSTENLKHQPGGGKVQIVYKPVDLSKVT |
| 259-288/4R | KIGSTENLKHQPGGGKVQIINKKLDLSNVQ |
| phospho 259-288/4R (pSer262) | KIGpSTENLKHQPGGGKVQIINKKLDLSNVQ |
| 270-300/4R | PGGGKVQIINKKLDLSNVQSKCGSKDNIKHV |
| 275-304/4R | VQIINKKLDLSNVQSKCGSKDNIKHVPGGG |
| 264-293/3R | ENLKHQPGGGKVQIVYKPVDLSKVTSKCGS |
| 264-293/4R | ENLKHQPGGGKVQIINKKLDLSNVQSKCGS |
| 281-305/4R | KLDLSNVQSKCGSKDNIKHVPGGGS |
| 282-311/4R | LDLSNVQSKCGSKDNIKHVPGGGSVQIVYK |
| 291-320/4R | CGSKDNIKHVPGGGSVQIVYKPVDLSKVTS |
| 301-330/4R | PGGGSVQIVYKPVDLSKVTSKCGSLGNIHH |
| 314-342/4R | DLSKVTSKCGSLGNIHHKPGGGQVEVKSE |
| 352-380/4R | SKIGSLDNITHVPGGGNKKIETHKLTFREN |

FIG. 8A

```
Human              265-NLKHQPGGGKVQIINKKLDLSNVQSKCGSKDNIKHVPGGGSVQIVYKPVD
Chimpanzee         572-NLKHQPGGGKVQIINKKLDLSNVQSKCGSKDNIKHVPGGGSVQIVYKPVD
Macaque            572-NLKHQPGGGKVQIINKKLDLSNVQSKCGSKDNIKHVPGGGSVQIVYKPVD
Gibbon             572-NLKHQPGGGKVQIINKKLDLSNVQSKCGSKDNIKHVPGGGSVQIVYKPVD
Orangutan          554-NLKHQPGGGKVQIINKKLDLSNVQSKCGSKDNIKHVPGGGSVQIVYKPVD
Giant_panda        596-NLKHQPGGGKVQIINKKLDLSNVQSKCGSKDNIKHVPGGGSVQIVYKPVD
Pig                541-NLKHQPGGGKVQIINKKLDLSNVQSKCGSKDNIKHVPGGGSVQIVYKPVD
Horse              241-NLKHQPGGGKVQIINKKLDLSNVQSKCGSKDNIKHVPGGGSVQIVYKPVD
Dog                237-NLKHQPGGGKVQIINKKLDLSNVQSKCGSKDNIKHVPGGGSVQIVYKPVD
Rabbit             228-NLKHQPGGGKVQIINKKLDLSNVQSKCGSKDNIKHVPGGGSVQIVYKPVD
Rat                228-NLKHQPGGGKVQIINKKLDLSNVQSKCGSKDNIKHVPGGGSVQIVYKPVD
Vole               226-NLKHQPGGGKVQIINKKLDLSNVQSKCGSKDNIKHVPGGGSVQIVYKPVD
Mouse              226-NLKHQPGGGKVQIINKKLDLSNVQSKCGSKDNIKHVPGGGSVQIVYKPVD
Ground_Squirrel    226-NLKHQPGGGKVQIINKKLDLSNVQSKCGSKDNIKHVPGGGSVQIVYKPVD
Cattle             244-NLKHQPGGGKVQIINKKLDLSNVQSKCGSKDNIKHVPGGGSVQIVYKPVD
Fowl               141-NLKHQPGGGKVQIINKKLDFSSVQSKCGSKDNIKHIPGGGSVQIVYKPVD
Finch              502-NLKHQPGGGKVQIINKKLDFSSVQSKCGSKDNIKHIPGGGSVQIVYKPVD
Zebra_fish         206-NIKHAPGGGNVQILDQKLDLTNVQARCGSKDNLKHVPGGGKVQILHKKID
African_clawed_frog 468-NIRHQPGGGKVQIVHKKVDLGNVQSKCGSKDNLKHVPGGGAIQITHRPID
Fruit_fly          157-NATYKPGGGHVKIESKKIDIKAAPRIEAKND--KYMPKGGEKKIVTTKLQ
Roundworm          269-N--HKAGGGNVEIFSEKR-LYNAQSKVGSLKNATHVAGGGNVQIENRKLD Human              LSKVTSKCGSLGNIHHKPGGGQVEVKSEKLDFKDRVQSKIGSLDNITHVPGGGN-368
Chimpanzee         LSKVTSKCGSLGNIHHKPGGGQVEVKSEKLDFKDRVQSKIGSLDNITHVPGGGN-703
Macaque            LSKVTSKCGSLGNIHHKPGGGQVEVKSEKLDFKDRVQSKIGSLDNITHVPGGGS-703
Gibbon             LSKVTSKCGSLGNIHHKPGGGQVEVKSEKLDFKDRVQSKIGSLDNITHVPGGGN-703
Orangutan          LSKVTSKCGSLGNIHHKPGGGQVEVKSEKLDFKDRVQSKIGSLDNITHVPGGGH-685
Giant_panda        LSKVTSKCGSLGNIHHKPGGGQVEVKSEKLDFKDRVQSKIGSLDNITHVPGGGN-727
Pig                LSKVTSKCGSLGNIHHKPGGGQVEVKSEKLDFKDRVQSKIGSLDNITHVPGGGN-673
Horse              LSKVTSKCGSLGNIHHKPGGGQVEVKSEKLDFKDRVQSKIGSLDNITHVPGGGH-372
Dog                LSKVTSKCGSLGNIHHKPGGGQVEVKSEKLDFKDRVQSKIGSLDNITHVPGGGN-368
Rabbit             LSKVTSKCGSLGNIHHKPGGGQVEVKSEKLDFKDRVQSKIGSLDNITHVPGGGN-359
Rat                LSKVTSKCGSLGNIHHKPGGGQVEVKSEKLDFKDRVQSKIGSLDNITHVPGGGN-359
Vole               LSKVTSKCGSLGNIHHKPGGGQVEVKSEKLDFKDRVQSKIGSLDNITHVPGGGN-357
Mouse              LSKVTSKCGSLGNIHHKPGGGQVEVKSEKLDFKDRVQSKIGSLDNITHVPGGGN-357
Ground_Squirrel    LSKVTSKCGSLGNIHHKPGGGQVEVKSEKLDFKDRVQSKIGSLDNITHVPGGGN-357
Cattle             LSKVTSKCGSLGNIHHKPGGGQVEVKSEKLDFKDRVQSKIGSLDNITHVPGGGN-375
Fowl               LSHVTSKCGSLGNIHHKPGGGQVEVKSEKLDFKDKVQSKIGSLDNISHVPGGGN-272
Finch              LSHVTSKCGSLGNIHHKPGGGQVEVKSEKLDFKDKVQSKIGSLDNISHVPGGGN-633
Zebra_fish         LSNVQSKCGSKDNLRHKPGGGNIEIRSEKLDF--KAQSKIGSMDNIKHTPGGGN-332
African_clawed_frog LTRVTSKCGSFVNIHHKPGGGNVELKSEKLEF-DKIQSKIGSLDNVTHVPGGGA-600
Fruit_fly          WN-AKSKIGSLENAAHKPGGGDKKIETLKMDFKDKAKPKVGSTANVKHQPGGGD-287
Roundworm          FSAASPKVGS--KTNYQPAKSDVKIVSERLTW--QAKSKVGSMDNAAHKPAGGN-396
```

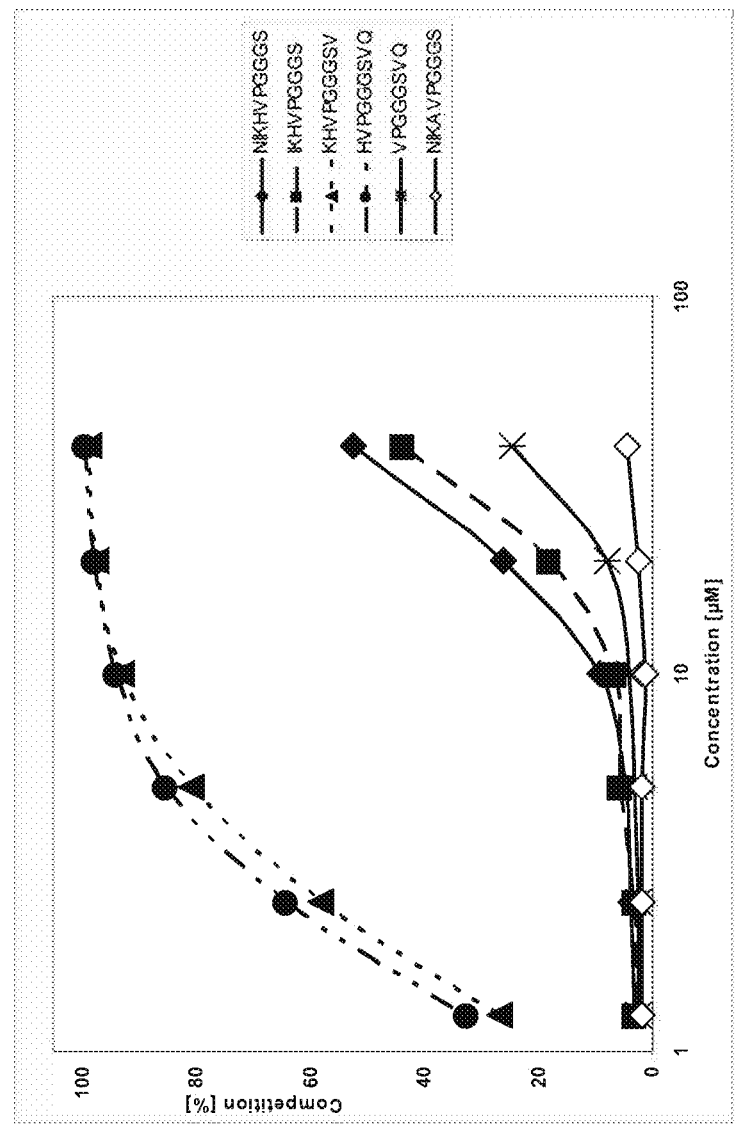

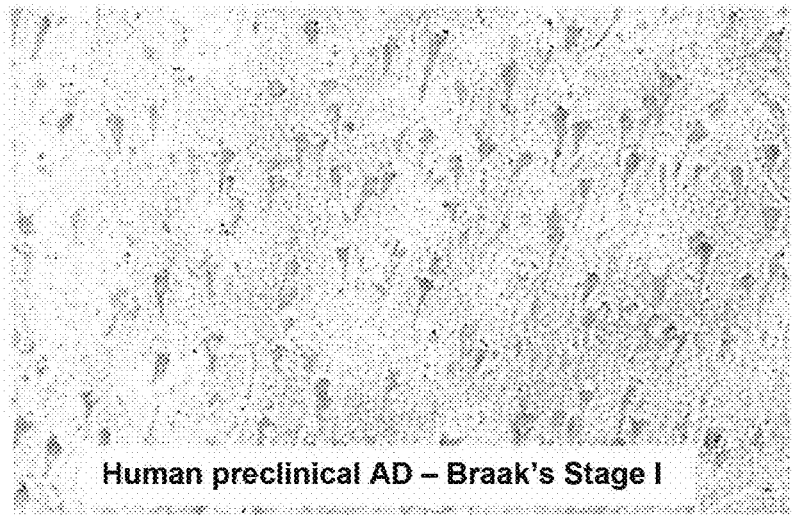
FIG. 11A Human preclinical AD – Braak's Stage I
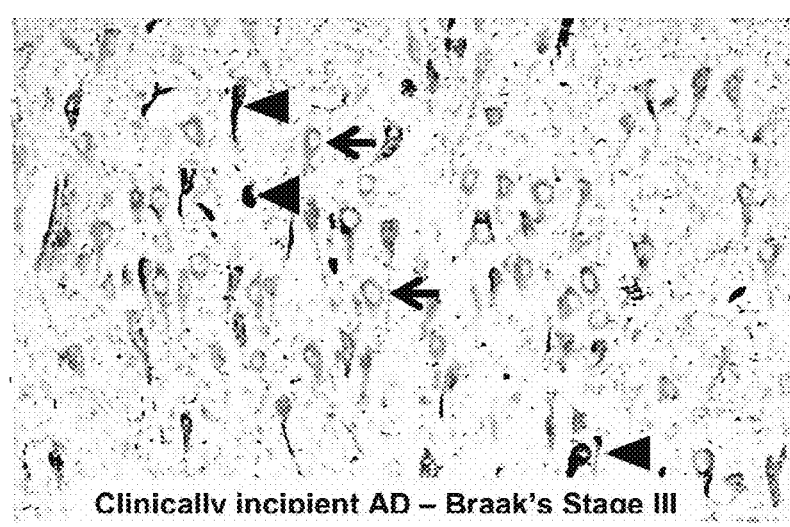
FIG. 11B Clinically incipient AD – Braak's Stage III
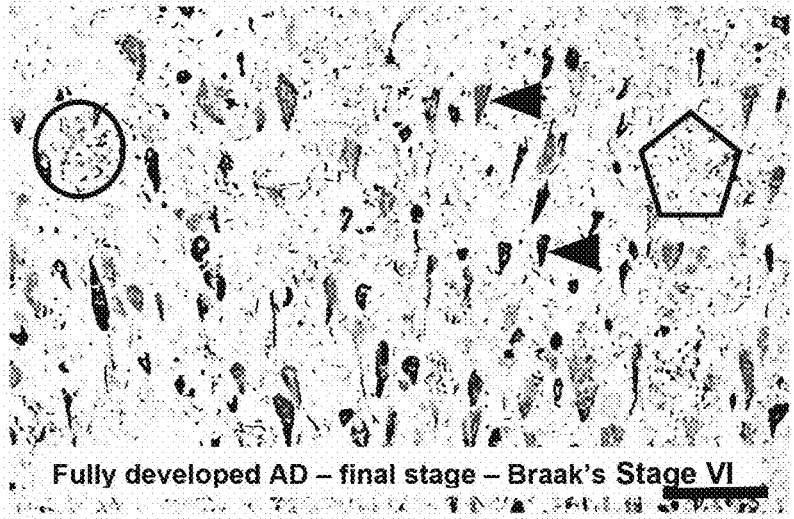
FIG. 11C Fully developed AD – final stage – Braak's Stage VI

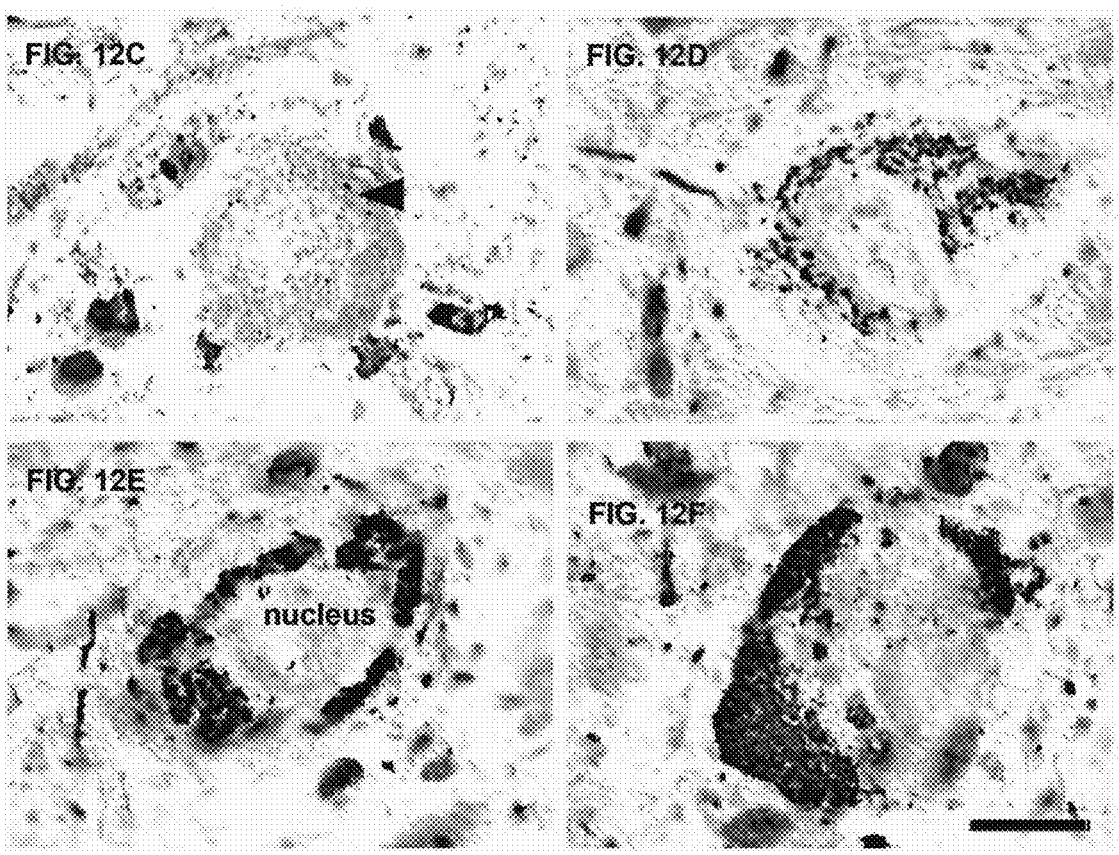

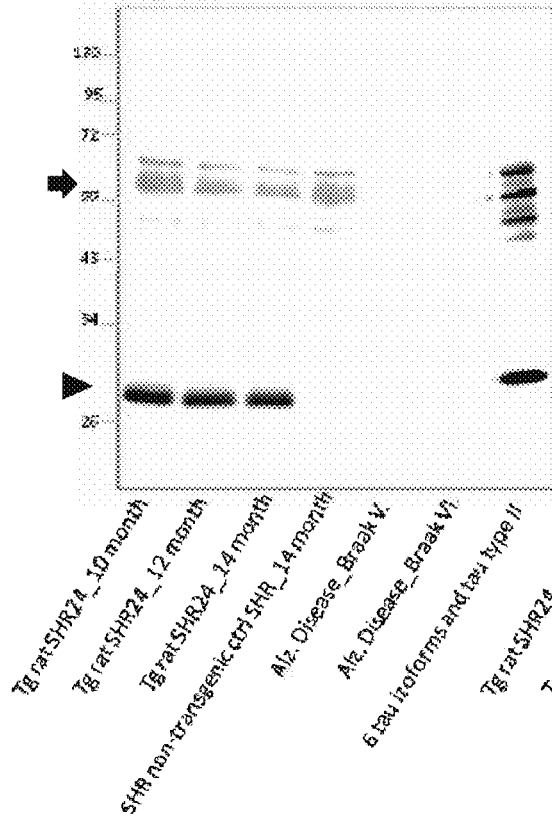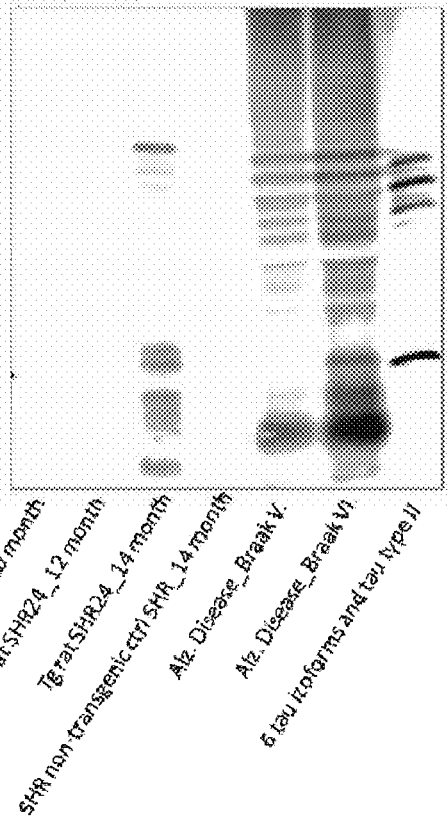

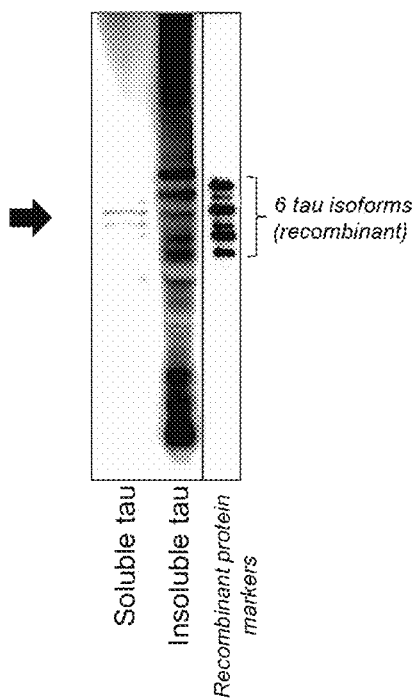
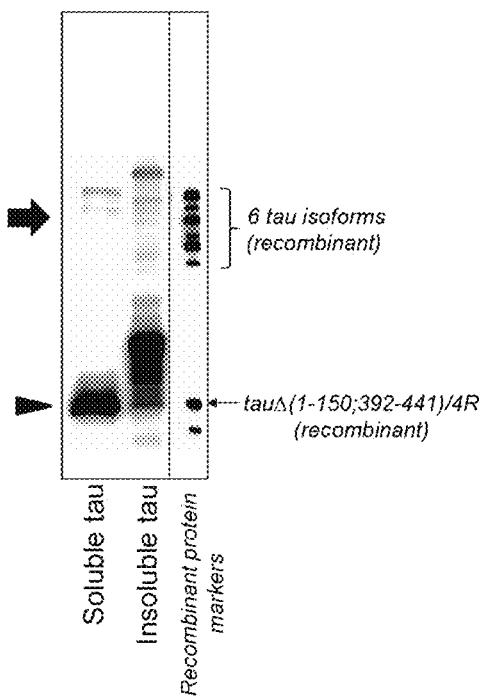

Alzheimer's disease Tau

FIG. 24A
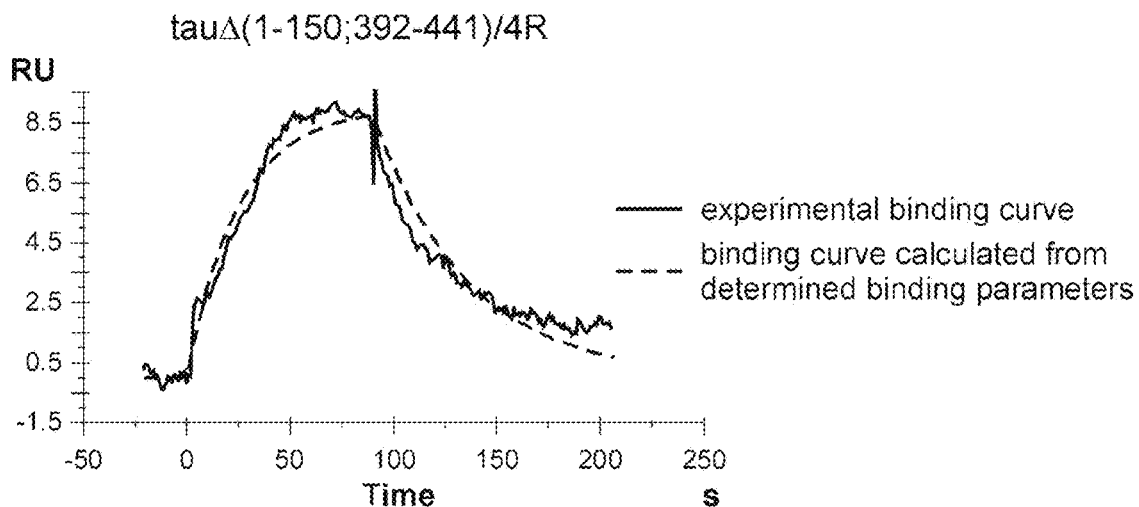
FIG. 24B
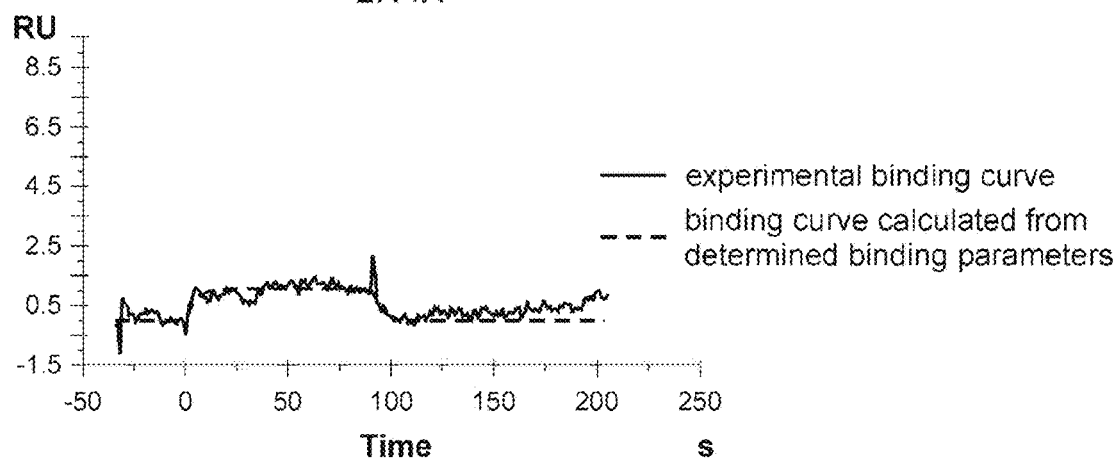
FIG. 24C
|  | $k_{ON}(s^{-1}M^{-1})$ | $k_{OFF}(s^{-1})$ | $K_A(M^{-1})$ |
|---|---|---|---|
| tauΔ(1-150;392-441)/4R | $1.8 \times 10^5$ | 0.02 | $8.1 \times 10^6$ |
| 2N4R | $5.7 \times 10^4$ | 0.2 | $2.7 \times 10^5$ |

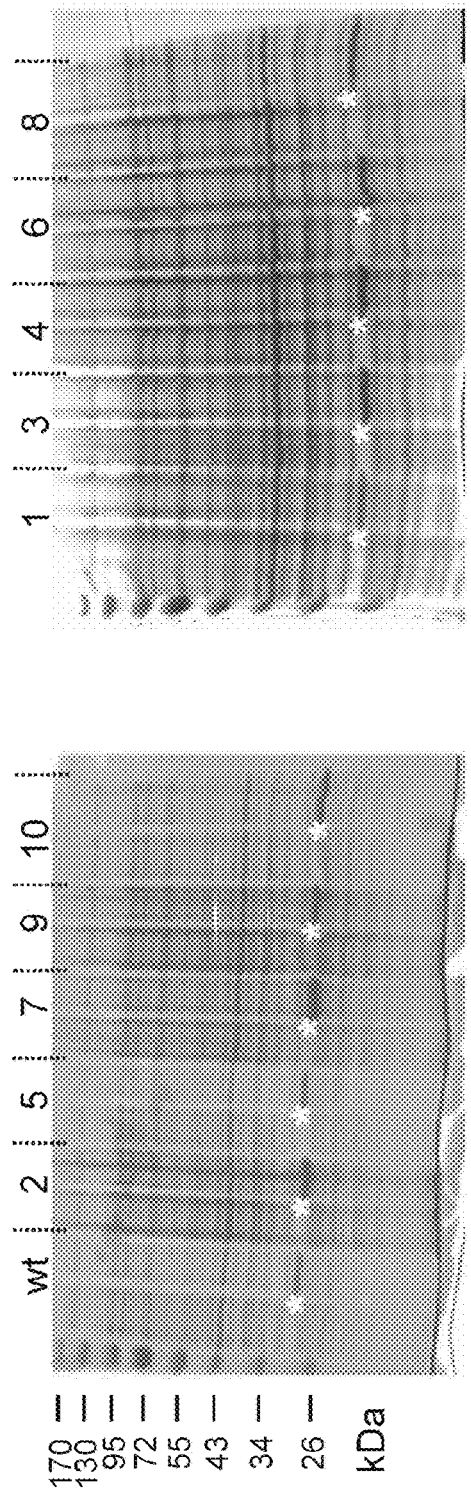
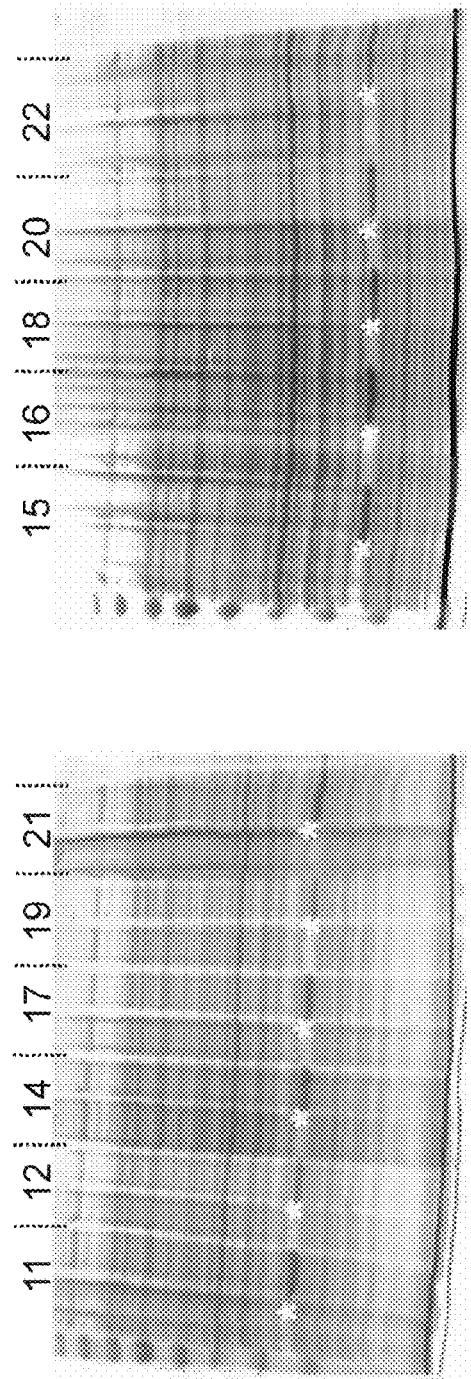
FIG. 25A

FIG. 26B

| SEQ ID NO | Immunogen | Reduction of insoluble tau (%) AD-relevant epitopes | | | | | |
|---|---|---|---|---|---|---|---|
| | | 347-353 | pT217 | pT231 | pS202/pT205 | pT181 |
| SEQ ID NO: 1 | Tau 251-280 | 71 | 42 | 11 | ND | 58 |
| SEQ ID NO: 2 | Tau 256-285 | 41 | 72 | 64 | 80 | 74 |
| SEQ ID NO: 2 | Tau 256-285/pS262 | 46 | 73 | 85 | 82 | 82 |
| SEQ ID NO: 3 | Tau 259-288 | 40 | 30 | 63 | 61 | 74 |
| SEQ ID NO: 4 | Tau 275-304 | 63 | 92 | 95 | 95 | 87 |
| SEQ ID NO: 108 | Tau 294-305 | 70 | 96 | 97 | 98 | 94 |
| SEQ ID NO: 5 | Tau 201-230/pT217 | 1 | -11 | 33 | -31 | 30 |
| SEQ ID NO: 6 | Tau 379-408/pS396/pS404 | -87 | -33 | -44 | 19 | -7 |
| SEQ ID NO: 7 | Tau 181-210/pS202/pT205 | -6 | -3 | -11 | -41 | -7 |
| SEQ ID NO: 8 | Tau 300-317 | -82 | 9 | -60 | 17 | -10 |

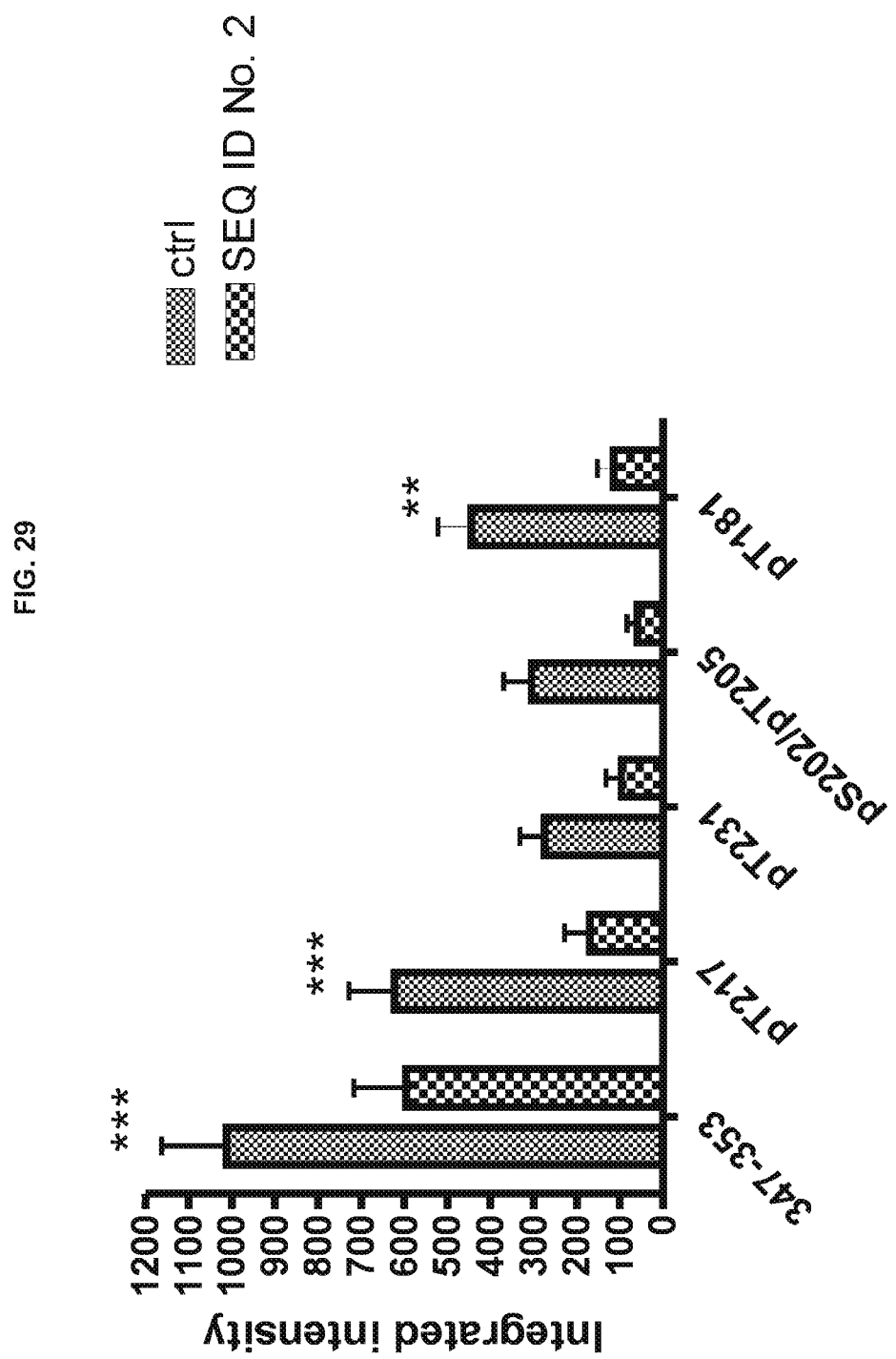

FIG. 56

| | Geometric mean antibody titers | | |
|---|---|---|---|
| | Solid phase | | |
| Serum dilutions | Peptide SEQ ID NO:108 | Tau Δ(1-150;392-441)/4R | Tau 2N4R |
| 100 | 0[a] | 0 | 0 |
| 200 | 0 | 0 | 0 |
| 400 | 0 | 0 | 0 |
| 800 | 0 | 0 | 2 |
| 1 600 | 0 | 0 | 1 |
| 3 200 | 1 | 0 | 3 |
| 6 400 | 0 | 4 | 1 |
| 12 800 | 2 | 2 | 1 |
| 25 600 | 5 | 4 | 2 |
| 51 200 | 2 | 0 | 0 |
| GMT[b] | 20800 | 12800 | 4200 |

Footnotes:
[a] Number of responders
[b] Geometric mean titre

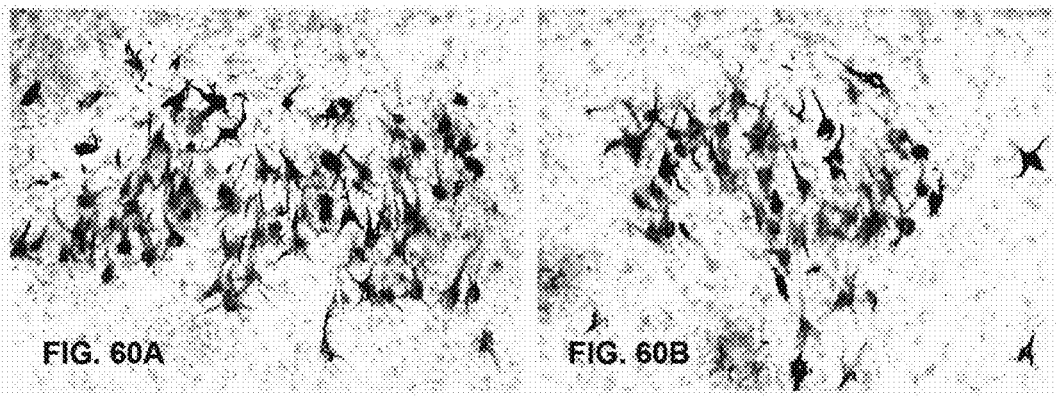
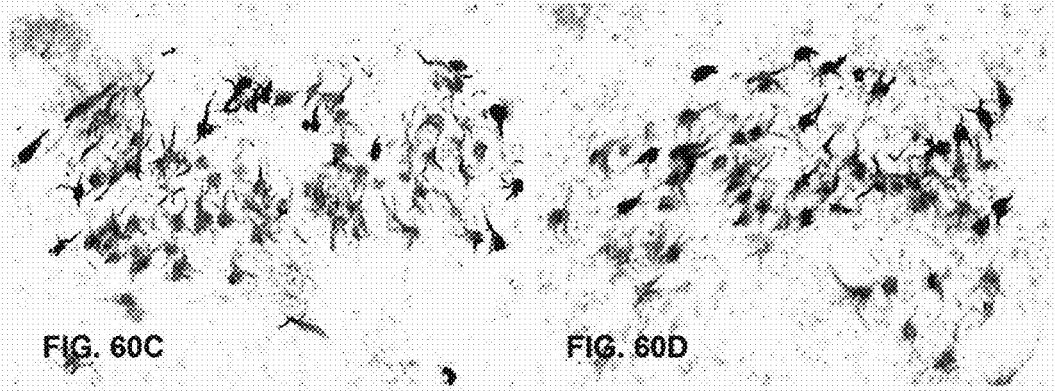
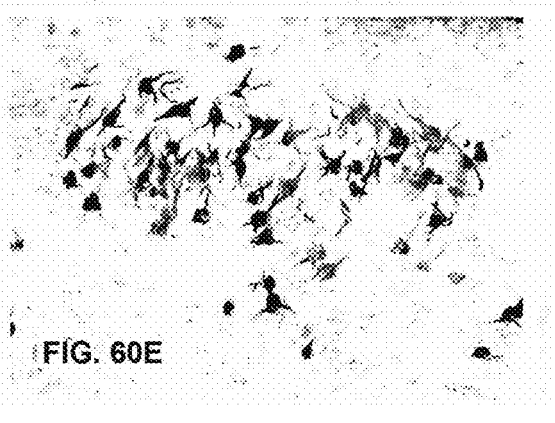

[GWSIHSPGGGSC (SEQ ID: 250)]

| | $K_A$ |
|---|---|
| tauΔ(1-150;392-441)4R | $1.1 \pm 0.3 \times 10^8 M^{-1}$ |
| 2N4R | $2.3 \pm 0.7 \times 10^6 M^{-1}$ |

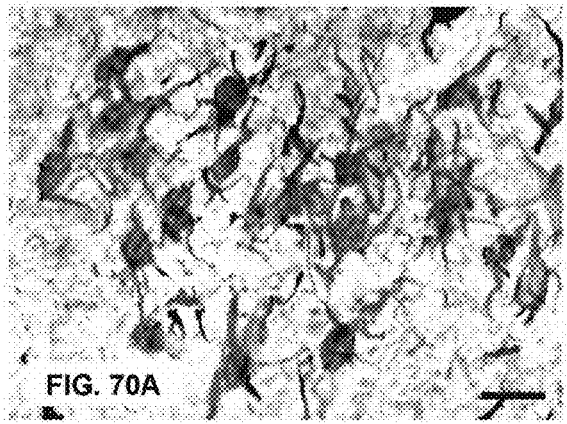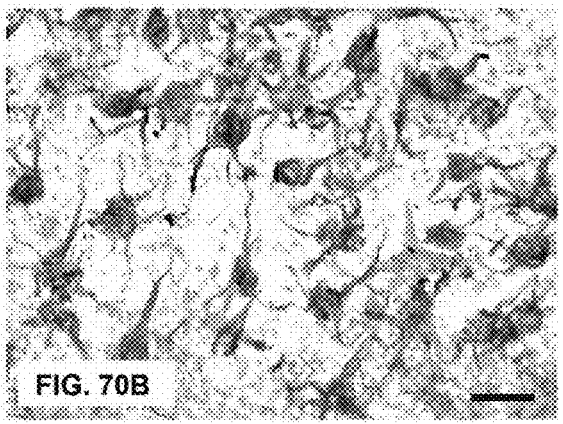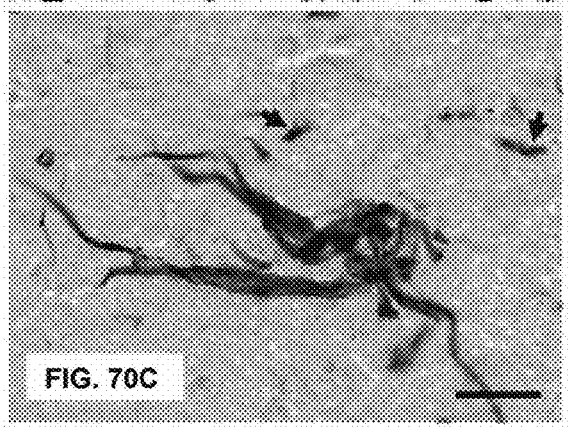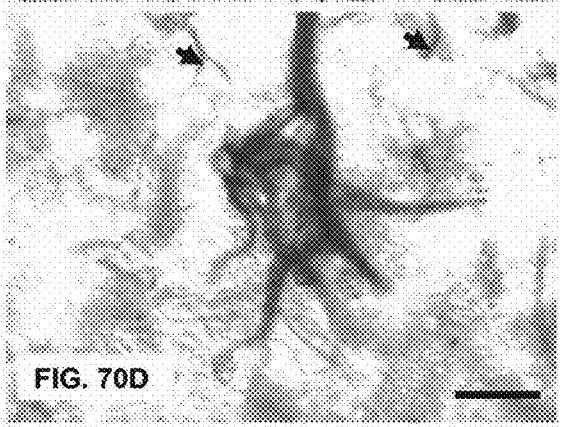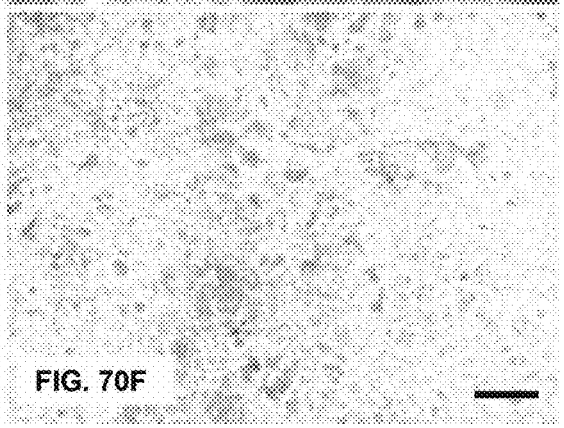

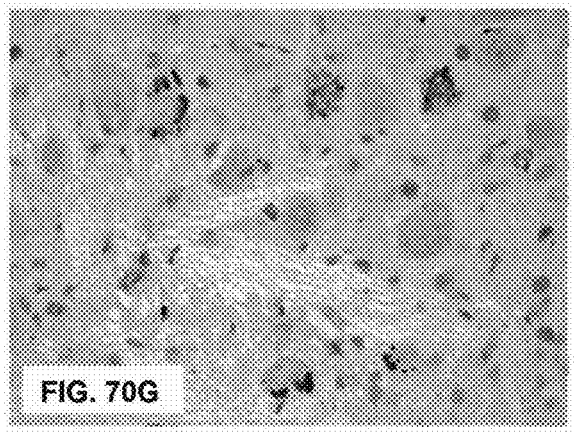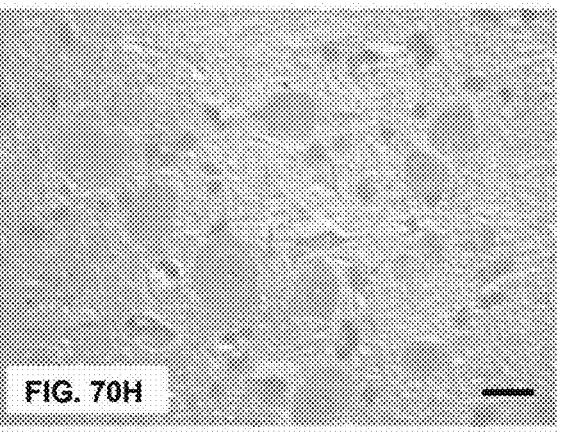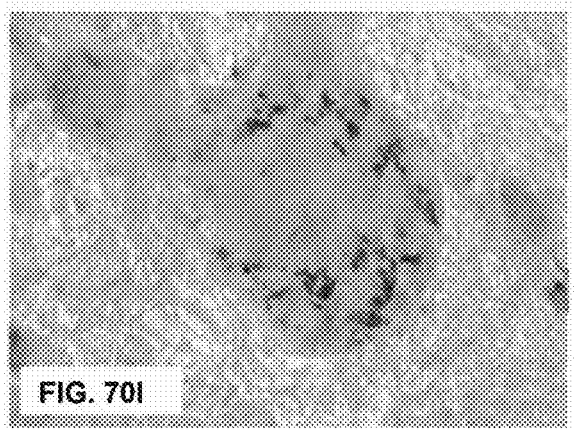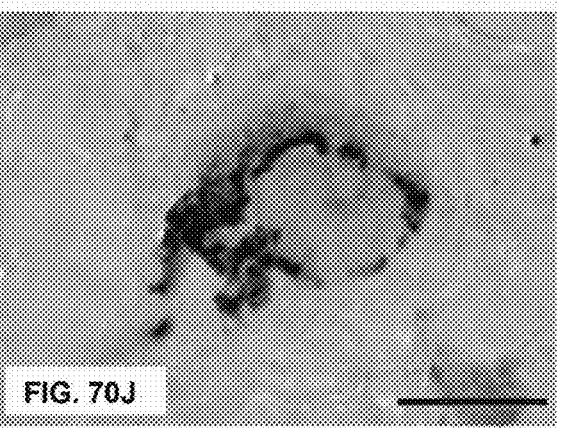

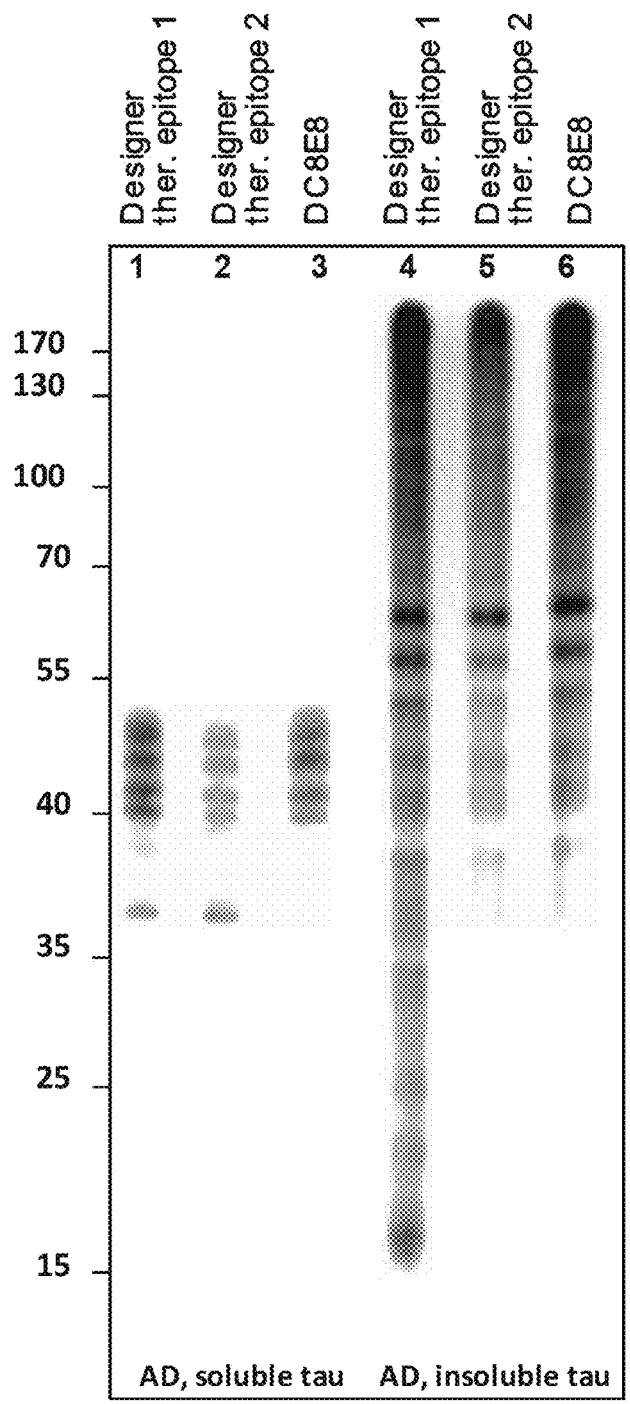

FIG. 75B

| Synthetic peptide | SEQ ID NO | Sequence |
|---|---|---|
| Tau263-274 | SEQ ID NO: 270 | TENLKHQPGGGK |
| Tau267-273 | SEQ ID NO: 271 | KHQPGGG |
| Tau268-273 | SEQ ID NO: 272 | HQPGGG |
| Tau268-272 | SEQ ID NO: 273 | HQPGG |
| Tau269-273 | SEQ ID NO: 274 | QPGGG |
| Tau264-305 | SEQ ID NO: 275 | ENLKHQPGGGKVQIINKKLDLSNVQSKCGSKDNIKHVPGGGS |
| Tau298-304 | SEQ ID NO: 276 | KHVPGGG |
| Tau299-304 | SEQ ID NO: 277 | HVPGGG |
| Tau299-303 | SEQ ID NO: 278 | HVPGG |
| Tau300-304 | SEQ ID NO: 279 | VPGGG |
| Tau295-313 | SEQ ID NO: 280 | DNIKHVPGGGSVQIVYKPV |
| Tau329-335 | SEQ ID NO: 281 | HHKPGGG |
| Tau330-335 | SEQ ID NO: 282 | HKPGGG |
| Tau361-367 | SEQ ID NO: 283 | THVPGGG |

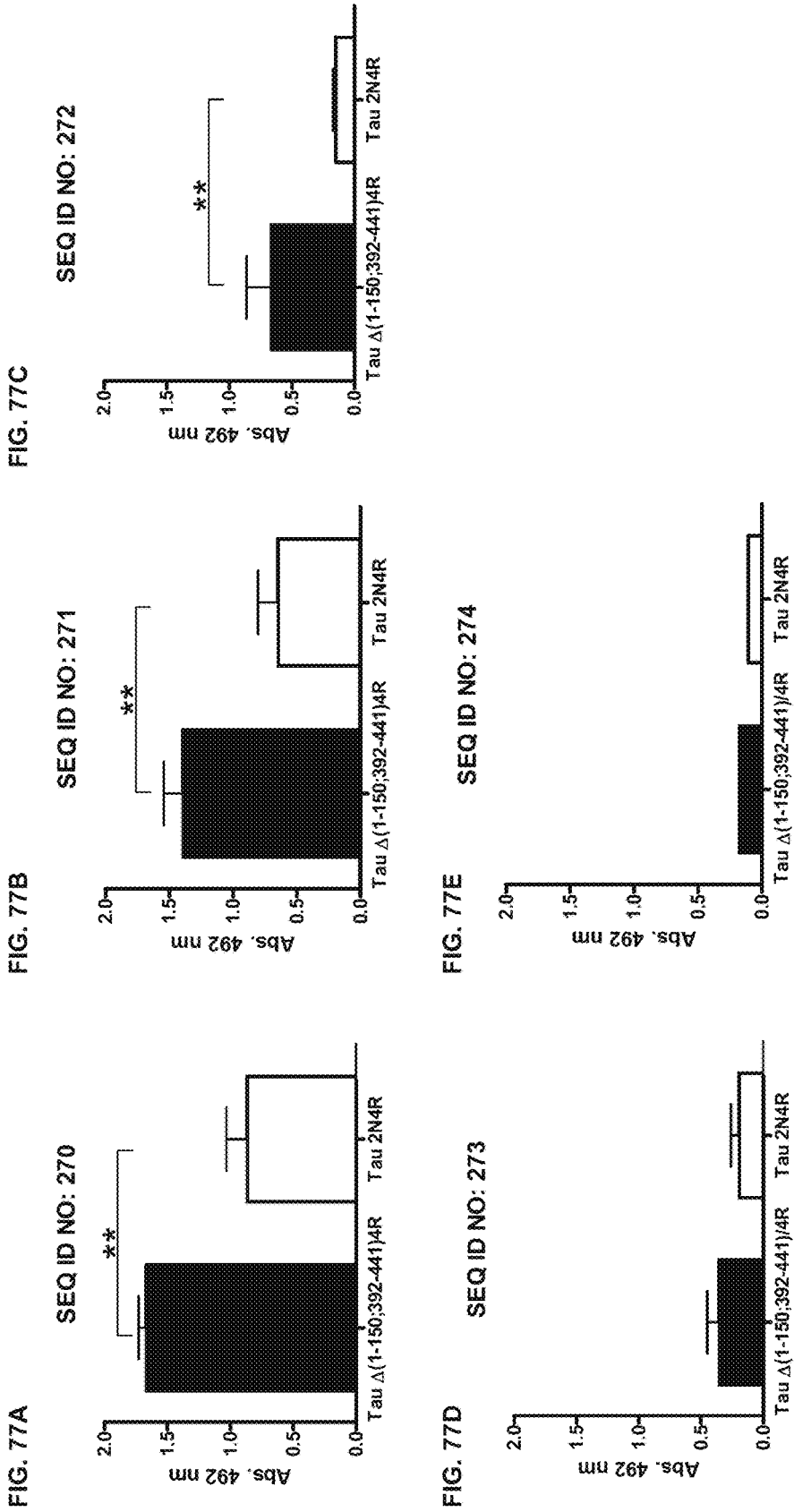

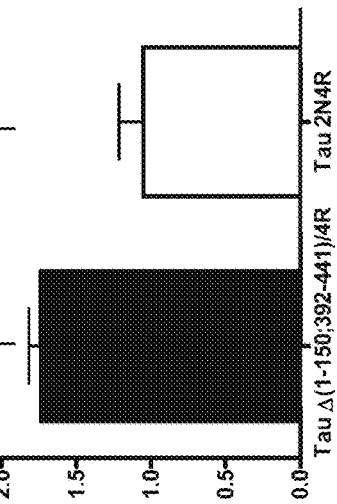
FIG. 77F
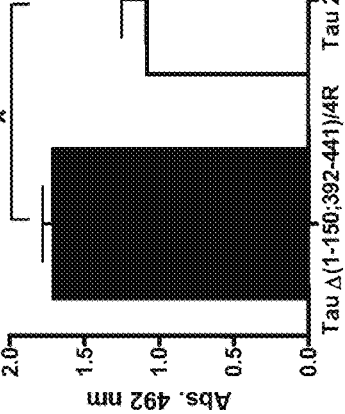
FIG. 77G
FIG. 77H
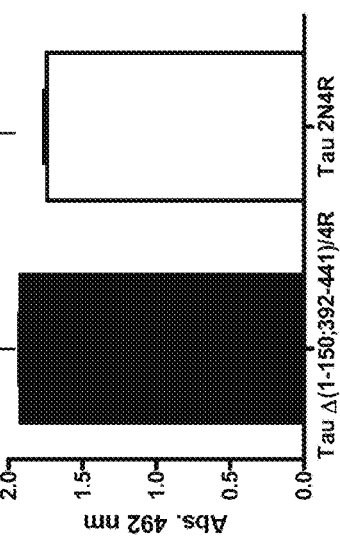
FIG. 77I
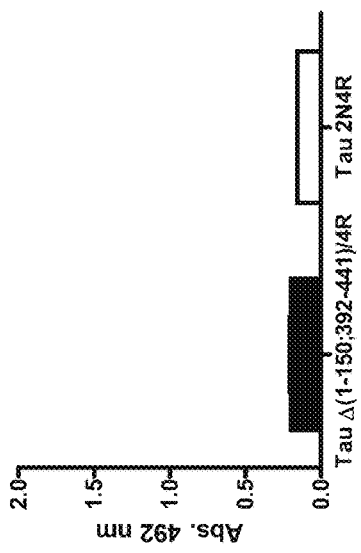
FIG. 77J
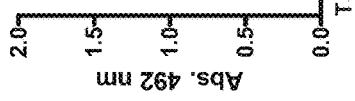
FIG. 77K
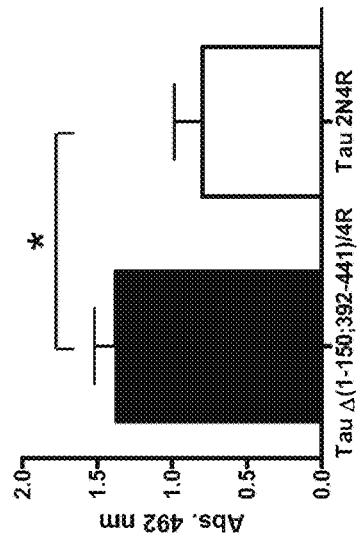

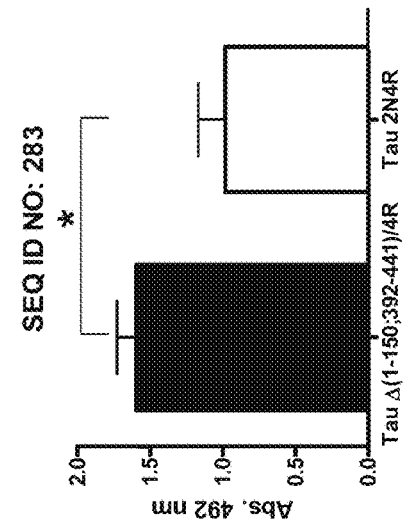
FIG. 77L  FIG. 77M
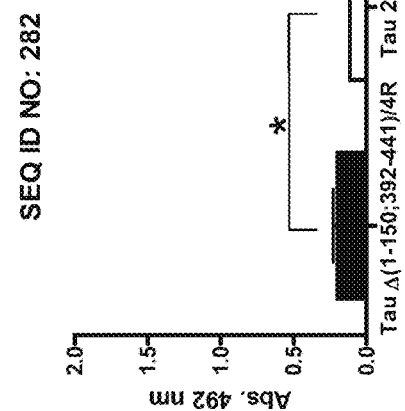
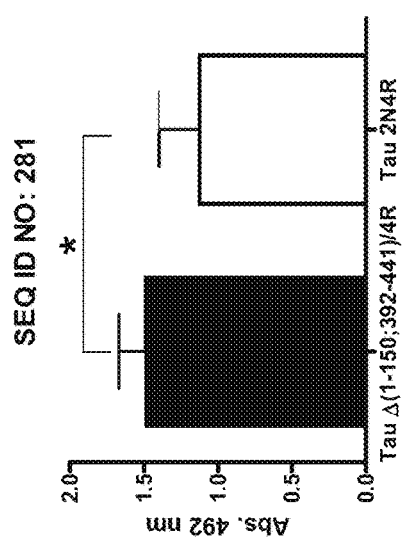
FIG. 77N

FIG. 78

| | Geometric mean antibody titers | |
|---|---|---|
| | solid phase | |
| Peptides | Tau Δ( 1-150; 392-441)/4R | Tau 2N4R |
| SEQ ID NO: 270 | 22286 | 4222 |
| SEQ ID NO: 271 | 12800 | 3200 |
| SEQ ID NO: 272 | 2786 | 264 |
| SEQ ID NO: 273 | 400 | <100 |
| SEQ ID NO: 274 | 152 | 0 |
| SEQ ID NO: 275 | >51200 | 16890 |
| SEQ ID NO: 280 | 51200 | 12800 |
| SEQ ID NO: 276 | 22286 | 4038 |
| SEQ ID NO: 277 | 12800 | 3805 |
| SEQ ID NO: 278 | 277 | 383 |
| SEQ ID NO: 279 | <100 | <100 |
| SEQ ID NO: 281 | 8445 | 2425 |
| SEQ ID NO: 282 | 174 | <100 |
| SEQ ID NO: 283 | 14703 | 4222 |

FIG. 81

Pathological forms of tau recognized by tau peptides-induced antibodies in Western blot

| Peptides | SHR 72 brain extract | AD brain extract |
|---|---|---|
| SEQ ID NO: 270 | + | + |
| SEQ ID NO: 271 | + | + |
| SEQ ID NO: 272 | + | + |
| SEQ ID NO: 273 | - | - |
| SEQ ID NO: 274 | - | - |
| SEQ ID NO: 275 | + | + |
| SEQ ID NO: 276 | + | + |
| SEQ ID NO: 277 | + | + |
| SEQ ID NO: 278 | - | - |
| SEQ ID NO: 279 | - | - |
| SEQ ID NO: 280 | + | + |
| SEQ ID NO: 281 | + | + |
| SEQ ID NO: 282 | - | - |
| SEQ ID NO: 283 | + | + |

+ positive
- negative

FIG. 83

Neurofibrillary tangles recognized by tau peptide-induced antibodies in human AD brain tissues

| Peptides | Intensity of staining | Number of NFTs |
|---|---|---|
| SEQ ID NO: 270 | Very intensive staining of NFTs | +++ |
| SEQ ID NO: 271 | Intensive staining of NFTs | ++ |
| SEQ ID NO: 272 | Weak staining of few NFTs | + |
| SEQ ID NO: 273 | No NFT staining | - |
| SEQ ID NO: 274 | No NFT staining | - |
| SEQ ID NO: 275 | Very intensive staining of NFTs | +++ |
| SEQ ID NO: 280 | Intensive staining of NFTs | +++ |
| SEQ ID NO: 276 | Intensive staining of NFTs | +++ |
| SEQ ID NO: 277 | Weak staining of NFTs | ++ |
| SEQ ID NO: 278 | No NFT staining | - |
| SEQ ID NO: 279 | No NFT staining | - |
| SEQ ID NO: 281 | Intensive staining of NFTs | ++ |
| SEQ ID NO: 282 | No NFT staining | - |
| SEQ ID NO: 283 | Very intensive staining of NFTs | +++ |

PROTEIN-BASED THERAPY AND DIAGNOSIS OF TAU-MEDIATED PATHOLOGY IN ALZHEIMER'S DISEASE

CROSS REFERENCE TO RELATED APPLICATIONS

This application is a division of U.S. patent application Ser. No. 14/345,561, which is a national stage application under 35 U.S.C. §371 of International Application No. PCT/IB2012/002246, filed Sep. 14, 2012, which claims the benefit under 35 U.S.C. §120 of U.S. patent application No. 61/536,339, filed Sep. 19, 2011, and of U.S. patent application No. 61/653,115, filed May 30, 2012, the content of each of which is incorporated herein by reference.

REFERENCE TO SEQUENCE LISTING SUBMITTED ELECTRONICALLY

An official copy of the sequence listing is submitted electronically via EFS-Web as an ASCII formatted sequence listing with a file named "SequenceListing.txt", created on Mar. 18, 2014, and having a size of 151 kilobytes. The sequence listing contained in this ASCII formatted document is part of the specification and is herein incorporated by reference in its entirety.

FIELD

The present invention features protein-based (e.g., antibodies, peptides) methods and means for interfering with the production and clearance of certain forms of tau that are involved in the promotion and/or development of pathological tau-tau aggregates in Alzheimer's disease, as well as methods for producing anti-tau antibodies that are useful for diagnosis and treatment of Alzheimer's disease. The invention further concerns methods and means for diagnosing Alzheimer's disease, including methods for staging and evaluating treatment progression.

BACKGROUND

Alzheimer's disease (AD) is a progressive neurodegenerative disorder that destroys higher brain structures, such as those involved in memory and cognition. The disease leads to deficits in cognitive function and declines in memory, learning, language, and in the ability to perform intentional and purposeful movements. AD is also accompanied by concomitant behavioral, emotional, interpersonal, and social deterioration. These cognitive and behavioral deficits render living difficult (Burns et al., 2002). Late-stage AD patients are often unable to speak, comprehend language, and handle their own basic personal care, eventually requiring full-time care and supervision, and are often dependent on family members and nursing homes. AD is the leading cause of senile dementia, and is predicted to increase in prevalence as the proportion of elderly persons in the population grows. The total number of persons with AD is predicted to increase at least threefold just between 2000 and 2050, rendering AD a world-wide public health problem (Sloane et al., 2002). Clinical management of AD remains largely supportive. That is, patients are given treatments aimed at prevention, control, or relief of complications and side effects from AD, and to improve their comfort and quality of life. There is still an unmet need for treatments that directly target the disease process and have disease-modifying effects.

AD is histologically characterized by the presence of extraneuronal plaques and intracellular and extracellular neurofibrillary tangles in the brain. Plaques are composed mainly of β amyloid (Aβ), whereas tangles comprise pathological forms of tau, such as pathological tau conformers and their aggregates. The relationship between plaques and tangles and the disease process remains unclear, although studies suggest a link between amyloid and tau pathogenesis (Hardy et al., 1998; Oddo et al., 2004; Rapoport et al., 2002; Roberson, et al., 2007; Shipton et al., 2011). A central role for Aβ in AD pathology was initially proposed in a hypothesis called the "Aβ cascade," wherein Aβ deposition is followed by tau phosphorylation and tangle formation, and then neuronal death (Hardy and Allsop, 1991; Hardy and Selkoe, 2002; for a review see, Walsh and Selkoe, 2004; also see Seabrook et al. 2007). Accordingly, initial therapeutic approaches for AD focused primarily on targeting Aβ. However, there is a documented lack of correlation between the extent of brain Aβ pathology in AD patients and clinical progression of the disease (Braak and Braak, 1991). In addition, asymptomatic individuals have shown extensive, often diffuse, amyloid deposition at autopsy (Braak and Braak, 1991), and at least in early-stage AD, neuronal loss and amyloid deposition occur in different regions of the brain (Carter and Lippa, 2001). Therefore targeting Aβ alone cannot suffice to alter the disease process in any or all patients. Nevertheless, the most advanced disease-targeting therapies undergoing clinical trials in AD patients remain those aimed at the production and clearance of Aβ. These therapies include passive immunotherapies, e.g., BAPINEUZUMAB, SOLANEUZUMAB, and PONEZUMAB, as well as the small molecule gamma-secretase inhibitor SEMAGACESTAT (for review see Citron et al., 2010).

A recognized role for tau in AD pathology has been demonstrated in numerous studies. For example, Braak showed that the closest correlate for AD neurodegeneration was the presence of tau tangles, and not of amyloid plaques (Braak and Braak, 1991). In another study, Aβ neurotoxicity in cultured neurons appeared to depend on tau (Rapoport et al., 2002). Recently, reducing endogenous tau prevented behavioral deficits in transgenic mice that expressed the human amyloid precursor protein, without altering their high Aβ levels (Roberson et al., 2007). Tau reduction also protected both transgenic and nontransgenic mice against excitotoxicity. Id. Santacruz et al. demonstrated that a reduction in the amount of tau restored memory function in a model of tauopathy (Santacruz et al., 2005). Thus, therapies aimed at reducing tau can represent an effective strategy for treating AD and other tau-related disease conditions.

Tau belongs to a family of intrinsically disordered proteins, characterized by the absence of a rigid three-dimensional structure in their physiological environment (Zilka et al., 2008) However, tau truncation and hyperphosphorylation can cause pathological transformations from an intrinsically disordered state to multiple soluble and insoluble misdisordered structures, including paired helical filaments (PHFs) and other aggregates (Wischik et al., 1988a; Wischik et al., 1988b; Novak et al., 1993; Skrabana et al., 2006; Zilka et al., 2008; Kovacech et al., 2010). These structural changes lead to a toxic gain of function, to a loss of physiological function of the native protein, or both (Zilka et al., 2008; Kovacech et al., 2010).

Tau's physiological function is in mediating the assembly of tubulin monomers into microtubules that constitute the neuronal microtubules network (Buee et al., 2000). Tau binds to microtubules through repetitive regions located in the C-terminal portion of the protein. Id. These repeat domains (R1-R4), are not identical to each other, but comprise highly conserved 31-32 amino acids (Taniguchi et al., 2005b). In the human brain, there are six unique isoforms of tau, which differ from each other in the presence or absence of certain amino acids in the N-terminal portion of tau, in combination with either three (R1, R3, and R4) or four (R1-R4) repeat domains, at the C-terminal end of the protein. See also FIG. 1, which shows the six human isoforms (2N4R, 1N4R, 2N3R, 0N4R, 1N3R, and 0N3R). It has been proposed that the most potent part of tau to induce microtubule polymerization is the 274-KVQIINKK-281 region (SEQ ID NO: 113), overlapping R1-R2. Id. In addition, tau's pathological and physiological functions appear to be influenced by the specific structural conformation, and the intrinsically disordered structure, adopted by the full length protein isoforms and their fragments. For example, Kontsekova et al. described a conformational region (encompassing residues 297-IKHVPGGGSVQIVYKPVDLSK-VTSKCGSL-325 (SEQ ID NO: 114)) within certain truncated tau molecules which had a significant relationship to the function of those truncated tau molecules on microtubule assembly (WO 2004/007547).

In addition to their physiological role, tau repeats are believed to participate in the formation of pathological tau aggregates and other structures. Thus, there is a need for tau-targeted therapeutic and diagnostic approaches that are capable of discriminating between physiological and pathological repeat-mediated activities. For example, the pronase resistant core of pathological paired helical filaments (PHFs) consists of the microtubule binding regions of 3- and 4-repeat tau isoforms (Jakes et al., 1991; Wischik, et al. 1988a; Wischik, et al. 1988b). Further, Novak et al. showed that the protease resistant core of the PHFs, which is 93-95 amino acids long, was restricted to three tandem repeats (Novak et al., 1993). Von Bergen et al. determined a minimal-tau peptide/interaction motif (306-VQIVYK-311; SEQ ID NO: 115), as well as a second site on tau (275-VQIINK-280) (SEQ ID NO: 116), which form beta-sheets and are described as potentially responsible for initiating the formation of PHFs, a pathological tau aggregate (Von Bergen et al., 2000; EP 1214598; WO 2001/18546). See FIG. 2 for a functional map of tau. Consequently, current strategies aim at generating anti-aggregating drugs that do not disrupt tau's intracellular role in microtubule stabilization.

Moreover, while under physiological circumstances tau is considered an intracellular cytoplasmic protein, intracellular tau can be released into the extracellular space and contribute to neurodegeneration (Gómez-Ramos et al., 2006). Indeed, neuronal loss has been linked to the topographic distribution of neurofibrillary tangles (made up of tau protein) in AD brains (West et al., 1994; Gómez-Isla et al., 1996, 1997). Further, the levels of total tau and phosphorylated tau are increased in the cerebrospinal fluid (CSF) of patients with AD (Hampel et al., 2010), and extracellular tau has been described as "ghost tangles" in the brain (Frost and Diamond, 2009), indicating that intracellular tau is released into extracellular space. In addition, extracellular tau aggregates can enter cells and stimulate fibrillization of intracellular tau, further seeding tau monomer for production of pathological tau aggregates (Frost et al., 2009). Such studies have highlighted that extracellular, insoluble tau could act as a transmissible agent to spread tau pathology throughout the brain in a prion-like fashion (Frost et al., 2009; Frost and Diamond, 2009). Clearance of extracellular tau tangles can reduce tau-associated extracellular and intracellular pathology. See, e.g., Asuni et al., 2007. Therefore, there is a need for treatments capable of decreasing extracellular tau, either by impeding its formation, promoting its clearance, or both, as well as for treatments that decrease intracellular disease tau.

All in all, although tau appears to play a pathological role in the clinical manifestation of AD, the development of drugs that work against tau has been slow, in part due to tau's importance in physiologic microtubule dynamics and to its complex biology (Dickey and Petrucelli, 2006). However, an increased understanding of the molecular mechanisms underlying the pathological transformations of tau has opened up the possibility of specifically targeting pathological modifications of tau for therapeutic purposes. As a result, a number of therapeutic approaches that directly or indirectly target the tau cascade have emerged (for review articles, see, e.g. Dickey and Petrucelli, 2006; Schneider and Mandelkow, 2008; Zilka et al., 2008), including compounds that prevent or reverse tau aggregation (Wischik et al., 1996; Necula et al. 2005; Pickhardt et al., 2005; Taniguchi et al., 2005a; Larbig et al., 2007) small-molecule type drugs that inhibit tau kinases or activate tau phosphatases (Iqbal and Grundke-Iqbal, 2004; Noble et al., 2005; Iqbal and Grundke-Iqbal, 2007), microtubule stabilizing drugs (Zhang et al., 2005), drugs that facilitate the proteolytic degradation of misfolded tau proteins (Dickey et al., 2005, Dickey et al. 2006; Dickey and Petrucelli, 2006), and immunosuppresive drugs (Zilka et al., 2008), as well as immunotherapeutic strategies including active and passive immunization (Schneider and Mandelkow et al., 2008; Zilka et al., 2008: Tabira, T. Immunization Therapy for Alzheimer disease: A Comprehensive Review of Active Immunization Strategies. Tohoku J. Exp. Med., 220: 95-106 (2010)).

More generally, novel monoclonal antibodies (mAbs) have been entering clinical studies at a rate of over 40 per year since 2007. At the end of 2010, at least 25 mAbs and five Fc fusion proteins were in Phase 2/3 or Phase 3 clinical studies in the US (Reichert, 2011). This trend demonstrates that passive immunotherapy is a growing approach in the treatment of human disorders, including AD. See, e.g., Citron et al., 2010. In fact, although AD treatments face the hurdle of overcoming the blood-brain-barrier (BBB), a growing number of pre-clinical and clinical studies report that antibody-mediated therapies can clear AD aggregates from the brain, and propose multiple mechanisms of action, such as (i) antibody uptake into the brain via an altered BBB permeability in AD, or BBB leakage; (ii) antibodies working as "peripheral sinks" for soluble plaque-forming amyloid species; (iii) entrance of antibody-secreting cells from the periphery into the brain, delivering antibodies locally; and (iv) transport of IgG within and across cells. See, e.g., Citron et al., 2010, and Asuni et al., 2007, for review. Accordingly, therapeutic antibodies targeting disease forms of tau represent a prospective approach for treatment and/or diagnosis of AD and other tauopathies (WO 2004/007547, US2008/0050383).

One of the immunotherapy approaches to target tau pathology is based on the notion that anti-tau antibodies could prevent tau aggregation, clear tau aggregates, or both. Although studies have described antibodies that bind to tau sequences, and some of those antibodies reportedly interfere with tau aggregation and clearance (Asuni et al., 2007), no monoclonal anti-tau antibody is yet reportedly undergoing in vivo pre-clinical or clinical trials in AD. Indeed, one mAb was predicted to have three binding sites within murine tau's microtubule-binding domain (namely, at R3, R4, and possibly R1), but it did not block microtubule binding. (Dingus et al., 1991). Dingus did not describe a role for this antibody on tau aggregation and thus, there is no reason to believe that the Dingus will block tau aggregation. In other reports, mAbs were generated that distinguish tau isoforms, but again there is no suggestion that these will have any effect on tau aggregation (DeSilva et al., 2003; Ueno et al., 2007). Taniguchi et al. demonstrated that certain anti-tau mAbs against R1 or R2, inhibited tau aggregation into PHFs in vitro, while promoting tau-induced tubulin assembly (Taniguchi et al., 2005b). Taniguchi's RTA-1 and RTA-2 antibodies bound specifically to R1 and R2, respectively. Neither antibody bound more than one tau repeat and none was reportedly tested for in vivo effects on either tau aggregation or clearance. Despite the existence of at least three anti-amyloid antibodies in clinical trials for passive immunization-based therapy of AD (i.e., one in which antibodies are administered to the patient), no clinical testing reports of passive, tau-based immunotherapies for AD are yet available.

An active immunization approach (i.e., one in which the patients body itself generates immunity against the target) was found to be effective in clearing Aβ deposits and reversing neuropathological lesions in several APP-transgenic mouse studies of AD (see, e.g. Schenk et al., 1999; Janus et al., 2000; Morgan et al., 2000; Sigurdsson et al., 2001). Recently, active immunotherapy with a phosphorylated tau epitope (Tau 379-408 [P-Ser 396, 404]) reduced the extent of aggregated tau in the brain and slowed the progression of the behavioral phenotype in mouse models of tau tangle pathology (Asuni et al., 2007; Boutajangout et al. 2010; US2008/0050383; US/2010/00316564). Treated animals produced anti-tau antibodies, which were detected in the brain and colocalized with antibodies that recognized pathological tau (Asuni et al., 2007). This immunotherapeutic approach was substantially more effective in the early stages of functional impairments in the animals (5 months) than at later stages (8 months), suggesting that clearance of early-stage pathological tau can be of therapeutic benefit (Asuni et al., 2007; Zilka et al., 2008). Indeed, there is awareness that not all tau is susceptible or perhaps even suitable for disruption and clearance. Some have suggested that disrupting tau aggregates could increase the abundance of toxic intermediate species, while others have suggested that detectable tau aggregates are not necessarily toxic and can even play a protective role (Lee et al., 2005). Thus, although immunotherapeutic approaches to target tau have shown pre-clinical promise, there is still a need for therapeutics that specifically target early, aberrant forms of tau whose elimination produces improved, lasting benefits. Nevertheless, there is still also a need to identify those tau species that are suitable targets for immunotherapy.

To this end, another consideration for developing mAbs against tau is the identification and characterization of the various structural forms of tau (physiological, early disease, late disease) and the stages of tau pathology that are targeted. Oddo et al. observed that while Aβ immunotherapy cleared Aβ plaques and early tau pathology in a transgenic mouse model of AD, mature tau aggregates remained intact (Oddo et al., 2004). Similarly, a genetic (not immunotherapeutic) reduction of tau expression in a P301L tau model of tauopathy improved memory, even though neurofibrillary tangles continued to accumulate (Santacruz et al., 2005).

Notwithstanding its prevalence, AD remains the largest unmet medical need in neurology (Citron, 2010). The most prevalent medical approach is to provide symptomatic therapy, which is not efficacious even after several years of treatment. New therapeutic approaches and strategies for AD need to go beyond the treatment of symptoms to prevent cognitive decline and counteract the fundamental pathological processes of the disease. In particular, there is a need for the development of molecules that either alone or in combination with other AD-targeted drugs interfere with at least some of the earliest stages of the disease. Such molecules would provide new, advantageous options in the early diagnosis (which could itself improve treatment outcomes), prevention, and treatment of AD.

SUMMARY OF THE INVENTION

In one embodiment, the invention provides an isolated antibody, wherein the antibody binds to one or more tau epitopes and is capable of two or more of the following:
 a) displaying a higher affinity for pathological tau than for physiological tau;
 b) inhibiting tau-tau aggregation; and
 c) mediating uptake and degradation of pathological tau protein by microglia; and wherein each tau epitope comprises an aggregation-promoting region of tau.

In an embodiment, this isolated antibody is such that each of the one or more epitopes is independently selected from epitopes within:
 i. position 267-273 or residues KHQPGGG (SEQ ID NO: 98), relative to $tau_{441}$;
 ii. position 298-304 or residues KHVPGGG (SEQ ID NO: 99), relative to $tau_{441}$
 iii. position 329-335 or residues HHKPGGG (SEQ ID NO: 100), relative to $tau_{441}$; and
 iv. position 361-367 or residues THVPGGG (SEQ ID NO: 101), relative to $tau_{441}$.

In certain embodiments, the isolated antibody having the properties described in the embodiments of the previous paragraphs is capable of binding to one or more forms of pathological tau chosen from misordered tau, misdisordered tau, sarkosyl-insoluble tau, neurofibrillary tangles, neuropil threads, and neuritic plaques in a brain biopsy of a human Alzheimer's disease patient, in a brain sample from an animal model of Alzheimer's disease, or in both. In certain embodiments, the isolated antibody is such that at least one of the epitopes that it recognizes is a conformational epitope.

In one embodiment, the invention provides an isolated antibody, wherein the antibody binds to one or more tau epitopes and is capable of two or more of the following:
 a) displaying a higher affinity for pathological tau than for physiological tau;
 b) inhibiting tau-tau aggregation; and
 c) mediating uptake and degradation of pathological tau protein by microglia; and wherein each tau epitope comprises an aggregation-promoting region of tau.

In an embodiment, this isolated antibody is such that each of the one or more epitopes is independently selected from epitopes within:
 i. position 268-273 or residues HQPGGG (SEQ ID NO: 223), relative to $tau_{441}$;
 ii. position 299-304 or residues HVPGGG (SEQ ID NO: 154), relative to $tau_{441}$
 iii. position 330-335 or residues HKPGGG (SEQ ID NO: 224), relative to $tau_{441}$; and
 iv. position 362-367 or residues HVPGGG (SEQ ID NO: 154), relative to $tau_{441}$.

In an embodiment, this isolated antibody is such that each of the one or more epitopes it binds to is independently selected from epitopes within:
 i. position 268-273 or residues HQPGGG (SEQ ID NO: 223), relative to $tau_{441}$;

ii. position 299-304 or residues HVPGGG (SEQ ID NO: 154), relative to tau$_{441}$
iii. position 330-335 or residues HKPGGG (SEQ ID NO: 224), relative to tau$_{441}$; and
iv. position 362-367 or residues HVPGGG (SEQ ID NO: 154), relative to tau$_{441}$;
and the antibody comprises:
a) an antibody light chain variable region comprising:
i. QSLLNSRTRKNY (SEQ ID NO: 117) or SEQ ID NO: 247 for CDR1;
ii. WAS (SEQ ID NO: 118) or SEQ ID NO: 253 for CDR2; and
iii. KQSFYLRT (SEQ ID NO: 119) or any one of SEQ ID NOs: 255, 257, 258, 259, and 260 for CDR3; and
b) an antibody heavy chain variable region comprising:
iv. GYIFTDYVIS (SEQ ID NO: 120), SEQ ID NO: 261, or SEQ ID NO: 262 for CDR1;
v. IFPRSGST (SEQ ID NO: 121), SEQ ID NO: 264, or SEQ ID NO: 265 for CDR2; and
vi. ARDYYGTSFAMDY (SEQ ID NO: 122), SEQ ID NO: 266, SEQ ID NO: 267, or SEQ ID NO: 269 for CDR3.

The invention also provides an isolated antibody that binds one or more epitopes on tau in a conformationally-specific manner wherein:
a) each of the one or more epitopes is independently selected from epitopes within:
i. position 267-273 or residues KHQPGGG (SEQ ID NO: 98), relative to tau$_{411}$;
ii. position 298-304 or residues KHVPGGG (SEQ ID NO: 99), relative to tau$_{441}$
iii. position 329-335 or residues HHKPGGG (SEQ ID NO: 100), relative to tau$_{441}$; and
iv. position 361-367 or residues THVPGGG (SEQ ID NO: 101), relative to tau$_{441}$;
b) zero, one, two, or three of the epitopes is/are linear epitope(s); and
c) one, two, three, or four of the epitopes is/are conformational epitope(s).

The invention also provides an isolated antibody that binds one or more epitopes on tau in a conformationally-specific manner wherein:
a) each of the one or more epitopes is independently selected from epitopes within:
i. position 268-273 or residues HQPGGG (SEQ ID NO: 223), relative to tau$_{441}$;
ii. position 299-304 or residues HVPGGG (SEQ ID NO: 154), relative to tau$_{441}$
iii. position 330-335 or residues HKPGGG (SEQ ID NO: 224), relative to tau$_{441}$; and
iv. position 362-367 or residues HVPGGG (SEQ ID NO: 154), relative to tau$_{441}$.
b) zero, one, two, or three of the epitopes is/are linear epitope(s); and
c) one, two, three, or four of the epitopes is/are conformational epitope(s).

In one embodiment, this antibody is DC8E8, wherein DC8E8 is an antibody produced by the hybridoma deposited under American Type Culture Collection Patent Deposit no. PTA-11994.

In certain embodiments, the isolated antibody binds to one or more of the same epitopes on tau as those bound by DC8E8. In an embodiment, the isolated antibody competes with monoclonal antibody DC8E8 for binding to tau.

The invention also provides an isolated antibody comprising in its epitope binding domain one or more complementarity determining region (CDR) sequences chosen from:

i.
                                        (SEQ ID NO: 117)
QSLLNSRTRKNY ii.
                                        (SEQ ID NO: 118)
WAS iii.
                                        (SEQ ID NO: 119)
KQSFYLRT iv.
                                        (SEQ ID NO: 120)
GYIFTDYVIS v.
                                        (SEQ ID NO: 121)
IFPRSGST;
and vi.
                                        (SEQ ID NO: 122)
ARDYYGTSFAMDY.

The invention also provides that any of the antibodies described in any embodiments described in the preceding paragraphs can be such that the isolated antibody comprises:
a) an antibody light chain variable region comprising:

(SEQ ID NO: 117)
  i.         QSLLNSRTRKNY for CDR1;

(SEQ ID NO: 118)
  ii.        WAS for CDR2; and (SEQ ID NO: 119)
  iii.       KQSFYLRT for CDR3;

b) an antibody heavy chain variable region comprising:

(SEQ ID NO: 120)
  iv.        GYIFTDYVIS for CDR1

(SEQ ID NO: 121)
  v.         IFPRSGST for CDR2; and (SEQ ID NO: 122)
  vi.        ARDYYGTSFAMDY for CDR3.

The invention also provides that any of the antibodies described in the previous embodiments can be such that the isolated antibody comprises:
a) one or more sequences of the light chain CDRs from the monoclonal antibody DC8E8, or one or more sequences having at least 80%, 90%, or 95% identity after optimum alignment with one of these light chain CDRs; and
b) one or more sequences of the heavy chain CDRs from the monoclonal antibody DC8E8, or one or more sequences having at least 80%, 90%, or 95% identity after optimum alignment with one of these heavy chain CDRs;
and wherein:
i. the light chain CDRs comprise a sequence chosen from QSLLNSRTRKNY (SEQ ID NO: 117), WAS (SEQ ID NO: 118), and KQSFYLRT (SEQ ID NO: 119); and ii. the heavy chain CDRs comprise a sequence chosen from GYIFTDYVIS (SEQ ID NO: 120), IFPRSGST (SEQ ID NO: 121), and ARDYYGTSFAMDY (SEQ ID NO: 122).

The invention also provides that any of the antibodies described in the previous embodiments can consist of or comprise a Fab, Fab', F(ab')$_2$, Fabc, Fv fragment, any other antigen-binding fragment; or an antigen-binding antibody portion thereof; having one or more of the following immunological binding characteristics:

1. the antibody binds one or more tau epitopes in a conformationally-specific manner, wherein:
   a) each of the one or more tau epitopes is independently selected from epitopes within:
      i. position 267-273 or residues KHQPGGG (SEQ ID NO: 98), relative to tau$_{441}$;
      ii. position 298-304 or residues KHVPGGG (SEQ ID NO: 99), relative to tau$_{44}$,
      iii. position 329-335 or residues HHKPGGG (SEQ ID NO: 100), relative to tau$_{441}$; and
      iv. position 361-367 or residues THVPGGG (SEQ ID NO: 101), relative to tau$_{441}$;
   b) zero, one, two, or three of the epitopes is a linear epitope;
   c) one, two, three, or four of the epitopes is a conformational epitope;
2. the antibody binds two or more tau epitopes and is capable of displaying a higher affinity for pathological tau than for physiological tau, wherein the two tau epitopes are selected from epitopes within:
   v. position 267-273 or residues KHQPGGG (SEQ ID NO: 98), relative to tau$_{441}$;
   vi. position 298-304 or residues KHVPGGG (SEQ ID NO: 99), relative to tau$_{441}$
   vii. position 329-335 or residues HHKPGGG (SEQ ID NO: 100), relative to tau$_{441}$; and
   viii. position 361-367 or residues THVPGGG (SEQ ID NO: 101), relative to tau$_{441}$.

The invention also provides that any of the antibodies described in the previous embodiments can consist of or comprise a Fab, Fab', F(ab')$_2$, Fabc, Fv fragment, any other antigen-binding fragment; or an antigen-binding antibody portion thereof; having one or more of the following immunological binding characteristics:

1. the antibody binds one or more tau epitopes in a conformationally-specific manner, wherein:
   a) each of the one or more tau epitopes is independently selected from epitopes within:
      i. position 268-273 or residues HQPGGG (SEQ ID NO: 223), relative to tau$_{411}$;
      ii. position 299-304 or residues HVPGGG (SEQ ID NO: 154), relative to tau$_{441}$;
      iii. position 330-335 or residues HKPGGG (SEQ ID NO: 224), relative to tau$_{441}$; and
      iv. position 362-367 or residues HVPGGG (SEQ ID NO: 154), relative to tau$_1$.
   b) zero, one, two, or three of the epitopes is a linear epitope;
   c) one, two, three, or four of the epitopes is a conformational epitope;
2. the antibody binds two or more tau epitopes and is capable of displaying a higher affinity for pathological tau than for physiological tau, wherein the two tau epitopes are selected from epitopes within:
   i. position 268-273 or residues HQPGGG (SEQ ID NO: 223), relative to tau$_{441}$;
      ii. position 299-304 or residues HVPGGG (SEQ ID NO: 154), relative to tau$_{441}$
      iii. position 330-335 or residues HKPGGG (SEQ ID NO: 224), relative to tau$_{441}$; and
      iv. position 362-367 or residues HVPGGG (SEQ ID NO: 154), relative to tau$_1$.

The invention also relates to any isolated antibody that competitively binds to tau against any of the isolated antibodies described in the previous embodiments. In one embodiment, the isolated antibody competitively binds to tau when tested against isolated DC8E8 for binding to tau.

In some embodiments, the antibody comprises a light chain comprising SEQ ID NO.: 141. In some embodiments, the antibody comprises a light chain comprising SEQ ID NO.:138. In some embodiments, the antibody comprises a light chain comprising SEQ ID NO.: 141 and a light chain comprising SEQ ID NO.:138.

The invention provides that the antibodies provided by the invention can be chosen from:
a) a monoclonal antibody;
b) a polyclonal antibody;
c) a recombinant antibody;
d) a chimeric antibody;
e) a humanized antibody;
f) a human antibody; and
g) an antigen-binding fragment or antigen-binding portion of anyone of (a) through (f).

Any of the isolated antibodies provided by the invention can be raised in a mammal. In certain embodiments, the isolated antibody is produced by a recombinant animal or by a recombinant host cell.

The invention provides that any of the isolated anti-tau antibodies provided herein can be such that they are detectably labeled with one or more labeling agents. In certain embodiments, at least one labeling agent is chosen from an enzyme, a radioisotope, a fluorophore, a nuclear magnetic resonance marker, and a heavy metal.

In some embodiments, the antibody comprises at least one drug (combination agent) attached to the antibody molecule.

The invention also provides isolated nucleic acids encoding at least one CDR, or at least the binding domain or variable region of an immunoglobulin chain of any of the anti-tau antibodies described in the previous embodiments. Also provided are isolated vectors comprising any of those nucleic acids. In some embodiments, the invention provides an isolated host cell comprising one or more of these isolated nucleic acids and vectors.

In certain embodiments, the invention provides an isolated cell line expressing any of the anti-tau antibodies described in the previous embodiments. In one embodiment, the isolated cell line is a hybridoma. In one embodiment, the isolated cell line is the hybridoma from which monoclonal antibody DC8E8 is produced, and which cell line has been deposited with the American Type Culture Collection, Manassas, Va., USA, on Jul. 13, 2011, with the ATCC Patent Deposit Designation PTA-11994.

The invention provides for the use of any of the anti-tau antibodies, nucleic acids, and cells provided herein, as a drug or in the manufacture of a medicament for the diagnosis, prevention, or treatment of Alzheimer's disease or a related tauopathy.

In some embodiments, the antibodies are comprised in a pharmaceutical composition, further comprising pharmaceutically acceptable carrier and/or diluent. In one embodiment, the pharmaceutical composition comprises a combination of antibodies and a pharmaceutically acceptable carrier and/or diluent, wherein the combination comprises at least two different antibodies, and wherein each of the antibodies is independently selected from the antibodies described in the previous embodiments. In one embodiment, at least one of the antibodies is DC8E8, or a human version of DC8E8, or a humanized version of DC8E8.

In some embodiments, the antibodies are comprised in a composition, further comprising a diluent and/or a carrier. The composition can be a pharmaceutical composition, a diagnostic composition, or any other composition. In some embodiments, the composition can further comprise at least one compound or agent selected from a detectable label, keyhole limpet hemocyanin, tetanus toxoid or a toxoid derived from other pathogenic bacteria, serum albumins, bovine serum albumin, an immunoglobulin molecule or fragment thereof, thyroglobulin, ovoglobulin, a universal T-cell epitope, a cytokine, a chemokine, interleukin 1-alpha (IL-1α), IL-1β, IL-2, IL-10, interferon-gamma (IFN-γ), granulocyte macrophage colony-stimulating factor (GM-CSF), macrophage inflammatory protein 1 alpha (MIP1α), MIP1β, and RANTES (regulated upon activation, normal T-cell expressed and secreted).

The invention also provides an article of manufacture (e.g., a kit) for pharmaceutical or diagnostic use, comprising packaging material and a container comprising a solution of a lyophilized form any one or more of the anti-tau antibodies provided herein. In certain embodiments, the container is a component of a device or system for delivery of the antibody to a subject.

In some embodiments, the invention provides a medical device comprising an anti-tau antibody as provided herein (see above), wherein the device is suitable for contacting or administering the antibody by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, and transdermal.

In one embodiment, the invention relates to a method of treating or preventing the progression of Alzheimer's disease or a related tauopathy in a subject, the method comprising administering to said subject an effective amount of at least one of the anti-tau antibodies provided herein. In some embodiments, the method is capable of reducing motor impairment, improving motor function, reducing cognitive impairment, improving cognitive function, or of a combination thereof.

In certain embodiments, the invention relates to a method of ameliorating at least one of the symptoms associated with Alzheimer's disease or a related tauopathy in a subject, the method comprising administering to said subject an effective amount of at least one of the anti-tau antibodies provided herein.

In still another embodiment, the invention provides a method of diagnosing or screening a subject for the presence of Alzheimer's disease or a related tauopathy in a subject, or for determining a subjects risk for developing Alzheimer's disease or a related tauopathy, the method comprising:
  a) contacting the subject, or a cell, tissue, organ, fluid, or any other sample of the subject, with an effective amount of at least one anti-tau antibody as provided herein; and
  b) determining the presence of a complex comprising pathological tau and the antibody, wherein the presence of the complex is diagnostic of Alzheimer's disease or a related tauopathy associated with the presence of pathological tau.

In a related embodiment, the invention provides a method of monitoring a subject for the presence, progression, regression, or stabilization of Alzheimer's disease or a related tauopathy in a subject, or for determining the stage of Alzheimer's disease or a related tauopathy in a subject, for the method comprising:
  a) contacting the subject, or a cell, tissue, organ, fluid, or any other sample of the subject, with an effective amount of at least one of the anti-tau antibodies provided herein; and
  b) determining the presence and/or characteristics of a complex comprising pathological tau and the antibody, wherein the presence of the complex is diagnostic of Alzheimer's disease or a related tauopathy associated with the presence of pathological tau.

In some embodiments, the antibody is administered intravenously, intramuscularly, subcutaneously, intraperitoneally, intranasally, intracerebroventricularly, intrathecally, or as an aerosol.

In some embodiments of the methods of treating or preventing the progression of Alzheimer's disease or a related tauopathy in a subject, and of the methods of ameliorating at least one of the symptoms associated with Alzheimer's disease or a related tauopathy in a subject, the effective amount of each antibody is at least 1 mg/kg body weight of the subject, per dose. In some embodiments, the effective amount of each antibody is at least 10 mg/kg body weight of the subject, per dose. In some embodiments, at least one of the antibodies is administered in multiple dosages over a period of at least six months. In some embodiments, the antibody is administered peripherally to a human subject to exert its beneficial effects. In some embodiments, the antibody, when administered peripherally to a human subject, binds to soluble tau, sarkosyl-insoluble tau, or to both. In some embodiments, the antibody, when administered peripherally to a human subject, binds to tau, wherein tau is in one or more pathological forms chosen from misordered tau, misdisordered tau, sarkosyl-insoluble tau, neurofibrillary tangles, neuropil threads, and neuritic plaques in a brain biopsy of a human Alzheimer's disease patient, in a brain sample from an animal model of Alzheimer's disease. In some embodiments, the antibody, when administered peripherally to a human subject, exerts one or more effector-function mediated beneficial effects on the subject. In some embodiments, the antibody is delivered to the periphery by injection/implantation of an antibody-expressing cell into the subject's brain. In some embodiments, the antibody-expressing cell is an hybridoma cell. In some embodiments, the hybridoma cell is a hybridoma expressing DC8E8.

In certain related embodiments, the invention provides an isolated peptide, wherein:
  a) the isolated peptide is a fragment of tau that is at least 6 amino-acid-residues-long, at least 7 amino-acid-residues-long, at least 9 amino-acid-residues-long, at least 10 amino-acid-residues-long, at least 12 amino-acid-residues-long, or 30 amino-acid-residues-long; and
  b) the isolated peptide comprises a tau therapeutic epitope.

In some related embodiments, the therapeutic epitope comprises a therapeutic epitope selected from those within:

i. position 267-273 or residues KHQPGGG (SEQ ID NO: 98), relative to $tau_{441}$;
ii. position 298-304 or residues KHVPGGG (SEQ ID NO: 99), relative to $tau_{441}$
iii. position 329-335 or residues HHKPGGG (SEQ ID NO: 100), relative to $tau_{441}$; and
iv. position 361-367 or residues THVPGGG (SEQ ID NO: 101), relative to $tau_{441}$.

In certain related embodiments, the invention provides an isolated peptide, wherein:
a) the isolated peptide is a fragment of tau that is at least 6 amino-acid-residues-long, at least 7 amino-acid-residues-long, at least 9 amino-acid-residues-long, at least 10 amino-acid-residues-long, at least 12 amino-acid-residues-long, or 30 amino-acid-residues-long; and
b) the isolated peptide comprises a tau therapeutic epitope.

In some related embodiments, the therapeutic epitope comprises a therapeutic epitope selected from those within:
i. position 268-273 or residues HQPGGG (SEQ ID NO: 223), relative to $tau_{441}$;
ii. position 299-304 or residues HVPGGG (SEQ ID NO: 154), relative to $tau_{441}$
iii. position 330-335 or residues HKPGGG (SEQ ID NO: 224), relative to $tau_{441}$; and
iv. position 362-367 or residues HVPGGG (SEQ ID NO: 154), relative to $tau_{441}$.

In some related embodiments, the therapeutic epitope is selected from:
i. position 268-273 or residues HQPGGG (SEQ ID NO: 223), relative to $tau_{441}$;
ii. position 299-304 or residues HVPGGG (SEQ ID NO: 154), relative to $tau_{441}$
iii. position 330-335 or residues HKPGGG (SEQ ID NO: 224), relative to $tau_{441}$; and
iv. position 362-367 or residues HVPGGG (SEQ ID NO: 154) relative to $tau_{441}$.

In other embodiments, the isolated peptide is a sequence selected from

```
SEQ ID NOs: 1-4, SEQ ID NOs: 9-101, and SEQ ID
NOs: 108-112, NIKAVPGGGS (SEQ ID NO: 200),
NIKHVPGGGS (SEQ ID NO: 201), IKHVPGGGS
(SEQ ID NO: 202), KHVPGGGSV (SEQ ID NO: 203),
HVPGGGSVQ (SEQ ID NO: 204), VPGGGSVQ
(SEQ ID NO: 205), GWSIHSPGGGSC (SEQ ID NO:
250), SVFQHLPGGGSC (SEQ ID NO: 251),
ANIKHVPGGGS (SEQ ID NO: 144), DAIKHVPGGGS
(SEQ ID NO: 146), DNAKHVPGGGS (SEQ ID NO:
149), DNIAHVPGGGS (SEQ ID NO: 151),
DNIKAVPGGGS (SEQ ID NO: 159), DNIKHAPGGGS
(SEQ ID NO: 161), and DNIKHVPGGGS (SEQ ID NO:
171).
```

In other embodiments, the isolated peptide is a sequence selected from

```
SEQ ID NO: 270 (TENLKHQPGGGK); SEQ ID NO: 271
(KHQPGGG), SEQ ID NO: 272 (HQPGGG); SEQ ID NO:
275 (ENLKHQPGGGKVQIINKKLDLSNVQSKCGSKDNIKHVPGGGS),
SEQ ID NO: 276 (KHVPGGG), SEQ ID NO: 277 (HVPGGG),
SEQ ID NO: 280 (DNIKHVPGGGSVQIVYKPV), SEQ ID NO:
281 (HHKPGGG), SEQ ID NO: 282 (HKPGGG), and SEQ ID
NO: 283 (THVPGGG).
```

In other embodiments, the isolated peptide is a sequence selected from

```
SEQ ID NO: 270 (TENLKHQPGGGK); SEQ ID NO: 271
(KHQPGGG), SEQ ID NO: 272 (HQPGGG); SEQ ID NO:
275 (ENLKHQPGGGKVQIINKKLDLSNVQSKCGSKDNIKHVPGGGS),
SEQ ID NO: 276 (KHVPGGG), SEQ ID NO: 277 (HVPGGG),
SEQ ID NO: 280 (DNIKHVPGGGSVQIVYKPV), SEQ ID NO:
281 (HHKPGGG), SEQ ID NO: 282 (HKPGGG), and SEQ ID
NO: 283 (THVPGGG);
``` and the therapeutic epitope is selected from:
i. position 268-273 or residues HQPGGG (SEQ ID NO: 223), relative to $tau_{441}$;
ii. position 299-304 or residues HVPGGG (SEQ ID NO: 154), relative to $tau_{441}$
iii. position 330-335 or residues HKPGGG (SEQ ID NO: 224), relative to $tau_{441}$; and
iv. position 362-367 or residues HVPGGG (SEQ ID NO: 154), relative to $tau_{441}$.

In other embodiments, the isolated peptide is a sequence selected from SEQ ID NO: 272 (HQPGGG) and SEQ ID NO: 277 (HVPGGG).

In certain embodiments, the isolated peptide is active in at least one assay, selected from assays that measure the peptide's:
a) ability to compete with tau for binding to the monoclonal antibody DC8E8;
b) ability to reduce the level of sarkosyl-insoluble tau, in vivo;
c) ability to promote tau clearance from the brain, in vivo;
d) ability to reduce the level of at least one biochemical marker of AD, in vivo;
e) ability to reduce neurofibrillary tangle (NFT) load, in vivo;
f) ability to improve at least one neurobehavioral parameter, in vivo;
g) ability to beneficially modify the course of AD in a subject;
h) ability to reduce the level of tau in the brain, in the cerebrospinal fluid, or in both; and/or
i) ability to serve as an immunogen in the making of an antibody capable of competing with monoclonal DC8E8 for binding to tau.

The invention also relates to compounds comprising any of the isolated peptides provided herein and a moiety. In certain embodiments, the moiety is N-terminal, C-terminal, or linked to an internal amino acid of the peptide, and wherein the moiety is selected from one or more of a cysteine residue, phospho group, keyhole limpet hemocyanin, tetanus toxoid or a toxoid derived from other pathogenic bacteria, serum albumins, bovine serum albumin, an immunoglobulin molecule or fragment thereof, thyroglobulin, ovoglobulin, a universal T-cell epitope, a cytokine, a chemokine, interleukin 1-alpha (IL-1α), IL-β, IL-2, IL-10, interferon-gamma (IFN-γ), granulocyte macrophage colony-stimulating factor (GM-CSF), macrophage inflammatory protein 1 alpha (MIP1α), MIP1β, and RANTES (regulated upon activation, normal T-cell expressed and secreted).

Also provided are pharmaceutical compositions comprising one or more of the isolated peptides and/or compounds provided by the invention and a pharmaceutically acceptable carrier, and/or a diluent, and/or an adjuvant. In some embodiments, the pharmaceutical composition is adapted to provide a dosage of the peptide or of the compound between 1 ng and 10 mg. In certain embodiments, the pharmaceutical composition is adapted to provide a dosage of the peptide or of the compound greater than 10 micrograms.

The invention also relates to an article of manufacture (e.g., a kit) for pharmaceutical or diagnostic use, comprising packaging material and a container comprising a solution of a lyophilized form of a peptide and/or compound provided by the invention. In some embodiments, the container is a component of a device or system for delivery of the peptide or the compound to a subject.

Also provided are medical devices comprising a peptide, a compound, and/or a peptide/compound composition as provided by the invention, wherein the device is suitable for contacting or administering the antibody by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, and transdermal.

In related embodiments, the invention provides a method of treating or preventing the progression of Alzheimer's disease or related tauopathies in a subject, the method comprising administering to said subject an effective amount of at least one peptide and/or at least one compound as provided by the invention. In some embodiments, the method is capable of reducing motor impairment, improving motor function, reducing cognitive impairment, improving cognitive function, or a combination thereof.

In related embodiments, the invention provides a method of ameliorating at least one of the symptoms associated with Alzheimer's disease or related tauopathies in a subject, the method comprising administering to said subject an effective amount of at least one peptide and/or at least one compound as provided by the invention.

In some of these methods of treatment, prevention, or amelioration of at least one of the symptoms associated with a method of ameliorating at least one of the symptoms associated with Alzheimer's disease or a related tauopathy in a subject, the method comprises administering to a human patient a peptide and/or a compound as provided by the invention, and/or an adjuvant that augments the immune response, which method effects an immune response comprising antibodies against pathological tau, thereby treating, preventing the progression, or ameliorating at least one of the symptoms associated with AD in the human patient.

The invention also provides a method of producing an antibody that is able to compete with DC8E8 for binding to tau, the method comprising immunizing a subject with at least one peptide and/or with at least one compound as provided by the invention. In some embodiments, at least one peptide is a peptide is chosen from any one of SEQ ID NOs: 1-4, SEQ ID NOs: 9-101, and SEQ ID NOs: 108-112, NIKHVPGGGS (SEQ ID NO: 201), IKHVPGGGS (SEQ ID NO: 202), KHVPGGGSV (SEQ ID NO: 203), HVPGGGSVQ (SEQ ID NO: 204), VPGGGSVQ (SEQ ID NO: 205), GWSIHSPGGGSC (SEQ ID NO: 250), SVFQHLPGGGSC (SEQ ID NO: 251), ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKAVPGGGS (SEQ ID NO: 159), DNIKHAPGGGS (SEQ ID NO: 161), and DNIKHVPGGGS (SEQ ID NO: 171). In one embodiment, the peptide is chosen from SEQ ID NOs: 1-4. In another embodiment, the peptide is SEQ ID NO. 108. In one embodiment, the peptide is GWSIHSPGGGSC (SEQ ID NO: 250). In certain embodiments, the peptide is SVFQHLPGGGSC (SEQ ID NO: 251). In certain embodiments the peptide is selected from SEQ ID NO: 270 (TENLKHQPGGGK); SEQ ID NO: 271 (KHQPGGG), SEQ ID NO: 272 (HQPGGG); SEQ ID NO: 275 (ENLKHQPGGG-KVQIINKKLDLSNVQSKCGSKDNIKHVPGGGS), SEQ ID NO: 276 (KHVPGGG), SEQ ID NO: 277 (HVPGGG), SEQ ID NO: 280 (DNIKHVPGGGSVQIVYKPV), SEQ ID NO: 281(HHKPGGG), SEQ ID NO: 282 (HKPGGG), and SEQ ID NO: 283 (THVPGGG). In other embodiments, the peptide is selected from SEQ ID NO: 272 (HQPGGG) and SEQ ID NO: 277 (HVPGGG).

Also provided is a method of isolating DC8E8, or isolating an antibody that is able to compete with DC8E8 for binding to tau, the method comprising contacting DC8E8 or the antibody with a peptide and/or with a compound as provided by the invention.

In related embodiments, the invention provides a method of diagnosing or screening a subject for the presence of Alzheimer's disease or related tauopathies in a subject, or for determining a subject's risk for developing Alzheimer's disease or related tauopathies, the method comprising:
  a) contacting the subject, or a cell, tissue, organ, fluid, or any other sample of the subject, with an effective amount of at least one antibody as provided by the invention; and
  b) determining the presence of a complex comprising pathological tau and the antibody, wherein the presence of the complex is diagnostic of Alzheimer's disease or related tauopathies associated with the presence of pathological tau.

In certain embodiments, the invention provides a method of monitoring a subject for the presence, progression, regression, or stabilization of Alzheimer's disease or related tauopathies, or for determining the stage of Alzheimer's disease or related tauopathies in a subject, the method comprising:
  a) contacting (e.g., administering) the subject, or a cell, tissue, organ, fluid, or any other sample of the subject, with an effective amount of at least one antibody as provided by at least one embodiment of the invention; and
  b) determining the presence and/or characteristics of a complex comprising pathological tau and the antibody, wherein the presence of the complex is diagnostic of Alzheimer's disease or related tauopathies associated with the presence of pathological tau.

In some embodiments of the method of monitoring a subject for the presence, progression, regression, or stabilization of Alzheimer's disease or related tauopathies, or for determining the stage of Alzheimer's disease or related tauopathies in a subject, the antibody, peptide, and/or compound is administered intravenously, intramuscularly, subcutaneously, intraperitoneally, intranasally, intracerebroventricularly, intrathecally, or as an aerosol. In some embodiments, the effective amount of each peptide and/or compound is at least 1 µg per dose, at least 10 µg per dose, at least 100 µg per dose. In some embodiments, the effective amount of each peptide and/or compound is at least 10 µg per dose in the presence of an adjuvant, and at least 100 µg per dose in the absence of an adjuvant. In some embodiments, at least one peptide or compound is administered in multiple dosages over a period of at least six months.

According to a related embodiment, the invention provides a method of treating or preventing the progression of Alzheimer's disease or related tauopathies in a subject, the method comprising administering to said subject an effective amount of at least one antibody, and/or at least one peptide, and/or at least one compound as provided by the invention, in combination with at least one combination agent chosen from acetylcholinesterase inhibitors, N-Methyl-D-aspartate (NMDA) receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid passive and active immunization, anti-amyloid aggregation inhibitors, and secretase inhibitors. In some embodiments, the method is capable of reducing motor impairment, improving motor function, reducing cognitive impairment, improving cognitive function, or a combination thereof.

In a related embodiment, the invention provides a method of ameliorating at least one of the symptoms associated with Alzheimer's disease or related tauopathies in a subject, the method comprising administering to said subject an effective amount of at least one antibody, at least one peptide, and/or at least one compound as provided by the invention, in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid-passive and -active immunization reagents, anti-amyloid aggregation inhibitors, and secretase inhibitors.

In some embodiments of the methods of treatment, prevention, or amelioration of at least one of the symptoms associated with Alzheimer's disease or related tauopathies in a subject, the method comprises administering to a human patient an effective amount of at least one antibody, at least one peptide, and/or at least one compound as provided by the invention, and/or an adjuvant that augments the immune response; in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid passive and -active immunization, anti-amyloid aggregation inhibitors, and secretase inhibitors; wherein the method effects an immune response comprising antibodies against pathological tau, thereby treating, preventing the progression, or ameliorating at least one of the symptoms associated with AD in the human patient.

In some embodiments of the methods of treatment, prevention, or amelioration of at least one of the symptoms associated with Alzheimer's disease or related tauopathies in a subject, the combination agent is administered prior to, simultaneously with, or after the administration of an antibody, a peptide, and/or a compound as provided by the invention.

In a related embodiment, the invention also provides a pharmaceutical composition comprising a pharmaceutically acceptable carrier and/or diluent; and
 a) an antibody as provided by the invention; and/or
 b) a peptide as provided by the invention; and/or
 c) a compound as provided by the invention;
 in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggre-
gation, inhibitors of protein kinases, inhibitors of heat shock proteins, anti-amyloid-passive and -active immunization reagents, anti-amyloid aggregation inhibitors, and secretase inhibitors. In some embodiments, the antibody is DC8E8. In certain embodiments, the antibody comprises at least one CDR from DC8E8. In some embodiments, the antibody comprise at least one variable chain (light or heavy) from DC8E8. In certain embodiments, a humanized or human version of DC8E8 can be used. In some embodiments, at least one peptide is chosen from any one of SEQ ID NOs: 1-4, SEQ ID NOs: 9-101, and SEQ ID NOs: 108-112, NIKHVPGGGS (SEQ ID NO: 201), IKHVPGGGS (SEQ ID NO: 202), KHVPGGGSV (SEQ ID NO: 203), HVPGGGSVQ (SEQ ID NO: 204), VPGGGSVQ (SEQ ID NO: 205), GWSIHSPGGGSC (SEQ ID NO: 250), SVFQHLPGGGSC (SEQ ID NO: 251), ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKAVPGGGS (SEQ ID NO: 159), DNIKHAPGGGS (SEQ ID NO: 161), and DNIKHVPGGGS (SEQ ID NO: 171). In one embodiment, the peptide is chosen from SEQ ID NOs: 1-4. In another embodiment, the peptide is SEQ ID NO. 108. In one embodiment, the peptide is GWSIHSPGGGSC (SEQ ID NO: 250). In certain embodiments, the peptide is SVFQHLPGGGSC (SEQ ID NO: 251). In certain embodiments the peptide is selected from SEQ ID NO: 270 (TENLKHQPGGGK); SEQ ID NO: 271 (KHQPGGG), SEQ ID NO: 272 (HQPGGG); SEQ ID NO: 275 (ENLKHQPGGGKVQIINKKLDLSNVQSKCGSKDNIKHVPGGGS), SEQ ID NO: 276 (KHVPGGG), SEQ ID NO: 277 (HVPGGG), SEQ ID NO: 280 (DNIKHVPGGGSVQIVYKPV), SEQ ID NO: 281(HHKPGGG), SEQ ID NO: 282 (HKPGGG), and SEQ ID NO: 283 (THVPGGG). In other embodiments, the peptide is selected from SEQ ID NO: 272 (HQPGGG) and SEQ ID NO: 277 (HVPGGG).

Additional objects and advantages of the embodiments will be set forth in part in the description which follows, and in part will be obvious from the description, or can be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the embodiments, as claimed.

The accompanying drawings, which are incorporated in and constitute a part of this specification, illustrate several embodiments and together with the description, serve to explain the principles of the embodiments. The publications discussed herein are provided solely for their disclosure prior to the filing date of the present application. They are all incorporated by reference in their entirety for all purposes. Nothing herein is to be construed as an admission that the present invention is not entitled to antedate such publication by virtue of prior invention. Further, the dates of publication provided can be different from the actual publication dates which can need to be independently confirmed.

BRIEF DESCRIPTION OF THE DRAWINGS

FIG. 2 discloses "VQIINK" and "VQIVYK" as SEQ ID NOS 116 and 115, respectively.

FIGS. 3A through 3D: The nucleotide and amino-acid sequences of DC8E8 variable regions and their alignment to the closest mouse germ line sequences. The figure shows nucleotide (SEQ ID NO: 165) (FIG. 3A, in A) and amino acid (SEQ ID NOS 141 (for the variable light chain) and 117-119 (for each of its CDRs, according to IMGT), respectively, in order of appearance); (FIG. 3A, in B) sequences of the variable light (VL) chain region of DC8E8 (alignment discloses SEQ ID NOS 166 and 168, respectively, in order of appearance); and (FIG. 3A, in C and FIG. 3B) alignment of DC8E8's variable light chain V-gene to the closest mouse germline sequence IGKV8-21*01 (alignment discloses SEQ ID NOS 166 and 167, respectively, in order of appearance; followed by the alignment of DC8E8's VL J-gene (SEQ ID NO:168) to closest mouse J gene, IGKJ1*01 (SEQ ID NO: 169). The figure shows the nucleotide (SEQ ID NO: 170) (FIG. 3B, in D) and amino acid sequence of DC8E8's (FIG. 3B, in E) variable heavy chain and its three CRDs (SEQ ID NOS 171 and 120-122, respectively, in order of appearance) sequences. In (FIG. 3C, in F) are shown the following alignments for DC8E8: first, the variable heavy (VH) chain V-gene of DC8E8 (SEQ ID NO 172) with the closest mouse germline sequence IGHV1-81*01 (SEQ ID NO 172); second, the variable heavy (VH) chain D-gene of DC8E8 (SEQ ID NO 174) with the closest mouse germline sequence IGHD2-14*01 (SEQ ID NO 175); and last, the variable heavy (VH) chain J-gene of DC8E8 (SEQ ID NO 176) with the closest mouse germline sequence IGHJ4*01 (SEQ ID NO 177). The sequence of DC8E8 kappa light chain constant region (SEQ ID NO: 178) (FIG. 3D, in G) and sequence of heavy chain constant region (SEQ ID NO: 179) (FIG. 3D, in H) are also shown. Complementarity determining regions (CDRs) are underlined in the protein sequences (B) and (E) and were identified according to IMGT numbering system.

FIG. 4: Alignment of DC8E8 Variable Light (VL) chain sequence (SEQ ID NOS 166 (V-gene) and 168 (J-gene), respectively, to the closest human germline VL gene (SEQ ID NOS 180-181, respectively, in order of appearance).

FIGS. 5A and 5B: Alignment of DC8E8 Variable Heavy (VH) chain sequence (SEQ ID NOS 172, 174, and 176, for V, D, and J genes, respectively) to the closest human germline VH gene (SEQ ID NOS 182-183 and 185, respectively, in order of appearance).

FIGS. 6A through 6E: Epitope mapping of DC8E8 by tau deletion mutants using ELISA. (FIG. 6A) Schematic of tau proteins used for DC8E8 epitope mapping, and (FIG. 6B through FIG. 6D) their amino acid sequence (SEQ ID NOS 186-197, 102, 104, and 198-199, respectively, in order of appearance). (FIG. 6E) ELISA readouts. DC8E8 recognizes the following tau proteins: Δ358-441, Δ421-441, Δ134-168, Δ1-220, Δ1-126, 2N4R, 2N3R, Δ(1-296;392-441) and Δ(1-150;392-441)/4R. DC8E8 does not recognize the following tau proteins: Δ222-427, Δ306-400, Δ228-441, Δ300-312, Δ257-400, Δ137-441, Δ283-441.

FIG. 14: Monoclonal antibody DC8E8 recognizes both soluble (A) and insoluble tau protein (B) in the brain samples isolated from transgenic rat model SHR24 (isocortex) and Alzheimer's disease patients (allocortex tissue including hippocampus, entorhinal and temporal cortex). Arrowhead—human truncated tau, arrow—rat endogenous tau. For soluble tau fractions 15 μg of protein were loaded per lane. For insoluble tau fractions the pellets were dissolved in 1× sodium dodecyl sulfate (SDS) samples loading buffer in 1/50 volume of the 1S, the same volume were loaded as in the case of soluble fractions. Monoclonal antibody DC8E8 recognizes both soluble and insoluble tau proteins in the brain samples isolated from Alzheimer's disease patients (allocortex tissue including hippocampus, entorhinal and temporal cortex) (C) and from transgenic rat model SHR72 (brain stem) (D). Arrow—physiological human tau proteins (A) and rat endogenous tau (B), arrowhead—human truncated tau (tauΔ(1-150;392-441)/4R) expressed as a transgene in the neurons of SHR72 rats (D). For soluble tau fractions 15 μg of total protein were loaded per lane. For insoluble tau fractions the pellets were dissolved in 1× sodium dodecyl sulfate (SDS) samples loading buffer in 1/50 volume of the 1S, the same volume were loaded as in the case of soluble fractions

FIG. 24: Recombinant scFv fragment of monoclonal antibody DC8E8 (scDC8E8v) exhibits tau binding properties similar to the DC8E8 antibody—selectively recognizes tauΔ(1-150;392-441)/4R. (A) Kinetic affinity determination by SPR of scDC8E8v binding to AD tauΔ(1-150;392-441)/4R. (B) Kinetic affinity determination by SPR of scDC8E8v binding to tau 2N4R. (C) Rate constants ($k_{ON}$ and $k_{OFF}$) and association equilibrium constant for scDC8E8v binding.

FIG. 29: Quantitative immunoblot analysis of insoluble tau prepared from the brain stems of transgenic rats (SHR72) treated with tau 256-VKSKIGSTEN-LKHQPGGGKVQIINKKLDLS-285 (SEQ ID NO:2) with adjuvant or control rats treated with adjuvant alone. Mean values are presented with standard error of the mean.

FIG. 56: Vaccination of transgenic rats SHR72 with tau peptide SEQ ID NO:108 induced formation of antibodies preferentially binding to pathological tau protein. Geometric mean antibody titers measured with ELISA show that antibodies elicited by vaccination with tau peptide SEQ ID NO:108 exhibited highest binding activity to immunogen (SEQ ID NO:108 peptide) and to pathological tauΔ(1-150; 392-441)/4R. Physiological tau (tau2N4R), which was used as a control, was more weakly recognized.

FIG. 60: Vaccination of transgenic rats SHR72 with tau peptide SEQ ID NO:108 induced antibodies recognizing pathological tau proteins in sections from human Alzheimer's disease brain tissues. Representative immunostaining of the rat serum Nos. 3 (A), 5 (B), 6 (C), 7 (D), and 8 (E) show that all tested rat serum antibodies recognized neurofibrillary tangles in Pre-α layer of the entorhinal cortex of an Alzheimer's disease patient. Pooled sera from rats immunized with adjuvant only were used as a negative control (F). Serial brain tissue sections from the entorhinal cortex were used. Scale bar 50 μm.

FIG. 70: Immunohistochemical staining of human AD diseased brain tissues with sera generated against designer therapeutic epitope 1 (GWSIHSPGGGSC, SEQ ID NO: 250) and designer therapeutic epitope 2 (SVFQHLPGGGSC, SEQ ID NO: 251). (A) Antisera against designer therapeutic epitope 1 recognized neurofibrillary pathology in the brain of AD patient. (C) High magnification of the neurofibrillary tangle and neuropil threads (arrows). (B) Antisera against designer therapeutic epitope 2 recognized neurofibrillary pathology in the brain of AD patient. (D) High magnification of the stained neurofibrillary tangle and neuropil threads (arrows). Antisera against designer therapeutic epitope 1 and designer therapeutic epitope 2 did not recognize normal tau in the control human brain (E, F). scale bar. 50 μm (A, B, E, F), 20 μm (C, D). (G) Serum generated against designer therapeutic epitope 2 (SVFQHLPGGGSC, SEQ ID NO: 251) recognizes neurofibrillary lesions in transgenic rats SHR72. (H) In age-matched control rat brains the antibody does not display intraneuronal staining. The serum recognizes oligomeric pre tangle stage (I), as well as intracellular (J). Scale bar 20 μm (A, B), 10 μm (C, D).

FIG. 71: Antibodies induced by designer therapeutic epitope 1 (GWSIHSPGGGSC, SEQ ID NO: 250) and designer therapeutic epitope 2 (SVFQHLPGGGSC, SEQ ID NO: 251) recognized soluble and sarkosyl-insoluble pathological tau isolated from the human Alzheimer's disease brain tissues.

FIGS. 77A through 77N: Induction of tau specific antibodies after immunization of C57BL mice with tau peptides. (FIG. 77A thorough FIG. 77E) 12-mer, 7-mer and 6-mer peptides (SEQ ID NOs: 270, 271 and 272, respectively) are immunogenic. The antibodies induced by immunization exhibit statistically significantly higher binding activity to pathological tauΔ(1-150; 392-441)/4R than to physiological tau 2N4R ($p<0.0079$; $p<0.0052$; $p<0.0079$, respectively). 5-mer peptides SEQ ID NOs: 273 and 274 are not immunogenic. (FIGS. 77F through 77K) 42-mer, 19-mer, 7-mer and 6-mer peptides (SEQ ID NOs: 275, 280, 276 and 277, respectively) are immunogenic. Antibodies induced by these peptides statistically significantly ($p<0.0079$, $p<0.0159$, $p<0.0079$ and $p<0.0379$, respectively) discriminated between pathological tauΔ(1-150;392-441)/4R and physiological tau 2N4R. 5-mer peptides SEQ ID NOs: 278 and 279 are not immunogenic. (FIGS. 77L through 77N) 7-mer peptides (SEQ ID NOs: 281 and 283) are immunogenic. Antisera against these peptides statistically significantly ($p<0.0379$, and $p<0.0286$, respectively) discriminated between pathological tauΔ(1-150;392-441)/4R and physiological tau 2N4R. The levels of antibodies to pathological tau and physiological tau induced by 6-mer peptide SEQ ID NO: 282 were very low. The graphs represent statistical evaluation of ELISA results for individual sera diluted at 1:800. Mean values are shown with standard error of the mean.

FIG. 78: Geometric mean antibody titers of tau specific antibodies after immunization of C57BL mice with tau peptides. Vaccination of C57BL mice with tau peptide SEQ ID NOs: 270, 271, 272, 275, 276, 277, 280, 281 and 283 induced formation of tau specific antibodies. Geometric mean antibody titers measured with ELISA show that antibodies elicited by vaccination with tau peptide SEQ ID NOs: 270, 271, 272, 275, 276, 277, 280, 281 and 283 exhibited higher binding activity to pathological tauΔ(1-150; 392-441)/4R than to physiological tau ($tau_2N4R$). Lower titers of tau specific antibodies were detected after immunization of mice with tau peptides SEQ ID NOs: 273, 274, 278, 279 and 282.

FIG. 81: Antibodies induced in mice immunized with tau peptides recognize pathological forms of tau in Western blotting. Vaccination of C57BL mice with tau peptides SEQ ID NOs: 270, 271, 272, 275, 276, 277, 280, 281 and 283 induced specific antibodies, which recognize pathological tau proteins isolated from human Alzheimer's disease brain tissue as well as from the brain stems of transgenic rats SHR72. Antisera after immunization of mice with peptides SEQ ID NOs: 273, 274, 278, 279 and 282 did not recognize pathological tau forms.

FIG. 83: Summary of immunohistochemical staining (and respective relative intensities) of brain tissues from a human AD patient with sera antibodies generated from immunization of C57BL mice with tau peptides SEQ ID NOS: 270, 271, 272, 273, 274, 275, 276, 277, 278, 279, 280, 281, 282, and 283.

DETAILED DESCRIPTION OF THE INVENTION

Figure 1:
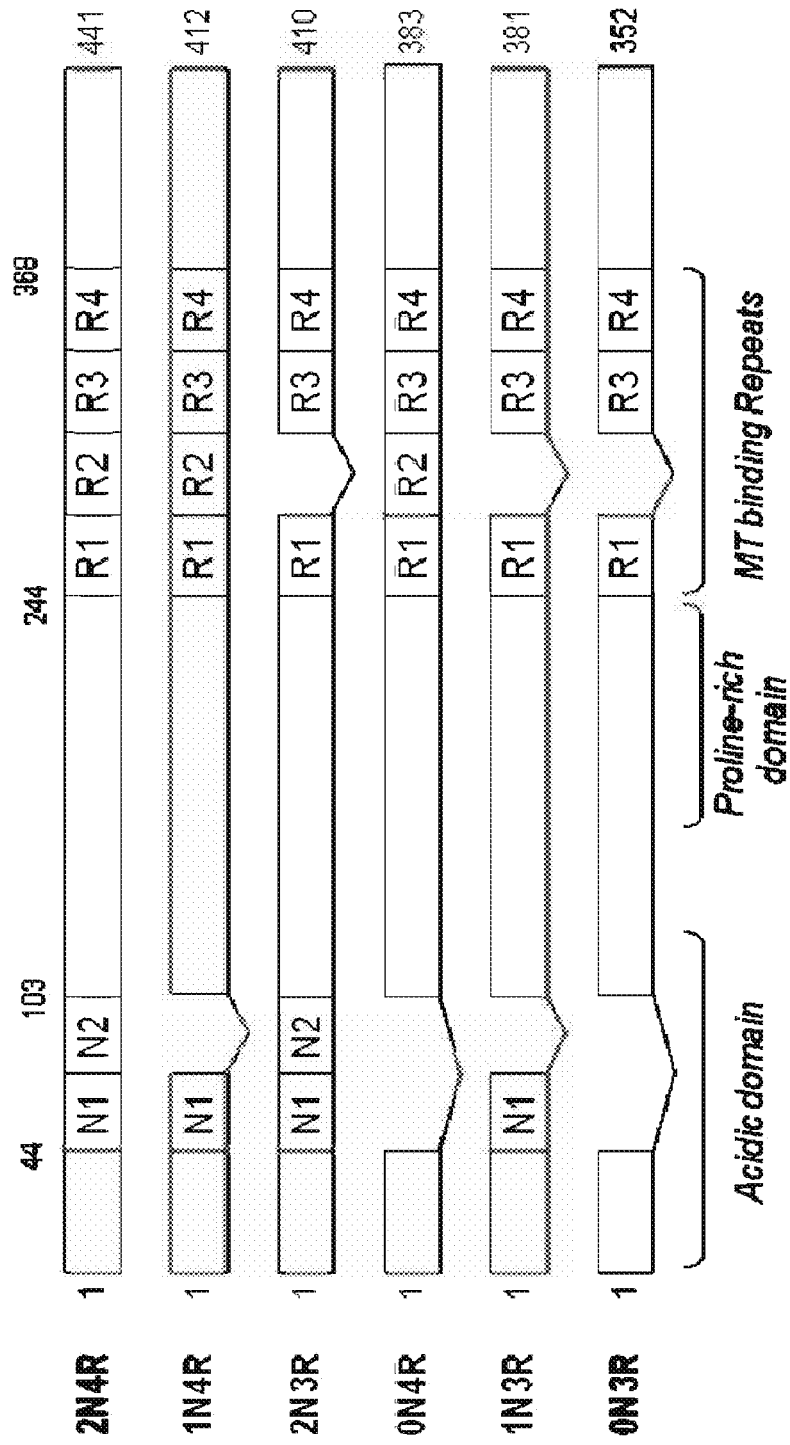
FIG. 1: Schematic of six isoforms of human tau.
Figure 2:
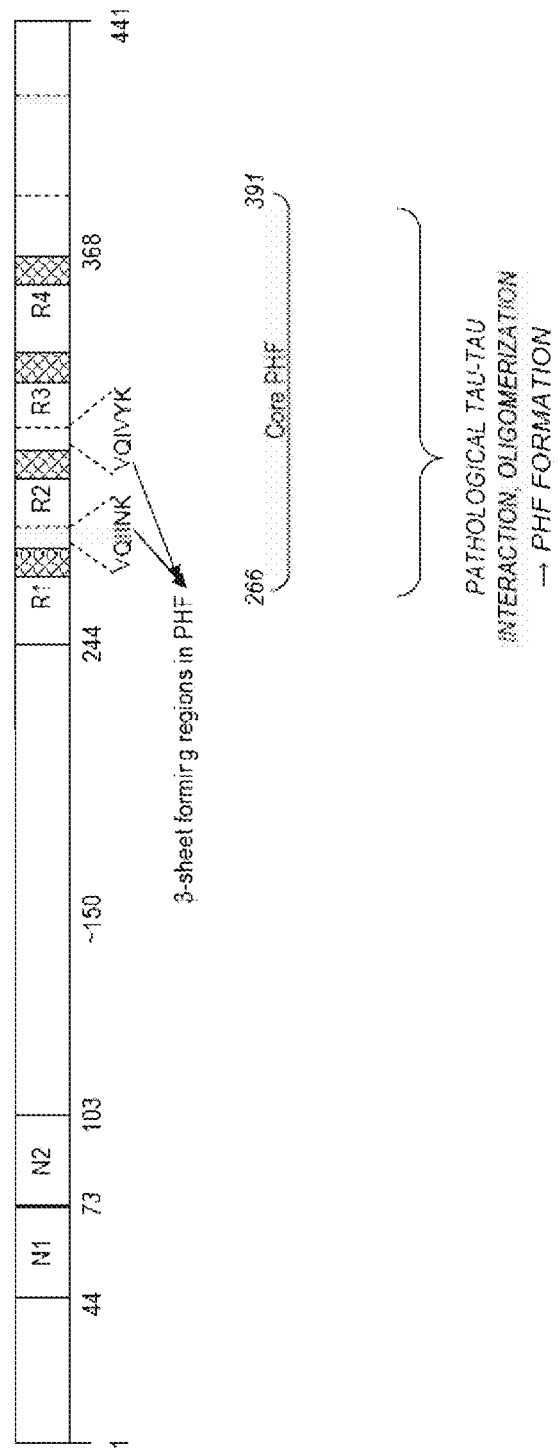
FIG. 2: Schematic functional map of human tau (2N4R).

The term "antibody" refers to an immunoglobulin, whether genetically engineered, natural, or wholly or partially synthetically or recombinantly produced. All derivatives, portions, and fragments thereof that maintain antigen-binding properties and at least one of the tau-related characteristic properties according to the invention are also included in the term. The term also encompasses any protein having a binding domain which is homologous or largely homologous to an immunoglobulin binding domain. These proteins can be derived from natural sources, or partly or wholly synthetically or recombinantly produced. An antibody can be monoclonal or polyclonal. The antibody can be a member of any immunoglobulin class, including any of the human classes: IgG, IgM, IgA, IgD, and IgE. Derivatives of the IgG class are preferred in some embodiments of the present invention.

The terms "isolated antibody" and "isolated peptide" refer to a protein or peptide produced from cDNA-, recombinant RNA-, or any other synthetic-origin, or some combination thereof; as well as to proteins and peptides that, by virtue of their origin, or source of derivation, either (1) are not associated with proteins found in nature, (2) are free of other proteins from the same source, e.g. free of murine proteins, (3) are expressed by a cell from a different species, or (4) do not occur in nature.

The antibodies according to the invention include, in addition, such antibodies having "conservative sequence modifications," nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a anti-tau antibody can be for example replaced with another amino acid residue from the same side chain family.

"Antibody fragments" and "antibody portions" comprise a portion of a full length antibody, generally at least the antigen binding portion/domain or the variable region thereof. Examples of antibody fragments include diabodies, single-chain antibody molecules, immunotoxins, and multi-specific antibodies formed from antibody fragments. In addition, antibody fragments comprise single chain polypeptides having the characteristics of a VH chain binding pathological tau, namely being able to assemble together with a VL chain or of a VL chain binding to pathological tau, namely being able to assemble together with a VH chain to form a functional antigen binding pocket and thereby providing the property of binding to pathological tau. The terms also comprise fragments that per se are not able to provide effector functions (e.g., ADCC/CDC) but provide this function after being combined with the appropriate antibody constant domain(s).

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" refers to antibodies in which the framework regions (FR) and/or the complementarity determining regions (CDR) have been modified to comprise the CDR of an immunoglobulin of different specificity as compared to that of the parent immunoglobulin. In one embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens and epitopes described herein as "therapeutic epitopes" on tau.

The term "human antibody", as used herein, is intended to include antibodies having variable and constant regions derived from human germline immunoglobulin sequences. The constant regions of the antibody can be, for example, constant regions of human IgG1 type. Such regions can be allotypic and are described by, e.g., Johnson, G., and Wu, T. T., Nucleic Acids Res. 28 (2000) 214-218 and the databases referenced therein, and are preferentially useful for some embodiments, as long as the properties of induction of ADCC and for example CDC according to the invention are retained.

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse such as a XENOMOUSE, a genetically modified mouse that produces antibodies having amino acid sequences of human antibodies, e.g., human framework (FR) and human constant region amino acid sequences) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, can not naturally exist within the human antibody germline repertoire in vivo.

The term "effector functions" includes, but is not limited to, C1q binding; complement dependent cytotoxicity (CDC); Fc receptor binding; antibody-dependent cell-mediated cytotoxicity (ADCC); phagocytosis; and down regulation of cell surface receptors (e.g. B cell receptor; BCR).

The term "epitope" is used here to refer to binding sites recognized by a binding protein or an antibody. Epitopes can be any molecule or grouping thereof, including, but not limited to, amino acids, amino acid side chains, sugars, and lipids, and can have a specific three-dimensional structure or conformation. Thus, an epitope can comprise any portion of a tau peptide/protein molecule that includes primary, secondary, tertiary, or quaternary structure, as those terms are generally known in the art. A "linear epitope" is made up of a continuous sequence of amino acid residues. A linear epitope is one that is present on physiological tau (e.g., is present in tau 2N/4R). A "conformational epitope" is an epitope to which the antibody or binding protein binds in a conformational-specific manner. In the case of protein-based epitopes, the binding can depend on the epitope-carrying-protein's secondary, tertiary, or quaternary structure. In other words, the antibody binds in a structure-specific manner, a tertiary-structure-specific manner, or a quaternary-structure-specific manner. A conformational epitope is one that is present in pathological tau (e.g., present in tauΔ(1-150;392-441)/4R)).

The term "therapeutic epitope" refers to regions within tau that were identified herein and were found to promote tau-tau aggregation, when in certain conformations (recognized by the DC8E8 antibody). Antibodies (and other binding proteins) that bind to one or more of these regions inhibit early and late stages of tau aggregation, including the conversion of tau monomer to dimer, and conversion to higher aggregate forms; i.e, the antibodies inhibit the conversion from physiological tau to pathological tau. These regions within tau can be involved in promoting tau fibrillization into paired helical filaments (PHFs), by promoting the formation of beta-sheets within adjacent regions of tau. Therapeutic epitopes are comprised within 267-KHQPGGG-273 (within $1^{st}$ repeat domain of tau protein), 298-KHVPGGG-304 (within $2^{nd}$ repeat domain of tau protein), 329-HHKPGGG-335 (within $3^{rd}$ repeat domain of tau protein), and 361-THVPGGG-367 (within $4^{th}$ repeat domain of tau protein. In some embodiments, the therapeutic epitopes are each comprised within 268-HQPGGG-273 (within $1^{st}$ repeat domain of tau protein), 299-HVPGGG-304 (within $2^{nd}$ repeat domain of tau protein), 330-HKPGGG-335 (within $3^{rd}$ repeat domain of tau protein), and 362-HVPGGG-367, respectively.

The term "displaying a higher affinity for pathological tau than for physiological tau" refers to a higher degree of interaction between the antibody and at least one form of pathological tau than between the antibody and at least one form of physiological tau. The interaction can be measured by, e.g., ELISA or surface plasmon resonance (SPR), as described in the EXAMPLES below.

The terms "specifically binds," "binds specifically," and "specific to," are interchangeable and mean that an antibody or antigen-binding fragment thereof (or other binding protein) forms a complex with an antigen or epitope that is relatively stable under physiologic conditions. Specific binding can be characterized by a dissociation constant of about $1 \times 10^{-6}$ M or smaller, for example less than about 100 nM, and most for example less than 10 nM. Methods for determining whether two molecules specifically bind are known in the art and include, for example, equilibrium dialysis, surface plasmon resonance, and the like. Typically, an antibody or antigen-binding fragment thereof provided by the invention is a molecule that binds the antigen or an epitope with such a dissociation constant of at least about $1 \times 10^{-6}$ M or smaller, but does not bind other molecules with such a dissociation constant.

"Preferentially bind" refers to binding with higher affinity to pathological tau than to physiological tau, for example, binding with higher affinity to tauΔ(1-150;392-441)/4R than to 2N4R.

A "universal T-cell epitope" is a sequence selected from Influenza Hemagluttinin: HA307-319 (PKYVKQNTLKLAT) (SEQ ID NO: 123); PADRE (AKXVAAWTLKAAA) (SEQ ID NO: 124); Malaria CS: T3 epitope (EKKIAKMEKASSVFNV) (SEQ ID NO: 125); Hepatitis B surface antigen: HBsA919_28 (FFLLTRILTI) (SEQ ID NO: 126); Heat Shock Protein 65: hsp65153_171 (DQSIGDLIAEAMDKVGNEG) (SEQ ID NO: 127); bacille Calmette-Guerin (QVHFQPLPPAVVKL) (SEQ ID NO: 128); Tetanus toxoid: T1830-844 (QYIKANSKFIGI-TEL) (SEQ ID NO: 129); Tetanus toxoid: T1947-967 (FNN-FTVSFWLRVPKVSASHLE) (SEQ ID NO: 130); and HIV gp120 T1 (KQIINMWQEVGKAMYA) (SEQ ID NO: 131).

The term "intrinsically disordered tau" refers to the normal/physiological form of tau protein, which lacks any defined 3D structure. It exists in the healthy brain (Kovacech et al., 2010).

"Misdisordered tau" refers to the forms of tau that differ conformationally from normal/physiological intrinsically disordered tau, and does not have a firm/defined 3D-structure. Misdisordered truncated tau is able to induce neurofibrillary degeneration in vivo. It does not exist in a healthy brain (Kovacech et al., 2010). "Misordered tau" refers to a structured pathological form of tau assembled into polymers of PHFs, which form NFTs. Misordered tau does not exist in a healthy brain (Kovacech et al., 2010).

"SHR24" refers to transgenic rat line that expresses tau type IIB (151-391/R3). The transgenic rats developed progressive age-dependent neurofibrillary degeneration in the cortical brain areas. Neurofibrillary tangles (NFTs) in SHR24 rats satisfy several key histological criteria used to identify neurofibrillary degeneration in human Alzheimer's disease including argyrophilia, Congo red birefringence, and Thioflavin S reactivity. These criteria can be used for analysis of neurofibrillary degeneration in subjects receiving any of the embodiments of the invention. Neurofibrillary tangles were also identified with antibodies used to detect pathologic tau in the human brain, including DC11, recognizing an abnormal tau conformation and antibodies that are specific for hyperphosphorylated forms of tau protein. Moreover, neurofibrillary degeneration was characterized by extensive formation of sarkosyl insoluble tau protein complexes consisting of rat endogenous and truncated tau species (Filipcik et al., 2010).

"SHR72" refers to transgenic rats that express human truncated tauΔ(1-150;392-441)/4R according to the International Patent Application PCT WO 2004/007547), in several brain regions and spinal cord. Generation of this rat line was described by Zilka et al., 2006, and tau pathology was described in Koson et al., 2008.

"Tau type IA" refers to N- and C-terminally double truncated tau proteins that have at least the first 236 N-terminal amino acids and at least the last 45 C-terminal amino acids of the 4 repeat containing $tau_{43}$ truncated. The molecules are detectable in Alzheimer's diseased brain tissue whereas the molecules are not detectable in normal healthy brain tissue (WO2004/007547 A2).

"Tau type IB" refers to N- and C-terminally double truncated tau proteins that have at least the first 236 N-terminal amino acids and at least the last 45 C-terminal amino acids of the 3 repeat containing $tau_{44}$ truncated. The molecules are detectable in Alzheimer's diseased brain tissue whereas the molecules are not detectable in normal healthy brain tissue (WO2004/007547 A2).

"Tau type IIA" refers to N- and C-terminally double truncated tau proteins that have at least the first 68 N-terminal amino acids and at least the last 40 C-terminal amino acids of the 4 repeat containing $tau_{43}$ truncated. The molecules are detectable in Alzheimer's diseased brain tissue whereas the molecules are not detectable in normal healthy brain tissue (WO2004/007547 A2).

"Tau type IIB" refers to N- and C-terminally double truncated tau proteins that have at least the first 68 N-terminal amino acids and at least the last 20 C-terminal amino acids of the 3 repeat containing $tau_{44}$ truncated. The molecules are detectable in Alzheimer's diseased brain tissue whereas the molecules are not detectable in normal healthy brain tissue (WO2004/007547 A2).

As used herein, the terms "treatment," "treating," and the like, refer to obtaining a desired pharmacologic and/or physiological effect. The effect can be prophylactic in terms of completely or partially preventing a disease or symptom thereof and/or can be therapeutic in terms of a partial or complete cure for a disease and/or adverse affect attributable to the disease. "Treatment," as used herein, also covers any treatment of AD or related tauopathies in a mammal, particularly in a human, and includes: (a) preventing the disease from occurring in a subject which can be predisposed to the disease or at risk of acquiring the disease but has not yet been diagnosed as having it; (b) inhibiting the disease, i.e., arresting its development; and (c) relieving the disease, i.e., causing regression of the disease. Preferred embodiments of "treatment" are further discussed below. In some embodiments, "treating" refers to administering a therapeutic agent to a patient suspected of suffering or already suffering from AD or another tauopathy. It can also refer to reducing, eliminating, or at least partially arresting, as well as to exerting any beneficial effect, on one or more symptoms of the disease and/or associated with the disease and/or its complications.

"Prevention" refers to administration to a patient susceptible to, or otherwise at risk of, a particular disease. Anyone in the general population is at risk for AD. Some individuals have an increased, genetic risk for AD. Prevention can eliminate or reduce the risk or delay the onset of disease. Delay of onset or progression can be measured based on standard times of disease progression in similar populations or individuals.

"Tauopathy" refers to a disease associated with the formation of pathological tau.

"Physiological tau" refers to any one of the 6 isoforms of normal human tau, namely:

2N4R (SEQ ID NO: 102)

1N4R (SEQ ID NO: 103)

2N3R (SEQ ID NO: 104)

0N4R (SEQ ID NO: 105)

1N3R (SEQ ID NO: 106)

0N3R (SEQ ID NO: 107)

Excluded from this definition are those that carry any one of the phosphorylations associated with Alzheimer's disease and other tauopathies.

"Pathological tau" includes pathological tau conformers and structures and encompasses all of the following: Tau Type IA, IB, IIA, and IIB, misordered, misdisordered tau (monomer, dimer, trimer, oligomer), misdisordered soluble tau, sarkosyl-insoluble tau, extracellular tau deposits, tau aggregates, paired helical filaments, neurofibrillary pathology, including neurofibrillary lesions, tangles, threads, fibrils, axonal spheriods, highly phosphorylated forms of truncated tau and of full-length tau, or any other form of tau associated with AD or another tauopathy.

"Linked" refers to attachment of a moiety to a peptide, antibody, or compound. The moiety can be coupled, or complexed, or covalently or non-covalently attached. The moiety can be chemically crosslinked or expressed or synthesized as a fusion with the peptide or antibody.

"Moiety" refers to any compound, organic, peptide, protein, nucleic acid, carrier, adjuvant, that is able to be attached to the peptide, antibody, or binding protein, but that is not the claimed peptide, antibody, or binding protein itself.

"Immunogenic" refers to something that can elicit an immune response. The immune response can be antibody- or cell-mediated, or both.

"Adjuvant" refers to a substance that is capable of increasing, amplifying, or modulating the immune response to the accompanying peptide.

"Other therapy" refers to additional therapies that the subject patients can receive.

"Clearance" refers to a reduction in levels or detection of pathological tau and/or a pathological tau structure. Clearance does not have to be a complete disappearance of pathological tau, i.e., it can be a partial disappearance.

The term "promoting" encompasses inducing, improving, or increasing.

"Brain tissue" refers to any neuronal tissue, e.g., from the brain, brain stem, and spinal cord.

The term "specific binding" and "high affinity", respectively, refers to antibody binding to a predetermined antigen, i.e. the tau epitope defined above. Typically, the antibody binds with a dissociation constant (KD) of $10^{-6}$ M or less, and binds to the predetermined antigen with a KD that is at least twofold less than its KD for binding to a nonspecific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen". As used herein "highly specific" binding means that the relative $K_D$ of the antibody for misdisordered tau is at least 4-fold less than the $K_D$ for binding that antibody to other ligands or to normal full-length tau.

The term "prokaryotic" is meant to include all bacteria which can be transformed or transfected with a DNA or RNA molecule for the expression of an antibody of the invention or one or more of the corresponding immunoglobulin chains. Prokaryotic hosts can include gram negative as well as gram positive bacteria such as, for example, *E. coli, S. typhimurium, Serrata marcescens* and *Bacillus subtilis*. The term "eukaryotic" is meant to include yeast, higher plant, insect and for example mammalian cells, most for example HEK 293, NSO, and CHO cells.

The term "chemical derivative" describes a molecule that contains additional chemical moieties that are not normally a part of the base molecule. Such moieties can improve the solubility, half-life, absorption, etc. of the base molecule. Alternatively the moieties can attenuate undesirable side effects of the base molecule or decrease the toxicity of the base molecule.

The terms "nucleic acid", "nucleic sequence", "nucleic acid sequence", "polynucleotide," "oligonucleotide", "polynucleotide sequence" and "nucleotide sequence" are used interchangeably in the present description, and refer to a precise sequence of nucleotides, modified or not, defining a fragment or a region of a nucleic acid, containing unnatural nucleotides or not, and being either a double-strand DNA, a single-strand DNA or transcription products of said DNAs.

The term "isolated polynucleotide" or "isolated nucleic acid" as used herein shall mean a polynucleotide of genomic, cDNA, or synthetic origin or some combination thereof, which by virtue of its origin either (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

Antibodies for Diagnostics, Passive Immunization, Drug Delivery, and AD-Therapy

Described herein are novel isolated antibodies, specific to one or more tau epitopes displayed by pathological forms of tau. These epitopes are located within regions of tau that are for the first time assigned a role in pathological tau aggregation, namely within: 267-KHQPGGG-273 (SEQ ID NO: 98) (i.e., epitope #1 is located within 267-KHQPGGG-273, which falls within the $1^{st}$ repeat domain of tau protein), 298-KHVPGGG-304 (SEQ ID NO: 99) (epitope #2, within the $2^{nd}$ repeat domain of tau protein), 329-HHKPGGG-335 (SEQ ID NO: 100) (epitope #3, within the $3^{rd}$ repeat domain of tau protein), and 361-THVPGGG-367 (SEQ ID NO: 101) (epitope #4, within the $4^{th}$ repeat domain of tau protein). These antibodies are capable of recognizing misordered and misdisordered tau in human AD brains, as well as in transgenic rat models of AD and related tauopathies, expressing human misdisordered truncated tauΔ(1-150;392-441)/3R or tauΔ(1-150;392-441)/4R. The isolated antibodies are also capable of interfering with one or several of the multiple tau-mediated activities contributing to AD pathology, including: (i) transition from either misordered or from physiological tau to misordered tau; (ii) formation of "pathological tau" monomers; dimers, trimers, and other tau multimers;" (iii) formation of insoluble tau aggregates; and (iv) promoting clearance of extracellular tau.

The disclosed invention is based, in part, on the discovery that antibodies that specifically bind to one of four previously unidentified functional regions of tau selected from 267-KHQPGGG-273 (SEQ ID NO: 98) (within $1^{st}$ repeat domain of tau protein), 298-KHVPGGG-304 (SEQ ID NO: 99) (within $2^{nd}$ repeat domain of tau protein), 329-HHKPGGG-335 (SEQ ID NO: 100) (within $3^{rd}$ repeat domain of tau protein), and 361-THVPGGG-367 (SEQ ID NO: 101) (within $4^{th}$ repeat domain of tau protein) are capable of inhibiting formation of pathological tau aggregates, and of detecting various pathological forms of tau, some of which are the earliest formed in the disease (e.g., pathological monomers). Hybridomas produced against human misdisordered tau II (151-391/4R), which is also referred in this application as tauΔ(1-150;392-441)/4R, were screened for the production of monoclonal antibodies specific to human PHFs both by immunohistochemistry (IHC) and Enzyme-linked Immuno Assays (ELISAs). The resulting set included mouse monoclonal antibody (mAb) DC8E8, which is of the IgG1 subclass. Epitope mapping of DC8E8 revealed it to bind four previously unidentified epitopes on human tau. Moreover, further functional analysis of DC8E8 revealed that each epitope represents a distinct functional region within tau. These regions, which can now be described as novel targets for AD diagnosis and therapy, and thus are referred to as "therapeutic epitopes," are comprised within 267-KHQPGGG-273 (SEQ ID NO: 98) (within $1^{st}$ repeat domain of tau protein), 298-KHVPGGG-304 (SEQ ID NO: 99) (within $2^{nd}$ repeat domain of tau protein), 329-HHKPGGG-335 (SEQ ID NO: 100) (within $3^{rd}$ repeat domain of tau protein), and 361-THVPGGG-367 (SEQ ID NO: 101) (within $4^{th}$ repeat domain of tau protein). In some embodiments, one or more of the therapeutic epitopes is comprised within 268-HQPGGG-273 (SEQ ID NO: 223) (within $1^{st}$ repeat domain of tau protein), 299-HVPGGG-304 (SEQ ID NO: 154) (within $2^{nd}$ repeat domain of tau protein), 330-HKPGGG-335 (SEQ ID NO: 224) (within $3^{rd}$ repeat domain of tau protein); and 362-HVPGGG-367 (SEQ ID NO: 154) (within $4^{th}$ repeat domain of tau protein). In some embodiments, at least one of the therapeutic epitopes is comprised within 299-HVPGGG-304 (SEQ ID NO: 154) (within $2^{nd}$ repeat domain of tau protein). In some embodiments, one or more of the therapeutic epitopes is 299-HVPGGG-304 (SEQ ID NO: 154).

Indeed, DC8E8 is capable of discriminating between pathological and normal tau proteins, suggesting that at least one of these four epitopes is conformational. In other words, DC8E8 revealed that at least one of the regions encompassed by each of the four therapeutic epitopes shows a conformation in pathological tau that is different from the shape(s) it assumes in intrinsically disordered tau (normal tau). DC8E8 is able to sense or detect that change in that it binds to pathological tau with a higher affinity than it binds to physiological tau. Moreover, DC8E8 binding to tau is capable of inhibiting tau-tau interactions leading up to the formation of pathological tau aggregates, as measured by DC8E8's ability to inhibit the formation of insoluble tau aggregates in vitro. For example, DC8E8 binding to normal tau is capable of preventing one or more of the conformational/shape changes discussed above for the regions encompassing the therapeutic epitopes.

In addition, binding of DC8E8 to normal tau at one or more of these regions or therapeutic epitopes impedes certain other conformational changes elsewhere in the molecule that are needed for the production of pathological tau. Without being bound by any specific mechanism, it is contemplated that one or more of these epitopes/regions within tau that are recognized by DC8E8, functions within tau as a promoter of tau-tau aggregation. For example, the structure/shape/conformation of one or more of these epitopes influences the structure of adjacent regions, such that fixing its shape within the tau molecule by binding of DC8E8 to it interferes with the adjacent region's (e.g., 274-281) ability or tendency to form beta-sheets, where beta-sheet formation is needed for tau-tau aggregation. Thus, it is contemplated that binding of DC8E8 to one of these four regions within normal tau is capable of preventing one of the earliest pathological changes in tau identified to date: a change that is needed to promote, or that itself promotes or allows for the formation of beta-sheets within tau. Moreover, it is also contemplated that binding of DC8E8 to one of these four regions within misdisordered/pathological tau, i.e., after one or more of the four has already changed to a pathological conformation, is still capable of inhibiting pathological tau-tau aggregation at least because it still inhibits beta-sheet formation, blocks tau-tau physical interaction, or both.

Thus, using DC8E8 as a tool to identify novel targets or functional regions within tau, four specific DC8E8 binding sites on tau were assigned a role in Alzheimer's disease. This was done through the recognition that one or more of these tau sites are involved in the formation of pathological tau monomers and multimers, at least because binding of DC8E8 to one or more of them is capable of inhibiting those processes. Moreover, antibodies (e.g., DC8E8) that bind to one or more of these therapeutic epitopes, are capable of promoting the clearance of pathological tau from the extracellular environment, at least because they are capable of mediating the uptake and degradation of pathological tau by microglia, in vitro; a decrease in extracellular and intracellular tau in the brain, in vivo; or both. In other words, these antibodies have the capacity to help reduce the damage that such pathological forms of tau cause to the brain.

Accordingly, described herein are antibodies that specifically bind to one or more therapeutic epitopes on tau, wherein each of the therapeutic epitopes is separately located within amino acid residues 267-KHQPGGG-273 (SEQ ID NO: 98) (epitope #1, within $1^{st}$ repeat domain of tau protein), 298-KHVPGGG-304 (SEQ ID NO: 99) (epitope #2, within $2^{nd}$ repeat domain of tau protein), 329-HHKPGGG-335 (SEQ ID NO: 100) (epitope #3, within $3^{rd}$ repeat domain of tau protein), and 361-THVPGGG-367 (SEQ ID NO: 101) (epitope #4, within $4^{th}$ repeat domain of tau protein). In some embodiments, the therapeutic epitopes #1 through 4 are comprised within 268-HQPGGG-273 (SEQ ID NO: 223) (within $1^{st}$ repeat domain of tau protein), 299-HVPGGG-304 (SEQ ID NO: 154) (within $2^{nd}$ repeat domain of tau protein), 330-HKPGGG-335 (SEQ ID NO: 224) (within $3^{rd}$ repeat domain of tau protein), and 362-HVPGGG-367 (SEQ ID NO: 154) (within $4^{th}$ repeat domain of tau protein). The antibodies can be monoclonal or polyclonal. Also included are antigen-binding antibody portions, antibody fragments, antibody variants, engineered proteins, and polymer scaffolds. These include any protein or peptide-containing molecule that comprises at least a portion of an immunoglobulin molecule, such as, but not limited to, at least one complementarity determining region (CDR) of a heavy or light chain or a ligand binding portion thereof, a heavy chain or light chain variable region, a heavy chain or light chain constant region, a framework region, or any portion thereof.

As a non-limiting example, a suitable antibody, antibody portion, fragment, or variant, as provided by the present invention, can bind to at least one of the described therapeutic epitopes. The term "antibody" also includes antibody digestion fragments, specified antibody portions and variants thereof, including antibody mimetics, or portions of antibodies that mimic the structure and/or function of an antibody or specified fragment or portion thereof, including single chain antibodies and fragments thereof. Functional fragments include antigen-binding fragments that bind to one or more therapeutic epitopes. For example, antibody fragments capable of binding to a therapeutic epitope, include, but are not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and re-aggregation), Fv or scFv (e.g., by molecular biology techniques) fragments, are provided by the present invention. See also, William E. Paul (ed.) Fundamental Immunology, $6^{th}$ Edition, Lippincott Williams & Wilkins, NY, N.Y. (2008), incorporated herein in its entirety. Certain fragments can be produced by enzymatic cleavage, synthetic or recombinant techniques, as routinely known in the art, or as provided herein. Antibodies can also be produced in a variety of truncated forms using antibody genes in which one or more stop codons have been introduced upstream of the natural stop site. For example, a combination gene encoding an F(ab')$_2$ heavy chain portion can be designed to include DNA sequences encoding the CH1 domain and/or hinge region of the heavy chain. The various portions of antibodies can be joined together chemically by conventional techniques, or can be prepared as a contiguous protein using routine genetic engineering techniques.

The basic antibody structural unit is known to comprise a tetramer. Each tetramer is composed of two identical pairs of polypeptide chains, each pair having one "light" (about 25-kDa) and one "heavy" chain (about 50-70 kDa). The amino-terminal portion of each chain includes a variable region of about 100 to 110 or more amino acids primarily responsible for antigen recognition. The carboxyl-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of IMGT. Alternative definitions are also known to one of ordinary skill in the art. See, e.g. Kabat Sequences of Proteins of Immunological Interest (National Institutes of Health; Bethesda; Md. (1987 and 1991)), or Chothia & Lesk J. Mol. Biol. 196:901-917 (1987); Chothia et al. Nature 342:878-883 (1989).

In some embodiments, a subject antibody comprises a light chain comprising an amino acid sequence having at least about 80%, at least about 85%, at least about 90%, at least about 95%, at least about 98%, or at least about 99% amino acid sequence identity to any one of SEQ ID NOs: 141, 143, 152, and 153. In some embodiments, a subject antibody comprises a light chain comprising an amino acid sequence that differs from any one of SEQ ID NOs:141, 143, 152, and 153 by only one, two, three, four, five, six, seven, eight, nine, or ten amino acids. Those of ordinary skill in the art can determine which amino acids in a light chain variable region can be altered. For example, by comparing the amino acid sequences of light chain variable regions of antibodies with the same specificity, those skilled in the art can determine which amino acids can be altered without altering the specificity. See the EXAMPLES for a comparison of CDR amino acid sequences of the exemplary DC8E8 antibody light chain. Furthermore, whether the specificity is altered can be determined using an antigen binding assay. In some embodiments, a subject antibody comprises a light chain comprising an amino acid sequence as set forth in any one of SEQ ID NOs:141, 143, 152, and 153.

In some embodiments, a subject antibody comprises a heavy chain comprising an amino acid sequence having at least about 80%, at least about 85%, at least about 90%, at least about 95%, at least about 98%, or at least about 99% amino acid sequence identity to any one of SEQ ID NOs: 138, 140, 147, and 148. In some embodiments, a subject antibody comprises a heavy chain comprising an amino acid sequence that differs from any one of SEQ ID NOs:138; 140, 147, and 148 by only one, two, three, four, five, six, seven, eight, nine; or ten amino acids. Those of ordinary skill in the art can determine which amino acids in a heavy chain variable region can be altered. For example; by comparing the amino acid sequences of heavy chain variable regions of antibodies with the same specificity, those skilled in the art can determine which amino acids can be altered without altering the specificity. See, e.g., FIGS. 3E and 25B for a comparison of CDR amino acid sequences of exemplary DC8E8 antibody heavy chain. Furthermore, whether the specificity is altered can be determined using an antigen binding assay. In some embodiments, a subject antibody comprises a heavy chain comprising an amino acid sequence as set forth in any one of SEQ ID NOs:138, 140, 147, and 148.

In some embodiments, a subject antibody comprises a light chain comprising an amino acid sequence as set forth in SEQ ID NO:141 and a heavy chain comprising an amino acid sequence as set forth in SEQ ID NO:138. In some embodiments, a subject antibody comprises a light chain comprising an amino acid sequence as set forth in SEQ ID NO:141 and a heavy chain comprising an amino acid sequence as set forth in SEQ ID NO:140. In some embodiments, a subject antibody comprises a light chain comprising an amino acid sequence as set forth in SEQ ID NO:141 and a heavy chain comprising an amino acid sequence as set forth in SEQ ID NO:147. In some embodiments, a subject antibody comprises a light chain comprising an amino acid sequence as set forth in SEQ ID NO:141 and a heavy chain comprising an amino acid sequence as set forth in SEQ ID NO:148. In some embodiments, a subject antibody comprises a light chain comprising an amino acid sequence as set forth in SEQ ID NO:143 and a heavy chain comprising an amino acid sequence as set forth in SEQ ID NO:138. In some embodiments, a subject antibody comprises a light chain comprising an amino acid sequence as set forth in SEQ ID NO:143 and a heavy chain comprising an amino acid sequence as set forth in SEQ ID NO:140. In some embodiments, a subject antibody comprises a light chain comprising an amino acid sequence as set forth in SEQ ID NO:143 and a heavy chain comprising an amino acid sequence as set forth in SEQ ID NO:147. In some embodiments, a subject antibody comprises a light chain comprising an amino acid sequence as set forth in SEQ ID NO:143 and a heavy chain comprising an amino acid sequence as set forth in SEQ ID NO:148. In some embodiments, a subject antibody comprises a light chain comprising an amino acid sequence as set forth in SEQ ID NO:152 and a heavy chain comprising an amino acid sequence as set forth in SEQ ID NO:138, In some embodiments, a subject antibody comprises a light chain comprising an amino acid sequence as set forth in SEQ ID NO:152 and a heavy chain comprising an amino acid sequence as set forth in SEQ ID NO:140. In some embodiments, a subject antibody comprises a light chain comprising an amino acid sequence as set forth in SEQ ID NO:152 and a heavy chain comprising an amino acid sequence as set forth in SEQ ID NO:147. In some embodiments, a subject antibody comprises a light chain comprising an amino acid sequence as set forth in SEQ ID NO:152 and a heavy chain comprising an amino acid sequence as set forth in SEQ ID NO:148. In some embodiments, a subject antibody comprises a light chain comprising an amino acid sequence as set forth in SEQ ID NO:153 and a heavy chain comprising an amino acid sequence as set forth in SEQ ID NO:138. In some embodiments, a subject antibody comprises a light chain comprising an amino acid sequence as set forth in SEQ ID NO:153 and a heavy chain comprising an amino acid sequence as set forth in SEQ ID NO:140. In some embodiments, a subject antibody comprises a light chain comprising an amino acid sequence as set forth in SEQ ID NO:153 and a heavy chain comprising an amino acid sequence as set forth in SEQ ID NO:147, In some embodiments, a subject antibody comprises a light chain comprising an amino acid sequence as set forth in SEQ ID NO:153 and a heavy chain comprising an amino acid sequence as set forth in SEQ ID NO:148.

In some embodiments, the subject antibody comprises a light chain variable region comprising at least one, at least two, or three CDRs chosen from SEQ ID NOs. 117-119. In some embodiments, the subject antibody comprises a heavy chain variable region comprising at least one, at least two, or three CDRs chosen from SEQ ID NOs. 120-122. Also provided are embodiments in which any one of these six CDRs is altered as described in EXAMPLE 14. In some embodiments, at least one of the altered CDRs in the light chain is chosen from SEQ ID NO: 247 for CDR1, SEQ ID NO: 253 for CDR2, and any one of SEQ ID NOs: 255, 257, 258, 259, and 260 for CDR3. In some embodiments, at least one of the altered CDRs in the heavy chain is chosen from SEQ ID NO: 261, or SEQ ID NO: 262 for CDR1, SEQ ID NO: 264, or SEQ ID NO: 265 for CDR2, and SEQ ID NO: 266, SEQ ID NO: 267, or SEQ ID NO: 269 for CDR3.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Song-sivilai & Lachmann Olin, Exp. Immunol. 79: 315-321 (1990), Kostelny et. J. Immunol. 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

The invention does not relate to antibodies in natural form, i.e., they are not taken from their natural environment but are isolated and obtained by purification from natural sources, or obtained by genetic recombination or chemical synthesis, and thus they can carry unnatural amino acids. Thus, as used herein, the twenty conventional amino acids and their abbreviations follow conventional usage, See Immunology-A Synthesis (2nd Edition, E. S. Golub and D. R. Gren, Eds., Sinauer Associates, Sunderland, Mass. (1991)), which is incorporated herein by reference. Stereoisomers (e.g., D-amino acids, Nle, Nva, Cha, Orn, Hie, Chg, Hch, or Har) of the twenty conventional amino acids, unnatural amino acids such as .alpha.-, .alpha.-disubstituted amino acids; N-alkyl amino acids, lactic acid, and other unconventional amino acids can also be suitable components for polypeptides of the present invention. Examples of unconventional amino acids include (i.e., are not limited to): 4-hydroxyproline, gamma.-carboxyglutamate, epsilon.-N,N, N-trimethyllysine, .epsilon.-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention Similarly; the present disclosure does not relate to nucleotide sequences in their natural chromosomal environment, i.e., in a natural state. The sequences of the present invention have been isolated and purified, i.e., they were sampled directly or indirectly, for example by a copy, their environment having been at least partially modified. Isolated nucleic acids obtained by recombinant genetics; by means, for example, of host cells, or obtained by chemical synthesis are also provided In relation to this disclosure, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math, 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, for example between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbial., 1999, Lett. 174:247-250) available on the site http://www.ncbi.nlm.nih.gov/gorf/bl2.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, for example 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated. As a non-limiting example, the table below summarizes the possible substitutions likely to be carried out without resulting in a significant modification of the biological activity of the corresponding modified antibody; inverse substitutions are naturally possible under the same conditions.

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

The invention provides an antibody produced by the mouse hybridoma cell line deposited with the American Type Culture Collection, (ATCC, 10801 University Blvd, Manassas, Va., USA) on Jul. 13, 2011, with the ATCC Patent Deposit Designation PTA-11994 (issued Jul. 29, 2011), as described in Examples 1-2. Other suitable antibodies can be produced by a cell line, a mixed cell line, an immortalized cell or clonal population of immortalized cells, as known in the art. See, e.g., Ausubel et al. (Ed.), Current Protocols in Molecular Biology, (John Wiley & Sons, Inc., New York, N.Y. (1987-2001)); Sambrook et al., Molecular Cloning; A Laboratory Manual, 2nd Edition, (Cold Spring Harbor, N.Y. (1989)) and Sambrook et at, Molecular Cloning—A Laboratory Manual (3rd Ed.), Vol. 1-3, Cold Spring Harbor Laboratory, Cold Spring Harbor, N.Y., 2000 (collectively, "Sambrook"); Harlow and Lane, Antibodies, A Laboratory Manual, (Cold Spring Harbor, N.Y. (1989)); Colligan, et al. (Eds.), Current Protocols in Immunology, (John Wiley & Sons, Inc., N.Y. (1994-2001)); Colligan et al., Current Protocols in Protein Science, (John Wiley & Sons, NY, N.Y., (1997-2001)), each entirely incorporated herein by reference.

In one approach for producing the antibodies provided by the invention, a hybridoma is produced by fusing a suitable immortal cell line (e.g., a myeloma cell line) with one of a variety of antibody-producing cells. Suitable immortal cell lines include, but not limited to, Sp2/0, Sp2/0-AG14, P3/NS1/Ag4-1, NSO, P3X63Ag8.653, MCP-11, S-194, heteromyelomas, fusion products thereof, or any cell or fusion cell derived therefrom, or any other suitable cell line as known in the art, and/or commercially available for this purpose (e.g., ATCC). Suitable antibody producing cells include, but are not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid; as recombinant or endogenous, viral, bacterial; algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded; hybridized, and the like or any combination of the same. See, e.g., Ausubel, supra, and Colligan, Immunology, supra, Chapter 2, entirely incorporated herein by reference.

Other approaches for producing the antibodies of the various embodiments described above include, but are not limited to, methods that select recombinant antibodies from peptide or protein libraries, including those commercially available from Cambridge antibody Technologies, Cambridgeshire, UK; MorphoSys, Martinsreid/Planegg, Del.; Biovation, Aberdeen, Scotland, UK; BioInvent, Lund; Sweden; Dyax Corp., Enzon, Affymax/Biosite; Xoma, Berkeley, Calif.; Ixsys; Applied Molecular Evolution; and the like; methods that rely upon immunization of transgenic animals that are capable of producing selectable sets of human antibodies (generally, these mice comprise at least one transgene comprising DNA from at least one human immunoglobulin locus that is functionally rearranged, or which can undergo functional rearrangement; the endogenous immunoglobulin loci in such mice can be disrupted or deleted to eliminate the capacity of the animal to produce antibodies encoded by endogenous genes); selection methods including ribosome display, single cell antibody producing technologies (e.g., selected lymphocyte antibody method ("SLAM")), and B-cell selection; subtractive immunization using cyclophosamide treatment; as well as any other methods routine in the art, including, but not limited to, those described in US Published Application No. 2005/0142609, which methods are entirely incorporated herein by reference).

In some embodiments, the antibodies are optimized full-length antibodies, chimeric or humanized, which can be produced by any one or a combination of known techniques, as listed and exemplified in, for example, Chapters 3, 4, and 5, of "Business Insights, Preclinical Development of Monoclonal Antibodies and Related Biologicals-Emerging technologies and new therapeutic candidates, by James Shirvill, 2010," the entire contents of which is incorporated by reference, such as: CDR grafting, such as UBC's SLAM technology, PDL's SMART technology, Arana Therapeutics plc's Superhumanization, Framework patching, techniques for making composit human antibodies, BioAtla LLC's ATLAb platform, humaneering, Mutational Lineage Guided (MLG) strategies, deimmunisation strategies, humanation strategies, human engineering (e.g., XOMA's HE technology), FcX, Biolex Therapeutics Inc (Pittsboro, N.C., US) LEX system, Potelligent approaches (e.g, BioWa), Complegent technology, BestMAb, ImmunoBody, EB66, Synageva Expression Platforms, Xencor Inc, XmAb, Sugar Engineered Antibodies (e.g, Seattle Genetics Inc (Bothell, Wash., US)). "Wox" (tryptophan oxidized) antibodies (e.g., InNexus Biotechnology Inc (Vancouver, BC, Canada)); and the like. In some embodiments, the antibodies are fully human monoclonal antibodies, and can be produced by one or a combination of technology platforms, as listed and exemplified in, for example, Chapter 4 of "Business Insights, Preclinical Development of Monoclonal Antibodies and Related Biologicals-Emerging technologies and new therapeutic candidates, by James Shirvill, 2010," and including, but not limited to: phage display (e.g., PDL, Dyax Corp; Cambridge, Mass., US); Molecule Based Antibody Screening (MBAS) (e.g., Affitech A/S, described in, e.g., EP0547201 and U.S. Pat. No. 6,730,483); cell based antibody selection (CBAS) platforms; Human Combinatorial Antibody Libraries (HuCAL; e.g., Morph® Sys AG); MAbstract platforms (e.g., Crucell NV), including those with the PER.C6 cell line; Adimab platforms; XenoMouse; UltiMAb platforms; SEBVI platforms; VelocImmune platforms, Open Monoclonal Technology platforms, Xenerex platforms; Cloning the Human Response platforms (e.g., IQ Therapeutics) and "Instant Immunity antibodies;" Viventia platforms (e.g., Fusogenics, UnLock, ImmunoMine); "Natural Human Antibodies" platforms (e.g., OncoMab, Patrys, Acceptys); MabIgX (e.g., Kenta Biotech); Reverse Translational Medicine platforms (e.g., Neuimmune Therapeutics); I-STAR (e.g., Theraclone Sciences); CellSpot (e.g., Trellis Bioscience); iBioLaunch (e.g., iBio Inc); and the like.

In some embodiments, the antibodies are modified by linking them to non-antibody agents, using one or more of the technology platforms and methods as described in Chapter 5 of "Business Insights, Preclinical Development of Monoclonal Antibodies and Related Biologicals-Emerging technologies and new therapeutic candidates, by James Shirvill, 2010," including: antibody drug conjugate (e.g., ADC, Seattle Genetics); targeted antibody payload (TAP; Immunogen Inc); Probodies (e.g., CytomX Therapeutics); antibody cloaking (e.g., BioTransformations); targeted photodynamic therapy (e.g., PhotoBiotics; AlbudAb (e.g., GSK); hyFc (e.g., Genexine); Ligand traps (e.g., BioLogix); CovX-Body (e.g., CovX); Dynamic Cross-Linking (e.g., InNexus Biotechnology); LEC Technology (e.g., Pivotal BioSciences, Morphotek); and the like.

In some embodiments, the antibody or its encoding cDNAs can be further modified. Thus, in a further embodiment, the invention provides methods of producing the antibodies of the various embodiments, wherein the methods comprise any one of the step(s) of producing a chimeric antibody, humanized antibody, or an analog of any one of those. In some embodiments, the production of chimeric antibodies is as described in international application WO89/09622. Methods for the production of humanized antibodies are described in, e.g., U.S. Pat. No. 6,548,640 or Canadian Patent No. 1340879 (CDR grafting).

In addition, the antibody or its encoding cDNAs can be further modified. Thus, in a further embodiment, the invention provides methods comprising any one of the step(s) of producing a single-chain antibody, Fab-fragment, bi-specific antibody, fusion antibody, labeled antibody or an analog of any one of those. As discussed above, the antibody of the invention can exist in a variety of forms besides complete antibodies; including, for example, Fv, Fab and F(ab)2, as well as in single chains. See e.g. international application WO88/09344. Furthermore, diabodies and V-like domain binding molecules are well-known to the person skilled in the art; see, e.g. U.S. Pat. No. 7,166,697.

In some embodiments, the antibodies (e.g., DC8E8) are modified or serve as the basis for making binding molecules with one or more of the antigen-binding properties described for the DC8E8 antibody. These binding proteins can be made by one or more of the techniques listed and exemplified in, for example, Chapter 6 of "Business Insights, Preclinical Development of Monoclonal Antibodies and Related Biologicals-Emerging technologies and new therapeutic candidates, by James Shirvill, 2010," including: Fab, TetraMABs (e.g., Galileo Oncologics); scFv; Immuna (e.g., ESBA Tech AG); [scFv]2, including binding molecules that bind any two of the four therapeutic epitopes of DC8E8; BITE (Affitech, Micromet AG); Avibodies (e.g., Avipep Pty); TandAb (e.g., Affimed Therapeutics); Flexibody (e.g., Affimed); V-NAR (e.g., AdAlta); Nanobody (Ablynx NV); Domain Antibodies (e.g, Diversys Ltd. GSK, U.S. Pat. No. 6,248,516 and EP0368684); Heteropolymer (e.g., Elusys Therapeutics Inc.); Unibody (e.g., GenMab A/S); Domain Exchanged Antibodies (e.g., Calmune Corporation, Science. 2003 Jun. 27;300(5628):2065-71); Small Modular ImmunoPharmaceuticals (SMTP) and SCORPION molecules (e.g., Trubion Pharmaceuticals); Dual Variable Domain Immunoglobulin, DVD-Ig (Abbott Laboratories); and the like.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. See, e.g., the EXAMPLES provided further below. Methods for introducing such modifications in the DNA sequence underlying the amino acid sequence of an immunoglobulin chain are known to the person skilled in the art. See, e.g., Sambrook (supra) and Ausubel (Supra). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment or removal of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus. See, e.g., international application WO00/30680 for corresponding technical details, incorporated herein by reference in its entirety.

In one embodiment, the invention relates to a method for the production of an antibody or a binding fragment or immunoglobulin chain(s) thereof, the method comprising
(a) culturing a cell as described above; and
(b) isolating said antibody or binding fragment or immunoglobulin chain(s) thereof from the culture.
In some embodiments, the isolation comprises contacting the antibody-containing sample with one of the peptides provided by the invention, to which the antibody binds to.

The transformed hosts can be grown in fermenters and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) can then be isolated from the growth medium, cellular lysates, or cellular membrane fractions. The isolation and purification of the, e.g., recombinantly expressed antibodies or immunoglobulin chains provided by the invention can be done by any conventional means such as, for example preparative chromatographic separations and immunological separations, like those involving the use of monoclonal or polyclonal antibodies directed against the constant region of the antibody of the invention.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies can then be used therapeutically (including extracorporally) or in developing and performing assay procedures.

The invention also provides antibodies coupled to other moieties for purposes such as drug targeting and imaging applications. Such coupling can be conducted chemically after expression of the antibody to site of attachment or the coupling product can be engineered into the antibody of the invention at the DNA level. The DNAs are then expressed in a suitable host system, and the expressed proteins are collected and renatured, if necessary.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

The invention provides also antibody-producing cell lines and recombinant cells, as a source of the antibodies provided by the present invention. The present invention further relates to diagnostic assays and kits that comprise the antibodies provided by the invention or an equivalent binding molecule and to therapeutic methods based thereon.

The invention also provides methods for producing antibodies that are capable of competing with DC8E8 and are also capable of inhibiting pathological tau-tau interactions. Those antibodies can be screened by their ability to sufficiently compete with DC8E8 for binding to tau and binding to one, two, three, or all four of the "therapeutic epitopes" identified herein.

The present invention also relates to polynucleotides encoding one or more of the antibody-based agents provided by the invention. In certain cases, the nucleotide for example encodes at least the binding domain or variable region of an immunoglobulin chain of the antibodies described above. Typically, said variable region encoded by the polynucleotide comprises at least one complementarity determining region (CDR) of the VH and/or VL of the variable region of the said antibody. The person skilled in the art knows that each variable domain (the heavy chain VH and light chain VL) of an antibody comprises three hypervariable regions, sometimes called complementarity determining regions or "CDRs" flanked by four relatively conserved framework regions or "FRs" and refer to the amino acid residues of an antibody which are responsible for antigen-binding. According to the Kabat numbering system, the hypervariable regions or CDRs of the human IgG subtype of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed Public Health Service, National Institutes of Health, Bethesda, Md. (1991) and/or those residues from a hypervariable loop, i.e. residues 26-32 (L1), 50-52 (L2) and 91-96 (L3) in the light chain variable domain and 26-32 (H1), 53-55 (H2) and 96-101 (H3) in the heavy chain variable domain as described by Chothia et al., J. Mol. Biol. 196 (1987), 901-917. In the IMGT unique numbering system, the conserved amino acids always have the same position, for instance cysteine 23 (1st-CYS), tryptophan 41 (CONSERVED-TRP), hydrophobic amino acid 89, cystein 104 (2nd-CYS), phenylalanine or tryptophan 118 (J-PHE or J-TRP). See, e.g., Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. The IMGT unique numbering is used in 2D graphical representations, designated as IMGT Colliers de Perles. See, e.g., Ruiz, M. and Lefranc, M.-P., Immunogenetics, 53, 857-883 (2002); Kaas, Q, and Lefranc, M.-P., Current Bioinformatics, 2, 21-30 (2007). It is also used for representing 3D structures. See, e.g., IMGT/3D structure-DB Kaas, Q., Ruiz, M. and Lefranc, M.-P., T cell receptor and MHC structural data. Nucl. Acids, Res., 32, D208-0210 (2004), Framework or FR residues are those variable domain residues other than and bracketing the hypervariable regions.

Accordingly, the invention also relates to an isolated nucleic acid characterized in that it is selected among the following nucleic acids (including any degenerate genetic code);

a) a nucleic acid, DNA or RNA, coding for an antibody according to the invention;
b) a nucleic acid complementary to a nucleic acid as defined in a);
c) a nucleic acid of at least 18 nucleotides capable of hybridizing under highly stringent conditions with at least one of the CDRs chosen from SEQ ID NOs, 117-122 and SEQ ID NOs. 247, 253, 255, 257-259, 122, 261, 262, 264, 265-267, and 269; and
d) a nucleic acid of at least 18 nucleotides capable of hybridizing under highly stringent conditions with at least the light chain of nucleic acid sequence SEQ ID 165 and/or the heavy chain of nucleic acid sequence SEQ ID No. 170, or a sequence with at least 80%, for example 85%, 90%, 95% and 98% identity after optimal alignment with sequences SEQ ID Nos. 165 and/or SEQ ID 170, for example with at least one of the CDRs therefrom according to the IMGT numbering.

Nucleic sequences exhibiting a percentage identity of at least 80%, for example 85%, 90%, 95% and 98%, after optimal alignment with a preferred sequence, means nucleic sequences exhibiting, with respect to the reference nucleic sequence, certain modifications such as, in particular, a deletion, a truncation, an extension, a chimeric fusion and/or a substitution, notably punctual. In some embodiments, these are sequences which code for the same amino acid sequences as the reference sequence, this being related to the degeneration of the genetic code, or complementarity sequences that are likely to hybridize specifically with the reference sequences, for example under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SOS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SOS, one 20-minute washing at 20° C. in 0.1×SSC+0.1% SDS. The last washing is carried out in 0.1×SSC+0.1% SOS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The affinity or avidity of an antibody for an antigen can be determined experimentally using any suitable method; see, for example, Pope M E, Soste M V, Eyford B A, Anderson N L, Pearson T W. (2009) J Immunol Methods. 341(1-2):86-96. and methods described herein. The measured affinity of a particular antibody-antigen interaction can vary if measured under different conditions, e.g., salt concentration, pH. Thus, measurements of affinity and other antigen-binding parameters, e.g., K sub 0, 1050, are for example made with standardized solutions of antibody and antigen, and a standardized buffer.

The invention also provides that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity can be enhanced by making amino acid substitutions within the CDRs or within the hypervariable loops (Chothia and Lesk, J. Mol. Biol. 196 (1987), 901-917) which partially overlap with the CDRs, as defined by Kabat. Thus, the present invention also relates to antibodies wherein one or more of the mentioned CDRs comprise one or more, for example not more than two amino acid substitutions. In some embodiments, the antibody of the invention comprises in one or both of its immunoglobulin chains two or all three CDRs of the variable regions as set forth in FIGS. 3B and 3E. In some embodiments, the antibody of the invention comprises in one or both of its immunoglobulin chains two or all three CDRs as set forth in FIG. 25B.

The polynucleotides or nucleic acids encoding the above described antibodies can be, e.g., DNA, cDNA, RNA or synthetically produced DNA or RNA or a recombinantly produced chimeric nucleic acid molecule comprising any of those polynucleotides either alone or in combination. In some embodiments, the polynucleotide is part of a vector. Such vectors can comprise further genes such as marker genes which allow for the selection of said vector in a suitable host cell and under suitable conditions.

In some embodiments, the polynucleotide is operatively linked to one or more expression control sequences, allowing expression in prokaryotic or eukaryotic cells. Expression of said polynucleotide comprises transcription of the polynucleotide into a translatable mRNA. Regulatory elements ensuring expression in eukaryotic cells, for example mammalian cells, are known to those skilled in the art. They usually comprise regulatory sequences ensuring initiation of transcription and optionally poly-A signals ensuring termination of transcription and stabilization of the transcript. Additional regulatory elements can include transcriptional as well as translational enhancers, and/or naturally associated or heterologous promoter regions.

In this respect, the person skilled in the art will appreciate that the polynucleotides encoding at least the variable domain of the light and/or heavy chain can encode the variable domains of both immunoglobulin chains or only one. Likewise, said polynucleotides can be under the control of the same promoter or can be separately controlled for expression. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells.

Beside elements that are responsible for the initiation of transcription, such regulatory elements can also comprise transcription termination signals, such as the SV40-poly-A site or the tk-poly-A site, downstream of the polynucleotide. Furthermore, depending on the expression system used, leader sequences capable of directing the polypeptide to a cellular compartment or secreting it into the medium can be added to the coding sequence of the polynucleotides and are known in the art. The leader sequence(s) is (are) assembled in appropriate phase with translation, initiation and termination sequences, and optionally, a leader sequence capable of directing secretion of translated protein, or a portion thereof, into the periplasmic space or extracellular medium. In some embodiments, the heterologous sequence can encode a fusion protein including a C- or N-terminal identification peptide imparting desired characteristics, e.g., stabilization or simplified purification of expressed recombinant product. In this context, suitable expression vectors are known in the art, and include, without limitation, the Okayama-Berg cDNA expression vector pcDV1 (Pharmacia), pCDM8, pRc/CMV, pcDNA1, pcDNA3 (Invitrogen), and pSPORT1 (GIBCO BRL).

In some embodiments, the expression control sequences can be eukaryotic promoter systems in vectors capable of transforming or transfecting eukaryotic host cells, but control sequences for prokaryotic hosts can also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms can follow. See, e.g., Beychok, Cells of Immunoglobulin Synthesis, Academic Press, N.Y., (1979).

Furthermore, the invention provides vectors, particularly plasmids, cosmids, viruses and bacteriophages used conventionally in genetic engineering that comprise a polynucleotide encoding a variable domain of an immunoglobulin chain of an antibody of the invention: optionally in combination with a polynucleotide of the invention that encodes the variable domain of the other immunoglobulin chain of an antibody of the invention. In some embodiments, said vector is an expression vector and/or a gene transfer or targeting vector. Expression vectors derived from viruses such as retroviruses, vaccinia virus, adeno-associated virus, herpes viruses, or bovine papilloma virus, can be used for delivery of the polynucleotides or vector of the invention into targeted cell population. Any methods that are known to those skilled in the art can be used to construct recombinant viral vectors. See, for example, the techniques described in Sambrook (supra) and Ausubel (supra). Alternatively, the polynucleotides and vectors provided by the invention can be reconstituted into liposomes for delivery to target cells. The vectors containing the polynucleotides provided by the invention (e.g., the heavy and/or light variable domain(s) of the immunoglobulin chains encoding sequences and expression control sequences) can be transferred into the host cell by known methods, which vary depending on the type of cellular host. For example, calcium chloride transfection is commonly utilized for prokaryotic cells, whereas calcium phosphate treatment or electroporation can be used for other cellular hosts.

The present invention furthermore relates to host cells transformed with a polynucleotide or vector provided by the invention. The host cell can be a prokaryotic or eukaryotic cell. The polynucleotide or vector that is present in the host cell can either be integrated into the genome of the host cell or it can be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. Depending upon the host employed in a recombinant production procedure, the antibodies or immunoglobulin chains encoded by the polynucleotide of the present invention can be glycosylated or can be non-glycosylated. Certain antibodies provided by the invention, or the corresponding immunoglobulin chains, can also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art. See, e.g., Sambrook. The genetic constructs and methods described therein can be utilized for expression of the antibodies provided by the invention, or their corresponding immunoglobulin chains, in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Manassas, Va., U.S.A., and other available version, incorporated herein by reference). Furthermore, transgenic animals, for example mammals, comprising cells of the invention can be used for the large scale production of the antibody of the invention.

Additionally, the present invention encompasses small peptides including those containing a binding molecule as described above, for example containing the CDR3 region of the variable region of any one of the mentioned antibodies, in particular CDR3 of the heavy chain since it has frequently been observed that, for certain antibodies, the heavy chain CDR3 (HCDR3) is the region having a greater degree of variability and a predominant participation in antigen-antibody interaction, Such peptides can be synthesized or produced by recombinant means to produce a binding agent useful according to the invention. Such methods are known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

The above described fusion proteins can further comprise a cleavable linker or cleavage site for proteinases, which can be called spacer moieties. These spacer moieties, in turn, can be either insoluble or soluble (Diener et al., Science 231 (1986); 148) and can be selected to enable drug release from the antibody at the target site. Examples of therapeutic agents which can be coupled to the antibodies of the present invention for immunotherapy are drugs, radioisotopes, lectins, and toxins. The drugs that can be conjugated to the antibodies and antigens of the present invention include compounds which are classically referred to as drugs such as mitomycin C, daunorubicin, and vinblastine. In using radioisotopically conjugated antibodies or antigens of the invention for, e.g., immunotherapy, certain isotopes can be more preferable than others depending on such factors as leukocyte distribution as well as isotype stability and emission, Depending on the autoimmune response, some emitters can be preferable to others. In general, alpha and beta particle emitting radioisotopes are preferred in immunotherapy. In certain preferred cases, the radioisotopes are short range, high energy alpha emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{166}$Re. In certain cases, the radiolabel is $^{64}$Cu. Other therapeutic agents which can be coupled to the antibody or antigen of the invention, as well as ex vivo and in vivo therapeutic protocols, are known, or can be ascertained, by those of ordinary skill in the art. Wherever appropriate, the person skilled in the art can use a polynucleotide of the invention encoding (and as the source for) any one of the above described antibodies, antigens, or the corresponding vectors, instead of the proteinaceous material itself.

The invention also relates to the use of a binding molecule or an antibody, as provided herein, for the preparation of a composition for use in vivo for suppressing formation of, or for otherwise reducing the levels of, misdisordered and/or misordered tau in a subject; or for extra-corporeal extraction of pathological tau compounds or their precursors from body fluids. These methods can be used for improving cognition or slowing or reversing cognitive decline associated with diseases. The antibody or binding molecules provided by the invention, or chemical derivatives thereof, can be administered directly to the blood or CSF and sequestered in a subsequent step by affinity capture from the blood or CSF, whereby misordered and misdisordered tau is sequestered together with the aforementioned binding molecule. Hence, the present invention also relates to a method of treating or preventing the onset or progression of Alzheimer's disease or related tauopathies in a subject comprising removing blood or CSF from the body of the subject, subjecting the blood and CSF and returning to the subject the blood and CSF, respectively, so obtained.

Molecules and particles with an antibody, peptide, or binding molecule/protein of the invention also have diagnostic utility. The invention provides antibodies that recognize and distinguish distinct forms of tau protein that are present at distinct stages of Alzheimer's disease. These antibodies are capable of detecting tau (and its various conformational changes) both in vitro and in vivo. The antibodies can distinguish between physiological and pathological tau in a variety of assays, including biochemical, immunoprecipitation, ELISA, Western blotting, and immunohistochemistry assays (e.g., fresh, fixed, frozen, paraffin-embedded), as well as in vivo imaging using, e.g., radiolabeled DC8E8 (including fragments of DC8E8 such as single chain DC8E8), which distinguishes physiological from pathological tau (see EXAMPLES). They are capable of doing so in both solid and fluid (e.g., blood, plasma, CSF, homogenates) animal (e.g., rodents, humans) samples and biopsies. Some of these detection assays are described in the EXAMPLES below. Other routine methods for detecting proteins are known to those of skill in the art, and thus can be routinely adapted to the antibodies, peptides, and tau-binding molecules, provided by the invention. The antibodies of the present invention can be labeled (e.g., fluorescent, radioactive, enzyme, nuclear magnetic, heavy metal) and used to detect specific targets in vivo or in vitro including immunochemistry-like assays in vitro (see, e.g., the EXAMPLES described below). Also, in vivo, they could be used in a manner similar to nuclear medicine imaging techniques to detect tissues, cells, or other material having misdisordered tau and deposits thereof. Targeting intracellular and extracellular misdisordered tau and neurofibrillary lesions with diagnostic imaging probes detectable by MRI or PET would provide a biological marker for a more definitive premortem diagnosis of AD, as well as means for monitoring the efficacy of therapies targeting tau protein. Thus, the invention provides for the use of the antibodies described herein for the preparation of a composition for, and in methods of, tau detection and/or targeting a diagnostic agent to pathological tau and neurofibrillary lesions of the brain for AD diagnosis. These compositions and methods can be used as part of a treatment protocol for AD and related tauopathies.

The invention provides antibodies suitable for use in immunoassays in which they can be utilized in liquid phase or bound to a solid phase carrier. Examples of immunoassays which can utilize the antibodies of the invention are competitive and non-competitive immunoassays in either a direct or indirect format, Examples of such immunoassays are the radioimmunoassay (RIA), the sandwich (immunometric assay), flow cytometry and the Western blot assay. The antibodies of the invention can be bound to one of many different carriers and used to isolate cells specifically bound thereto. Examples of known carriers include glass, polystyrene, polyvinyl chloride, polypropylene, polyethylene, polycarbonate, dextran, nylon, amyloses, natural and modified celluloses, polyacrylamides, agaroses, and magnetite. The carrier can be either soluble or insoluble for the purposes of the invention. There are many different labels and methods of labeling known to those of ordinary skill in the art.

Examples of the types of labels that can be used in the present invention include enzymes, radioisotopes and radionuclides, colloidal metals, fluorescent compounds, chemiluminescent compounds, biotinyl groups, predetermined polypeptide epitopes recognized by a secondary reporter (e.g., leucine zipper pair sequences, binding sites for secondary antibodies, metal binding domains, epitope tags), and chemi/electrochemi/bioluminescent compounds. The enzymes include peroxidase (e.g, HRP), luciferase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase. Alternatively, the label is biotin, digoxigenin, or 5-bromo-desoxyuridine, Fluorescent labels can be also combined with the antibodies and tau-binding proteins provided by the invention, including rhodamine, lanthanide phosphors, fluorescein and its derivatives, fluorochromes, rhodamine and its derivatives, green fluorescent protein (GFP), Red Fluorescent Protein (RFP) and others, dansyl, umbelliferone. In such conjugates, the antibodies/binding proteins of the invention can be prepared by methods known to a person skilled in the art. They can then be bound with enzymes or fluorescent labels directly; via a spacer group or a linkage group such as polyaldehyde, glutaraldehyde, ethylenediaminetetraacetic acid (EDTA) or diethylenetriaminepentaacetic acid (DPTA); or in the presence of other binding agents such as those routinely known in the art. Conjugates carrying fluorescein labels can be prepared by, for example, reaction with an isothiocyanate. In certain situations, the label or marker can also be therapeutic.

Others conjugates can include chemiluminescent labels such as luminol and dioxetane, bioluminescent labels such as luciferase and luciferin, or radioactive labels such as iodine$^{123}$, iodine$^{125}$, iodine$^{126}$, iodine$^{133,\ 131}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium[47], tellurium[121m], tellurium[122m], tellurium[125m], thulium[165], thulium[167], thulium[168], fluorine[18], yttrium[199] and iodine[131]. Existing methods known to a person skilled in the art for labeling antibodies with radioisotypes, either directly or via a chelating agent such as the EDTA or DTPA mentioned above, can be used for as diagnostic radioisotopes. See, e.g., labeling with [I[125]]Na by the chloramine-T technique [Hunter W. M. and Greenwood F. C. (1962) Nature 194:495]; labeling with technetium[99m] as described by Crockford et al. (U.S. Pat. No. 4,424,200); and bound via DTPA as described by Hnatowich (U.S. Pat. No. 4,479,930).

The invention also provides antibodies and other tau-binding molecules that can also be used in a method for the diagnosis of a disorder in an individual by obtaining a body fluid sample from the individual, which can be a blood sample, a lymph sample or any other body fluid sample and contacting the body fluid sample with an antibody of the instant invention under conditions enabling the formation of antibody-antigen complexes. The presence and/or amount of such complexes is then determined by methods known in the art; a level significantly higher than that formed in a control sample indicating the presence of disease in the tested individual. Thus, the present invention relates to an in vitro immunoassay comprising an antibody of the invention.

Furthermore, the present invention relates to in vivo imaging techniques employing any one of the tau-binding molecules of the present invention. For example, the medical imaging technique Positron emission tomography (PET) which produces a three-dimensional image of body parts is based on the detection of radiation from the emission of positrons. Typically, a biomolecule is radioactively labeled, e.g. it incorporates a radioactive tracer isotope, Upon administration of the labeled biomolecule to the subject; typically by injection into the blood circulation, the radioactively labeled biomolecule becomes concentrated in tissues of interest. The subject is then placed in the imaging scanner, which detects the emission of positrons. In one embodiment, a labeled, for example $^{64}$Cu labeled binding molecule such as an antibody is administered to a subject and detection of the binding molecule and thus misdisordered or misordered tau is performed by placing the subject in an imaging scanner and detecting the emission of positrons, thereby indicating a neurological disorder if emission is detected. The present invention thus encompasses a method for PET imagining, comprising the step of administering a $^{64}$Cu-labelled or equivalent labeled binding molecule of the present invention to a subject.

The present invention also provides an article of manufacture, such as pharmaceutical and diagnostic packs or kits comprising one or more containers filled with one or more of the above described ingredients, i.e. binding molecule, antibody or binding fragment thereof, polynucleotide, vector or cell, as provided by the invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition or kit of the present invention is suitable for the diagnosis, prevention, and treatment of Alzheimer's disease and related tauopathies.

The biological activity of the binding molecules, e.g., antibodies provided by the invention suggests that they have sufficient affinity to make them candidates for drug localization/drug delivery to cells or tissue. The targeting and binding to misdisordered tau deposits could be useful for the delivery of therapeutically or diagnostically active agents and gene therapy/gene delivery. Thus, the invention provides for the use of the antibodies described herein for the preparation of a composition for, and in methods of, detection and/or targeting a therapeutic or diagnostic agent to pathological tau and neurofibrillary lesions of the brain. These compositions and methods can be used as part of a treatment protocol for AD and related tauopathies.

Accordingly, the present invention relates to compositions comprising one or more of the aforementioned compounds, including binding molecules, antibodies, binding fragments; chemical derivatives thereof; polynucleotides, vectors, and cells. Certain compositions can further comprise one or more pharmaceutically acceptable carriers and one or more pharmaceutically acceptable diluents. Certain chemical derivatives comprise chemical moieties that are not normally a part of the base molecule or cell (e.g, of the antibody, binding molecule, polynucleotides, vectors, and cells) but are linked to them by routine methods. Such moieties can function to, for example, improve the solubility, half-life, visualization, detectability, and/or absorption, of the base molecule or cell. Alternatively, the moieties can attenuate undesirable side effects of the base molecule or decrease the toxicity of the base molecule.

The invention also provides pharmaceutical compositions comprising combinations of the antibodies provided herein with further agents, such as with interleukins or interferons, depending on the intended use of the pharmaceutical composition. For example, for use in the treatment of Alzheimer's disease the additional agent can be selected from the group consisting of small organic molecules, anti-tau antibodies, anti-beta-amlyoid antibodies, and combinations thereof. Other agents include, but are not limited to, acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid-passive and -active immunization reagents, anti-amyloid aggregation inhibitors, and secretase inhibitors. Hence, in an embodiment, the present invention relates to the use of the binding molecule, antibody or binding fragment of the present invention or of a binding molecule having substantially the same binding specificities of any one thereof, the polynucleotide, the vector or the cell of the present invention for the preparation of a pharmaceutical or diagnostic composition for treating or preventing the progression of Alzheimer's disease or related tauopathies; for the amelioration of symptoms associated with Alzheimer's disease or related tauopathies; for diagnosing or screening a subject for the presence of Alzheimer's disease or related tauopathies for determining a subject's risk for developing Alzheimer's disease or related tauopathies.

Peptides for Diagnostics, Active Immunization, and AD-Therapy

The present invention is based in part on the discovery that certain fragments of tau are active in inducing an immune response to pathological tau when injected into rat models of AD, and would be expected to do so in humans. These immunogenic tau fragments, which comprise one or more of the regions of tau identified above, through DC8E8, as promoters or at least participants in the development and progression of AD, were found capable of (i) promoting clearance of extracellular tau deposits within AD brains (rat models); (ii) inducing the production of protective antibodies against AD in an animal model; and/or (iii) slowing the progression of AD in the recipient subjects, as measured by one or more biochemical and neurological assays, in an animal model. They can also directly physically interfere with the ability of tau to form pathological tau-tau interactions along these regions The invention provides immunogens or immunogenic peptides derived from newly identified regions of the tau protein that are important for the formation of the core of PHFs and promote PHF assembly in vitro. Strategically targeting these regions ("therapeutic epitopes") can lead to the successful treatment of AD and related tauopathies. Immunogens can be screened for therapeutic efficacy in an animal model, such as the transgenic rat models described below.

In an embodiment of the present invention, tau peptides for example encompass one of the following amino acid sequences, within which is separately comprised each of the four therapeutic epitopes: a) SEQ ID NO:98 tau 267-KHQPGGG-273, b) SEQ ID NO:99 tau 298-KHVPGGG-304, c) SEQ ID NO:100 tau 329-HHKPGGG-335, and d) SEQ ID NO:101 tau 361-THVPGGG-367 (numbered according to the longest human tau isoform tau 2N4R, 441 residues-long, see SEQ ID NO:102). In another embodiment, tau peptides comprise at least one therapeutic epitope; wherein the therapeutic epitope is selected from SEQ ID NO:223 tau 268-HQPGGG-273, SEQ ID NO:154 tau 299-HVPGGG-304, SEQ ID NO:224 tau 330-HKPGGG-335, and SEQ ID NO:154 tau 362-HVPGGG-367.

The invention provides 30-amino acid long immunogens, such as any one of the SEQ ID NOs shown in the Table 1. Each one of the immunogens included in Table 1 is an isolated fragment of tau that contains one of the therapeutic epitopes, located within SEQ ID NO:98, SEQ ID NO:99, SEQ ID NO:100, and SEQ ID NO:101.

TABLE 1

Tau 30-mer peptides each carrying one therapeutic epitope

| SEQ ID NO | Immunogen | Sequences |
|---|---|---|
| SEQ ID NO: 1 | Tau251-280 | PDLKNVKSKIGS TENLKHQPGGGKVQIINK |
| SEQ ID NO: 2 | Tau256-285 | VKSKIGSTENLKHQP GGGKVQIINK KLDLS |
| SEQ ID NO: 3 | Tau259-288 | KIGSTENLKHQP GGGKVQIINK KLDLSNVQ |
| SEQ ID NO: 4 | Tau275-304 | VQIINKKLDL SNVQSKCGSK DNIKHVPGGG |
| SEQ ID NO: 9 | Tau244-273 | QTAPVPMPDLKNVKSKIGSTENLKHQPGGG |
| SEQ ID NO: 10 | Tau245-274 | TAPVPMPDLKNVKSKIGSTENLKHQPGGGK |
| SEQ ID NO: 11 | Tau246-275 | APVPMPDLKNVKSKIGSTENLKHQPGGGKV |
| SEQ ID NO: 12 | Tau247-276 | PVPMPDLKNVKSKIGSTENLKHQPGGGKVQ |
| SEQ ID NO: 13 | Tau248-277 | VPMPDLKNVKSKIGSTENLKHQPGGGKVQI |
| SEQ ID NO: 14 | Tau249-278 | PMPDLKNVKSKIGSTENLKHQPGGGKVQII |
| SEQ ID NO: 15 | Tau250-279 | MPDLKNVKSKIGSTENLKHQPGGGKVQIIN |
| SEQ ID NO: 16 | Tau252-281 | DLKNVKSKIGSTENLKHQPGGGKVQIINKK |
| SEQ ID NO: 17 | Tau253-282 | LKNVKSKIGSTENLKHQPGGGKVQIINKKL |
| SEQ ID NO: 18 | Tau254-283 | KNVKSKIGSTENLKHQPGGGKVQIINKKLD |
| SEQ ID NO: 19 | Tau255-284 | NVKSKIGSTENLKHQPGGGKVQIINKKLDL |
| SEQ ID NO: 20 | Tau257-286 | KSKIGSTENLKHQPGGGKVQIINKKLDLSN |
| SEQ ID NO: 21 | Tau258-287 | SKIGSTENLKHQPGGGKVQIINKKLDLSNV |
| SEQ ID NO: 22 | Tau260-289 | IGSTENLKHQPGGGKVQIINKKLDLSNVQS |
| SEQ ID NO: 23 | Tau261-290 | GSTENLKHQPGGGKVQIINKKLDLSNVQSK |
| SEQ ID NO: 24 | Tau262-291 | STENLKHQPGGGKVQIINKKLDLSNVQSKC |
| SEQ ID NO: 25 | Tau263-292 | TENLKHQPGGGKVQIINKKLDLSNVQSKCG |
| SEQ ID NO: 26 | Tau264-293 | ENLKHQPGGGKVQIINKKLDLSNVQSKCGS |
| SEQ ID NO: 27 | Tau265-294 | NLKHQPGGGKVQIINKKLDLSNVQSKCGSK |
| SEQ ID NO: 28 | Tau266-295 | LKHQPGGGKVQIINKKLDLSNVQSKCGSKD |
| SEQ ID NO: 29 | Tau267-296 | KHQPGGGKVQIINKKLDLSNVQSKCGSKDN |
| SEQ ID NO: 30 | Tau 276-305 | QIINKKLDLSNVQSKCGSKDNIKHVPGGGS |
| SEQ ID NO: 31 | Tau 277-306 | IINKKLDLSNVQSKCGSKDNIKHVPGGGSV |

TABLE 1-continued

Tau 30-mer peptides each carrying one therapeutic epitope

| SEQ ID NO | Immunogen | Sequences |
|---|---|---|
| SEQ ID NO: 32 | Tau 278-307 | INKKLDLSNVQSKCGSKDNIKHVPGGGSVQ |
| SEQ ID NO: 33 | Tau 279-308 | NKKLDLSNVQSKCGSKDNIKHVPGGGSVQI |
| SEQ ID NO: 34 | Tau 280-309 | KKLDLSNVQSKCGSKDNIKHVPGGGSVQIV |
| SEQ ID NO: 35 | Tau 281-310 | KLDLSNVQSKCGSKDNIKHVPGGGSVQIVY |
| SEQ ID NO: 36 | Tau 282-311 | LDLSNVQSKCGSKDNIKHVPGGGSVQIVYK |
| SEQ ID NO: 37 | Tau 283-312 | DLSNVQSKCGSKDNIKHVPGGGSVQIVYKP |
| SEQ ID NO: 38 | Tau 284-313 | LSNVQSKCGSKDNIKHVPGGGSVQIVYKPV |
| SEQ ID NO: 39 | Tau 285-314 | SNVQSKCGSKDNIKHVPGGGSVQIVYKPVD |
| SEQ ID NO: 40 | Tau 286-315 | NVQSKCGSKDNIKHVPGGGSVQIVYKPVDL |
| SEQ ID NO: 41 | Tau 287-316 | VQSKCGSKDNIKHVPGGGSVQIVYKPVDLS |
| SEQ ID NO: 42 | Tau 288-317 | QSKCGSKDNIKHVPGGGSVQIVYKPVDLSK |
| SEQ ID NO: 43 | Tau 289-318 | SKCGSKDNIKHVPGGGSVQIVYKPVDLSKV |
| SEQ ID NO: 44 | Tau 290-319 | KCGSKDNIKHVPGGGSVQIVYKPVDLSKVT |
| SEQ ID NO: 45 | Tau 292-321 | GSKDNIKHVPGGGSVQIVYKPVDLSKVTSK |
| SEQ ID NO: 46 | Tau 293-322 | SKDNIKHVPGGGSVQIVYKPVDLSKVTSKC |
| SEQ ID NO: 47 | Tau 294-323 | KDNIKHVPGGGSVQIVYKPVDLSKVTSKCG |
| SEQ ID NO: 48 | Tau 295-324 | DNIKHVPGGGSVQIVYKPVDLSKVTSKCGS |
| SEQ ID NO: 49 | Tau 296-325 | NIKHVPGGGSVQIVYKPVDLSKVTSKCGSL |
| SEQ ID NO: 50 | Tau 297-326 | IKHVPGGGSVQIVYKPVDLSKVTSKCGSLG |
| SEQ ID NO: 51 | Tau 298-327 | KHVPGGGSVQIVYKPVDLSKVTSKCGSLGN |
| SEQ ID NO: 52 | Tau 307-336 | QIVYKPVDLSKVTSKCGSLGNIHHKPGGGQ |
| SEQ ID NO: 53 | Tau 308-337 | IVYKPVDLSKVTSKCGSLGNIHHKPGGGQV |
| SEQ ID NO: 54 | Tau 309-338 | VYKPVDLSKVTSKCGSLGNIHHKPGGGQVE |
| SEQ ID NO: 55 | Tau 310-339 | YKPVDLSKVTSKCGSLGNIHHKPGGGQVEV |
| SEQ ID NO: 56 | Tau 311-340 | KPVDLSKVTSKCGSLGNIHHKPGGGQVEVK |
| SEQ ID NO: 57 | Tau 312-341 | PVDLSKVTSKCGSLGNIHHKPGGGQVEVKS |
| SEQ ID NO: 58 | Tau 313-342 | VDLSKVTSKCGSLGNIHHKPGGGQVEVKSE |
| SEQ ID NO: 59 | Tau 314-343 | DLSKVTSKCGSLGNIHHKPGGGQVEVKSEK |
| SEQ ID NO: 60 | Tau 315-344 | LSKVTSKCGSLGNIHHKPGGGQVEVKSEKL |
| SEQ ID NO: 61 | Tau 316-345 | SKVTSKCGSLGNIHHKPGGGQVEVKSEKLD |
| SEQ ID NO: 62 | Tau 317-346 | KVTSKCGSLGNIHHKPGGGQVEVKSEKLDF |
| SEQ ID NO: 63 | Tau 318-347 | VTSKCGSLGNIHHKPGGGQVEVKSEKLDFK |
| SEQ ID NO: 64 | Tau 319-348 | TSKCGSLGNIHHKPGGGQVEVKSEKLDFKD |
| SEQ ID NO: 65 | Tau 320-349 | SKCGSLGNIHHKPGGGQVEVKSEKLDFKDR |
| SEQ ID NO: 66 | Tau 321-350 | KCGSLGNIHHKPGGGQVEVKSEKLDFKDRV |
| SEQ ID NO: 67 | Tau 322-351 | CGSLGNIHHKPGGGQVEVKSEKLDFKDRVQ |
| SEQ ID NO: 68 | Tau 323-352 | GSLGNIHHKPGGGQVEVKSEKLDFKDRVQS |

TABLE 1-continued

Tau 30-mer peptides each carrying one therapeutic epitope

| SEQ ID NO | Immunogen | Sequences |
|---|---|---|
| SEQ ID NO: 69 | Tau 324-353 | SLGNIHHKPGGGQVEVKSEKLDFKDRVQSK |
| SEQ ID NO: 70 | Tau 325-354 | LGNIHHKPGGGQVEVKSEKLDFKDRVQSKI |
| SEQ ID NO: 71 | Tau 326-355 | GNIHHKPGGGQVEVKSEKLDFKDRVQSKIG |
| SEQ ID NO: 72 | Tau 327-356 | NIHHKPGGGQVEVKSEKLDFKDRVQSKIGS |
| SEQ ID NO: 73 | Tau 328-357 | IHHKPGGGQVEVKSEKLDFKDRVQSKIGSL |
| SEQ ID NO: 74 | Tau 329-358 | HHKPGGGQVEVKSEKLDFKDRVQSKIGSLD |
| SEQ ID NO: 75 | Tau339-368 | VKSEKLDFKDRVQSKIGSLDNITHVPGGGN |
| SEQ ID NO: 76 | Tau340-369 | KSEKLDFKDRVQSKIGSLDNITHVPGGGNK |
| SEQ ID NO: 77 | Tau341-370 | SEKLDFKDRVQSKIGSLDNITHVPGGGNKK |
| SEQ ID NO: 78 | Tau342-371 | EKLDFKDRVQSKIGSLDNITHVPGGGNKKI |
| SEQ ID NO: 79 | Tau343-372 | KLDFKDRVQSKIGSLDNITHVPGGGNKKIE |
| SEQ ID NO: 80 | Tau344-373 | LDFKDRVQSKIGSLDNITHVPGGGNKKIET |
| SEQ ID NO: 81 | Tau345-374 | DFKDRVQSKIGSLDNITHVPGGGNKKIETH |
| SEQ ID NO: 82 | Tau346-375 | FKDRVQSKIGSLDNITHVPGGGNKKIETHK |
| SEQ ID NO: 83 | Tau 347-376 | KDRVQSKIGSLDNITHVPGGGNKKIETHKL |
| SEQ ID NO: 84 | Tau 348-377 | DRVQSKIGSLDNITHVPGGGNKKIETHKLT |
| SEQ ID NO: 85 | Tau 349-378 | RVQSKIGSLDNITHVPGGGNKKIETHKLTF |
| SEQ ID NO: 86 | Tau 350-379 | VQSKIGSLDNITHVPGGGNKKIETHKLTFR |
| SEQ ID NO: 87 | Tau351-380 | QSKIGSLDNITHVPGGGNKKIETHKLTFRE |
| SEQ ID NO: 110 | Tau352-381 | SKIGSLDNITHVPGGGNKKIETHKLTFREN |
| SEQ ID NO: 89 | Tau353-382 | KIGSLDNITHVPGGGNKKIETHKLTFRENA |
| SEQ ID NO: 90 | Tau354-383 | IGSLDNITHVPGGGNKKIETHKLTFRENAK |
| SEQ ID NO: 91 | Tau355-384 | GSLDNITHVPGGGNKKIETHKLTFRENAKA |
| SEQ ID NO: 92 | Tau356-385 | SLDNITHVPGGGNKKIETHKLTFRENAKAK |
| SEQ ID NO: 93 | Tau357-386 | LDNITHVPGGGNKKIETHKLTFRENAKAKT |
| SEQ ID NO: 94 | Tau358-387 | DNITHVPGGGNKKIETHKLTFRENAKAKTD |
| SEQ ID NO: 95 | Tau359-388 | NITHVPGGGNKKIETHKLTFRENAKAKTDH |
| SEQ ID NO: 96 | Tau360-389 | ITHVPGGGNKKIETHKLTFRENAKAKTDHG |
| SEQ ID NO: 97 | Tau361-390 | THVPGGGNKKIETHKLTFRENAKAKTDHGA |

In some embodiments, the immunogenic peptide is chosen from SEQ ID NO:1 tau 251-PDLKNVKSKIGSTENLKHQPGGGKVQIINK-280; SEQ ID NO:2 tau 256-VKSKIGSTENLKHQPGGGKVQIINKKLDLS-285; SEQ ID NO:3 tau 259-KIGSTENLKHQPGGGKVQIINKKLDLSNVQ-288; and SEQ ID NO:4 tau 275-VQIINKKLDLSNVQSKCGSKDNIKHVPGGG-304.

The invention also provides for shorter and longer immunogenic peptides for use in the present invention that contain one or more of the amino acid sequences SEQ ID NO:98 267-KHQPGGG-273, or amino acids SEQ ID NO:99 298-KHVPGGG-304, or amino acids SEQ ID NO:100 329-HHKPGGG-335, or amino acids SEQ ID NO:101 361-THVPGGG-367 can be derived from any one of the six isoforms of human tau protein. In one embodiment, an immunogenic peptide comprises at least one therapeutic epitope, wherein the therapeutic epitope is selected from SEQ ID NO:223 tau 268-HQPGGG-273, SEQ ID NO:154 tau 299-HVPGGG-304, SEQ ID NO:224 tau 330-HKPGGG-335, and SEQ ID NO:154 tau 362-HVPGGG-367. In one embodiment, the immunogenic peptide comprises a sequence selected from SEQ ID NO:109 Tau 314-DLSKVTSKCGSLGNIHHKPGGGQVEVKSE-342; SEQ ID NO:110 Tau 352-SKIGSLDNITHVPGGGNKKIETHKLTFREN-380; SEQ ID NO:111 Tau 325-LGNIHHKPGGGQ-336; SEQ ID NO:112 Tau 357-LDNITHVPGGGN-368;

SEQ ID NO:108 Tau 294-305 KDNIKHVPGGGS. In some embodiments, at least one immunogenic peptide is chosen from any one of SEQ ID NOs: 1-4, SEQ ID NOs: 9-101, and SEQ ID NOs: 108-112, NIKHVPGGGS (SEQ ID NO: 200), NIKHVPGGGS (SEQ ID NO: 201), IKHVPGGGS (SEQ ID NO: 202), KHVPGGGSV (SEQ ID NO: 203), HVPGGGSVQ (SEQ ID NO: 204), VPGGGSVQ (SEQ ID NO: 205), GWSIHSPGGGSC (SEQ ID NO: 250), and SVFQHLPGGGSC (SEQ ID NO: 251), ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKAVPGGGS (SEQ ID NO: 159), DNIKHAPGGGS (SEQ ID NO: 161), and DNIKHVPGGGS (SEQ ID NO: 171).

The amino acid sequences corresponding to the human tau isoforms are given in SEQ ID NOs:102-107

```
SEQ ID NO: 102 (2N4R):
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L

SEQ ID NO: 103 (1N4R):
MAEPRQEFEV MEDHAGTYGL GDRKDQGGYT MHQDQEGDTD

AGLKESPLQT PTEDGSEEPG SETSDAKSTP TAEAEEAGIG

DTPSLEDEAA GHVTQARMVS KSKDGTGSDD KKAKGADGKT

KIATPRGAAP PGQKGQANAT RIPAKTPPAP KTPPSSGEPP

KSGDRSGYSS PGSPGTPGSR SRTPSLPTPP TREPKKVAVV

RTPPKSPSSA KSRLQTAPVP MPDLKNVKSK IGSTENLKHQ

PGGGKVQIIN KKLDLSNVQS KCGSKDNIKH VPGGGSVQIV

YKPVDLSKVT SKCGSLGNIH HKPGGGQVEV KSEKLDFKDR

VQSKIGSLDN ITHVPGGGNK KIETHKLTFR ENAKAKTDHG

AEIVYKSPVV SGDTSPRHLS NVSSTGSIDM VDSPQLATLA

DEVSASLAKQ GL

SEQ ID NO: 104 (2N3R):
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIVYK

PVDLSKVTSK CGSLGNIHHK PGGGQVEVKS EKLDFKDRVQ

SKIGSLDNIT HVPGGGNKKI ETHKLTFREN AKAKTDHGAE

IVYKSPVVSG DTSPRHLSNV SSTGSIDMVD SPQLATLADE

VSASLAKQGL

SEQ ID NO: 105 (0N4R):
MAEPRQEFEV MEDHAGTYGL GDRKDQGGYT MHQDQEGDTD

AGLKAEEAGI GDTPSLEDEA AGHVTQARMV SKSKDGTGSD

DKKAKGADGK TKIATPRGAA PPGQKGQANA TRIPAKTPPA

PKTPPSSGEP PKSGDRSGYS SPGSPGTPGS RSRTPSLPTP

PTREPKKVAV VRTPPKSPSS AKSRLQTAPV PMPDLKNVKS

KIGSTENLKH QPGGGKVQII NKKLDLSNVQ SKCGSKDNIK

HVPGGGSVQI VYKPVDLSKV TSKCGSLGNI HHKPGGGQVE

VKSEKLDFKD RVQSKIGSLD NITHVPGGGN KKIETHKLTF

RENAKAKTDH GAEIVYKSPV VSGDTSPRHL SNVSSTGSID

MVDSPQLATL ADEVSASLAK QGL

SEQ ID NO: 106 (1N3R):
MAEPRQEFEV MEDHAGTYGL GDRKDQGGYT MHQDQEGDTD

AGLKESPLQT PTEDGSEEPG SETSDAKSTP TAEAEEAGIG

DTPSLEDEAA GHVTQARMVS KSKDGTGSDD KKAKGADGKT

KIATPRGAAP PGQKGQANAT RIPAKTPPAP KTPPSSGEPP

KSGDRSGYSS PGSPGTPGSR SRTPSLPTPP TREPKKVAVV

RTPPKSPSSA KSRLQTAPVP MPDLKNVKSK IGSTENLKHQ

PGGGKVQIVY KPVDLSKVTS KCGSLGNIHH KPGGGQVEVK

SEKLDFKDRV QSKIGSLDNI THVPGGGNKK IETHKLTFRE

NAKAKTDHGA EIVYKSPVVS GDTSPRHLSN VSSTGSIDMV

DSPQLATLAD EVSASLAKQG L

SEQ ID NO: 107 (0N3R):
MAEPRQEFEV MEDHAGTYGL GDRKDQGGYT MHQDQEGDTD

AGLKAEEAGI GDTPSLEDEA AGHVTQARMV SKSKDGTGSD

DKKAKGADGK TKIATPRGAA PPGQKGQANA TRIPAKTPPA

PKTPPSSGEP PKSGDRSGYS SPGSPGTPGS RSRTPSLPTP

PTREPKKVAV VRTPPKSPSS AKSRLQTAPV PMPDLKNVKS

KIGSTENLKH QPGGGKVQIV YKPVDLSKVT SKCGSLGNIH

HKPGGGQVEV KSEKLDFKDR VQSKIGSLDN ITHVPGGGNK

KIETHKLTFR ENAKAKTDHG AEIVYKSPVV SGDTSPRHLS

NVSSTGSIDM VDSPQLATLA DEVSASLAKQ GL
```

The use of peptide-based vaccines to elicit immune responses in diseases for which no conventional vaccines are yet available is attractive (Brown, 1994; BenYedidia, et at, 1997). However, in many cases small peptides are poor immunogens because they act as haptens that lack the necessary Th-cell epitopes and/or that are captured with low efficiency by antigen presenting cells (ARC). In one embodiment of the present invention, the immunogenic epitopes can be longer polypeptides that include a protective epitope of tau peptide, or analogue together with other amino acids.

Some of the agents described herein for inducing an immune response contain the appropriate epitope for inducing an immune response against pathological tau and tau deposits but are too small to be immunogenic. In this case, a peptide immunogen can be linked to a suitable carrier to help elicit an immune response. In certain embodiments, suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1α and β peptides, IL-2, γINF, IL-10, GM-CSF, and chemokines, such as M1P1 α and β and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the .epsilon.-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein.

For example, also provided are immunogens that include fusion proteins comprising a tau peptide carrying a protective B cell epitope linked to a promiscuous non-natural Pan DR Th-cell epitope that induces a B-cell response against the protective epitope. In a further alternative, the invention provides immunogens that can be designed as polymers (Jackson et a., 1997), multiple antigen peptide systems (MAP) (Tam and Recent, 1996), immunostimulating complexes (ISCOM) (Barr, I. G. and Mitchell, 1996) and possibly other branched amphoteric polypeptides (Wilkinson et al., 1998), or chimeric peptides produced by co-linearization of the epitopes (Marussig et al., 1997).

In certain embodiments, the therapeutic peptides can be applied alone or in combination, bound or not to a pharmaceutically acceptable carrier including KLH, tetanus toxoid, albumin binding protein, bovine serum albumin, dendrimer (MAP; Biol, Chem. 358; 581) as well as adjuvant substances, or their combinations, described e.g. in O'Hagan et al. (2003) (in particular the endogenous immunopotentiating compounds and dispensing systems described therein) and in Wilson-Welderer et al. (2009) (in particular those indicated in table 2 and 3 of said document) or mixtures thereof.

In certain embodiments, an immunogenic agent of the present invention can be bound or linked to a suitable carrier by chemical crosslinking to increase the immune response against pathological tau, including tau deposits. In certain embodiments, the bound or linked pharmaceutically acceptable carrier is keyhole limpet hemocyanin (KLH), tetanus toxoid, bovine serum albumin (BSA), immunoglobulin (Ig) molecule, thyroglobulin, or ovoglobulin. Other carriers for stimulation of immune response include cytokines (such as IL-1, IL-2, IL-10 IFNγ, GM-CSF) and chemokines (such as M1P1α and β).

Tau peptides or analogs can be synthesized by solid phase peptide synthesis or recombinant expression, or can be obtained from natural sources, Automatic peptide synthesizers are commercially available from numerous suppliers, such as Applied Biosystems, EZBiolab, or Antagene. Recombinant expression systems can include bacteria, such as *E. coli*, yeast, insect cells, or mammalian cells. Procedures for the manipulation of DNA and preparation DNA constructs for recombinant expression are described by Sambrook et al. (1989), methods for the production of recombinant proteins are described in detail in *Current Protocols in Protein Science* (Chapter 5 "Production of Recombinant Proteins", UNITS 5.1-5.24, DOI: 10.1002/0471140864, also available online at onlinelibrary.wiley.com/book/10.1002/0471140864/toc).

The immunogenic agents of the present invention can be expressed by a virus or bacteria as a vector or carrier. A nucleic acid encoding the immunogenic peptide is incorporated into a genome or episome of the virus or bacteria. Finally, the immunogenic peptides can be expressed as a secreted protein or as a fusion protein with an outer surface protein of a virus or can be displayed as a transmembrane protein of bacteria. Viruses or bacteria used in such methods are generally nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include *Salmonella* and *Shigella*. Alternatively, fusion of an immunogenic peptide to HBsAg of HBV is suitable.

A further aspect of the present invention relates to the therapeutic agent or immunogen, which can also be an analogue of the various peptides described in the various embodiments (e.g., SEQ ID No: 1-4; 9-97) or of fragments thereof.

The present invention is also based on the discovery of novel peptides, designated in this application as designer therapeutic epitopes. Despite having a primary sequence that is different from that of tau and tau fragments, this invention features designer therapeutic epitopes that are capable of having a shape (e.g.; an intrinsically disordered structure, a tertiary structure, a conformation) that mimics that of one or more of the tau "therapeutic epitopes" described above. By mimicking one or more of these regions, these designer therapeutic epitopes can be useful to generate antibodies against them, such as antibodies that compete with DC8E8. These peptides are able to compete with tau or tau fragments for binding to the DC8E8 antibody, disclosed above.

Also included are immunogenic designer therapeutic epitopes capable of inducing an immune response to pathological tau when injected into rat models of AD and which would be expected to do so in humans. In addition, also disclosed are mouse antibodies/antisera, produced in response to immunization with one or more designer therapeutic epitopes, and capable of (i) recognizing one or more epitopes that are or mimic those of DC8E8; (ii) discriminating between pathological tau and normal tau; and/or (iii) recognizing neurofibrillary lesions in human AD brain and/or in transgenic rat models of AD.

The invention also provides compositions for the prevention, treatment, and/or diagnosis of Alzheimer's disease, wherein the composition comprises (i) a means for treating Alzheimer's disease in a subject by inhibiting tau-tau aggregation; and (2) a pharmaceutically acceptable carrier and/or diluent. The invention also provides compositions for the prevention, treatment, and/or diagnosis of Alzheimer's disease, wherein the composition comprises (i) a means for treating Alzheimer's disease in a subject by binding to one or more "therapeutic epitopes" in pathological tau; and (2) a pharmaceutically acceptable carrier and/or diluents. The invention also provides compositions for the prevention, treatment, and/or diagnosis of Alzheimer's disease, wherein the composition comprises (i) a means for decreasing tau-tau aggregation by binding to one or more "therapeutic epitopes" in pathological tau; and (2) a pharmaceutically acceptable carrier and/or diluents.

Formulations

Agents of the invention can be administered as pharmaceutical formulations comprising a therapeutic agent (e.g., antibody or peptide, as described above) and one or more of other pharmaceutically acceptable components. See Remington's Pharmaceutical Science (15th ed., Mack Publishing Company; Easton, Pa., 1980). These formulations include, for example, powders, pastes, ointments, jellies, waxes, oils, lipids, lipid (cationic or anionic) containing vesicles (such as LIPOFECTIN), DNA conjugates; anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J. Pharm Sci. 89(8):967-78 (2000), Powell et al. "Compendium of excipients for parenteral formulations" FDA J Pharm Sci Technol. 52:238-311 (1998) and the citations therein for additional information related to formulations, excipients and carriers known to pharmaceutical chemists.

A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7.sup.th ed., Lippincott, Williams, & Wilkins; and Handbook of Pharmaceutical Excipients (2000) A. H, Kibbe et al., eds., 3 ed. Amer. Pharmaceutical Assoc.

The chosen formulation depends on the intended mode of administration and therapeutic application. The formulations can also include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The pharmaceutical composition or formulation can also include other carriers, adjuvants, or nontoxic, nontherapeutic, nonimmunogenic stabilizers and the like. However, some reagents suitable for administration to animals, such as Complete Freund's adjuvant are not typically included in compositions for human use.

Examples of suitable pharmaceutical carriers are known in the art and include phosphate buffered saline solutions, water, emulsions, such as oil/water emulsions, various types of wetting agents, sterile solutions etc. Compositions comprising such carriers can be formulated by known conventional methods. More carriers are described further below.

Adjuvants

Therapeutic agents, immunogens, of the invention can be administered in combination with adjuvants, i.e., substances that do not themselves cause adaptive immune responses, but amplify or modulate the response to an accompanying antigen. A variety of adjuvants can be used in combination with the therapeutic peptides and antibodies in the present invention, in order to elicit an immune response. Preferred adjuvant(s) augment the intrinsic response to an immunogen without causing conformational changes in the immunogen that would affect the qualitative form of the response.

In certain embodiments, the adjuvant is an aluminum salt (alum), such as aluminum hydroxide, aluminum phosphate, and aluminum sulphate (Hunter, 2002). Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Other adjuvants are oil-in-water emulsions and include (a) MF59 (WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer such as Model 110Y microfuidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi InunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), for example MPL+CWS (Detox™). In some embodiments, the adjuvant is a saponin, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

Alternatively, tau peptides and their immunogenic analogues can be coupled to an adjuvant. For example, a lipopeptide version of a tau peptide "A" can be prepared by coupling palmitic acid or other lipids directly to the N-terminus of "A" as described for hepatitis B antigen vaccination (Livingston, J. Immunol. 159, 1383-1392 (1997)). However, such coupling should not substantially change the conformation of the tau peptide "A" so as to affect the nature of the immune response thereto.

An adjuvant can be administered with an immunogen as a single composition, or can be administered before, concurrent with, or after administration of the immunogen. Immunogen and adjuvant can be packaged and supplied in the same vial or can be packaged in separate vials and mixed before use. Immunogen and adjuvant are typically packaged with a label, indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al., Advanced Drug Delivery Reviews 32:173-186 (1998), which is hereby incorporated by reference in its entirety) alone or optionally in combination with any of alum, QS21, and MPL and all combinations thereof are suitable for human administration.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

Combinations

The invention provides for compositions and methods of treatment that combine the antibodies and peptides described herein with other treatments for AD and related tauopathies. For example, currently, tau-related therapeutic strategies mainly focus on the drugs that inhibit tau kinases or activate phosphatases (Iqbal and Grundke-Iqbal, 2004, 2005, 2007; Noble et al. 2005), the drugs that stabilize microtubules (Zhang et al. 2005), the drugs that facilitate the proteolytic degradation of misfolded tau protein (Dickey et al. 2005; Dickey and Petrucelli, 2006; Dickey et al. 2006), compounds that prevent or reverse tau aggregation (Wischik et al. 1996; Pickhardt et al, 2005; Taniguchi et al. 2005; Necula et al. 2005; Larbig et al. 2007) or vaccine-mediated clearance of aggregated tau (Asuni et al. 2007), Therefore, the invention provides that multiple targeting (e.g., targeting both tau and beta-amyloid) can substantially increase treatment efficiency.

In the case of Alzheimer's disease and related tauopathies, in which pathological soluble tau and insoluble tau (tau deposits) occur in the brain, agents of the invention can also be administered in conjunction with other agents that increase passage of the agents of the invention across the blood-brain barrier.

Methods of Administration

Agents for inducing an immune response (passive or active), for reducing the level of tau, or for any of the methods of prevention, treatment, or diagnosis (in vivo) described herein, can be administered by parenteral, topical, intradermal, intravenous, oral, subcutaneous, intraperitoneal, intranasal or intramuscular means for prophylactic and/or therapeutic treatment. A typical route of administration is subcutaneous although others can be equally effective. Another typical route is intramuscular injection. This type of injection is most typically performed in the arm or leg muscles. Intravenous injections as well as intraperitoneal injections, intraarterial, intracranial, or intradermal injections are also effective in generating an immune response. In some methods, agents are injected directly into a particular tissue where deposits have accumulated.

Aerosol formulations such as nasal spray formulations include purified aqueous or other solutions of the active agent with preservative agents and isotonic agents. Such formulations are for example adjusted to a pH and isotonic state compatible with the nasal mucous membranes. Formulations for rectal or vaginal administration can be presented as a suppository with a suitable carrier.

For parenteral administration, therapeutic peptides of the present invention can be administered as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions, Agents of the invention can also be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water; alcoholic/aqueous solutions, emulsions or suspensions, including saline and buffered media. Parenteral vehicles include sodium chloride solution, Ringer's dextrose, dextrose and sodium chloride, lactated Ringers, or fixed oils. Intravenous vehicles include fluid and nutrient replenishers; electrolyte replenishers (such as those based on Ringers dextrose), and the like. Preservatives and other additives can also be present such as, for example, antimicrobials, anti-oxidants, chelating agents, and inert gases and the like.

Typically, compositions are prepared as injectables; either as liquid solutions or suspensions; solid forms suitable for solution in, or suspension in, liquid vehicles prior to injection can also be prepared. The preparation also can be emulsified or encapsulated in liposomes or micro particles such as polylactide; polyglycolide; or copolymer for enhanced adjuvant effect; as discussed above (see Langer; Science 249, 1527 (1990) and Hanes, Advanced Drug Delivery Reviews 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, for example 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules; sustained release formulations or powders and contain 10%-95% of active ingredient; for example 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin patch or using transferosomes (Paul et al., Eur. J. Immunol. 25, 3521-24 (1995); Cevc et al., Biochem. Biophys. Acta 1368, 201-15 (1998)). Subcutaneous administration of a subject antibody, peptide, or compound, is accomplished using standard methods and devices, e.g., needle and syringe, a subcutaneous injection port delivery system, and the like. Intramuscular administration is accomplished by standard means, e.g., needle and syringe, continuous delivery system, etc. In some embodiments, a subject antibody, peptide, and/or compound, is delivered by a continuous delivery system. The term "continuous delivery system" is used interchangeably herein with "controlled delivery system" and encompasses continuous (e.g., controlled) delivery medical devices (e.g., pumps) in combination with catheters, injection devices, and the like, a wide variety of which are known in the art. Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present methods of drug delivery can be accomplished using any of a variety of refillable, pump systems. Pumps provide consistent, controlled release over time.

The agents can also be administered by the now standard procedure of drilling a small hole in the skull to administer a drug. In a preferred aspect, the binding molecule, especially antibody or antibody-based drug of the present invention can cross the blood-brain barrier, which allows for intravenous or oral administration.

In pharmaceutical dosage forms, the agents (antibodies, peptides, compounds provided by the invention) can be administered in the form of their pharmaceutically acceptable salts, or they can also be used alone or in appropriate association, as well as in combination, with other pharmaceutically active compounds. The methods and excipients described herein are merely exemplary and are in no way limiting. A subject antibody, peptide, or compound, can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration can comprise the active agent in a composition as a solution in sterile water; normal saline or another pharmaceutically acceptable carrier. The term "unit dosage form," or "dose," as used herein, refers to physically discrete units suitable as unitary dosages for human and animal subjects, each unit containing a predetermined quantity of a subject antibody calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

Immune responses against pathological tau proteins and tau deposits can also be induced by administration of nucleic acids encoding therapeutic tau peptides. Such nucleic acids can be DNA or RNA. A nucleic acid segment encoding the immunogen is linked to regulatory elements, such as a promoter and enhancer that allow expression of such a DNA segment in the intended target cells of a patient. Usually, promoter and enhancer elements from immunoglobulin genes (light or heavy chain) or the CMV major intermediate early promoter and enhancer are suitable to direct expression in the blood cells, which are the desirable target for induction of an immune response. The linked regulatory elements and coding sequences are often cloned into a vector.

A number of viral vector systems are available including retroviral systems (see, e.g., Lawrie et al., Cur, Opin. Genet, Develop. 3:102-109 (1993), which is hereby incorporated by reference in its entirety); adenoviral vectors (Bett et al., J. Virol. 67:5911 (1993), which is hereby incorporated by reference in its entirety); adeno-associated virus vectors (Zhou et al., J. Exp. Med. 179:1867 (1994), which is hereby incorporated by reference in its entirety), viral vectors from the pox family including vaccinia virus and the avian pox viruses, viral vectors from the alpha virus genus, such as those derived from Sindbis and Semliki Forest Viruses (Dubensky et al., J. Virol 70:508-519 (1996), which is hereby incorporated by reference in its entirety); Venezuelan equine encephalitis virus (see U.S. Pat. No. 5,643,576 to Johnston et al., which is hereby incorporated by reference in its entirety) and rhabdoviruses, such as vesicular stomatitis virus (see WO 96/34625 to Rose, which is hereby incorporated by reference in its entirety) and papillomaviruses (Ohe, et al., Human Gene Therapy 6:325-333 (1995); WO 94/12629 to Woo et al.; and Xiao & Brandsma, Nucleic Acids. Res. 24:2630-2622 (1996), which are hereby incorporated by reference in their entirety).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly(lactide-co-glycolides), see, e.g., McGee et al., J. Micro Encap. (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun (see U.S. Pat. No. 6,436,709). In this application, the DNA encoding an immunogen is precipitated onto the surface of microscopic metal beads. The microprojectiles are accelerated with a shock wave or expanding helium gas, and penetrate tissues to a depth of several cell layers (reviewed in Haynes et al., 1996). For example, the Accel™ Gene Delivery Device manufactured by Agacetus, Inc, (Middleton, Wis.) or Helios Gene Gun manufactured by Bio-Rad Laboratories, Inc. (Hercules, Calif.) are suitable. For therapeutic purposes, DNA can also be delivered by electroporation (e.g. as described in Trollet et al., 2008 and references therein). Alternatively, naked DNA can pass through skin into the blood stream simply by spotting the DNA onto skin with chemical or mechanical irritation (see WO 95/05853) or tattooing (e.g. as described by van den Berg et al., 2009).

In a different variation, DNA or vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, for example after verification of the expression of the immunogen and usually after selection for cells which have incorporated the vector.

Another promising although potentially riskier approach for human treatment has been to transfect dentritic cells (DCs, through straight DNA delivery or using viral strategies) to produce the antigen themselves (Xing et al., 2005), thus providing a continuous supply of intact antigen presented through MHC I.

Subjects Amenable to Treatment

Subjects amenable to treatment include individuals at risk of Alzheimer's disease or related tauopathies but not showing symptoms, as well as patients already showing symptoms. In the case of Alzheimer's disease, virtually anyone is at risk of suffering from Alzheimer's disease if he or she lives long enough. Therefore, the present treatments or therapies can even be administered prophylactically to the general population without any assessment of the risk of the subject patient. The vaccines presented in this patent can be especially useful for individuals who have a known genetic risk of Alzheimer's disease. Such individuals include those having relatives who suffered from this disease, and those whose risk is determined by the presence of genetic or biochemical markers. Genetic markers of risk of early onset familial Alzheimer's disease include mutations in the APP gene, presenilin genes PS1 and PS2, and markers for late onset Alzheimer's disease in the ApoE4 gene (recently reviewed by Bertram and Tanzi, 2008). Additional risk factors include family history of AD, hypercholesterolemia or atherosclerosis. Individuals presently suffering from Alzheimer's disease can be recognized from characteristic dementia, as well as the presence of the risk factors described above. In addition, a number of diagnostic tests are available for identifying individuals who have AD. These include measurement of total tau, phospho-tau and amyloid β (1-42) levels in CSF. Elevated tau and/or phospho-tau and decreased amyloid β (1-42) levels indicate the presence of AD. Individuals suffering from Alzheimer's disease can also be diagnosed by MMSE, ADRDA or other criteria.

In asymptomatic patients, treatment can begin at any age (e.g., 10, 20, 30). However, it may not be necessary to begin treatment until a patient reaches 40, 50, 60 or 70, Treatment can entail multiple dosages over a period of time. Treatment can be monitored by assaying antibody, or activated T-cell or B-cell responses to the therapeutic agent (e.g., tau peptide) over time. If the response falls, a booster dosage is indicated. In the case of potential Down's syndrome patients, who are at higher risk for AD or related tauopathies, treatment can begin pre-natally, by administering therapeutic agent to the mother, or shortly after birth.

In some embodiments, DC8E8 (or a chimeric, humanized, human, or other derivative/portion/fragment thereof) is the antibody or passive vaccine intended for use in aged immunosenescent Alzheimer's disease (AD) patients showing significant decrease in the levels of the co-stimulatory molecule CD28 on T-cells. A decrease in co-stimulatory molecule CD28 is indicative of impaired immune response (Saurwein-Teissl et al., 2002). $CD8^+CD28^-$ T cell clones which are frequently $CD45RA^+$ (immunophenotype: $CD8^+$ $CD28^-CD45RA^+$) produce large amount of pro-inflammatory cytokine IFN-γ and marginal amounts of IL-5. These clones accumulate during normal aging and induce imbalance in the production of $Th_1$ and $Th_2$ cytokines. Thus, the accumulating $CD8^+CD28^-CD45RA^+$ T cell clones along with the dwindling population of naïve B cells (Siegrist and Aspinall, 2009) are the major contributors to the decline of immune functions that affects about one third of elderly population (Weng et al., 2009, Saurwein-Teissl et al., 2002).

Accordingly, passive immunotherapy (e.g., with DC8E8 (or a chimeric; humanized, human, or other derivative/portion/fragment thereof) provides a means to circumvent the failing immune system of a large population of AD patients and target the pathological tau proteins causing neurofibrillary degeneration.

In some embodiments, one of the tau therapeutic epitopes (or a peptide comprising one of the tau therapeutic epitopes described herein) is used as an active vaccine; intended for use in aged immunocompetent Alzheimer's disease patients. The immunophenotype of immunocompetent patients is $CD8^+CD28^+CD45RA^+$. Therefore levels of co-stimulatory molecule CD28 on $CD8^+$ T cells will be determined and used as a selection marker of patients for active vaccination.

Furthermore, prior to the treatment; CSF and blood taken from patients will be tested for antibodies against *Borrelia, Treponema, Chlamydia*, Herpesvirus and other brain pathogens to exclude individuals with chronic infectious and inflammatory CNS disorders that can mimic or aggravate the symptoms of AD (Balin et al., 2008; Itzhaki and Wozniak, 2008; Miklossy, 2008; Andreasen, 2010). CNS infections often compromise the function of the blood-brain barrier (BBB), especially *Chlamydia* infections of the brain endothelial cells, which can can lead to an increased influx of monocytes into the brain parenchyma and thus can influence the local immune response (Balin et al., 2008), It has also been shown that elderly subjects with higher levels of IgG to cytomegalovirus (CMV) suffered faster rates of cognitive decline (Itzhaki and Wozniak; 2008). Therefore, in order to prevent adverse effects after immunization with one of the agents provided by the invention (e.g. uncontrolled immune reaction to normal tau) the Alzheimer's disease patients with CNS infections or those tested positively for antibodies against the aforementioned pathogens will be treated with a highly selective vaccine.

Prior to the treatment, CSF and blood taken from patients can be tested for antibodies against *Borrelia, Treponema, Chlamydia*, Herpesvirus and other brain pathogens to exclude individuals with chronic infectious and inflammatory CNS disorders that can mimic or aggravate the symptoms of AD (Balin et al., 2008; Itzhaki and Wozniak, 2008; Miklossy, 2008; Andreasen, 2010). In order to prevent possible adverse effects promoted by various chronic infections, this group of patients will be treated with a more selective antibody or therapeutic-epitope-containing vaccine. In some instances, the active vaccine is a designer epitope (e.g., see EXAMPLES), inducing the production of strictly selective antibodies targeting the therapeutic epitope on pathological tau proteins. In some embodiments, the vaccine does not contain any amino acid sequence shared with normal/physiological tau protein.

Treatment Regimes

In prophylactic applications, pharmaceutical compositions or medicaments are administered to a patient susceptible to, or otherwise at risk of, a particular disease in an amount sufficient to eliminate or reduce the risk or delay the outset of the disease. In therapeutic applications, compositions or medicaments are administered to a patient suspected of, or already suffering from such a disease in an amount sufficient to cure, or at least partially arrest, the symptoms of the disease and its complications. An amount adequate to accomplish this is defined as a therapeutically or pharmaceutically effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions, vary depending upon many factors, including means of administration, target site, physiological state of the patient, whether the patient is human or an animal, other medications administered, and whether the treatment is prophylactic or therapeutic. Usually, the patient is a human. Treatment dosages need to be titrated to optimize safety and efficacy. Accordingly, treatment with an antibody or tau-binding protein will typically entail multiple dosages over a period of time. For passive immunization with an antibody, the dosage ranges from about 0.0001 to 100 mg/kg, and more usually 0.01 to 5 mg/kg of the host body weight. In some applications, the amount of antibody or tau-binding protein can be administered at a dosage of at least 0.1 mg/kg of body weight, at a dosage of at least 0.5 mg/kg of body weight, 1 mg/kg of body weight, or any combination of dosages between 0.1 and 10 mg/kg of body weight. In some methods, the antibody or tau-binding protein can be administered in multiple dosages (equal or different) over a period of at least 1 month, at least 3 months, or at least 6 months. The total number of doses over any one treatment period can be, for example, between 4 and 6, although other numbers can be used depending on the factors discussed above. Treatment can be monitored by any of the methods described further below.

The amount of immunogen depends on whether adjuvant is also administered, with higher dosages being required in the absence of adjuvant. The amount of an immunogen for administration sometimes varies from 1 µg-500 µg per patient and more usually from 5-500 µg per injection for human administration. Occasionally, a higher dose of 1-2 mg per injection is used. Typically about 10, 20, 50 or 100 µg is used for each human injection. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response. In some embodiments, the active vaccine will be formulated with a suitable carrier, preferentially KLH, and aluminum hydroxide as an adjuvant. Preferentially, 100 µg peptide/dose/patient (but also 1 µg, 10 µg 100 µg and 1 mg will be applied in pre-clinical phase and 10 µg 100 µg 200 µg in Phase I toxicity studies) will be applied once in 4 weeks, 5 doses in total.

Doses for nucleic acids encoding immunogens range from about 10 ng to 1 g, 100 ng to 100 mg, 1 µg to 10 mg, or 30-300 µg DNA per patient. Doses for infectious viral vectors vary from $10-10^9$, or more, virions per dose. Treatment can be monitored by assaying antibody, or activated T-cell or B-cell responses to the therapeutic agent over time. If the response falls, a booster dose can be indicated.

Ultimately, the dosage regimen will be determined by the attending physician and by clinical factors. As is known in the medical arts, dosages for any one patient depend upon many factors, including the patients size, body surface area, age, the particular compound to be administered, sex, time and route of administration, general health, and other drugs being administered concurrently. A typical dose can be, for example, in the range of 0.001 to 1000 mg; however, doses below or above this exemplary range are envisioned, especially considering the aforementioned factors. Generally, the regimen as a regular administration of the pharmaceutical composition should be in the range of 1 mg to 10 mg units per day. If the regimen is a continuous infusion, it should also be in the range of 1 mg to 10 mg per kilogram of body weight per minute, respectively. Progress can be monitored by periodic assessment.

In addition, co-administration or sequential administration of other agents can be desirable. In some embodiments, a therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. In some embodiments, the therapeutic agent in the composition is present in an amount sufficient to restore normal behavior and/or cognitive properties in case of Alzheimer's disease and related tauopathies.

The invention provides different measures that can be relied upon for evaluation of treatment effectiveness with any of the agents provided by the invention. Examples include, but are not limited to, decreased levels of one or more pathological tau forms (e.g., within the brain), increased clearance of pathological tau from the brain and/or CSF; improved cognitive performance measures, such as cognitive functions (tested by, for example, Clinical Dementia Rating—CDR, Alzheimer's disease Assessment Scale—Cognitive Subscale—ADAS-Cog Mini Mental State Examination—MMSE); improved motor function tests (e.g., Grip strength test, Timed Up & Go (TUG) test, TUG manual, Talking while Walking test, Unified Parkinson's disease Rating Scale UPDRS); improved performance of basic activities of daily living (ADL) tests (e.g, hygiene, dressing, continence, eating, meal preparation, telephoning, going on an outing, finance, and correspondence; Disability Assessment in Dementia tests); and lessened severity/grading of AD impaired grip strength, locomotion, and apraxia (which have direct correlations with the animal models and assays described below, in the EXAMPLES), memory decline, aphasia, agnosia, disorientation in time and space, and depression.

For purposes of assessing treatment effectiveness, the levels and distribution of tau (within the brain, and in body fluids) can be assayed by any of the methods described herein, and/or by any other methods available to detect tau. For example, the levels of tau could be measured in vivo (Positron emission tomography) using novel imaging radiotracer 18F-THK523, which selectively binds tau and tau pathology in vitro, ex vivo (tissue slices) and in vivo (transgenic mice) (Fodero-Tavoletti et al., 2011, Brain), Tau could be identified in the cerebrospinal fluid and in the blood as well using ELISA kits recognizing either total tau or phospho-tau.

Indeed, neurobehavioral impairment in transgenic rats has parallels with motor impairment in Alzheimers disease patients, which has implications for clinical trials and treatment protocols with any of the therapeutic agents provided herein (including, but not limited to, agents for active vaccination. In humans, Alzheimer's disease is characterized clinically by progressive memory impairment and cognitive decline, behavioral changes and psychological symptoms (disturbances in mood, emotion, appetite, wake sleep cycle, confusion, agitation and depression) and impaired motor function (apraxia, myoclonus, gait impairment, decreased muscle strength, extrapyramidal features such as bradykinesia, rigidity and resting tremor) (Goldman et al., 1999; Boyle et al., 2009). Many studies have reported that motor signs are commonly observed in Alzheimer's disease (AD) and become more prominent as the disease progresses (Goldman et al., 1999; Wilson et al., 2003; Louis et at, 2004; Pettersson et al., 2005; Scarmeas et al., 2004; Scarmeas et al., 2005; Waite et al., 2005; Alfaro-Acha et al., 2006; Wang et al., 2006; Buchman et al., 2007a; Boyle et al., 2009). Notably, the motor signs can precede the cognitive impairment and predict cognitive and functional decline, institutionalization and mortality in Alzheimer disease (Morris et al., 1989; Soininen et al., 1992; Kraemer et al., 1994; Chui et al., 1994; Scarmeas et al., 2004; Scarmeas et al., 2005). It has been shown that decreased muscle strength precedes the development of cognitive impairment (Buchman et al., 2007b; Boyle et al., 2009).

The development of motor signs in AD has been associated with neuronal degeneration and neuronal loss in the brainstem (Zarow et al, 2003; Burns et al. 2005; Grudzien et al. 2007; Simic et al., 2009; Wai et al., 2009; Braak and DelTredici, 2011). Moreover, several studies have suggested that neurofibrillary degeneration originates in the brainstem and precedes cortical neurodegeneration (Hertz, 1989; Simic et al., 2009; Braak and DelTredici, 2011).

These findings show that motor impairment represents a key hallmark in AD pathogenesis. Moreover, functional impairment of some motor domains can precede dementia and predict cognitive decline. Active immunotherapy with the peptides (including therapeutic epitopes) described herein can improve motor impairment of transgenic rats expressing human pathological tau. Thus, direct targeting of the brain stem pathology by active immunotherapy can prevent, slow, or delay, motor as well as cognitive impairment in human AD patients. Thus, testing of motor functions can be included in the battery of tests that can be used for the evaluation of the clinical efficacy of the agents (e.g.; tau clearance agents, active and passive vaccines) described herein.

Also, one of ordinary skill in the art is aware of well-established correlations between the levels and distribution of pathological tau, (e.g., NFT in cortexihippocampus) and disease progression. The density of pathological tau (NFT pathology) has been correlated with cognitive deficit and the severity of the Alzheimer's disease (Braak and Braak, 1991; Bierer et al., 1995; Berg et al., 1998; Duyckaerts et al., 1998; Giannakopoulos et al., 1998, 2003). Pathological tau (e.g., NFTs, neuropil threads) in the entorhinal cortex and hippocampus are inversely associated with longitudinal changes in memory (Reitz et al., 2009). Similarly; in the brain stem, pathological tau (NFT) occurs in the dorsal raphe nucleus at a very early stage; the other raphe nuclei are subsequently affected. These lesions explain the serotoninergic deficit found in AD (Duykaerts et al., 2009). The extrapyramidal symptoms have been correlated with the substantia nigra tau pathology (Liu et al., 1997). Accordingly, a treatment agent that can affect one or more of these AD distribution patterns will likely have a beneficial effect in AD.

EXAMPLES

Example 1: Preparation of Recombinant Human Tau Proteins

Human full-length tau (2N4R, 2N3R) and tau deletion mutants: Tau recombinant proteins (FIGS. 1 and 6A through 6E) were generated from clone T40 (Goedert, 1989), which was subcloned into the expression plasmid pET-17b (Novagen) and expressed in bacteria. Each tau deletion mutant was verified by DNA-sequencing. All tau deletion mutants and tau peptides are numbered according to the longest human tau isoform 2N4R, which is 441 amino acids in length and thus is also called $tau_{441}$ (D'Souza, 2005). Tau deletion mutants and peptides derived from the isoform 2N3R are marked by "3R" to indicate that the second microtubule binding repeat (amino acids 275-305 of 2N4R) is missing. Production of tau proteins involved the following steps: a) expression of tau in bacteria; b) tau purification by ion exchange chromatography; c) tau purification by gel-filtration; d) concentration and storage of isolated tau; and e) immunoaffinity purification (this is an exception adopted only for tauΔ(1-150;392-441)/4R, which was used in the microglia uptake experiments, see Example 10, FIG. 17).

a) Bacterial Expression of human full-length tau (either 2N4R or 2N3R) and recombinant tau deletion mutants: human tau (above) expression plasmids were transformed into *Escherichia coli* (*E. coli*), production strain BL21 (DE3). Bacterial cells containing the appropriate expression plasmid were cultivated and induced as described in "Molecular Cloning: A Laboratory Manual" by Sambrook and Russell (2001). A single colony of BL21(DE3) bacteria, transformed with pET-17b plasmid driving expression of a tau protein or its fragment, were grown at 37° C. in 500 ml of Luria broth medium with 100 μg/ml ampicillin at 300 rpm and induced by the addition of isopropyl-β-D-1-thiogalactopyranoside (IPTG) to a final concentration of 0.4 mM. After further incubation at 37° C. for 3 hours, bacteria were collected by centrifugation at 3,000×g for 15 min at 4° C.

b) Cation-exchange chromatography purifications of the basic and neutral tau proteins (full-length tau isoforms, tauΔ358-441, tauΔ306-400, tauΔ421-441, tauΔ300-312, tauΔ134-168, tauΔ1-220, tauΔ1-126, tauΔ(1-150; 392-441)/4R, tauΔ(1-150; 392-441)/3R and tauΔ(1-296;392-441)/4R) were done essentially as previously described (Krajciova et al., 2008). After expression, the bacterial pellets were resuspended in 10 ml of lysis buffer (50 mM 1,4-piperazinediethanesulfonic acid (PIPES) pH 6.9, 50 mM sodium chloride (NaCl), 1 mM ethylenediaminetetraacetic acid (EDTA), 5 mM dithiothreitol (DTT), 0.1 mM phenylmethylsulfonyl fluoride (PMSF), 5% (v/v) glycerol), quickly frozen in liquid nitrogen, and stored at −80° C. until used for purification of tau proteins. For tau protein purification, the frozen bacterial suspensions were quickly thawed and placed on ice. Bacterial cell walls were broken by sonication on ice by using Sonopuls HD 2200, tip TT-13 (Bandelin, Germany) set to 50% duty cycle, 50 W power output, 6 times for 30 s with 30 s pauses. The lysates were clarified by centrifugation (21,000×g for 15 min at 4° C.) and the supernates were filtered through a 0.45 μm membrane filter. Large-scale purification of the recombinant tau proteins was done at 6° C. using an AKTA-FPLC workstation (Amersham Biosciences, Sweden). The filtered lysates were loaded at a 3 ml/min flow rate onto a 5-ml HiTrap SP HP column (GE Healthcare, Uppsala, Sweden) equilibrated with the lysis buffer, and washed extensively with 60 ml of the lysis buffer until the baseline at 280 nm became stable. Bound tau proteins were eluted by a gradient (0-30% within 15 ml) of Buffer B (lysis buffer supplemented with 1 M NaCl). Individual 1 ml fractions were collected and analyzed by sodium dodecyl sulfate-polyacrylamide gel electrophoresis (SOS-PAGE). To remove nucleic acids, which copurify with positively charged tau proteins, the fractions containing tau protein were pooled and purified by a second cation-exchange chromatography step, using a 5-ml HiTrap SP HP column (GE Healthcare, Uppsala, Sweden) with a less steep gradient of Buffer B (0-30% in 45 ml).

c) Anion-exchange chromatography purification of the acidic tau proteins (tauΔ222-427, tauΔ228-441, tauΔ257-400, tauΔ137-441, tauΔ283-441) was done as previously described (Csokova, et, al 2004). After expression, bacterial pellets were resuspended in 10 ml of histidine lysis buffer (20 mM histidine, pH 6.0, 50 mM NaCl, 1 mM EDTA, 5 mM OTT, 0.1 mM PMSF, and 5% (v/v) glycerol). Bacterial cell walls were broken by sonication on ice by using Sonopuls HD 2200, tip TT-13 (Bandelin, Germany) set to 50% duty cycle, 50 W power output, 6 times for 30 s with 30 s pauses. The lysates were clarified by centrifugation (21,000×g for 15 min at 4° C.). Bacterial lysates were precipitated by 1% streptomycin sulfate (Medexport, Russia), incubated on ice for 5 min, clarified by centrifugation (21,000×g for 15 min at 4° C.), and filtered through a 0.45 μm membrane filter. The filtered streptomycin precipitated lysates were loaded at 3 ml/min flow rate onto a 5 ml HiTrap QSepharose HP column (Amersham Biosciences, Sweden) and washed extensively with 30-50 ml histidine lysis buffer until the A280 baseline became stable. Tau proteins were eluted with a two-step salt gradient (0.05-0.5M NaCl in 40 ml followed by 0.5-1M NaCl in 20 ml) in histidine lysis buffer.

d) In the final gel-filtration step of purification (the same for all tau proteins), pooled tau protein fractions obtained by ion exchange chromatography, were injected onto a gel-filtration column (HiLoad 26/60 Superdex 200 prep grade column, GE Healthcare) at 3 ml/min in either PIPES or Histidine lysis buffer for basic/neutral or acidic tau proteins, respectively, supplemented with 100 mM NaCl. Eluted tau proteins were pooled.

e) For tau protein concentration after gel-filtration purification, pooled fractions were diluted with 1.5 volumes of 2.5% glycerol, and loaded again on a HiTrap SP HP column (basic and neutral tau proteins) or on a HiTrap Q HP column (acidic tau proteins). The concentrated recombinant tau protein was then eluted from the column with a 1 M NaCl step gradient. Finally, the buffer was exchanged to phosphate-buffered saline (PBS, 8.09 mM disodium phosphate ($Na_2HPO_4$), 1.47 mM potassium dihydrogen phosphate ($KH_2PO_4$), 136.89 mM NaCl, 2.7 mM potassium chloride (KCl)) saturated with argon, using a 5 ml HiTrap Desalting column (GE Healthcare). Protein quantitation of purified samples was done using bicinchoninic acid (BCA) quantitation kits (Pierce, USA), with bovine serum albumin (BSA) as a standard, Tau proteins were aliquoted into working aliquots, snap-frozen in liquid nitrogen, and stored at −70° C.

f) In order to remove possible bacterial contaminants from the recombinant tauΔ(1-150;392-441)/4R used for the measurements of tau uptake by microglia (Example 10, FIGS. 17A and 17B), the recombinant tau protein was purified by a modified method, as follows. After the first cation-exchange chromatography step, the fractions containing tau were pooled and 1/20 volume of ice-cold 5% polyethylenimine was added while stirring. The stirring continued for another 30 min, on ice. The sample was centrifuged at 20,000×g for 15 min at 4° C. The supernate was collected and injected onto a HiLoad 26/60 Superdex 200 prep grade column (GE Healthcare) at 3 ml/min in the PIPES lysis buffer supplemented with 100 mM NaCl but lacking DTT or any other reducing agent, After gel filtration, fractions with tau protein were pooled and loaded onto an immunoaffinity column (at a flow rate of 0.5 ml/min) containing DC25 antibody (epitope 347-353 of 2N4R tau, Axon Neuroscience, Vienna, Austria) immobilized on CNBr-activated Sepharose. The column was pre-equilibrated in 20 mM Tris-HCl, pH 7.4, 150 mM NaCl, 0.1% Tween 20 (TBS-Tween). After binding, the column was washed with 5 column volumes of TBS-Tween and the bound tau proteins were eluted with 0.1 M glycine, pH 2.7. The collected fractions were neutralized by adding 1/30 volume of 1 M Tris-HCl pH 8.8 and pooled, Lastly, the buffer was exchanged to PBS (saturated with argon), using an HiTrap Desalting column, 5 ml (GE Healthcare). Protein quantitation of purified samples was done using a bicinchoninic acid (BCA) quantitation kit (Pierce, USA), with BSA as a standard. The protein was aliquoted into working aliquots, snap-frozen in liquid nitrogen, and stored at −70° C.

The purified DC25 antibody (Axon Neuroscience, Vienna, Austria) used for the DC25 affinity column (supra) was prepared as follows. Serum free DC25 hybridoma culture supernate was adjusted to pH 7.5 by adding 0.2 volume of PBS, precleared by centrifugation at 20,000×g for 10 minutes at 4° C., and the supernate filtered through a 0.2 μm filter. The pre-cleared DC25 hybridoma culture supernate was loaded onto a PBS-equilibrated HiTrap Protein G HP column (5 ml, GE Healthcare) at 1 ml/min. After loading was complete, the column was washed with 4 column volumes of PBS, and the bound antibody was eluted with 100 mM glycine pH 2.7. Eluted fractions were neutralized with 1 M Tris-HCl pH 9, pooled, and buffer exchanged into PBS using a HiTrap Desalting column (5 ml, GE Healthcare). The purified DC25 antibody was stored in small aliquots at −70° C.

Example 2: Preparation of Hybridoma Cell Lines Producing Monoclonal Antibodies Against Human TauΔ(1-150;392-441)/4R, Screening of Monoclonal Antibodies by ELISA, and Initial Characterization of Monoclonal Antibody DC8E8

Six-week-old Balb/c mice were primed subcutaneously with 50 μg of recombinant tauΔ(1-150;392-441)/4R (prepared as described in Example 1) in complete Freund's adjuvant (SIGMA), and boosted five times at five-week intervals with 50 µg of the same antigen in incomplete Freund's adjuvant. Three days before the fusion, mice were injected intravenously with 50 µg of the same antigen in PBS. Spleen cells from immunized mice were fused with NS/0 myeloma cells according to the method of Kontsekova et al. (1988). Splenocytes ($10^8$) were mixed with $2\times10^7$ NS/0 myeloma cells (ratio 5:1) and fused for 1 minute in 1 ml of 50% polyethylene glycol (PEG) 1550 (Serva) in serum free Dulbecco's modified Eagle's medium (DMEM) supplemented with 10% dimethyl sulphoxide. The fused cells were resuspended in DMEM containing 20% horse serum, L-glutamine (2 mM), hypoxanthine (0.1 mM), aminopterin (0.04 mM), thymidine (0.016 mM), and gentamycin (40 U/ml), at a density of $2.5\times10^5$ spleen cells per well on 96-well plates. The cells were incubated for 10 days at 37° C. and growing hybridomas were screened for the production of anti-tauΔ (1-150:392-441)/4R-specific monoclonal antibodies by an enzyme-linked immunosorbent assay (ELISA).

An ELISA was used to detect monoclonal antibodies in hybridoma culture supernates directed against tauΔ(1-150; 392-441)/4R (a misdisordered form of tau). Microtiter plates were coated overnight with tauΔ(1-150;392-441)/4R (5 µg/ml, 50 µl/well) at 37° C. in PBS. After blocking with 1% nonfat dried milk to reduce nonspecific binding, the plates were washed with PBS-0.05% Tween 20 and incubated with 50 µl/well of hybridoma culture supernate for 1 hr at 37° C. Bound monoclonal antibodies were detected with sheep anti-mouse immunoglobulin (Ig) conjugated with horse radish peroxidase (HRP, DAKO). The reaction was developed with orthophenylenediamine solution as a peroxidase substrate and stopped with 50 µl of 2 M $H_2SO_4$. Absorbance at 492 nm was measured using a Multiscan MCC/340 ELISA reader (Labsystems). Readouts with an absorbance value of at least twice the value of the negative controls (PBS) were considered positive. Positive hybridoma cultures were further tested by immunohistochemistry (accordingly to method of Zilka et al., 2003) and subcloned in soft agar according to the procedure described in Kontsekova et at (1991).

The monoclonal antibody DC8E8 (produced by the mouse hybridoma cell line deposited with the American Type Culture Collection on Jul. 13, 2011, with the ATCC Patent Deposit Designation PTA-11994) was identified among the positive hybridoma cultures so produced and selected, DC8E8 was further characterized as described below. The antibody isotype was determined to be murine IgG1 by ELISA using a mouse Ig isotyping kit (ISO-2, SIGMA).

Example 3: Sequencing of Variable Regions of D8E8 and its Humanization by CDR-Grafting a) Determination of the nucleotide and amino acid sequences of the light and heavy chain variable regions of DC8E8 (FIGS. 3A through 3D). The nucleotide sequence of DC8E8's variable regions (FIGS. 3A and 3B) was determined by DNA sequencing of cDNA synthesized using total RNA extracted from the mouse hybridoma cell line PTA-11994 (ATCC), which expresses the DC8E8 monoclonal antibody. Total RNA was extracted using TRIZOL® Reagent (Invitrogen, USA). Synthesis of the first strand cDNA was carried out using the "High capacity cDNA reverse transcription" kit according to the manufacturer's protocol (Applied Biosystems, USA), The composition of the reagents for the 2× reverse transcription master-mix was as follows (quantities per 20 µL reaction): 2 µL of 10×RT buffer; 0.8 µL of 25×dNTP Mix (100 mM); 2 µl of 10×RT Random Primers (50 µM); 1 µL of MultiScribe™ Reverse Transcriptase (50 U/µL); 4.2 µL of nuclease-free $H_2O$. For reverse transcription, 10 µL of the 2× reverse transcription master-mix was mixed with RNA sample (2 µg/10 µL) and cDNA was synthesized under the following conditions: 10 min at 25° C., 120 min at 37° C., 5 min at 85° C., and final cooling to 4° C. Amplification of the genes encoding the variable regions of the light and heavy chains was done by polymerase chain reaction (PCR) using Phusion® High-Fidelity DNA Polymerase (Finnzymes, Finland). The forward primers (8E8L-sense 5'-ACATTGTGATGTCACA-GTCTCCATCCTCC-3' (SEQ ID NO: 132) and 8E8H-sense 5'-CTCCTCCAATTGCAGCAGTCTGG-3'(SEQ ID NO: 133)) were designed according to the protein sequence of the N-terminal ends of DC8E8 light (DIVMSQSPSS) (SEQ ID NO: 134) and heavy (QVQLQQSGPE) (SEQ ID NO: 135) chains. The N-terminal protein sequences were determined using Edman degradation (light chain) and MALDI in-source decay (heavy chain). Using this information, the most similar proteins to the light and heavy chains were identified in the Genebank along with their corresponding nucleotide sequences. The most probable nucleotide sequences of the mouse V-genes (light and heavy) were then identified in the IMGT/LIGM-DB database (www.imgt.org). These genes were used for the design of the forward primers (corrections were made using the N-terminal protein sequences of DC8E8). The reverse primers for the light and heavy chains (Kappa-antisense 5'-GGAATTCGTTGAAGCTCTT-GACAATGGGTG-3' (SEQ ID NO: 136) and G1-antisense 5'-GGAATTCACATATGCAAGGCTTACAACCAC-3 (SEQ ID NO: 137)) were derived from kappa and IgG1 chains constant regions, respectively.

The FOR products were sequenced and the resulting DNA sequences of variable regions of light and heavy chains of DC8E8 are shown in FIGS. 3A and 3D, respectively. The alignment of DC8E8 to the closest mouse germline light chain IGKV8-21*01 and heavy chain IGHV1-81*01 are shown in FIGS. 3C and 3F, respectively. Complementarity determining regions (CDRs) are underlined in the DC8E8 light and heavy chains protein sequences (FIGS. 3A and 3B, respectively). CDRs and framework regions (FR) were identified according to the ImMunoGeneTics (IMGT) numbering system (see, e.g., Lefranc M. P. The IMGT unique numbering for immunoglobulins, T-cell receptors, and Ig-like domains. The Immunologist 7, 132-136, 1999 (1999)).

b) Humanization of DC8E8. To identify a suitable candidate human immunoglobulin for production of a humanized DC8E8 through grafting of the mouse DC8E8 complementarity determining regions (CDRs), the human germline gene with the highest sequence identity to DC8E8 was determined using ClustalX2 pairwise alignment of the DC8E8 nucleotide sequence against a selected set of human immunoglobulin genes extracted from IMGT/LIGM-DB flat file release 201112-6 (www.imgt.org). IgKv4-1*01 was identified as the closest human germline gene for the DC8E8 light chain (FIG. 4), and IgHV1-69*10 was identified as the closest germline gene for the DC8E8 heavy chain (FIGS. 5A and 5B). The following approach (Method 1 and Method 2) was designed and can be used to prepare one or more humanized versions of the DC8E8 antibody, After expression in an appropriate antibody expression system (e.g., mammalian expression vectors used for antibody expression in vitro (e.g., HEK293 cells) or in vivo (transgenic animals)), the resulting humanized, recombinant antibodies, can be tested for activity (e.g., biochemical and therapeutic activity) according to any of the methods used for characterization of DC8E8's activity.

Method 1: CDR grafting and mutations in the framework region (FR), if necessary (CDRs are in bold underlined, FR mutations are in bold):

```
Heavy chain variable region
(SEQ ID NOS 138-140, respectively, in order of appearance):
DC8E8_heavy       QVQLQQSGPELVKPGTSVKMPCKASGYIFTDYVISWVKQRTGQGLEWIGEIFPRSGSTYY
human_germ_heavy  QVQLVQSGAEVKKPGSSVKVSCKASGGTFSSYAISWVRQAPGQGLEWMGGIIPILGIANY
                  **** ***.*: ***:***:.*****  *:.*.****.* .******:* *:*  * : *

SEQ ID No. 140    QVQLVQSGPEVKKPGSSVKVPCKASGYIFTDYVISWVRQATGQGLEWMGEIFPRSGSTNY

DC8E8_heavy       NEKFKGKATLTADKSSNTAYMQLSSVTSEDSAVYFCARDYYGTSFAMDYWGQGTSVTVSS
human_germ_heavy  AQKFQGRVTITADKSTSTAYMELSSLRSEDTAVYYCARENHCYYYGMDVWGQGTTVTVSS
                   :**:*:.*:*****:.****:***: ***:***:***: :   :.** *****:*****

SEQ ID No. 140    AQKFQGRVTITADKSTSTAYMELSSLRSEDTAVYYCARDYYGTSFAMDYWGQGTTVTVSS

Light chain variable region
(SEQ ID NOS 141-143, respectively, in order of appearance):
DC8E8_light       DIVMSQSPSSLAVSAGEKVTMSCKSSQSLLNSRTRKNYLAWYQQKPGQSPKLLIYWASTR
human_germ_light  DIVMTQSPDSLAVSLGERATINCKSSQSVLYSSNNKNYLAWYQQKPGQPPKLLIYWASTR
                  ****:***.***** **:.*:.******:* *  ..*************.***********

SEQ ID No. 143    DIVMTQSPDSLAVSLGERATINCKSSQSLLNSRTRKNYLAWYQQKPGQSPKLLIYWASTR

DC8E8_light       ESGVPDRFTGSGSGTDFTLTISSVQAEDLAVYYCKQSFYLRTFGGGTKLDIK
human_germ_Light  ESGVPDRFSGSGSGTDFTLTISSLQAEDVAVYYCQQYYSTLTFGGGTKVEIK
                  ********:**************:****:*****:* :   *******::**

SEQ ID No. 143    ESGVPDRFSGSGSGTDFTLTISSLQAEDVAVYYCKQSFYLRTFGGGTKVEIK
```

Method 2: The mouse (FIG. 3) and human (FIGS. 4 and 5) germline immunoglobulins with the highest sequence identity with DC8E8 were found and aligned to the DC8E8 protein sequence. The CDR regions were identified following the IMGT numbering system. The most probable antigen-contacting residues within the DC8E8 combining site were identified on the basis of the work of MacCallum et al, J. Mol. Biol. 1996.

Various amino acid candidates for mutation in the humanized version of DC8E8 were identified on the basis of the following combined criteria:

i. their presence in the CDR and probability of contact with antigen
ii. their presence in the Vernier zone
iii. whether or not they were mutated in the mouse germline Two levels of mutation candidates were identified according to the above criteria:

X-type residues (in bold):
Residues different between DC8E8 and the closest mouse germline, non-similar amino acids Residues in the CDR and contacting antigen. CDRs are in lowercase bold italic in the DC8E8 sequence below.

Y-type residues (in bold underlined):
Residues identical between DC8E8 and the closest mouse germline, but different in the closest human germline and located in the Vernier zone (non-similar amino acid)

Residues different between DC8E8 and the closest mouse germline (similar/conserved amino acid)

Two humanized sequences for each chain were identified with mutations predicted to affect DC8E8's activity:
SEQ ID Nos. 147, 152: Only X type of residues will be mutated
SEQ ID Nos. 148, 153: Both X and Y type of residues will be mutated

```
Heavy chain variable region
(SEQ ID NOS 138, 145, 139, respectively, in order of appearance):
DC8E8_heavy       QVQLQQSGPELVKPGTSVKMPCKASgyiftdyvisWVKQRTGQGLEWIGifprsgstYY
mouse_germ_heavy  QVQLQQSGAELARPGASVKLSCKASGYTFTSYGISWVKQRTGQGLEWIGEIYPRSGNTYY
human_germ_heavy  QVQLVQSGAEVKKPGSSVKVSCKASGGTFSSYAISWVRQAPGQGLEWMGGIIPILGIANY
                  **** ***.*: :**:***:.*****  *:.* ****:* .******:* * *  * : *

SEQ ID No. 147    QVQLVQSGPEVVKPGSSVKMPCKASGYIFSDYAISWVRQRTGQGLEWMGEIFPRSGSTNY
SEQ ID No. 148    QVQLVQSGPEVVKPGSSVKMPCKASGYIFSDYAISWVRQRTGQGLEWMGEIFPRSGSTYY

DC8E8_heavy       NEKFKGKATLTADKSSNTAYMQLSSVTSEDSAVYFCardyygtsfamdyWGQGTSVTVSS
mouse_germ_heavy  NEKFKGKATLTADKSSSTAYMELRSLTSEDSAVYFCARDYYGTYYAMDYINGQGTSVTVSS
human_germ_heavy  AQKFQGRVTITADKSTSTAYMELSSLRSEDTAVYYCARENHCYYYGMDVWGQGTTVTVSS
                   :**:*:.*:*****:.****:* *: ***:***:***: :   :.** *****:*****

SEQ ID No. 147    AQKFQGRVTITADKSTSTAYMELSSLRSEDTAVYYCARDYYGTSYGMDVWGQGTTVTVSS
SEQ ID No. 148    NQKFQGRVTITADKSTNTAYMQLSSLTSEDTAVYYCARDYYGTSYGMDVWGQGTTVTVSS

Light chain variable region
(SEQ ID NOS 141, 150, 142, respectively, in order of appearance):
DC8E8_light       DIVMSQSPSSLAVSAGEKVTMSCKSSqsllnsrtrknyLAWYQQKPGQSPKLLIYwasTR
mouse_germ_light  DIVMSQSPSSLAVSAGEKVTMSCKSSQSLLNSRTRKNYLAWYQQKPGQSPKLLIYWASTR
```

```
human_germ_light  DIVMTQSPDSLAVSLGERATINCKSSQSVLYSSNNKNYLAWYQQKPGQSPKLLIYWASTR
                  ****:***.***** **:.*:.******:* * ..************.***********

SEQ ID No. 152    DIVMTQSPDSLAVSLGERATINCKSSQSVLNSRNNKNYLAWYQQKPGQPPKLLIYWASTR
SEQ ID No. 153    DIVMTQSPDSLAVSLGERATISCKSSQSVLNSRNNKNYLAWYQQKPGQSPKLLIYWASTR

DC8E8_light       ESGVPDRFTGSGSGTDFTLTISSVQAEDLAVYYCkqsfylrtFGGGTKLDIK
mouse_germ_light  ESGVPDRFTGSGSGTDFTLTISSVQAEDLAVYYCKQSYNLRTFGGGTKLEIK
human_germ_light  ESGVPDRFSGSGSGTDFTLTISSLQAEDVAVYYCQQYYSTLTFGGGTKVEIK
                  ********:***************:****:*****:*  ;  *******:.**

SEQ ID No. 152    ESGVPDRFSGSGSGTDFTLTISSLQAEDVAVYYCKQSFYLRTFGGGTKVEIK
SEQ ID No. 153    ESGVPDRFSGSGSGTDFTLTISSLQAEDVAVYYCKQSFYLRTFGGGTKVEIK
```

Figure 6E:
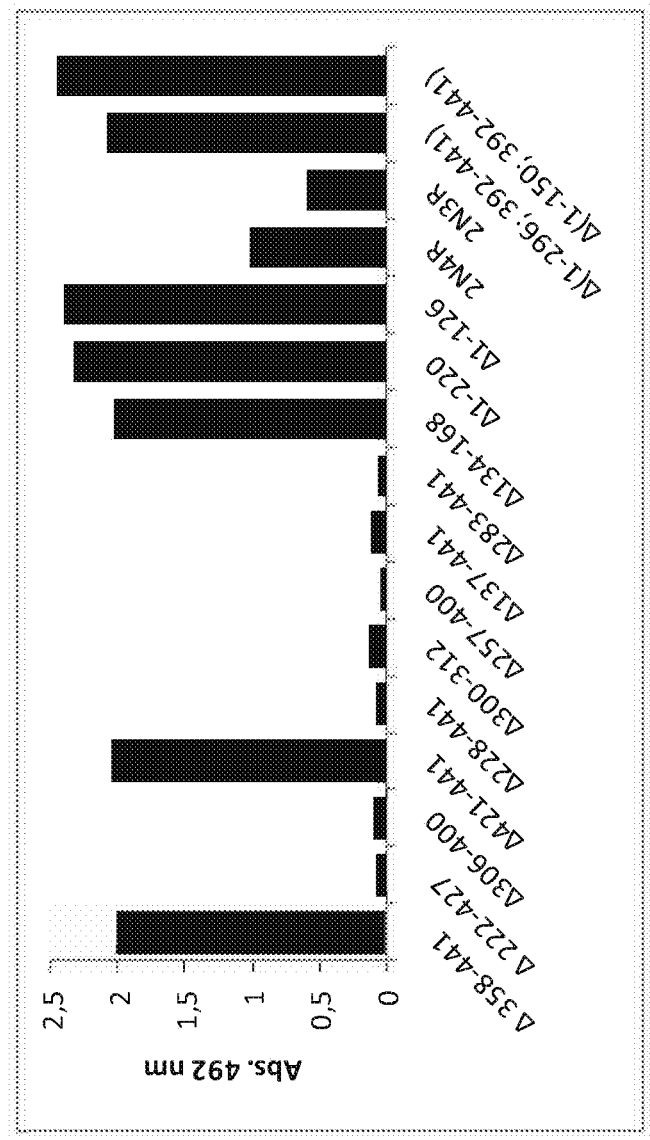

Example 4: Mapping of the DC8E8 Epitope Using Recombinant Tau Deletion Mutants and Tau-Derived Peptides Deletion mutants of human tau protein 2N4R, as well as tau derived peptides (Antagene; Inc. (Sunnyvale; CA) and EZBiolab, (USA)) were used for epitope mapping of DC8E8 using ELISA (FIGS. 6, 7, and 8). Recombinant human tau isoforms (2N4R; 2N3R) and tau deletion mutants (FIGS. 6A through 6E) were prepared as described in Example 1, Peptides (FIG. 7A, 7B) were synthesized by EZBiolabs (USA) with purity higher than 85%.

Microtiter plates were coated overnight at 37° C. with either recombinant tau proteins or with tau peptides (5 µg/ml in PBS, 50 µl/well). After blocking with 1% nonfat dried milk to reduce nonspecific binding; the plates were washed with PBS-0.05% Tween 20 and incubated with 50 µl/well of DC8E8 hybridoma culture supernate, for 1 hr at 37° C. Bound monoclonal antibody was detected with sheep anti-mouse Ig HRP-conjugated (DAKO). The reaction was developed with orthophenylenediamine solution as a peroxidase substrate and stopped with 50 µl of 2 M $H_2SO_4$. Absorbance was measured at 492 nm using a Multiscan MCC/340 ELISA reader (Labsystems). Readouts with an absorbance value of at least twice the value of the negative controls (PBS) were considered positive.

Figure 7C:
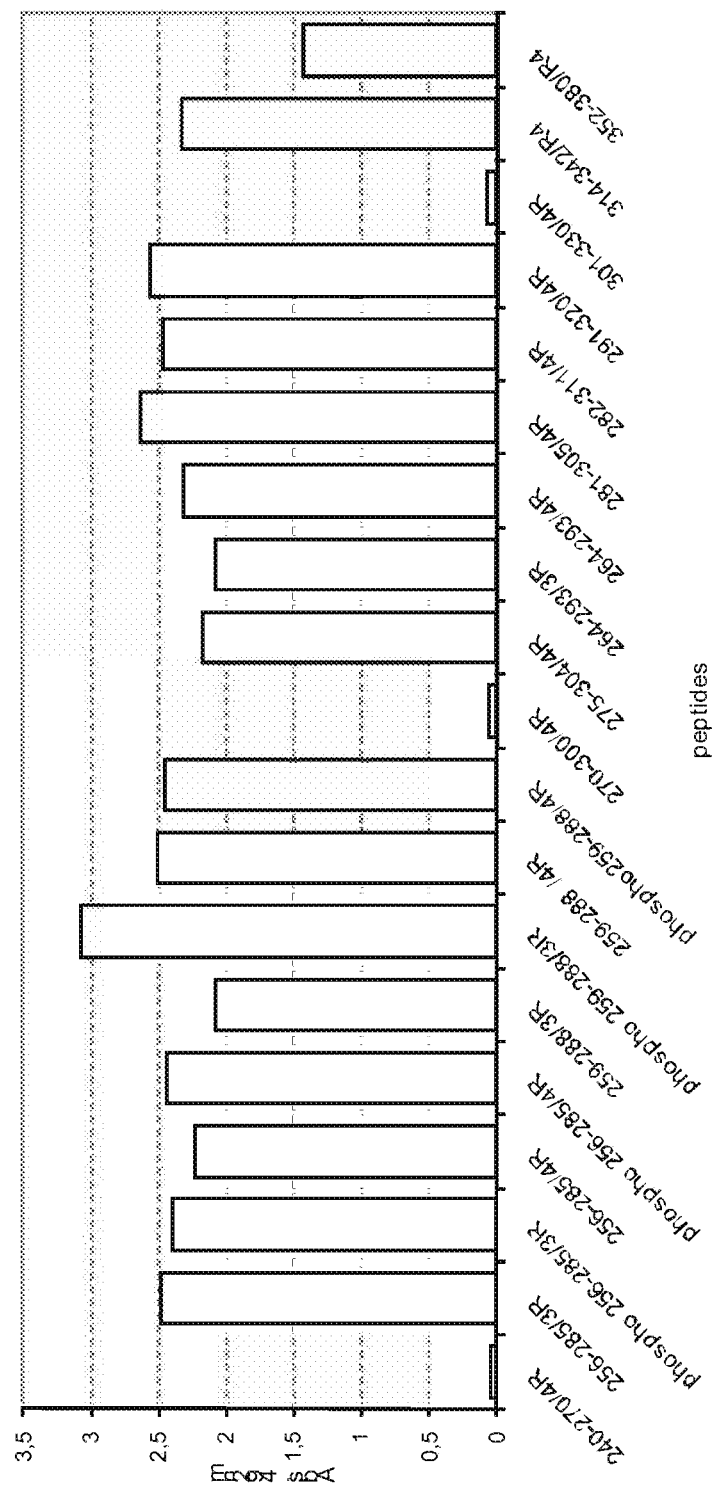
FIGS. 7: (A) and (B) Schematic of synthetic peptides (SEQ ID NOS 206, 207, 208, 2, 210, 211, 212, 3, 214, 215, 4, 217, 26, 219, 36, 221, 222, 109, and 88, respectively, in order of appearance) for epitope mapping and their sequence, respectively. (C) Epitope mapping of DC8E8 with synthetic peptide by ELISA. (D) Schematic of epitopes that DC8E8 is capable of binding to within tau. DC8E8 is capable of binding to any one of four separate binding regions, each of which is a separate epitope, named epitope 1 through 4. The four epitopes each are separately located within the 1$^{st}$ (epitope #1), 2$^{nd}$ (epitope #2), 3$^{rd}$ (epitope #3), and 4$^{th}$ (epitope #4) repeat domains of protein tau. As shown, the four DC8E8 epitopes are each respectively encompassed within one of each of the following amino acid sequences: 267-KHQPGGG-273 (SEQ ID NO: 98) (within 1$^{st}$ repeat domain of tau protein), 298-KHVPGGG-304 (SEQ ID NO: 99) (within 2$^{nd}$ repeat domain of tau protein), 329-HHK-PGGG-335 (SEQ ID NO: 100) (within 3$^{rd}$ repeat domain of tau protein) and 361-THVPGGG-367 (SEQ ID NO: 101) (within 4$^{th}$ repeat domain of tau protein), respectively.
Figure 7D:
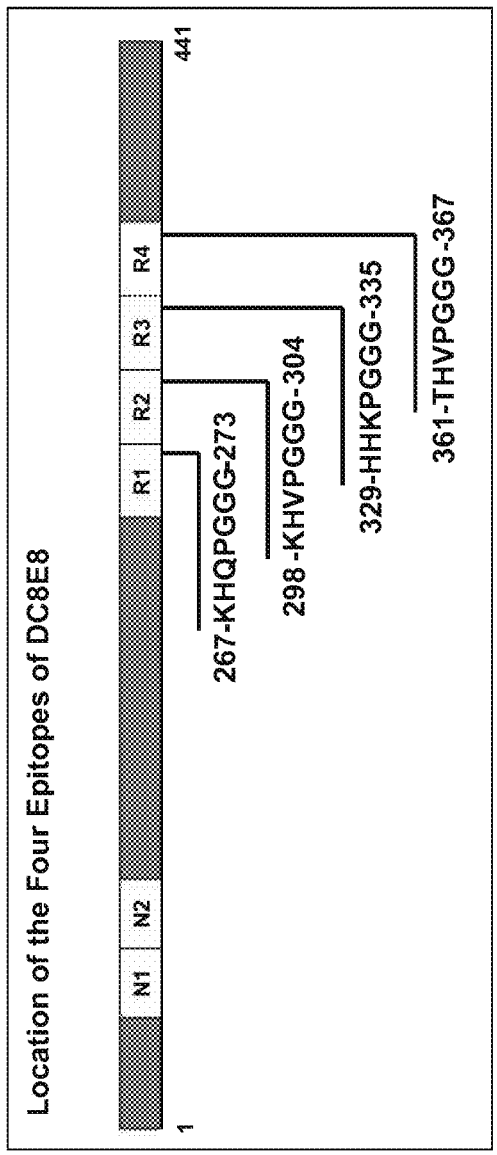

DC8E8 recognized the following human tau proteins: Δ358-441, 4421-441, Δ134-168, Δ1-220, Δ1-126, Δ(1-296; 392-441)/4R and Δ(1-150;392-441)/4R, but failed to recognize the tau proteins with deletions Δ222-427, Δ306-400, Δ228-441, Δ300-312, Δ257-400; Δ137-441, and Δ283-441 (FIG. 6E). DC8E8 recognized the physiological tau isoforms 2N4R and 2N3R to a lesser extent than it recognized the pathological/misdisordered tauΔ(1-296;392-441)/4R, tauΔ(1-150;392-441)/4R and the tau deletion mutants (Δ358-441, Δ421-441; Δ134-168, Δ1-220; Δ1-126) of tau 2N4R (FIG. 6E). More detailed epitope mapping, using tau peptides, revealed that DC8E8 did not recognize tau peptides 240-270, 270-300, and 301-330 (FIG. 7A, 7B, 7C). Together, these findings suggest that DC8E8 has four binding sites or epitopes on human tau, each of which is located in the microtubule-binding repeat domain region of the tau protein, and each of which epitopes is separately located within one of the following tau sequences: 267-KHQPGGG-273 (SEQ ID NO: 98) (1st repeat domain of tau protein), 298-KHVPGGG-304 (SEQ ID NO: 99) (2nd repeat domain of tau protein), 329-HHKPGGG-335 (SEQ ID NO: 100) (3rd repeat domain of tau protein), and 361-THVPGGG-367 (SEQ ID NO: 101) (4th repeat domain of tau protein) (FIG. 7D). Moreover, because DC8E8 binds to the truncated forms of tau better than to the full-length 3-repeat and 4-repeat tau, these results also suggest that DC8E8 binds better to disease forms of tau than to physiological tau (tau39 (2N3R) and tau40 (2N4R)). Also, because tau is thought to change conformation from physiological tau (intrinsically disordered) to disease tau (misdisordered and misordered, Kovacech et al., 2010), these results suggest that one or more of the binding sites for DC8E8 (the DC8E8 epitopes) has a different conformation in physiological tau than it does in disease tau, and that DC8E8 is capable of detecting that conformational change.

Because these tau repeat domains are conserved across species (FIG. 8A), DC8E8 is likely to react against tau proteins from such diverse species as rat, mouse, cow, chimpanzee, frog, and others. An alignment of tau proteins of various animal species was done using software ClustalW2 (available, for example, at www.ebi.ac.uk/Tools/msa/clustalw2/). Human tau is represented by the longest tau isoform expressed in human brain neurons (2N4R, 441 amino acids). Tau proteins of other species were selected from public databases. The sequences within which each of the four epitopes recognized by DC8E8 antibody is located are boxed.

Additional point mutations and deletions were done on certain tau-derived peptides (8-mers, 9-mers, and 10-mers) to further define the DC8E8 epitopes, as assessed by each peptide's ability to compete with tauΔ(1-150;392-441/4R) for binding to DC8E8. Peptides were synthesized by EZBiolabs (USA) with purity higher than 85%. The competition ELISA was carried out according to the following standard protocol. ELISA plates (IWAKI high bind plate, #3801-096, Bertoni GmbH, Austria) were coated overnight at 4° C. with 100 µl/well of 5 µg/ml of recombinant purified tauΔ(1-150; 392-441/4R) in PBS. The IWAKI high bind plates were washed 4 times with PBS/Tween 20 (0.05% v/v), and blocked with PBS/Tween 20 for 2 h at 25° C. Each of the peptides was separately dissolved in PBS at a final concentration of 5 mM. Serial dilutions (2-fold) of the peptides in PBS/Tween 20 were prepared in polypropylene plates with conical well bottom (Greiner, #651201) (concentration range 80 µM, 40 µM, 20 µM, 10 µM, 5 µM, and 2.5 µM). 100 µl of each dilution were added per well. Purified DC8E8 monoclonal antibody (purification was done as described below in Example 5) was diluted to a concentration of 2 µg/ml in PBS/Tween 20 and 100 µl of this diluted antibody was mixed with each serial dilution of peptides resulting in 200 µl mixtures with 100 ng of antibody/100 µl containing each respective test peptide at a concentration of 40 µM, 20 µM, 10 µM, 5 µM, 2.5 µM, and 1.25 µM. The antibody/peptide mixtures were incubated for 1 hr at 25° C. on a rotating platform set to 250 rpm. One hundred microliters (100 µl) of antibody/peptide mixtures were transferred from the polypropylene plates into tauΔ(1-150;392-441/4R)-coated and PBS/Tween 20-blocked IWAKI high bind plates, and incubated for 1 hr at 25° C. on a rotating platform set to 250 rpm. The plates were washed 4× times with PBS/Tween 20. The samples (in the plates) were incubated for 1 hr at 25° C. on a rotating platform (set to 250 rpm) with 100 µl of Polyclonal Goat Anti-Mouse Immunoglobulins/HRP (Dako, #P0447) diluted 1:4,000 in PBS/Tween 20. The plates were washed 4× times with PBS/Tween. The samples/plates were then incubated with 100 µl of a 1.5 mg/2 ml solution of o-PDA (o-phenylenediamine, SIGMA, P1526) in 0.1 M Na-Acetate pH 6.0 (Roth, #6779) supplemented with 1.5 µl/2 ml of 30% $H_2O_2$ (SIGMA, H-0904) for 10 minutes at 25° C., in the dark. The reaction was stopped by adding 100 µl of 2 M $H_2SO_4$ (Merck, 1.00731.1000). The extent of reaction was followed by reading the absorbance of the samples/plates at 490 nm (e.g. using the Victor Multilabel Counter (Wallac).

FIG. 8B shows the results of the competition ELISA performed with the following six peptides: NIKAVPGGGS (SEQ ID NO: 200), NIKHVPGGGS (SEQ ID NO: 201), IKHVPGGGS (SEQ ID NO: 202), KHVPGGGSV (SEQ ID NO: 203), HVPGGGSVQ (SEQ ID NO: 204), and VPGGGSVQ (SEQ ID NO: 205). The peptides KHVPGGGSV (SEQ ID NO: 203) and HVPGGGSVQ (SEQ ID NO: 204), encompassing tau therapeutic epitope #2, competed with at least one of the original therapeutic epitopes present on tauΔ(1-150;392-441/4R). Removal of the underlined histidine from the epitope of SEQ ID NO: 204 lead to a loss of competing activity (see peptide VPGGGSVQ, SEQ ID NO: 205). A point mutation changing a histidine to alanine (at corresponding tau position 299, in "epitope #2") lead to a loss of competing activity (peptide NIKAVPGGGS, SEQ ID NO: 200). Peptides containing 2 or 3 amino acids before "histidine 299" (towards the N terminus) also competed with the original epitope (peptides IKHVPGGGS (SEQ ID NO: 202) and NIKHVPGGGS (SEQ ID NO: 201), respectively). These results suggest that the minimal epitope of DC8E8 falling within the second tau repeat (epitope #2) is within a 6-mer sequence, namely HVPGGG (SEQ ID NO: 154).

The aforementioned mapping experiments suggested the presence of the amino acid sequence PGGG within one ore more of epitopes of the DC8E8 antibody. Furthermore, this amino acid sequence is present in all four epitopes on tau protein bound by DC8E8 (see SEQ ID NOs: 98, 99, 100, 101). In order to determine the residues in the N-terminal region of the DC8E8 epitopes, alanine scanning experiments were done on tau peptide 295-DNIKHVPGGGS-305, which comprises the DC8E8 epitope (within 298-KHVPGGG-304, SEQ ID NO: 99) that falls within the $2^{nd}$ repeat domain of tau.

The binding capacity of the mutant peptides to DC8E8 was assessed by each peptide's ability to compete with tauΔ(1-150;392-441/4R) for binding to DC8E8. Seven peptides were synthesized by EZBiolabs (USA) with purity higher than 85%: ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKAVPGGGS (SEQ ID NO: 159), DNIKHAPGGGS (SEQ ID NO: 161), and the peptide with the original sequence DNIKHVPGGGS (SEQ ID NO: 171). The competition ELISA was carried out according to the following standard protocol. ELISA plates (IWAKI high bind plate, #3801-096, Bertoni GmbH, Austria) were coated overnight at 4° C. with 100 µl/well of 5 µg/ml of recombinant purified tauΔ(1-150;392-441/4R) in PBS. The IWAKI high bind plates were washed 4 times with PBS/Tween 20 (0.05% v/v), and blocked with PBS/Tween 20 for 2 h at 25° C. Each of the peptides was separately dissolved in PBS at a final concentration of 5 mM. Serial dilutions (2-fold) of the peptides in PBS/Tween 20 were prepared in polypropylene plates with conical well bottom (Greiner, #651201) (concentration range 320 µM, 160 µM, 80 µM, 40 µM, 20 µM, 10 µM, 5 µM, and 2.5 µM). 100 µl of each dilution were added per well. Purified DC8E8 monoclonal antibody (purification was done as described below in Example 5) was diluted to a concentration of 2 µg/ml in PBS/Tween 20 and 100 µl of this diluted antibody was mixed with each serial dilution of peptides resulting in 200 µl mixtures with 100 ng of antibody/1000 containing each respective test peptide at a concentration of 160 µM, 80 µM, 40 µM, 20 µM, 10 µM, 5 µM, 2.5 µM, and 1.25 µM. The antibody/peptide mixtures were incubated for 1 hr at 25° C. on a rotating platform set to 250 rpm, One hundred microliters (100 µl) of antibody/peptide mixtures were transferred from the polypropylene plates into tauΔ(1-150;392-441/4R)-coated and PBS/Tween 20-blocked IWAKI high bind plates, and incubated for 1 hr at 25° C. on a rotating platform set to 250 rpm. The plates were washed 4× times with PBS/Tween 20. The samples (in the plates) were incubated for 1 hr at 25° C. on a rotating platform (set to 250 rpm) with 100 µl of Polyclonal Goat Anti-Mouse Immunoglobulins/HRP (Dako, #P0447) diluted 1:4,000 in PBS/Tween 20. The plates were washed 4× times with PBS/Tween. The samples/plates were then incubated with 100 µl of a 1.5 mg/2 ml solution of 0-PDA (o-phenylenediamine, SIGMA, P1526) in 0.1 M Na-Acetate pH 6.0 (Roth, #6779) supplemented with 1.5 µl/2 ml of 30% $H_2O_2$ (SIGMA, H-0904) for 10 minutes at 25° C., in the dark. The reaction was stopped by adding 100 µl of 2 M $H_2SO_4$ (Merck, 1.00731.1000). The extent of reaction was followed by reading the absorbance of the samples/plates at 490 nm (e.g. using the Victor Multilabel Counter (Wallac).

Figure 8C:
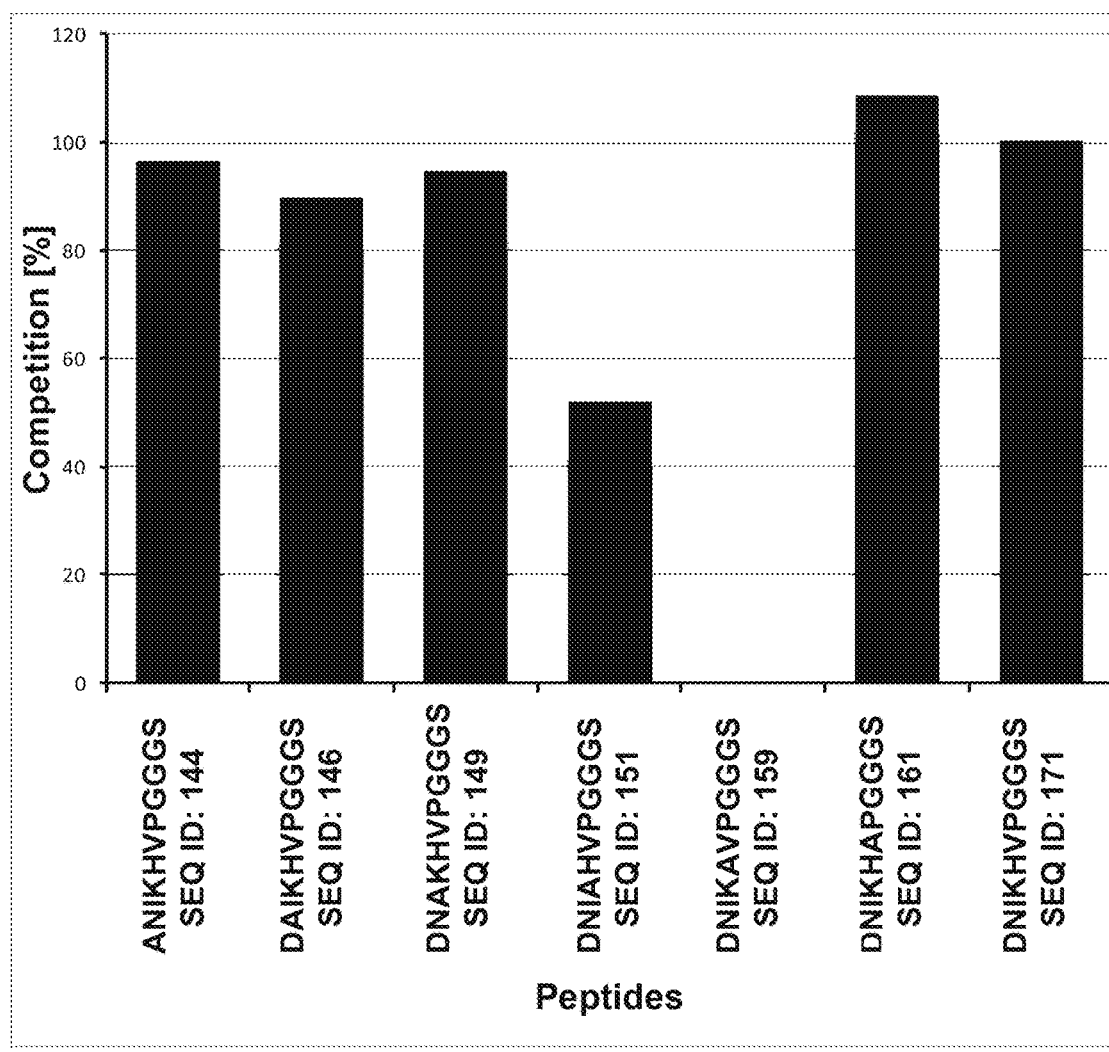
FIG. 8: (A) Alignment of human tau amino acid sequence (SEQ ID NO: 225) to tau protein sequence from other species (SEQ ID NOS 226-245, respectively, in order of appearance). The full length of human tau protein was used for the alignment; only amino acids 265-368 of human tau from the alignment are shown. The regions comprising the four separate DC8E8 epitopes on human tau and the aligned sequences are boxed and shown in bold. (B) Competition ELISA showing the ability of six tau peptides (SEQ ID NOS 201-205 and 200, respectively, in order of appearance) to compete with tauΔ(1-150;392-441)/4R (SEQ ID NO: 199) for binding to antibody DC8E8, capable (C) Competition ELISA showing the ability of seven tau peptides (SEQ ID NOS 144, 146, 149, 151, 159, 161, and 171) to compete with tauΔ(1-150;392-441)/4R for binding to antibody DC8E8, capable of recognizing at least one of the tau epitopes involved in tau-tau aggregation of recognizing at least one of the tau epitopes involved in tau-tau aggregation.

FIG. 8C shows the results of the competition ELISA performed with the following seven peptides: ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKAVPGGGS (SEQ ID NO: 159), DNIKHAPGGGS (SEQ ID NO: 161), and ANIKHVPGGGS (SEQ ID NO: 171). A point mutation changing a histidine to alanine (at corresponding tau position 299, in "epitope #2") lead to a complete loss of competing activity with tauΔ(1-150;392-441/4R) for binding to DC8E8 (peptide DNIKAVPGGGS, SEQ ID NO: 159). Mutations that changed amino acids D, N, I, K and V to alanine did not abolish the competing activity of the respective mutant peptides (peptides ANIKHVPGGGS (SEQ ID NO: 144), DAIKHVPGGGS (SEQ ID NO: 146), DNAKHVPGGGS (SEQ ID NO: 149), DNIAHVPGGGS (SEQ ID NO: 151), DNIKHAPGGGS (SEQ ID NO: 161). These results suggest that the minimal epitope of DC8E8 falling within the second tau repeat (epitope #2) is within a 6-mer sequence, namely HVPGGG (SEQ ID NO: 154), and that DC8E8 binds to HXPGGG (SEQ ID NO:164).

Example 5: DC8E8 Recognizes Misdisordered TauΔ(1-150;151-391)/4R, as Assessed by Surface Plasmon Resonance Surface plasmon resonance (SPR) can be used for the detection of protein binding and to determine the thermodynamic parameters of protein complexes (e.g., antibody-antigen complexes) by direct monitoring of the binding event in real time. This technology is routinely used to characterize both diagnostic and therapeutic antibodies (See, e.g., Karlsson and Larsson, Affinity Measurement Using Surface Plasmon Resonance, in Methods in Molecular Biology, Vol. 248: Antibody Engineering: Methods and Protocols. Edited by: B. K. C. Lo © Humana Press Inc., Totowa, N.J., (2008)).

For SPR experiments, the DC8E8 monoclonal antibody (mAb) was purified from serum-free hybridoma supernate on a Protein G affinity column, as follows. The hybridoma supernate was adjusted to pH 7.5, the solution was pre-cleared by centrifugation, filtered through a 0.45 μm membrane filter, and loaded onto a 5 ml Protein G Sepharose column. DC8E8 mAb was eluted from the column with 0.1 M Glycine-HCl, pH 2.7. Eluted fractions were immediately neutralized with 1M Tris-HCl pH 9.0. Pooled fractions were dialyzed against PBS, concentrated by ultrafiltration, and stored at −70° C. The concentration of the antibody was determined by measuring absorbance at 280 nm, using the formula $c(mg/ml)=A_{280nm}/1.43$.

A BIACORE3000 instrument with a CM5 sensor chip (Biacore AB, Uppsala) was used for the SPR assays. Amine-coupling reagents (EDC, NHS, ethanolamine pH 8.5), P20 detergent, and 10 mM sodium acetate pH 5.0 were obtained from Biacore AB, These experiments were done at 25° C. in PBS pH 7.4 with 0.005% of P20 (PBS-P) as the running buffer. Typically, 5,000 RU (response units) of polyclonal anti-mouse antibody (No. Z 0420; DakoCytomation, Glostrup, Denmark) was coupled at pH 5.0 via primary amines simultaneously in two flow cells, one of which was used as a reference measurement.

In each analysis cycle, purified DC8E8 was captured in the analytical flow cell to reach an immobilization level of 230-250 RU. For $K_A$ determinations, as well as for the determination of kinetic rate constants ($k_{ON}$ and $k_{OFF}$), two-fold serial dilutions of either tau proteins (against which DC8E8 affinity was tested), or PBS-P as a control, were injected at a flow rate 50 μl/min over the sensor chip. Kinetic binding data were double referenced according to Myszka, 1999 and fitted by BIA evaluation software 4.1 (Biacore AB) to a two-phase reaction model. Kinetic rate constants were approximated globally, maximal responses were fitted locally, and the bulk response was set to zero.

Figure 9A:
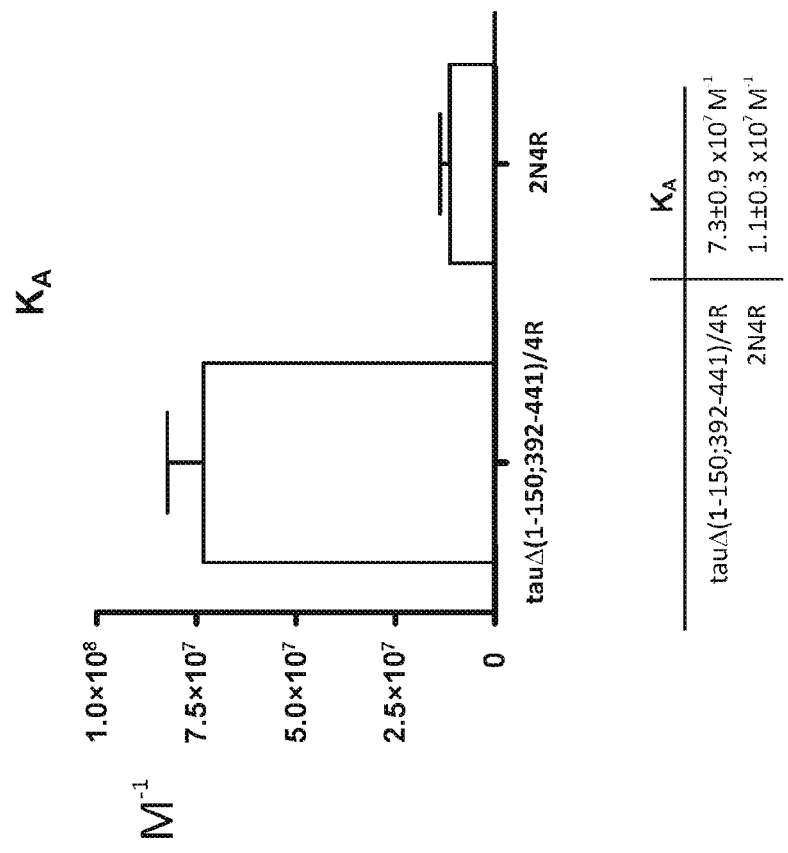
FIG. 9: (A). Surface plasmon resonance (SPR) to characterize DC8E8's binding to tauΔ(1-150;392-441)/4R and 2N4R. (B). Surface plasmon resonance (SPR) to characterize DC8E8's binding to tauΔ(1-150;392-441)/3R and 2N3R.
Figure 9B:
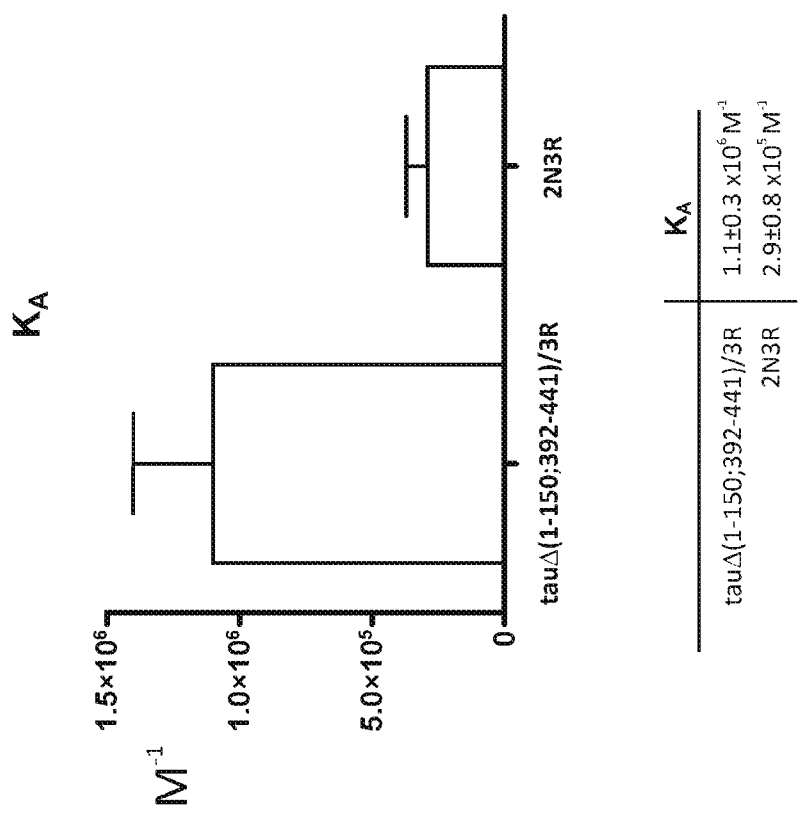

In order to quantify DC8E8's affinity for each of the tested tau proteins, the association equilibrium binding constants ($K_A$) were determined for DC8E8 binding to the four repeat tau protein isoform 2N4R, three repeat tau protein isoform 2N3R, as well as to misdisordered tauΔ(1-150;392-441)/4R and misdisordered tauΔ(1-150;392-441)/3R. All tau proteins used for SPR were prepared according to Example 1. The affinity of DC8E8 was highest for four repeat tauΔ(1-150; 392-441)/4R, followed by the full-length four repeat tau isoform 2N4R, then for three repeat tauΔ(1-150;392-441)/3R, and lastly for the three repeat full-length tau isoform 2N3R (FIG. 9A, 9B). These results confirmed: (1) the specificity of DC8E8 for the misdisordered form of tau, and (2) the selectivity of DC8E8 for misdisordered tau (i.e., disease or pathological tau) over the full-length tau (i.e., normal or physiological tau).

Figure 10A:
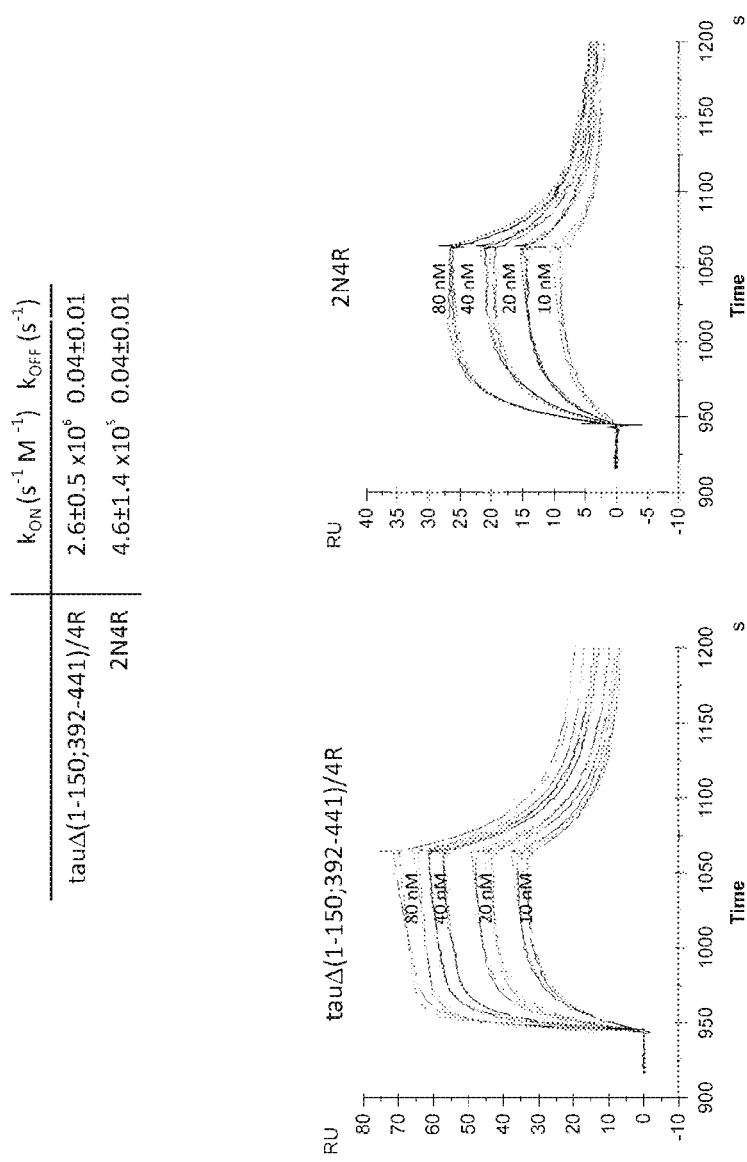
FIG. 10: (A). Association and dissociation rates of DC8E8 binding to tauΔ(1-150;392-441)/4R and to tau 2N4R, as determined by SPR. (B). Association and dissociation rates of DC8E8 binding to tauΔ(1-150;392-441)/3R and to tau 2N3R, as determined by SPR. The concentrations used in the measurements are indicated in the plots, dashed lines were interpolated by computer program BIA evaluation software 4.1 (Biacore AB) from measured data for kinetic parameter calculations.
Figure 10B:
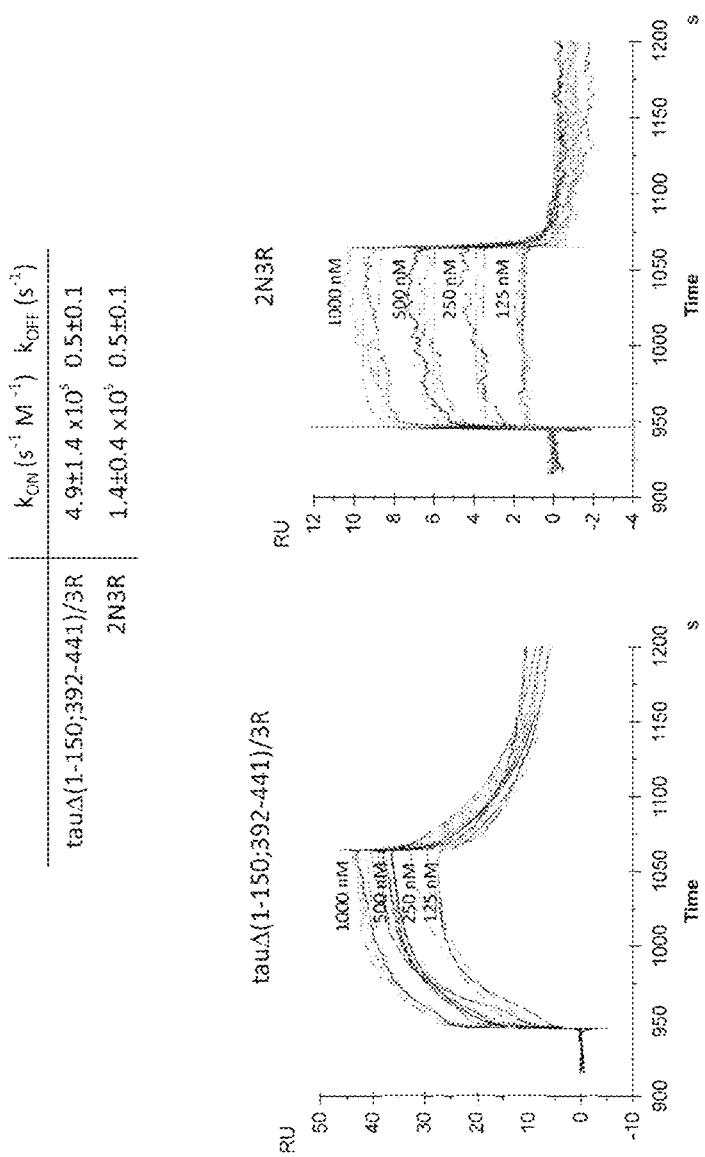

Real time monitoring of binding events using SPR enabled the measurement of the kinetic rate of association (kON) and dissociation (kOFF) between DC8E8 and several tau proteins. DC8E8's binding kinetics revealed an altered conformation for misdisordered tauΔ(1-150;392-441)/4R and tauΔ(1-150;392-441)13R, when compared to physiological 2N4R tau, which is indicated by more easily accessible DC8E8 epitope(s) in the misdisorderd tau proteins. This is reflected by the faster binding and higher kON for the misdisordered tau proteins compared to their full-length counterparts. Moreover, the presence of an extra binding site for DC8E8 on the four-repeat tau protein species resulted in a 10-times slower dissociation of 4R tau species from the complex with DC8E8 and a corresponding 10-times lower kOFF (FIG. 10A, 10B; the dashed lines were interpolated from measured data by kinetic parameter calculations using a computer program BIAEvaluation v4.1).

Example 6: DC8E8 Recognizes all Developmental Stages of Neurofibrillary Degeneration in Human Alzheimer's Disease Brain Human brain tissue (on paraffin blocks) were obtained from the Netherlands brain bank. The blocks were cut on a microtome. Paraffin-sections (8 μm) of the hippocampus-entorhinal cortex from Alzheimer's disease brain (Braak's stage VI) and non-demented control (Braak's stage I and III) were treated with cold (+4° C.) 99% formic acid for 1 min at room temperature (25° C.). The tissue sections were incubated in blocking solution (5% BSA, 0.3% Triton X-100 in 50 nM Tris-HCl) and then overnight with purified primary antibody DC8E8 (7.8 mg/ml; prepared as described in Example 5), which was diluted 1:2,000 in blocking solution. Subsequently, the sections were incubated with a biotinylated secondary antibody (Vectastain Elite ABC Kit, Vector Laboratories) at room temperature for an hour and then reacted with avidin-biotin peroxidase-complex for 60 minutes (Vectastain Elite ABC Kit, Vector Laboratories), both at room temperature (25° C.). The immunoreaction was visualized with peroxidase substrate kit (Vector VIP, Vector laboratories, Ca, USA) and counterstained with methyl green (Vector Laboratories). The sections were examined with an Olympus BX71 microscope.

Figure 11D:
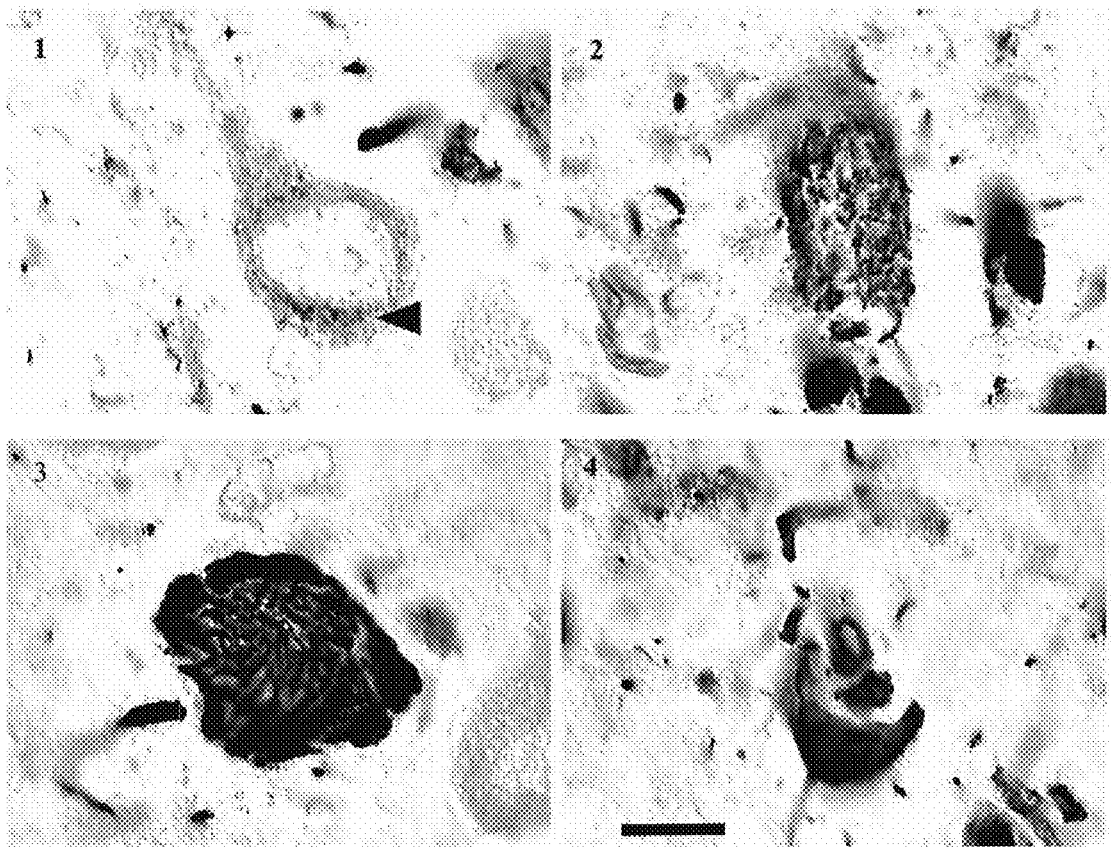
FIG. 11: Monoclonal antibody DC8E8 is able to discriminate between preclinical AD, clinically incipient AD and fully developed final stage AD. DC8E8 displays staining of early stages (tau monomers, dimers) of pathological tau in human preclinical AD—Braak's Stage I. (A). The antibody recognizes the stage of pathological tau oligomers (arrows) and the stage of pathological tau polymers (tangles) (arrowhead) (B). In fully developed Alzheimer's disease (final stage—Braak's Stage VI), DC8E8 recognizes mainly pathological tau polymers in forms of the neurofibrillary tangles (arrowhead), neuritic plaques (inside the circle) and neuritic threads (inside the pentagon) (C). Scale bar: 100 μm. Monoclonal antibody DC8E8 recognizes all developmental stages of tangle formation in Alzheimer's disease (D). DC8E8 recognizes early developmental stages of tangle formation—monomeric, dimeric and early oligomeric stage (D1), and late oligomeric, pre-tangle stage (D2), as well as late developmental stages of pathological tau polymers—intracellular (D3) and extracellular neurofibrillary tangles (D4). Arrowhead indicates small oligomeric tau aggregates inside pyramidal hippocampal neurons (D1). Scale bar: 10 μm

Monoclonal antibody DC8E8 discriminated between pre-clinical AD, clinically incipient AD, and fully developed final stage of AD. Immunohistochemical study showed that DC8E8 detected early stages (tau monomers, dimers) of pathological tau in human preclinical AD—Braak's Stage I. (FIG. 11A). The brain contains only a limited number of neurofibrillary tangles (NFTs) in the entorhinal cortex and no NFTs in the hippocampus (Braak's stage I). In the clinically incipient AD brain, where a few NFTs were found in the hippocampus (Braak's stage III), the DC8E8 mAb recognized both the stage of pathological tau oligomers (arrows) and the stage of pathological tau polymers (tangles) (FIG. 11B). In fully developed Alzheimer's disease brain, where extensive neurofibrillary degeneration is present, DC8E8 recognizes mainly pathological tau polymers in the form of neurofibrillary tangles, neuritic plaques, and neurotic threads (FIG. 11C). Thus, mAb DC8E8 recognizes all developmental stages of neurofibrillary lesions in human Alzheimer's disease brain tissue, including monomeric; dimeric, early-oligomeric stage (FIG. 11D, panel 1) and late-oligomeric pre-tangle stage (FIG. 11D, panel 2); as well as late developmental stages of pathological tau polymers—intracellular (FIG. 11D, panel 3) and extracellular neurofibrillary tangles (FIG. 11D, panel 4). This reactivity of mAb DC8E8 is thus useful for both diagnostic and therapeutic applications of this antibody.

Example 7: DC8E8 Recognizes all Developmental Stages of Neurofibrillary Degeneration in the Brain of Transgenic Rats SHR72, as Seen in Human Alzheimer's Disease The SHR24 Transgenic Rat Line:
this line expresses tauΔ(1-150;392-441)/3R, a protein described in International Patent Application POT WO 2004/007547. Generation and characterization of this transgenic line has been described in Filipcik et al., 2010. These transgenic rats develop progressive age-dependent neurofibrillary degeneration in the cortical brain areas. Neurofibrillary tangles (NFTs) satisfied several key histological criteria used to identify neurofibrillary degeneration in human Alzheimer's disease including argyrophilia, Congo red birefringence, and Thioflavin S reactivity. Neurofibrillary tangles were also identified with antibodies used to detect pathologic tau in the human brain, including DC11, which recognizes a disease tau conformation (Vechterova et al. 2003; Kovacech et al. 2010), and antibodies that are specific for hyperphosphorylated forms of tau protein. Moreover, neurofibrillary degeneration was characterized by extensive formation of sarkosyl insoluble tau protein complexes consisting of rat endogenous and transgenic truncated tau species (Filipcik et al., 2010). The most prominent histopathological feature of these transgenic rats is extensive neurofibrillary pathology—neurofibrillary tangles in the cortex. The median survival time of transgenic rats is 222.5 days (SD=43.56) and the longest survival period reaches 475 days (Filipcik et al., 2010).

The SHR72 Transgenic Rat Line:

These transgenic rats express human truncated tauΔ(1-150;392-441)/4R according to International Patent Application POT WO 2004/007547) in several brain regions and spinal cord. Generation of this rat line was described by Zilka et al., 2006, and tau pathology was described in Koson et al., 2008. The most prominent histopathological feature of these transgenic rats is extensive neurofibrillary pathology; e.g.; neurofibrillary tangles. The appearance of NFTs satisfied several histological criteria used to identify neurofibrillary degeneration in human AD including argyrophilic, Congo red birefringence, and Thioflavin S reactivity. NFTs were also identified with antibodies used to detect pathologic tau in the human brain, including DC11, recognizing an abnormal tau conformation (see U.S. Pat. No. 7,446,180), and antibodies that are specific for hyperphosphorylated forms of tau protein. Moreover, neurofibrillary degeneration was characterized by extensive formation of sarcosyl-insoluble tau protein complexes consisting of rat endogenous and human truncated tau species. In a heterozygote line of this model the most extensive neurofibrillary pathology was observed in the brainstem and spinal cord (Zilka et al., 2006). The transgene expression levels, the NFT load, and the rats' life span have been previously determined. The median survival time for the transgenic rats (line SHR72) was 222.5 days (SD=24.48) (Koson et al., 2008).

Transgenic rat lines SHR24 (express tauΔ(1-150;392-441)/3R) and SHR72 (express tauΔ(1-150;392-441)/4R) develop extensive neurofibrillary degeneration in the brain and spinal cord, Transgenic rat line SHR24 displays severe neurodegeneration in the isocortex, brainstem and spinal cord, while SHR72 transgenic rats develop NFT mainly in the brainstem and spinal cord but not in cortex. Progression of sensorimotor and neurological impairment is similar in both transgenic lines; however SHR72 transgenic rats show shorter lifespan.

In the transgenic rat studies presented in this application, hemizygous transgenic rats were used (SHR24 and SHR72). All rats were housed under standard laboratory conditions with free access to water and food and were kept under diurnal lighting conditions (12 hour light/dark cycles with light starting at 7:00 a.m.). Efforts were made to minimize the number of rats utilized and to limit their discomfort, pain, and suffering.

Immunohistochemistry of Rat Brain Tissue with DC8E8:

transgenic rats (7 months old) were perfused transcardially with PBS for 1 min under deep anesthesia followed by perfusion with 100 ml of 4% paraformaldehyde (pH 7.4). After perfusion, the head was cut off and the brain was quickly removed. The brain was cut sagittally into two equal-sized hemispheres using disposable scalpel blades. The brain tissues were post-fixed in 4% paraformaldehyde, embedded in paraffin, and cut into sections on a microtome. Immunohistochemistry and histopathology were done on 8 μm paraffin-embedded tissue sections. Tissue sections were pre-treated for 20 min with an antigen unmasking solution (Vector laboratories, CA, USA) and for 1 min with cold (+4° C.) 90% formic acid (Applichem, Germany), at room temperature (25° C.). After blocking, the sections were incubated overnight with purified monoclonal antibody DC8E8 (7.8 mg/ml) that was diluted 1:2000 in blocking solution (5% bovine serum albumin, 0.3% Triton X 100 in 50 nM Tris-HCl). After washing, the sections were incubated with a biotinylated secondary antibody (Vectastain Elite ABC Kit, Vector Laboratories) at room temperature for an hour, and then reacted with an avidin-biotin peroxidase-complex solution for 60 minutes (Vectastain Elite ABC Kit, Vector Laboratories), at room temperature (25° C.). The immunoreaction was visualized with a peroxidase substrate kit (Vector VIP, Vector laboratories, Ca, USA), and the sections were counterstained with methyl green (Vector Laboratories). Sections were examined with an Olympus BX71 microscope.

Figure 12A:
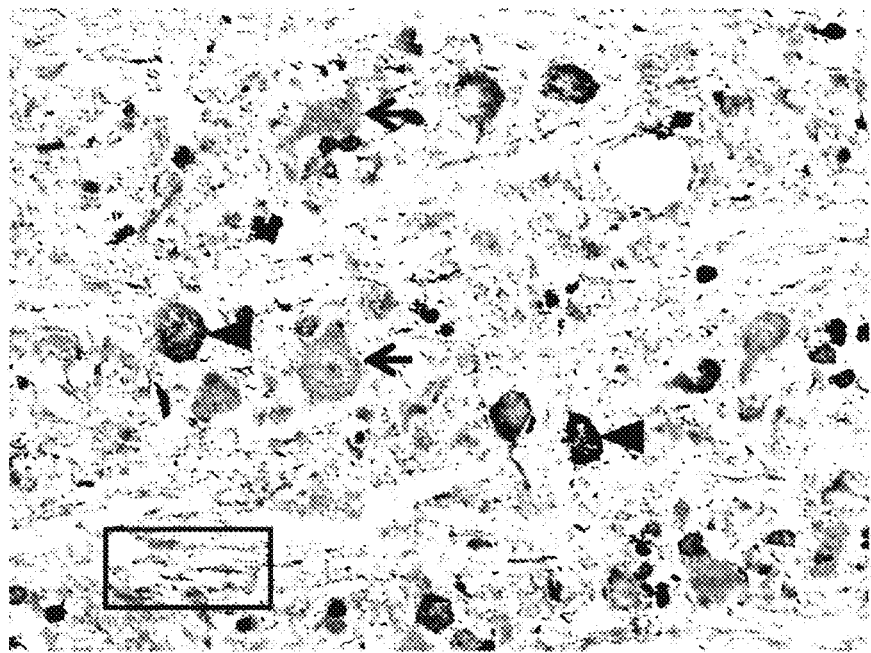
FIG. 12: (A) Monoclonal antibody DC8E8 recognizes neurofibrillary degeneration in transgenic rats SHR72. DC8E8 recognizes tau oligomeric stage (arrows) and tangle stage (arrowhead) of tau neurodegeneration. Moreover, the antibody reacts with misfolded tau that is located in the axonal fibers (inside the rectangle). (B) In age-matched control rat brains the antibody does not display intraneuronal staining. Scale bar 20 μm. DC8E8 also recognizes all developmental stages of tangle formation in transgenic rat brain (SHR 72) as in human Alzheimer's disease. DC8E8 recognizes early developmental stages of tangle formation—monomeric, dimeric and early oligomeric stage (C) and late oligomeric pre tangle stage (D), as well as late developmental stages of pathological tau polymers—intracellular (E) and extracellular neurofibrillary tangles (missing nucleus) (F). Arrowhead in (C) indicates small oligomeric tau aggregates inside the neurons (A). Scale bar: 10 μm
Figure 12B:

In the transgenic rat brain (SHR72), mAb DC8E8 recognized the disease stage of pathological tau oligomers (arrows) and the disease stage of pathological tau polymers (tangles) (FIG. 12A). Moreover, DC8E8 reacted with misfolded tau that is located in the axonal fibers. In age-matched control rat brains the antibody did not stain neuronal soma or axonal processes (FIG. 12B).

As in human Alzheimers disease brain (see supra), mAb DC8E8 recognized all developmental stages of neurofibrillary lesions in the brain of SHR72 transgenic rats, including diseased monomeric, dimeric, and early-oligomeric stage (FIG. 12C) and late-oligomeric pre tangle stage tau (FIG. 12D), as well as late developmental stages of pathological tau polymers intracellular (FIG. 12E) and extracellular neurofibrillary tangles (FIG. 12F).

Figure 13A:
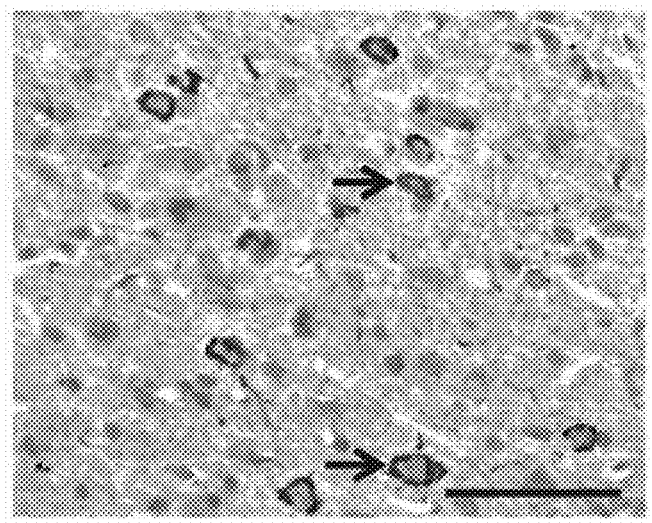
FIG. 13: (A) DC8E8 staining of neurofibrillary tangles in the cortex of SHR24 transgenic rats, which express tauΔ(1-150;392-441)/3R. (B) DC8E8 recognized neurofibrillary tangles in the brainstem of the transgenic rats SHR72, which express tauΔ(1-150;392-441)/4R. Tissue sections were counterstained with methylgreen. Arrows—neurofibrillary tangles. Scale bar: 50 μm
Figure 13B:
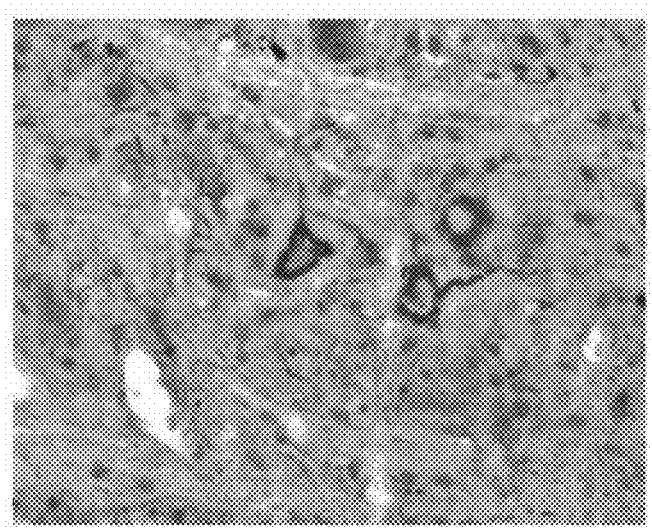

DC8E8 also recognized neurofibrillary tangles in the brain of transgenic rats expressing tauΔ(1-150;392-441)/3R) (SHR24, FIG. 13A; SHR72, FIG. 13B).

Example 8: DC8E8 Recognizes Both Soluble Misdisordered Tau and Insoluble Tau Species in Human Alzheimer's Disease and in Brains of Tau Transgenic Rats Soluble tau and insoluble tau complexes were isolated either from human AD brains or from disease tau transgenic rat brains (SHR24 and SHR72 lines described in Example 7), using the sarkosyl method (Greenberg and Davies, 1990). For protein extraction, frozen human AD brain tissues (allocortex, samples of Braak stages V and VI obtained form the Netherlands brain bank) and tissues from transgenic SHR24 rats (isocortex, 10, 12 and 14 months old) and from transgenic SHR72 rats (brain stem, 7.5 months old) were homogenized in 10 volumes of cold extraction buffer (10 mM Tris pH 7.4, 0.8 M NaCl, 1 mM EGTA, and 10% sucrose). The homogenates were centrifuged for 20 min at 20,000×g and 50 μl of the supernates were used for the analysis of soluble tau.

To prepare sarkosyl-insoluble tau, the remaining supernates were supplemented with N-lauroylsarcosine (SIGMA) to a final concentration of 1% and incubated for 1 h at room temperature, while shaking. After centrifugation at 100, 000×g for 1 h, the resulting supernates were discarded, and the pellets comprise the sarkosyl-insoluble tau fraction.

Soluble tau and sarkosyl-insoluble tau fractions were analyzed by immunoblotting. Soluble tau fractions were diluted with an equal volume of 2×SDS-sample loading buffer (with β-mercaptoethanol) (Laemmli, 1970) and 15 μg of proteins were loaded per lane. For sarkosyl-insoluble tau fractions, the pellets were dissolved in 1×SDS-sample loading buffer, in 1/50 volume of the soluble fraction used for the preparation of the insoluble tau fraction. Then, equal volumes of soluble tau and sarkosyl-insoluble tau fractions were used for immunoblot analysis, which corresponded to 15 μg of total protein in the soluble fraction (see Filipcik et al. 2010). Samples were heated at 95° C. for 5 min, loaded onto 5-20% gradient SOS polyacrylamide gels, and electrophoresed in a Tris-glycine-SDS buffer system for 40 minutes at 25 mA. Proteins were transferred to a polyvinylidene fluoride (PVDF) membrane (1 h at 150 mA in 10 mM CAPS, pH 12). After the transfer; the membranes were blocked in 5% non-fat dry milk in phosphate-buffered-saline (PBS; 136.89 mM NaCl, 2.7 mM KCl, 8.09 mM $Na_2HPO_4$, 1.47 mM $KH_2PO_4$) for 1 h at room temperature, and then incubated for 1 h with DC8E8 hybridoma culture supernate, diluted 1:1 with TBST-milk (20 mM pH 7.4, 150 mM NaCl, 0.1% Tween 20, 5% non-fat dried milk), followed by three washes with large volumes of PBS. The membranes were incubated (1 h at room temperature) with HRP-conjugated goat anti-mouse Ig (DAKO, Denmark), diluted 1:4,000 with PBS, as a secondary antibody. This incubation was followed by washing (three times) with 0.2% Igepal CA-630 (SIGMA) in PBS. The blots were developed with SuperSignal West Pico Chemiluminescent Substrate (Pierce, U.S.A), and the protein signals detected using a LAS3000 imaging system (FUJI Photo Film Co., Japan). The chemiluminescence signal intensities were quantified using AIDA (Advanced Image Data Analyzer, Raytest, Straubenhardt, Germany) software.

DC8E8 recognized both soluble human tauΔ(1-150;392-441)/3R and physiological rat tau isoforms in SHR24 transgenic rats (FIG. 14A). Moreover, DC8E8 recognized tauΔ(1-150;392-441)/3R and pathological rat tau proteins in the sarkosyl-insoluble tau fractions from SHR24 rat brains (FIG. 14B). Importantly, DC8E8 strongly recognized pathological human tau proteins in the sarkosyl-insoluble tau fraction in the human AD brains (Braak stages V and VI, FIGS. 14B and 14C). DC8E8 recognized both soluble human tauΔ(1-150;392-441)/4R and full-length (physiological) rat tau isoforms in SHR72 transgenic rats (FIG. 14D). Significantly, DC8E8 specifically recognized pathological tauΔ(1-150; 392-441)/4R and pathological forms of rat tau in the sarkosyl-insoluble tau fractions from SHR72 rat brains (FIG. 14D).

Example 9: DC8E8 Inhibits Pathological Tau-Tau Interactions

The Tau Fibrillization Assay.

An in vitro tau fibrillization assay was used to determine whether DC8E8 had an inhibitory effect on pathological tau-tau interactions. The assay is based on an intrinsic property of tau proteins, namely their ability to undergo a conformational change upon interaction with polyanions, such as the sulfated glycosaminoglycan heparin. This altered conformation on one tau molecule further leads to its pathological interactions with another tau molecule, stabilization of the tau-tau complex through formation of cross-β sheet structures in the microtubule binding regions of the interacting tau molecules, and, lastly, formation of Alzheimer's disease-like paired helical filaments (PHFs) (Skrabana et al., 2006). The formation of the beta-sheet-rich structures can be detected by fluorescent dyes, like Thioflavin T.

The assay to measure the effect of DC8E8 on pathological tau-tau interactions was setup in PBS (filtered through a 0.2 μm filter) containing: 20 μM (final concentration) of either one of the tested recombinant tau proteins (tauΔ(1-150; 392-441)/4R or tauΔ(1-296;392-441)/4R), purified as described in Example 1; 5 μM heparin (Heparin sodium salt from porcine intestinal mucosa, ≥150 IU/mg, dry basis, from SIGMA); and 12.5 μM (final concentration) Thioflavin T. Each reaction (80 μl final volume) was incubated for 20 h at 37° C. in sealed black solid polystyrene plates (384 wells, Greiner BioOne). Thioflavin T fluorescence was measured using a fluorescence reader (Fluoroskan Ascent FL (Labsystems)), with an excitation wavelength of 450 nm, emission at 510 nm, and 200 ms measurement time. For determining the inhibitory activity of mAb DC8E8 on pathological tau-tau interactions, purified DC8E8 (Example 5) was added to the reaction mix at 20 μM final concentration, prior to the incubation at 37° C. Two antibodies were used as controls: DC51 (recognizing an envelope protein of the rabies virus; Macikova et al., 1992) and DC11 (recognizing certain truncated conformationally altered forms of tau, U.S. Pat. No. 7,446,180).

Figure 15A:
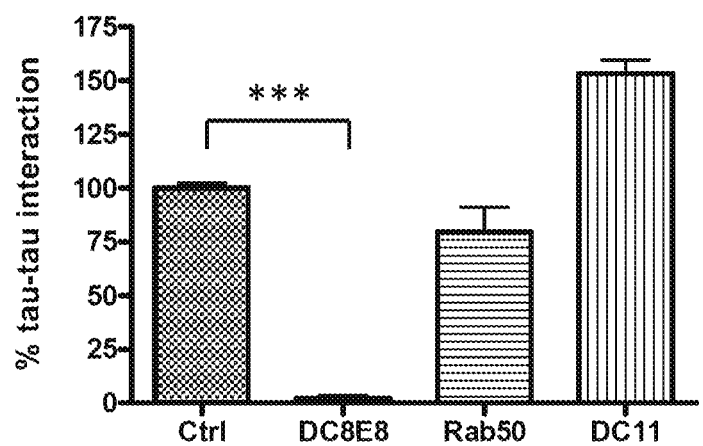
FIG. 15: DC8E8 inhibits pathological tau-tau interaction in fluorescence-based tau fibrillization assay. TauΔ(1-150:392-441)/4R (FIG. 15A) or tauΔ(1-296:392-441)/4R (FIG. 15B) were induced by heparin to undergo a conformational change and fibrilize as measured by Thioflavin T fluorescence; mAbs DC8E8, Rab50, and DC11 were tested for their ability to prevent the pathological conformation change.
Figure 15B:
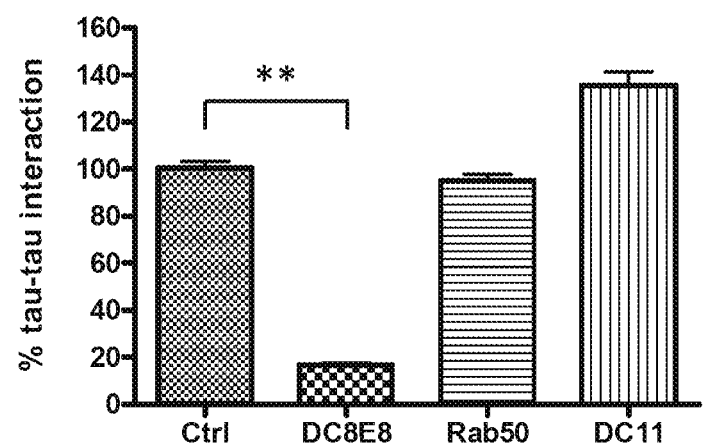

The amount of conformationally altered and fibrilized tau was measured by Thioflavin T fluorescence in the absence ("Ctrl") and in the presence ("DC8E8") of DC8E8 (FIGS. 15A and 15B). mAb DC8E8, added at 20 μM final concentration, prevented the pathological conformational change and fibrillization of both misdisordered tau proteins, reducing the amount of fibrillized pathological tau forms to less than 5% and 16% for tauΔ(1-150;392-441)/4R and tauΔ(1-296;392-441)/4R, respectively. This inhibitory activity of DC8E8 was statistically significant when analyzed by a non-parametric t-test ("DC8E8", p<0.001 and p p<0.01 in FIGS. 15A and 15B, respectively). An irrelevant antibody, Rab50 (Macikova et al., 1992), which does not bind tau, did not prevent the conformational change of tau, resulting in unaltered Thioflavin T fluorescence ("Rab50"). The antibody DC11, which recognizes certain pathologically altered conformations of tau (Vechterova et al., 2003 and U.S. Pat. No. 7,446,180), further promoted the formation of fibrilized tau; this effect can reflect a stabilization of the pathological conformation of tau required for the abnormal tau-tau interaction and fibril formation by DC11.

Figure 16:
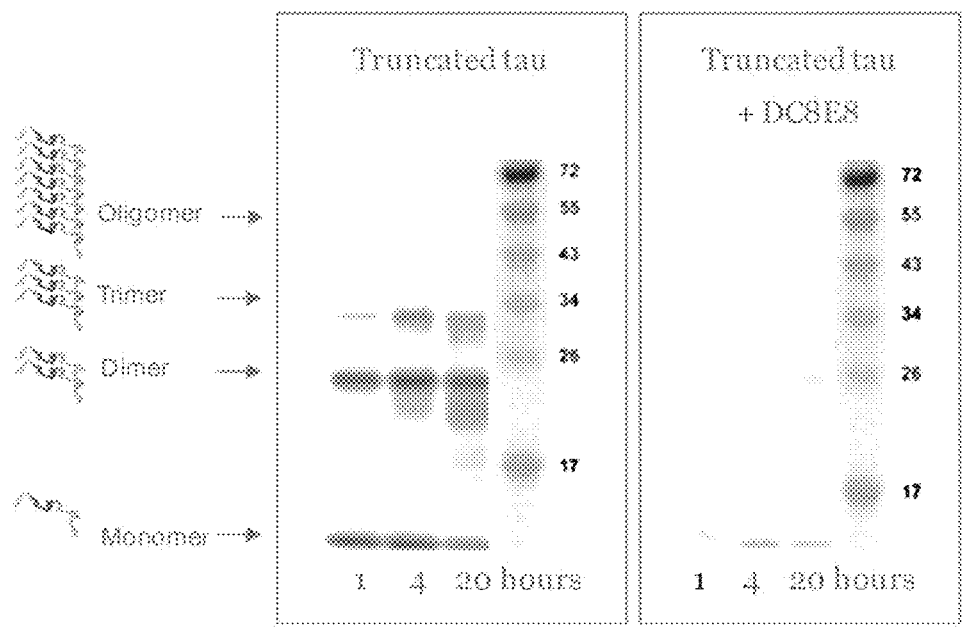
FIG. 16: Analysis of the inhibitory potential of DC8E8 to prevent the formation of tau dimers, trimers, and oligomers by truncated tau protein tauΔ(1-296;392-441)/4R by immunoblotting using HRP-conjugated mAb DC25.

DC8E8 also inhibited the formation of tau dimers, trimers, and oligomers by misdisordered tauΔ(1-296;392-441/4R) (FIG. 16). Recombinant tau Δ(1-296;392-441)/4R was incubated for 1, 4, and 20 h either in the presence or in the absence of DC8E8 as described above for the fibrillization assay. At the time points indicated, the reaction was stopped by addition of SDS-sample loading buffer. For protein analysis, 10 μl of each fibrillization reaction was loaded onto 5-20% gradient SOS polyacrylamide gels and electrophoresed in Tris-glycine-SDS buffer system for 40 minutes at 25 mA. After protein transfer to PVDF membranes (1 h at 150 mA in 10 mM CAPS, pH 12), the membranes were blocked in 5% non-fat dry milk in PBS for 1 h at room temperature, and then incubated for 1 h with HRP-conjugated DC25 (Skrabana et al. (2006) diluted 1:1,000 in PBS, followed by three washes with large volumes of PBS. The blots were developed with SuperSignal West Pico Chemiluminescent Substrate (Pierce, U.S.A), and the chemiluminescence signals detected using a LAS3000 imaging system (FUJI Photo Film Co., Japan), The chemiluminescence signal intensities were quantified using AIDA (Advanced Image Data Analyzer, Raytest, Straubenhardt, Germany) software.

These results reveal that one or more of the four binding sites that DC8E8 recognizes/binds to in human tau is involved in monomer tau conformational changes, tau fibrillization, and in the formation of tau aggregates (dimers, trimers, and other oligomers). In other words, one or more of the four regions of tau encompassed by residues 267-KHQPGGG-273 (SEQ ID NO: 98) (1$^{st}$ repeat domain of tau protein), 298-KHVPGGG-304 (SEQ ID NO: 99) (2$^{nd}$ repeat domain of tau protein), 329-HHKPGGG-335 (SEQ ID NO: 100) (3$^{rd}$ repeat domain of tau protein), and 361-THVPGGG-367 (SEQ ID NO: 101) (4$^{th}$ repeat domain of tau protein) promotes and/or is involved in tau fibrillization and formation of tau aggregates (dimers, trimers, and other oligomers).

Example 10: DC8E8 Mediates Uptake and Degradation of Misdisordered Tau

Mouse BV2 microglia cells were treated in 6-well plates for different time periods with either 1 μM recombinant tauΔ(1-150;392-441)/4R alone; or with a mixture/complex of tauΔ(1-150;392-441)/4R and DC8E8. The medium was collected and the cells were washed first with PBS, and then for 1 min with mild acid wash solution (0.5 M NaCl, 0.2 M acetic acid, pH 3). The washed cells were then lysed in TTL buffer (20 mM Tris pH 7.4, 150 mM NaCl, 1 mM EDTA, 1 mM DTT, 0.5% Triton X-100, 50 mM NaF, 1 mM Na$_3$VO$_4$, Roche—protease inhibitor complete) and quickly frozen in liquid nitrogen. The resulting cell extracts were analyzed on 12% SOS-PAGE gel and Western blot as described previously (Koson et al., 2008). Briefly, the proteins were transferred onto nitrocellulose membranes (Millipore, Billerica; MA, USA) and stained with Ponceau S to confirm uniform protein transfer, and then the membranes were probed with DC25 hybridoma culture supernate recognizing tau residues 347-353, and referred to as a pan-tau antibody (Axon Neuroscience; Vienna, Austria). Western blotting with an anti-GADPH antibody (1:1,000, Abcam) was used as a protein loading control. Incubation with DC25 primary antibody was followed by washes and incubation with a polyclonal goat anti-mouse IgG secondary antibody, which was HRP-conjugated (1:3,000; Dako, Glostrup, Denmark). The blots were developed with SuperSignal West Pico Chemiluminescent Substrate (Pierce; U.S.A), and the chemiluminescence signals detected using a LAS3000 imaging system (FUJI Photo Film Co., Japan).

Figure 17A:
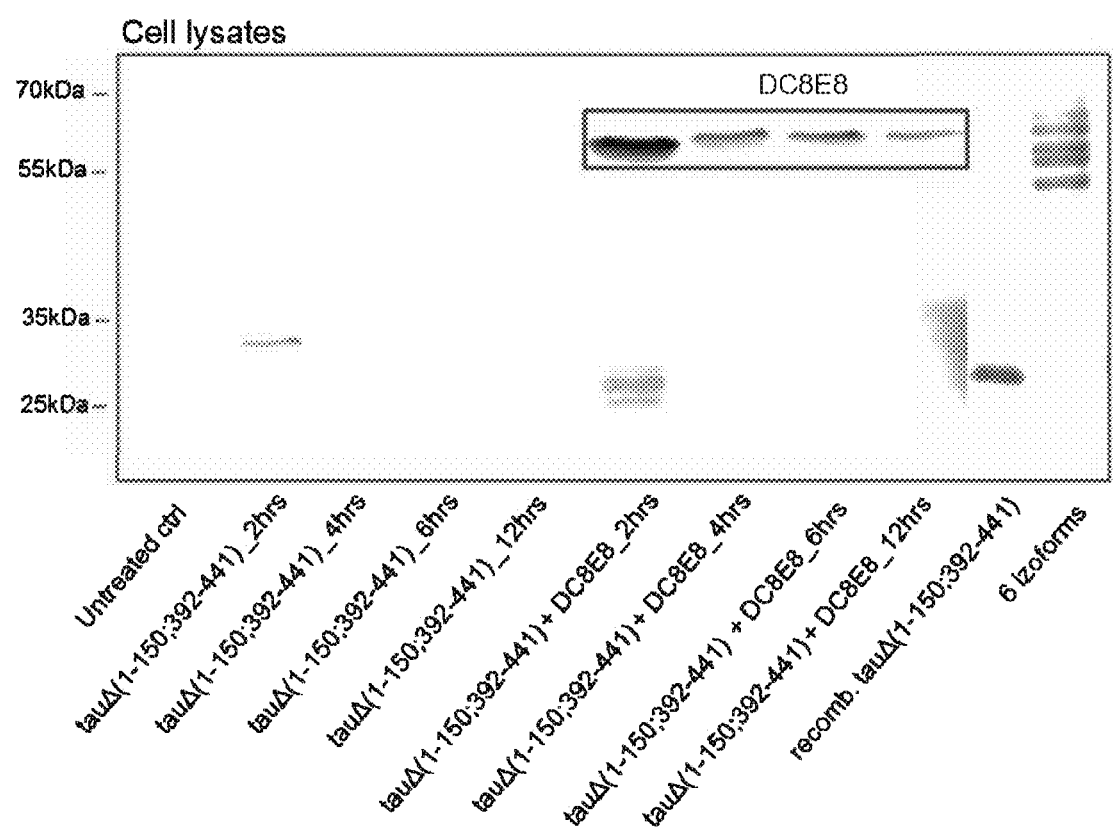
FIG. 17: Uptake and degradation of TauΔ(1-150;392-441)/4R by microglia BV2 cells. TauΔ(1-150;392-441)/4R was added to mouse BV2 cells either alone (1 μM) or in complex with monoclonal antibody DC8E8 (1 μM tauΔ(1-150;392-441)/4R+1 μM DC8E8). After incubation for various lengths of time (2, 4, 6 and 12 hours), the BV2 cells were acid-washed, cellular proteins were extracted and the levels of internalized tau were analyzed by Western blotting with pan-tau antibody DC25. TauΔ(1-150;392-441)/4R was immunolabeled in cell lysates (intracellular tau) (A) and in cell cultivation medium (extracellular tau) (B). DC8E8 antibody was visualized with anti-mouse HRP-conjugated antibody. 20 μg of protein were loaded per lane.

TauΔ(1-150;392-441)/4R was added to cultures of mouse BV2 cells at the concentration of 1 μM either alone or with 1 μM mAb DC8E8, as described in the previous paragraph. After incubation for 2, 4, 6, and 12 hours; the cellular proteins were extracted, and the levels of internalized tau were analyzed by Western blotting. Pan-tau antibody DC25 showed the presence of misdisordered tau inside the microglial cells. The western blot profile revealed that the degradation of misdisordered tau was faster in the presence of DC8E8 (FIG. 17A).

Figure 17B:
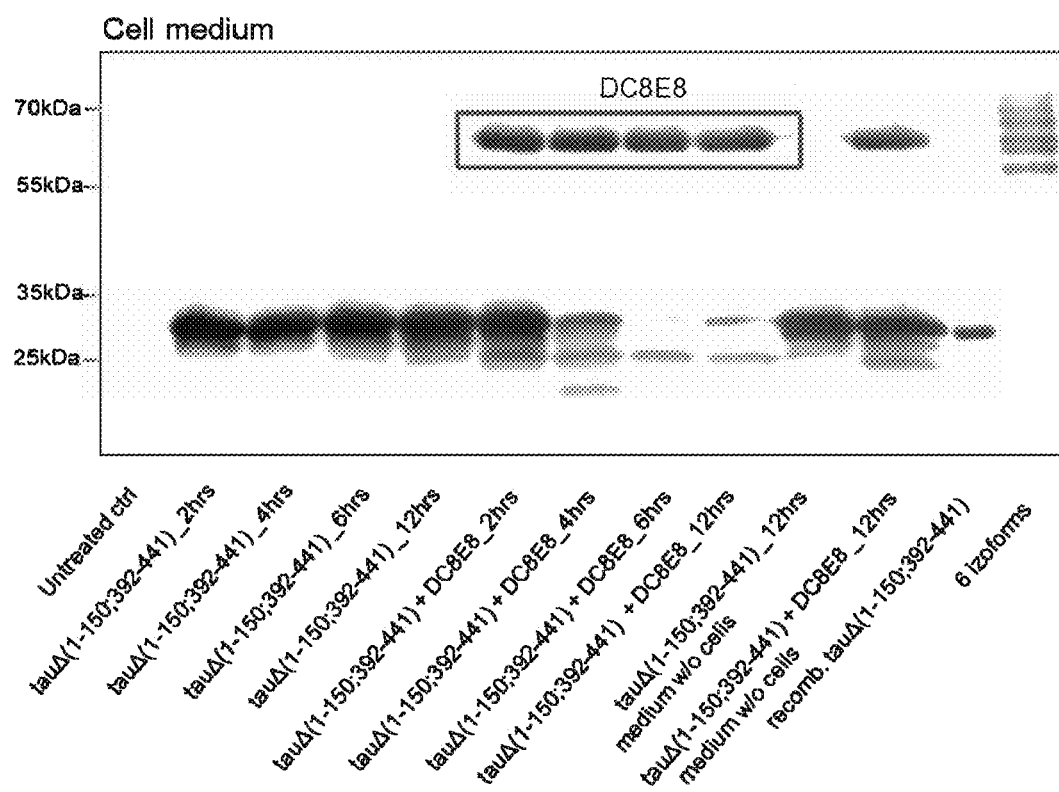

The DC8E8 antibody itself was also found present inside the BV2 cells. FIG. 17A. Moreover, DC8E8 reduced the load of soluble misdisordered tau in the cell medium; which can reflect the activation of the extracellular proteolytic machinery (FIG. 17B).

Example 11: DC8E8 is Stable at 37° C.

Figure 18:
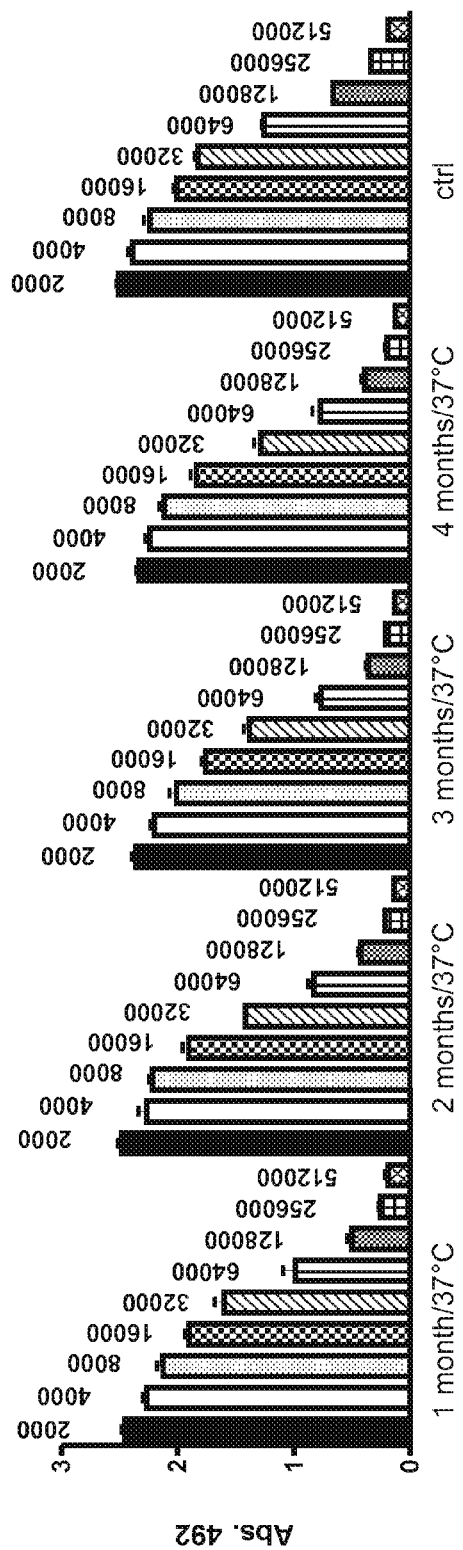
FIG. 18: Stability (shelf-life) of DC8E8 at 37° C., as tested by ELISA. The antibody recognized tauΔ(1-150;392-441)/4R after several months of storage (1, 2, 3 and 4 months). The bars represent serial dilutions of the antibody as indicated. The measurements were performed in triplicate.

DC8E8 (purified as described in Example 5) was diluted to concentration of 2 mg/ml in PBS and aliquots (100 μl) were incubated at 37° C. At various 1-month intervals, aliquots were frozen at −20° C. An aliquot of DC8E8 (2 mg/ml) kept stored at −20° C. throughout the duration of the experiment was used as a "control," After 4 months (when all samples were collected) analysis of DC8E8 activity (binding to recombinant tauΔ(1-150;392-441)/4R as a solid phase), hence shelf-life stability at 37° C., was done by ELISA, as described in Example 2. Each DC8E8 aliquot was diluted 2,000-fold (i.e., 2,000× or 1:2,000), 4,000×, 8,000×, 16,000×, 32,000×, 64,000×, 128,000×, 256,000×, and 512,000×. DC8E8 was active (as measured by its ability to bind tauΔ(1-150;392-441)/4R) and thus stable even after 4 months of incubation at the 37° C., as compared to the "control" (FIG. 18).

Example 12: DC8E8 is Capable of Binding to and Immunoprecipitating Both Soluble and Insoluble Tau from Human AD Brain and from the Brain of SHR72 Rats, Under Native Ex Vivo-Like Conditions Sarkosyl-insoluble misfolded tau proteins were biochemically isolated either from human AD brains or from tau transgenic rat brains (line SHR72 described in Example 7) using the sarkosyl method (Greenberg and Davies, 1990). For protein extraction, unfixed frozen human AD brain (transentorhinal cortex, Braak stage V, obtained from the Netherlands Brain Bank, Netherlands) and SHR72 transgenic rat (isocortex, 7.5 months old animals) tissues were homogenized in 10 volumes of ice-cold extraction buffer [10 mM Tris pH 7.4, 0.8 M NaCl, 1 mM EGTA, and 10% sucrose (supplemented with 50 mM NaF, 1 mM Na$_3$VO$_4$, and the cocktail of protease inhibitors Complete® without EDTA (from Roche)], The homogenates were centrifuged for 20 min at 20,000×g to remove membraneous material. To prepare sarkosyl-insoluble tau fractions, the supernates were supplemented with N-lauroylsarcosine (SIGMA) to a final concentration of 1% and incubated for 1 h at room temperature, while shaking. After centrifugation at 100,000×g for 1 h, the resulting supernates were discarded and the pellets were washed once in 3 ml of phosphate-buffered saline (PBS, 8.09 mM Na$_2$HPO$_4$, 1.47 mM KH$_2$PO$_4$, 136.89 mM NaCl, 2.7 mM (KCl)), The pellets, which represent the brain protein fraction enriched in oligomeric and polymeric misfolded tau species (i.e. the disease tau proteins), were then re-suspended in 1 ml of PBS (supplemented with 50 mM NaF, 1 mM Na$_3$VO$_4$ and the cocktail of protease inhibitors Complete® without EDTA (Roche)) by sonication for 2 minutes on ice using a Bandelin Sonopuls HD2200/UW2200 equipped with a MS72 probe, at 20% duty cycle with the output set at 20% (Bandelin Electronic, Germany).

The resulting suspensions (both from human AD brain and from the brain of rat AD model); enriched in the disease tau proteins; were split into two 500 μl portions and each portion received 25 μg of one of two purified antibodies: either DC8E8 or control antibody Rab50 (recognizing an envelope protein of the rabies virus; Macikova et al., 1992). The suspensions were incubated with the antibodies with head-over-tail rotation at 6° C. for 2 hours. In order to isolate the formed antibody-disease tau complexes, 50 μl of 50% suspension of Protein G Mag Sepharose beads (GE Healthcare) equilibrated in PBS were added into each suspension reaction, which were further incubated at 6° C. for 1 hour. The beads with bound antibody-tau complexes were harvested and washed three times with PBS (supplemented with 50 mM NaF, 1 mM Na$_3$VO$_4$, 0.02% IGEPAL CA-630 (SIGMA) and the cocktail of protease inhibitors Complete® without EDTA (Roche)). The bound antibody complexes were eluted from the beads by three separate 5-min incubations in 100 μl of 200 mM formic acid pH 2.7. The 100 μl eluates were pooled, lyophilized, the proteins dissolved in SDS-PAGE sample loading buffer (Laemmli, 1970), separated on 12% SDS-PAGE gels, transferred onto nitrocellulose membranes, and the tau proteins detected by incubation with the pan-tau antibody DC25 (epitope 347-353 of 2N4R tau, Axon Neuroscience, Vienna, Austria), HRP-conjugated as above (Kementec, Denmark). Incubation (1 h at room temperature) was followed by washing (three times) with 0.2% Igepal CA-630 (SIGMA) in PBS. The blots were developed with a SuperSignal West Pico Chemiluminescent Substrate system (Pierce, U.S.A) and the signals detected using aLAS3000 imaging system (FUJI Photo Film Co., Japan).

Figure 19B:
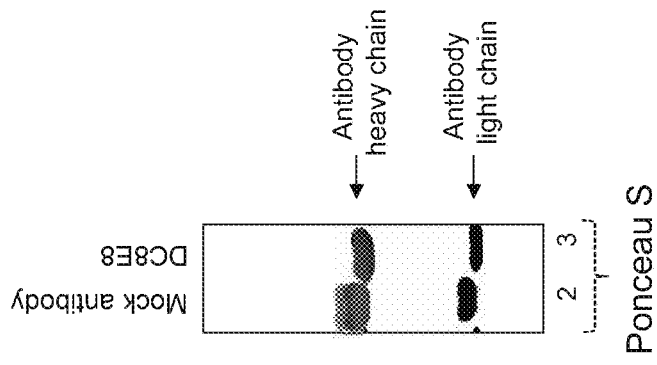
FIG. 19: DC8E8 recognizes and targets misfolded (diseased) tau in the brain tissues of the human Alzheimer's disease. (A) Western blot analysis with pan-tau DC25 antibody:
1) Biochemical extraction of pathological tau from the brain tissues of human Alzheimer's disease (Greenberg and Davies, 1989);
2) Mock antibody (Rab50) does not recognize tau;
3) DC8E8 recognizes and targets misfolded (diseased) tau in brain tissues of human Alzheimer's disease; and
(B) Ponceau S staining: 2),3) Control of antibody amount (Rab50 and DC8E8) used in the experiment.
Figure 19A:
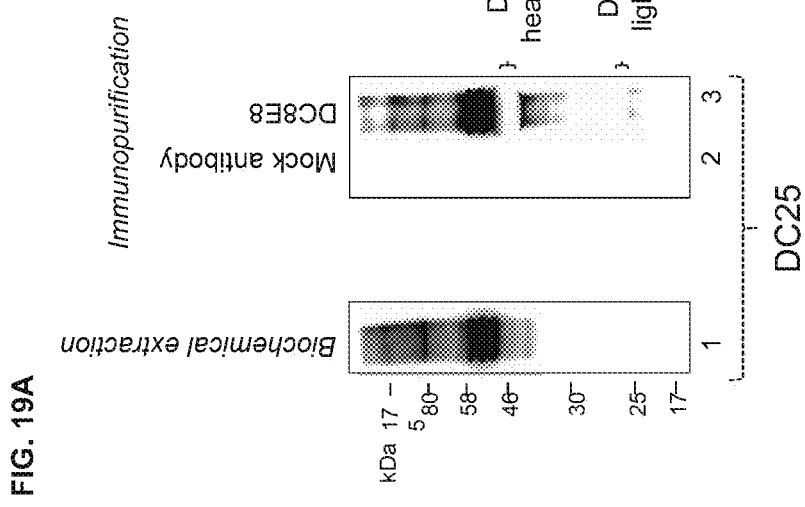

DC8E8 recognizes; targets; and binds all forms of the disease tau proteins: oligomeric and polymeric misfolded tau species present in the brain of a patient with Alzheimer's disease (FIG. 19A). Lane 1 in FIG. 19A shows biochemically extracted pathological tau species from human AD brain. Lane 3 shows tau species recognized, bound by, and isolated by immunoprecipitation with DC8E8. The pattern of DC8E8-bound/immunoprecipitated disease tau species was that of the biochemically extracted tau proteins. These results show efficient ex vivo recognition by DC8E8 of the pathological tau species in the human brain, i.e., in extracts where the proteins are in vivo-like, unmodified form, showing that DC8E8 has useful therapeutic properties, being able to target the disease tau species in vivo. The control antibody Rab50 ("Mock antibody", lane 2) does not recognize any of the tau proteins present in the brain extract, confirming that binding of DC8E8 to tau proteins is specific.

FIG. 19B shows the amount of mock antibody (Rab50) and DC8E8 (lanes 2 and 3, respectively) used for the immunopurification of tau proteins. The positions of the heavy and light chains of DC8E8 are also marked in lane 3 of FIG. 19A. The presence of the higher amount of antibody chains distorts the pattern of disease tau.

Figure 20A:
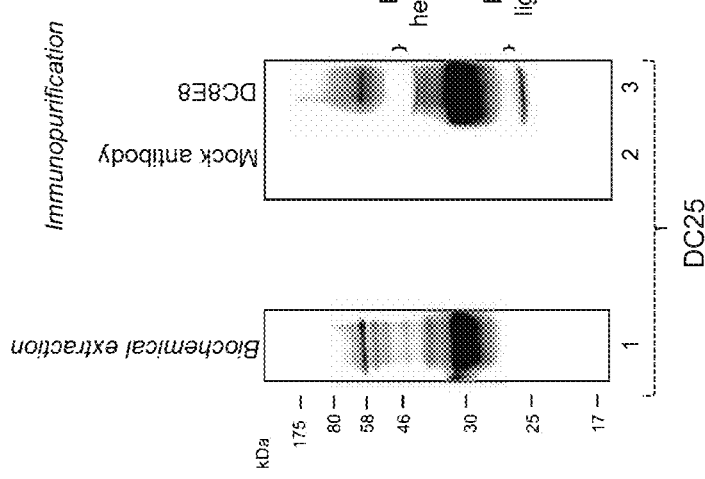
FIG. 20: DC8E8 recognizes and targets misfolded (diseased) tau in brain tissues of the SHR72 rat model of AD. (A) Western blot analysis with pan-tau DC25 antibody:
4) Biochemical extraction of pathological tau from brain tissues of human Alzheimers disease (Greenberg and Davies, 1989);
5) Mock antibody (Rab50) does not recognize tau;
6) DC8E8 recognizes and targets misfolded (diseased) tau in brain tissues of human Alzheimer's disease; and
(B) Ponceau S staining: 2),3) Control of antibody amount (Rab50 and DC8E8) used in the experiment.

DC8E8 also recognizes and targets all forms of misfolded (diseased) tau in the brain of the SHR72 rat model of Alzheimers disease. FIG. 20A, lane 1 shows biochemically extracted disease tau species from the brain of the transgenic rats. Incubation of DC8E8 antibody with the transgenic rat brain extract allowed immunopurification of disease tau species present in the brain (FIG. 20A, lane 3). The DC8E8 purified tau species showed a pattern identical to that of biochemically isolated tau proteins (FIG. 20A, lane 1), which confirms that DC8E8 recognizes and binds all pathological tau species present in the transgenic rat brain. The slight distortion of the tau proteins banding pattern is caused by the presence of DC8E8 antibody heavy and light chains (marked in FIG. 20A, lane 3). Mock antibody Rab50 (FIG. 20A, lane 2) did not bind any of the tau proteins.

Figure 20B:
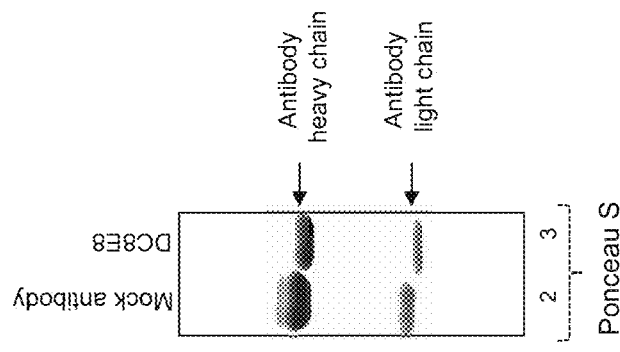

FIG. 20B shows the amount of mock antibody (Rab50) and DC8E8 (lanes 2 and 3, respectively) used for the immunopurification of tau proteins from the brain extract of rats of the transgenic model of Alzheimer's disease. The positions of the heavy and light chains of DC8E8 are also marked in lane 3 of FIG. 20A. The presence of the higher amount of the antibody chains slightly distorted the pattern of disease tau.

Example 13: DC8E8 Monoclonal Antibody Removes Pathological Tau from the Brain of Transgenic Rats SHR72

Hybridoma cells producing either DC8E8 or Rab50 (a negative control antibody, recognizing virus rabbles) were cultivated in DMEM containing 10% NHS and 1% glutamine. The cells were counted in a Bürker counting chamber. Cell suspensions containing 500,000 cells per milliliter were spun down at 100×g for 5 min and the pellets were resuspended in 1 ml of PBS. The cell suspensions were spun down again at 100×g for 5 min, and the pellets resuspended in 5 μl of PBS.

Transgenic rats SHR72 (6 months old) were used for these experiments (3 rats per group). At least one hour before surgery, an immunosuppressive drug—Sandimmun (15 mg/kg)—was applied to the rats subcutaneously. Transgenic rats were anaesthetized by mixture of Tiletamine-Zolazepam (100 mg/ml)/Xylazine (20 mg/ml) in 3:5 ratio, injected intraperitoneally. Dosing of anesthetics was as follows: Zoletil (30 mg/kg) and Xylariem (10 mg/kg). The heads of the anesthetized rats were fixed in a stereotactic apparatus (David Kopf Instruments, Tujunga, Calif., USA) by placing fixating arms into the ear canals of each animal. Holes were drilled on each animal's head, using the surgical drill, according to chosen stereotactic coordinates (lateral 5 mm; anterior-posterior 4 mm; dorsoventral −5 mm, relative to bregma). The hybridoma cell suspensions, producing either DC8E8 ($10^5$ cells) or Rab50 ($10^5$ cells), were bilaterally injected into the fimbria of hippocampi of the rats' brains. Shortly after operation, Ketonal (5 mg/kg) was administer intramuscularly. Sandimmun (15 mg/kg) was applied subcutaneously for 8 days after application. Enroxil (20 mg/kg/24 h) was administered in drinking water for 10 days.

Two weeks after the surgical procedure, the rats were anaesthetized by a mixture of Zoletil (30 mg/kg) and Xylariem (10 mg/kg). After 2-5 minutes, rats were mounted on a dissecting stage, and their abdominal cavity was opened. Before perfusion the blood was collected for analysis of tau and antibody levels in the blood serum. A perfusion needle was placed into the left heart ventricle, and the rats were perfused with PBS fort minutes using a peristaltic pump (Type pp1-05, Zalimp, speed—10×, degree 7-22 ml/1 min of perfusion liquid). Each rat was decapitated, its skull was opened by paean, and the brain (with part of the spinal cord) carefully removed. Brains were cut sagitally into two parts; the right side was fixed in 4% PFA (4° C.) overnight. The left side was cut and the brainstem and two cortical areas were quickly frozen in liquid nitrogen.

Figure 21A:
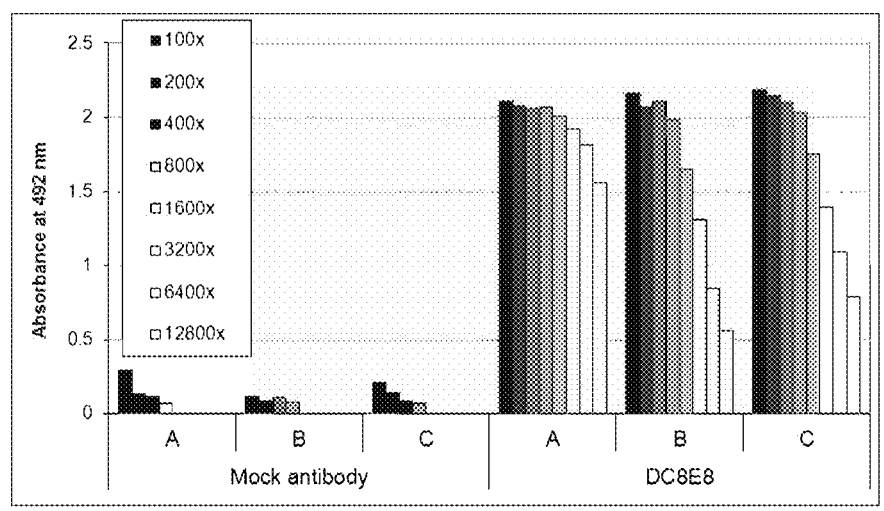
FIG. 21: In vivo, DC8E8 targets pathological forms of tau in the brain of transgenic rats (SHR72) and transports pathological tau from the brain to the peripheral blood. (A) Concentration of the DC8E8 antibody in the serum of DC8E8 treated animals reached 466, 200 and 273 μg/ml, respectively. (B) In vivo transport of the DC8E8-tau complexes from the brain into the peripheral blood was observed. Pathological tau reached the average concentration of 350 μg/ml of the serum. Active transport of tau by DC8E8 eliminates pathological tau proteins from the brain. On the other hand, no tau proteins were detected in the sera of the animals treated with mock antibody (Rab50), which recognizes the rabies virus (Macikova et al., 1992). Concentration of tau in the sera of the treated animals was determined by Innotest hTAU ELISA (Innogenetics, Belgium). The graph shows means with standard errors of the mean (SEM). Each of the 8 bars for rats A-C indicates a different sequential serum dilution (from 100-fold through 12,800-fold, from left to right).

The amount of DC8E8 antibody in the serum of the treated animals was determined by ELISA, as described below in Example 19 using taut (1-150; 392-441)4R as a solid phase. The serum of each animal (A, B, C) was serially diluted from 100× to 12,800× (FIG. 21A). The serum concentration of DC8E8 antibody was determined using purified DC8E8 as a standard, DC8E8 reached concentrations of 466, 200, and 273 ng/ml in treated animals (A, B, C, of the DC8E8 treatment group, respectively).

Figure 21B:
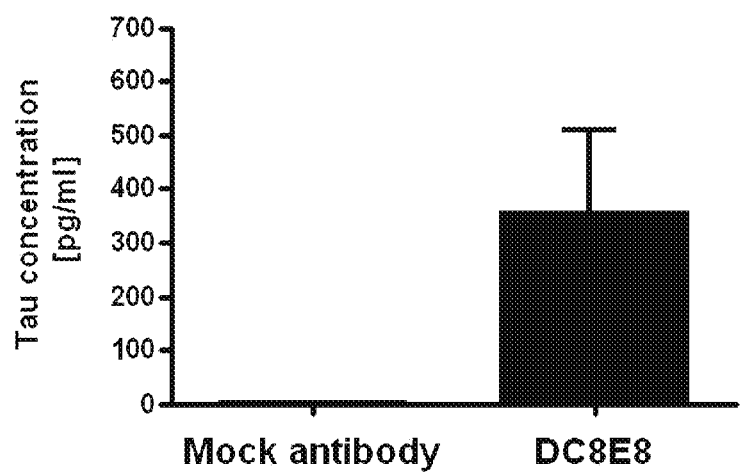

The concentration of tau in the sera of each treated animal was also determined. This was done using a Innotest hTAU ELISA kit (Innogenetics, Belgium), according to the manufacturer's protocol. Treatment with DC8E8 caused transport of the antibody—tau complexes into the blood, where tau reached the average concentration of 350 μg/ml. This effect of DC8E8 helps to eliminate pathological tau proteins from the brain. On the other hand, no tau proteins were detected in the sera of the animals treated with mock antibody (Rab50), which recognizes the envelope protein of the rabies virus (Macikova et al., 1992), The graph shows means with standard errors of the mean (SEM) (FIG. 21B).

The fixed brain tissues were embedded in paraffin and cut on a microtome. Immunohistochemistry was done on 8 μm paraffin-embedded sections. Tissue sections were pretreated for 20 minutes with boiling antigen unmasking solution (Vector Laboratories, Burlingame, Calif., USA) and for 1 minute with 85% formic acid (Applichem, Darmstadt, Germany). After blocking, the tissue sections were incubated with mAb DC8E8 overnight, followed by washes and incubation (1 hour, at room temperature) with biotinylated secondary antibody (Vectastain Elite ABC Kit, Vector Laboratories). After washing, the sections were reacted with an avidin-biotin peroxidase-complex (Vectastain Elite ABC Kit, Vector Laboratories) for 60 minutes at room temperature. The immunoreaction was visualized with peroxidase substrate kit VIP (Vector VIP, Vector Laboratories, Burlingame, Calif., USA). The superior olivary complex was used for quantification of DC8E8 intraneuronal signal. The total signal as quantified in individual motor neurons, at least 15 neurons per section. The image analysis was done using AIDA (Advanced Image Data Analyzer, Raytest, Straubenhardt, Germany) software. The counting was done on sections of all treated animals and then statistically evaluated using nonparametric Mann-Whitney test.

Figure 22A:
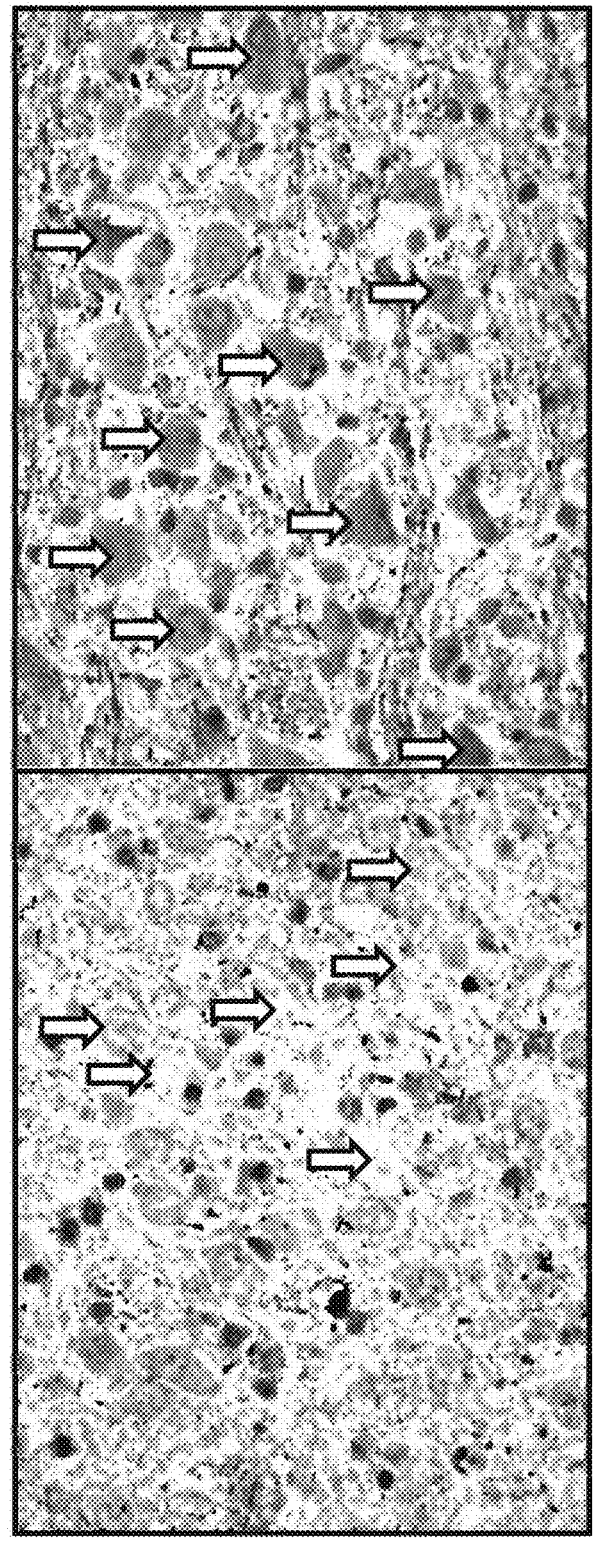
FIG. 22: DC8E8 monoclonal antibody removes pathological tau from the brain of transgenic rats (SHR72). (A) Intracerebral application of DC8E8 (left panel) removes (arrows) pathological tau from the neurons in comparison with mock treated animals (right panel). (B) Quantification of the amount of pathological tau in the neurons of the mock-treated and DC8E8-treated animals showed radical reduction in the amount of pathological tau in animals treated with DC8E8 (p<0.0001).
Figure 22B:
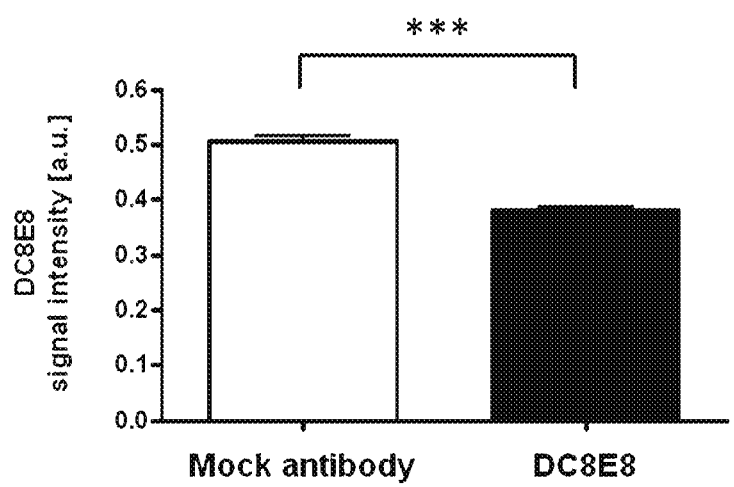

The quantification (FIG. 22B) of the amount of pathological tau in the superior olivary complex of sections from the mock-treated (FIG. 22A, right panel) and DC8E8-treated (FIG. 22A, left panel) animals showed a reduction in the amount of pathological tau in the tested brain area in all three animals treated with DC8E8 compared to mock-treated animals (p<0.0001) (FIGS. 22A and 22B).

Example 14: Mapping of the Residues within the DC8E8 Combining Site that Influence DC8E8's Recognition of Tau's Therapeutic Epitopes a) Cloning of the Single Chain DC8E8 Antibody and Mutagenesis of the Antibody Combining Site.

A functional single chain version (scDC8E8v) of the full-length DC8E8 mAb was prepared to help map the amino acid residues of mAb DC8E8 essential for the recognition of tau proteins. This was done using cDNAs of DC8E8's light and heavy chains prepared as described in Example 3.

The variable regions of DC8E8 were further amplified by PCR using cloning primers bearing restriction sites for NcoI (forward primer: 5'-ATATTACCATGGACATTGTGATGT-CACAG-3' (SEQ ID NO: 155)) and XhoI (reverse primer: 5'-ATATTATTCTCGAGGGAGACGGTGACTGAGGT-3' (SEQ ID NO: 156)) restriction enzymes and oligonucleotide linker sequences (VH-LINK-F: 5'-GGCGGCGGCGGCTC-CGGTGGTGGTGGTTCCATGCAGGTCCAATTGCA-GCAG-3' (SEQ ID NO: 157); VL-LINK-R: 5'-GGAGC-CGCCGCCGCCAGAACCACCACCACCAGAACCACC ACCACCCCGTTTGAT GTCCAGCTTGGTGCC-3' (SEQ ID NO: 158)), which were used to join heavy and light chain variable regions (the linker sequence was designed according to Krebber et al. 1997). After digestion of the isolated FOR products (using NcoI and XhoI enzymes) and purification via agarose gel electrophoresis, the fragments were cloned into a NcoI- and XhoI-digested pET22b plasmid, using T4-DNA-Ligase (Fermentas, Germany). The bacterial strain DH5α was used for the amplification of the resulting plasmid and the correct insert position in the selected clones was verified by restriction enzyme analysis. The correctness of the sequence of the resulting single-chain DC8E8 construct (scDC8E8v) was verified by DNA sequencing using a 3130 Genetic Analyzer (Applied Biosystems, USA).

b) Identification, by Alanine Scanning Mutagenesis, of Residues in DC8E8 Combining Site that Influence DC8E8's Recognition of Pathological Tau.

For the identification of residues that influence DC8E8 binding to tau, Ala scanning mutagenesis was done on select sites (in bold and underlined, see below) of scDC8E8v. The amino acids selected for Ala substitution were identified on the basis of the work of MacCallum et a/(J. Mol. Biol. 1996). The mutagenesis of scDC8E8v was done by overlap extension method using mutant oligonucleotides in PCR by standard procedures described in "Molecular Cloning: A Laboratory manual" by Sambrook and Russell (2001).

The mutant single chains are listed below, relative to each original DC8E8 sequence. The mutated residues are in bold and underlined. The names of the mutant single chains consist of the number of the construct, variable heavy or light chain acronym (VH or VL), the single-letter code of the original amino acid in DC8E8 followed by its position in the light and heavy chain sequence SEQ ID Nos. 141 and No. 138, respectively, and then A for the substituting alanine. For example, mutant 1-VL-N31A corresponds to single chain mutant number 1, where the variable light chain was mutated at position 31 (relative to DC8E8), by replacing Asparagine 31 (N31) with Alanine (A)):

DC8E8 Light Chain Variable Region (CDRs are Underlined):
[SEQ ID No. 141]:

```
         1         10        20        30        40        50
         DIVMSQSPSSLAVSAGEKVTMSCKSSQSLLNSRTRKNYLAWYQQKPGQSPKLL 60        70        80        90        100
                   IYWASTRESGVPDRFTGSGSGTDFTLTISSVQAEDLAVYYCKQSFYLRTFGGG

110
                   TKLDIK
```

Mutations in CDR1 [SEQ ID No. 117] (the mutated residues are in bold and underlined):

```
QSLLNSRTRKNY (SEQ ID NO: 117)
(original DC8E8 sequence of CDR1)
                                        [SEQ ID NO. 247]
1-VL-N31A

[SEQ ID NO. 248]
2-VL-R33A

[SEQ ID NO. 249]
3-VL-Y38A
```

Mutation in Framework region FR2 preceding CDR2: LAWYQQKPGQSPKLLY (SEQ ID NO: 160) (original DC8E8 sequence of framework region FR2)

```
                                        [SEQ ID NO. 252]
4-VL-Y55A
```

Mutation in CDR2 [SEQ ID No. 118]: WAS (SEQ ID NO: 118) (original DC8E8 sequence of CDR2)

Mutations in CDR3 [SEQ ID No. 119]: KQSFYLRT (SEQ ID NO: 119) (original DC8E8 sequence of CDR3)

```
5-VL-W56A                               [SEQ ID NO. 253]

6-VL-K95A                               [SEQ ID NO. 254]

7-VL-Q96A                               [SEQ ID NO. 255]

8-VL-S97A                               [SEQ ID NO. 256]

9-VL-F98A                               [SEQ ID NO. 257]

10-VL-Y99A                              [SEQ ID NO. 258]

11-VL-L100A                             [SEQ ID NO. 259]

12-VL-R101A                             [SEQ ID NO. 260]
```

DC8E8 Heavy chain variable region (CDRs are underlined):
[SEQ ID No. 138]:

```
1         10        20        30        40        50
QVQLQQSGPELVKPGTSVKMPCKASGYIFTDYVISWVKQRTGQGLEWIGEIFP 60        70        80        90        100
RSGSTYYNEKFKGKATLTADKSSNTAYMQLSSVTSEDSAVYFCARDYYGTSFA

110
MDYWGQGTSVTVSS
```

Mutations in CDR1 [SEQ ID No. 120] (the mutated residues are in bold and underlined):

```
    GYIFTDYVIS (SEQ ID NO: 120)
    (original DC8E8 sequence of CDR1)
                                        [SEQ ID NO. 261]
    14-VH-Y32A

[SEQ ID NO. 262]
    15-VH-V33A
```

Mutation in Framework region FR2 preceding CDR2: WVKQRTGQGLEWIGE (SEQ ID NO: 162) (original DC8E8 sequence of framework region FR2)

```
                                        [SEQ ID NO. 263]
    16-VH-E50A
```

Mutations in CDR2 [SEQ ID No. 121]: IFPRSGST (SEQ ID NO: 121) (original DC8E8 sequence of CDR2)

```
                                        [SEQ ID NO. 264]
    17-VH-F52A

[SEQ ID NO. 265]
    18-VH-S57A
```

Mutations in CDR3 [SEQ ID No. 122]: ARDYYGTSFAMDY (SEQ ID NO: 122) (original DC8E8 sequence of CDR3)

```
                                        [SEQ ID NO. 266]
    19-VH-D99A

[SEQ ID NO. 267]
    20-VH-Y100A

[SEQ ID NO. 268]
    21-VH-Y101A

[SEQ ID NO. 269]
    22-VH-G102A
```

Analytical and Preparative Expression of Recombinant DC8E8 Antibody Variants:

The pET22b-scDC8E8v DNA constructs of wild type antibody and its mutants (all of which are His-tagged) were transformed into E. coli cells of the production strain BL21 (DE3). The resulting clones were first verified for the production of recombinant scDC8E8v. Individual colonies obtained after transformation were inoculated into 2 ml of LB medium supplemented with 100 µg/ml of ampicillin and grown at 37° C. for 5 hours with constant agitation (Sambrook and Russell 2001). A 100 µl aliquot of each culture was removed, mixed with 2/3 of the volume of 100% glycerol and stored frozen at −80° C. for later use. The expression of the recombinant protein was induced by the addition of isopropyl-β-D-1-thiogalactopyranoside (IPTG) to a final concentration of 1 mM and incubation continued for an additional 3 hours. The cells were collected by centrifugation in a benchtop centrifuge at 4° C. for 1 min at 10,000×g, the supernate was discarded, the cell pellet was resuspended in 1×SDS-sample buffer (Laemmli 1970) and boiled for 5 minutes. The samples were centrifuged for 5 minutes at 10,000×g and supernates (bacterial lysates) analyzed by SDS-polyacrylamide gel electrophoresis (SOS-PAGE). The separated proteins were visualized by staining with Coomassie Brilliant Blue R250 (SIGMA).

Figure 23A:
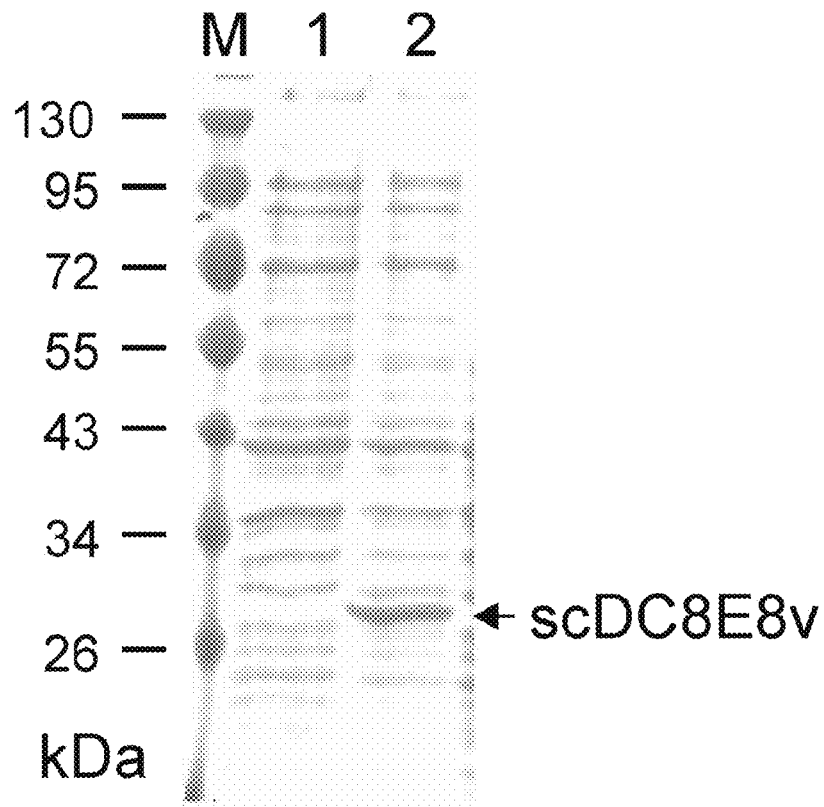
FIG. 23: Recombinant scFv fragment (scDC8E8v) of monoclonal antibody DC8E8, expressed in bacteria, recognizes pathological misdisordered tauΔ(1-150;392-441)/4R. (A) Coomassie Brilliant Blue staining of crude lysates of control BL21 bacteria and bacteria harbouring scDC8E8v expression plasmid, separated by 10% SDS-PAGE: lane 1, crude lysate of control BL21 bacteria; lane 2, crude lysate of BL21 bacteria expressing scDC8E8v; and lane M, protein molecular weight marker (Page Ruller Prestained Protein Ladder #SM0672, Fermentas. (B) Ponceau S stained nitrocellulose membrane containing tau proteins: lane 1, tauΔ(1-150;392-441)/4R, 500 ng; lane 2, tauΔ(1-150;392-441)/4R, 250 ng; lane 3, tauΔ(1-150;392-441)/4R, 125 ng; lane 4 tauΔ228-441, 50 ng; and lane M, protein molecular weight marker. (C) Western blot/Nitrocellulose membrane containing tau proteins, loaded as in B), detected with lysate from bacteria expressing scDC8E8v. (D) Western blot/Nitrocellulose membrane containing tau proteins, loaded as in B), developed with negative control bacterial lysate.

For preparative expression of each scDC8E8v antibody (native and mutant), bacterial cells containing the respective expression plasmids were cultivated and induced as described in "Molecular Cloning: A Laboratory manual" by Sambrook and Russell (2001). Transformed cells were grown at 37° C. in 100-500 ml of LB medium with 100 µg/ml ampicillin at 230 rpm. When absorbance of the culture at 600 nm reached 0.8-1.0, IPTG was added to a final concentration of 1 mM to induce the expression of scDC8E8v. After further incubation at 37° C. for 3 hours, the cells were collected by centrifugation at 3,000 g for 15 min at 4° C. The cell pellet was resuspended in 10 ml of lysis buffer (50 mM PIPES pH 6.9, 50 mM NaCl, 0.1 mM PMSF) and sonicated on ice 6 times for 30 s with 30 s pauses using a TT-13 tip (50% duty cycle, 50 W power output, Sonopuls HD 2200, Bandelin, Germany). The lysate was clarified by centrifugation (21,000×g for 15 min at 4° C.). Lysates were filtered through a 0.45 µm membrane filter and stored at −80° C. until use. For examination of the successful induction and the level of expression, 1 ml of the induced culture was collected, cells harvested by centrifugation as above, resuspended in 100 µl of 1×SDS sample buffer, boiled for 5 minutes at 95° C. and then analyzed by SOS-PAGE (FIG. 23A). The cytoplasmic lysate was used for the binding/detection of tau proteins (by western blot analysis) and for the SPR determination of the recombinant antibodies' affinity for tau, both of which are measures of the activity of the native and mutant scDC8E8v antibodies.

Example 15: Recombinant scFV Fragment of Monoclonal Antibody DC8E8 (scDC8E8V) Recognizes Pathological Tau (TauΔ(1-150;392-441)/4R)

Figure 23B:
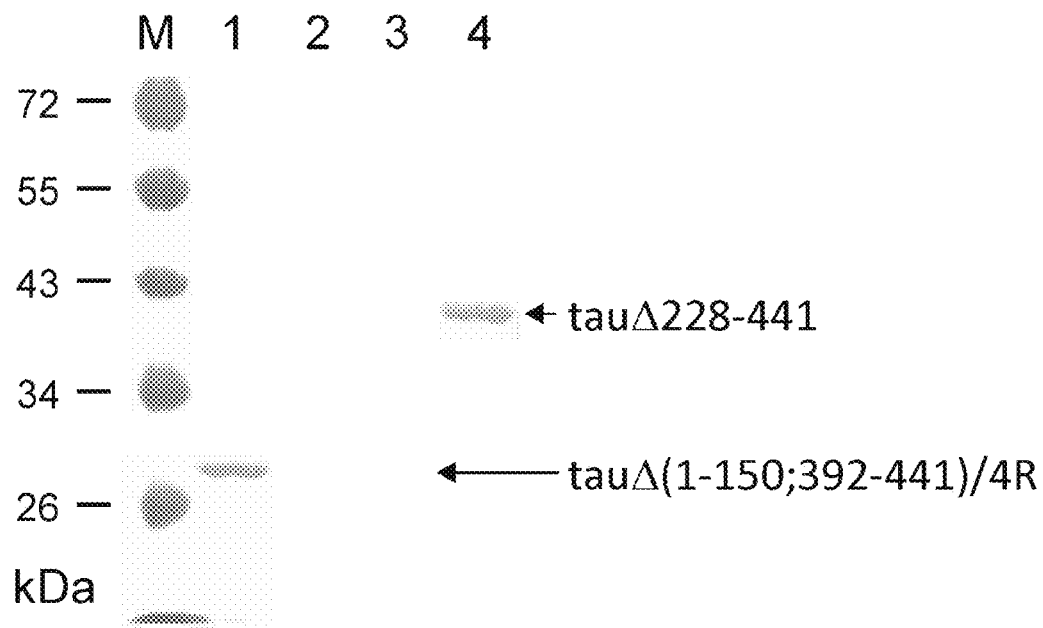
Figure 23D:
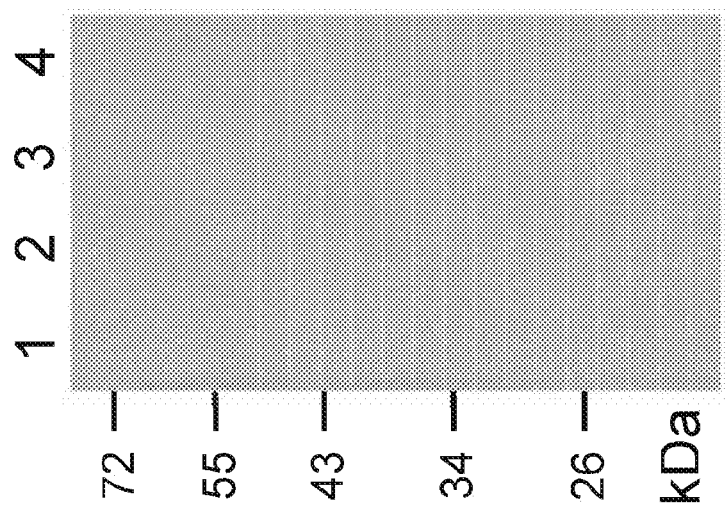
Figure 23C:
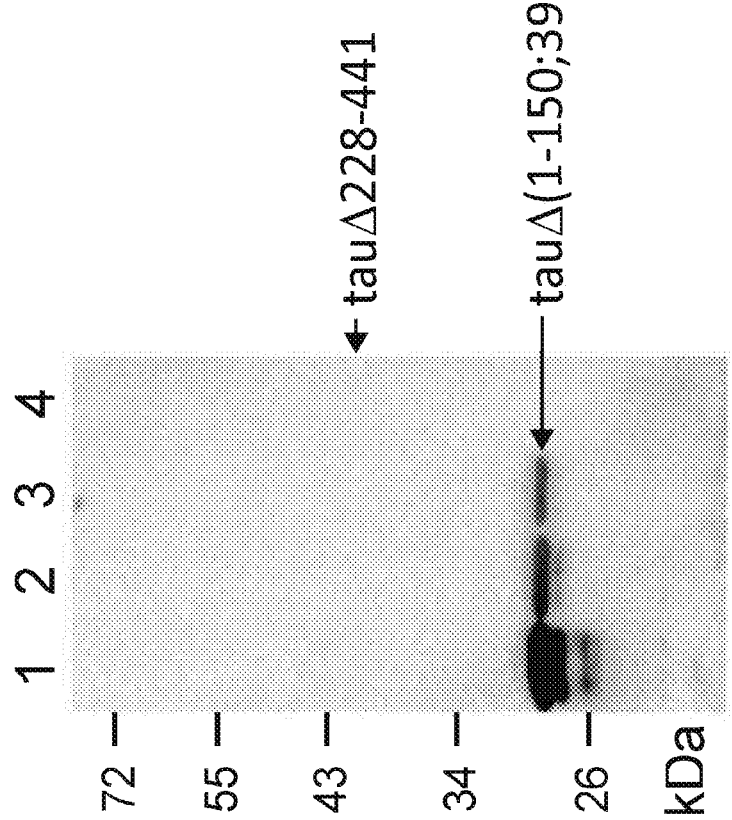

For determination of the binding properties of scDC8E8v to pathological forms of tau, the protein lysate from bacteria expressing scDC8E8v was diluted 16-fold into TBS-T buffer (20 mM Tris pH 7.4, 150 mM NaCl, 0.1% Tween 20) and was used to overlay the nitrocellulose membrane containing 500, 250, and 125 ng of recombinant truncated tau protein (tauΔ(1-150;392-441)/4R) and recombinant C-terminally truncated tau protein (tauΔ228-441) (Ponceau S staining of the proteins, FIG. 23B). Bound scDC8E8v was detected by immunoblotting with an anti-6×hisTag (SEQ ID NO: 163) antibody (No. A00174; GenScript, Piscataway, N.J., USA) and visualized with anti-rabbit HRP-conjugated antibody (DAKO Cytomation, Denmark) (FIG. 23C). The blots were developed with SuperSignal West Pico Chemiluminescent Substrate (Pierce, U.S.A) detected using anLAS3000 imaging system (FUJI Photo Film Co., Japan).

Western blot analysis showed that recombinant single chain antibody (scDC8E8v) detects truncated tau [tauΔ(1-150;392-441)/4R]. The binding is specific, since scDC8E8v does not recognize the control truncated tau protein tauΔ228-441, which does not contain any of the four therapeutic epitopes recognized by intact DC8E8 (FIG. 23C lane 4). Probing the nitrocellulose membrane containing the tau proteins (loaded as shown in FIG. 23B) with lysate from control bacteria not expressing scDC8E8v did not produce any signal (FIG. 23D).

Example 16: Recombinant Scfv Fragment of Monoclonal Antibody DC8E8 (scDC8E8v) Exhibits Tau Binding Properties Similar to the DC8E8 Antibody-Selectively Recognizes Pathological Tau (TauΔ(1-150;392-441)/4R) and Significantly Discriminates it from Physiological, Native Tau (Tau2N4R)

To quantify the tau binding properties of recombinant single chain antibody scDC8E8v, kinetic affinity determinations were done by SPR (Biacore 3000, Biacore, Sweden) to measure scDC8E8v's binding to the pathological truncated tau (tauΔ(1-150;392-441)/4R) (FIG. 24A) and to the normal human four repeat tau isoform 2N4R (FIG. 24B). To this end, 11,000 RU of the rabbit polyclonal anti-His tag antibody (No. A00174; GenScript, Piscataway, N.J., USA) were immobilized on a CM5 sensor chip. All experiments were done at 25° C. in PBS pH 7.4 with 0.005% of P20 (PBS-P) as the running buffer. Recombinant His-tagged scDC8E8v was captured in the analytical flow cell to reach an immobilization level of 60 RU, and known concentrations of each tau protein, or of a PBS-P control sample, were injected at a flow rate of 100 µl/min over the sensor chip. Kinetic binding data were double referenced and fitted by the BIA evaluation software 4.1 (Biacore AB) to a 1:1 interaction model. Kinetic rate constants were approximated globally, maximal responses were fitted locally, and bulk response was set to zero.

Figure 25B:
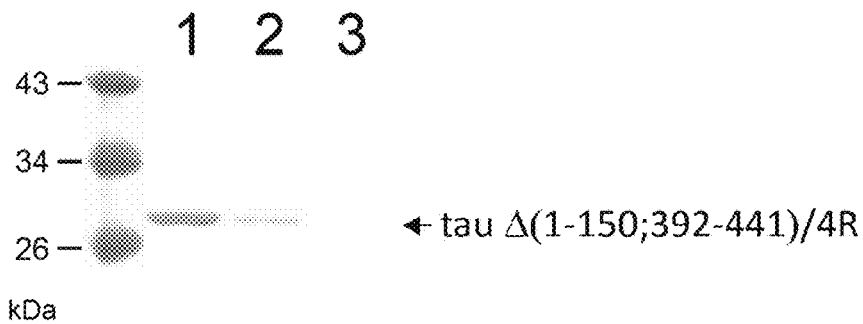
FIG. 25: Identification of residues in scDC8E8v combining site that influence scDC8E8v/DC8E8's recognition of misdisordered tau. (A) Coomassie Brilliant Blue staining of polyacrylamide gels after separation of proteins from crude lysate of BL21 bacteria harboring scDC8E8v expression plasmid (wt) and its mutant forms. Each numbered lane corresponds to the respective clone number, (e.g. lane 2 corresponds to 2-VL-R33A). Expressed single chain proteins are indicated by asterisks. Control bacterial cultures do not express single chain proteins. (B) Ponceau S stained nitrocellulose membrane containing tau proteins: lane 1, tauΔ(1-150;392-441)/4R, 500 ng; lane 2, tauΔ(1-150;392-441)/4R, 250 ng; lane 3, tauΔ(1-150;392-441)/4R, 125 ng. (C) Western Blot on nitrocellulose membranes containing tau proteins, loaded as in B), detected with lysates from bacteria expressing either scDC8E8v (wt gel) or one of its mutant forms (blots 1-VL-N31A through 22-VH-G102A).
Figure 25C:
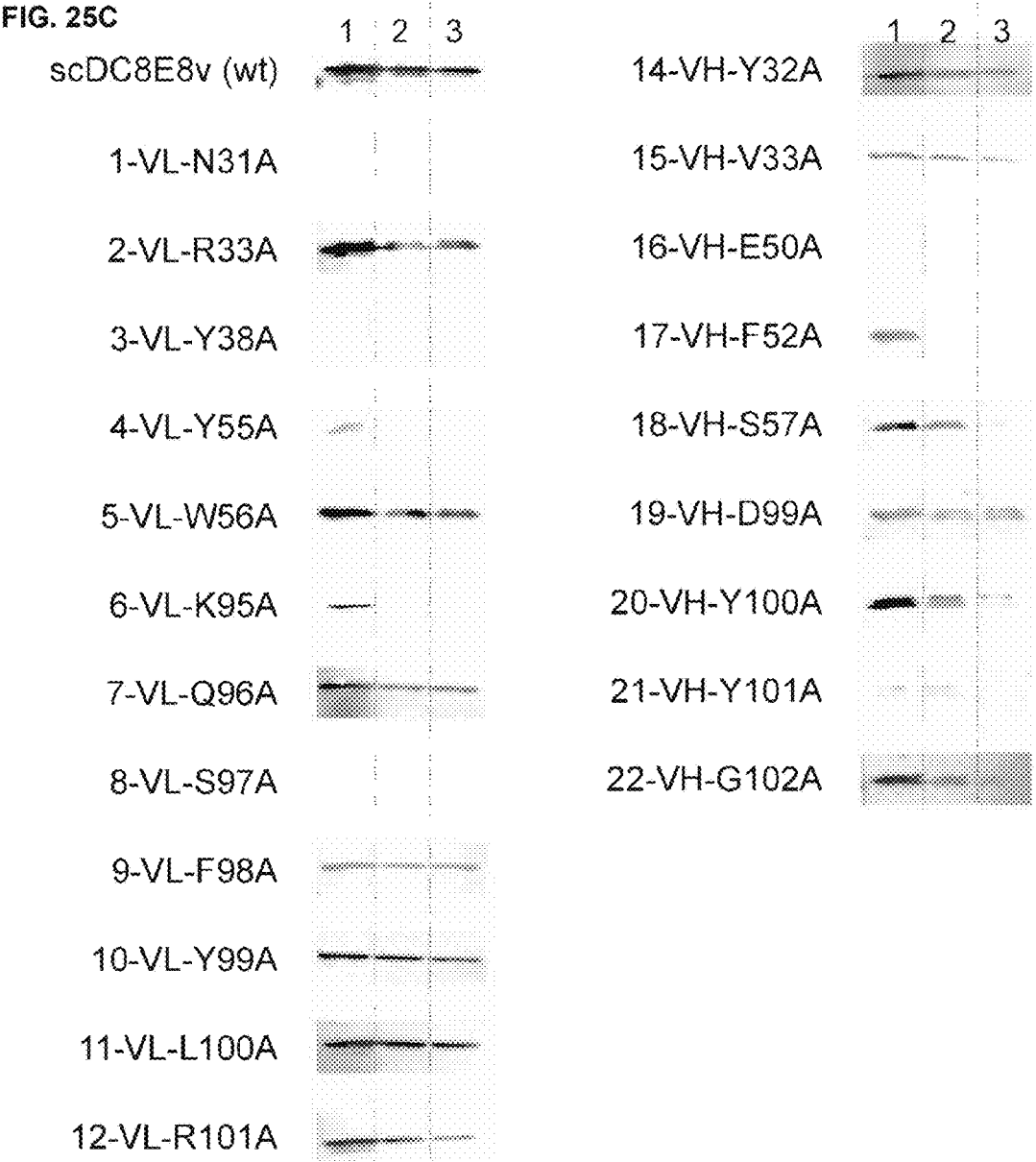

The kinetic measurements showed a higher association rate constant and a lower dissociation rate constant of scDC8E8v toward pathological AD tauΔ(1-150;392-441)/4R than toward normal tau 2N4R (FIG. 240). Consequently, the affinity of scDC8E8v for truncated AD tau is higher (higher value of equilibrium association constant $K_A$) than for the full-length tau isoform 2N4R. These measurements confirmed that the single chain version of DC8E8 antibody (scDC8E8v) shows a binding preference for conformationally altered, pathological tau proteins, like the parental full-length DC8E8 antibody. Recombinant scDC8E8v is thus suitable for identification of amino acid residues within the DC8E8 antibody combining site responsible for its binding properties Example 17: Identification of Residues in the scDC8E8v Combining Site that Influence scDC8E8v/DC8E8's Recognition of Pathological Tau Epitopes Several amino-acid residues that influence the DC8E8-antigen interaction have been determined by alanine scanning mutagenesis of the residues of scDC8E8v combining site. The potential antigen-contacting residues in the light and heavy chains were identified on the basis of the work of MacCallum et al (J. Mol. Biol. 1996) and mutated to alanine, as described in Example 14. The mutant versions of scDC8E8v were subsequently expressed in BL21 *E. coli* strain (FIG. 25A, single chain proteins are indicated by asterisks). The binding properties of the mutated scDC8E8v were analyzed by western blotting (FIG. 25B-C). FIG. 25B shows PonceauS staining of nitrocellulose membranes containing various amounts of truncated tauΔ(1-150;392-441)/4R protein. Identical membranes were used for detection of the truncated tau by the various mutant single chain antibodies (FIG. 25C).

Based on these results, the amino acid residues in the variable region of DC8E8 were classified into three main categories, as follows:

Category 1: The residues listed in this category (in bold) contributed the most for binding of scDC8E8v to pathological truncated AD tau (tauΔ(1-150;392-441)14R). Mutation of any one of these residues to alanine most prevented recognition of DC8E8 epitopes on tau protein.

Category 1 residues in DC8E8 light chain:

Asparagine at the position 31 in CDRL1 [SEQ ID No. 117]

Tyrosine at the position 38 in CDRL1 [SEQ ID No. 117]

Serine at the position 97 in CDRL3 [SEQ ID No. 119]

Category 1 residues in DC8E8 heavy chain:

Glutamic acid at the position 50 in FRH2 preceding CDRH2 [SEQ ID No. 121]

Tyrosine at the position 101 in CDRH3 [SEQ ID No. 122]

Category 2: The residues listed in this category contribute to binding of scDC8E8v to pathological tau (tauΔ(1-150: 392-441)/4R). Mutation of any one of these residues to alanine reduces reactivity of scDC8E8v toward truncated AD tau (tauΔ(1-150;392-441)/4R), but prevents it to a lesser degree than mutations to Category 1 residues:

Category 2 residues in DC8E8 light chain:
Tyrosine at the position 55 in framework region FRL2 preceding CDRL2 [SEQ ID No. 118]

Lysine at the position 95 in CDRL3 [SEQ ID No. 119]

Category 2 residues in DC8E8 heavy chain:

Serine at the position 57 in CDRH2 [SEQ ID No. 121]

Tyrosine at the position 100 in CDRH3 [SEQ ID No. 122]

Glycine at the position 102 in CDRH3 [SEQ ID No. 122]

Category 3: The residues listed in this last category contribute the least to binding of scDC8E8v to pathological AD tau (tauΔ(1-150;392-441)/4R). The mutation of these residues to alanine does not change the reactivity of scDC8E8v toward truncated tau (tauΔ(1-150;392-441)/4R):

Category 3 residues in the Light chain:

Arginine at the position 33 in CDRL1 [SEQ ID No. 117]

Tryptophane at the position 56 in CDRL2 [SEQ ID No. 118]

Glutamine at the position 96 in CDRL3 [SEQ ID No. 119]

Phenylalanine at the position 98 in CDRL3 [SEQ ID No. 119]

Tyrosine at the position 99 in CDRL3 [SEQ ID No. 119]

Leucine at the position 100 in CDRL3 [SEQ ID No. 119]

Arginine at the position 101 in CDRL3 [SEQ ID No. 119]

Category 3 residues in the Heavy chain;

Tyrosine at the position 32 in CDRH1 [SEQ ID No. 120]

Valine at the position 33 in CDRH1 [SEQ ID No. 121]

Phenylalanine at the position 52 in CDRH2 [SEQ ID No. 121]

Aspartic acid at the position 99 in CDRH3 [SEQ ID No. 122]

Example 18: Active Vaccination with Therapeutic Tau Epitopes: Preparation of Immunogens for Vaccines Based on One of the DC8E8 Binding Epitopes on Tau and Vaccine Administration a. Peptides:

Peptide immunogens consisting of synthetic fragments of human tau protein 2N4R were synthesized by Antagene, Inc. (Sunnyvale, Calif.) and EZBiolab; USA, with purity higher than 95%. Each peptide sequence was designed to encompass at least one of the sequences believed to be involved and/or promote tau fibrillization/aggregation (novel target "therapeutic epitopes"), and which epitopes were identified above as binding sites to DC8E8 and by the assays described in Examples 1-11. See FIG. 26A. These four sequences are also referred to herein as "therapeutic epitopes" (see below). These epitopes represent tau-tau interaction motifs (aggregation epitopes), which are important for tau fibrillization/PHF assembly. Therefore, targeting these strategic therapeutic epitopes can lead to the successful treatment of AD and related tauopathies. Furthermore, usage of such a specific anti-tau therapy would prove safer than widely aimed therapies relying on randomly selected tau epitopes, because targeting some tau epitopes has been thought to provoke an autoimmune response and potentially aggravate the disease (Furlan et al., 2003; Gruden et al., 2004).

Accordingly, to further determine the therapeutic potential of tau-based immunotherapy, several sets of tau peptides were designated for use as immunogens. All of the residues refer to those of full-length tau 2N4R, which has 441 amino acid residues. A first set of immunogens was made up of SEQ ID NO:1 tau 251-PDLKNVKSKIGSTENLKHQPGGGKVQIINK-280: SEQ ID NO:2 tau 256-VKSKIGSTENLKHQPGGGKVQIINKKLDLS-285; SEQ ID NO:3 tau 259-KIGSTENLKHQPGGGKVQIINKKLDLSNVQ-288; SEQ ID NO:4 tau 275-VQIINKKLDLSNVQSKCGSKDNIKHVPGGG-304; SEQ ID NO:5 tau 201-GSPGTPGSRS RTPSLPTPPTREPKKVAVVR-230; SEQ ID NO:6 tau 379-RENAKAKTDHGAEI VYKSPVVSGDTSPRHL-408; SEQ ID NO:7 tau 181-TPPSSGEPPKSGDRSGYSSPGSPGTPGSRS-210, SEQ ID NO:8 tau 300-VPGGGSVQIVYKPVDLSK-317; and SEQ ID NO:108 tau 294-KDNIKHVPGGGS-305, Some of these sequences carry phoshorylated epitopes previously found in AD tau pathology. Thus, tau peptide SEQ ID NO:5 contains phosphorylated threonine at position 217, tau peptide SEQ ID NO:6 contains phosphorylated serine residues at position 396 and 404, and tau peptide SEQ ID NO:7 contains phosphorylated serine at position 202 and threonine at position 205. Tau peptide SEQ ID NO:2 was synthesized in unphosphorylated and phosphorylated form. The phosphorylated form contains phosphorylated serine residue at position 262.

Within this set, one subset of immunogens (tau peptides SEQ ID NOs:1-4 and 108) encompass one of the therapeutic epitopes represented either by SEQ ID NO:98, (tau 267-KHQPGGG-273) or SEQ ID NO:99 (tau 298-KHVPGGG-304). The another subset of tau peptides (SEQ ID NOs:5-7) encompass phosphorylated sites, found in Alzheimer's disease and other tauopathies. Tau peptide SEQ ID NO:8 does not carry any of the mentioned epitopes and was used as a control. (FIG. 26.

The second set of peptides was made up of SEQ ID NOs: 9 through 97, which represent overlapping sequences spanning residues 244-390 of human tau 2N4R. Each of these peptides comprises one of the tau therapeutic epitope sequences in a different tau-based environment. In other words, in each subset, each of the epitopes #1 through #4 is surrounded by different tau residues on both its N- and C-terminus. (FIG. 26).

b. Conjugation for Use as a Vaccine:

Tau peptides SEQ ID NOs: 2, 4, and 108 were conjugated to keyhole limpet hemocyanin (KLH) via a cysteine link.

To this end, tau peptides SEQ ID NO: 2, 4, 7, and 108 were synthetized as cysteinated peptides with an extra N-terminally located cysteine residue with the aim to obtain oriented attachment of the peptide on the surface of the KLH protein. Peptides were coupled to the KLH carrier via bifunctional cross-linker N-[γ-maleimidobutyryloxy]succinimide ester (GMBS). To prepare the conjugation reaction, 20 mg of KLH (Calbiochem) were dissolved in conjugation buffer (PBS with 0.9 M NaCl, 10 mM EDTA) to a concentration of 10 mg/ml by gentle mixing for 10 minutes. For preparation of maleimide-activated KLH, 2 mg of active bi-functional cross-linker GMBS were dissolved in 50 μl of anhydrous dimethylformamide and mixed with 2 ml of KLH solution for 1 hour at room temperature. Subsequently, un-reacted GMBS was removed on a 5 ml HiTrap Desalting column (GE Healthcare) equilibrated in conjugation buffer. Conjugations were carried out at a 1:1 ratio of peptide to maleimide-activated KLH (w/w, 20 mg of peptide) for 2 h at room temperature (25° C.). The resulting conjugates were dialyzed against a 100-fold excess of PBS, with four dialysis buffer changes to remove unconjugated peptide. After dialysis, the conjugates were centrifuged at 21,000×g for 15 min at 2° C. Completeness of conjugation was confirmed by the absence of free peptide in the dialysis buffer, measured using LC-MS/MS. The conjugates were aliquoted and stored at −20° C. until used.

c. Vaccine Preparation:

To prepare immunization doses with Aluminum/Alum adjuvant AdjuPhos (Brenntag Biosector, Denmark), 200 μg of each respective tau peptide conjugate (dissolved in 150 μl of PBS) were emulsified at a 1:1 (vol/vol) ratio with Adju-Phos adjuvant, in a final dose volume of 300 µl. Each suspension/emulsion was incubated with rotation at 4° C. overnight to allow the peptide to adsorb onto the aluminum phosphate particles.

To prepare immunization doses with Complete Freund's adjuvant, 200 µg of each respective tau peptide conjugate (dissolved in 150 µl of PBS) was emulsified 1:1 (vol/vol) with Complete Freund's adjuvant, in a final dose volume of 300 µl. For subsequent booster doses, the immunogen was prepared similarly, but was emulsified with Incomplete Freund's adjuvant.

d. Vaccine Administration:

Prepared vaccine doses were injected into tau transgenic rats carrying a human truncated tau transgene (SHR72 line described above in Example 7, expressing tauΔ(1-150;392-441)/4R (Zilka et al., 2006). The rats received the first subcutaneous injection of 200 µg of immunogen in a final volume of 300 µl at 2 months of age, followed by the second injection three weeks later, and thereafter on a monthly schedule. The control transgenic rats received the adjuvant mixed 1:1 with PBS. The evaluation of the efficacy of the immunotherapy is described in Example 19.

Isolation and Purification of Fetal Rat Tau, for Use as Internal Standard in the Quantitative Analysis of Insoluble Tau in Vaccine-Treated Rats:

Fetal rat tau purification was done essentially as described in Ivanovova et al., 2008, using 1% perchloric acid. Brain tissue obtained from 1-7 day old rat pups was homogenized in ice-cold 1% perchloric acid (1.5 g tissue per 5 ml of perchloric acid, PCA) and allowed to stand on ice for 20 min. The homogenate was spun at 15,000×g for 20 min, and the clear supernate was concentrated and simultaneously the buffer was changed to washing buffer (20 mM Tris, pH 7.4, 150 mM NaCl, 0.1% Tween 20) using an Amicon Ultra Centrifugal Filter device (Millipore). The filtered PCA brain extracts, containing about 10 mg of total proteins, were loaded at a flow rate of 0.2 ml/min onto a Poly-Prep column C10/10 (GE Healthcare) packed with Sepharose carrying immobilized pan-tau mAb DC25 (see above). Unbound proteins were washed off with 10-15 ml washing buffer until the absorbance of the eluting fractions (at 280 nm) became stable, Fetal tau, bound to mAb DC25, was eluted with 0.1 M glycine, pH 2.6, Eluted 0.5 ml fractions were immediately neutralized with 50 µl of 1 M Tris-HCl, pH 9, and assayed by SDS-PAGE. Fractions containing fetal tau were concentrated using Amicon Ultra Centrifugal Filter devices (Millipore) with simultaneous buffer exchange to PBS. Fetal tau purified by affinity chromatography was precipitated according to Chen et al., (2005) by addition of four volumes of ice-cold acetone containing 10% trichloroacetic acid. The mixture was incubated at −20° C. for 2 hours and centrifuged at 15,000×g for 20 min at 2° C. The supernate was discarded and the precipitate was resuspended in 1 ml of ice-cold acetone, allowed to stand on ice for 20 min and again centrifuged as above. The resulting pellet was dried at room temperature and dissolved in a volume of PBS equal to that volume before precipitation.

Example 19: General Methods of Evaluating Tau Peptide Vaccines in Transgenic Rat Models of Alzheimer's Disease Active vaccines were evaluated by the following approaches: (a) biochemically, by evaluating the effect of their administration on the levels of phosphorylated forms of insoluble tau using immunoblot analysis of rat brain samples with phosphorylation-specific monoclonal antibodies AT270, 00209, DC217, and AT8, and total amount of insoluble tau using the pan-tau monoclonal antibody DC25; (b) neurobehaviorally, using a NeuroScale evaluation; (c) immunohistochemically, including NFT quantification; and (d) by analysis of the induced antibody response. Passive vaccines can also be evaluated pre-clinically by one or more of these approaches, among others.

(a). Biochemical Analysis:

Insoluble tau fractions were prepared using the sarkosyl method (Greenberg and Davies, 1990), from the brain stems of transgenic (SHR72) rats immunized with test peptides, as well as from mock-treated SHR72 rats (injected with adjuvant only (control)), as described in Example 8. Sarkosyl-insoluble tau samples were analyzed by immunoblotting using various monoclonal antibodies, as described below. The results of this analysis for immunogenic peptides SEQ ID NOs 1-8 and 108 are summarized in FIG. 26B, The levels of insoluble tau have been shown to correlate with progression of tau pathology in SHR72 transgenic rats. Koson et al., 2008.

Immunoblot Analysis:

Samples of sarkosyl-insoluble tau fractions were dissolved in 1× sodium dodecyl sulfate (SOS) sample loading buffer (Laemmli, 1970) in 1/50 volume of the soluble fraction (see Filipcik et al. 2010) and heated at 95° C. for 5 min, 6 µl of each were then loaded onto 5-20% gradient SDS polyacrylamide gels and electrophoresed in Tris-glycine-SDS buffer system for 40 minutes at 25 mA. Proteins were transferred to PVDF membranes (1 h at 150 mA in 10 mM CAPS, pH 12). After the transfer, the membranes were blocked in 5% non-fat dry milk in PBS for 1 h at room temperature and then incubated for 1 h with primary (tau-specific) monoclonal antibodies (see below for more detailed descriptions of each antibody), followed by three washes with a large volume of PBS. After washes, HRP-conjugated goat anti-mouse Ig (DAKO, Denmark) diluted 1:4000 with PBS was used as a secondary antibody. Incubation (1 h at room temperature) was followed by washing (three times) with 0.2% Igepal in PBS. The blots were developed with SuperSignal West Pico Chemiluminescent Substrate (Pierce, U.S.A) and the signal detected using a LAS3000 imaging system (FUJI Photo Film Co., Japan). The signal intensities were quantified using AIDA software (Advanced Image Data Analyzer, Raytest, Straubenhardt, Germany). Fetal tau (0.6 µg/lane) was used as an internal standard for quantification analysis.

Monoclonal antibodies AT8 and AT270 were purchased from Innogenetics (Belgium) and both were used for immunoblot analysis. AT8 was also used for immunohistochemistry. AT8 recognizes phosphorylated serine 202 and threonine 205 located in the proline-rich domain of tau, which contributes to a major part of tau's microtubule-binding affinity. AT270 recognizes phosphorylated threonine 181 located also in the proline-rich domain. Both antibodies bind soluble and insoluble tau. The phosphorylation-specific monoclonal antibodies DC209 (recognizes pT231), DC217 (recognizes pT217) used in this study were prepared by Axon Neuroscience, GmbH (Vienna, Austria). Pan-tau antibody DC25 (Axon Neuroscience, GmbH) recognizes an epitope in the fourth microtubule-binding repeat repeat at the C-terminus of tau protein (347-353) in all forms of soluble and insoluble tau. DC25 antibody recognizes tau proteins independent of their phosphorylation level.

(b). Neurobehavioral Evaluation:

Neurobehavioral responses in the rats were assessed 10 days after the final vaccine dose using the NeuroScale, which is a battery of behavioral tests originally designed for transgenic rats expressing human truncated tau protein (Korenova et al., 2009). The NeuroScale is composed of sensorimotor (beam walking test), neuromuscular (prehensile traction test), and neurological tasks (placing, righting, postural, pinna, startle, and hindlimb escape extension reflex), enriched with basic observational assessments.

The general observation involved assessment of posture and limb functions; the neurological examination included the basic reflex response, all graded on a 1-point scale (normal response 0; delayed or incomplete response 1 point). Assessment of the hind-limb escape extension reflex was graded on a 3-point scale (normal response 0-1; deficit 2-3 points).

For the beam walking test, three sorts of traversing segments were used (3×3 cm, 4×2 cm, and a round beam of 3.5 cm diameter). The maximum number of points was 10 (5 points for latency+5 points for hind-limb slips on one beam type). The lower the score obtained from the beam walking test, the better the sensorimotor-coordination ability of the tested animal. The sum of points possible to achieve was 30.

For the prehensile traction test, a rat was allowed to grasp, with its forepaws, a horizontal steel wire (3 mm in diameter) suspended 76 cm above a padded surface. Latency to fall from the wire was measured. The maximal number of points awardable was 5, reflecting serious impairment of neuromuscular functionality and muscular weakness. The longer the latency to fall, the lower the score obtained from the task, reflecting forelimb muscular strength and the agility of the tested animal.

The NeuroScale score was calculated from the scores obtained in the individual tests. A maximum total score of 49 points was possible by adding the contribution of the observational assessment, the neurological examination, the three series of beam walking test and the prehensile traction test. The more severe the neurobehavioral impairment, the higher the NeuroScale score.

(c). Immunohistochemistry:

For the collection of brain samples, the rats were perfused transcardially with PBS for 2 minutes under deep anesthesia. After perfusion, the rat brains were removed and cut sagittally into two equal-sized hemispheres. The brainstem and the cerebellum of the right hemisphere were collected for biochemical analyses. The left hemisphere was fixed with 4% paraformaldehyde overnight at 4° C., followed by a treatment with 25% sucrose for 48 hours to provide cryoprotection. The material was then frozen in cold 2-methylbutane (−42° C.) for 30 s and sectioned on a cryomicrotome. Sagittal sections (40 μm) were cut in a cryostat at −18° C. Free-floating sections were used for immunohistochemical studies.

Immunohistochemical staining was done on frozen brain sections of treated and control rats. Koson et at, 2008, have shown that the number of NFT in the brain of SHR72 transgenic rats correlates with the time of demise of the animals (i.e., the more NFTs, the earlier the animal's demise). In order to analyze neurofibrillary changes in the rat brains, sagittal sections of the brain were prepared. Free floating tissue sections were treated with cold (+4° C.) 80% formic acid for 30 s at room temperature (25° C.). Brain sections were incubated for 20 minutes at room temperature in PBS containing 0.3% Triton X-100 and 1% $H_2O_2$, followed by a 30-minute incubation in blocking solution (PBS containing 0.3% Triton X-100, 1% horse serum), followed by overnight incubation at 4° C. with either purified AT8 antibody (0.2 μg/ml in blocking buffer) or hybridoma culture supernatant DC217 (1:100 in blocking buffer). Both antibodies showed similar immunostaining pattern in the brain stem of transgenic rats. After washing, the sections were immunostained using the standard avidin biotin peroxidase method (ABC Elite, Vector Laboratories, Burlingame, Calif.). The reaction product was visualized using an avidin-biotin system and Vector VIP as a chromogen (Vector Laboratories). Sections were then examined with an Olympus BX 51 microscope.

(d). Antibody Response:

The transgenic rats were bled before the commencement of the study (i.e., prior to the first injection) and two weeks after the last injection. The antibody response to the administered immunogen/vaccine was determined by ELISA using serially diluted plasma samples. Peptide immunogens, recombinant tau protein tauΔ(1-150;392-441)/4R, and recombinant full-length tau isoform 2N4R, were separately coated onto 96 well plates MAKI, Japan) at a concentration of 10 μg/ml in PBS overnight at 37° C. After blocking with 1% nonfat dried milk in PBS, the plates were washed with PBS-0.05% Tween 20 and incubated with 50 μl/well of serial plasma dilutions (1:200-1:128,000 in blocking buffer) for 1 hr at 37° C. After incubation and washing, peroxidase-conjugated secondary antibody (rabbit anti-rat Ig, DAKO, Denmark) was diluted 1:1000 and applied to the wells (50 μl/well) for 1 hr at 37° C. The reaction was developed with o-phenylenediamine in a peroxidase substrate solution (0.1 M phosphate buffer) and stopped with 50 μl 2M $H_2SO_4$. Absorbance at 492 nm was measured using a Multiscan MCC/340 ELISA reader (Labsystems). Absorbance readings of at least twice the value of the negative controls were considered positive.

Affinity measurements were performed using SPR, as described above in Example 5. Briefly, experiments were performed at 25° C. in phosphate-buffered saline pH 7.4 with 0.005% of P20 (PBS-P) as the running buffer. 3000 RU (response units) of polyclonal anti-mouse antibody (No. Z 0420; DakoCytomation, Glostrup, Denmark) were coupled at a concentration of 5 μg/ml (prepared by 40-times dilution of 200 μg/ml 0.5×PBS stock in 10 mM sodium acetate buffer pH 4.5) via primary amines, simultaneously in two flow cells, one of which was used as a reference in the measurement. In each analysis cycle, 1000-fold diluted sera were captured in the analytical flow cell to reach an immobilization level ~850 RU, which approached saturation. For the $K_A$ determinations, as well as for the determination of kinetic rate constants, 100 nM solutions of tau immunogenic peptides or tau proteins were injected at a flow rate of 100 μl/min over the sensor chip. PBS-P injection was used for background signal subtraction in the double referencing procedure (Myszka J Mol Rec 1999). Kinetic data were fitted by a BIA evaluation software 4.1 (Biacore AB) to a 1:1 reaction model. Kinetic rate constants were approximated globally, maximal responses were fitted locally, and the bulk response was set to zero.

Example 20: Tau Peptide Vaccines Comprising at Least One of Four Therapeutic Epitope Sequences are Beneficial in Transgenic Rats that Model Human Alzheimer's Disease a. SEQ ID NO:1 Tau 251-PDLKNVSKIGSTEN-LKHQPGGGKVQIINK-280.

Transgenic rats (SHR72) were immunized with tau peptide SEQ ID NO:1 formulated with Adju-phos adjuvant.

Figure 26A:
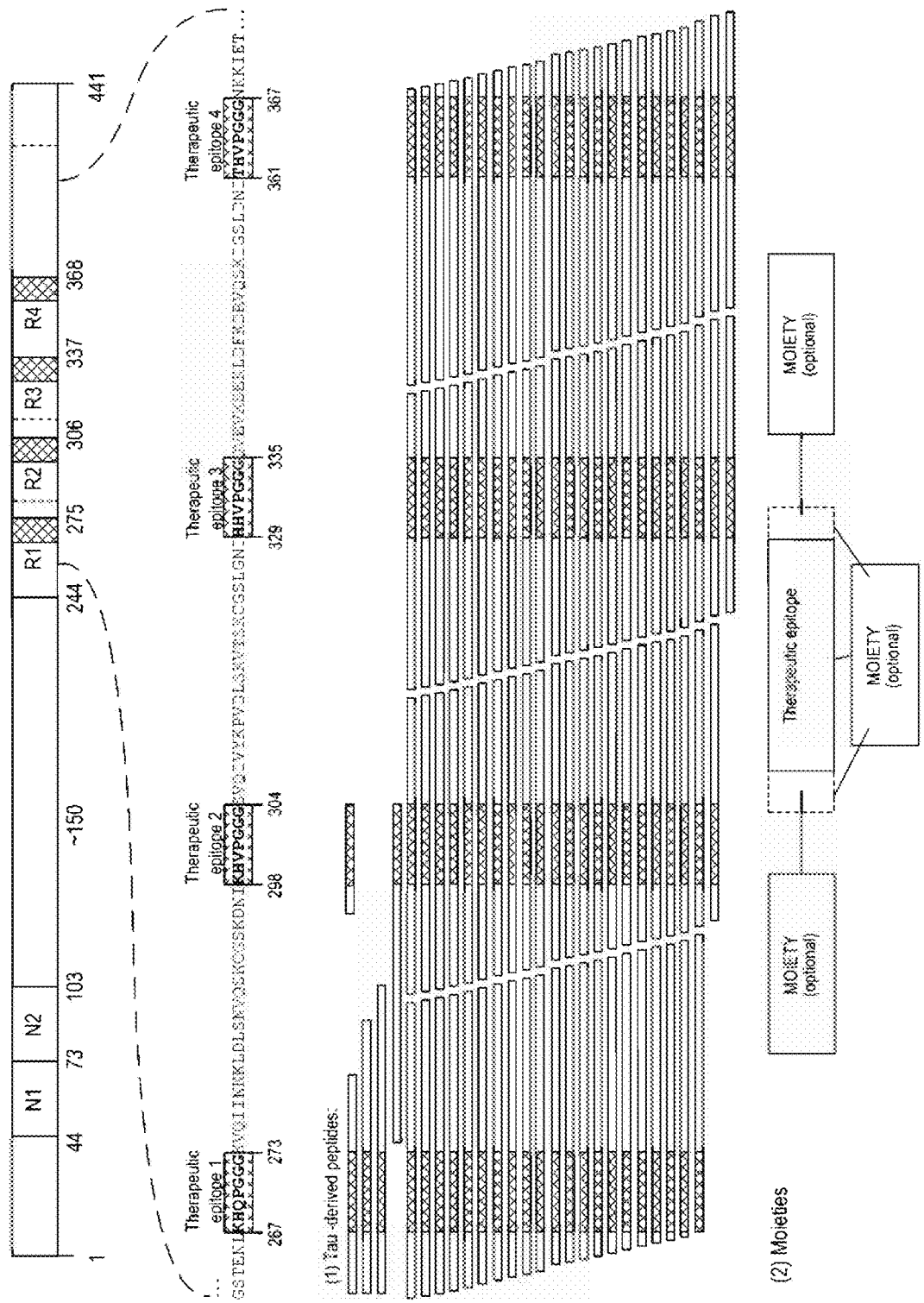
FIG. 26: (A) Schematic of tau 2N4R (SEQ ID NO: 102) with the four DC8E8 epitopes shown in hatched boxes within the enlarged region between residues 261 and 373 (SEQ ID NO. 246): SEQ ID NOs 98-101, respectively. (1) Schematic of overlapping tau-derived peptide immunogens comprising at least one of the four regions of tau recognized by the DC8E8 antibody, for use as active vaccines or to purify DC8E8 antibodies and the like; (2) general possibilities for other modified and designer peptides and compounds, with optional moieties. (B) Summary of immunoblot analysis of insoluble tau prepared from the brain stems of transgenic rats (SHR72, expressing tauΔ(1-150;392-441)/4R) treated with peptides SEQ ID NOs 1-8 and 108. Immunoblot analysis was performed with various mAbs to determine the reduction of insoluble tau of the following AD-relevant epitopes: mAb DC25 (tau 347-353), mAb DC217 (tau pThr217), mAb DC209 (tau pThr 231), mAb AT8 (tau pSer202/pThr205) and mAb AT270 (tau pThr181). (C) Densitometric immunoblot analysis of insoluble tau prepared from the brain stems of rats treated with tau 251-PDLKNVKSKIGSTENLKHQPGGGKVQIINK-280 (SEQ ID NO:1) combined with adjuvant and from control rats treated with adjuvant alone. Mean values are presented with standard error of the mean.
Figure 26C:
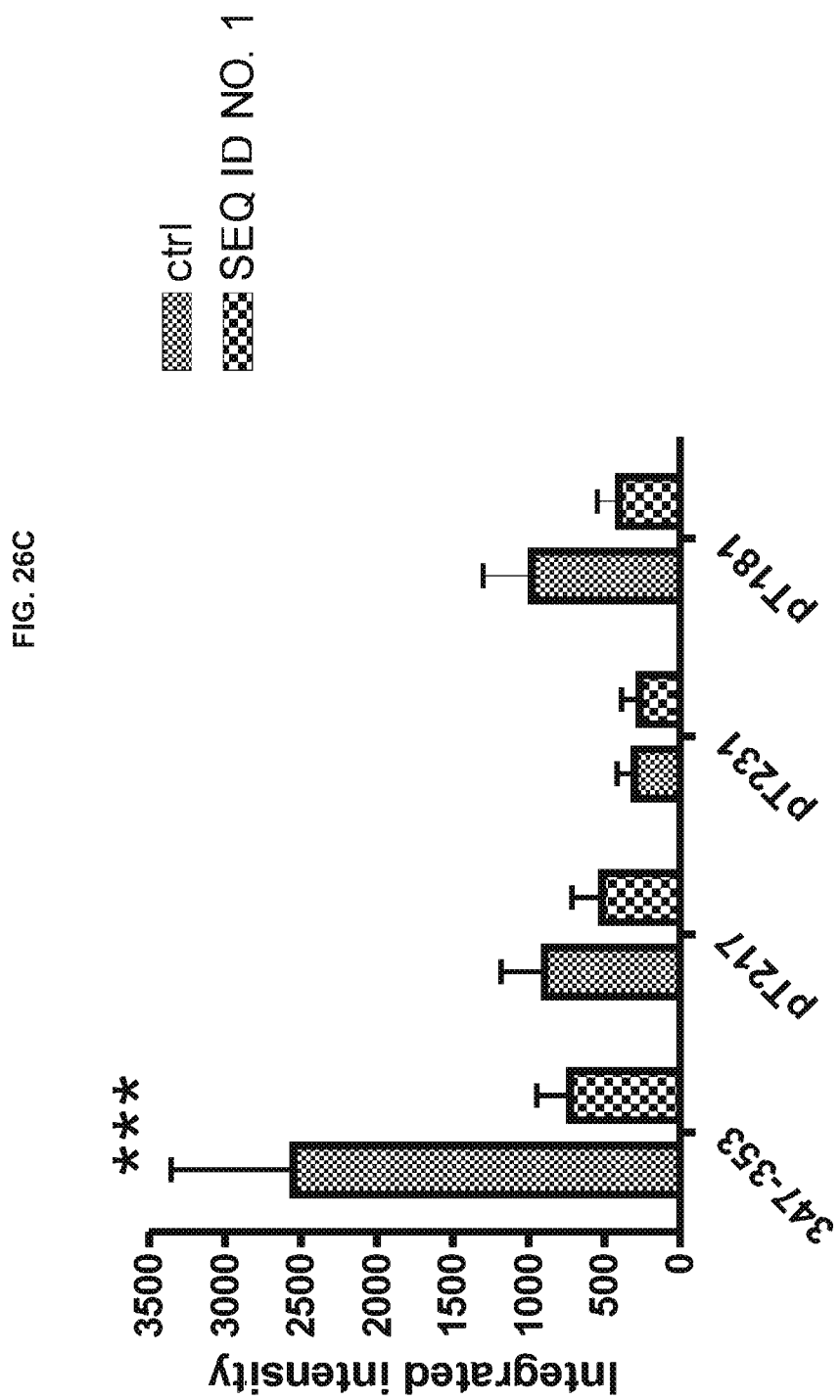

The conversion of tau from soluble to sarkosyl-insoluble pathologic forms is seen as an important step in the development of tau pathology and appears to depend on several factors, such as the concentration of tau, the truncation of tau, and the extent of tau phosphorylation (Alonso et al. 2001; Koson et al. 2008; Kovacech and Novak 2010). The results of immunoblot quantitative analysis of insoluble tau in the sarkosyl insoluble brain fractions harvested from the group of rats immunized with tau peptide SEQ ID NO:1 and from the control group are shown in FIG. 26C. The vaccination reduced the amount of insoluble tau in rats immunized with tau251-280 (SEQ ID NO.1) compared to control rats, which received adjuvant alone (FIG. 26C). This reduction was observed both for overall levels of insoluble tau (as assessed by the DC25 pan-tau antibody, recognizing residues 347-353) as well as for all other tested AD-relevant tau epitopes (surrogate markers of AD) described in FIGS. 26B and 26C and known to be present in sarkosyl-insoluble fractions. Indeed, immunization with tau peptide SEQ ID NO:1 induced a statistically significant (p<0.001) reduction in insoluble tau, which was observed at the total insoluble tau level (71%) using pan-tau monoclonal antibody DC25 (FIG. 26 B, 26C), Analysis with DC217 (pThr217), AT270 (pThr181), revealed a trend towards a reduction in the levels of phosphorylation at Thr217 (42%) and pThr181 (58%) of insoluble tau in the immunized rats compared to the control rats. A weaker treatment effect (11%) was observed at the insoluble tau protein phosphoepitope pThr231 (FIG. 26B). These results suggest that the vaccine activated a mechanism responsible for the inhibition of tau aggregation and/or a mechanism involved in decreasing the levels of tau proteins prone to tau-tau interaction.

Figure 27A:
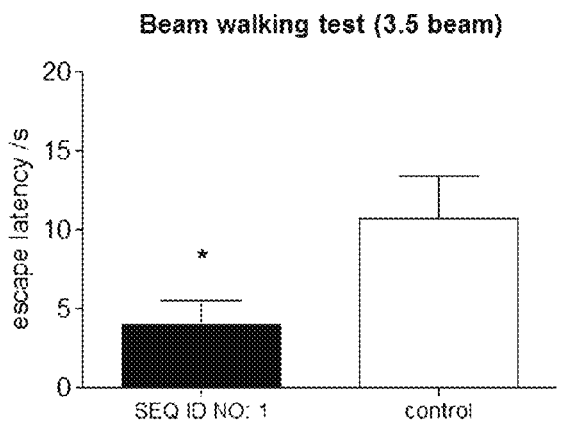
FIG. 27: Neurobehavioral evaluation of transgenic rats (SHR72) modeling AD treated with tau 251-PDLKNVK-SKIGSTENLKHQPGGGKVQIINK-280 (SEQ ID NO: 1). Ten days after 5$^{th}$ dose of the immunogen, the transgenic rats were used for behavioral testing. Diagrams represent mean±SEM. All statistical data were obtained using nonparametric Mann-Whitney U-test. (A) Beam walking test (3.5 beam). (B) Number of hindlimb slips (3.5 beam). (C) Neuroscale.
Figure 27B:
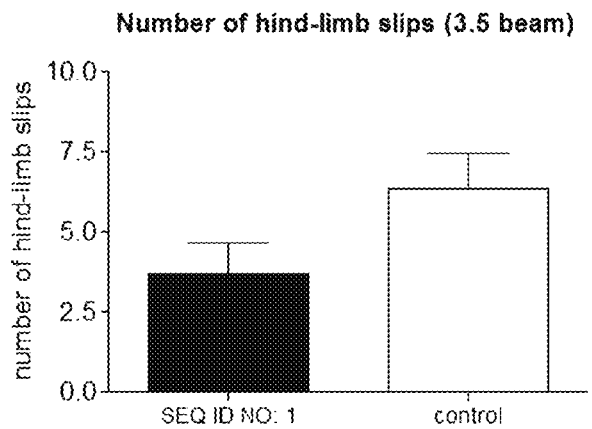
Figure 27C:
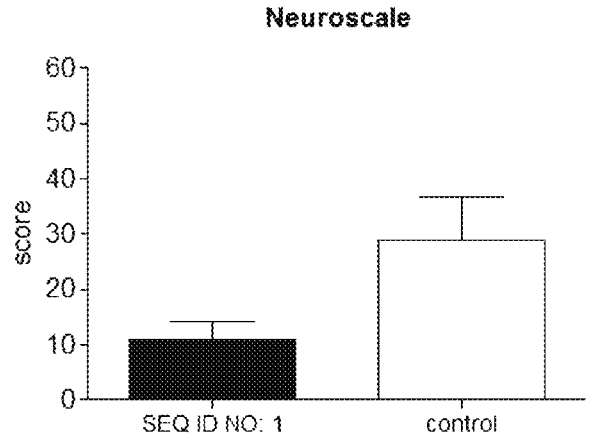

Rats treated with the tau peptide immunogen SEQ ID NO:1 showed statistically significant decreased escape latencies in the beam walking test (* p=0.045) compared to control rats (FIG. 27A). Similarly, the number of hind-limb slips was reduced in the vaccinated group compared to controls; however, this difference was marginally statistically significant (p=0.059, FIG. 27B). The NeuroScale score (described in Example 19, above) was calculated from the values obtained in the beam walking tests, prehensile traction tests and neurological examinations (basic reflexes, hind-limb escape extension reflex). The immunization improved the NeuroScale score of the rats treated with peptide SEQ ID NO:1 compared to the control group, but this improvement was not statistically significant (p=0.065, FIG. 27C), The total NeuroScale score confirmed the neurobehavioral improvement of treated rats compared to untreated rats. All statistical data were obtained using the nonparametric Mann-Whitney U-test.

The neurobehavioral parameters correlated with the insoluble tau levels in the brain stem. Treated rats with low levels of insoluble tau showed lower escape latency and hind-limb slips compared to controls. These findings indicate that the reduction of highly insoluble, misfolded tau leads to functional improvements in immunized rats, which could have therapeutic value. Immunotherapy with tau peptide SEQ ID NO:1 resulted in improvement in neurobehavioral parameters of treated rats. This effect followed the reduction in insoluble tau levels in the brains of the immunized rats. These findings indicate that lowering insoluble tau levels has therapeutic benefit.

Figure 28:
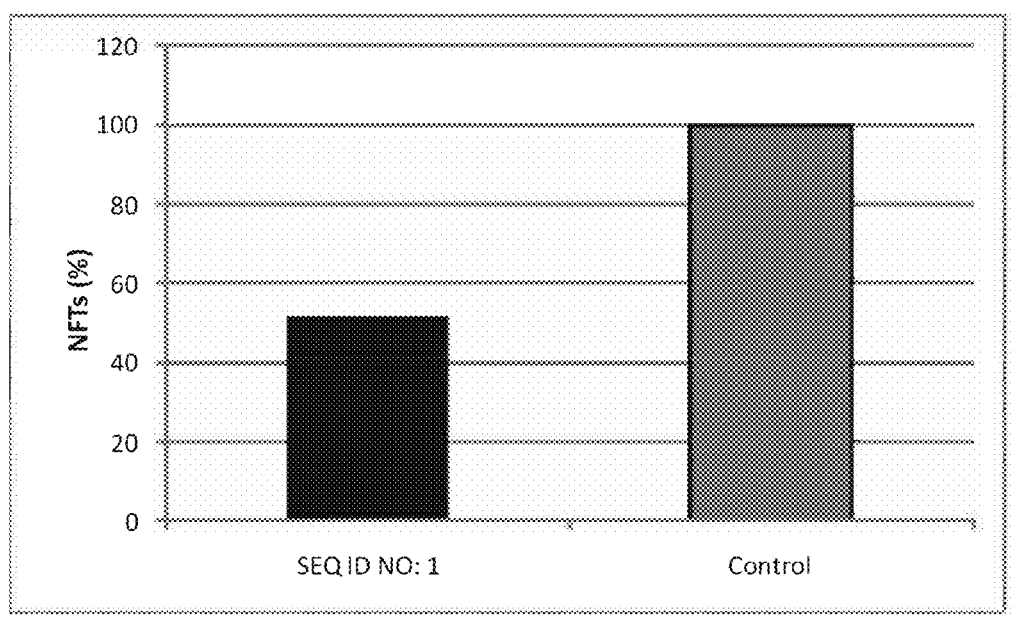
FIG. 28: Vaccination of transgenic rats SHR72 with tau peptide SEQ ID NO:1 resulted in 49% reduction of neurofibrillary tangle (NFT) load. Antibody AT8 was used for evaluation of NFTs in the brain tissues of transgenic rats SHR72.

The efficacy of the immunotherapy with tau peptide SEQ ID NO:1 was further tested at the immunohistochemical level (FIG. 28). Neurofibrillary tangles (NFTs) were analyzed using anti-tau antibodies ATB, DC217, which recognize phosphorylated epitopes on pathological tau, in the brainstems of treated and mock-treated control transgenic rats SHR 72, which received adjuvant/PBS only. The number of NFTs was determined using a semiquantitative method. Three quantitative levels were assigned: 1) none or few neurofibrillary tangles (up to 3 in the brain stem); 2) moderate (many NFTs mainly in the reticular formation of brain stem); and 3) severe (many NFTs in all areas of the brain stem). "Extensive" means moderate to severe stage of neurofibrillary neurodegeneration. Immunohistochemical analysis showed a 50% reduction of neurofibrillary tangle load in vaccine-treated group of transgenic animals.

The decrease of insoluble tau levels measured biochemically correlated with the immunohistochemical analysis results. The data from immunization with SEQ ID NO:1 show the treatment capacity of this peptide, containing DC8E8 epitope No. 1.

b. SEQ ID NO:2 Tau 256-VKSKIGSTENLKHQPGGG-KVQIINK KLDLS-285.

Transgenic rats (SHR72) were immunized with tau peptide SEQ ID NO:2 conjugated to the carrier KLH (as described above).

Immunoblot analysis revealed that the vaccine reduced the amount of insoluble tau in immunized rats compared with control rats that received adjuvant alone. FIG. 29 shows a reduction in all monitored epitopes present in insoluble/aggregated tau. Quantitative analysis of pan-tau DC25 immunoreactivity revealed 41% reduction of insoluble tau (statistically significant, p<0.001) in immunized rats compared to control rats that received adjuvant alone (FIG. 26B). Likewise, immunoreactivity of other antibodies recognizing phosphorylated AD-specific epitopes on insoluble tau was reduced (FIG. 26B and FIG. 29). Additionally, the treatment had an impact on the level of another tau phosphoepitope, which is created by two phosphoresidues Ser202/Thr205 and which is known as a marker of AD pathology. The vaccine induced a 80% reduction of this epitope in immunized transgenic rats, in comparison to non-treated animals. Similarly, the levels of the phosphorylated tau epitopes Thr217, Thr231, and Thr181, were decreased by 72% (p<0.001), 64%, and 74% (p<0.01), respectively. These results suggest that the vaccine induced a mechanism responsible for the inhibition of tau aggregation and/or a mechanism lowering tau species prone to pathological tau-tau interaction.

Figure 30A:
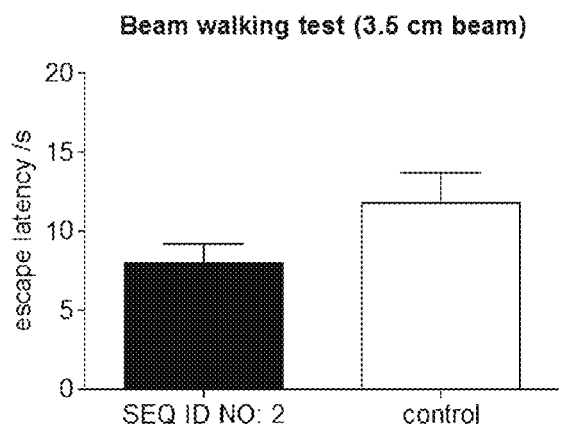
FIG. 30: Neurobehavioral evaluation of transgenic rats (SHR72) treated with tau 256-VKSKIGSTEN-LKHQPGGGKVQIINKKLDLS-285 (SEQ ID NO:2). All statistical data were obtained using nonparametric Mann-Whitney U-test. (A) Beam walking test (3.5 beam). (B) Number of hindlimb slips (3.5 beam). (C) Neuroscale.
Figure 30B:
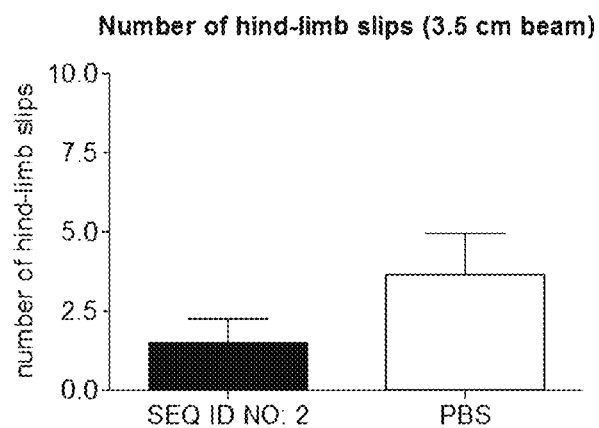
Figure 30C:
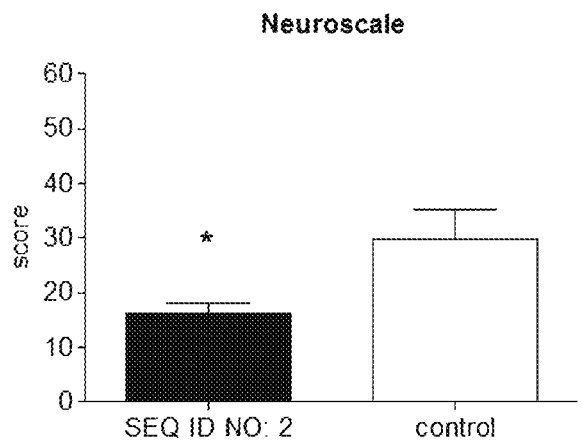

The rats were subjected to behavioral analyses, and FIG. 30 shows results obtained in the beam walking test (FIG. 30A), hind-limb slips test (FIG. 30B) and neuroscale analysis (FIG. 30C, * p, 0.05). A positive trend in beam walking escape latency was observed (p=0.096) in the group of rats treated with the tau peptide SEQ ID NO:2. The immunization reduced the number of hind-limb slips in traverse beam test; however, the difference was not statistically significant (p=0.25) in comparison to the control group. Motor impairment tests together with the prehensile traction test and neurological examination were summarized into Neuroscale score. FIG. 30 shows the statistically significant improvement in Neuroscale score of the rats treated with tau peptide SEQ ID NO: 2 compared to the control group (* p=0.036). In general, the immunization with tau peptide SEQ ID NO: 2 improved the overall motor performance. Improvement on neurobehavioral level correlated with decrease in the amount of insoluble tau (AD-template tau) in immunized animals compared to controls. These findings indicate that lowering insoluble tau levels can have therapeutic benefit.

Figure 31:
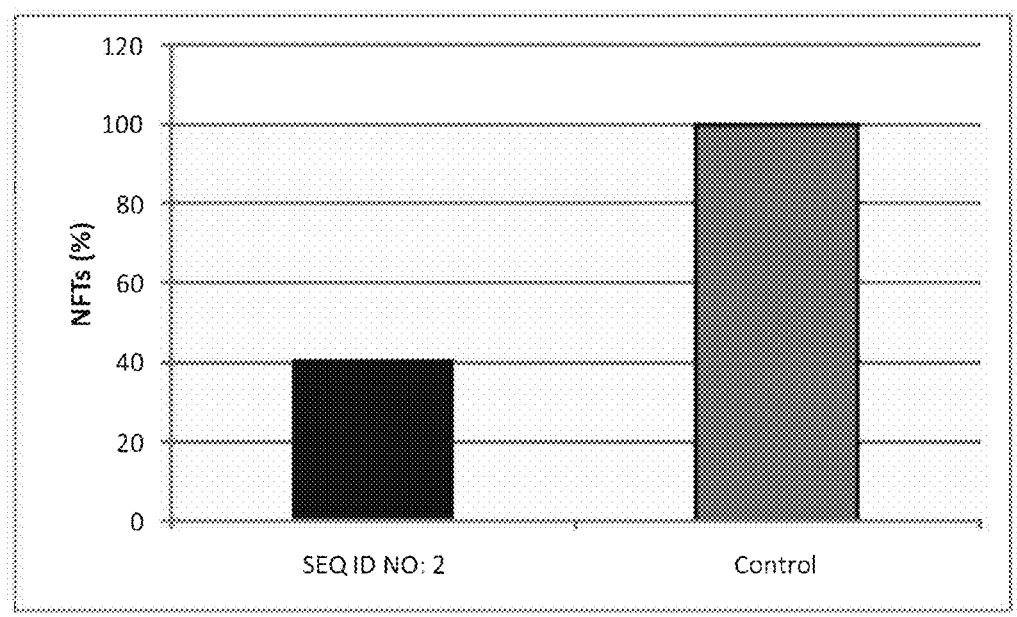
FIG. 31: Vaccination of transgenic rats SHR72 with tau peptide SEQ ID NO:2 resulted in 60% reduction of neurofibrillary tangle (NFT) load. Antibody AT8 was used for evaluation of NFTs in the brain tissues of transgenic rats SHR72.

The efficacy of the immunotherapy with tau peptide SEQ ID NO:2 was further tested at the immunohistochemical level (FIG. 31). For this purpose, two different anti-tau antibodies were used (AT8, DC217), which recognize both phosphorylated soluble and insoluble tau. Neurofibrillary pathology; in these rats (SHR72), is localized mainly in the brainstem and spinal cord and partially in the cerebellum (data not shown), The number of NFTs was determined using a semiquantitative method. Three quantitative levels were assigned: 1) none or few neurofibrillary tangles (up to 3 in the brain stem); 2) moderate (many NFTs mainly in the reticular formation of brain stem); and 3) severe (many NFTs in all areas of the brain stem). "Extensive" means moderate to severe stage of neurofibrillary neurodegeneration. Immunotherapy with peptide SEQ ID NO:2 decreased the number of transgenic rats with extensive NFTs in the brainstem by almost 60% (FIG. 31).

These results demonstrate that vaccination with tau peptide SEQ ID NO:2 shows several desirable vaccine outcomes: 1) reduction in insoluble tau in the brains of immunized transgenic rats at the biochemical level; 2) alleviation of sensorimotor deficits in the immunized trangenic rats at the behavioral level; and 3) reduction in the numbers of neurofibrillary lesions at the immunohistochemical level.

SEQ ID NO:2 Tau 256-VKSKIGSTENLKHQPGGGK-VQIINKKLDLS-285 with Phosphorylated Ser262.

SEQ ID NO:2 containing phosphorylated serine at position 262 was conjugated to KLH.

Figure 32:
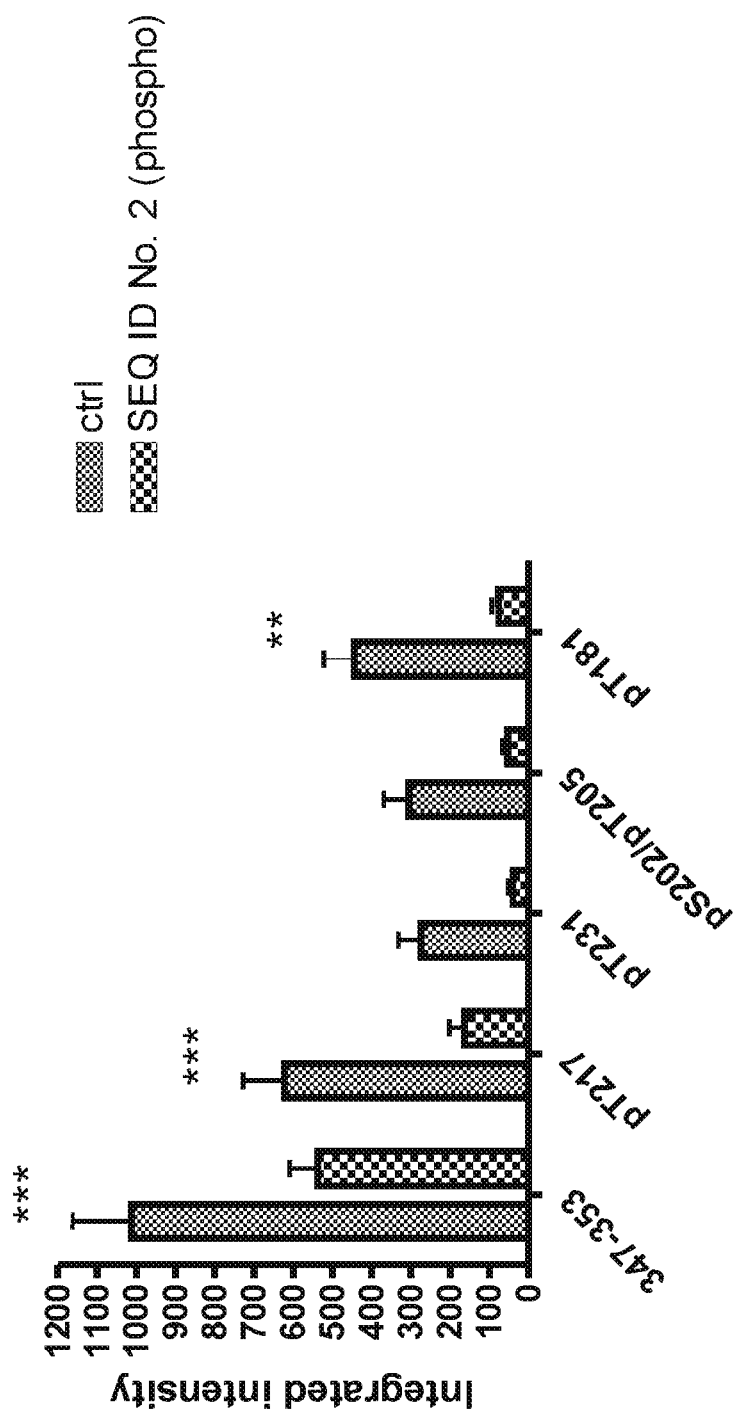
FIG. 32: Quantitative immunoblot analysis of insoluble tau prepared from the brain stems of transgenic rats (SHR72) treated with tau 256-VKSKIGSTEN-LKHQPGGGKVQIINKKLDLS-285 with phosphorylated Ser262 (SEQ ID NO:2) with adjuvant or control rats treated with adjuvant alone. Mean values are presented with standard error of the mean.

Immunoblot of rat brain sarkosyl-insoluble tau fractions with the DC25 antibody revealed that the vaccine statistically significantly reduced the total amount of insoluble tau by 46% (p<0.01) in the immunized animals compared to control transgenic rats that received adjuvant alone (FIG. 32 and FIG. 26B, DC25-based measurements ("347-353" data). Likewise, quantification of the signals of DC209 (pThr231), DC217 (pThr217), AT8 (pSer202, pThr205) and AT270 (pT181) showed lower levels of insoluble phosphorylated tau in the immunized group of animals compared to controls (FIG. 26B). However, reduction of the levels of phosphorylated insoluble tau at pThr217 (p<0.001; 73%), pThr231 (84%), pSer202/pThr205 (82%) and pThr181 (p<0.01; 82%) was more pronounced than the decrease observed in total insoluble tau. These changes in the levels of phosphoepitopes involved in the AD tau misfolding cascade are a useful indicator of the treatment effect. Reduction of AD-relevant tau epitopes shows that the vaccine activated a mechanism responsible for the inhibition of tau aggregation and/or a mechanism decreasing levels of tau prone to pathological interactions with endogenous tau.

Figure 33:
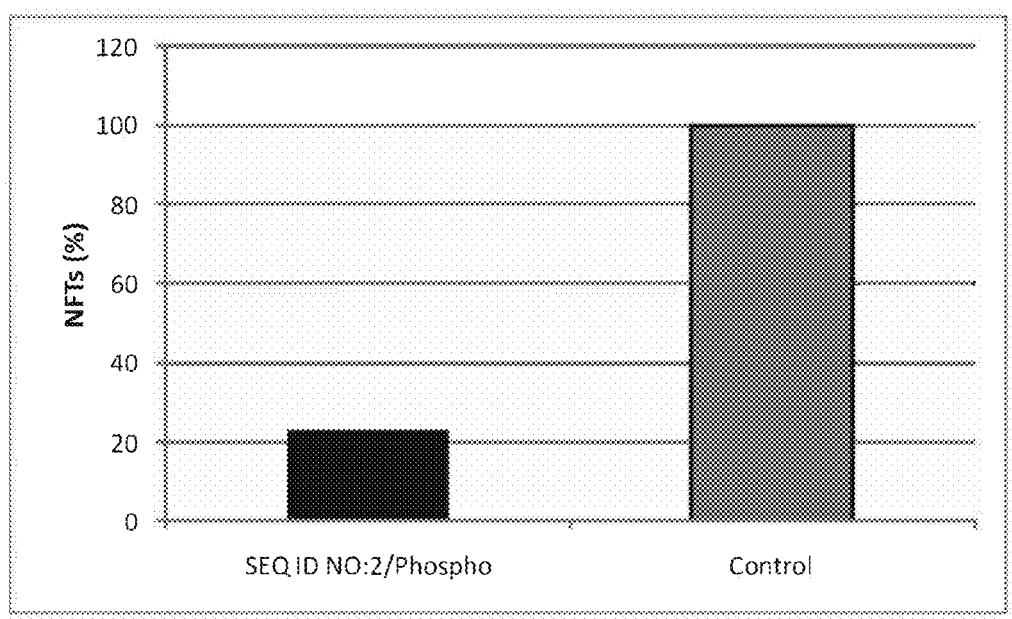
FIG. 33: Vaccination of transgenic rats SHR72 with tau peptide SEQ ID NO:2/Phospho resulted in 77% reduction of neurofibrillary tangle (NFT) load. Antibody AT8 was used for evaluation of NFTs in the brain tissues of transgenic rats SHR72.

The immunohistochemical profile (FIG. 33) shows that immunotherapy with the phosphopeptide SEQ ID NO: 2 led to a decrease in the number of transgenic rats with extensive NFTs in the brainstem. A 78% decrease in the number of transgenic rats with extensive NFTs was observed in the immunized group, when compared to the control non-immunized group. The immunization halted the development of the brain tau pathology in immunized animals. A similar effect was obtained at the biochemical level, with a reduction of insoluble tau on the AD-relevant epitopes analyzed (FIGS. 26B and 32).

These results demonstrate that vaccination with tau phosphopeptide SEQ ID NO:2/pSer262 provoked: 1) a reduction in insoluble tau in the brains of immunized transgenic rats at the biochemical level; and 2) a positive treatment effect on the numbers of neurofibrillary lesions at the immunohistochemical level.

d. SEQ ID NO:3 Tau 259-KIGSTENLKHQPGGGKVQI-INKKLDLSNVQ-288.

Transgenic rats (SHR72 line) were immunized with tau peptide SEQ ID NO:3 formulated with alum adjuvant (Adju-Phos).

Figure 34:
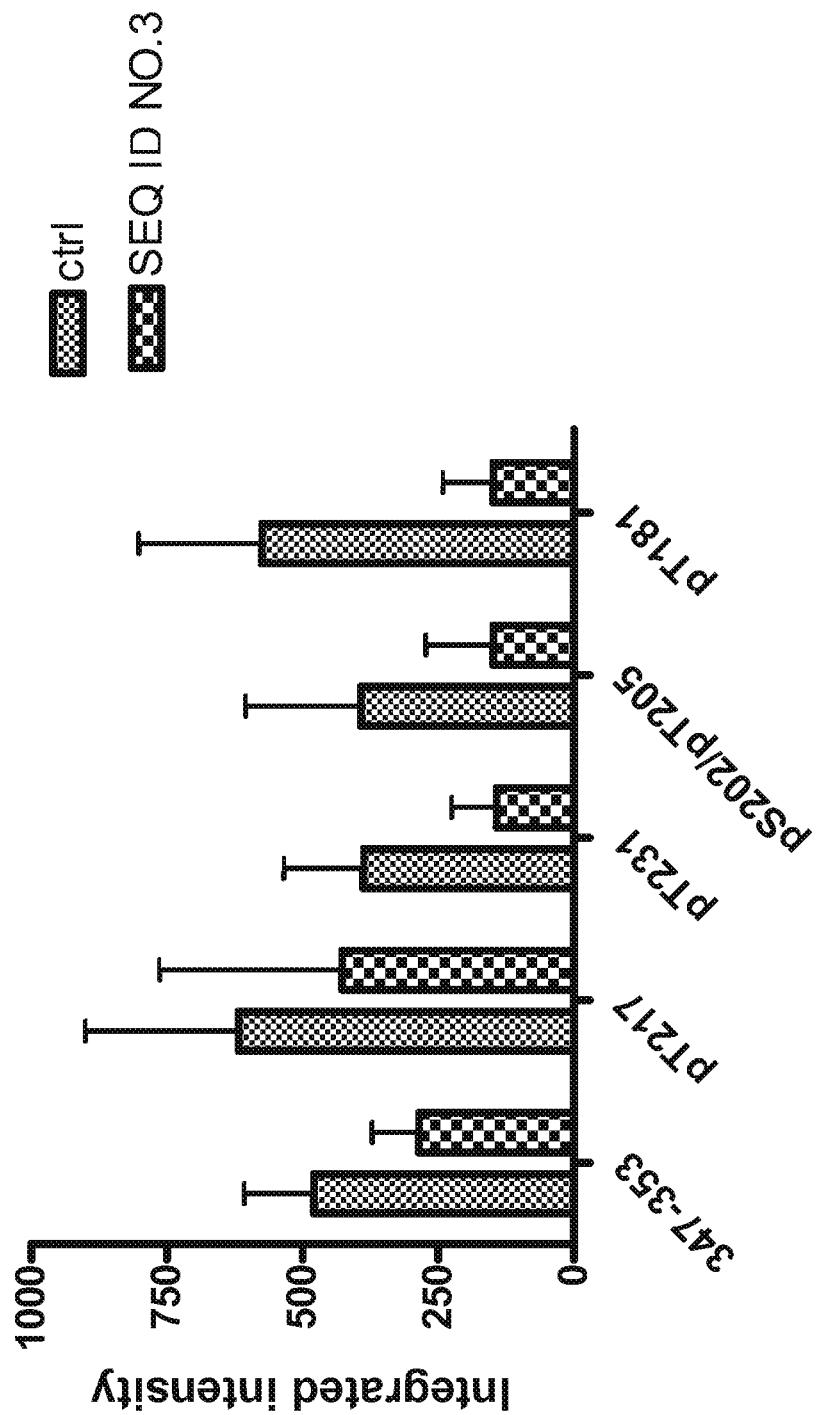
FIG. 34: Quantitative immunoblot analysis of insoluble tau prepared from the brain stems of transgenic rats (SHR72) treated with tau 259-KIGSTENLKHQPGGGK-VQIINKKLDLSNVQ-288 (SEQ ID NO:3) with adjuvant or control rats treated with adjuvant alone. Mean values are presented with standard error of the mean.

FIG. 34 demonstrates that immunotherapy reduces insoluble tau in the immunized rats compared to control rats that received adjuvant alone. A decrease in the insoluble tau level was detected for all analyzed tau epitopes (i.e, for 347-353/DC25 antibody, pT217/DC217 antibody, pT231/DC209 antibody, pS202/pT205/AT8 antibody, and pT181/AT270 antibody). The level of total insoluble tau was reduced by 40%, as revealed by immunodetection with pan-tau antibody DC25. Similarly, the vaccine induced a 30% reduction in tau protein phosphorylated at pT217, as shown in FIG. 26B and FIG. 34. The treatment had a greater effect on the levels of insoluble tau forms phosphorylated at Thr231 (63%), Thr181 (74%), and Ser202/Thr205 (61%) in immunized rats, compared to the non-immunized rats (FIG. 26B and FIG. 34). These findings show that a reduction in insoluble tau can lead to additional alterations in the levels of tau proteins leading to pathology and, thus, can have therapeutic significance. The reduction of AD-relevant tau epitopes shows that the vaccine activated a mechanism responsible for the inhibition of tau aggregation and/or a mechanism decreasing levels of tau prone to pathological interactions with endogenous tau.

Figure 35A:
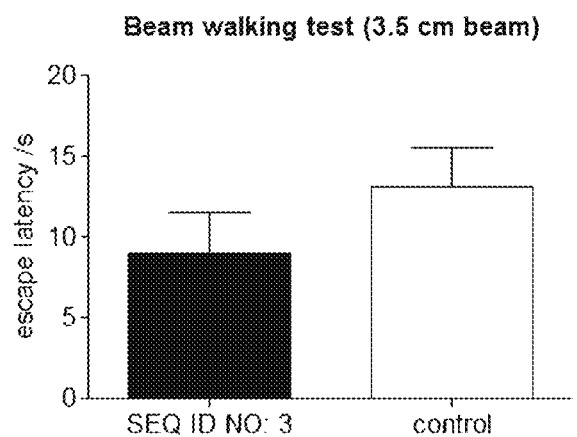
FIG. 35: Neurobehavioral evaluation of transgenic rats (SHR72) treated with tau 259-KIGSTENLKHQPGGGK-VQIINKKLDLSNVQ-288 (SEQ ID NO:3). All statistical data were obtained using nonparametric Mann-Whitney U-test. (A) Beam walking test (3.5 beam). (B) Number of hindlimb slips (3.5 beam). (C) Neuroscale.
Figure 35B:
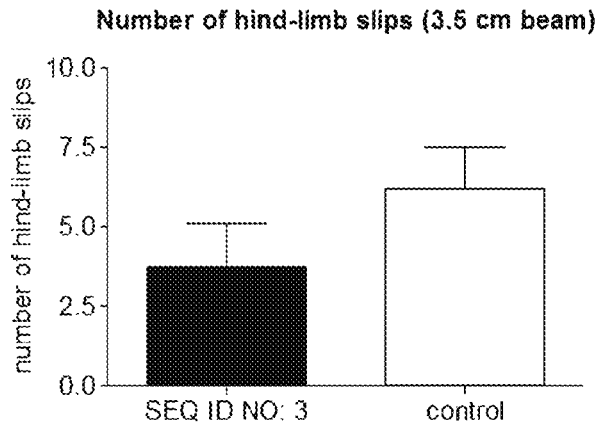
Figure 35C:
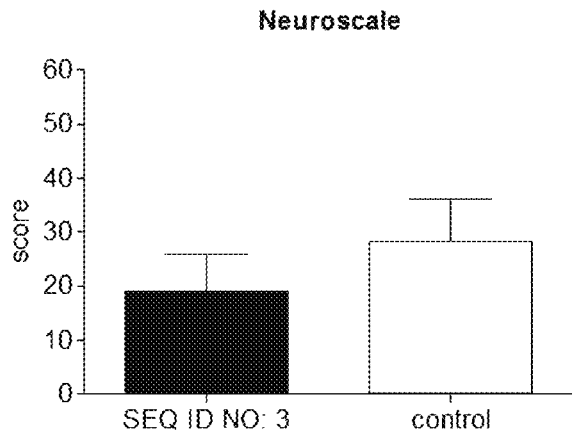

FIG. 35A-C shows results obtained by neurobehavioral evaluation. In the group of rats treated with the peptide SEQ ID NO: 3, a positive trend in beam walking escape latency was observed; however, without a statistically significant difference between the peptide-treated and non-treated/control rats (FIG. 35A; p=0.21). Similarly, treatment led to a decrease in numbers of hind limb slips in the group of immunized rats compared to nontreated rats, but this effect was not statistically significant (FIG. 35B, p=0.15). The total Neuroscale score confirmed the neurobehavioral improvement in rats treated with tau peptide SEQ ID NO: 3 compared to untreated rats (p=0.11 in both cases). However, the difference in Neuroscale score was not statistically significant (p=0.19). Immunotherapy with tau peptide SEQ ID NO: 3 resulted in better sensorimotor coordination of the treated rats compared to control rats in the beam walking test, as well as in the hind-limb slips test; these results were confirmed by the Neuroscale score.

Figure 36:
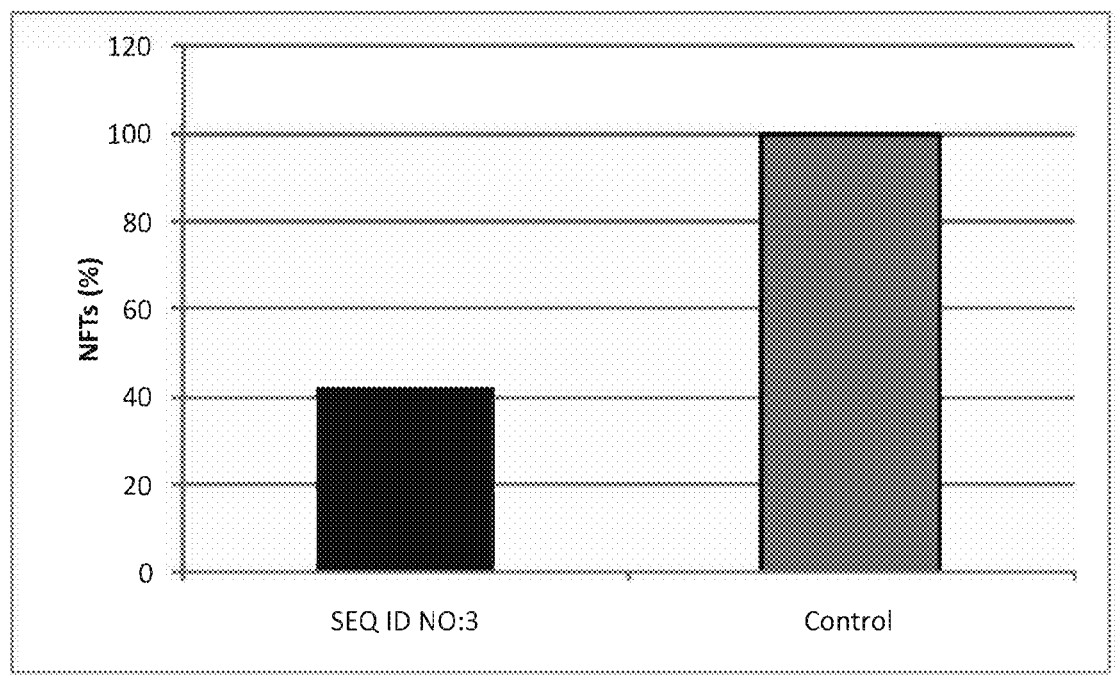
FIG. 36: Vaccination of transgenic rats SHR72 with tau peptide SEQ ID NO:3 resulted in 58% reduction of neurofibrillary tangle (NFT) load. Antibody AT8 was used for evaluation of NFTs in the brain tissues of transgenic rats SHR72.

Moreover, the immunohistochemical profile revealed that immunotherapy with the phosphopeptide SEQ ID NO: 3 lead to a 58% reduction of NFTs in the brain stem of vaccine-treated animals (FIG. 36). These results show that immunization with SEQ ID NO:3, which contains DC8E8 epitope No. 1, significantly reduced pathologic polymeric tau assembled into NFTs. Furthermore, this positive treatment effect was also shown at the biochemical level, represented by a statistically significant reduction of insoluble pathological tau.

e. SEQ ID NO:4 tau 275-VQIINKKLDLSNVQSKCG-SKDNIKHVPGGG-304.

Tau peptide SEQ ID NO:4 was conjugated to KLH and was used for immunization with alum adjuvant (AdjuPhos).

Figure 37:
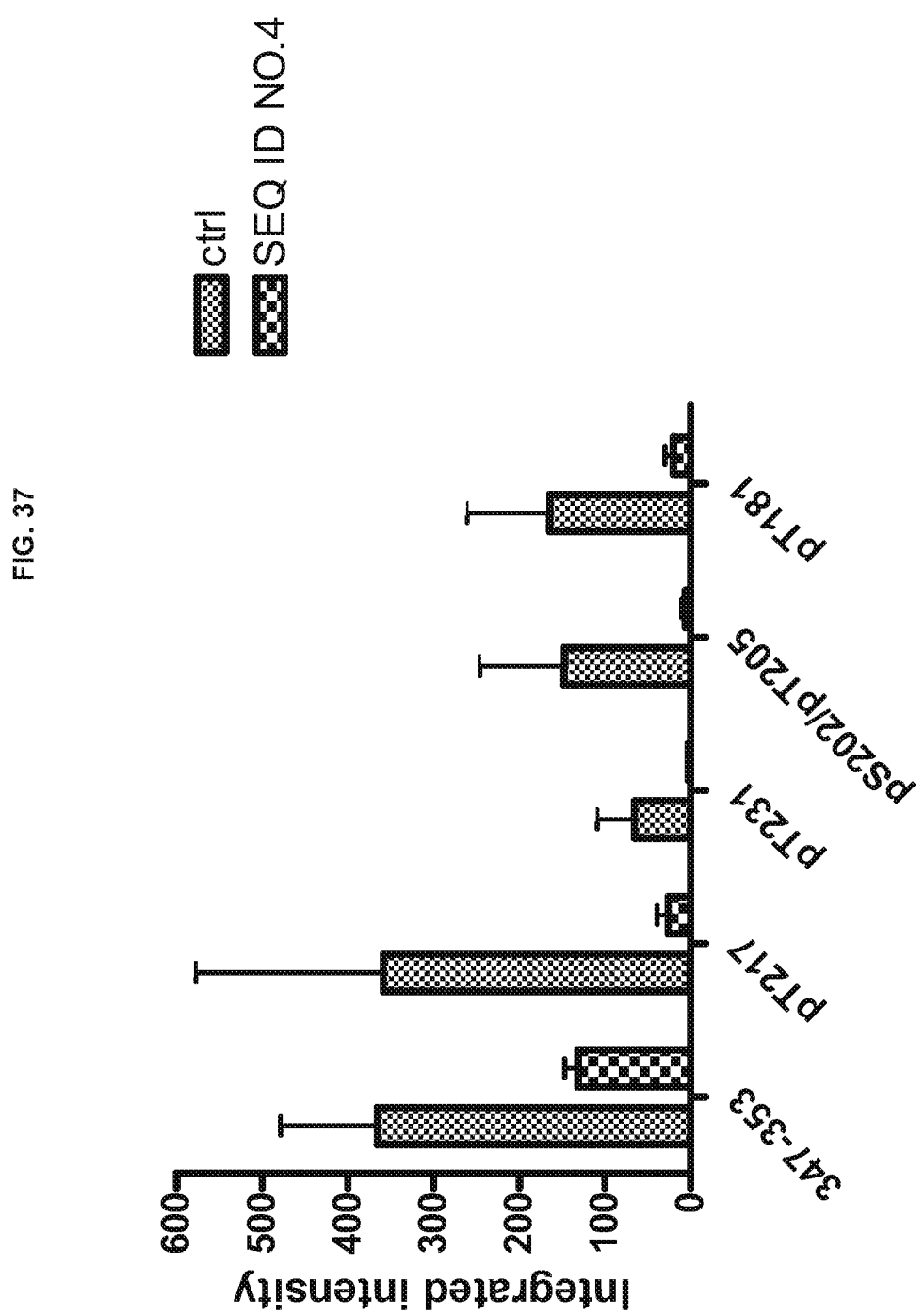
FIG. 37: Quantitative immunoblot analysis of insoluble tau prepared from the brain stems of transgenic rats (SHR72) treated with tau 275-VQIINKKLDL SNVQSKCGSKDNIKHVPGGG-304 (SEQ ID NO:4) or control rats treated with adjuvant alone. Mean values are presented with standard error of the mean.

FIG. 37 and FIG. 26B show that immunotherapy with SEQ ID NO:4 leads to a reduction in the amount of insoluble tau in the immunized rats, compared to control rats that received adjuvant alone. The data show that a decrease in the insoluble tau level was detected for all analyzed tau epitopes. Total insoluble tau levels were reduced by 63%, as revealed by immunoreactivity with pan-tau antibody DC25. Similarly, the vaccine induced reductions in tau protein phosphorylated at pThr217 (92%), Thr231 (95%), Thr181 (87%), and Ser202/Thr205 (95%), as shown in FIG. 26B. It has been shown previously that the level of insoluble tau correlates with the progress of tau pathology (Zilka et al., 2006). The present results show that immunotherapy directed at the therapeutic tau epitope comprised within SEQ ID NO: 99 can decrease the levels of insoluble tau and retards the progress of tau pathology.

Figure 38A:
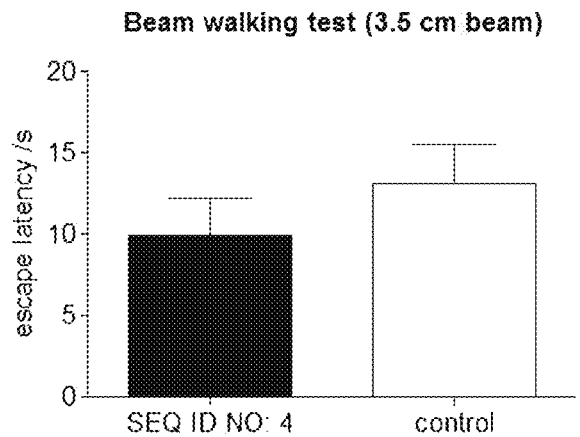
FIG. 38. Vaccination of transgenic rats SHR72 with tau peptide SEQ ID NO:4 showed moderate improvement in neurobehavioral parameters. (A) Beam walking test (3.5 cm beam). (B) Number of hind-limb slips (3.5 cm beam). (C) Neuroscale. Data are presented as mean values with standard error of the mean.
Figure 38B:
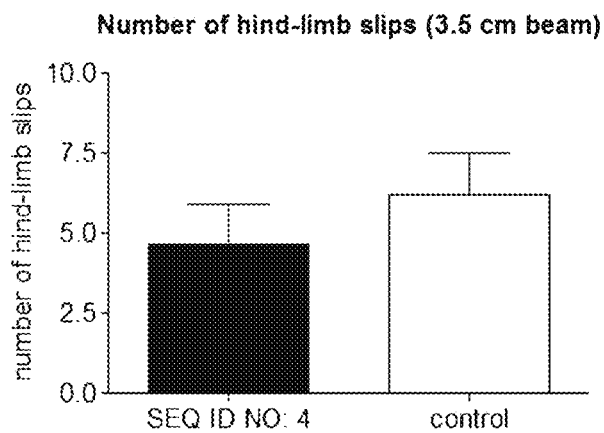
Figure 38C:
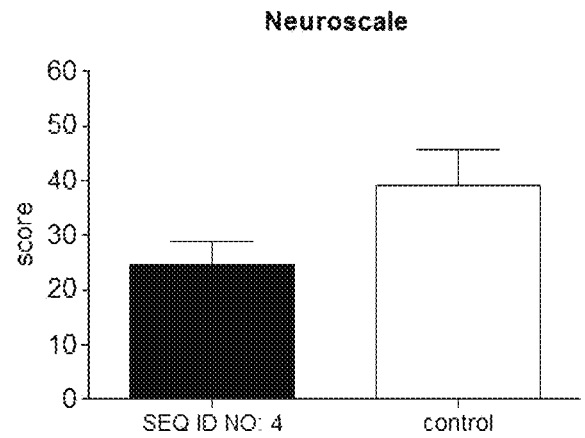

Complex motor impairment was measured by the set of standard motor tests combined with the neurological examination in the composite score—Neuroscale. At 6.5 months of age, transgenic rats SHR72 treated with tau peptide SEQ ID NO:4 were subject to behavioral tests with aim to determine the effect of this immunotherapy. Rats treated with the tau peptide immunogen SEQ ID NO:4 showed decreased escape latencies in the beam walking test, compared to the transgenic rats that received adjuvant alone (controls) (FIG. 38A). Similarly, positive results in number of hind-limb slips was observed in the vaccinated group in comparison with transgenic treatment controls (FIG. 38B). The total Neuroscale score was calculated from the data obtained in the beam walking tests, prehensile traction tests, and neurological examinations (basic reflexes, hind-limb escape extension reflex). The immunization improved the Neuroscale score of the rats treated with peptide SEQ ID NO:4, compared to the control treatment group (FIG. 38C). The total Neuroscale score confirmed the neurobehavioral improvement of treated transgenic rats when compared to untreated transgenic rats.

Figure 39:
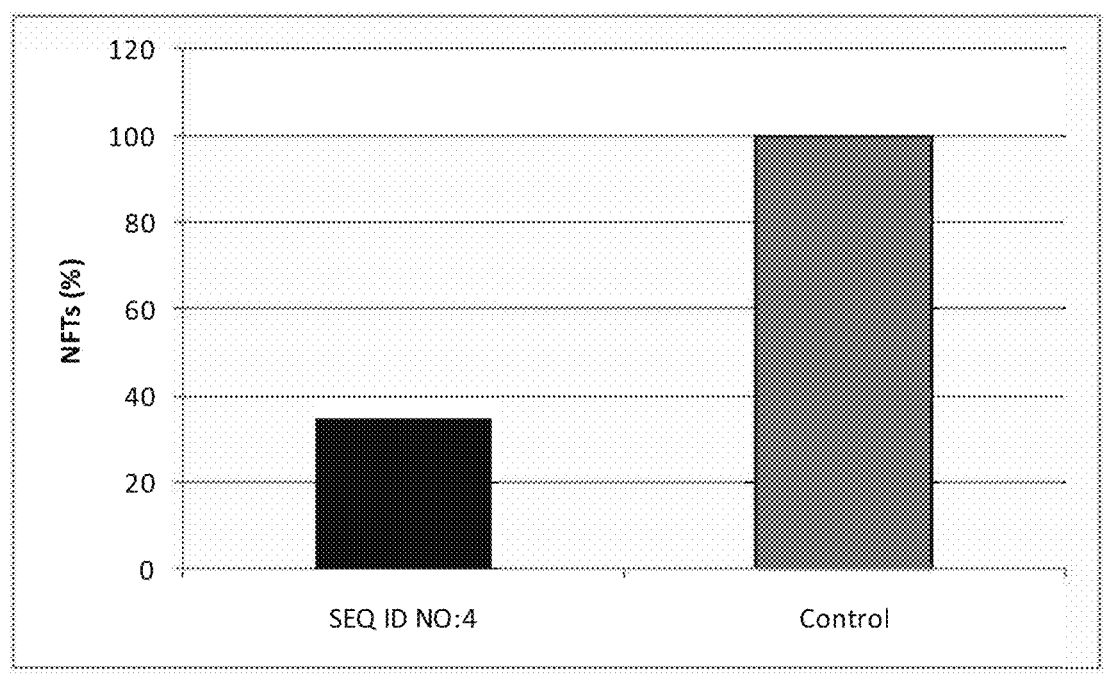
FIG. 39: Vaccination of transgenic rats SHR72 with tau peptide SEQ ID NO:4 resulted in 66% reduction of neurofibrillary tangle (NFT) load. Antibody AT8 was used for evaluation of NFTs in the brain tissues of transgenic rats SHR72.

The efficacy of the immunotherapy with tau peptide SEQ ID NO:4 was further tested at the immunohistochemical level (FIG. 39). Neurofibrillary tangles (NFTs) were analyzed using anti-tau antibodies AT8 and DC217, which recognize phosphorylated epitopes on pathological tau, in the brain stems of vaccine-treated and adjuvant-treated (control) SHR72 rats. Brain tissue from animals which received adjuvant only contained AT8- and DC217-positive NFTs in all areas of the brain stem, and mainly in the reticular formation of brain stem. Immunohistochemical analysis showed a 66% reduction of neurofibrillary pathology in the vaccine-treated transgenic rats SHR72 (FIG. 39).

The changes of insoluble tau levels in the brain stem of transgenic rat line SHR72 are a sensitive indicator of treatment effect. Insoluble total tau, as well as phosphorylated tau levels (pathological monomers, dimers, oligomers and polymers), were both effectively reduced in the brain stem by treatment with tau peptide SEQ ID NO:4 (63-95% reduction; FIG. 26B). The decrease of insoluble tau levels measured biochemically correlated with the results obtained from immunohistochemical analysis. This analysis showed more than 60% reduction of neurofibrillary pathology in the brain stem of vaccine-injected transgenic rats (FIG. 38). The data from immunization with SEQ ID NO:4, show the treatment capacity of this peptide, containing DC8E8 epitope No. 2.

f. SEQ ID NO:5 Tau 201-GSPGTPGSRSRTPSLPTPP-TREPKKVAVVR-230 Carrying Phosphorylated Threonine at Position 217.

The tau peptide SEQ ID NO:5, phosphorylated at position of threonine 217, was administered to SHR72 transgenic rats using alum adjuvant (AdjuPhos).

Figure 40:
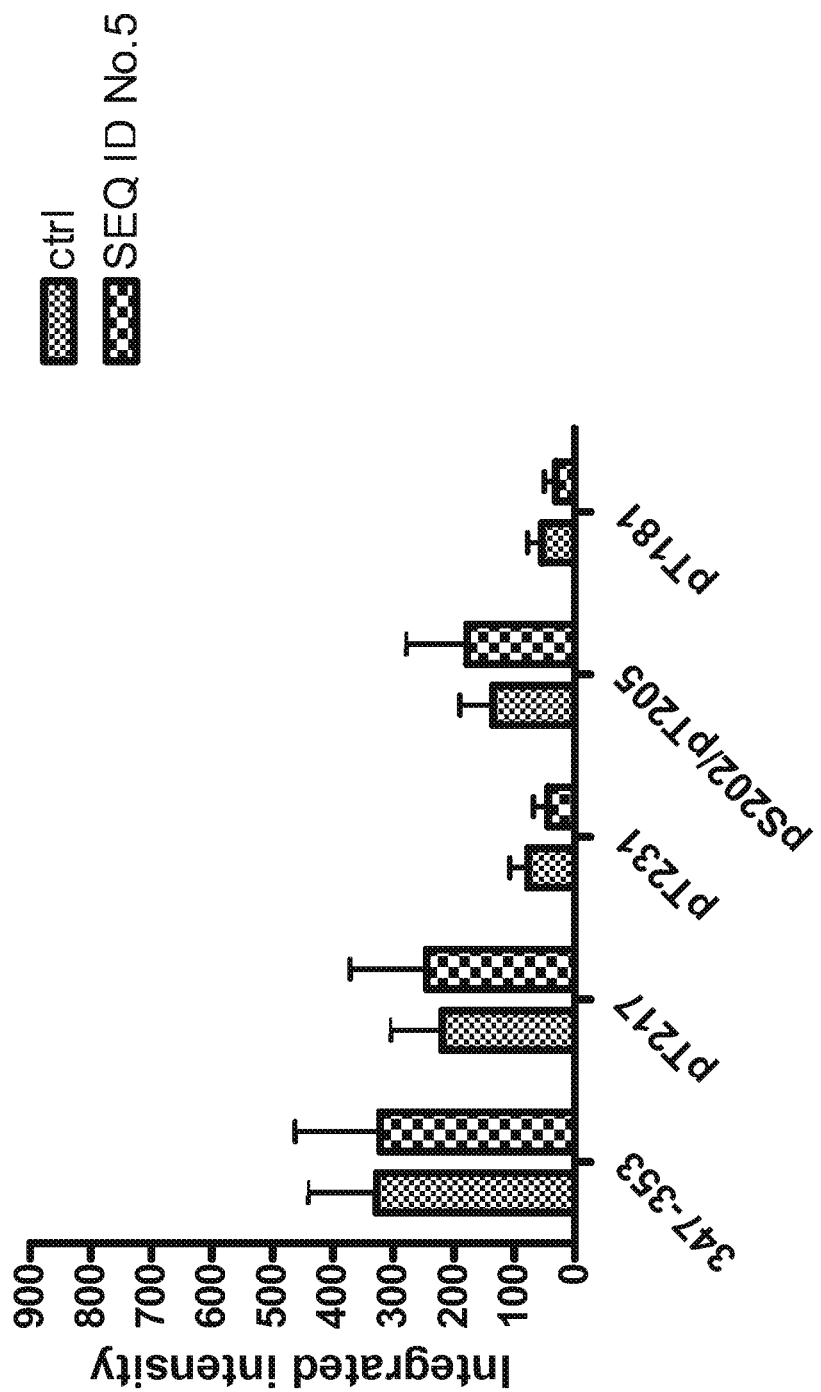
FIG. 40: Immunoblot analysis of insoluble tau prepared from the brain stem of transgenic rats (SHR72) immunized with tau 201-GSPGTPGSRSRTPSLPTPPT REPKKVAVVR-230/carrying phosphorylated threonine at position 217 (SEQ ID NO:5) with adjuvant or control rats treated with adjuvant alone. Mean values are presented with standard error of the mean.

Immunoblot analysis showed that immunization with the phosphopeptide SEQ ID NO:5 did not affect the amount of total insoluble tau (detected with the DC25 antibody) compared with control Tg rats that received adjuvant alone (FIG. 40 and FIG. 26B). However, analysis with antibodies DC209 and AT270 revealed about 30% reduction in the phospho-tau pThr231 and pThr181 levels in the insoluble tau fraction (FIG. 26B). On the other hand, treatment induced a moderate increase in insoluble tau phosphorylated at threonine 217 (11% increase) and tau carrying phospho-sites Ser202/Thr205 (31% increase) compared to control transgenic rats. This finding would suggest an ambiguous or neutral vaccine effect of the immunization with phospho-peptide SEQ ID NO: 5 on the assessed AD-relevant markers, which peptide does not encompass any of the tau aggregation epitopes #1 through #4, identified above (Examples 1 through 11) as therapeutic epitopes.

Figure 41A:
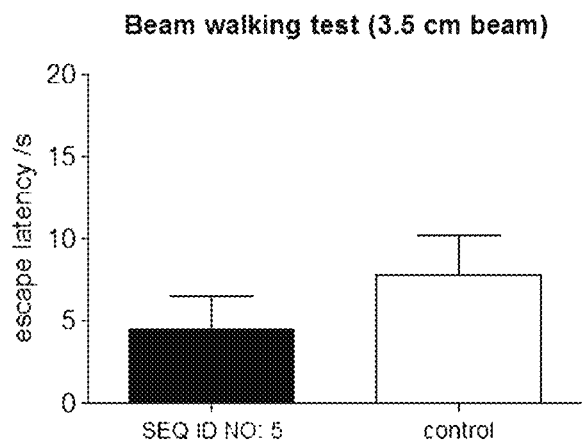
FIG. 41: Neurobehavioral evaluation of transgenic rats (SHR72) treated with tau 201-GSPGTPGSRSRTPSLPTPPT REPKKVAVVR-230/carrying phosphorylated threonine at position 217 (SEQ ID NO:5). All statistical data were obtained using nonparametric Mann-Whitney U-test. (A) Beam walking test (3.5 beam). (B) Number of hindlimb slips (3.5 beam). (C) Neuroscale.
Figure 41B:
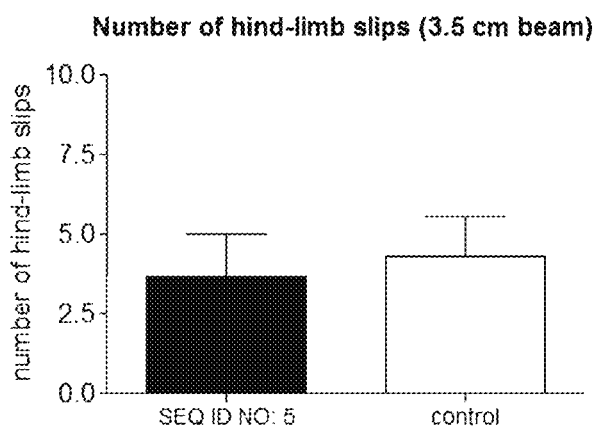
Figure 41C:
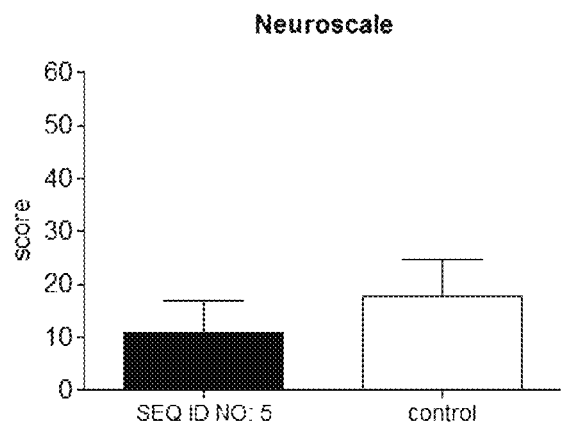

Neurobehavioral analyses of rats treated with phosphorylated tau peptide SEQ ID NO: 5 showed that there was no significant improvement in neurobehavioral functions in the treated group in beam walking test (FIG. 41A, p=0.19) or in the number of hind-limb slips when compared to the control group (FIG. 41B). The total NeuroScale score (FIG. 41C) confirmed no neurobehavioral improvement of treated rats compared to mock-immunized rats (p=0.28).

Figure 42:
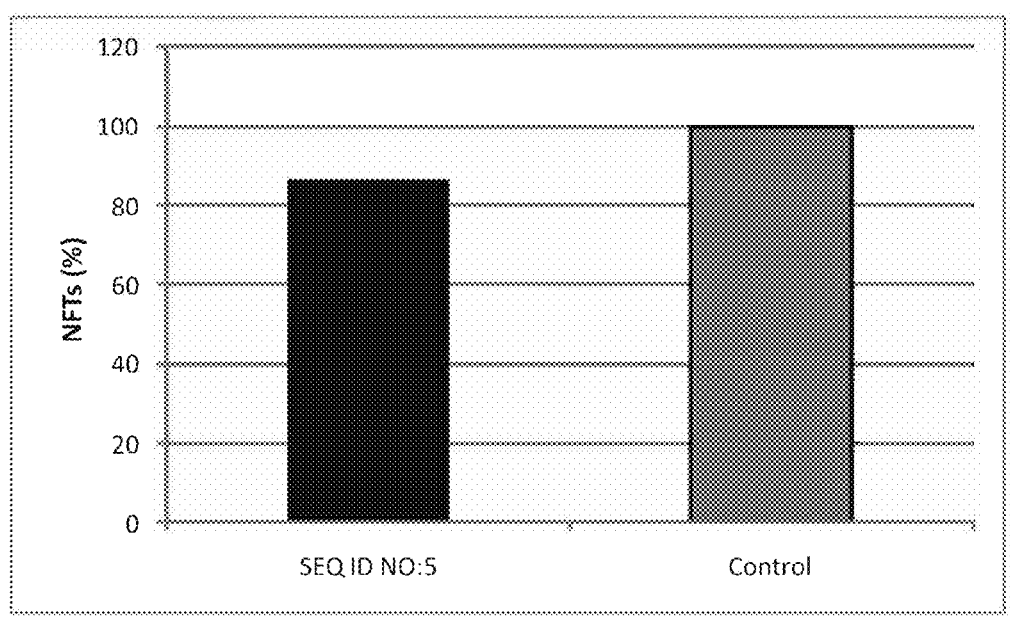
FIG. 42: Vaccination of transgenic rats SHR72 with tau peptide SEQ ID NO:5 showed no effect on neurofibrillary tangle (NFT) load. Antibody AT8 was used for evaluation of NFTs in the brain tissues of transgenic rats SHR72.

Immunotherapy with tau phosphopeptide SEQ ID NO:5 did not reduce the number of transgenic rats (SHR72) with extensive NFTs in the brainstem when compared to control transgenic rats by immunohistochemistry (FIG. 42).

These results show that vaccination with tau peptide SEQ ID NO: 5 pT217, which lacks all of the therapeutic epitopes (SEQ NO:98-101), does not result in a statistically significant improvement of neurobehavioral function and only a reduction of approximately 11% in the number of neurofibrillary lesions at the immunohistochemical level. No effect was observed on biochemical level with respect to a reduction of insoluble tau, as assessed by the DC25 antibody.

g. SEQ NO:6 Tau 379-RENAKAKTDHGAEIVYKSPV-VSGDTSPRHL-408 Carrying Phosphorylated Serine Residues at Position 396 and 404.

Tau peptide phosphorylated at position of 396 and 404 was administered to SHR72 using alum adjuvant (Adju-Phos). SEQ ID NO:61 pS396/pS404 lacks any of the therapeutic epitopes represented by SEQ NO:98-101, but contains a phosphoepitope over-represented in AD brain tau proteins (Greenberg et al. 1992; Otvos et al. 1994).

Figure 43:
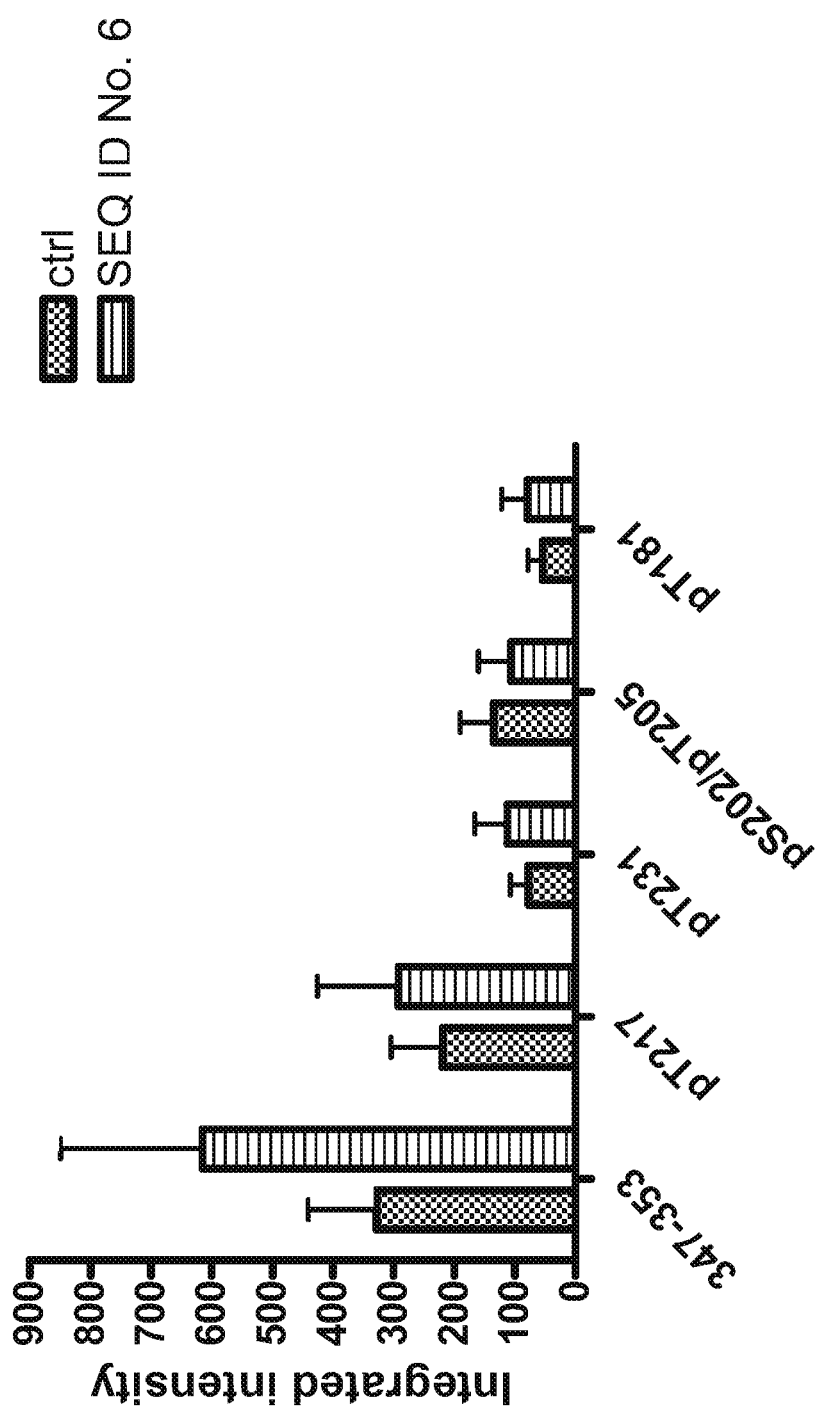
FIG. 43: Immunoblot analysis of insoluble tau prepared from the brain stem of transgenic rats (SHR72) immunized with tau 379-RENAKAKTDHGAEIVYKSPVV SGDTSPRHL-408 carrying phosphorylated serine residues at position 396 and 404 (SEQ ID NO:6) and adjuvant or control rats treated with adjuvant alone. Mean values are presented with standard error of the mean.

In contrast to the decrease in the amount of sarkosyl-insoluble tau observed with peptides SEQ ID NOs, 1-4, immunization with phosphorylated peptide SEQ ID NO. 6 led to an increase in the amount of insoluble tau in immunized rats compared to control rats; which received adjuvant alone. Immunoblot analysis revealed a trend towards an overall increase in insoluble phospho-tau levels (FIG. 43 and FIG. 26B), Immunization led to an increase in total tau levels in the insoluble tau fraction, as revealed by pan-tau mAb D025. An increase was also observed at tau epitopes pT217 (33% increase), Thr231 (44% increase), and Thr181 (7% increase). However; AD-relevant epitope pS202/pT205 was an exception (FIG. 26B). The level of tau protein carrying this phosphoepitope was reduced by 19% compared to control rats. Increased levels of multiple disease-relevant pathological insoluble tau protein indicate an undesirable negative effect of this vaccine on the rats.

Figure 44A:
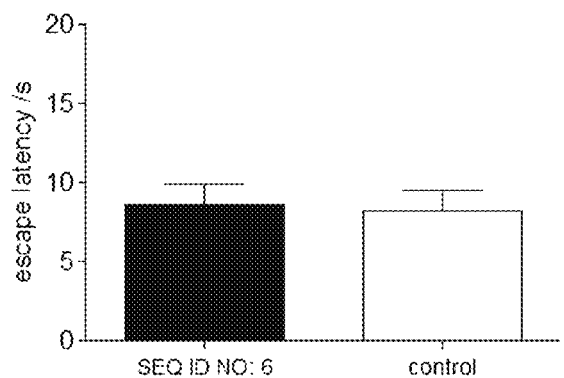
FIG. 44: Neurobehavioral evaluation of transgenic rats (SHR72) treated with tau SEQ ID NO:6 phosphorylated at Ser396/Ser404. All statistical data were obtained using nonparametric Mann-Whitney U-test. (A) Beam walking test (3.5 beam). (B) Number of hindlimb slips (3.5 beam). (C) Neuroscale.
Figure 44B:
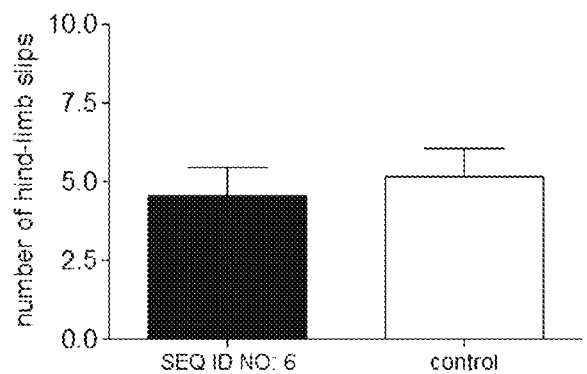
Figure 44C:
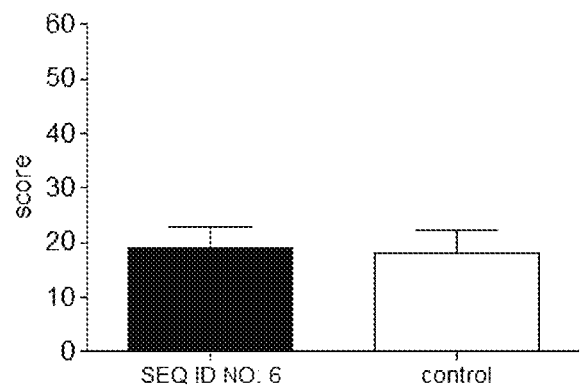

The neurobehavioral response of rats treated with tau peptide SEQ ID NO:6/pS396/pS404 and controls was evaluated (FIGS. 44A, B, and C). Immunotherapy showed no statistically significant differences between the treated and control rats in beam walking escape latency (p=0.82) or in the number of hind-limb slips (p=0.75). These results were confirmed by the Neuroscale score (p=0.96), in which no statistically significant differences in overall neurobehavioral performance were observed between immunized and control rats, Thus, the treatment with peptide SEQ ID NO: 6/pS396/pS404 had no statistically significant influence on the beam walking test escape latency, number or hind-limb slips, or overall motor performance of the tested rats.

Figure 45:
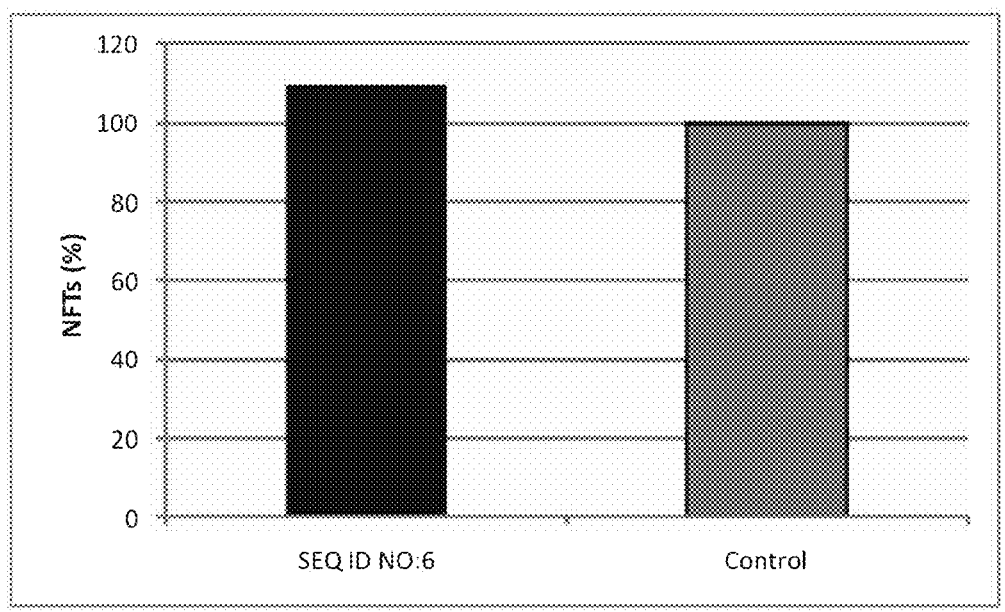
FIG. 45: Vaccination of transgenic rats SHR72 with tau peptide SEQ ID NO:6 showed no reduction of neurofibrillary tangle (NFT) load. Antibody AT8 was used for evaluation of NFTs in the brain tissues of transgenic rats SHR72.

FIG. 45 shows the percentage of transgenic rats with extensive tau pathology, as assessed by immunohistochemistry with AT8. Immunotherapy with tau peptide SEQ ID NO:6/pS396/pS404 increased the tangle load by 9% relative to the control group. Thus, the negative effect of the SEQ ID NO:6/pS396/pS404 at the immunohistochemical level was confirmed at the biochemical and neurobehavioral levels.

These results demonstrate that vaccination with tau phosphopeptide SEQ ID NO:6/pS396/pS404, which lacks any of the therapeutic tau epitopes depicted in SEQ ID NO: 98-101, shows: 1) no therapeutic effect on insoluble tau in the brains of immunized rats; 2) no effect at the behavioral level; and 3) no reduction, but rather a 9% increase in tangle load. Therefore, this phosphoepitope, which has been reported to be AD-specific (Greenberg et al. 1992; Otvos et al. 1994), did not induce a therapeutic effect.

h. SEQ ID NO:7 Tau 181-TPPSSGEPPKSGDRSGYS-SPGSPGTPGSRS-210 Carrying a Phosphorylated Serine Residue at Position 202 and a Phosphorylated Threonine Residue at Position 205.

Figure 46:
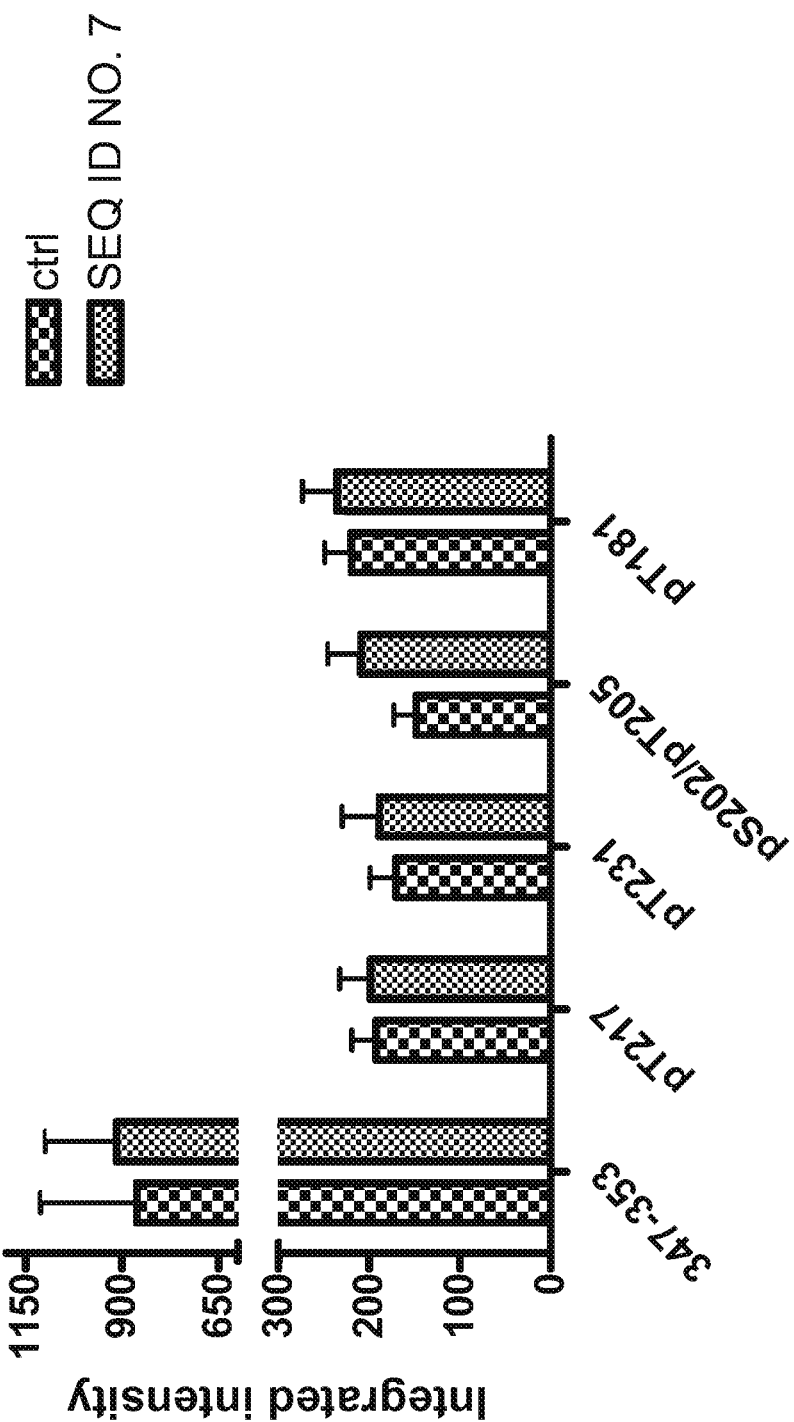
FIG. 46: Immunoblot analysis of insoluble tau prepared from the brain stem of rats (SHR72) immunized with tau 181-TPPSSGEPPKSGDRSGYSSPGSPGTPGSRS-210 carrying phosphorylated serine residue at position 202 and threonine residue at 205 (SEQ ID NO:7) with adjuvant or control rats treated with adjuvant alone. Mean values are presented with standard error of the mean.

The resulting tau peptide SEQ ID NO:7/pS202/pT205, lacks any of the therapeutic epitopes presented in the SEQ ID NO:98-101. The phosphopeptide was conjugated to KLH and administered to transgenic rats (SHR72 line) in Freund's adjuvant The quantitative analysis of tau immunoreactivity in the brain stem by immunoblot did not show any therapeutic effect. (FIG. 46). The levels of total tau (DC25 epitope, 6% increase) and tau proteins phosphorylated on disease-relevant tau epitopes pT217 (3% increase), Thr231 (11% increase), and Thr181 (7% increase), was slightly increased in immunized rats compared to controls (FIGS. 46 and 26B). Immunization induced a higher increase in insoluble tau protein phosphorylated at Ser202/Thr205 (41% increase).

Figure 47A:
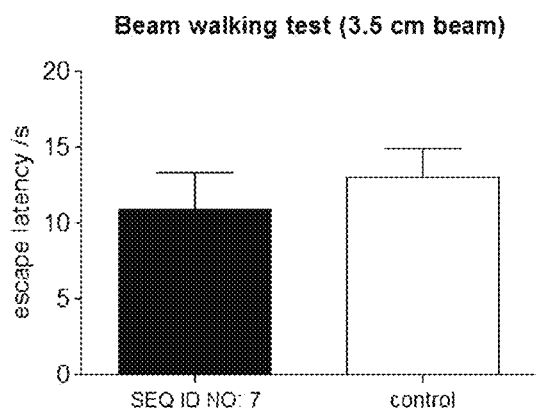
FIG. 47: Neurobehavioral evaluation of SHR72 rats treated with tau 181-TPPSSGEPPKSGDRSGYSSPGSPGTPGSRS-210 carrying phosphorylated serine residue at position 202 and threonine residue at 205 (SEQ ID NO:7). All statistical data were obtained using nonparametric Mann-Whitney U-test. (A) Beam walking test (3.5 beam). (B) Number of hindlimb slips (3.5 beam). (C) Neuroscale.
Figure 47B:
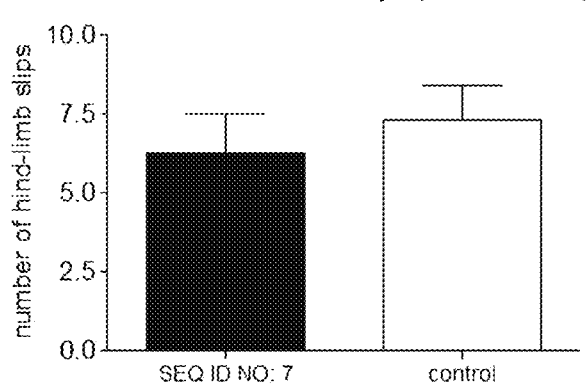
Figure 47C:
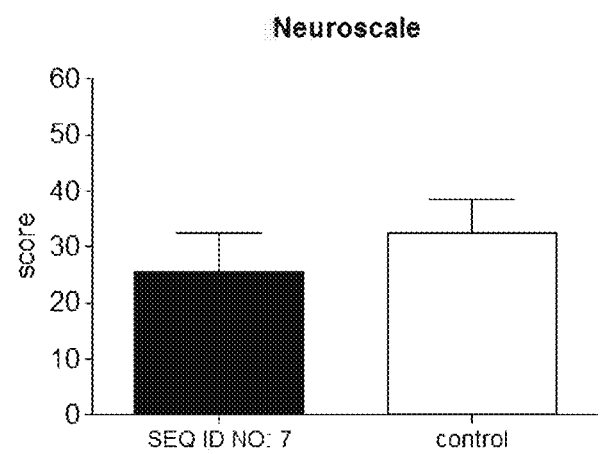

Immunotherapy with phosphorylated peptide SEQ ID NO: 7 did not significantly influence the sensorimotor function of the rats (FIG. 47). Immunized rats showed an apparent improvement in neurobehavioral parameters compared to controls. However, the groups were not statistically different, as no statistically significant difference was observed between treated rats and controls in the beam walking escape latencies (p=0.47, FIG. 47A), as well as in the number of hind-limb slips (p=0.54, FIG. 47B) and NeuroScale score (p=0.3, FIG. 47C).

Figure 48:
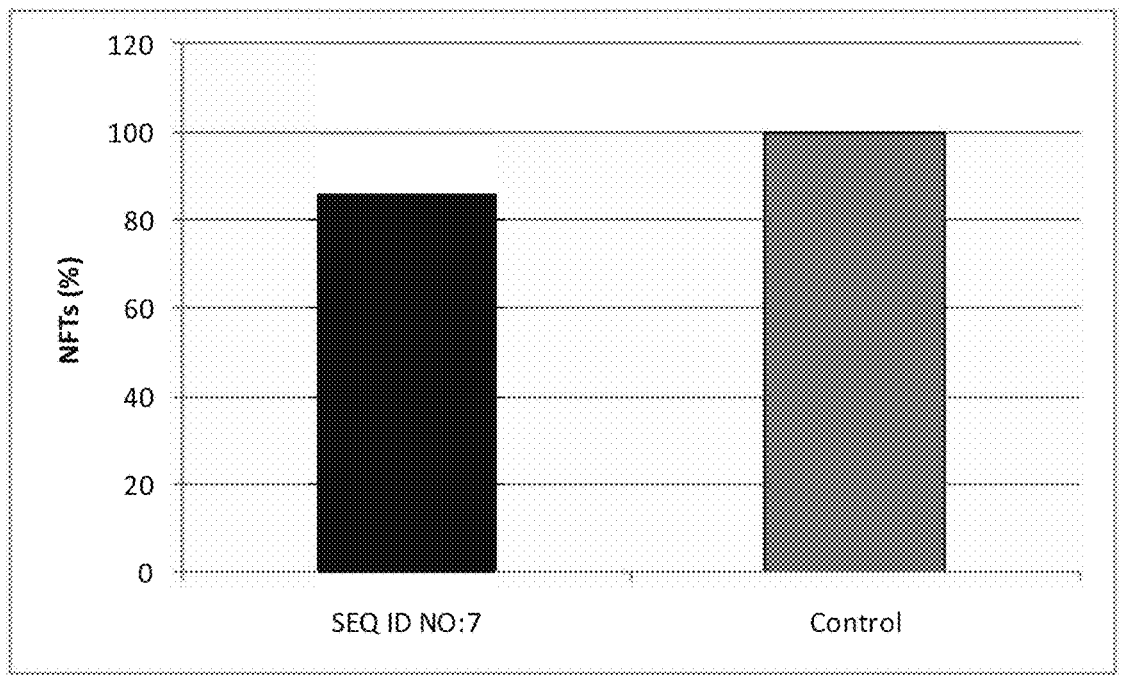
FIG. 48: Vaccination of transgenic rats SHR72 with tau peptide SEQ ID NO:7 showed no effect on neurofibrillary tangle (NFT) load. Antibody AT8 was used for evaluation of NFTs in the brain tissues of transgenic rats SHR72.

Peptide SEQ ID NO:7 carries a phosphorylated tau epitope which does not contain any of the DC8E8 epitopes. Examination of the brain stems of the treated SHR72 rats revealed that the immunotherapy with tau peptide SEQ ID NO:7 was not able to reduce the neurofibrillary tangle load (FIG. 48). Brain tissue from vaccinated and control animals contained nearly identical numbers of AT8 and DC217-positive NFTs in all areas of the brain stem, mainly in the reticular formation, Vaccine containing SEQ ID NO:7, lacking DC8E8 epitopes, did not show any beneficial effect in the treated animals.

These results demonstrate, that vaccination with tau phosphopeptide SEQ ID NO:7/pS202/pT205 produces: 1) no change in the levels of insoluble tau in the brains of immunized rats at the biochemical level; and 2) no effect at the behavioral level. This phosphopeptide provides additional evidence that the phospho-sites represented by pS202/pThr205 are not sufficient to elicit an immune reaction eliminating pathological tau proteins and/or positively influencing the neurobehavioral status of the rats. In contrast, the therapeutic tau epitopes (SEQ ID NOs:98-101) achieve this effect.

i. SEQ ID NO:8 Tau 300-VPGGGSVQIVYKPVDLSK-317.

Figure 49:
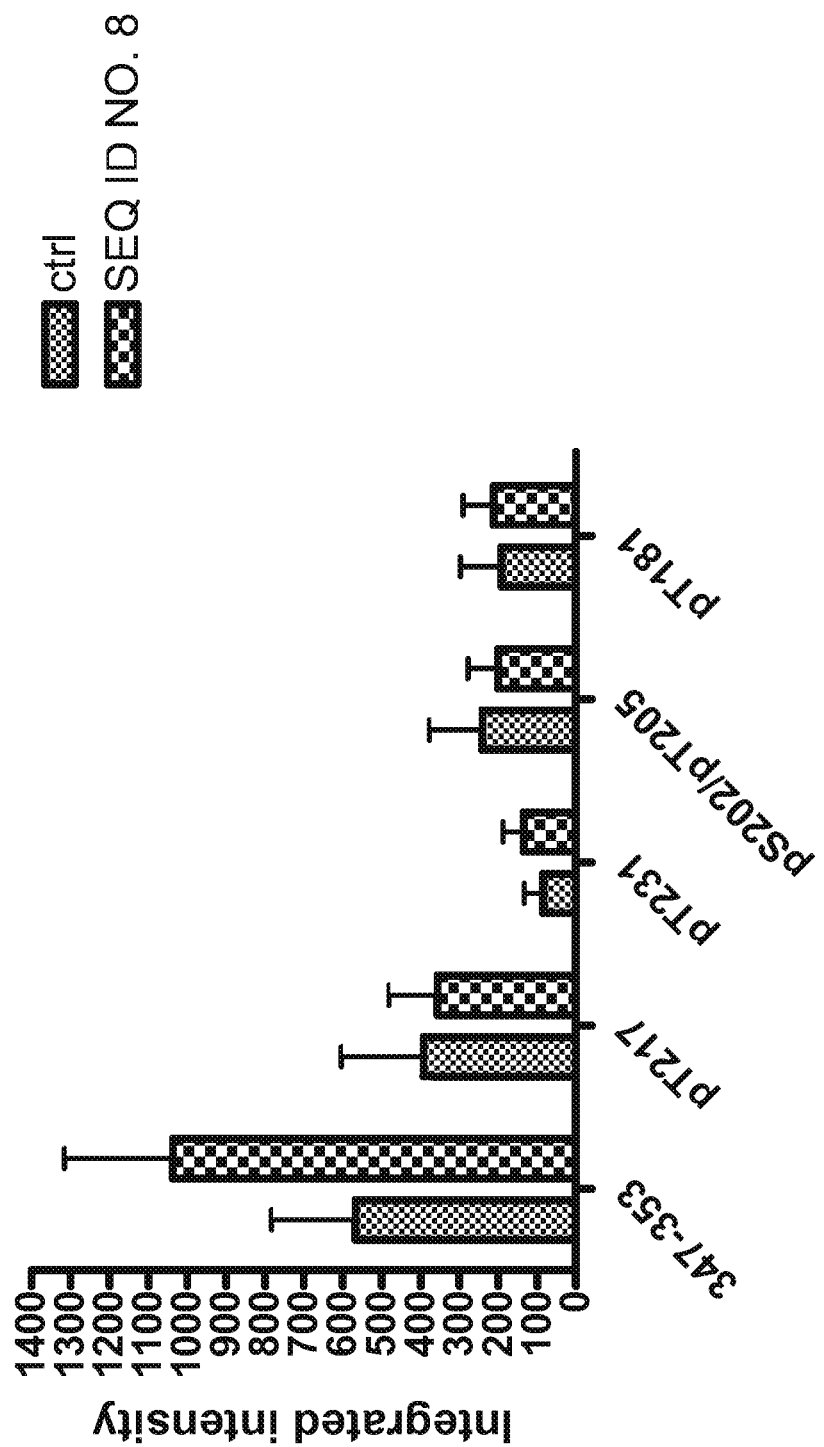
FIG. 49: Immunoblot analysis of insoluble tau prepared from the brain stem of rats (SHR72) immunized with tau 300-VPGGGSVQIVYKPVDLSK-317 (SEQ ID NO:8) with adjuvant or control rats treated with adjuvant alone. Mean values are presented with standard error of the mean.

Immunotherapy with a shorter tau peptide, which was used as a control because it does not carry a complete tau 6-mer within which one of the four tau "therapeutic epitopes" could reside, nor a phosphorylated epitope, was carried out to determine its ability to affect the levels of pathological insoluble tau and neurofibrillary deposits in the brain. The level of total insoluble tau detected by pan-tau mAb DC25 was significantly increased (82%) in immunized rats compared to the controls that received adjuvant alone (FIG. 49 and FIG. 26B). Similarly, immunotherapy induced an increase in the levels of insoluble tau phosphorylated at T231 (60%) and a smaller increase in insoluble tau phosphorylated at position of T181 (10%), Quantitative analysis with a different set of antibodies, DC217 (pT217) and AT8 (pS202/pT205) did not reveal any effect on these epitopes in insoluble tau (FIG. 26B).

Figure 50A:
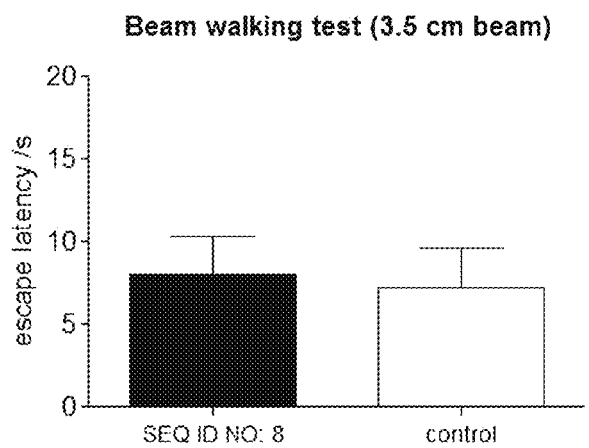
FIG. 50: Neurobehavioral evaluation of transgenic AD rats (SHR72) treated with tau 300-VPGGGSVQIVYKPVDLSK-317 (SEQ ID NO:8). All statistical data were obtained using nonparametric Mann-Whitney U-test. (A) Beam walking test (3.5 beam). (B) Number of hindlimb slips (3.5 beam). (C) Neuroscale.
Figure 50B:
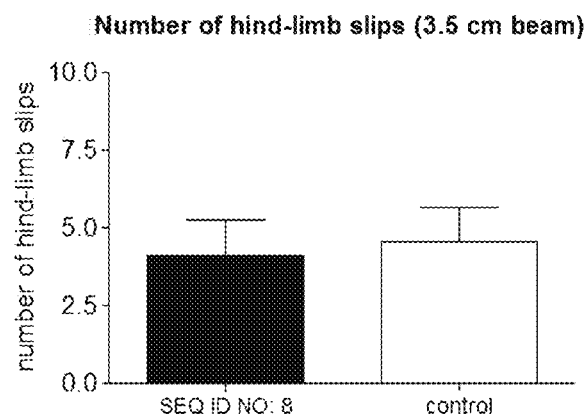
Figure 50C:
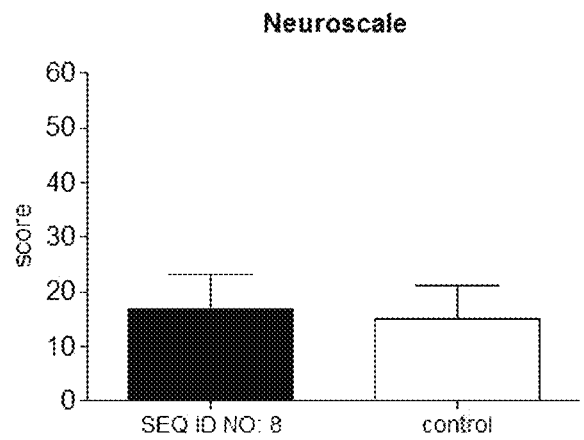

Animals were subjected to behavioral analysis (FIGS. 50A, B, C). Rats treated with peptide SEQ ID NO: 8 showed no statistically significant difference in escape latencies in the beam walking test (p=0.6) compared to controls. The difference in the number of hind-limb slips was also not statistically significant (p=0.49) compared to controls. Similarly, there was no statistically significant difference in the NeuroScale score (p=0.9). Thus, administration of the peptide SEQ ID NO: 8 did not statistically significantly influence the motor performance of the rats.

These results demonstrate that vaccination with tau peptide SEQ ID NO:8, which lacks all of the therapeutic epitopes (within SEQ ID NOs:98-101), produced: 1) no change on insoluble tau in the brains of immunized rats at the biochemical level; and 2) no effect at the neurobehavioral level.

Figure 51:
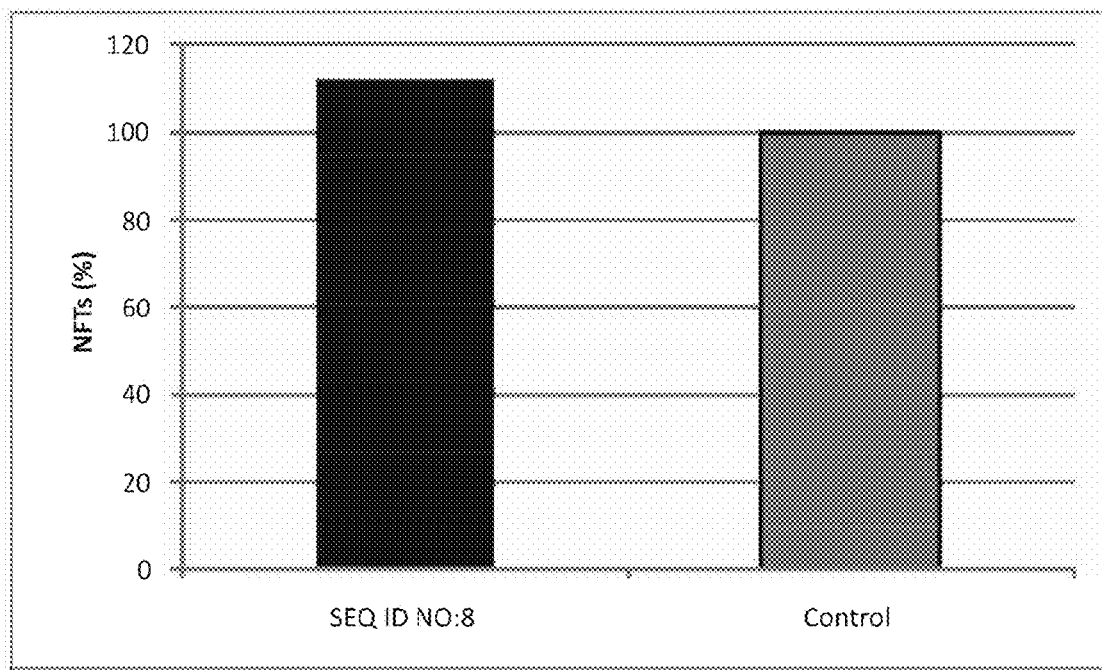
FIG. 51: Vaccination of transgenic rats SHR72 with tau peptide SEQ ID NO:8 showed no reduction of neurofibrillary tangle (NFT) load. Antibody AT8 was used for evaluation of NFTs in the brain tissues of transgenic rats SHR72.

The effect of the peptide vaccine on NFT load in brain stem of treated and mock-control animals (received adjuvant only) was evaluated by imunohistochemistry. The results showed that immunotherapy with tau peptide SEQ ID NO:8 did not reduce the amount of neurofibrillary tangles (FIG. 51). Treated and mock-control animals developed nearly identical number of neurodegenerative changes in all areas of the brain stem, mainly in the reticular formation of the brain stem as revealed by AT8 and DC217 staining.

Vaccination with SEQ ID NO:8, which does not encompass any complete therapeutic epitopes (SEQ ID NO:98-101), did not show any beneficial effect in the treated animals. Thus, the results of the immunizations with peptides SEQ ID NO:5-8 show that the presence of at least one complete therapeutic epitope (located within SEQ ID NO:98-101) is needed for the desired positive effect of the vaccine—reduction of tau pathology and improvement in at least one neurobehavioral parameters.

j. SEQ ID NO:108 Tau 294-KDNIKHVPGGGS-305.

SHR72 rats were immunized with tau peptide SEQ ID NO:108 conjugated to the carrier KLH, formulated with alum adjuvant and administered in dose of 100 µg per animal.

Vaccination of Transgenic Rats SHR72 with Tau Peptide SEQ ID NO:108 Statistically Significantly Reduced Insoluble Pathological Tau (p<0.001).

Figure 52:
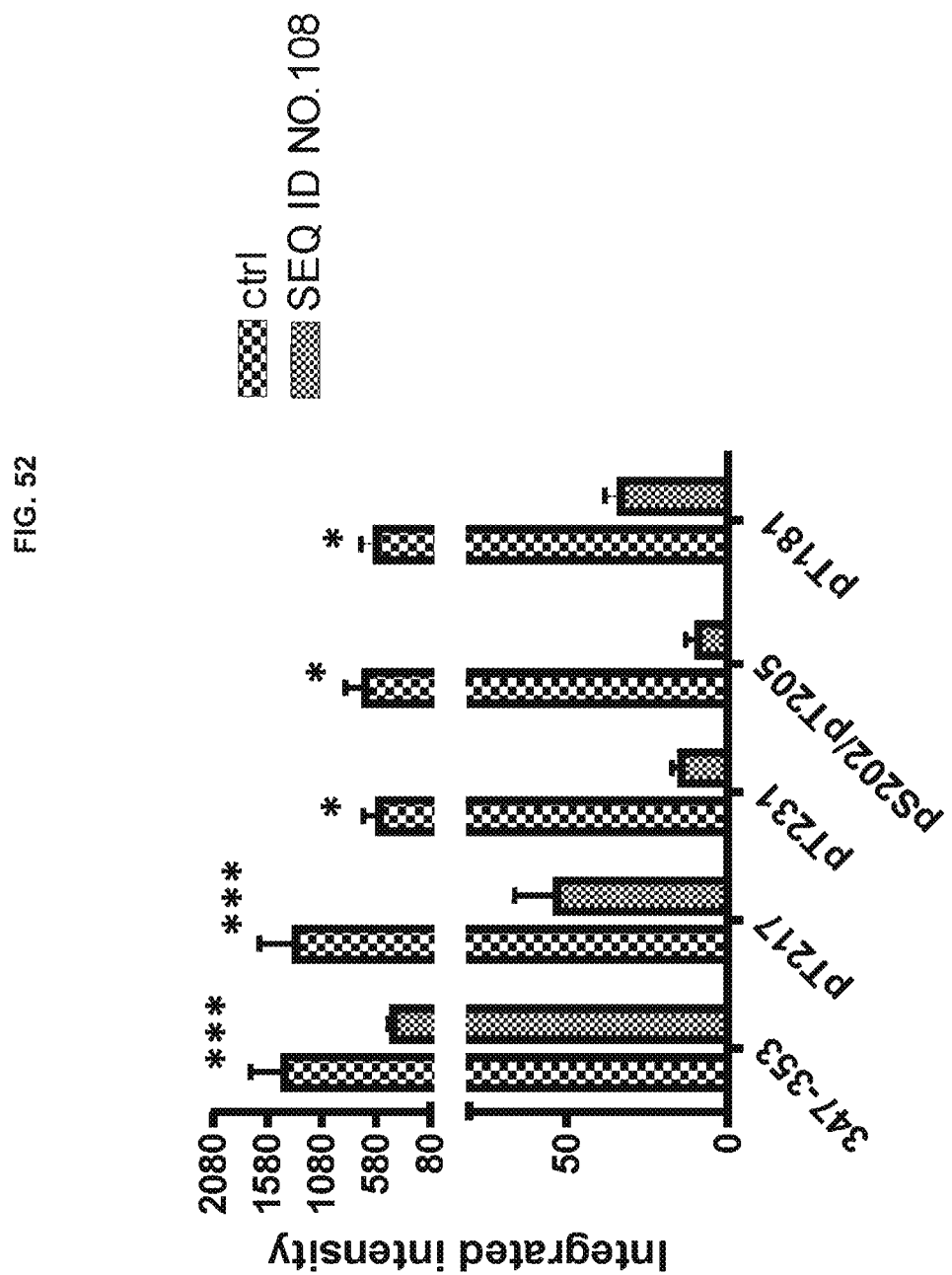
FIG. 52: Vaccination of transgenic rats SHR72 with tau peptide (SEQ ID NO:108) statistically significantly reduced insoluble pathological tau (p<0.001). Pathological insoluble tau was extracted from the brains of transgenic rats SHR72 immunized with tau peptide and analyzed by immunoblotting. Mean values are presented with standard error of the mean.

Since the Alzheimer disease pathology in SHR 72 is caused by pathological insoluble tau forms (represented by monomers, dimers, oligomers and polymers of pathological tau), the impact of treatment with the 12-mer passive vaccine SEQ ID NO:108 on the insoluble tau levels was analyzed. The brain stem of the transgenic animals immunized with the respective immunogen and control group immunized with adjuvant alone were used for the extraction of sarkosyl-insoluble pathological tau (as described above), The results of the quantitative immunoblot analysis from the group of transgenic rats immunized with tau peptide SEQ ID NO:108 and control group are shown in FIGS. 52 and 26B, The vaccination statistically significantly reduced the pathological insoluble tau in immunized animals compared to the control transgenic rats that received adjuvant alone (FIG. 52). This reduction was observed at all analyzed AD relevant tau epitopes, Immunization with tau peptide SEQ ID NO:108 induced significant reduction of insoluble pathological tau ($p<0.001$; 70%) revealed by measurement with pan-tau monoclonal antibody D025 (FIG. 52), Moreover, analysis with phospho-dependent mAbs D0217 (pThr217) and AT8 (pSer202/pThr205) revealed significant reduction of the levels of pathological tau species phosphorylated at Thr217 ($p<0.001$; 96%) and at Ser202/pThr205 ($p<0.05$; 98%) in insoluble tau of immunized rats compared to the controls (FIG. 52). Statistically significant reduction was also observed at the levels of insoluble pathological tau carrying pThr231($p<0.05$; 97%) and pThr181 ($p<0.05$; 94%). These results show that the vaccine induced immune response results in statistically significant reduction of early forms of pathological tau (represented by monomers, dimers, oligomers) and late forms of pathological tau polymers (represented by PRFs).

Vaccination of Transgenic Rats SHR72 with Tau Peptide SEQ ID NO:108 Statistically Significantly Improved Neurobehavioral Parameters ($p<0.05$).

Figure 53A:
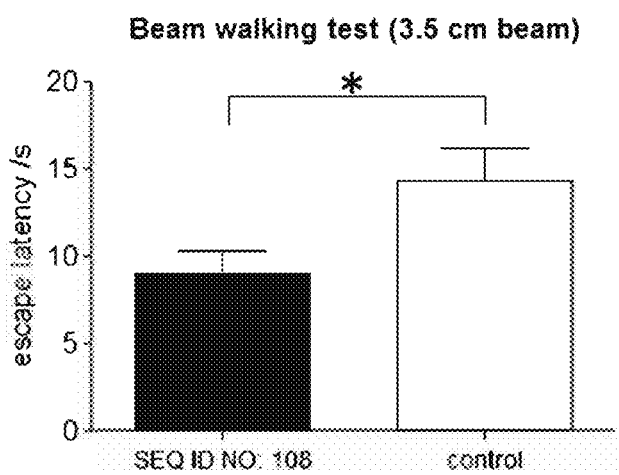
FIG. 53: Vaccination of transgenic rats SHR72 with tau peptide (SEQ ID NO:108) statistically significantly improved neurobehavioral parameters (p<0.05). (A) Beam walking test (3.5 cm beam). (B) Number of hind-limb slips (3.5 cm beam). (C) Neuroscale. Data are presented as mean values with standard error of the mean.
Figure 53B:
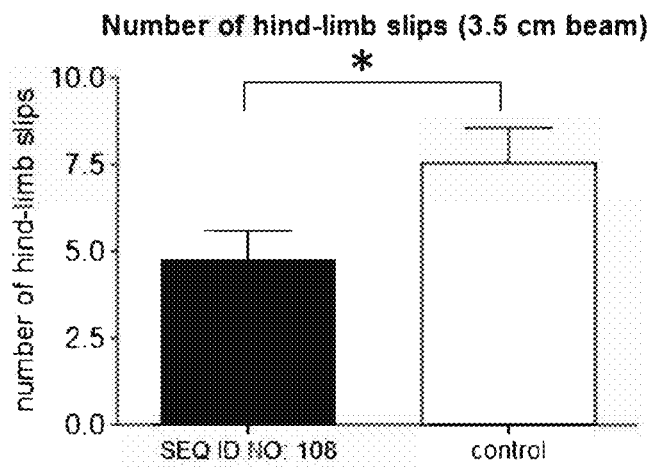
Figure 53C:
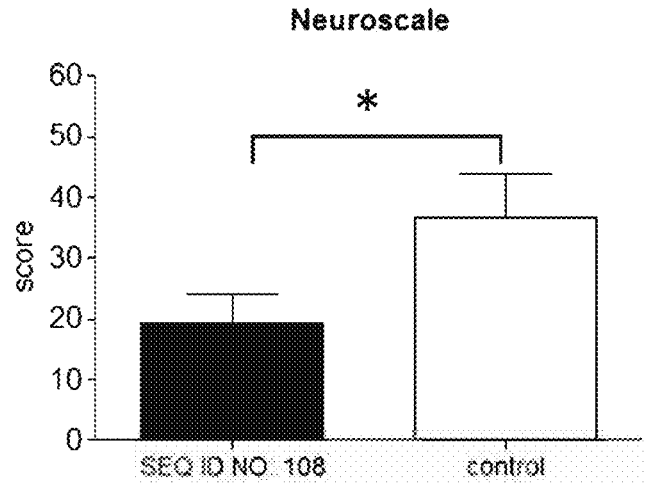

Motor impairment was measured by the set of standard motor tests combined with the neurological examination in the composite score—Neuroscale. At 6.5 months of age, transgenic rats SHR72 treated with tau peptide SEQ ID NO:108 were subject to behavioral tests with aim to determine the effect of immunotherapy. Rats treated with the tau peptide immunogen SEQ ID NO: 108 showed significantly decreased escape latencies in the beam walking test (*$p=0.04$) compared to the transgenic rats that received adjuvant alone (controls) (FIG. 53). Similarly, a positive trend in number of hind-limb slips was observed in the vaccinated group in comparison with transgenic treatment controls, this difference was significant (*$p=0.045$; FIG. 53), The total Neuroscale score was calculated from the data obtained in the beam walking tests, prehensile traction tests and neurological examinations (basic reflexes, hind-limb escape extension reflex). The immunization significantly improved the Neuroscale score of the rats treated with peptide SEQ ID NO: 108 compared to the control treatment group (*$p=0.047$) (FIG. 53C). The total Neuroscale score confirmed the neurobehavioral improvement of treated transgenic rats when compared to untreated transgenic rats. All statistical data were obtained using nonparametric Mann-Whitney U-test.

Neurobehavioral parameters correlated with the insoluble pathological tau levels in the brain stem of the treated transgenic animals. Animals treated with vaccine peptide SEQ ID NO: 108 exhibited low levels of insoluble pathological tau, which was associated with lower escape latency and lower number of hind-limb slips in comparison with control treatment animals. These findings show that the reduction of insoluble pathological tau leads to the statistically significant improvements of neurobehavioral deficits in the group of transgenic animals immunized with the 12-mer peptide (SEQ ID NO: 108) vaccine, showing its therapeutic value.

Vaccination of Transgenic Rats SHR72 with Tau Peptide SEQ ID NO:108 Resulted in 60% Reduction of Neurofibrillary Tangle (NFT) Load.

Figure 54:
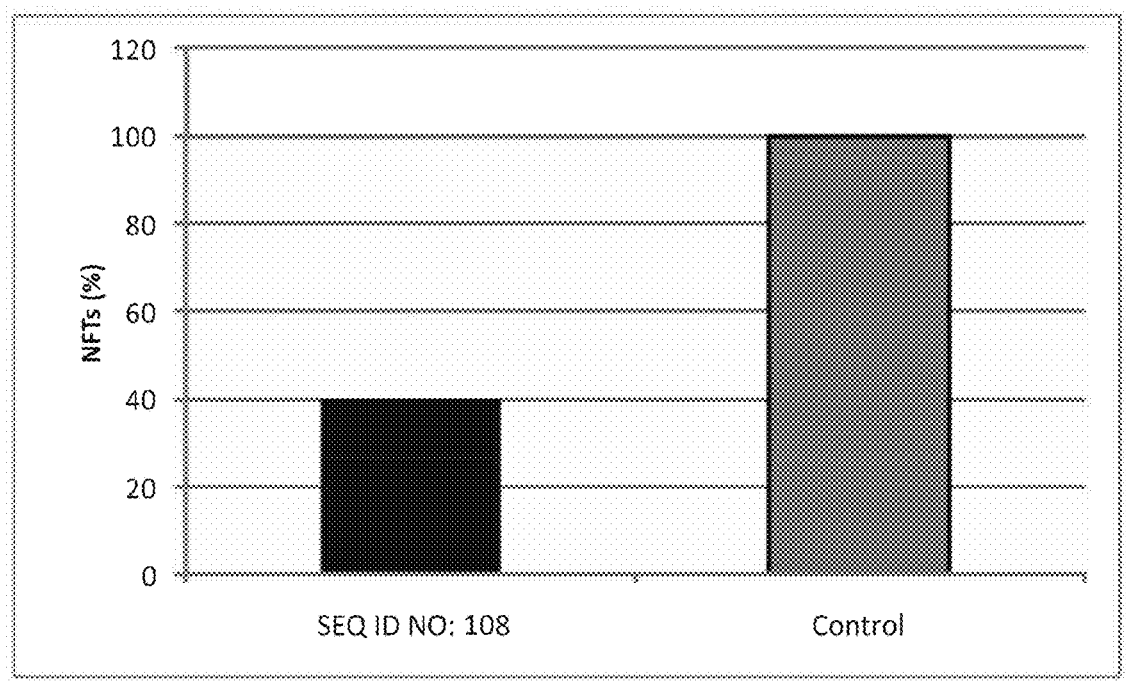
FIG. 54: Vaccination of transgenic rats SHR72 with tau peptide (SEQ ID NO:108) resulted in 60% reduction of neurofibrillary tangle (NFT) load. Antibody AT8 was used for evaluation of NFTs in the brain tissues of transgenic rats SHR72.

Immunohistochemical analysis of the neurofibrillary tau pathology (neurofibrillary tangles, NFT) in the brain stem showed reduction of NFTs achieved in the vaccine treated SHR72 rats (FIG. 54). The number of immunized transgenic rats with extensive NFTs in the brain stem compared to the adjuvant treated animals was decreased by more than 60%. The immunization reduced tau pathology (pathological tau polymers, PHFs) in the brain of the transgenic animals immunized with SEQ ID NO: 108 peptide vaccine.

The results show that immunotherapy with tau peptide SEQ ID NO:108 efficiently reduced the tau pathology in SHR72 rats. Vaccination led to a statistically significant reduction in the insoluble pathological tau levels in the brains of the immunized animals as well as in the reduction of neurofibrillary tangle load (PHFs). The reduction in the amount of pathological tau proteins resulted in a statistically significant improvement of neurobehavioral parameters of the treated transgenic rats. Thus, administration of tau peptide SEQ ID NO: 108 has capacity for the treatment of AD.

Example 21: Immunotherapy with AD Therapeutic Peptides is Immunogenic and Induces the Production of Disease-Tau-Specific Antibodies in Transgenic Rats a. After five doses of tau peptide vaccine, analysis of the peptide's immunogenicity in the treated rats was carried out. Sera from immunized rats were used for antibody titer determination. Sera from rats immunized with adjuvant alone were used as a control. The titers of specific anti-tau antibodies were determined by ELISA, as described in Example 19. Serial dilutions of each serum were tested against AD tauΔ(1-150; 392-441)/4R and recombinant full-length tau 2N4R, previously coated onto microtiter well plates. The assayed immunogens induced the production of specific anti-tau antibodies.

For Example, Anti-Tau Specific Antibodies were Generated after Immunization with 275-VQIINKKLDLSN-VQSKCGSKDNIKHVPGGG-304 (SEQ ID NO: 4).

Figure 55:
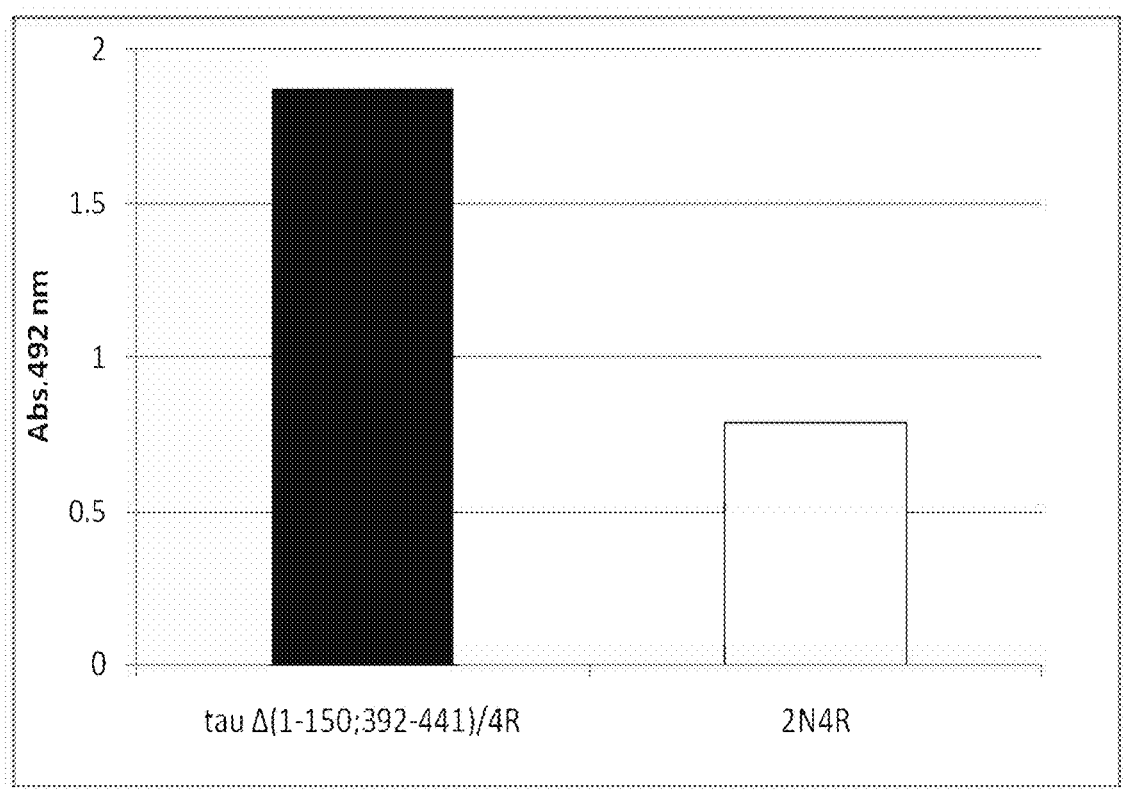
FIG. 55: ELISA of antisera generated from immunization of transgenic rats (SHR72) with peptide tau 275-VQIINKKLDLSNVQSKCGSKDNIKHVPGGG-304 (SEQ ID NO:4) shows a difference in the antisera's binding to human pathological tauΔ(1-150; 392-441)/4R and human physiological tau 2N4R.

Antibodies induced by tau peptide SEQ ID NO: 4 exhibited approximately 3-fold higher binding activity to misdisordered tauΔ(1-150; 392-441)/4R than to tau 2N4R (FIG. 55; 1:3.200 dilution). These results further suggest that this vaccine induced antibodies which possess therapeutic potential to recognize and eliminate/neutralize pathological tau proteins in Alzheimer's disease.

Also, vaccination of transgenic rats SHR72 with tau peptide SEQ ID NO:108 induced formation of antibodies preferentially binding to pathological tau protein, over physiological tau. After five doses of vaccine, analysis of the immunogenicity was done in each of the vaccinated rats. Animals were bled two weeks after the last booster dose and collected sera were used for geometric mean antibody titer (GMT) determination. The titers of specific anti-tau antibodies were determined by ELISA, as described in Example 19. Serial dilutions (1:100 to 1:51,200) of each serum were tested against pathological tauΔ(1-150; 392-441)/4R and physiological tau 2N4R, used as a solid phase. Titers were defined as the reciprocal of the dilution of serum that gives half of the maximum Optical Density (Absorbance). To calculate geometric mean antibody titers, titer readings smaller than 100 were assigned as value 10. As shown in FIG. 56, the antibody titer to pathological tauΔ(1-150; 392-441)/4R (GMT 12800) was three-fold higher than that to full-length tau 2N4R (GMT 4200). Antibody titers were also measured against the unconjugated peptide SEQ ID NO:108 using the same methodology described in Example 19. FIG. 56 shows that the highest antibodies titers were generated against tau peptide SEQ ID NO:108 (GMT 20800). No antibody responses were observed in the transgenic rats immunized with adjuvant only (GMT 10; data not shown). Vaccination with peptide SEQ ID NO:108, carrying DC8E8 epitope No. 2 (within SEQ ID NO: 99), induced antibodies preferentially recognizing pathological tau protein, thus discriminating between pathological tauΔ(1-150; 392-441/4R) and physiological tau 2N4R. Moreover, results showed that SEQ ID NO:108 is immunogenic and therefore possesses therapeutic potential to eliminate pathological tau proteins in Alzheimer's disease.

Figure 57:
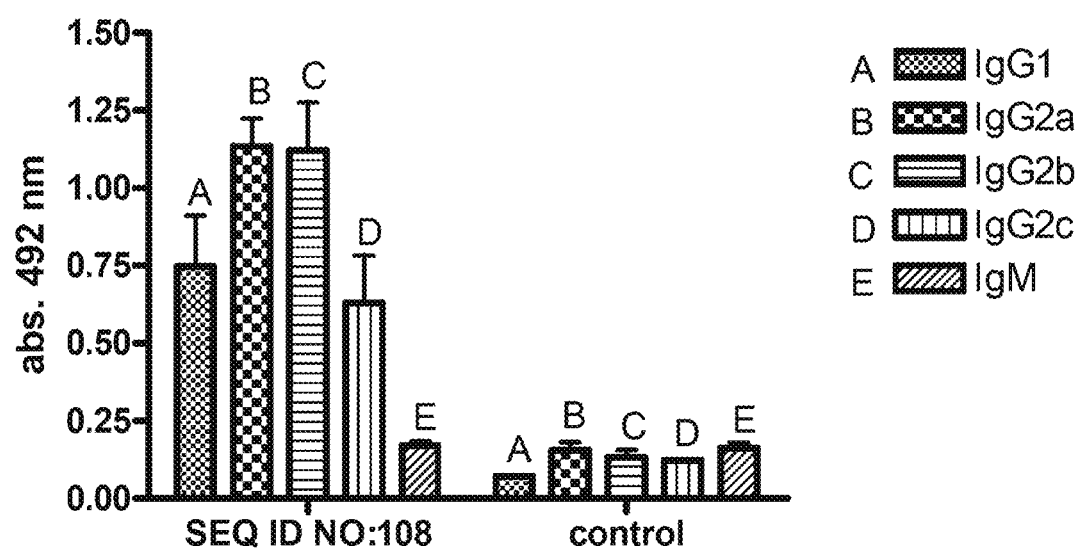
FIG. 57: Vaccination of transgenic rats SHR72 with tau peptide SEQ ID NO: 108 preferentially induced formation of IgG antibody isotypes specific to pathological tau. The isotype profile of antibodies induced by tau peptide SEQ ID NO:108 is shown. Sera from individual rats were diluted 1:800 and binding activity to pathological tauΔ(1-150; 392-441)/4R was analyzed by ELISA.

Moreover, vaccination of transgenic rats SHR72 with tau peptide SEQ ID NO:108 preferentially induced formation of IgG antibody isotypes specific to pathological tau. To determine the specific isotypes of the antibodies produced in response to peptide SEQ ID NO:108, sera from rats of the immunized and control groups were serially diluted from 1:100 to 1:12,800, and tested in duplicates by ELISA (as described in Example 19) against pathological tauΔ(1-150; 392-441)/4R. To detect rat IgG1, IgG2a, IgG2b, IgG2c, and IgM isotypes, anti-rat subclass specific HRP-conjugated secondary antibodies were diluted 1:5,000 in PBS (Pierce, anti IgG1-PA1-84708, anti IgG2a PA1-84709, anti IgG2b PA1-84710, anti-IgG2c PA1-84711 and anti-IgM-PA1-84712). FIG. 57 shows results for the representative 1:800 dilution. The data demonstrate that the peptide SEQ ID NO:108 conjugated to KLH induced a broad spectrum of anti-tau antibody isotypes. The vaccine generated high levels of antibody isotypes (IgG1, IgG2a, IgG2b and IgG2c), which are considered to be the high affinity antibodies. By contrast, isotypic profile showed very low levels of IgM antibodies. These are considered to have low affinity to the antigen. The presence of high titers of IgG antibodies with preferential affinity to pathological tau indicated that the immune response induced by the vaccine is directed against pathological tau species. The control sera obtained from mock-immunized rats (which received adjuvant alone) were negative.

Figure 58:
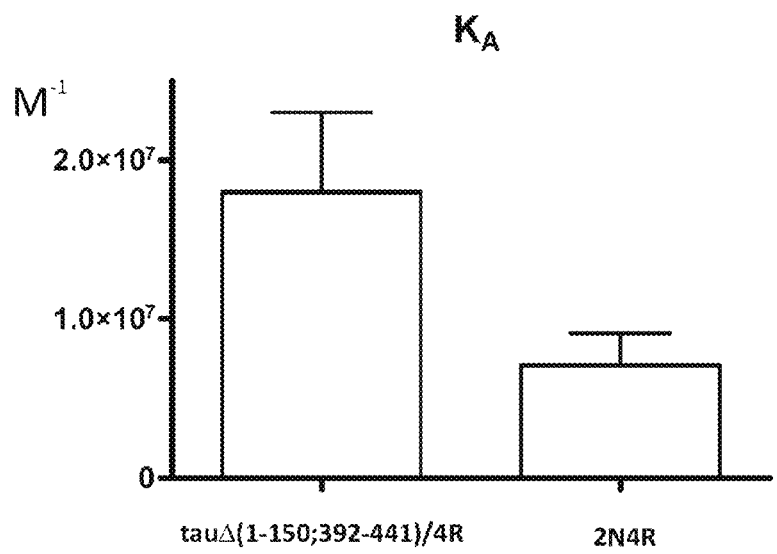
FIG. 58: SPR affinity determination of antisera generated from immunization of SHR72 rats with peptide tau 275-VQIINKKLDLSNVQSKCGSKDNIKHVPGGG-304 (SEQ ID NO:4) for binding to human tauΔ(1-150;392-441)/4R and human tau 2N4R.
Figure 59A:
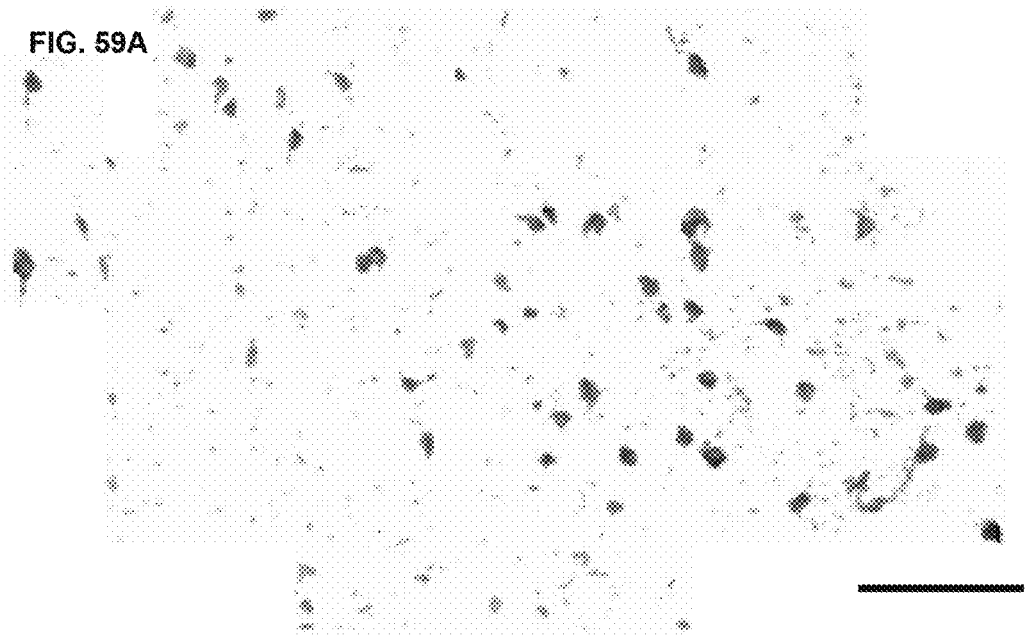
FIG. 59: Immunohistochemical staining of brains from a human AD patient with rat antibodies generated from immunization of transgenic rats (SHR72) with tau 275-VQIINKKLDL SNVQSKCGSKDNIKHVPGGG-304 (SEQ ID NO: 4). (A) The antisera recognized neurofibrillary lesions in Alzheimer's disease brain, hippocampus. (B) Higher magnification showed neurofibrillary tangles. Scale bars: 100 μm (A), 10 μm (B).
Figure 59B:
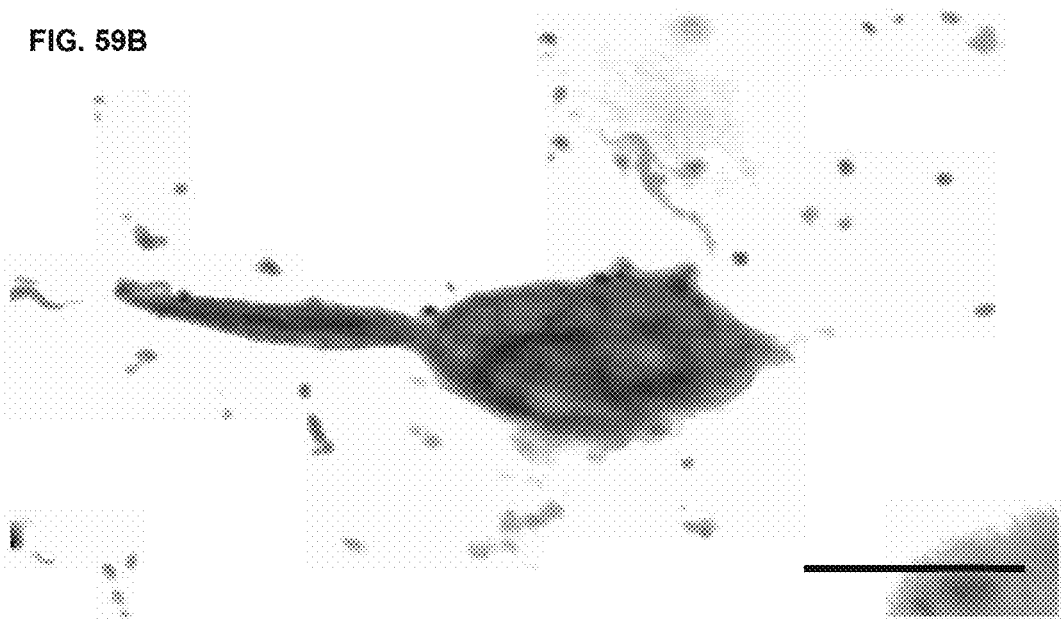

These data were further used for determination of polarization (Th1/Th2 phenotype) of the immune response. The levels of IgG1 and IgG2a isotypes induced by immunization indirectly suggest the contributions of Th1 cytokines versus Th2 cytokines to immune response. In general, production of IgG1 antibodies is induced by Th2 cytokines and production of IgG2a antibodies is induced by Th1 cytokines. Therefore, the ratio of IgG1 and IgG2a isotypes was calculated by dividing OD values for IgG1 by OD values for IgG2a. These data suggest (the ratio=0.625), that immune response is slightly shifted toward Th1 phenotype.

b. Real time monitoring of binding events using surface plasmon resonance enabled measurement of the kinetic rate of association ($k_{ON}$) and dissociation ($k_{OFF}$) of antibodies from the pooled sera of rats immunized with tau peptide 275-VQIINKKLDLSNMSKCGSKDNIKHVPGGG-304 (SEQ ID NO:4). The analysis showed a distinction between the recognition of tauΔ(1-150;392-441)/4R and physiological tau isoform 2N4R (FIG. 58). The antibodies induced by immunization exhibited a preferential affinity for tauΔ(1-150;392-441)/4R, binding this tau protein with three-times higher affinity for truncated AD tau compared to their affinity for the corresponding full-length isoform 2N4R. This binding difference was determined to be, in part, due to the approximately five-times greater $k_{ON}$ rate for tauΔ(1-150;392-441)/4R (data not shown).

c. To further determine the specificity of antibodies induced in rats immunized with therapeutic tau peptides, the antisera can be used for immunohistochemical staining of frozen sections of hippocampus from human AD brain. For example, antibodies induced after immunization with SEQ ID NO: 4 were evaluated by this assay. The hippocampus from human AD brain was fixed with 4% paraformaldehyde 4° C. for 2 days, followed by a treatment with 25% sucrose for 72 hours to provide cryoprotection. The material was then frozen in cold 2-methylbutane (−42° C.) for 30 seconds and sectioned on cryomicrotome. Coronal sections (40 μm) were cut in a cryostat at −18° C. Free-floating sections were used for immunohistochemical studies. Free floating tissue sections were treated with cold (+4° C.) 99% formic acid for 1 min. at room temperature (25° C.). Brain sections were incubated for 20 minutes at room temperature in 0.01 M of PBS, pH 7.4, containing 0.3% Triton X-100 and 1% $H_2O_2$, followed by a 30-minute incubation in the blocking solution (0.01 M PBS, containing 0.3% Triton X-100, 1% horse serum), followed by overnight incubation with sera from transgenic rats immunized with vaccine containing peptide SEQ ID NO: 4 (diluted 1:1000) at 4° C. After washing, the sections were immunostained using the standard avidin biotin peroxidase method (ABC Elite, Vector Laboratories, Burlingame, Calif.). The reaction product was visualized using avidin-biotin and Vector VIP as a chromogen (Vector Laboratories). Sections were then examined with an Olympus BX 51 microscope. Immunohistochemical staining showed that the antibodies induced by immunization with peptide SEQ ID NO:4 specifically recognized pathological tau structures, i.e. neurofibrillary lesions in the hippocampus of Alzheimer's disease brain (FIGS. 59A, 59B). Sera from control rats, which received adjuvant alone, was used as a negative control, and it did not recognize any neuronal pathology (data not shown).

Vaccination of Transgenic Rats SHR72 with Tau Peptide SEQ ID NO:108 Induced Antibodies Recognizing Pathological Tau Proteins in the Sections from the Human Alzheimer's Disease Brain Tissues.

To further determine the specificity of antibodies induced in rats immunized with therapeutic tau peptide SEQ ID NO:108, their sera were used for immunohistochemical staining of the entorhinal cortex using frozen sections of human AD brain (Braak stage VI). Free floating tissue sections were incubated with sera (diluted 1:1000) from immunized transgenic rats at 4° C. The individual sera from the animals vaccinated with SEQ ID NO: 108 were used separately, while sera from animals vaccinated with adjuvant only were pooled. After immunostaining using the standard avidin-biotin peroxidase method (ABC Elite, Vector Laboratories, Burlingame, Calif.) the sections were examined with Olympus BX 51 microscope. Immunohistochemical staining showed that the antibodies induced by immunization with peptide SEQ ID NO:108 specifically recognized pathological tau structures, i.e. neurofibrillary lesions in the entorhinal cortex of Alzheimers disease brain. FIGS. 60A through 60E shows representative immunostaining with the rat sera collected from five vaccinated transgenic rats SHR72. Sera of the animals vaccinated with SEQ ID NO:108 decorated the neurofibrillary pathology very intensively, confirming that the antibodies efficiently targeted pathological tau proteins. Sera from control rats, which received adjuvant alone, were used as negative controls. They did not recognize any neurofibrillary pathology (FIG. 60F).

Antibodies Induced by the SEQ ID NO:108 Vaccine Recognize Pathological Tau Proteins Extracted from Brains of SHR72 and from Human AD Brains.

Figure 61:
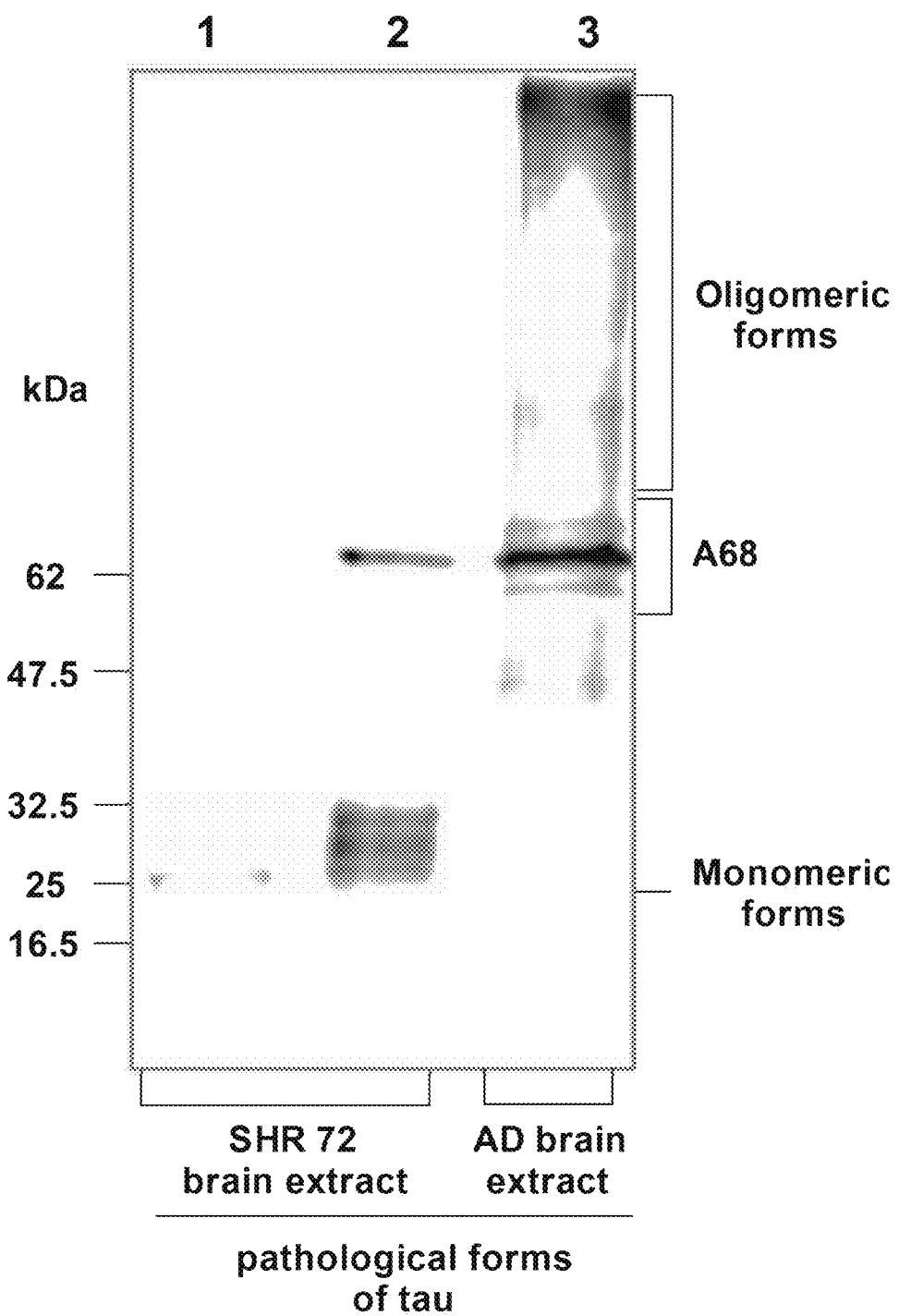
FIG. 61: Vaccination of transgenic rats SHR72 with tau peptide SEQ ID NO:108 induced specific antibodies recognizing pathological tau proteins in human Alzheimer's disease brains as well as in the brains of transgenic rats SHR72. Pathological tau was extracted from human and rat brain tissues and analyzed by immunoblotting with pooled sera from peptide SEQ ID NO:108 immunized transgenic rats SHR72. The sera antibodies recognized monomeric (lane No. 1, 2 and No. 3) and oligomeric (lane No. 2 and No. 3) pathological tau including AD characteristic A68 pathological tau.
Figure 62:
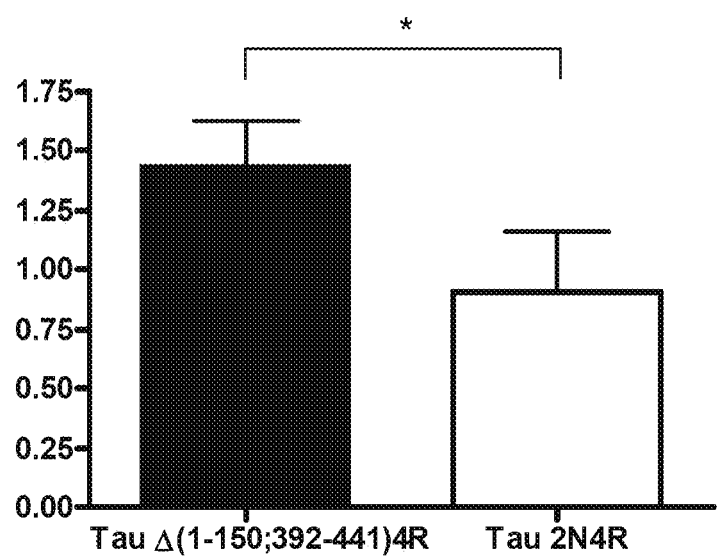
FIG. 62: Immunization of mice with tau peptide SEQ ID NO:109 induced antibodies with statistically significantly higher binding activity to pathological tauΔ(1-150; 392-441)/4R than to physiological tau 2N4R (p=0.0115). The graph represents statistical evaluation of ELISA results for individual sera diluted at 1:800. Mean values are shown with standard error of the mean.
Figure 63:
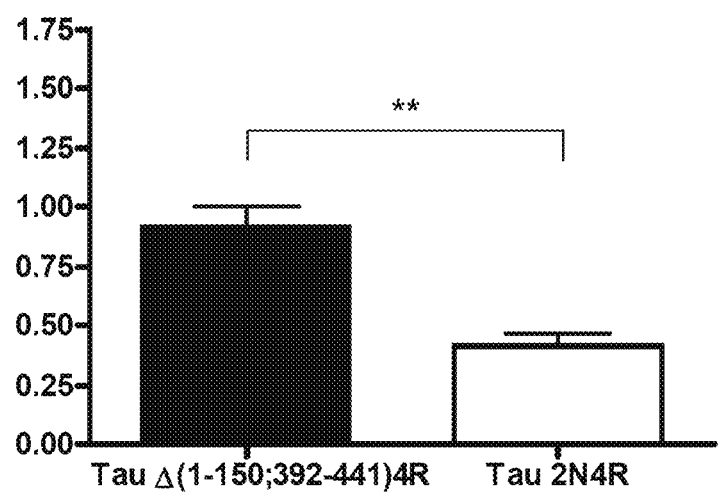
FIG. 63: Immunization of mice with tau peptide SEQ ID NO:110 induced antibodies exhibiting statistically significantly higher binding activity to pathological tauΔ(1-150; 392-441)/4R than to physiological tau 2N4R (p=0.0029). The graph represents statistical evaluation of ELISA results for individual sera diluted at 1:800. Mean values are shown with standard error of the mean.
Figure 64:
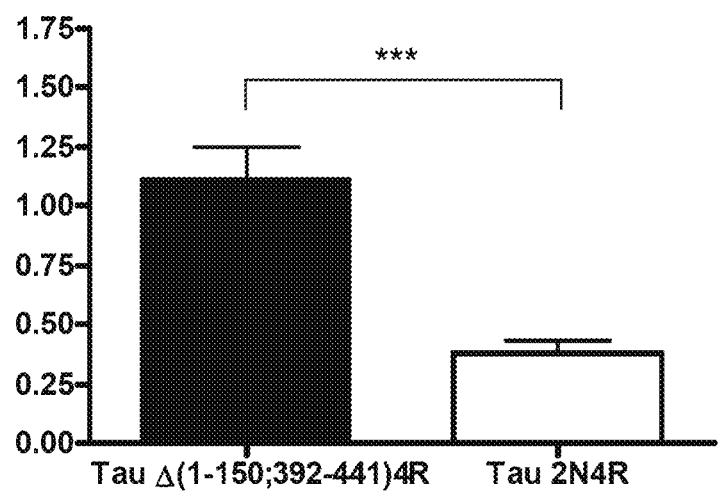
FIG. 64: Immunization of mice with tau peptide SEQ ID NO:111 induced antibodies exhibiting statistically significantly higher binding activity to pathological tauΔ(1-150; 392-441)/4R than to physiological tau 2N4R (p=0.0007). The graph represents statistical evaluation of ELISA results for individual sera diluted at 1:800. Mean values are shown with standard error of the mean.
Figure 65:
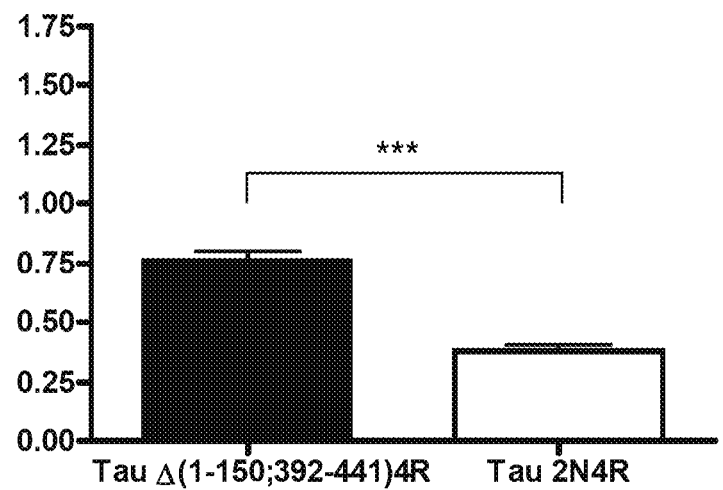
FIG. 65: Immunization of mice with tau peptide SEQ ID NO:112 induced antibodies exhibiting statistically significantly higher binding activity to pathological tauΔ(1-150; 392-441)/4R than to physiological tau 2N4R (p<0.001). The graph represents statistical evaluation of ELISA results for individual sera diluted at 1:800. Mean values are shown with standard error of the mean.

The specificity of the sera from rats immunized with tau peptide SEQ ID NO:108 was further examined on pathological forms of soluble and insoluble pathological tau using immunoblot method (as described in Example 19). The brain stems of SHR72 rats in the late stage of the pathology were used for the extraction of soluble insoluble pathological tau proteins. Temporal cortex of human AD brain (Braak stage VI; obtained from the Netherlands Brain Bank, Netherlands) was used for the extraction of human pathological AD tau. The soluble and insoluble pathological tau proteins were prepared using the same method as described in Example 8. For soluble tau fractions 15 μg of total proteins were loaded per lane. For insoluble tau fractions the pellets were dissolved in 1× sodium dodecyl sulfate (SDS) sample loading buffer (Laemmli, 1970) in 1/50 volume of the soluble fraction used for the preparation of the insoluble tau fraction and equal volume was loaded onto SDS-PAGE. Pooled sera from immunized animals were diluted 1:1000 in PBS and used as a primary antibody. Incubation with primary antibody was followed by polyclonal rabbit anti-rat immunoglobulins conjugated to horseradish peroxidase (1:3000; Dako, Glostrup, Denmark). Western blot signal was digitized with LAS3000 CCD imaging system (Fujifilm, Japan). The results of this immunoblot analysis are shown in FIG. 61.

The results (FIG. 61) show that antibodies generated against peptide carrying DC8E8 epitope 2 (SEQ ID NO:99) recognize the pathological tau proteins extracted from SHR72 and from AD brains tissues. The induced antibodies recognized monomeric forms of pathological tau (lane No. 1, 2 and No. 3) as well as oligomeric forms of pathological tau (lane No. 2 and No. 3) including the A68 tau triplet characteristic for AD. These findings have key impact on immunotherapy using this rat model of Alzheimer's disease. High affinity antibodies generated by vaccine target all forms of pathological tau proteins. They target monomeric forms of pathological tau proteins and thus prevent pathological tau-tau interaction (oligomerization) leading to reduction of insoluble tau levels in vaccinated rat and consequently to improvement of neurobehavioral parameters. The generated antibodies also bind oligomeric forms of pathological tau and target them for degradation, e.g. by microglia, as it was described in Example 10 for mAb DC8E8.

Example 22: Immunotherapy with AD Therapeutic Peptides Induces the Production of Disease-Tau-Specific Antibodies in Mice Peptides SEQ ID NO:109, SEQ ID NO:110 (SEQ ID NO: 88 corresponds to SEQ ID NO: 110 plus an additional N-terminal Cys for conjugation), SEQ ID NO:111, and SEQ ID NO:112, carrying one of the therapeutic epitopes within either SEQ ID NO: 100 or 101, induced production of antibodies in immunized mice. The resulting antibodies show statistically significantly higher binding activity to pathological tauΔ(1-150; 392-441)/4R than to physiological tau 2N4R.

```
                                              SEQ ID NO: 109
Tau 314-DLSKVTSKCGSLGNIHHKPGGGQV
EVKSE-342

SEQ ID NO: 110
Tau 352-SKIGSLDNITHVPGGGNKKIETHK
LTFREN-381
```

```
                                              SEQ ID NO: 111
Tau 325-LGNIHHKPGGGQ-336

SEQ ID NO: 112
Tau 357-LDNITHVPGGGN-368

SEQ ID NO: 100
Tau 329-HHKPGGG-335

SEQ ID NO: 101
Tau 361-THVPGGG-367
```

Indeed, with the aim to further determine the immunogenic potential of peptides carrying one or more therapeutic DC8E8 epitopes (e.g., within 7-mer: SEQ ID NO: 100 and SEQ ID NO: 101), twelve and thirty amino acids long peptides (SEQ ID NO:109, SEQ ID NO:110, SEQ ID NO:111 and SEQ ID NO:112) carrying one of the DC8E8 therapeutic epitopes were designed. Tau peptides SEQ ID NO:109 (30 amino acids) and SEQ ID NO:111 (12 amino acids) contain within them the therapeutic epitope in SEQ ID NO:100. Tau peptides SEQ ID NO:110 (30 amino acids) and SEQ ID NO:112 (12 amino acids) contain within them the therapeutic epitope in SEQ ID NO:101, Peptides were conjugated to KLH via their N-terminal Cys residue as described in Examples 18-19. Vaccines for immunizations were prepared with peptide-KLH conjugates, containing 100 μg of conjugated peptide, in 100 μl of PBS and emulsified 1:1 (vol/vol) with Freund's adjuvant in a final dose volume of 200 μl. Five Balb/c mice were used per treatment group. The first immunization was done using the peptide-conjugate in PBS formulated with Freund's complete adjuvant. The two following immunizations, in two-week intervals, were performed using the peptide-conjugate in PBS formulated with Freund's incomplete adjuvant. As a control, vaccine containing adjuvant-only was used. Sera were collected 10 days after the last immunization and antibody response were measured by ELISA as described in Example 19. Sera from individual mice were serially diluted from 1:100 to 1:12,800 and tested in duplicates, To determine the specificity of sera, the pathological tauΔ(1-150;392-441/4R) and physiological tau 2N4R were used as the solid phase. FIGS. 62 through 65 show a summary of the results for sera at 1:800 dilution. The ELISA results were statistically evaluated using the Mann-Whitney non-parametric test.

All tested peptides generated tau-specific antibodies in immunized mice. Antibodies induced by vaccinations with tau peptides SEQ ID NO:109, SEQ ID NO:110, SEQ ID NO:111, and SEQ ID NO:112 exhibited statistically significantly higher binding activity to pathological tauΔ(1-150; 392-441)/4R than to physiological tau 2N4R (FIG. 62-65), Moreover, shortening of the peptides from 30 amino acids (SEQ ID NO:109, SEQ ID NO:110) to 12 amino acids (SEQ ID NO:111 and SEQ ID NO:112) led to significantly higher production of specific antibodies, which preferentially recognized pathological tau (SEQ ID NO:109, p=0.0115; SEQ ID NO:110, p=0.0029; SEQ ID NO:111, p=0.0007; SEQ ID NO:112, p<0.001). Altogether, these results showed that the peptides SEQ ID NO:109 and SEQ ID NO:111 (carrying the therapeutic epitope within SEQ ID NO:100) and peptides SEQ ID NO:110 and SEQ ID NO:112 (carrying the therapeutic epitope within SEQ ID NO:101) are immunogenic and possess therapeutic activity targeting pathological tau proteins present in the brains of patients suffering from Alzheimer's disease.

Example 23: Identification of Designer Peptides (Designer Therapeutic Epitopes) Capable of Competing with Pathological Tau for Binding to at Least One DC8E8 Epitope Two additional peptides (11-mess) were designed based on the conserved amino acid residues between epitope #1 (within KHQPGGG, SEQ ID NO:98), #2 (within KHVPGGG, SEQ ID NO:99), #3 (within HHKPGGG, SEQ ID NO:100) and #4 (within THVPGGG, SEQ ID NO:101). In their design, five residues contributing for the binding of DC8E8 to these epitopes were kept fixed: histidine, proline, and three glycine residues in the sequence HxPGGG (SEQ ID NO: 164). Peptides were synthesized by EZBiolabs (USA) with purity higher than 85%. The two designer therapeutic epitopes are GWSIHSPGGGSC (SEQ ID NO: 250) and SVFQHLPGGGSC (SEQ ID NO: 251).

These peptides were analyzed for their ability to compete with pathological tau by competition ELISA. ELISA plates (IWAKI high bind plate, #3801-096, Bertoni GmbH, Austria) were coated with 100 µl/well of 5 µg/ml of recombinant purified tauΔ(1-150;392-441)4R in PBS overnight at 4° C. The coated ELISA plates were washed 4 times with PBS/Tween 20 (phosphate-buffered saline supplemented with 0.05% V/V Tween 20), and blocked with PBS/Tween 20 for 2 h at 25° C. Each of the peptides was separately dissolved in PBS at the final concentration of 5 mM. Serial 2-fold dilutions of the peptides in PBS/Tween 20 in polypropylene plates (Greiner, #651201) were prepared (concentration range 80 µM, 40 µM, 20 µM, 10 µM, 5 µM, and 2.5 µM). 100 µl of each peptide dilution was mixed with 100 µl of 2 µg/ml purified DC8E8 monoclonal antibody (purification was done as described in Example 5). The resulting 200 µl of mixture then contained 1 µg/ml DC8E8 antibody and 40 µM, 20 µM, 10 µM, 5 µM, 2.5 µM and 1.25 µM peptides. tauΔ(1-150; 392-441)4R was included as a positive control. The antibody/peptide mixtures were incubated for 1 hr at 25° C. on a rotating platform set to 250 rpm. One hundred microliters of the antibody/peptide mixtures were then transferred into the prepared ELISA plates and incubated for 1 hr at 25° C. on a rotating platform set to 250 rpm. The ELISA plates were washed 4× times with PBS/Tween 20. The ELISA plates were then incubated with 100 µl of Polyclonal Goat Anti-Mouse Immunoglobulins/HRP (Dako, #P0447) diluted 1:4000 in PBS/Tween 20 and incubated for 1 hr at 25° C. on a rotating platform set to 250 rpm. The ELISA plates were washed 4× times with PBS/Tween20. The ELISA plates were then incubated with 100 µl of 1.5 mg/2 ml o-PDA (o-phenylenediamine, SIGMA, P1526) in 0.1 M Na-Acetate pH=6.0 (Roth, #6779) supplemented with 1.5 µl/2 ml of 30% $H_2O_2$ (SIGMA, H-0904) for 10 minutes at 25° C. in dark. The reaction was stopped by adding 100 µl of 2M $H_2SO_4$ (Merck, 1.00731.1000). The developed signal was measured by reading at 490 nm (e.g. using the Victor Multilabel Counter (Wallac).

Figure 66:
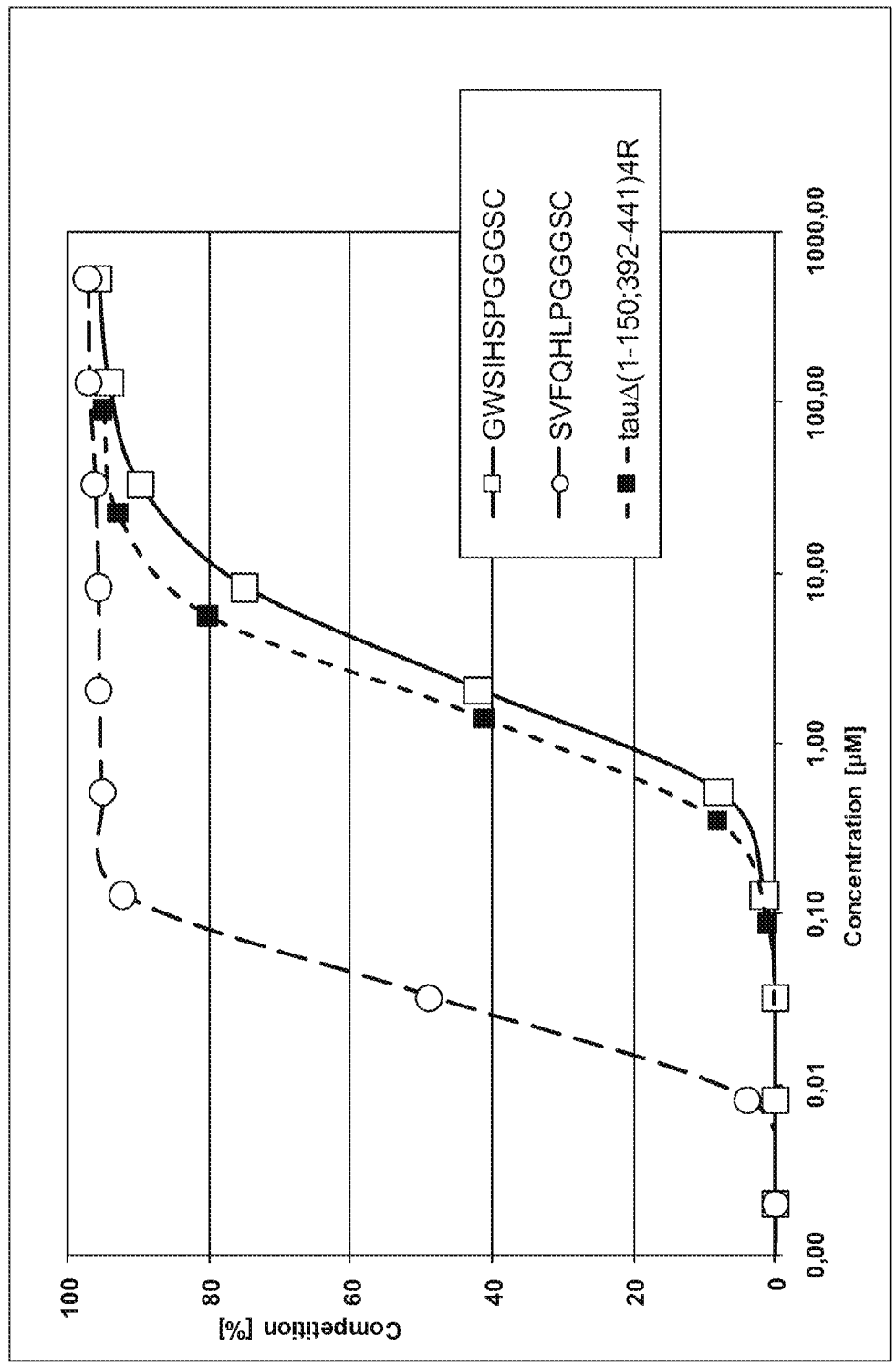
FIG. 66: Designer therapeutic epitopes GWSIHSPGGGSC (SEQ ID NO: 250) and SVFQHLPGGGSC (SEQ ID NO: 251) competed with pathological tauΔ(1-150; 392-441)4R for binding to antibody DC8E8.

The two designer peptides, namely GWSIHSPGGGSC (SEQ ID NO: 250) and SVFQHLPGGGSC (SEQ ID NO: 251), were both able to compete with tauΔ(1-150;392-44)4R for binding to DC8E8 (FIG. 66). The peptide GWSIHSPGGGSC (SEQ ID NO: 250), termed designer therapeutic epitope 1, showed the most similar affinity for DC8E8 compared to tauΔ(1-150;392-441)4R. The affinity of the peptide SVFQHLPGGGSC (SEQ ID NO: 251), termed designer therapeutic epitope 2, for DC8E8 was more than one order of magnitude higher than the affinity of disease tau (tauΔ(1-150;392-441)4R for this antibody.

Example 24: In Vivo Testing of Designer Therapeutic Epitopes 1 and 2 for Immunogenicity and Specificity of the Immune Response The designer therapeutic epitope 1 (GWSIHSPGGGSC, SEQ ID NO: 250) and designer therapeutic epitope 2 (SVFQHLPGGGSC, SEQ ID NO: 251) were conjugated to KLH via their C-terminal Cys residue (as described in Example 18) and used to immunize Balb/c mice. Three mice were used for each designer therapeutic epitope. Immunizations were done as follows. Vaccines for immunizations were prepared with designer therapeutic epitope-KLH conjugates, containing 100 µg of the conjugated peptide in 100 µl of PBS and emulsified 1:1 (vol/vol) with Freund's adjuvant in a final dose volume of 200 µl. The first immunization was done using the designer therapeutic epitope-KLH conjugate in PBS formulated with Freund's complete adjuvant. The four following immunizations, in four-week intervals, were performed using the designer therapeutic epitope-KLH conjugates in PBS formulated with Freund's incomplete adjuvant. For control immunization; PBS was used instead of designer therapeutic epitope-conjugates. Sera were prepared 14 days after the last immunization.

1. Antibodies Discriminate Pathological Tau.

Figure 67:
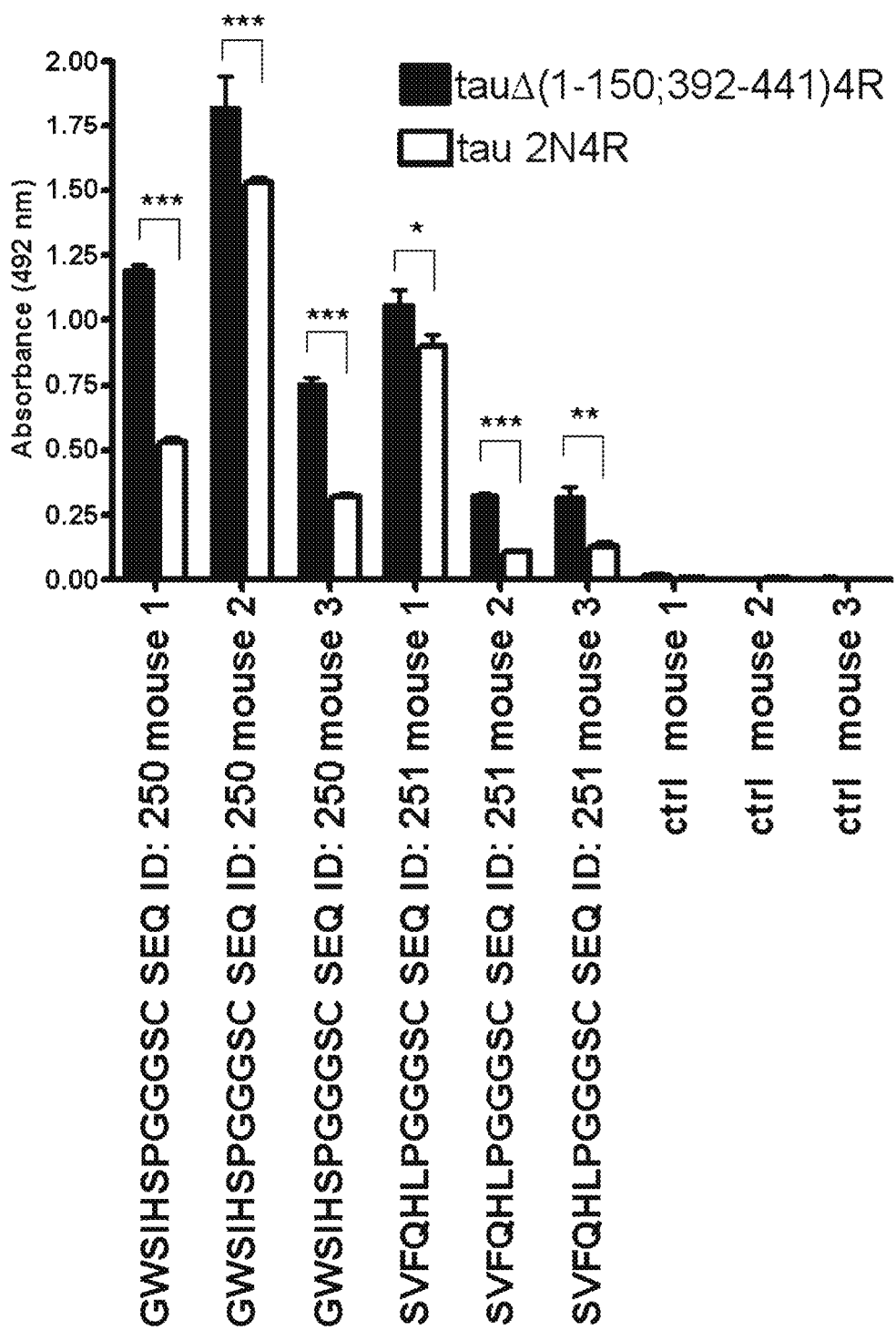
FIG. 67: Designer therapeutic epitopes GWSIHSPGGGSC (SEQ ID NO: 250) and SVFQHLPGGGSC (SEQ ID NO: 251) induced production of antibodies that statistically significantly discriminated between pathological tauΔ(1-150;392-441)4R and physiological tau 2N4R, as assayed by ELISA. Sera (at 1:3200 dilution) from mice immunized with one of the peptides 250 and 251 were tested for antibodies specific for tau proteins: pathological tauΔ(1-150;392-441)4R and physiological tau 2N4R by ELISA.

To determine the specificity of sera, two tau proteins were used: recombinant pathological tauΔ(1-150;392-441)4R and physiological Tau 2N4R. The sera from each mouse were serially diluted from 1:100 to 1:12.800 and tested in triplicates. Antibody titers were determined using Polyclonal Goat Anti-Mouse Immunoglobulins/HRP (Dako, #P0447) diluted 1:4; 000. FIG. 67 shows representative results for 1:3200 dilution.

Both designer therapeutic epitopes generated a high immune response in immunized mice. Furthermore, both tested designer therapeutic epitopes induced antibodies that recognized pathological tauΔ(1-150;392-441)4R with higher affinity compared to physiological Tau 2N4R (FIG. 67). This discrimination is statistically significant for sera from all immunized animals. Altogether, and in combination with the results obtained with the activity observed with DC8E8, these results show that both designer therapeutic epitopes 1 and 2 are immunogenic and induce antibody response with therapeutic potential to target pathological tau proteins in the brains of Alzheimer's disease patients.

Figure 68:
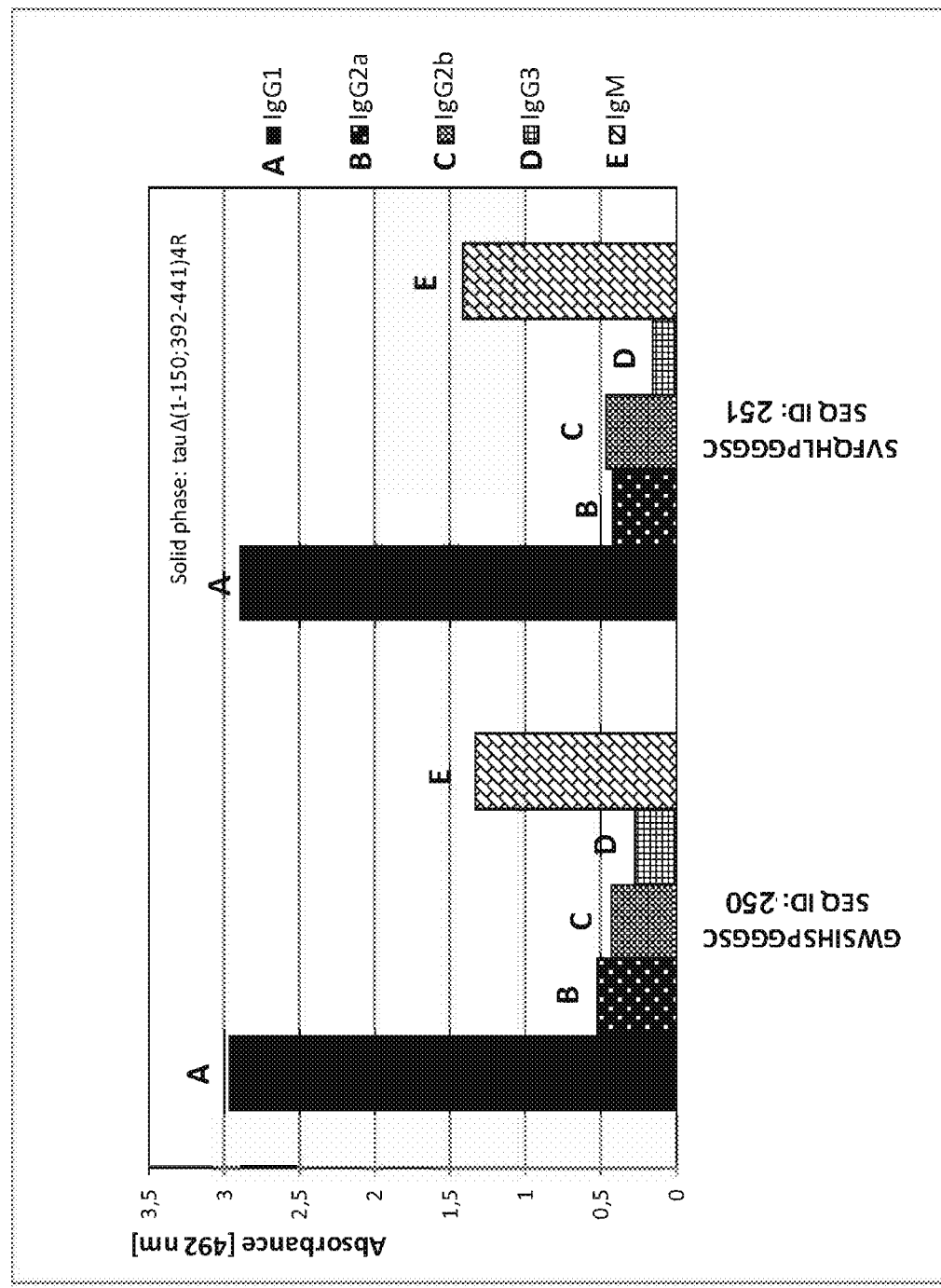
FIG. 68: Immunization with designer therapeutic epitopes GWSIHSPGGGSC (SEQ ID NO: 250) and SVFQHLPGGGSC (SEQ ID NO: 251) induced the most robust production of IgG1-isotype antibodies.

2. Antibody Isotype:

To determine the specific isotypes of the antibodies produced in response to these designer therapeutic epitopes 1 and 2, sera from mice of the same group were pooled, serially diluted from 1:100 to 1:12.800, and tested in triplicates by antibody isotype ELISA. To detect mouse IgM, IgG1, IgG2a, IgG2b, and IgG3 isotypes, anti-mouse subclass specific HRP-conjugated secondary antibodies were used (antibodies purchased from Lifespan Biosciences, anti IgG1 #LS-059107, anti IgG2a-# LS-059112, anti IgG2b-#LS-059117, anti-IgG3-#LS-059125 and anti-IgM-#LS-055875). Antisera obtained from control mice were negative. FIG. 68 shows representative results for 1:800 dilution. The data obtained with pooled sera demonstrated that immunization with both tested designer therapeutic epitopes induced a broad spectrum of anti-tau antibody isotypes and that the isotype profile was very similar in all tests. Both designer therapeutic epitopes generated mainly IgG1 antibodies in comparison with IgG2a, IgG2b and IgG3 responses. (FIG. 68).

3. Designer Therapeutic Epitopes Induce Antibody Response Statistically Highly Significantly Discriminating Between Pathological and Physiological Tau.

Analysis of the affinities of the antibodies generated against designer therapeutic epitopes was done by surface plasmon resonance on BIACORE3000 using a CM5 sensor chip (Biacore AB, Uppsala) as described in Examples 5 and 19. In each analysis cycle, mouse antiserum against either GWSIHSPGGGSC (SEQ ID NO: 250), designer therapeutic epitope 1 (diluted 100-fold) or SVFQHLPGGGSC (SEQ ID NO:251), designer therapeutic epitope 2 (diluted 100-fold), (pooled antisera from 3 mice), was captured in the analytical flow cell to reach immobilization level ~950 RU, which approached saturation. As a reference, an irrelevant antibody Rab50 (Macikova et al., 1992), which does not bind tau, was captured in the reference flow cell. For the $K_A$ determination as well as for the determination of the kinetic rate constants $k_{ON}$ and $k_{OFF}$, 100 nM solutions of either pathological tauΔ(1-150;392-441)4R or physiological Tau 2N4R, were injected at a flow rate 100 µl/min over the sensor chip.

Figure 69A:
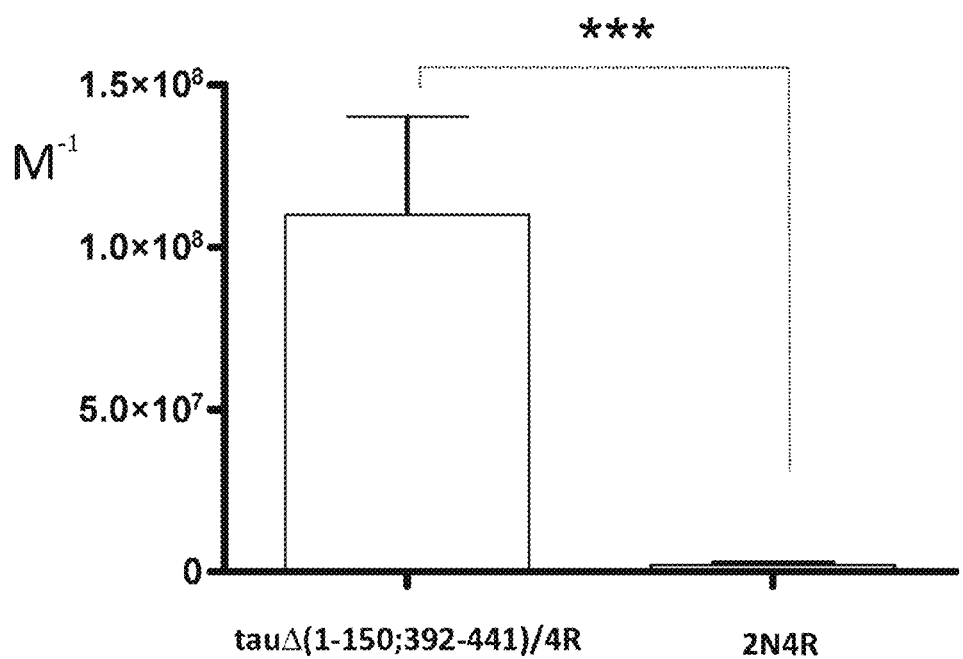
FIG. 69: Quantitative SPR (Surface Plasmon Resonance) measurements show that antibodies induced by designer therapeutic epitope 1 (GWSIHSPGGGSC, SEQ ID NO: 250) (FIG. 69A) and designer therapeutic epitope 2 (SVFQHLPGGGSC, SEQ ID NO: 251) (FIG. 69B) statistically significantly (p<0.001 and p<0.01, respectively) discriminated between pathological tauΔ(1-150;392-441)/4R and physiological 2N4R tau.
Figure 69B:
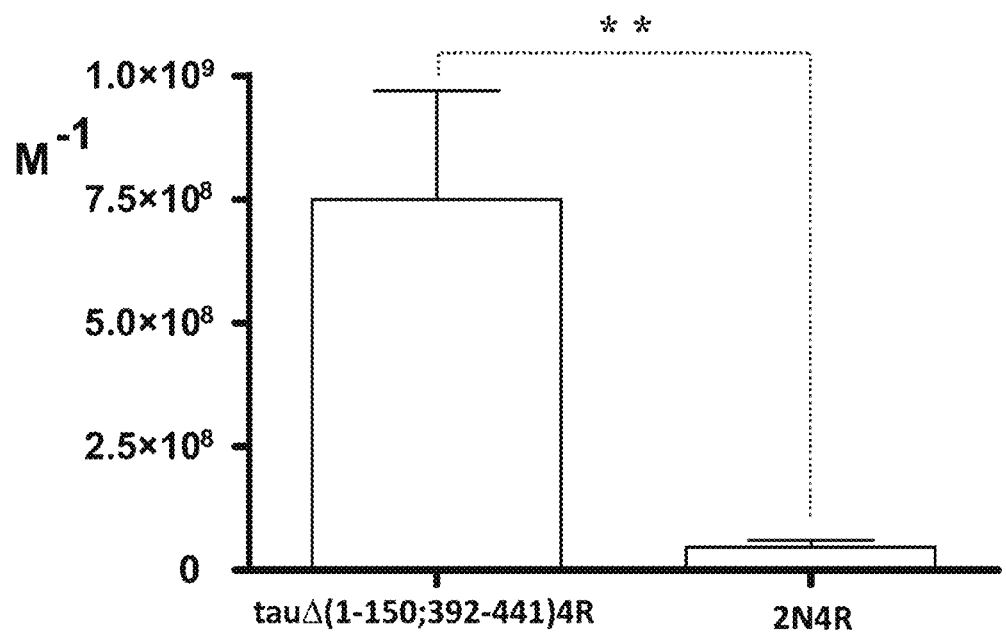

The antibodies induced by vaccination with designer therapeutic epitopes 1 and 2 discriminated between pathological tauΔ(1-150;392-441)4R and physiological Tau 2N4R (FIGS. 69A and 69B). Affinity of antibodies present in antiserum against designer therapeutic epitope 1 (GWSIHSPGGGSC, SEQ ID NO: 250) measured by surface plasmon resonance, exhibited nearly 50-times higher affinity to pathological tau, compared to physiological tau, which is highly statistically significant ($p<0.001$). Affinity of antibodies present in antiserum against designer therapeutic epitope 2 (SVFQHLPGGGSC (SEQ ID NO:251) measured by surface plasmon resonance, exhibited nearly 15-times higher affinity to pathological tau, compared to physiological tau, which is highly statistically significant ($p<0.01$).

4. Designer Therapeutic Epitopes Induce Antibody Response Recognizing Pathological Tau Species in Human AD Brains.

To determine the specificity of the antibodies generated in mice immunized with designer therapeutic epitopes, immunohistochemical staining was done on frozen sections of human AD brains.

The human AD brain tissue samples (entorhinal cortex, AD Braak VI, provided by the Netherlands Brain Bank) were fixed with 4% paraformaldehyde in PBS for 2 days at 4° C. and then cryoprotected (25% sucrose), frozen in cold 2-methylbutane (−42° C.) and sectioned on cryotome. Free floating tissue sections (40 µm) were treated with cold (4° C.) 99% formic acid for 1 min at room temperature (25° C.). The sections were immunostained using the standard avidin-biotin peroxidase method (ABC Elite, Vector Laboratories, Burlingame, Calif.). Mouse antisera against designer therapeutic epitope 1 (SEQ ID: 250) and designer therapeutic epitope 2 (SEQ ID NO: 251), each pooled from 3 immunized mice, were diluted 1:2000 in the blocking solution (5% bovine serum albumin, 0.3% Triton X-100 in PBS). Sections were then examined with an Olympus BX 51 microscope.

Immunohistochemical staining showed that mouse immunosera generated against both designer therapeutic epitopes GWSIHSPGGGSC (SEQ ID NO: 250) and SVFQHLPGGGSC (SEQ ID NO: 251) specifically recognized pathological tau structures, i.e. neurofibrillary tangles and neuropil threads, in the entorhinal cortex of Alzheimer's disease brain (FIGS. 70A through 70D). Antisera against designer therapeutic epitope 1 and designer therapeutic epitope 2 did not recognize normal tau in the control human brain. (FIGS. 70E and 70F).

5. Designer Therapeutic Epitope 2 (SVFQHLPGGGSC, SEQ ID NO: 251) Induces Antibody Response Recognizing Pathological Tau Species in the Brains of Transgenic Rat Model of Alzheimer's Disease.

To determine the specificity of the antibodies generated in mice immunized with designer therapeutic epitopes, immunohistochemical staining was done on paraffin embedded sections of the brains of transgenic rats SHR72.

Transgenic rats of the strain SHR72 (7 months old) were perfused transcardially with PBS for 1 min under deep anesthesia followed by perfusion with 100 ml of 4% paraformaldehyde (pH 7.4). After perfusion, the head was cut off and the brain was quickly removed. The brain was cut sagittally into two equal-sized hemispheres using disposable scalpel blades. The brain tissues were post-fixed in 4% paraformaldehyde, embedded in paraffin, and cut into sections on a microtome. Immunohistochemistry and histopathology were done on 8 µm paraffin-embedded tissue sections. Tissue sections were pre-treated for 20 min with an antigen unmasking solution (Vector laboratories, CA, USA) and for 1 min with cold (+4° C.) 90% formic acid (Applichem, Germany), at room temperature (25° C.). After blocking, the sections were incubated overnight with serum generated against designer therapeutic epitope 2 (SVFQHLPGGGSC, SEQ ID NO: 251) that was diluted 1:1000 in blocking solution (5% bovine serum albumin, 0.3% Triton X 100 in 50 nM Tris-HCl). After washing, the sections were incubated with a biotinylated secondary antibody (Vectastain Elite ABC Kit, Vector Laboratories) at room temperature for an hour, and then reacted with an avidin-biotin peroxidase-complex solution for 60 minutes (Vectastain Elite ABC Kit, Vector Laboratories), at room temperature (25° C.). The immunoreaction was visualized with a peroxidase substrate kit (Vector VIP, Vector laboratories, Ca, USA). Sections were examined with an Olympus BX71 microscope.

In the transgenic rat brain (SHR72), serum generated against designer therapeutic epitope 2 (SVFQHLPGGGSC, SEQ ID NO: 251) recognized neurofibrillary tangles (FIG. 70G). In age-matched control rat brains the antibody did not stain neuronal cells (FIG. 70H).

Serum generated against designer therapeutic epitope 2 (SVFQHLPGGGSC, SEQ ID NO: 251) recognized oligomeric pre tangle stage tau (FIG. 70I), as well as intracellular neurofibrillary tangles (FIG. 70J).

6. Antibodies Induced by Designer Therapeutic Epitopes 1 and 2 Recognize Soluble and Insoluble Pathological Tau in Human AD Brain:

Sarkosyl soluble and insoluble pathological tau was isolated from the temporal cortex of human Alzheimers disease (obtained from the Netherlands Brain Bank) and analyzed by immunoblotting, as described in Example 8.

The membrane containing soluble and insoluble pathological tau protein fractions were incubated either with DC8E8 hybridoma supernate diluted 1:1 with 5% non-fat dry milk in PBST or with pooled mouse antisera generated against designer therapeutic epitope 1 (SEQ ID NO: 250, GWSIHSPGGGSC) or with pooled mouse antisera generated against designer therapeutic epitope 2 (SVFQHLPGGGSC, SEQ ID NO: 251) whereby both pooled antisera were diluted 1:100 in 5% non-fat dry milk in PBST. Membranes were washed and then incubated with peroxidase-conjugated goat anti-mouse IgG (DAKO, Denmark) diluted 1:4000. The blots were developed with Super-Signal West Pico Chemiluminescent Substrate (Pierce, U.S.A) detected using the LAS3000 imaging system (FUJI Photo Film Co., Japan). The signal intensities were quantified using AIDA software (Advanced Image Data Analyzer, Raytest, Straubenhardt, Germany).

The results of this immunoblot analysis are shown in FIG. 71. These results show that antibodies generated against both designer therapeutic epitopes 1 (i.e., GWSIH-SPGGGSC) (SEQ ID NO: 250) and 2 (i.e. SVFQHLPGGGSC) (SEQ ID NO: 251) recognize the same pathological tau proteins as DC8E8. All the GWSIH-SPGGGSC (SEQ ID NO: 250) antisera, SVFQHLPGGGSC (SEQ ID NO: 251) antisera and DC8E8 antibody specifically recognized pathological tau proteins present in sarkosyl soluble and insoluble tau fraction isolated from AD brain tissues (FIG. 71).

7. Antibodies Induced by Designer Therapeutic Epitopes 1 and 2 Recognize Soluble and Insoluble Pathological Tau in Brains of Tau Transgenic Rats.

Sarkosyl soluble and insoluble pathological tau was isolated from the brains of tau transgenic rat brains (SHR72 line described in Example 7) as described in Example 8.

Figure 72:
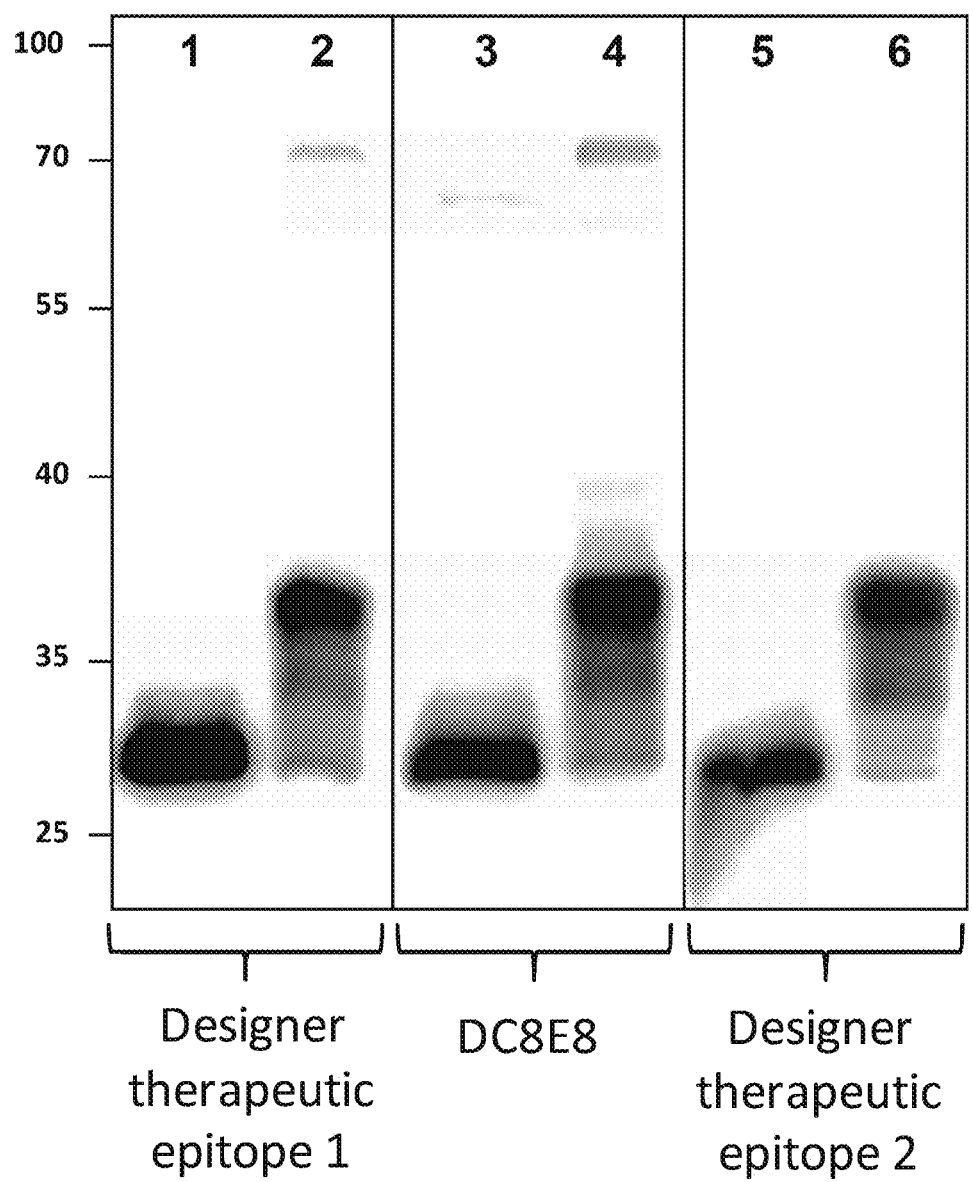
FIG. 72: Antibodies induced by designer therapeutic epitope 1 (GWSIHSPGGGSC, SEQ ID NO: 250) and designer therapeutic epitope 2 (SVFQHLPGGGSC, SEQ ID NO: 251) recognized soluble (Lane 1, 3, 5) and insoluble (Lane 2, 4, 6) pathological tau isolated from the brains of the Alzheimer's disease rat model (SHR72).

The results of the immunoblot analysis (described in the Example 8) are shown in FIG. 72. These results show that antibodies induced by designer therapeutic epitopes 1 (i.e., GWSIHSPGGGSC) (SEQ ID NO: 250) and 2 (i.e. SVFQHLPGGGSC) (SEQ ID NO: 251) recognize the same pathological tau proteins as DC8E8 (FIG. 72). Targeting of monomeric and oligomeric pathological tau protein prevent generation of pathological tau aggregates resulting in decreased tau pathology leading to therapeutic effect and treatment of AD in human.

Example 25: In Vivo Efficacy of Designer Therapeutic Epitopes in Transgenic Rats Modeling AD Immunotherapy with Designer Therapeutic Epitopes Showed Improvement in Neurobehavioral Parameters of Treated Rats.

Designer therapeutic epitope 2 (SEQ ID NO: 251) was selected for the immunotherapy in transgenic rats SHR 72. Rats were immunized subcutaneously with vaccine doses containing designer therapeutic epitope 2 (SEQ ID NO: 251) conjugated to KLH combined with Adju-phos adjuvant. Vaccines were prepared as described in Example 18. One dose contained 100 μg of conjugated designer therapeutic epitope 2. Complex motor impairment was measured by the set of standard motor tests combined with the neurological examination in the composite score—Neuroscale. At 6.5 months of age, transgenic rats SHR72 treated with vaccine containing designer therapeutic epitope 2 (SEQ ID NO: 251) were subjected to behavioral tests with aim to determine the effect of immunotherapy.

Figure 73A:
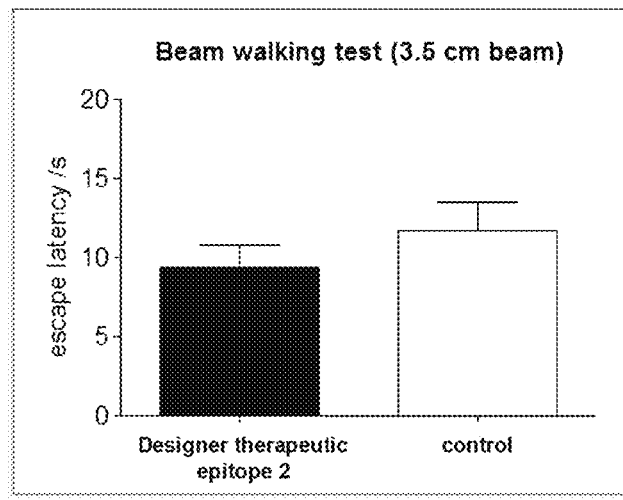
FIG. 73: Immunotherapy with designer therapeutic epitope 2 (SVFQHLPGGGSC, SEQ ID NO: 251) showed significant improvement in neurobehavioral parameters (Neuroscale) of treated SHR72 rats. (A) Beam walking test. (B) Number of hind-limb slips (p<0.05). (C) Neuroscale. Rats treated with the designer therapeutic epitope 2 (SEQ ID NO: 251) showed: a) decreased escape latencies by 27% in the beam walking test, b) reduced number of the hind-limb slips by 44% (p<0.05), and c) the reduced Neuroscale score by 26% than the transgenic control rats that received adjuvant alone. All statistical data were obtained using nonparametric Mann-Whitney U-test.
Figure 73B:
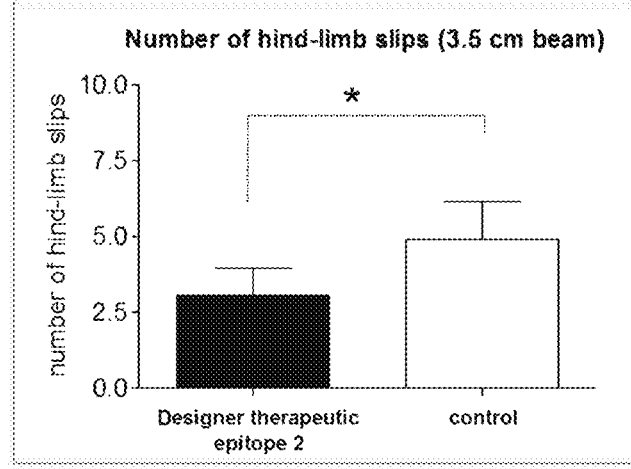
Figure 73C:
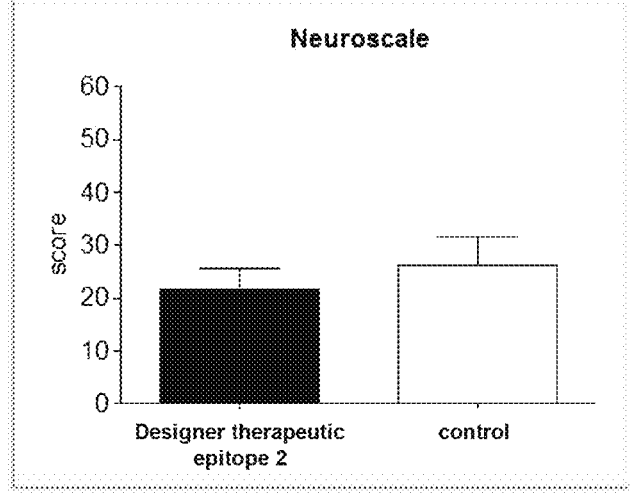

Rats treated with the designer therapeutic epitope 2 (SEQ ID NO: 251) showed decreased escape latencies by 27% in the beam walking test than the transgenic control rats that received adjuvant alone (FIG. 73A), The number of the hind-limb slips was statistically significantly reduced (p<0.05) by 44% in the vaccinated group in comparison with transgenic controls (FIG. 73B). The Neuroscale score was calculated from the values obtained in the beam walking tests, prehensile traction tests and neurological examinations (basic reflexes, hind-limb escape extension reflex). The immunization significantly improved the Neuroscale score of the rats treated with peptide SEQ ID NO: 251 by 26% compared to the control group (FIG. 73C). Total Neuroscale score confirmed the neurobehavioral improvement of treated transgenic rats when compared to untreated transgenic rats. All statistical data were obtained using nonparametric Mann-Whitney U-test.

Immunotherapy with Designer Therapeutic Epitope 2 Showed Statistically Significant Reduction (p<0.05) of Pathological Tau in the Brains of Treated Alzheimer Transgenic Rats.

To confirm the effect of the immunization with designer therapeutic epitope 2 (SEQ ID NO: 251) on the levels of insoluble pathological tau, we used immunoblot analysis of the rat brain samples. Brain tissue (the brain stem) of the transgenic animals immunized with designer therapeutic epitope 2 (SEQ ID NO: 251) and control group of transgenic animals immunized with adjuvant alone were used for the preparation of sarkosyl-insoluble tau fraction as described in Example 8. Immunoblot analysis was done as described in Example 19. The statistical analysis was done by T-test. Phosphorylation dependent monoclonal antibodies AT8, DC209, DC217 and pan-tau monoclonal antibody DC25 were used in the study.

Figure 74:
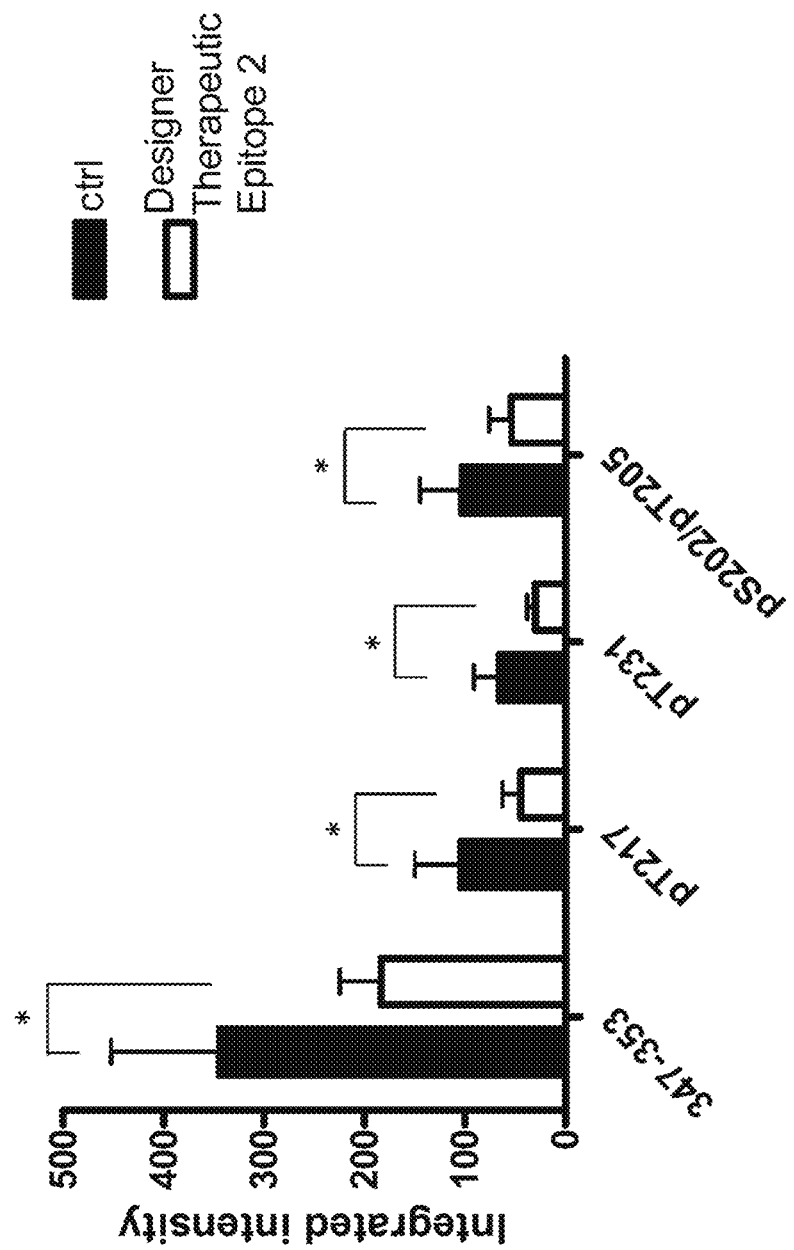
FIG. 74: Immunotherapy with designer therapeutic epitope 2 (SVFQHLPGGGSC, SEQ ID NO: 251) showed a statistically significant reduction of pathological tau in brains of immunized Alzheimer transgenic SHR72 rats. Immunotherapy statistically significantly (p<0.05) reduced the amount of pathological insoluble tau in immunized animals compared to the control transgenic rats that received adjuvant alone. The reduction of pathological insoluble tau was observed at all analyzed tau epitopes (P<0.05).

The results of immunoblot quantitative analysis of insoluble tau levels from the group of transgenic rats immunized with designer therapeutic epitope 2 (SEQ ID NO: 251) and control group are shown in FIG. 74. Immunotherapy reduced statistically significantly the amount of insoluble tau in immunized animals compared to the control transgenic rats that received adjuvant alone The reduction of insoluble tau was observed at all analyzed tau epitopes. Reductions at 347-353 epitope and phospho-tau epitopes were statistically significant (P<0.05). Observed reduction was as follows: at 347-353 tau epitope by 46% (P<0.05), at pT217 tau epitope by 57% (P<0.05), at p231-tau epitope by 55% (P<0.05), at pS202/pT205 tau epitope by 47% (P<0.05).

These results show that the vaccine induced pathological tau specific antibodies which led to reduction of pathological tau. The reduction of pathological tau levels in the brain of treated Alzheimer's disease rat model correlated with neurobehavioral parameters. Treated animals with low levels of insoluble tau showed shorter escape latency and statistically significantly reduced number of hind-limb slips (p<0.05), in comparison with control animals. These findings show that the immunization with designer therapeutic epitope leads to the reduction of insoluble pathological tau and to neurobehavioral improvement in treated animals, which underlines the therapeutic potential of the vaccine for the treatment of the human Alzheimers disease and related tauopathies.

Figure 75A:
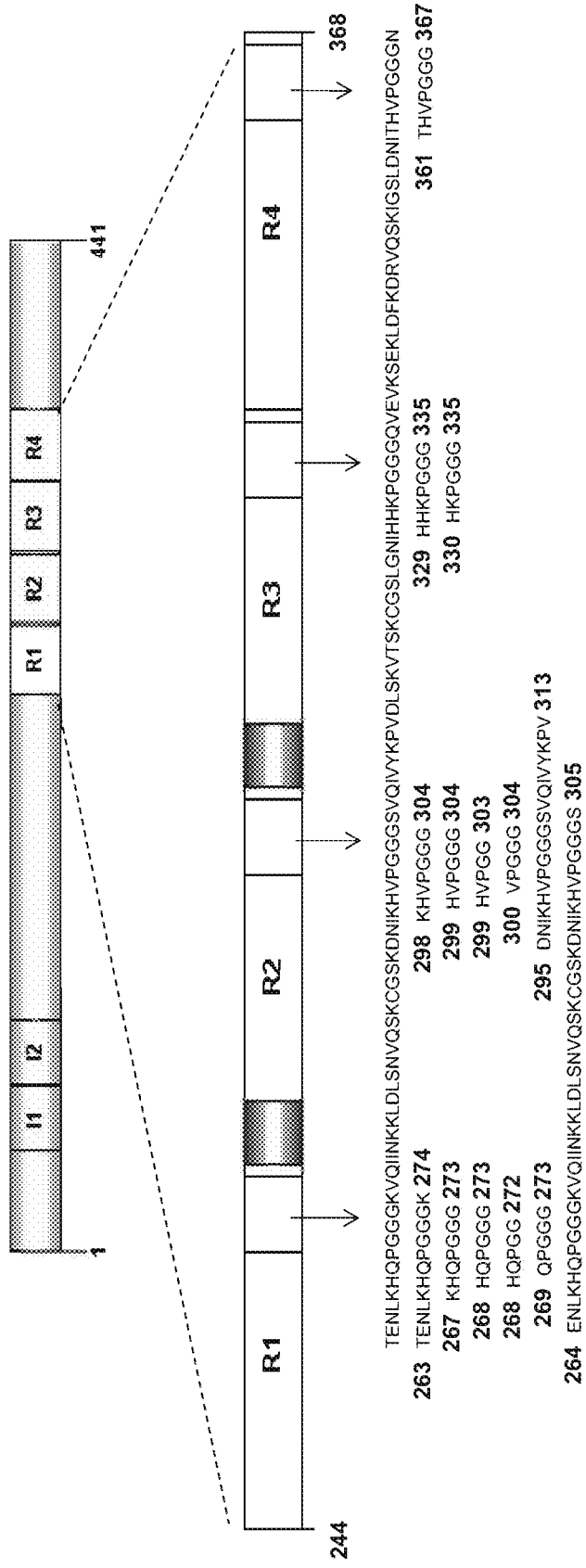
FIG. 75: (A) Schematic of synthetic peptides used for further evaluation of DC8E8's minimal epitope (therapeutic core unit) and immunogenic potency determination and (B) their amino acid sequences.

Example 26: Further Characterization of DC8E8 Minimal Epitopes (for Therapeutic Core Units To further characterize DC8E8's minimal epitopes, a panel of tau peptides with different lengths (42-mer, 19-mer, 12-mers, 7-mers, 6-mers and 5-mers), derived from the microtubule binding repeat regions (MTBR1, MTBR2, MTBR3, MTBR4) of human tau protein 2N4R were designed (FIG. 75 A, B). Peptides were synthesized by EZBiolabs (USA) with purity higher than 95%. All peptide were analyzed for their ability to compete with pathological tauΔ(1-150;392-441)/4R for binding to DC8E8 by competition ELISA. ELISA plates (Sarstedt, #821581001) were coated with 50 μl/well of 5 μg/ml of recombinant purified tauΔ(1-150;392-441)/4R) in PBS overnight at 37° C. The coated plates were washed 5 times with PBS/Tween 20 (0.05% v/v), and blocked with PBS/Tween 20 (0.05% v/v) for 1 h at 25° C. Each of the peptides was separately dissolved in PBS at a final concentration of 1 mM. Serial dilutions (2.5×) of peptides in PBS/Tween 20 were prepared in polypropylene microtiter plates with conical well bottom (Greiner, #651201) within the concentration range of 200 µM; 80 µM; 32 µM; 12.8 µM; 5.12 µM; 2.048 µM; 0.8192 µM; 0.32768 µM). The validation monoclonal antibody DC8E8 was diluted to a concentration of 0.6 µg/ml in PBS and 60 µl of this diluted antibody was added into each well to serial dilution of peptides resulting in 120 µl/well of mixture. The antibody/peptide mixtures were incubated for 1 hr at 25° C. on a rotating platform set to 230 rpm. 50 µl/well of antibody/peptide mixtures were transferred from polypropylene plates into tauΔ(1-150;392-441)/4R coated and PBS/Tween 20 blocked ELISA plates (in duplicates) and incubated for 1 hr at 25° C. The plates were washed 5× times with PBS/Tween 20 and incubated with 50 µl/well of Polyclonal Goat Anti-Mouse Immunoglobulins/HRP (Dako, #P0447) diluted 1:1000 in PBS/Tween 20 for 1 hr at 25° C., After washing, the plates were then incubated with 50 µl/well of 1 mg/2 ml o-PDA (o-phenylenediamine, Sigma, P1526) in 0.1 M Na-Acetate pH=6.0 (Roth, #6779) supplemented with 1.5 µl/2 ml of 30% $H_2O_2$ (Sigma, H-0904) for 20 minutes at 25° C. in dark. The reaction was stopped by adding 50 µl/well of 2M $H_2SO_4$ (Merck, 1.00731.1000) followed by reading the plates at 492 nm (e.g. Powerwave HT, Bio-Tek).

Figure 76:
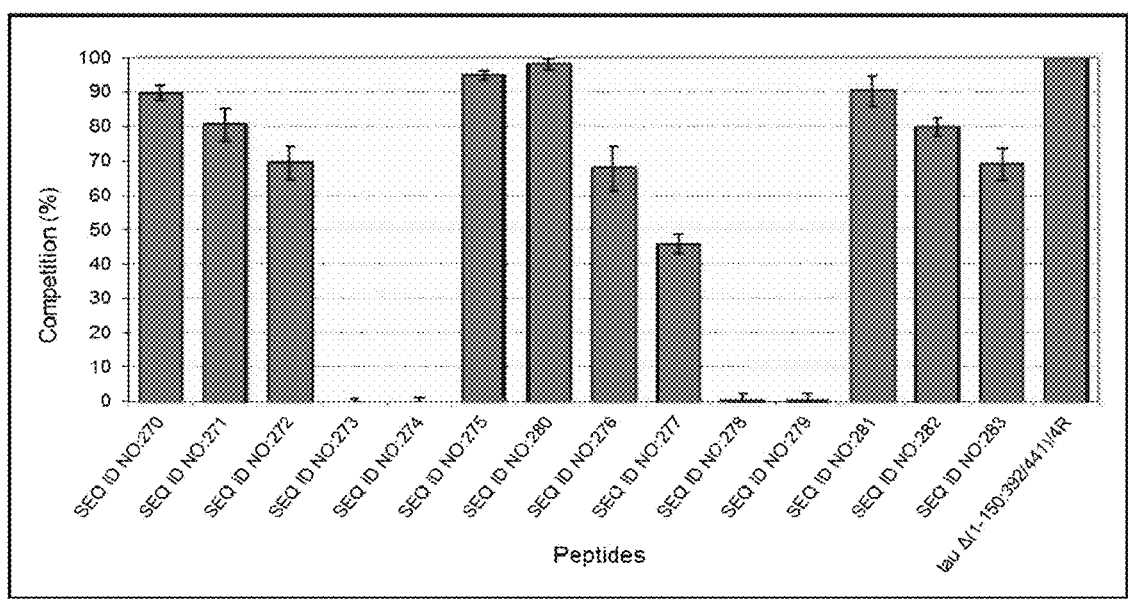
FIG. 76: Determination of DC8E8 minimal epitope (therapeutic core unit) using synthetic peptides by competitive ELISA. Ten tau peptides (SEQ ID NOs: 270, 271, 272, 275, 276, 277, 280, 281, 282 and 283) that contain at least 6 amino acids of the DC8E8 recognition sequence are capable to compete with pathological tauΔ(1-150;392-441)/4R for binding to antibody DC8E8. Tau peptides containing only 5 amino acids of the DC8E8 recognition sequence (SEQ ID NOs: 273, 274, 278 and 279) do not compete with tauΔ(1-150;392-441)/4R (SEQ ID NO: 199) for binding to antibody DC8E8.

FIG. 76 shows the results of the competition ELISA performed with the following peptides: TENLKHQPGGGK (SEQ ID NO: 270), KHQPGGG (SEQ ID NO: 271), HQFGGG (SEQ ID NO: 272), HQPGG (SEQ ID NO: 273), QPGGG (SEQ ID NO: 274), ENLKHQPGGGKVQIINKKLDLSNVQSKCGSKDNIKHVPGGGS (SEQ ID NO: 275), KHVPGGG (SEQ ID NO: 276), HVPGGG (SEQ ID NO: 277), HVPGG (SEQ ID NO: 278), VPGGG (SEQ ID NO: 279), DNIKHVPGGGSVQIVYKPV (SEQ ID NO: 280), HHKPGGG (SEQ ID NO: 281), HKPGGG (SEQ ID NO: 282) and THVPGGG (SEQ ID NO: 283). All analyzed peptides that encompassed tau therapeutic epitopes competed with pathological tauΔ(1-150;392-441/4R). As shown in FIG. 76, even 6-mer peptides (SEQ ID NO: 272, SEQ ID NO: 277 and SEQ ID NO: 282) were able to compete with tau Δ(1-150;392-441)/4R for binding to DC8E8. However, removal of either histidine (5-mer peptides SEQ ID NOs: 274, 279) or the last glycine (5-mer peptides SEQ ID NOs: 273, 278) led the to a loss of competing activity with tauΔ(1-150;392-441/4R) for binding to DC8E8 (the 5-mer peptides were derived from SEQ ID NO: 272 and SEQ ID NO: 277 with removed amino acids His and Gly underlined, see above). These results suggest that the 5-mers peptides did not generate the therapeutic 3D structure that is recognized by DC8E8 on pathological tau. On the other hand, peptides comprising six amino acid residues create therapeutic 3D structure responsible for the biological activity measured by competitive ELISA and form minimal epitopes (therapeutic core units) of DC8E8. In their design, five amino acid residues are important for DC8E8 recognition, which are conserved (histidine, proline, and the three glycine residues in the sequence HxPGGG).

CONCLUSION

The data suggest that the minimal DC8E8 epitope on human tau consists of 6 amino acids, which comprise the residues HQPGGG (located within MTBR1), HVPGGG (within MTBR2), HKPGGG (within MTBR3) and HVPGGG (within MTBR4). Thus, the DC8E8 binding site (=epitope) is present four times in 2N4R tau and three times in 2N3R tau. This suggests that the required amino acids within the 6-mer sequence are the histidine and all three glycines.

Example 27: Determination of the Immunogenicity of Peptides Carrying DC8E8 Minimal Epitopes a) Peptides Carrying DC8E8's Minimal Epitopes are Immunogenic:

With the aim to determine the immunogenic potential of individual tau peptides, peptides were conjugated to KLH via their N-terminal Cys residue.

Towards this end, tau peptides were synthetized as cysteinated peptides with an extra N-terminally located cysteine residue with the aim to obtain oriented attachment of the peptide on the surface of the KLH protein. Peptides were coupled to the KLH carrier via bifunctional cross-linker N-[γ-maleimidobutyryloxy]succinimide ester (GMBS). To prepare the conjugation reaction, 20 mg of KLH (Calbiochem) were dissolved in conjugation buffer (PBS with 0.9 M NaCl, 10 mM EDTA) to a concentration of 10 mg/ml by gentle mixing for 10 minutes. For preparation of maleimide-activated KLH, 2 mg of active bi-functional cross-linker GMBS were dissolved in 50 µl of anhydrous dimethylformamide and mixed with 2 ml of KLH solution for 1 hour at room temperature. Subsequently, un-reacted GMBS was removed on a 5 ml HiTrap Desalting column (GE Healthcare) equilibrated in conjugation buffer. Conjugations were carried out at a 1:1 ratio of peptide to maleimide-activated KLH (w/w, 20 mg of peptide) for 2 h at room temperature (25° C.). The resulting conjugates were dialyzed against a 100-fold excess of PBS, with four dialysis buffer changes to remove unconjugated peptide. After dialysis, the conjugates were centrifuged at 21,000×g for 15 min at 2° C. The conjugates were aliquoted and stored at −20° C. until used.

Vaccines for immunizations were prepared with peptide-KLH conjugates, containing 100 µg of conjugated peptide, in 100 µl of PBS and emulsified 1:1 (vol/vol) with Freund's adjuvant in a final dose volume of 200 µl. Five C57/BL mice were used per treatment group. The first immunization was performed using the peptide-conjugate in PBS formulated with Freund's complete adjuvant. The two following immunizations, in one-week intervals, were performed using the peptide-conjugate in PBS formulated with Freund's incomplete adjuvant. Animals were bled one week after the last booster dose and collected sera were used for antibody titer determination. The titers of specific anti-tau antibodies were determined by ELISA, as described in Example 19. Serial dilutions (1:100 to 1:102400) of each serum were tested against pathological tauΔ(1-150; 392-441)/4R and physiological tau 2N4R, used as a solid phase. FIGS. 77A through 77N shows a summary of the results for sera at 1:800 dilution. The ELISA results were statistically evaluated using the Mann-Whitney non-parametric test. Titers were defined as the reciprocal of the dilution of serum giving one half of maximum OD and summarized in FIG. 78.

Figure 79A:
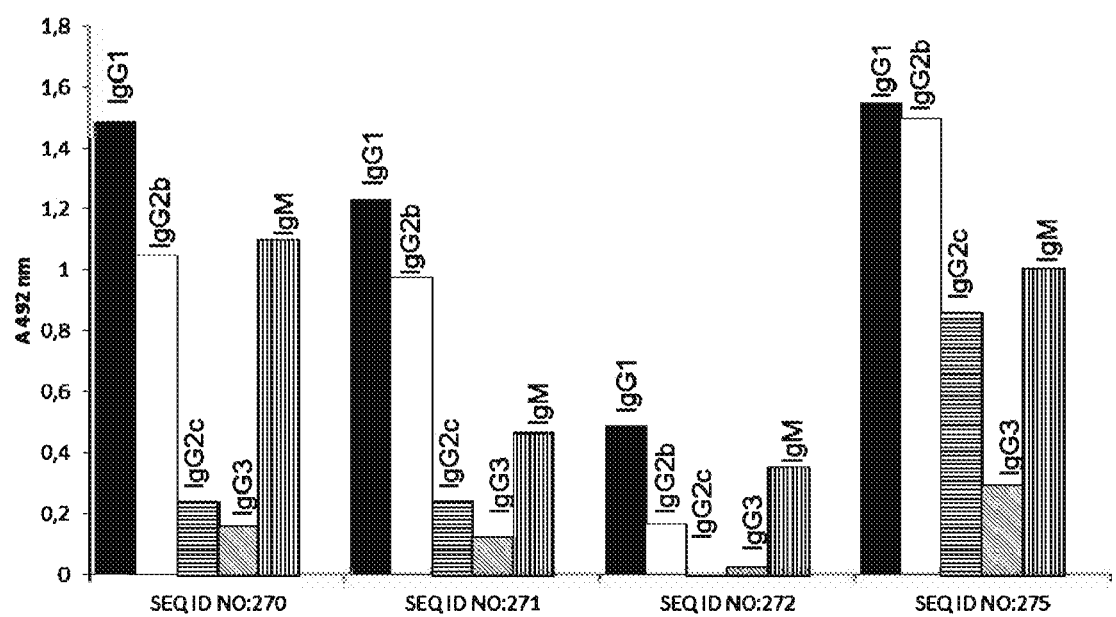
FIGS. 79A and 79B: The isotype profile of antibodies induced by tau peptides is shown. Immunization of C57/BL mice with tau peptides carrying minimal DC8E8 epitope preferentially induced formation of IgG1 and IgG2b antibody isotypes specific to pathological tau. Pooled sera from individual mice were diluted 1:800 and binding activity to pathological tauΔ(1-150; 392-441)/4R was analyzed by ELISA.
Figure 79B:
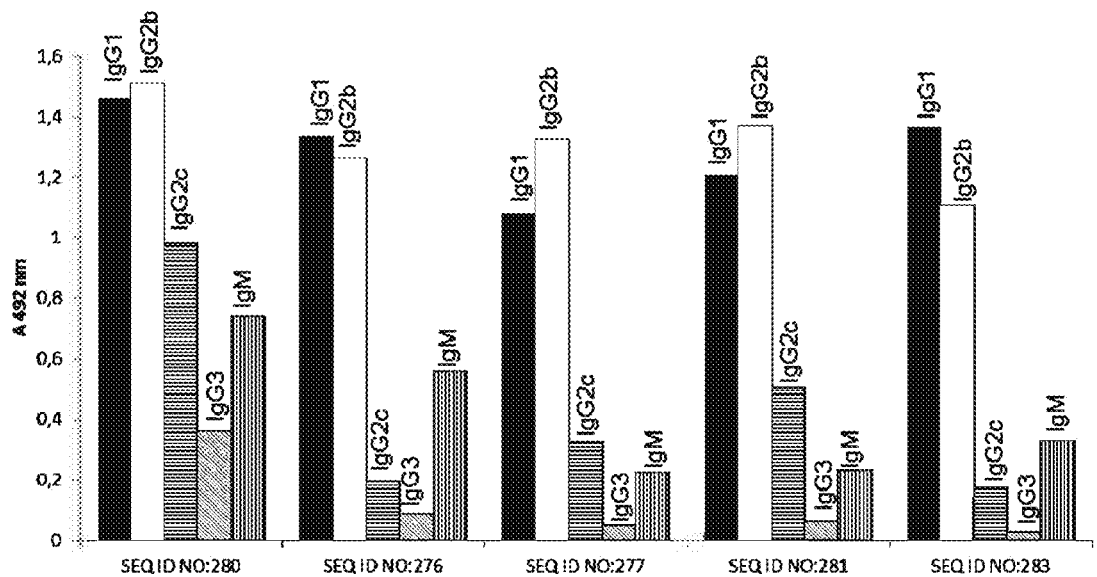
Figure 80:
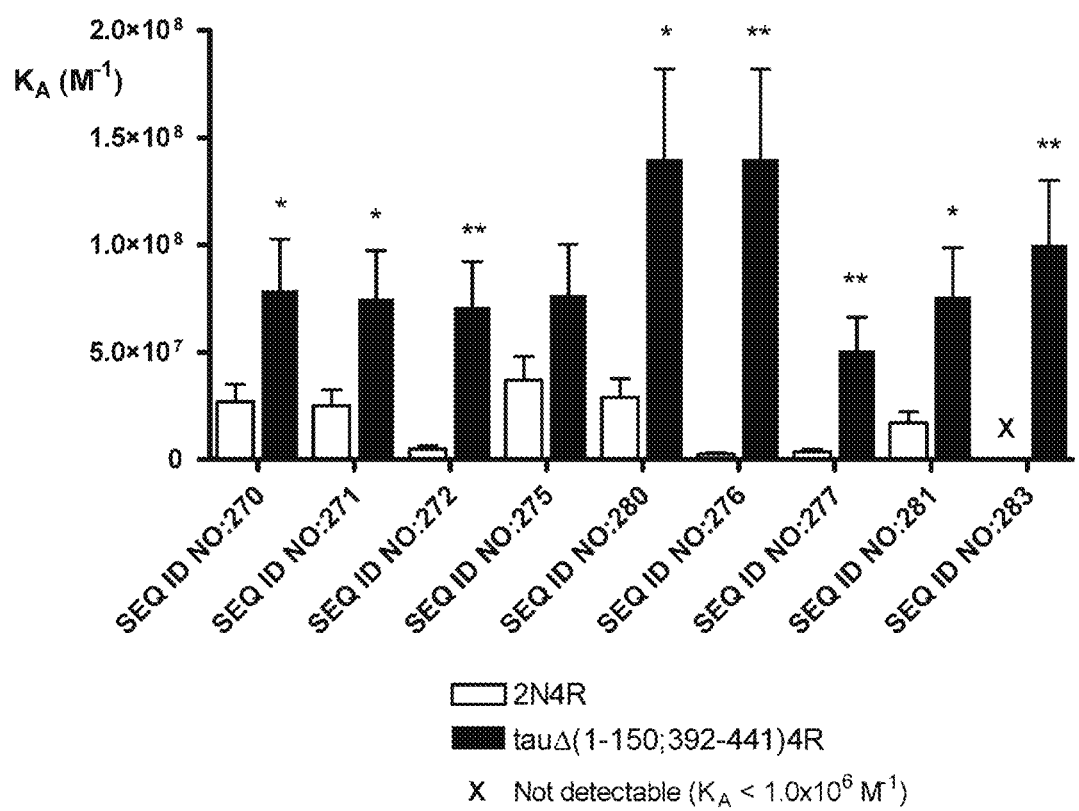
FIG. 80: Quantitative evaluation of the binding capacity of antibodies, which were induced in mice C75BL immunized with tau peptides, to tauΔ(1-150;392-441)/4R and 2N4R. Surface plasmon resonance (SPR) measurements showed that antibodies against tau peptides SEQ ID NOs: 270, 271, 272, 275, 276, 277, 280, 281 and 283 statistically significantly (** . . . $p<0.001$ and * . . . $p<0.01$) discriminated between pathological tauΔ(1-150;392-441)/4R and physiological 2N4R tau. KA—the association equilibrium binding constant.

Immunization of mice with tau peptides TENLKHQPGGGK (SEQ ID NO: 270), KHQPGGG (SEQ ID NO: 271), ENLKHQPGGGKVQIINKKLDLSNVQSKCGS KDNIKHVPGGGS (SEQ ID NO: 275), KHVPGGG (SEQ ID NO: 276), HVPGGG (SEQ ID NO: 277), DNIKHVPGGGSVQIVYKPV (SEQ ID NO: 280), HHKPGGG (SEQ ID NO: 281) and THVPGGG (SEQ ID NO: 283) induced high levels of tau specific antibodies in immunized mice. Furthermore, induced antibodies exhibited higher affinity to pathological tauΔ(1-150; 392-441)/4R than to physiological tau 2N4R (FIG. 77A-C). This discrimination was statistically significant for sera from all immunized animals (SEQ ID NO: 270, p<0.0079; SEQ ID NO: 271, p<0.0052; SEQ ID NO: 275, p<0.0079; SEQ ID NO: 276, p<0.0079; SEQ ID NO: 277, p<0.0379; SEQ ID NO: 280, p<0.0159; SEQ ID NO: 281, p<0.0379, and SEQ ID NO: 283, p<0.0286). Generally, the geometric mean antibody titers to pathological tauΔ(1-150; 392-441)/4R were three- to five-fold higher than that to physiological tau 2N4R (FIG. 78). As shown in FIG. 78, the highest antibody titers to pathological tau were induced by tau peptide SEQ ID NO: 275 (GMT 51200), SEQ ID NO: 280 (GMT 51200), SEQ ID NO: 270 (GMT 22286) and SEQ ID NO: 276 (GMT 22286). 5-mer peptides (SEQ ID NOS: 273, 274, 278, 279), which appear to lack the therapeutic 3D structure, were not able to induce tau specific antibodies in immunized animals. Altogether, these results showed that the peptides (SEQ ID NOS: 270, 271, 272, 275, 276, 277, 280, 281 and 283) carrying the minimal therapeutic epitopes (therapeutic core units) are immunogenic and induce antibodies with therapeutic potential to target pathological tau proteins in the brains of Alzheimer's disease patients. The aforementioned epitope mapping experiments showed that peptide SEQ ID NO: 282 creates a therapeutic 3D structure (e.g., at least partially mimicks the minimal DC8E8 epitope), nevertheless, it did not induce a specific antibody response in immunized mice (GMT for pathological tau was 174, FIG. 78).

b) Isotypic Profile:

Vaccination of C57/BL mice with tau peptides SEQ ID NOS: 270, 271, 275, 276, 277, 280, 281 and 283 preferentially induced formation of IgG1 and IgG2b antibody isotypes specific to pathological tau. To determine the specific isotypes of the antibodies produced in response to peptides sera from mice were pooled and diluted from 1:100 to 1:12.800, and tested in duplicates by ELISA (as described in Example 19) against pathological tauΔ(1-150; 392-441)/4R. To detect mice IgG1, IgG2b, IgG2c, IgG3 and IgM isotypes, anti-mouse subclass specific HRP conjugated secondary antibodies were diluted 1:5,000 in PBS (antibodies purchased from Lifespan Biosciences). FIG. 79 shows results for the representative 1:800 dilution. The data suggest that the peptides conjugated to KLH induced a broad spectrum of anti-tau antibody isotypes. In general, the vaccination with peptides generated highest levels of antibody isotypes (IgG1, IgG2b), which are considered to be the high affinity antibodies. The presence of high titers of IgG1 and IgG2b antibodies with preferential affinity to pathological tau indicated that the immune response induced by the vaccine is directed against pathological tau species. The control sera obtained from mock-immunized mice (which received adjuvant alone) were negative (data not shown).

c) Peptides Carrying Therapeutic Epitopes Induce Antibodies Discriminating Between Pathological and Physiological Tau:

Real time monitoring of binding events using surface plasmon resonance enabled measurement of the kinetic rate of association (kON) and dissociation (kOFF) of antibodies from the pooled sera of mice C57/BL immunized with individual tau peptides TENLKHQPGGGK (SEQ ID NO: 270), KHQPGGG (SEQ ID NO: 271), HQPGGG (SEQ ID NO: 272), HQPGG (SEQ ID NO: 273), QPGGG (SEQ ID NO: 274), ENLKHQPGGGKVQIINKKLDLSNVQSKCG-SKDNIKHVPGGGS (SEQ ID NO: 275), KHVPGGG (SEQ ID NO: 276), HVPGGG (SEQ ID NO: 277), HVPGG (SEQ ID NO: 278), VPGGG (SEQ ID NO: 279), DNIKHVPGGGSVQIVYKPV (SEQ ID NO: 280), HHKPGGG (SEQ ID NO: 281), HKPGGG (SEQ ID NO: 282) and THVPGGG (SEQ ID NO: 283). The analysis was done by surface plasmon resonance on BIACORE3000 using a CM5 sensor chip (Biacore AB, Uppsala) as described in Examples 5 and 19. The analysis showed that antibodies induced by immunization with the peptides were able to discriminate between the recognition of tauΔ(1-150;392-441)/4R and physiological tau isoform 2N4R (FIG. 80). The antibodies induced by immunization with peptides SEQ ID NOS: 270, 271, 272, 275, 276, 277, 280, 281 and 283, carrying the minimal therapeutic epitopes, exhibited a preferential affinity for tauΔ(1-150;392-441)/4R, compared to their affinity for the corresponding physiological tau 2N4R. This discrimination was statistically significant for sera from the peptides: SEQ ID NO: 270 (p=0.0392), SEQ ID NO:271 (p=0.0363), SEQ ID NO: 272 (p=0.0022), SEQ ID NO: 276 (p=0.0013), SEQ ID NO: 277 (p=0.0023), SEQ ID NO:280 (p=0.0104), SEQ ID NO:281 (p=0.0123) and SEQ ID NO: 283 (p=0.0011). The obtained results are in accordance with previous immunogenicity experiments summarized in FIG. 77A-C and FIG. 78.

d) Peptide-Induced Antibodies Recognize Pathological Forms of Tau by Western Blot:

Antibodies induced by immunization of mice C57/BL with individual tau peptides were examined for pathological forms of tau using immunoblot method (as described in Example 19). The brain stems of SHR72 rats in the late stage of neurofibrillary pathology were used for the extraction of insoluble pathological tau proteins. Temporal cortex of human AD brain (Braak stage VI; obtained from the Netherlands Brain Bank, Netherlands) was used for the extraction of human pathological AD tau. Extracted tau proteins were prepared according to sarcosyl method (Greenberg and Davies 1990). Pooled sera from immunized animals were diluted 1:1000 in PBS and used as a primary antibody, Incubation with primary antibody was followed by polyclonal rabbit anti-rat immunoglobulins conjugated to horseradish peroxidase (1:3000; Dako, Glostrup, Denmark). The horseradish peroxidase-conjugated antibodies were then visualized by chemiluminescence using SuperSignal West Pico Chemiluminescence Substrate (Thermo Scientific, Belgium). The signal was digitized with LAS3000 CCD imaging system (Fujifilm, Japan). Summarized results are provided in FIG. 81. Antibodies elicited by vaccination with peptides likely creating therapeutic 3D structure of DC8E8 epitope(s) (SEQ ID NOS: 270, 271, 272, 275, 276, 277, 280, 281 and 283) recognized all pathological forms of tau protein extracted from SHR72 and from AD brain tissues, including the A68 tau triplet characteristic for AD. Nevertheless, peptide SEQ ID NO: 282 which appears to create a therapeutic 3D structure (competes with tau Δ(1-150;392-441)/4R for binding to DC8E8), did not induce specific antibody response in this immunized mice, thus reactivity was negative. Similarly, 5-mers peptides that were not able to induce tau specific antibody response were negative in this analysis.

e) Peptide-Induced Antibodies Recognize Pathological Tau Proteins in the Sections from the Human Alzheimer's Disease Brain Tissues:

Tau-specific antibodies elicited by vaccination of mice C57/BL with individual peptides were tested on human brain tissue (paraffin blocks) obtained from the Netherlands brain bank. The blocks were cut on a microtome. Paraffin-sections (8 μm) of the hippocampus-CA1 sector from Alzheimer's disease brain (Braak stage V) were treated with cold (+4° C.) 99% formic acid for 1 min at room temperature (25° C.). The tissue sections were incubated in blocking solution (5% BSA, 0.3% Triton X-100 in 50 nM Tris-HCl) and then overnight with serum diluted 1:1000 in blocking solution.

Figure 82A:
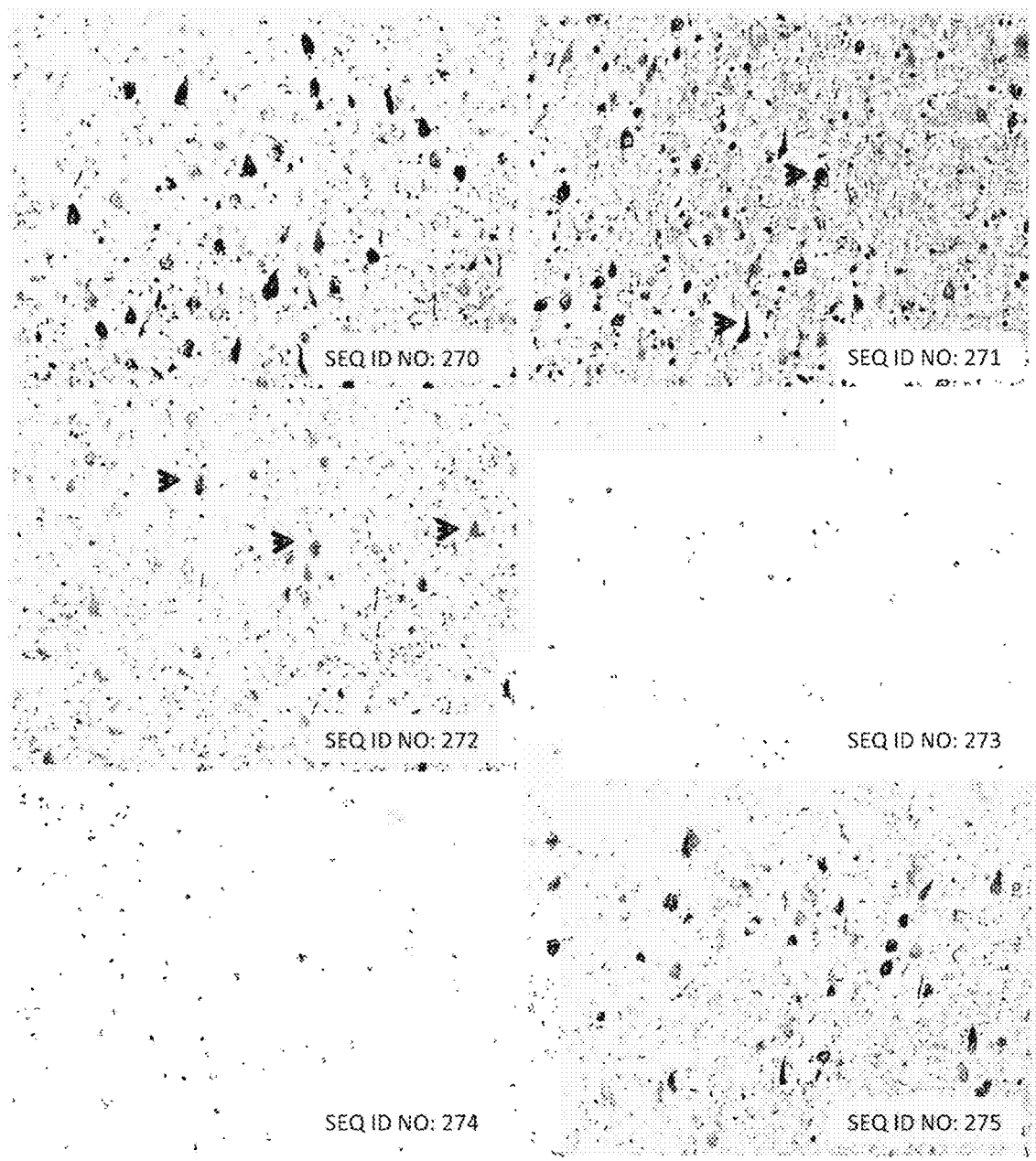
FIGS. 82A-C: Neurofibrillary tangles recognized by tau peptide-induced antibodies in human AD brain tissues. Vaccination of C57BL mice with tau peptides SEQ ID NOs: 270, 271, 272, 275, 276, 277, 280, 281 and 283 induced antibodies recognizing neurofibrillary lesions in hippocampus of Alzheimer's disease brain. Sera from mice immunized with adjuvant only were used as a negative control. Brain tissue sections from the hippocampus CA1 were used. Scale bar 100 μm.
Figure 82B:
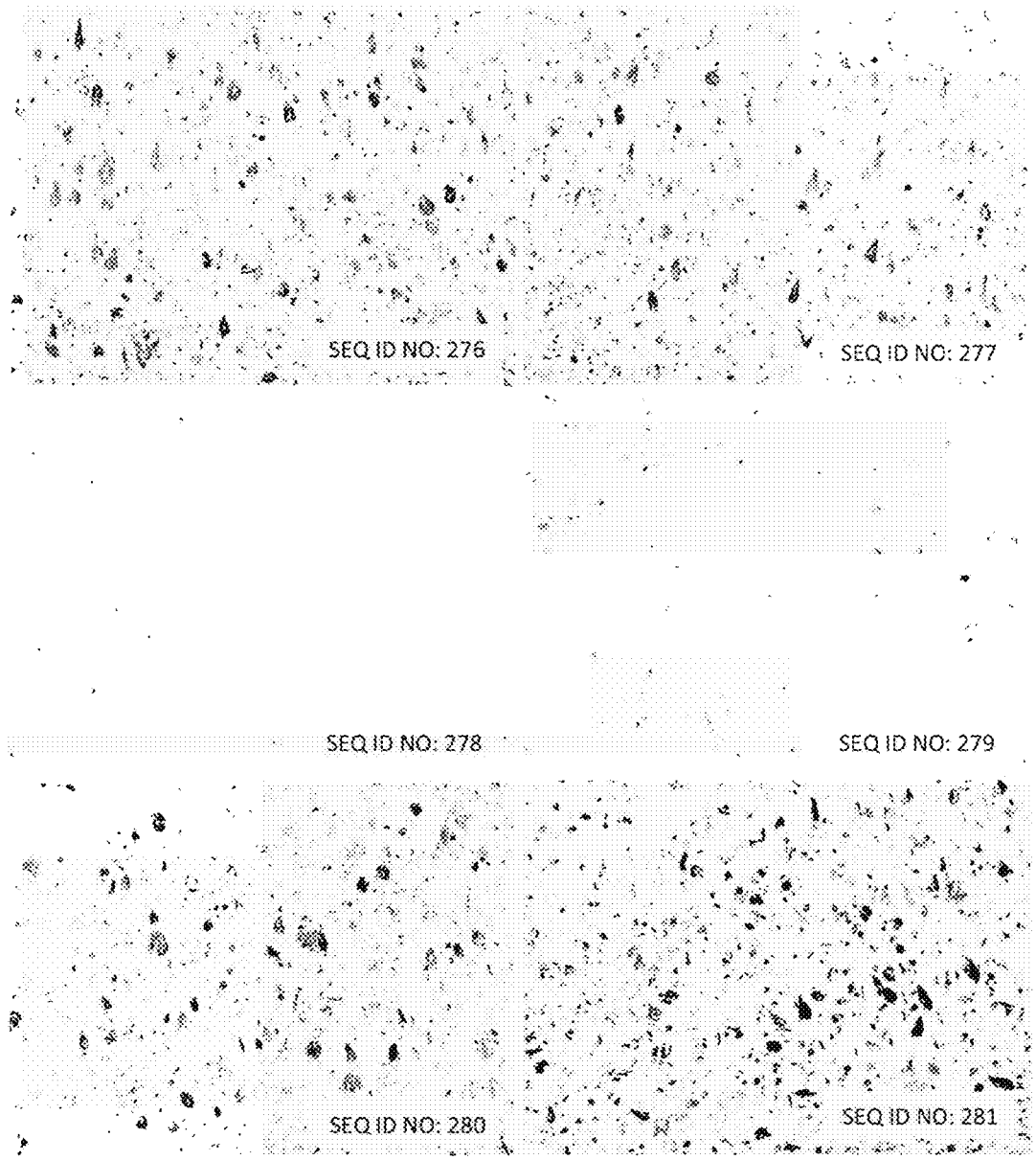
Figure 82C:
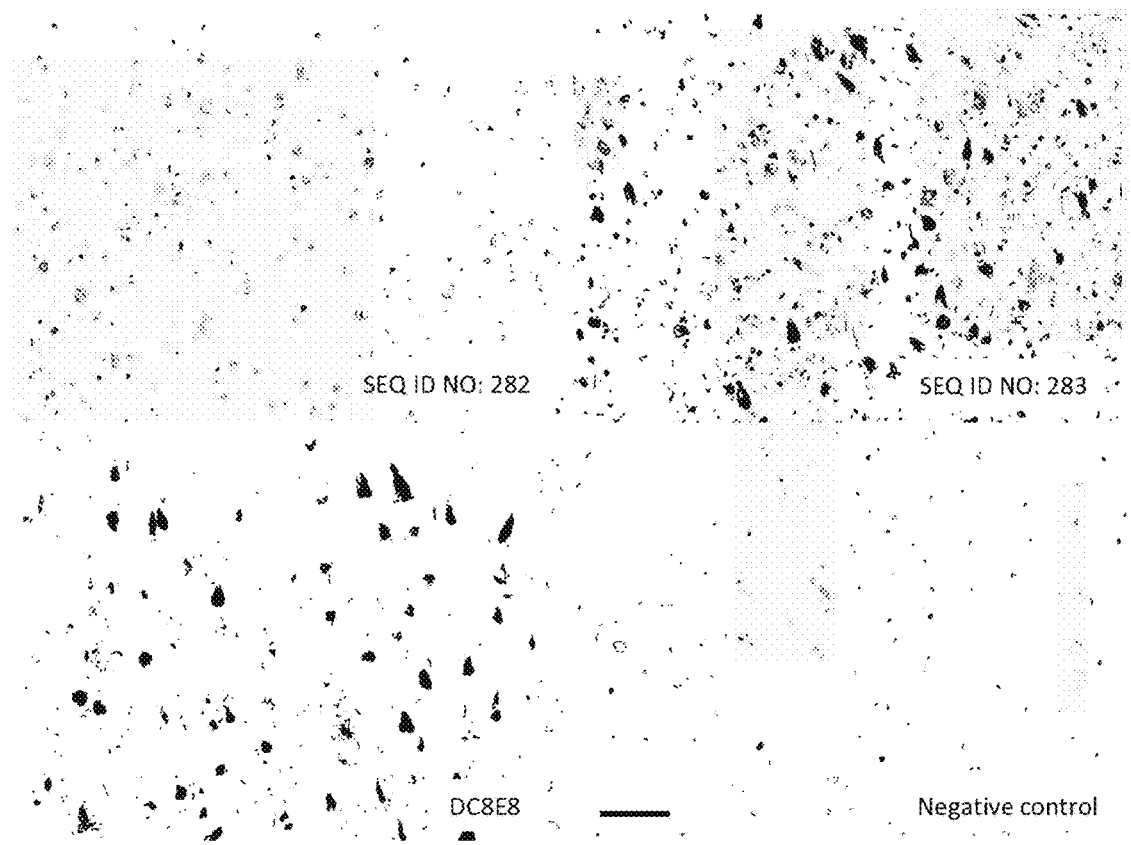

Subsequently, the sections were incubated with a biotinylated secondary antibody (Vectastain Elite ABC Kit, Vector Laboratories) at room temperature for one hour and then reacted with avidin-biotin peroxidase-complex for another one hour (Vectastain Elite ABC Kit, Vector Laboratories), both at 25° C. The immunoreaction was visualized with peroxidase substrate kit (Vector VIP, Vector laboratories, Ca, USA) and counterstained with methyl green (Vector Laboratories). The sections were examined with an Olympus BX71 microscope. Immunohistochemical staining (FIG. 82A-C, FIG. 83) suggests that the antibodies induced by immunization with peptide SEQ ID NOS: 270, 271, 275, 276, 280, 281 and 283 specifically recognized pathological tau structures, i.e. neurofibrillary tangles in hippocampus of Alzheimer's disease brain tissue. Sera of the animals vaccinated with aforementioned peptides decorated the neurofibrillary pathology intensively, confirming that the antibodies targeted pathological tau proteins, Antibodies induced by vaccination with peptides SEQ ID NOS: 272 and 277 show weaker intensity of staining of pathological tau structures in brain tissues. Peptides that induced lower levels of tau specific antibody response or did not induce tau specific antibody response (SEQ ID NOS: 273, 274, 278, 279 and 282) were negative in this analysis. Sera from mice, which received adjuvant alone, were used as negative controls. They did not recognize neurofibrillary pathologies (FIG. 82C).

All references cited herein, including patents, patent applications, papers, text books, and the like, and the references cited therein, to the extent that they are not already, are hereby incorporated herein by reference in their entirety. In addition, the following references, which are cited to in the previous paragraphs in a more abbreviated form, are also incorporated by reference herein in their entirety, including the references cited in such references.

Alfaro-Acha et al. Handgrip Strength and Cognitive Decline in Older Mexican Americans. J Gerontol A Biol Sci Med Sci. (2006); 61(8): 859-865.

Alonso A, Zaidi T, Novak M, Grundke-Iqbal I, Iqbal K. 2001. Hyperphosphorylation induces self-assembly of tau into tangles of paired helical filaments/straight filaments, Proc Natl Acad Sci USA 98: 6923-6928.

Al-Lazikani, B., Lesk, A. M., and Chothia, C. (1997), Standard conformations for the canonical structures of immunoglobulins. Journal of molecular biology 273, 927-948.

Andreasen N, Blennow K, Zetterberg H. 2010. Neuroinflammation Screening in Immunotherapy Trials against Alzheimer's disease. Int J Alzheimers Dis. 2010:638379.

Asuni A A, Boutajangout A, Quartermain D, Sigurdsson E M. Immunotherapy targeting pathological tau conformers in a tangle mouse model reduces brain pathology with associated functional improvements. J Neurosci 27:9115-9129 (2007).

Balin B J, Little C S, Hammond C J, Appelt D M, Whittum-Hudsond J A, Gerard H C, Hudson A R 2008. *Chlamydophila Pneumoniae* and the Etiology of Late-Onset Alzheimer's disease. J Alzheimer's Dis 13:371-380.

Berg, L., et al. Clinicopathologic Studies in Cognitively Healthy Aging and Alzheimer disease. ARCH NEURO/ VOL 55, March 1998.

Bertram L, Tanzi R E. Thirty years of Alzheimer's disease genetics: the implications of systematic meta-analyses. Nat Rev Neurosci 9:768-778 (2008).

Bierer, L. M., et al. Neocortical Neurofibrillary Tangles Correlate With Dementia Severity in Alzheimer's disease. Arch Neuro/Vol. 52, January 1995.

Boyle, P., et al. Association of Muscle Strength With the Risk of Alzheimer disease and the Rate of Cognitive Decline in Community-Dwelling Older Persons. (REPRINTED) ARCH NEURO/VOL 66 (NO. 11), November 2009.

Braak H, Braak E (1999) Temporal sequence of Alzheimer's disease-related pathology. In: Neurodegenerative and age-related changes in structure and function of the cerebral cortex, vol. 14 (Peters, A. and Morrison, J. H., eds), pp 475-512 New York: Kluwer Academic/Plenum Publications.

Braak, H., et al. Neuropathological stageing of Alzheimer-related changes. Acta Neuropathol 82:239-259 (1991).

Braak, H., et al. The pathological process underlying Alzheimer's disease in individuals under thirty. Acta Neuropathol (2011) 121:171-181, Buchman, A., et al., Frailty is Associated With Incident Alzheimer's disease and Cognitive Decline in the Elderly. Psychosomatic Medicine 69:483-489 (2007).

Buchman, A., et al., Grip Strength and the Risk of Incident Alzheimer's disease. Neuroepidemiology; 29:66-73 (2007)

Buee, L., Bussiere, T., Buee-Scherrer, V., Delacourte, A., Hof, P. R. (2000). Tau protein isoforms, phosphorylation and role in neurodegenerative disorders. Brain Research. Brain Research Reviews. 33, 95-130.

Burns, A., Zaudig, M. 2002. Mild cognitive impairment in older people. Lancet. 360(9349), 1963-5, Burns, J. M., et al. The pathology of the substantia nigra in Alzheimer disease with extrapyramidal signs. Neurology 2005; 64; 1397.

Carter J, Lippa C F. Beta-amyloid, neuronal death and Alzheimer's disease. Curr Mol Med 1:733-737 (2001).

Cevc G, Gebauer D, Stieber J, Schatzlein A, Blume G (1998) Ultraflexible vesicles, Transfersomes, have an extremely low pore penetration resistance and transport therapeutic amounts of insulin across the intact mammalian skin, Biochem. Biophys. Acta 1368, 201-15.

Chui, H. C., et al. Extrapyramidal Signs and Psychiatric Symptoms Predict Faster Cognitive Decline in Alzheimer's disease. Arch Neurol/Vol 51, July 1994.

Citron, M, (2010). Alzheimer's disease: strategies for disease modification. Nature Rev Drug Discovery 9, 387-398.

Clavaguera, F., Bolmont, T., Crowther, R. A., Abramowski, D., Probst, A., Fraser, G., Stalder, A. K., Beibel, M., Staufenbiel, M., Jucker, M., Goedert, M., Tolnay, M. (2009). Transmission and spreading of tauopathy in transgenic mouse brain. Nat Cell Biol 11(7), 909-13.

Csokova N, Skrabana R, Liebig H D, Mederlyova A, Kontsek P, Novak M. Rapid purification of truncated tau proteins: model approach to purification of functionally active fragments of disordered proteins, implication for neurodegenerative diseases. Protein Expr Purif 35:366-372 (2004).

Current Protocols in Protein Science 2001 May; Chapter 5

Dickey C A, Ash P, Klosak N, Lee W C, Petrucelli L, Hutton M, Eckman C B (Pharmacologic reductions of total tau levels; implications for the role of microtubule dynamics in regulating tau expression. Mol Neurodegener 1:6.2006).

Dickey C A, Eriksen J, Kamal A, Burrows F, Kasibhatla S, Eckman C B, Hutton M, Petrucelli L (Development of a high throughput drug screening assay for the detection of changes in tau levels—proof of concept with HSP90 inhibitors. Curr Alzheimer Res 2:231-238.2005).

Dickey C A, Petrucelli L. Current strategies for the treatment of Alzheimer's disease and other tauopathies. Expert Opin Ther Targets 10:665-676 (2006).

Dodart J C, Bales K R, Gannon K S, Greene S J, DeMattos R B, Mathis C, DeLong C A, Wu S, Wu X, Holtzman D M, Paul S M (Immunization reverses memory deficits without reducing brain Abeta burden in Alzheimer's disease model. Nat Neurosci 5:452-457 (2002), Duyckaerts, C., et al. Classification and basic pathology of Alzheimer disease. Acta Neuropathol (2009) 118:5-36.

Duyckaerts, C., et al. Diagnosis and Staging of Alzheimer disease. Neurobiology of Aging, Vol. 18, No, S4, pp. 533-542 (1997)

Duyckaerts, C., et al. The progression of the lesions in Alzheimer disease: insights from a prospective clinico-pathological study. J. Neural Transm (1998) [Suppl] 53:119-126, D'Souza, I., and Schellenberg, G. D. (2005). Regulation of tau isoform expression and dementia. Biochimica et biophysica acta 1739, 104-115.

Ferri C P, Prince M, Brayne C, Brodaty H, Fratiglioni L, Ganguli M, Hall K, Hasegawa K, Hendrie H, Huang Y, Jorm A, Mathers C, Menezes P R, Rimmer E, Scazufca M (Global prevalence of dementia: a Delphi consensus study. Lancet 366:2112-2117(2005), Filipcik P, Zilka N, Bugos O, Kucerak J, Koson P, Novak P, Novak M. (2010) First transgenic rat model developing progressive cortical neurofibrillary tangles. Neurobiol Aging. 2010 Dec. 31. [Epub ahead of print]

Fodero-Tavoletti, M. T., et al. F-THK523: a novel in vivo tau imaging ligand for Alzheimer's disease, Brain 134; 1089-1100 (2011)

Frenkel D, Dewachter I, Van Leuven F, Solomon B (Reduction of beta-amyloid plaques in brain of transgenic mouse model of Alzheimer's disease by EFRH-phage immunization, Vaccine 21:1060-1065 (2003).

Frost, B., Diamond, M. I. (2009). The expanding realm of prion phenomena in neurodegenerative disease. Prion 3(2):74-7.

Frost, B., Jacks, R. L., Diamond, M. I. (2009). Propagation of tau misfolding from the outside to the inside of a cell. J Biol Chem 284(19), 12845-52

Furlan R, Brambilla E, Sanvito F, Roccatagliata L, Olivieri S, Bergami A, Pluchino S, Uccelli A, Comi G, Martino G (Vaccination with amyloid-beta peptide induces autoimmune encephalomyelitis in C57/BL6 mice. Brain 126: 285-291 (2003), Gelinas D S, DaSilva K, Fenili D, St George-Hyslop P, McLaurin J (Immunotherapy for Alzheimer's disease. Proc Natl Acad Sci USA 101 Suppl 2:14657-14662 (2004).

Giannakopoulos, P., et al. Pathologic Correlates of Apraxia in Alzheimer disease. ARCH NEURO/VOL 55, May 1998.

Giannakopoulos, P., Herrmann, F. R., Bussiere, T., Bouras, C., Kövari, E., Peri, D. P., Morrison, J. H., Gold, G., Hof, P. R. (2003). Tangle and neuron numbers, but not amyloid load, predict cognitive status in Alzheimer's disease. Neurology 60, 1495-500.

Glenn G M, Rao M, Matyas G R, Alving C R. (1998). Skin immunization made possible by cholera toxin. Nature 391:851.

Goedert, M., Spillantini, M. G., Jakes, R., Rutherford, D., Crowther, R. A. (1989a). Multiple isoforms of human microtubule-associated protein tau: sequences and localization in neurofibrillary tangles of Alzheimer's disease. Neuron. 3, 519-526.

Goedert, M., Spillantini, M. G., Potier, M. C., Ulrich, J., Crowther, R. A. (1989b.) Cloning and sequencing of the cDNA encoding an isoform of microtubule-associated protein tau containing four tandem repeats: differential expression of tau protein mRNAs in human brain. EMBO J. 8, 393-399.

Goldman, W. P., et at, Motor dysfunction in mildly demented AD individuals without extrapyramidal signs. Neurology (1999):53; 956.

Gomez-Isla T, Hollister R, West H, Mui S, Growdon J H, Petersen R C, Parisi J E, Hyman B T. Neuronal loss correlates with but exceeds neurofibrillary tangles in Alzheimer's disease. Ann Neural 41:17-24 (1997).

Gómez-Isla, T., Price, J. L., McKeel Jr, D. W., Morris, J. C., Growdon, J. H., Hyman, B. T, (1996). Profound loss of layer II entorhinal cortex neurons occurs in very mild Alzheimer's disease. J Neurosci 16(14), 4491-500.

Gómez-Ramos, A., Díaz-Hernández, M., Cuadros, R., Hernández, F., and Avila, J. (2006). Extracellular tau is toxic to neuronal cells. FEBS Lett 580(20), 4842-50.

Gómez-Ramos, A., Díaz-Hernández, M., Rubio, A., Díaz-Hernández, J. I., Miras-Portugal, M. T., Avila, J. (2009). Characteristics and consequences of muscarinic receptor activation by tau protein. Eur Neuropsychopharmacol 19(10):708-17, Gómez-Ramos, A., Díaz-Hernández, M., Rubio, A., Miras-Portugal, M. T., Avila, J. (2008). Extracellular tau promotes intracellular calcium increase through M1 and M3 muscarinic receptors in neuronal cells. Mol Cell Neurosci 37(4), 673-81.

Goode, B. L., Chau, M., Denis, P. E., Feinstein, S. C. 2000. Structural and functional differences between 3-repeat and 4-repeat tau isoforms. Implications for normal tau function and the onset of neurodegenerative disease. J Biol Chem 275, 38182-38189.

Goode, B. L., Feinstein, S. C. (1994). Identification of a novel microtubule binding and assembly domain in the developmentally regulated inter-repeat region of tau. J Cell Biol. 124, 769-782.

Greenberg S G, Davies P. A preparation of Alzheimer paired helical filaments that displays distinct tau proteins by polyacrylamide gel electrophoresis. Proc Natl Acad Sci USA 87:5827-5831 (1990).

Greenberg S G, Davies P, Schein J D, Binder L I. (1992). Hydrofluoric acid-treated tau PHF proteins display the same biochemical properties as normal tau. The Journal of Biological Chemistry 267: 564-569.

Gruden M A, Davudova T B, Malisauskas M, Zamotin V V, Sewell R D, Voskresenskaya N I, Kostanyan I A, Sherstnev W, Morozova-Roche L A. Autoimmune responses to amyloid structures of Abeta(25-35) peptide and human lysozyme in the serum of patients with progressive Alzheimer's disease. Dement Geriatr Cogn Disord 18:165-171 (2004).

Grudzien, A., et al. Locus coeruleus neurofibrillary degeneration in aging, mild cognitive impairment and early Alzheimer's disease. Neurobiology of Aging 28 (2007) 327-335.

Grundke-Iqbal I, Iqbal K, Tung Y C, Quinlan M, Wisniewski H M, Binder L I. Abnormal phosphorylation of the microtubule-associated protein tau (tau) in Alzheimer cytoskeletal pathology. Proc Natl Acad Sci USA 83:4913-4917 (1986).

Hampel, H., Blennow, K., Shaw, L. M., Hoessler, Y. C., Zetterberg, H., Trojanowski, J. Q. (2010). Total and phosphorylated tau protein as biological markers of Alzheimer's disease. Exp Gerontol 45(1), 30-40.

Hardy J, Allsop D. Amyloid deposition as the central event in the aetiology of Alzheimer's disease. Trends Pharmacol Sci 12:383-388 (1991).

Hardy J, Duff K, Hardy K G, Perez-Tur J, Hutton M. Genetic dissection of Alzheimer's disease and related dementias: amyloid and its relationship to tau. Nat Neurosci 1:355-358 (1998).

Hardy J, Selkoe D J. The amyloid hypothesis of Alzheimer's disease: progress and problems on the road to therapeutics. Science 297:353-356 (2002).

Haynes J R, McCabe D E, Swain W F, Widera G, Fuller J T. Particle-mediated nucleic acid immunization. J Biotechnol 44:37-42.1996).

Hertz, L. Is Alzheimer's disease an anterograde degeneration, originating in the brainstem, and disrupting metabolic and functional interactions between neurons and glial cells? Brain Research Reviews, 14 (1989) 335-353.

Hunter R L. Overview of vaccine adjuvants: present and future. Vaccine 2002; 20 Suppl. 3:57-12.

Iqbal K, Grundke-Iqbal I. Developing pharmacological therapies for Alzheimer disease. Cell Mol Life Sci 64:2234-2244 (2007).

Iqbal K, Grundke-Iqbal I. Inhibition of neurofibrillary degeneration: a promising approach to Alzheimer's disease and other tauopathies. Curr Drug Targets 5:495-502 (2004).

Ivanovova N, Handzusova M, Hanes J, Kontsekova E, Novak M. High-yield purification of fetal tau preserving its structure and phosphorylation pattern. J Immunol Methods 339:17-22 (2008).

Itzhaki R F; Wozniak M A. 2008. Herpes Simplex Virus Type 1 in Alzheimer's disease: The Enemy Within. J Alzheimers Dis. 13:393-405, Jacobsen J S, Reinhart P, Pangalos M N. Current concepts in therapeutic strategies targeting cognitive decline and disease modification in Alzheimer's disease. NeuroRx 2:612-626 (2005).

Jakes, R., Novak, M., Davison, M., Wischik, C. M. (1991). Identification of 3- and 4-repeat tau isoforms within the PHF in Alzheimer's disease. EMBO J 10, 2725-2729.

Jansen F K, Blythman H E; Carrière D, Casellas P, Gros O; Gros P, Laurent J C, Paolucci F, Pau B, Poncelet P, Richer G, Vidal H, Voisin G A. (1982). Immunotoxins: hybrid molecules combining high specificity and potent cytotoxicity. Immun. Rev. 62; 185-216

Janus C, Pearson J, McLaurin J, Mathews P M, Jiang Y, Schmidt S D, Chishti M A, Horne P, Heslin D, French J, Mount H T, Nixon R A, Mercken M, Bergeron C, Fraser P E; St George-Hyslop P, Westaway D (A beta peptide immunization reduces behavioural impairment and plaques in a model of Alzheimer's disease. Nature 408: 979-982.2000).

Jensen F C, Savary J R, Diveley J P, Chang J C (1998). Adjuvant activity of incomplete Freund's adjuvant, Advanced Drug Delivery Reviews, 32:173-186.

Krebber A, Bornhauser S, Burmester J, Honegger A, Willuda J, Bosshard H R, Pluckthun A. Reliable cloning of functional antibody variable domains from hybridomas and spleen cell repertoires employing a reengineered phage display system. J Immunol Methods. 1997 Feb. 14;201(1): 35-55

Kawasaki G (1991). International Patent Application Publication No. WO91/05058.

Kontsekova, E. (2002) International Patent Application Publication No. WO/2004/007547.

Korenova M, Zilka N, Stozicka Z, Bugos O, Vanicky I, Novak M (NeuroScale, the battery of behavioural tests with novel scoring system for phenotyping of transgenic rat model of tauopathy. J Neurosci Methods 177:108-114.2009).

Kosik, K. S., Kowall, N. W., McKee, A. (1989a). Along the way to a neurofibrillary tangle: a look at the structure of tau, Ann Med. 21, 109-112.

Koson P, Zilka N, Kovac A, Kovacech B, Korenova M, Filipcik P, Novak M. Truncated tau expression levels determine life span of a rat model of tauopathy without causing neuronal loss or correlating with terminal neurofibrillary tangle load. Eur J Neurosci 28:239-246 (2008).

Kovac, A., Zilkova, M., Deli, M. A., Zilka, N., Novak, M. (2009), Human truncated tau is using a different mechanism from amyloid-beta to damage the blood-brain barrier. J Alzheimers Dis 18(4), 897-906.

Kovacech B, Novak M. (2010). Tau truncation is a productive posttranslational modification of neurofibrillary degeneration in Alzheimers disease. Curr Alzheimer Res 7: in press.

Kovacech B, Skrabana R, Novak M. (2010). Transition of tau protein from disordered to misordered in Alzheimers disease. Neurodegener Dis 7: 24-27.

Kraemer, H. C., et al, 'How Far' vs 'How Fast' in Alzheimer's disease, Arch Neurol/Vol 51, March (1994).

Krajciova, G., Skrabana, R.; Filipcik, P., and Novak, M. (2008). Preserving free thiols of intrinsically disordered tau protein without the use of a reducing agent. Anal Biochem 383, 343-345.

Laemmli U K. Cleavage of structural proteins during the assembly of the head of bacteriophage T4. Nature 227: 680-685 (1970).

Langer R, Cleland J L, Hanes J. (1997). New advances in microsphere-based single-dose vaccines. Advanced Drug Delivery Reviews 28, 97-119.

Langer R. New methods of drug delivery, (1990) Science 249:1527-33.

Larbig G, Pickhardt M, Lloyd D G, Schmidt B, Mandelkow E, Screening for inhibitors of tau protein aggregation into Alzheimer paired helical filaments: a ligand based approach results in successful scaffold hopping. Curr Alzheimer Res 4:315-323 (2007), Lee H G, Perry G, Moreira P I, Garrett M R, Liu O, Zhu X, Takeda A, Nunomura A, Smith M A Tau phosphorylation in Alzheimer's disease: pathogen or protector? Trends Mol Med 11:164-169 (2005).

Liu, Y., et al. Pathological Correlates of Extrapyramidal Signs in Alzheimer's disease. Ann Neurol (1997); 4 1:368-374.

Livingston, B. D., Crimi, C., Grey, H., Ishioka, G., Chisari, F. V., Fikes, J., Grey, H., Chesnut, R. W., and Sette, A. The hepatitis B virus-specific CTL responses induced in humans by lipopeptide vaccination are comparable to those elicited by acute viral infection. J. Immunol. 159: 1383-1392 (1997).

Louis, E. D., et al. Parkinsonian Signs in Older People in a Community-Based Study. (REPRINTED) ARCH NEUROL/VOL 61, (August 2004).

MacCallum R M, Martin A C, Thornton J M. Antibody-antigen interactions: contact analysis and binding site topography. J Mol Biol. (1996) Oct. 11; 262(5):732-45.

Macikova I., Dedek L., Kontsekova E., Kontsek P., Ciampor F, Novak M., Vrzal V. (1992) Common and different antigenic properties of the rabies virus glycoprotein between strains SAD-Vnukovo and Pitman-Moore. Acta virol. 36, 541-55, März W, Scharnagl H, Kirça M, Bohl J, Gross W, Ohm T G. 1996. Apolipoprotein E polymorphism is associated with both senile plaque load and Alzheimer-type neurofibrillary tangle formation. Ann N Y Acad Sci. 777:276-80, Matsuo E S, Shin R W, Billingsley M L, Van deVoorde A, O'Connor M, Trojanowski J Q, Lee V M Biopsy-derived adult human brain tau is phosphorylated at many of the same sites as Alzheimer's disease paired helical filament tau. Neuron 13:989-1002 (1994), Miklossy J. 2008. Chronic Inflammation and Amyloidogenesis in Alzheimer's disease—Role of Spirochetes. J Alzheimer's Dis 13:381-391 381

Moe, J. G., Chatterjee, I., Davidowitz, E. J., Arancio, O. (2009). Modulation of synaptic function by extracellular tau enriched in oligomers. Alzheimer Dem 5 (4), P499

Morgan D, Diamond D M, Gottschall P E, Ugen K E, Dickey C, Hardy J, Duff K, Jantzen P, DiCarlo G, Wilcock D, Connor K, Hatcher J, Hope C, Gordon M, Arendash G W. A beta peptide vaccination prevents memory loss in an animal model of Alzheimer's disease. Nature 408:982-985 (2000).

Morgan D. 2011. Immunotherapy for Alzheimer's disease. J Intern Med. 269(1):54-63.

Morris, J. C., et al. Clinical and Pathological Aspects of Parkinsonism in Alzheimer's disease. Arch Neurol-Vol 46 (June 1989).

Mouri A, Noda Y, Hara H, Mizoguchi H, Tabira T, Nabeshima T. Oral vaccination with a viral vector containing Abeta cDNA attenuates age-related Abeta accumulation and memory deficits without causing inflammation in a mouse Alzheimer model. FASEB J 21:2135-2148 (2007).

Myszka, D. G. (1999) Improving biosensor analysis. J. Mol. Recognit. 12, 279-84.

Necula M, Chirita O N, Kuret J Cyanine dye N744 inhibits tau fibrillization by blocking filament extension: implications for the treatment of tauopathic neurodegenerative diseases. Biochemistry 44:10227-10237 (2005).

Nicolau O, Greferath R, Balaban T S, Lazarte J E, Hopkins R J A liposome-based therapeutic vaccine against beta-amyloid plaques on the pancreas of transgenic NORBA mice. Proc Natl Acad Sci USA 99:2332-2337 (2002).

Noble W, Planel E, Zehr O, Olm V, Meyerson J, Suleman F, Gaynor K, Wang L, LaFrancois J, Feinstein B, Burns M, Krishnamurthy P, Wen Y, Bhat R, Lewis J. Dickson D, Duff K (Inhibition of glycogen synthase kinase-3 by lithium correlates with reduced tauopathy and degeneration in vivo. Proc Natl Acad Sci USA 102:6990-6995 (2005).

Novak, M., Kabat, J., Wischik, C. M. (1993). Molecular characterization of the minimal protease resistant tau unit of the Alzheimer's disease paired helical filament, EMBO J 12, 365-70.

Oddo S, Billings L, Kesslak J P, Cribbs D H, LaFerla F M. Abeta immunotherapy leads to clearance of early, but not late, hyperphosphorylated tau aggregates via the proteasome. Neuron 43:321-332 (2004).

Oddo S, Caccamo A, Shepherd J D, Murphy M P, Golde T E, Kayed R, Metherate R, Mattson M P, Akbari Y. LaFerla F M. Triple-transgenic model of Alzheimer's disease with plaques and tangles: intracellular Abeta and synaptic dysfunction. Neuron 39:409-421 (2003).

O'Hagan D T, Valiante N M (Recent advances in the discovery and delivery of vaccine adjuvants. Nat Rev Drug Discov 2:727-735 (2003).

O'Mahony, DJ. (1995) International Patent Application Publication No. WO9717613

Otvos L, Jr., Feiner L, Lang E, Szendrei G I, Goedert M, Lee V M. (1994). Monoclonal antibody PHF-1 recognizes tau protein phosphorylated at serine residues 396 and 404. Journal of neuroscience research 39: 669-673.

Paul A, Cevc G, Bachhawat B K. (1995). Transdermal immunization with large proteins by means of ultradeformable drug carriers. Eur J Immunol. December; 25(12):3521-4.

Pettersson, A. F., et al. Motor Function in Subjects with Mild Cognitive Impairment and Early Alzheimer's disease. Dement Geriatr Cogn Disord (2005); 19:299-304.

Pickhardt M, von Bergen M, Gazova Z, Hascher A, Biernat J, Mandelkow E M, Mandelkow E Screening for inhibitors of tau polymerization. Curr Alzheimer Res 2:219-226 (2005).

Price J L, Morris J C Tangles and plaques in nondemented aging and "preclinical" Alzheimer's disease. Ann Neurol 45:358-368 (1999).

Rapoport M, Dawson H N, Binder L I, Vitek M P, Ferreira A Tau is essential to beta-amyloid-induced neurotoxicity. Proc Natl Acad Sci USA 99:6364-6369 (2002).

Reichert, J. M. (2011). Antibody-based therapeutics to watch in 2011. mAbs 3(1), 76-99.

Reitz, C., et al. Memory performance is related to amyloid and tau pathology in the hippocampus. (March 2009); J. Neurol. Neurosurg. Psychiatry 2009; 80; 715-721; originally published online.

Roberson E D, Scearce-Levie K, Palop J J, Yan F, Cheng I H, Wu T, Gerstein H, Yu G Q, Mucke L Reducing endogenous tau ameliorates amyloid beta-induced deficits in an Alzheimer's disease mouse model. Science 316:750-754 (2007).

Sambrook J, Russell D (2001) Moleclular cloning: A laboratory manual. Cold Spring Harbor, N.Y.: Cold Spring Harbor Laboratory Press.

Santacruz K, Lewis J, Spires T, Paulson J, Kotilinek L, Ingelsson M, Guimaraes A, DeTure M, Ramsden M, McGowan E, Forster C, Yue M, Orne J, Janus C, Mariash A, Kuskowski M, Hyman B, Hutton M, Ashe K H Tau suppression in a neurodegenerative mouse model improves memory function. Science 309:476-481 (2005).

Saurwein-Teissl M, Lung T L, Marx F, Gschösser C, Asch E, Blasko I, Parson W, Böck G, Schönitzer D, Trannoy E, Grubeck-Loebenstein B. 2002. Lack of antibody production following immunization in old age: association with CD8(+)CD28(-) T cell clonal expansions and an imbalance in the production of Th1 and Th2 cytokines. J Immunol. 168(11):5893-9, Scarmeas, N., et al. Motor signs during the course of Alzheimer disease. Neurology. (2004); 63(6): 975-982.

Scarmeas, N., et al. Motor signs predict poor outcomes in Alzheimer disease. Neurology. (2005); 64(10): 1696-1703. doi:10.1212/01.WNL.0000162054.15428.E9.

Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P Immunization with amyloid-beta attenuates Alzheimer-disease-like pathology in the PDAPP mouse, Nature 400: 173-177 (1999).

Schenk D, Hagen M, Seubert P Current progress in beta-amyloid immunotherapy. Curr Opin Immunol 16:599-606 (2004).

Schneider, A., Mandelkow, E., (2008). Tau-based treatment strategies in neurodegenerative diseases. Neurotherapeutics 5(3), 443-57.

Seabrook G R, Ray W J, Shearman M, Hutton M Beyond amyloid: the next generation of Alzheimer's disease therapeutics. Mol Inter 7:261-270 (2007).

Selkoe D J Alzheimer's disease: a central role for amyloid. J Neuropathol Exp Neurol 53:438-447 (1994), Shipton O A, Leitz J R, Dworzak J, Acton C E, Tunbridge E M, Denk F, Dawson H N, Vitek M P, Wade-Martins R, Paulsen O, Vargas-Caballero M (Tau Protein Is Required for Amyloid {beta}-Induced Impairment of Hippocampal Long-Term Potentiation. J Neurosci 31:1688-1692 (2011).

Siegrist C A, Aspinall R. (2009). B-cell responses to vaccination at the extremes of age. Nat Rev Immunol. 9(3): 185-94

Sigurdsson E M, Knudsen E, Asuni A, Fitzer-Attas C, Sage D, Quartermain D, Goni F, Frangione B, Wisniewski T (An attenuated immune response is sufficient to enhance cognition in an Alzheimer's disease mouse model immunized with amyloid-beta derivatives. J Neurosci 24:6277-6282 (2004), Sigurdsson E M, Scholtzova H, Mehta P D, Frangione B, Wisniewski T Immunization with a nontoxic/nonfibrillar amyloid-beta homologous peptide reduces Alzheimer's disease-associated pathology in transgenic mice. Am J Pathol 159:439-447 (2001), Simic, G., et al, Annotation—Does Alzheimer's disease begin in the brainstem? Neuropathol Appl Neurobiol, 2009 December; 35(6): 532-554. doi:10.1111/j.1365-2990.2009.01038.x.

Skrabana, R., Sevcik, I., Novak, M. (2006). Intrinsically disordered proteins in the neurodegenerative processes: formation of tau protein paired helical filaments and their analysis. Cell Mol Neurobiol 26, 1085-1097.

Skrabana; R., M. Skrabanova-Khuebachova; et al. (2006). "Alzheimer's-disease-associated conformation of intrinsically disordered tau protein studied by intrinsically disordered protein liquid-phase competitive enzyme-linked immunosorbent assay." Anal Biochem 359(2): 230-7.

Sloane P D, Zimmerman S. Suchindran C, Reed P, Wang L; Boustani M, Sudha S The public health impact of Alzheimer's disease, 2000-2050: potential implication of treatment advances. Annu Rev Public Health 23:213-231 (2002).

Soininen, H.; et al. Extrapyramidal signs in Alzheimer's disease: a 3-year follow-up study. J Neural Transm [P-D Sect] (1992) 4:107-119.

Steinhilb M L, Dias-Santagata D, Fulga T A, Felch D L, Feany M B (Tau phosphorylation sites work in concert to promote neurotoxicity in vivo. Mol Biol Cell 18:5060-5068 (2007a).

Steinhilb M L, Dias-Santagata D, Mulkearns E E, Shulman J M, Biernat J, Mandelkow E M, Feany M B. S/P and T/P phosphorylation is critical for tau neurotoxicity in *Drosophila*. J Neurosci Res 85:1271-1278 (2007b).

Taniguchi S, Suzuki N, Masuda M, Hisanaga S; Iwatsubo T, Goedert M, Hasegawa M. Inhibition of heparin-induced tau filament formation by phenothiazines, polyphenols, and porphyrins. J Biol Chem 280:7614-7623 (2005a).

Taniguchi T; Sumida M, Hiraoka S, Tomoo K; Kakehi T, Minoura K, Sugiyama S, Inaka K, Ishida T, Saito N, Tanaka C (Effects of different anti-tau antibodies on tau fibrillogenesis: RTA-1 and RTA-2 counteract tau aggregation. FEBS Lett 579:1399-1404 (2005b).

Trollet C, Scherman D, Bigey P Delivery of DNA into muscle for treating systemic diseases: advantages and challenges. Methods Mol Biol 423:199-214 (2008).

van den Berg J H, Nujien B, Beijnen J H, Vincent A, van Tinteren H, Kluge J; Woerdeman L A, Hennink W E; Storm G, Schumacher T N; Haanen J B. Optimization of intradermal vaccination by DNA tattooing in human skin. Hum Gene Ther 20:181-189 (2009).

Van Nest G., Ott G., Barchweld G. (1990) Patent Application Publication No, WO9014837

Vechterova L, Kontsekova E, Zilka N, Ferencik M, Ravid R, Novak M. (2003). DC11: a novel monoclonal antibody revealing Alzheimer's disease-specific tau epitope. Neuroreport 14: 87-91.

Wai, M., et al. Co-localization of hyperphosphorylated tau and caspases in the brainstem of Alzheimer's disease patients. Biogerontology (2009) 10:457-469, Waite, L. M., et al. Gait slowing as a predictor of incident dementia: 6-year longitudinal data from the Sydney Older Persons Study. Journal of the Neurological Sciences 229-230 (2005) 89-93

Walsh D M, Selkoe D J. Deciphering the molecular basis of memory failure in Alzheimer's disease. Neuron 44:181-193 (2004).

Wang, Li, et al. Performance-Based Physical Function and Future Dementia in Older People. (REPRINTED) ARCH INTERN MED/VOL 166 (May 22, 2006).

Weiner H L, Lemere C A, Maron R, Spooner E T, Grenfell T J, Mori C, Issazadeh S, Hancock W W, Selkoe D J (Nasal administration of amyloid-beta peptide decreases cerebral amyloid burden in a mouse model of Alzheimer's disease. Ann Neurol 48:567-579 (2000).

Weng N P, Akbar A N, Goronzy J. 2009. CD28(−) T cells: their role in the age-associated decline of immune function. Trends Immunol. 30(7):306-12.

West, M. J., Coleman, P. D., Flood, D. G., Troncoso, J. C. (1994). Differences in the pattern of hippocampal neuronal loss in normal ageing and Alzheimer's disease. Lancet 344, 769-72.

Wilson, R. S., et al. Parkinsonian-like Signs and Risk of Incident Alzheimer disease in Older Persons. (REPRINTED) ARCH NEUROL/VOL 60 (April 2003).

Wilson Welder J H, Torres M P, Kipper M J, Mallapragada S K, Wannemuehler M J, Narasimhan B. Vaccine adjuvants: current challenges and future approaches. J Pharm Sci 98:1278-1316 (2009).

Wischik C M, Edwards P C, Lai R Y, Roth M, Harrington C R (Selective inhibition of Alzheimer disease-like tau aggregation by phenothiazines. Proc Natl Acad Sci USA 93:11213-11218 (1996).

Wischik, C. M., Novak, M., Edwards, P. C., Klug, A., Tichelaar, W., Crowther, R. A. (1988a). Structural characterization of the core of the paired helical filament of Alzheimer disease, Proc Natl Acad Sci USA 85, 4884-8.

Wischik, C. M., Novak, M., Thøgersen, H. C., Edwards, P. C., Runswick, M. J., Jakes, R., Walker, J. E., Milstein, C., Roth, M., Klug, A. (1988b). Isolation of a fragment of tau derived from the core of the paired helical filament of Alzheimer disease, Proc Natl Acad Sci USA 85, 4506-10.

Xing Z, Santosuosso M, McCormick 5, Yang T C, Millar J, Hitt M, Wan Y, Bramson J, Vordermeier H M. Recent advances in the development of adenovirus- and poxvirus-vectored tuberculosis vaccines. Curr Gene Ther 5:485-492 (2005).

Zarow, C., et al. Neuronal Loss Is Greater in the Locus Coeruleus Than Nucleus Basalis and Substantia Nigra in Alzheimer and Parkinson diseases. (REPRINTED) ARCH NEURO/VOL 60, March 2003.

Zhang B, Maiti A, Shively S, Lakhani F, McDonald-Jones G, Bruce J, Lee E B, Xie S X, Joyce S, Li C, Toleikis P M, Lee V M, Trojanowski J Q. Microtubule-binding drugs offset tau sequestration by stabilizing microtubules and reversing fast axonal transport deficits in a tauopathy model. Proc Natl Acad Sci USA 102:227-231 (2005).

Zhang J, Wu X, Qin C, Qi J, Ma S, Zhang H, Kong Q, Chen D, Ba D, He W (A novel recombinant adeno-associated virus vaccine reduces behavioural impairment and beta-amyloid plaques in a mouse model of Alzheimer's disease. Neurobiol Dis 14:365-379 (2003).

Zielinski C, Scheiner O, Jensen-Jarolim E, Breiteneder H, Pehamberger H. (2003). Patent Application Publication No. WO03/020750

Zilka N, Vechterová L, Kontseková E, Novák M. (2003) A rapid immunohistochemical primary screening assay for hybridomas. J Immunol Methods. 272(1-2):49-53.

Zilka N, Filipcik P, Koson P, Fialova L, Skrabana R, Zilkova M, Rolkova G, Kontsekova E, Novak M. Truncated tau from sporadic Alzheimer's disease suffices to drive neurofibrillary degeneration in viva. FEBS Lett 580:3582-3588 (2006).

Zilka, N., et at Chaperone-like Antibodies Targeting Misfolded Tau Protein: New Vistas in the Immunotherapy of Neurodegenerative Foldopathies. Journal of Alzheimer's disease 15 (2008) 169-179.

Zilkova, M., Koson, P., Zilka, N. 2006. The hunt for dying neurons: insight into the neuronal loss in Alzheimer's disease. Bratisl Lek Listy 107(9-10), 366-73.

---

What is claimed is:

1. An anti-tau antibody comprising:

a) an antibody light chain variable region comprising:

i.    QSLLNSRTRKNY for CDR1; (SEQ ID NO: 117)

ii.    WAS for CDR2; and (SEQ ID NO: 118)

iii.    KQSFYLRT for CDR3; and (SEQ ID NO: 119)

b) an antibody heavy chain variable region comprising:

iv.    GYIFTDYVIS for CDR1 (SEQ ID NO: 120)

v.    IFPRSGST for CDR2; and (SEQ ID NO: 121)

vi.    ARDYYGTSFAMDY for CDR3. (SEQ ID NO: 122)

2. The antibody according to claim 1, wherein the antibody is DC8E8, and wherein DC8E8 is an antibody produced by the hybridoma deposited under American Type Culture Collection Patent Deposit no. PTA-11994.

3. The antibody according to claim 1, wherein the antibody competes with monoclonal antibody DC8E8 for binding to tau.

4. An Fab, Fab', F(ab')$_2$, Fabc, Fv fragment, or any other antigen-binding fragment of the antibody of claim 1.

5. The antibody according to claim 1, wherein the antibody is chosen from:

a) a monoclonal antibody;

b) a polyclonal antibody;

c) a recombinant antibody;

d) a chimeric antibody;

e) a humanized antibody; and f) an antigen-binding fragment or antigen-binding portion of anyone of (a) through (e).

6. The antibody according to claim 1, wherein the antibody is raised in a mammal.

7. The antibody according to claim 1, wherein the antibody is produced by a recombinant animal or by a recombinant host cell.

8. The antibody according to claim 1, further comprising at least one drug attached to the antibody.

9. A cell line expressing the antibody of claim 1.

10. A pharmaceutical composition comprising the antibody according to claim 1 and a pharmaceutically acceptable carrier and/or diluent.

11. A method of treating Alzheimer's disease or another tauopathy in a subject, the method comprising administering to said subject an effective amount of at least one antibody according to claim 1.

12. A method of ameliorating at least one of the symptoms associated with Alzheimer's disease or another tauopathy in a subject, the method comprising administering to said subject an effective amount of at least one antibody according to claim 1.

13. A method of diagnosing or screening a subject for the presence of Alzheimer's disease or another tauopathy in a subject, or for determining a subject's risk for developing Alzheimer's disease or another tauopathy, the method comprising:
   a) contacting the subject, or a cell, tissue, organ, fluid, or any other sample of the subject, with an an effective amount of at least one antibody according to claim 1; and
   b) determining the presence of a complex comprising pathological tau and the antibody, wherein the presence of the complex is diagnostic of Alzheimer's disease or a related tauopathy associated with the presence of pathological tau.

14. A method of monitoring a subject for the presence, progression, regression, or stabilization of Alzheimer's disease or another tauopathy in a subject, or for determining the stage of Alzheimer's disease or another tauopathy in a subject, the method comprising:
   a) contacting the subject, or a cell, tissue, organ, fluid, or any other sample of the subject, with an effective amount of at least one antibody according to claim 1; and
   b) determining the presence and/or distribution of a complex comprising pathological tau and the antibody, wherein the presence and/or distribution of the complex in the sample is used to monitor the subject for the presence, progression, regression, or stabilization of Alzheimer's disease or another tauopathy, or for determining the stage of Alzheimer's disease or another tauopathy associated with the presence of pathological tau.

15. A method of treating Alzheimer's disease or another tauopathy in a subject, the method comprising administering to said subject an effective amount of at least one antibody according to claim 1, in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid passive and active immunization, anti-amyloid aggregation inhibitors, and secretase inhibitors.

16. A pharmaceutical composition comprising a pharmaceutically acceptable carrier and/or diluent and an antibody according to claim 1 in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloid-passive and -active immunization reagents, anti-amyloid aggregation inhibitors, and secretase inhibitors.

17. The antibody according to claim 1, wherein the antibody binds to one or more of the same epitopes on tau as those bound by DC8E8.

18. A method of diagnosing or screening a subject for the presence of Alzheimer's disease or another tauopathy in a subject, or for determining a subject's risk for developing Alzheimer's disease or another tauopathy, the method comprising:
   a) contacting the subject, or a cell, tissue, organ, fluid, or any other sample of the subject, with an effective amount of at least one antibody according to claim 17; and
   b) determining the presence of a complex comprising pathological tau and the antibody, wherein the presence of the complex is diagnostic of Alzheimer's disease or another tauopathy associated with the presence of pathological tau.

19. A method of monitoring a subject for the presence, progression, regression, or stabilization of Alzheimer's disease or another tauopathy in a subject, or for determining the stage of Alzheimer's disease or another tauopathy in a subject, for the method comprising:
   a) contacting the subject, or a cell, tissue, organ, fluid, or any other sample of the subject, with an effective amount of at least one antibody according to claim 17 and
   b) determining the presence and/or distribution of a complex comprising pathological tau and the antibody, wherein the presence and/or distribution of the complex in the sample is used to monitor the subject for the presence, progression, regression, or stabilization of Alzheimer's disease or another tauopathy, or for determining the stage of Alzheimer's disease or another tauopathy associated with the presence of pathological tau.

20. The antibody according to claim 1, wherein the antibody is detectably labeled with one or more labeling agents.

21. The antibody of claim 20, wherein at least one labeling agent is chosen from an enzyme, a radioisotope, a fluorophore, a nuclear magnetic resonance marker, and a heavy metal.

22. A composition comprising at least one antibody according to claim 1 and a diluent or a carrier.

23. The composition of claim 22, further comprising at least one compound or agent selected from a detectable label, keyhole limpet hemocyanin, tetanus toxoid or a toxoid derived from other pathogenic bacteria, serum albumins, bovine serum albumin, an immunoglobulin molecule or fragment thereof, thyroglobulin, ovoglobulin, a universal T-cell epitope, a cytokine, a chemokine, IL-1α, IL-1β, IL-2, IL-10, IFN-γ, GM-CSF, MIP1α, MIP1β, and RANTES.

24. A method of ameliorating at least one of the symptoms associated with Alzheimer's disease or another tauopathy in a subject, the method comprising administering to said subject an effective amount of at least one antibody according to any one of claims 2-3, 1, 4, and 5-8, or a composition according to any one of claims 10, 22, and 23, in combination with at least one combination agent chosen from acetylcholinesterase inhibitors, NMDA receptor antagonists, transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of heat shock proteins, anti-amyloidpassive and -active immunization reagents, anti-amyloid aggregation inhibitors, and secretase inhibitors.

* * * * *

SEQUENCE LISTING

```
<160> NUMBER OF SEQ ID NOS: 283

<210> SEQ ID NO 1
<211> LENGTH: 30
<212> TYPE: PRT
<213> ORGANISM: Homo sapiens

<400> SEQUENCE: 1

Pro Asp Leu Lys Asn Val Lys Ser Lys Ile Gly Ser Thr Glu Asn Leu
1               5                   10                  15

Lys His Gln Pro Gly Gly Gly Lys Val Gln Ile Ile Asn Lys
            20                  25                  30

<210> SEQ ID NO 2
<211> LENGTH: 30
<212> TYPE: PRT
<213> ORGANISM: Homo sapiens

<400> SEQUENCE: 2

Val Lys Ser Lys Ile Gly Ser Thr Glu Asn Leu Lys His Gln Pro Gly
1               5                   10                  15

Gly Gly Lys Val Gln Ile Ile Asn Lys Lys Leu Asp Leu Ser
            20                  25                  30

<210> SEQ ID NO 3
<211> LENGTH: 30
<212> TYPE: PRT
<213> ORGANISM: Homo sapiens

<400> SEQUENCE: 3

Lys Ile Gly Ser Thr Glu Asn Leu Lys His Gln Pro Gly Gly Gly Lys
1               5                   10                  15

Val Gln Ile Ile Asn Lys Lys Leu Asp Leu Ser Asn Val Gln
            20                  25                  30

<210> SEQ ID NO 4
<211> LENGTH: 30
<212> TYPE: PRT
<213> ORGANISM: Homo sapiens

<400> SEQUENCE: 4

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly
            20                  25                  30

<210> SEQ ID NO 5
```

```
<211> LENGTH: 30
<212> TYPE: PRT
<213> ORGANISM: Homo sapiens

<400> SEQUENCE: 5

Gly Ser Pro Gly Thr Pro Gly Ser Arg Ser Arg Thr Pro Ser Leu Pro
1               5                   10                  15

Thr Pro Pro Thr Arg Glu Pro Lys Lys Val Ala Val Val Arg
            20                  25                  30

<210> SEQ ID NO 6
<211> LENGTH: 30
<212> TYPE: PRT
<213> ORGANISM: Homo sapiens

<400> SEQUENCE: 6

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 7
<211> LENGTH: 30
<212> TYPE: PRT
<213> ORGANISM: Homo sapiens

<400> SEQUENCE: 7

Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser
            20                  25                  30

<210> SEQ ID NO 8
<211> LENGTH: 18
<212> TYPE: PRT
<213> ORGANISM: Homo sapiens

<400> SEQUENCE: 8

Val Pro Gly Gly Gly Ser Val Gln Ile Val Tyr Lys Pro Val Asp Leu
1               5                   10                  15

Ser Lys

<210> SEQ ID NO 9
<211> LENGTH: 30
<212> TYPE: PRT
<213> ORGANISM: Homo sapiens

<400> SEQUENCE: 9

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly
            20                  25                  30

<210> SEQ ID NO 10
<211> LENGTH: 30
<212> TYPE: PRT
<213> ORGANISM: Homo sapiens

<400> SEQUENCE: 10

Thr Ala Pro Val Pro Met Pro Asp Leu Lys Asn Val Lys Ser Lys Ile
1               5                   10                  15

Gly Ser Thr Glu Asn Leu Lys His Gln Pro Gly Gly Gly Lys
```

<210> SEQ ID NO 11
<211> LENGTH: 30
<212> TYPE: PRT
<213> ORGANISM: Homo sapiens

<400> SEQUENCE: 11

Ala Pro Val Pro Met Pro Asp Leu Lys Asn Val Lys Ser Lys Ile Gly
1               5                   10                  15

Ser Thr Glu Asn Leu Lys His Gln Pro Gly Gly Gly Lys Val
            20                  25                  30

<210> SEQ ID NO 12
<211> LENGTH: 30
<212> TYPE: PRT
<213> ORGANISM: Homo sapiens

<400> SEQUENCE: 12

Pro Val Pro Met Pro Asp Leu Lys Asn Val Lys Ser Lys Ile Gly Ser
1               5                   10                  15

Thr Glu Asn Leu Lys His Gln Pro Gly Gly Gly Lys Val Gln
            20                  25                  30

<210> SEQ ID NO 13
<211> LENGTH: 30
<212> TYPE: PRT
<213> ORGANISM: Homo sapiens

<400> SEQUENCE: 13

Val Pro Met Pro Asp Leu Lys Asn Val Lys Ser Lys Ile Gly Ser Thr
1               5                   10                  15

Glu Asn Leu Lys His Gln Pro Gly Gly Gly Lys Val Gln Ile
            20                  25                  30

<210> SEQ ID NO 14
<211> LENGTH: 30
<212> TYPE: PRT
<213> ORGANISM: Homo sapiens

<400> SEQUENCE: 14

Pro Met Pro Asp Leu Lys Asn Val Lys Ser Lys Ile Gly Ser Thr Glu
1               5                   10                  15

Asn Leu Lys His Gln Pro Gly Gly Gly Lys Val Gln Ile Ile
            20                  25                  30

<210> SEQ ID NO 15
<211> LENGTH: 30
<212> TYPE: PRT
<213> ORGANISM: Homo sapiens

<400> SEQUENCE: 15

Met Pro Asp Leu Lys Asn Val Lys Ser Lys Ile Gly Ser Thr Glu Asn
1               5                   10                  15

Leu Lys His Gln Pro Gly Gly Gly Lys Val Gln Ile Ile Asn
            20                  25                  30

<210> SEQ ID NO 16
<211> LENGTH: 30
<212> TYPE: PRT
<213> ORGANISM: Homo sapiens

<400> SEQUENCE: 16

-continued

Asp Leu Lys Asn Val Lys Ser Lys Ile Gly Ser Thr Glu Asn Leu Lys
1               5                   10                  15

His Gln Pro Gly Gly Lys Val Gln Ile Ile Asn Lys Lys
            20                  25                  30

<210> SEQ ID NO 17
<211> LENGTH: 30
<212> TYPE: PRT
<213> ORGANISM: Homo sapiens

<400> SEQUENCE: 17

Leu Lys Asn Val Lys Ser Lys Ile Gly Ser Thr Glu Asn Leu Lys His
1               5                   10                  15

Gln Pro Gly Gly Gly Lys Val Gln Ile Ile Asn Lys Lys Leu
            20                  25                  30

<210> SEQ ID NO 18
<211> LENGTH: 30
<212> TYPE: PRT
<213> ORGANISM: Homo sapiens

<400> SEQUENCE: 18

Lys Asn Val Lys Ser Lys Ile Gly Ser Thr Glu Asn Leu Lys His Gln
1               5                   10                  15

Pro Gly Gly Gly Lys Val Gln Ile Ile Asn Lys Lys Leu Asp
            20                  25                  30

<210> SEQ ID NO 19
<211> LENGTH: 30
<212> TYPE: PRT
<213> ORGANISM: Homo sapiens

<400> SEQUENCE: 19

Asn Val Lys Ser Lys Ile Gly Ser Thr Glu Asn Leu Lys His Gln Pro
1               5                   10                  15

Gly Gly Gly Lys Val Gln Ile Ile Asn Lys Lys Leu Asp Leu
            20                  25                  30

<210> SEQ ID NO 20
<211> LENGTH: 30
<212> TYPE: PRT
<213> ORGANISM: Homo sapiens

<400> SEQUENCE: 20

Lys Ser Lys Ile Gly Ser Thr Glu Asn Leu Lys His Gln Pro Gly Gly
1               5                   10                  15

Gly Lys Val Gln Ile Ile Asn Lys Lys Leu Asp Leu Ser Asn
            20                  25                  30

<210> SEQ ID NO 21
<211> LENGTH: 30
<212> TYPE: PRT
<213> ORGANISM: Homo sapiens

<400> SEQUENCE: 21

Ser Lys Ile Gly Ser Thr Glu Asn Leu Lys His Gln Pro Gly Gly Gly
1               5                   10                  15

Lys Val Gln Ile Ile Asn Lys Lys Leu Asp Leu Ser Asn Val
            20                  25                  30

<210> SEQ ID NO 22

```
<211> LENGTH: 30
<212> TYPE: PRT
<213> ORGANISM: Homo sapiens

<400> SEQUENCE: 22

Ile Gly Ser Thr Glu Asn Leu Lys His Gln Pro Gly Gly Gly Lys Val
1               5                   10                  15

Gln Ile Ile Asn Lys Lys Leu Asp Leu Ser Asn Val Gln Ser
            20                  25                  30

<210> SEQ ID NO 23
<211> LENGTH: 30
<212> TYPE: PRT
<213> ORGANISM: Homo sapiens

<400> SEQUENCE: 23

Gly Ser Thr Glu Asn Leu Lys His Gln Pro Gly Gly Gly Lys Val Gln
1               5                   10                  15

Ile Ile Asn Lys Lys Leu Asp Leu Ser Asn Val Gln Ser Lys
            20                  25                  30

<210> SEQ ID NO 24
<211> LENGTH: 30
<212> TYPE: PRT
<213> ORGANISM: Homo sapiens

<400> SEQUENCE: 24

Ser Thr Glu Asn Leu Lys His Gln Pro Gly Gly Gly Lys Val Gln Ile
1               5                   10                  15

Ile Asn Lys Lys Leu Asp Leu Ser Asn Val Gln Ser Lys Cys
            20                  25                  30

<210> SEQ ID NO 25
<211> LENGTH: 30
<212> TYPE: PRT
<213> ORGANISM: Homo sapiens

<400> SEQUENCE: 25

Thr Glu Asn Leu Lys His Gln Pro Gly Gly Gly Lys Val Gln Ile Ile
1               5                   10                  15

Asn Lys Lys Leu Asp Leu Ser Asn Val Gln Ser Lys Cys Gly
            20                  25                  30

<210> SEQ ID NO 26
<211> LENGTH: 30
<212> TYPE: PRT
<213> ORGANISM: Homo sapiens

<400> SEQUENCE: 26

Glu Asn Leu Lys His Gln Pro Gly Gly Gly Lys Val Gln Ile Ile Asn
1               5                   10                  15

Lys Lys Leu Asp Leu Ser Asn Val Gln Ser Lys Cys Gly Ser
            20                  25                  30

<210> SEQ ID NO 27
<211> LENGTH: 30
<212> TYPE: PRT
<213> ORGANISM: Homo sapiens

<400> SEQUENCE: 27

Asn Leu Lys His Gln Pro Gly Gly Gly Lys Val Gln Ile Ile Asn Lys
1               5                   10                  15
```

```
Lys Leu Asp Leu Ser Asn Val Gln Ser Lys Cys Gly Ser Lys
            20                  25                  30

<210> SEQ ID NO 28
<211> LENGTH: 30
<212> TYPE: PRT
<213> ORGANISM: Homo sapiens

<400> SEQUENCE: 28

Leu Lys His Gln Pro Gly Gly Gly Lys Val Gln Ile Ile Asn Lys Lys
 1               5                  10                  15

Leu Asp Leu Ser Asn Val Gln Ser Lys Cys Gly Ser Lys Asp
            20                  25                  30

<210> SEQ ID NO 29
<211> LENGTH: 30
<212> TYPE: PRT
<213> ORGANISM: Homo sapiens

<400> SEQUENCE: 29

Lys His Gln Pro Gly Gly Gly Lys Val Gln Ile Ile Asn Lys Lys Leu
 1               5                  10                  15

Asp Leu Ser Asn Val Gln Ser Lys Cys Gly Ser Lys Asp Asn
            20                  25                  30

<210> SEQ ID NO 30
<211> LENGTH: 30
<212> TYPE: PRT
<213> ORGANISM: Homo sapiens

<400> SEQUENCE: 30

Gln Ile Ile Asn Lys Lys Leu Asp Leu Ser Asn Val Gln Ser Lys Cys
 1               5                  10                  15

Gly Ser Lys Asp Asn Ile Lys His Val Pro Gly Gly Gly Ser
            20                  25                  30

<210> SEQ ID NO 31
<211> LENGTH: 30
<212> TYPE: PRT
<213> ORGANISM: Homo sapiens

<400> SEQUENCE: 31

Ile Ile Asn Lys Lys Leu Asp Leu Ser Asn Val Gln Ser Lys Cys Gly
 1               5                  10                  15

Ser Lys Asp Asn Ile Lys His Val Pro Gly Gly Gly Ser Val
            20                  25                  30

<210> SEQ ID NO 32
<211> LENGTH: 30
<212> TYPE: PRT
<213> ORGANISM: Homo sapiens

<400> SEQUENCE: 32

Ile Asn Lys Lys Leu Asp Leu Ser Asn Val Gln Ser Lys Cys Gly Ser
 1               5                  10                  15

Lys Asp Asn Ile Lys His Val Pro Gly Gly Gly Ser Val Gln
            20                  25                  30

<210> SEQ ID NO 33
<211> LENGTH: 30
<212> TYPE: PRT
<213> ORGANISM: Homo sapiens
```

<400> SEQUENCE: 33

Asn Lys Lys Leu Asp Leu Ser Asn Val Gln Ser Lys Cys Gly Ser Lys
1               5                   10                  15

Asp Asn Ile Lys His Val Pro Gly Gly Gly Ser Val Gln Ile
            20                  25                  30

<210> SEQ ID NO 34
<211> LENGTH: 30
<212> TYPE: PRT
<213> ORGANISM: Homo sapiens

<400> SEQUENCE: 34

Lys Lys Leu Asp Leu Ser Asn Val Gln Ser Lys Cys Gly Ser Lys Asp
1               5                   10                  15

Asn Ile Lys His Val Pro Gly Gly Gly Ser Val Gln Ile Val
            20                  25                  30

<210> SEQ ID NO 35
<211> LENGTH: 30
<212> TYPE: PRT
<213> ORGANISM: Homo sapiens

<400> SEQUENCE: 35

Lys Leu Asp Leu Ser Asn Val Gln Ser Lys Cys Gly Ser Lys Asp Asn
1               5                   10                  15

Ile Lys His Val Pro Gly Gly Gly Ser Val Gln Ile Val Tyr
            20                  25                  30

<210> SEQ ID NO 36
<211> LENGTH: 30
<212> TYPE: PRT
<213> ORGANISM: Homo sapiens

<400> SEQUENCE: 36

Leu Asp Leu Ser Asn Val Gln Ser Lys Cys Gly Ser Lys Asp Asn Ile
1               5                   10                  15

Lys His Val Pro Gly Gly Gly Ser Val Gln Ile Val Tyr Lys
            20                  25                  30

<210> SEQ ID NO 37
<211> LENGTH: 30
<212> TYPE: PRT
<213> ORGANISM: Homo sapiens

<400> SEQUENCE: 37

Asp Leu Ser Asn Val Gln Ser Lys Cys Gly Ser Lys Asp Asn Ile Lys
1               5                   10                  15

His Val Pro Gly Gly Gly Ser Val Gln Ile Val Tyr Lys Pro
            20                  25                  30

<210> SEQ ID NO 38
<211> LENGTH: 30
<212> TYPE: PRT
<213> ORGANISM: Homo sapiens

<400> SEQUENCE: 38

Leu Ser Asn Val Gln Ser Lys Cys Gly Ser Lys Asp Asn Ile Lys His
1               5                   10                  15

Val Pro Gly Gly Gly Ser Val Gln Ile Val Tyr Lys Pro Val
            20                  25                  30

```
<210> SEQ ID NO 39
<211> LENGTH: 30
<212> TYPE: PRT
<213> ORGANISM: Homo sapiens

<400> SEQUENCE: 39

Ser Asn Val Gln Ser Lys Cys Gly Ser Lys Asp Asn Ile Lys His Val
1               5                   10                  15

Pro Gly Gly Gly Ser Val Gln Ile Val Tyr Lys Pro Val Asp
            20                  25                  30

<210> SEQ ID NO 40
<211> LENGTH: 30
<212> TYPE: PRT
<213> ORGANISM: Homo sapiens

<400> SEQUENCE: 40

Asn Val Gln Ser Lys Cys Gly Ser Lys Asp Asn Ile Lys His Val Pro
1               5                   10                  15

Gly Gly Gly Ser Val Gln Ile Val Tyr Lys Pro Val Asp Leu
            20                  25                  30

<210> SEQ ID NO 41
<211> LENGTH: 30
<212> TYPE: PRT
<213> ORGANISM: Homo sapiens

<400> SEQUENCE: 41

Val Gln Ser Lys Cys Gly Ser Lys Asp Asn Ile Lys His Val Pro Gly
1               5                   10                  15

Gly Gly Ser Val Gln Ile Val Tyr Lys Pro Val Asp Leu Ser
            20                  25                  30

<210> SEQ ID NO 42
<211> LENGTH: 30
<212> TYPE: PRT
<213> ORGANISM: Homo sapiens

<400> SEQUENCE: 42

Gln Ser Lys Cys Gly Ser Lys Asp Asn Ile Lys His Val Pro Gly Gly
1               5                   10                  15

Gly Ser Val Gln Ile Val Tyr Lys Pro Val Asp Leu Ser Lys
            20                  25                  30

<210> SEQ ID NO 43
<211> LENGTH: 30
<212> TYPE: PRT
<213> ORGANISM: Homo sapiens

<400> SEQUENCE: 43

Ser Lys Cys Gly Ser Lys Asp Asn Ile Lys His Val Pro Gly Gly Gly
1               5                   10                  15

Ser Val Gln Ile Val Tyr Lys Pro Val Asp Leu Ser Lys Val
            20                  25                  30

<210> SEQ ID NO 44
<211> LENGTH: 30
<212> TYPE: PRT
<213> ORGANISM: Homo sapiens

<400> SEQUENCE: 44

Lys Cys Gly Ser Lys Asp Asn Ile Lys His Val Pro Gly Gly Gly Ser
1               5                   10                  15
```

Val Gln Ile Val Tyr Lys Pro Val Asp Leu Ser Lys Val Thr
            20                  25                  30

<210> SEQ ID NO 45
<211> LENGTH: 30
<212> TYPE: PRT
<213> ORGANISM: Homo sapiens

<400> SEQUENCE: 45

Gly Ser Lys Asp Asn Ile Lys His Val Pro Gly Gly Gly Ser Val Gln
1               5                   10                  15

Ile Val Tyr Lys Pro Val Asp Leu Ser Lys Val Thr Ser Lys
            20                  25                  30

<210> SEQ ID NO 46
<211> LENGTH: 30
<212> TYPE: PRT
<213> ORGANISM: Homo sapiens

<400> SEQUENCE: 46

Ser Lys Asp Asn Ile Lys His Val Pro Gly Gly Gly Ser Val Gln Ile
1               5                   10                  15

Val Tyr Lys Pro Val Asp Leu Ser Lys Val Thr Ser Lys Cys
            20                  25                  30

<210> SEQ ID NO 47
<211> LENGTH: 30
<212> TYPE: PRT
<213> ORGANISM: Homo sapiens

<400> SEQUENCE: 47

Lys Asp Asn Ile Lys His Val Pro Gly Gly Gly Ser Val Gln Ile Val
1               5                   10                  15

Tyr Lys Pro Val Asp Leu Ser Lys Val Thr Ser Lys Cys Gly
            20                  25                  30

<210> SEQ ID NO 48
<211> LENGTH: 30
<212> TYPE: PRT
<213> ORGANISM: Homo sapiens

<400> SEQUENCE: 48

Asp Asn Ile Lys His Val Pro Gly Gly Gly Ser Val Gln Ile Val Tyr
1               5                   10                  15

Lys Pro Val Asp Leu Ser Lys Val Thr Ser Lys Cys Gly Ser
            20                  25                  30

<210> SEQ ID NO 49
<211> LENGTH: 30
<212> TYPE: PRT
<213> ORGANISM: Homo sapiens

<400> SEQUENCE: 49

Asn Ile Lys His Val Pro Gly Gly Gly Ser Val Gln Ile Val Tyr Lys
1               5                   10                  15

Pro Val Asp Leu Ser Lys Val Thr Ser Lys Cys Gly Ser Leu
            20                  25                  30

<210> SEQ ID NO 50
<211> LENGTH: 30
<212> TYPE: PRT
<213> ORGANISM: Homo sapiens

<400> SEQUENCE: 50

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly
            20                  25                  30

<210> SEQ ID NO 51
<211> LENGTH: 30
<212> TYPE: PRT
<213> ORGANISM: Homo sapiens

<400> SEQUENCE: 51

Lys His Val Pro Gly Gly Gly Ser Val Gln Ile Val Tyr Lys Pro Val
1               5                   10                  15

Asp Leu Ser Lys Val Thr Ser Lys Cys Gly Ser Leu Gly Asn
            20                  25                  30

<210> SEQ ID NO 52
<211> LENGTH: 30
<212> TYPE: PRT
<213> ORGANISM: Homo sapiens

<400> SEQUENCE: 52

Gln Ile Val Tyr Lys Pro Val Asp Leu Ser Lys Val Thr Ser Lys Cys
1               5                   10                  15

Gly Ser Leu Gly Asn Ile His His Lys Pro Gly Gly Gly Gln
            20                  25                  30

<210> SEQ ID NO 53
<211> LENGTH: 30
<212> TYPE: PRT
<213> ORGANISM: Homo sapiens

<400> SEQUENCE: 53

Ile Val Tyr Lys Pro Val Asp Leu Ser Lys Val Thr Ser Lys Cys Gly
1               5                   10                  15

Ser Leu Gly Asn Ile His His Lys Pro Gly Gly Gly Gln Val
            20                  25                  30

<210> SEQ ID NO 54
<211> LENGTH: 30
<212> TYPE: PRT
<213> ORGANISM: Homo sapiens

<400> SEQUENCE: 54

Val Tyr Lys Pro Val Asp Leu Ser Lys Val Thr Ser Lys Cys Gly Ser
1               5                   10                  15

Leu Gly Asn Ile His His Lys Pro Gly Gly Gly Gln Val Glu
            20                  25                  30

<210> SEQ ID NO 55
<211> LENGTH: 30
<212> TYPE: PRT
<213> ORGANISM: Homo sapiens

<400> SEQUENCE: 55

Tyr Lys Pro Val Asp Leu Ser Lys Val Thr Ser Lys Cys Gly Ser Leu
1               5                   10                  15

Gly Asn Ile His His Lys Pro Gly Gly Gly Gln Val Glu Val
            20                  25                  30

```
<210> SEQ ID NO 56
<211> LENGTH: 30
<212> TYPE: PRT
<213> ORGANISM: Homo sapiens

<400> SEQUENCE: 56

Lys Pro Val Asp Leu Ser Lys Val Thr Ser Lys Cys Gly Ser Leu Gly
1               5                   10                  15

Asn Ile His His Lys Pro Gly Gly Gly Gln Val Glu Val Lys
            20                  25                  30

<210> SEQ ID NO 57
<211> LENGTH: 30
<212> TYPE: PRT
<213> ORGANISM: Homo sapiens

<400> SEQUENCE: 57

Pro Val Asp Leu Ser Lys Val Thr Ser Lys Cys Gly Ser Leu Gly Asn
1               5                   10                  15

Ile His His Lys Pro Gly Gly Gly Gln Val Glu Val Lys Ser
            20                  25                  30

<210> SEQ ID NO 58
<211> LENGTH: 30
<212> TYPE: PRT
<213> ORGANISM: Homo sapiens

<400> SEQUENCE: 58

Val Asp Leu Ser Lys Val Thr Ser Lys Cys Gly Ser Leu Gly Asn Ile
1               5                   10                  15

His His Lys Pro Gly Gly Gly Gln Val Glu Val Lys Ser Glu
            20                  25                  30

<210> SEQ ID NO 59
<211> LENGTH: 30
<212> TYPE: PRT
<213> ORGANISM: Homo sapiens

<400> SEQUENCE: 59

Asp Leu Ser Lys Val Thr Ser Lys Cys Gly Ser Leu Gly Asn Ile His
1               5                   10                  15

His Lys Pro Gly Gly Gly Gln Val Glu Val Lys Ser Glu Lys
            20                  25                  30

<210> SEQ ID NO 60
<211> LENGTH: 30
<212> TYPE: PRT
<213> ORGANISM: Homo sapiens

<400> SEQUENCE: 60

Leu Ser Lys Val Thr Ser Lys Cys Gly Ser Leu Gly Asn Ile His His
1               5                   10                  15

Lys Pro Gly Gly Gly Gln Val Glu Val Lys Ser Glu Lys Leu
            20                  25                  30

<210> SEQ ID NO 61
<211> LENGTH: 30
<212> TYPE: PRT
<213> ORGANISM: Homo sapiens

<400> SEQUENCE: 61

Ser Lys Val Thr Ser Lys Cys Gly Ser Leu Gly Asn Ile His His Lys
```

```
                1               5                  10                 15
Pro Gly Gly Gly Gln Val Glu Val Lys Ser Glu Lys Leu Asp
                20                 25                 30

<210> SEQ ID NO 62
<211> LENGTH: 30
<212> TYPE: PRT
<213> ORGANISM: Homo sapiens

<400> SEQUENCE: 62

Lys Val Thr Ser Lys Cys Gly Ser Leu Gly Asn Ile His His Lys Pro
1               5                   10                  15
Gly Gly Gly Gln Val Glu Val Lys Ser Glu Lys Leu Asp Phe
                20                  25                  30

<210> SEQ ID NO 63
<211> LENGTH: 30
<212> TYPE: PRT
<213> ORGANISM: Homo sapiens

<400> SEQUENCE: 63

Val Thr Ser Lys Cys Gly Ser Leu Gly Asn Ile His His Lys Pro Gly
1               5                   10                  15
Gly Gly Gln Val Glu Val Lys Ser Glu Lys Leu Asp Phe Lys
                20                  25                  30

<210> SEQ ID NO 64
<211> LENGTH: 30
<212> TYPE: PRT
<213> ORGANISM: Homo sapiens

<400> SEQUENCE: 64

Thr Ser Lys Cys Gly Ser Leu Gly Asn Ile His His Lys Pro Gly Gly
1               5                   10                  15
Gly Gln Val Glu Val Lys Ser Glu Lys Leu Asp Phe Lys Asp
                20                  25                  30

<210> SEQ ID NO 65
<211> LENGTH: 30
<212> TYPE: PRT
<213> ORGANISM: Homo sapiens

<400> SEQUENCE: 65

Ser Lys Cys Gly Ser Leu Gly Asn Ile His His Lys Pro Gly Gly Gly
1               5                   10                  15
Gln Val Glu Val Lys Ser Glu Lys Leu Asp Phe Lys Asp Arg
                20                  25                  30

<210> SEQ ID NO 66
<211> LENGTH: 30
<212> TYPE: PRT
<213> ORGANISM: Homo sapiens

<400> SEQUENCE: 66

Lys Cys Gly Ser Leu Gly Asn Ile His His Lys Pro Gly Gly Gly Gln
1               5                   10                  15
Val Glu Val Lys Ser Glu Lys Leu Asp Phe Lys Asp Arg Val
                20                  25                  30

<210> SEQ ID NO 67
<211> LENGTH: 30
<212> TYPE: PRT
```

```
<213> ORGANISM: Homo sapiens

<400> SEQUENCE: 67

Cys Gly Ser Leu Gly Asn Ile His His Lys Pro Gly Gly Gly Gln Val
1               5                   10                  15

Glu Val Lys Ser Glu Lys Leu Asp Phe Lys Asp Arg Val Gln
            20                  25                  30

<210> SEQ ID NO 68
<211> LENGTH: 30
<212> TYPE: PRT
<213> ORGANISM: Homo sapiens

<400> SEQUENCE: 68

Gly Ser Leu Gly Asn Ile His His Lys Pro Gly Gly Gly Gln Val Glu
1               5                   10                  15

Val Lys Ser Glu Lys Leu Asp Phe Lys Asp Arg Val Gln Ser
            20                  25                  30

<210> SEQ ID NO 69
<211> LENGTH: 30
<212> TYPE: PRT
<213> ORGANISM: Homo sapiens

<400> SEQUENCE: 69

Ser Leu Gly Asn Ile His His Lys Pro Gly Gly Gly Gln Val Glu Val
1               5                   10                  15

Lys Ser Glu Lys Leu Asp Phe Lys Asp Arg Val Gln Ser Lys
            20                  25                  30

<210> SEQ ID NO 70
<211> LENGTH: 30
<212> TYPE: PRT
<213> ORGANISM: Homo sapiens

<400> SEQUENCE: 70

Leu Gly Asn Ile His His Lys Pro Gly Gly Gly Gln Val Glu Val Lys
1               5                   10                  15

Ser Glu Lys Leu Asp Phe Lys Asp Arg Val Gln Ser Lys Ile
            20                  25                  30

<210> SEQ ID NO 71
<211> LENGTH: 30
<212> TYPE: PRT
<213> ORGANISM: Homo sapiens

<400> SEQUENCE: 71

Gly Asn Ile His His Lys Pro Gly Gly Gly Gln Val Glu Val Lys Ser
1               5                   10                  15

Glu Lys Leu Asp Phe Lys Asp Arg Val Gln Ser Lys Ile Gly
            20                  25                  30

<210> SEQ ID NO 72
<211> LENGTH: 30
<212> TYPE: PRT
<213> ORGANISM: Homo sapiens

<400> SEQUENCE: 72

Asn Ile His His Lys Pro Gly Gly Gly Gln Val Glu Val Lys Ser Glu
1               5                   10                  15

Lys Leu Asp Phe Lys Asp Arg Val Gln Ser Lys Ile Gly Ser
            20                  25                  30
```

```
<210> SEQ ID NO 73
<211> LENGTH: 30
<212> TYPE: PRT
<213> ORGANISM: Homo sapiens

<400> SEQUENCE: 73

Ile His His Lys Pro Gly Gly Gln Val Glu Val Lys Ser Glu Lys
1               5                   10                  15

Leu Asp Phe Lys Asp Arg Val Gln Ser Lys Ile Gly Ser Leu
            20                  25                  30

<210> SEQ ID NO 74
<211> LENGTH: 30
<212> TYPE: PRT
<213> ORGANISM: Homo sapiens

<400> SEQUENCE: 74

His His Lys Pro Gly Gly Gly Gln Val Glu Val Lys Ser Glu Lys Leu
1               5                   10                  15

Asp Phe Lys Asp Arg Val Gln Ser Lys Ile Gly Ser Leu Asp
            20                  25                  30

<210> SEQ ID NO 75
<211> LENGTH: 30
<212> TYPE: PRT
<213> ORGANISM: Homo sapiens

<400> SEQUENCE: 75

Val Lys Ser Glu Lys Leu Asp Phe Lys Asp Arg Val Gln Ser Lys Ile
1               5                   10                  15

Gly Ser Leu Asp Asn Ile Thr His Val Pro Gly Gly Gly Asn
            20                  25                  30

<210> SEQ ID NO 76
<211> LENGTH: 30
<212> TYPE: PRT
<213> ORGANISM: Homo sapiens

<400> SEQUENCE: 76

Lys Ser Glu Lys Leu Asp Phe Lys Asp Arg Val Gln Ser Lys Ile Gly
1               5                   10                  15

Ser Leu Asp Asn Ile Thr His Val Pro Gly Gly Gly Asn Lys
            20                  25                  30

<210> SEQ ID NO 77
<211> LENGTH: 30
<212> TYPE: PRT
<213> ORGANISM: Homo sapiens

<400> SEQUENCE: 77

Ser Glu Lys Leu Asp Phe Lys Asp Arg Val Gln Ser Lys Ile Gly Ser
1               5                   10                  15

Leu Asp Asn Ile Thr His Val Pro Gly Gly Gly Asn Lys Lys
            20                  25                  30

<210> SEQ ID NO 78
<211> LENGTH: 30
<212> TYPE: PRT
<213> ORGANISM: Homo sapiens

<400> SEQUENCE: 78
```

Glu Lys Leu Asp Phe Lys Asp Arg Val Gln Ser Lys Ile Gly Ser Leu
1               5                   10                  15

Asp Asn Ile Thr His Val Pro Gly Gly Gly Asn Lys Lys Ile
            20                  25                  30

<210> SEQ ID NO 79
<211> LENGTH: 30
<212> TYPE: PRT
<213> ORGANISM: Homo sapiens

<400> SEQUENCE: 79

Lys Leu Asp Phe Lys Asp Arg Val Gln Ser Lys Ile Gly Ser Leu Asp
1               5                   10                  15

Asn Ile Thr His Val Pro Gly Gly Gly Asn Lys Lys Ile Glu
            20                  25                  30

<210> SEQ ID NO 80
<211> LENGTH: 30
<212> TYPE: PRT
<213> ORGANISM: Homo sapiens

<400> SEQUENCE: 80

Leu Asp Phe Lys Asp Arg Val Gln Ser Lys Ile Gly Ser Leu Asp Asn
1               5                   10                  15

Ile Thr His Val Pro Gly Gly Gly Asn Lys Lys Ile Glu Thr
            20                  25                  30

<210> SEQ ID NO 81
<211> LENGTH: 30
<212> TYPE: PRT
<213> ORGANISM: Homo sapiens

<400> SEQUENCE: 81

Asp Phe Lys Asp Arg Val Gln Ser Lys Ile Gly Ser Leu Asp Asn Ile
1               5                   10                  15

Thr His Val Pro Gly Gly Gly Asn Lys Lys Ile Glu Thr His
            20                  25                  30

<210> SEQ ID NO 82
<211> LENGTH: 30
<212> TYPE: PRT
<213> ORGANISM: Homo sapiens

<400> SEQUENCE: 82

Phe Lys Asp Arg Val Gln Ser Lys Ile Gly Ser Leu Asp Asn Ile Thr
1               5                   10                  15

His Val Pro Gly Gly Gly Asn Lys Lys Ile Glu Thr His Lys
            20                  25                  30

<210> SEQ ID NO 83
<211> LENGTH: 30
<212> TYPE: PRT
<213> ORGANISM: Homo sapiens

<400> SEQUENCE: 83

Lys Asp Arg Val Gln Ser Lys Ile Gly Ser Leu Asp Asn Ile Thr His
1               5                   10                  15

Val Pro Gly Gly Gly Asn Lys Lys Ile Glu Thr His Lys Leu
            20                  25                  30

<210> SEQ ID NO 84
<211> LENGTH: 30

```
<212> TYPE: PRT
<213> ORGANISM: Homo sapiens

<400> SEQUENCE: 84

Asp Arg Val Gln Ser Lys Ile Gly Ser Leu Asp Asn Ile Thr His Val
1               5                   10                  15

Pro Gly Gly Gly Asn Lys Lys Ile Glu Thr His Lys Leu Thr
            20                  25                  30

<210> SEQ ID NO 85
<211> LENGTH: 30
<212> TYPE: PRT
<213> ORGANISM: Homo sapiens

<400> SEQUENCE: 85

Arg Val Gln Ser Lys Ile Gly Ser Leu Asp Asn Ile Thr His Val Pro
1               5                   10                  15

Gly Gly Gly Asn Lys Lys Ile Glu Thr His Lys Leu Thr Phe
            20                  25                  30

<210> SEQ ID NO 86
<211> LENGTH: 30
<212> TYPE: PRT
<213> ORGANISM: Homo sapiens

<400> SEQUENCE: 86

Val Gln Ser Lys Ile Gly Ser Leu Asp Asn Ile Thr His Val Pro Gly
1               5                   10                  15

Gly Gly Asn Lys Lys Ile Glu Thr His Lys Leu Thr Phe Arg
            20                  25                  30

<210> SEQ ID NO 87
<211> LENGTH: 30
<212> TYPE: PRT
<213> ORGANISM: Homo sapiens

<400> SEQUENCE: 87

Gln Ser Lys Ile Gly Ser Leu Asp Asn Ile Thr His Val Pro Gly Gly
1               5                   10                  15

Gly Asn Lys Lys Ile Glu Thr His Lys Leu Thr Phe Arg Glu
            20                  25                  30

<210> SEQ ID NO 88
<211> LENGTH: 31
<212> TYPE: PRT
<213> ORGANISM: Homo sapiens

<400> SEQUENCE: 88

Cys Ser Lys Ile Gly Ser Leu Asp Asn Ile Thr His Val Pro Gly Gly
1               5                   10                  15

Gly Asn Lys Lys Ile Glu Thr His Lys Leu Thr Phe Arg Glu Asn
            20                  25                  30

<210> SEQ ID NO 89
<211> LENGTH: 30
<212> TYPE: PRT
<213> ORGANISM: Homo sapiens

<400> SEQUENCE: 89

Lys Ile Gly Ser Leu Asp Asn Ile Thr His Val Pro Gly Gly Gly Asn
1               5                   10                  15

Lys Lys Ile Glu Thr His Lys Leu Thr Phe Arg Glu Asn Ala
```

<210> SEQ ID NO 90
<211> LENGTH: 30
<212> TYPE: PRT
<213> ORGANISM: Homo sapiens

<400> SEQUENCE: 90

Ile Gly Ser Leu Asp Asn Ile Thr His Val Pro Gly Gly Gly Asn Lys
1               5                   10                  15

Lys Ile Glu Thr His Lys Leu Thr Phe Arg Glu Asn Ala Lys
            20                  25                  30

<210> SEQ ID NO 91
<211> LENGTH: 30
<212> TYPE: PRT
<213> ORGANISM: Homo sapiens

<400> SEQUENCE: 91

Gly Ser Leu Asp Asn Ile Thr His Val Pro Gly Gly Gly Asn Lys Lys
1               5                   10                  15

Ile Glu Thr His Lys Leu Thr Phe Arg Glu Asn Ala Lys Ala
            20                  25                  30

<210> SEQ ID NO 92
<211> LENGTH: 30
<212> TYPE: PRT
<213> ORGANISM: Homo sapiens

<400> SEQUENCE: 92

Ser Leu Asp Asn Ile Thr His Val Pro Gly Gly Gly Asn Lys Lys Ile
1               5                   10                  15

Glu Thr His Lys Leu Thr Phe Arg Glu Asn Ala Lys Ala Lys
            20                  25                  30

<210> SEQ ID NO 93
<211> LENGTH: 30
<212> TYPE: PRT
<213> ORGANISM: Homo sapiens

<400> SEQUENCE: 93

Leu Asp Asn Ile Thr His Val Pro Gly Gly Gly Asn Lys Lys Ile Glu
1               5                   10                  15

Thr His Lys Leu Thr Phe Arg Glu Asn Ala Lys Ala Lys Thr
            20                  25                  30

<210> SEQ ID NO 94
<211> LENGTH: 30
<212> TYPE: PRT
<213> ORGANISM: Homo sapiens

<400> SEQUENCE: 94

Asp Asn Ile Thr His Val Pro Gly Gly Gly Asn Lys Lys Ile Glu Thr
1               5                   10                  15

His Lys Leu Thr Phe Arg Glu Asn Ala Lys Ala Lys Thr Asp
            20                  25                  30

<210> SEQ ID NO 95
<211> LENGTH: 30
<212> TYPE: PRT
<213> ORGANISM: Homo sapiens

<400> SEQUENCE: 95

Asn Ile Thr His Val Pro Gly Gly Asn Lys Lys Ile Glu Thr His
1               5                   10                  15

Lys Leu Thr Phe Arg Glu Asn Ala Lys Ala Lys Thr Asp His
            20                  25                  30

<210> SEQ ID NO 96
<211> LENGTH: 30
<212> TYPE: PRT
<213> ORGANISM: Homo sapiens

<400> SEQUENCE: 96

Ile Thr His Val Pro Gly Gly Gly Asn Lys Lys Ile Glu Thr His Lys
1               5                   10                  15

Leu Thr Phe Arg Glu Asn Ala Lys Ala Lys Thr Asp His Gly
            20                  25                  30

<210> SEQ ID NO 97
<211> LENGTH: 30
<212> TYPE: PRT
<213> ORGANISM: Homo sapiens

<400> SEQUENCE: 97

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala
            20                  25                  30

<210> SEQ ID NO 98
<211> LENGTH: 7
<212> TYPE: PRT
<213> ORGANISM: Homo sapiens

<400> SEQUENCE: 98

Lys His Gln Pro Gly Gly Gly
1               5

<210> SEQ ID NO 99
<211> LENGTH: 7
<212> TYPE: PRT
<213> ORGANISM: Homo sapiens

<400> SEQUENCE: 99

Lys His Val Pro Gly Gly Gly
1               5

<210> SEQ ID NO 100
<211> LENGTH: 7
<212> TYPE: PRT
<213> ORGANISM: Homo sapiens

<400> SEQUENCE: 100

His His Lys Pro Gly Gly Gly
1               5

<210> SEQ ID NO 101
<211> LENGTH: 7
<212> TYPE: PRT
<213> ORGANISM: Homo sapiens

<400> SEQUENCE: 101

Thr His Val Pro Gly Gly Gly
1               5

<210> SEQ ID NO 102
<211> LENGTH: 441
<212> TYPE: PRT
<213> ORGANISM: Homo sapiens

<400> SEQUENCE: 102

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380
```

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
        435                 440

<210> SEQ ID NO 103
<211> LENGTH: 412
<212> TYPE: PRT
<213> ORGANISM: Homo sapiens

<400> SEQUENCE: 103

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
            85                  90                  95

Arg Met Val Ser Lys Ser Lys Asp Gly Thr Gly Ser Asp Asp Lys Lys
        100                 105                 110

Ala Lys Gly Ala Asp Gly Lys Thr Lys Ile Ala Thr Pro Arg Gly Ala
    115                 120                 125

Ala Pro Pro Gly Gln Lys Gly Gln Ala Asn Ala Thr Arg Ile Pro Ala
130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
            165                 170                 175

Pro Gly Ser Arg Ser Arg Thr Pro Ser Leu Pro Thr Pro Pro Thr Arg
        180                 185                 190

Glu Pro Lys Lys Val Ala Val Val Arg Thr Pro Pro Lys Ser Pro Ser
    195                 200                 205

Ser Ala Lys Ser Arg Leu Gln Thr Ala Pro Val Pro Met Pro Asp Leu
210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
            245                 250                 255

Asn Val Gln Ser Lys Cys Gly Ser Lys Asp Asn Ile Lys His Val Pro
        260                 265                 270

Gly Gly Gly Ser Val Gln Ile Val Tyr Lys Pro Val Asp Leu Ser Lys
    275                 280                 285

Val Thr Ser Lys Cys Gly Ser Leu Gly Asn Ile His His Lys Pro Gly
290                 295                 300

Gly Gly Gln Val Glu Val Lys Ser Glu Lys Leu Asp Phe Lys Asp Arg

```
                305                 310                 315                 320
        Val Gln Ser Lys Ile Gly Ser Leu Asp Asn Ile Thr His Val Pro Gly
                        325                 330                 335

Gly Gly Asn Lys Lys Ile Glu Thr His Lys Leu Thr Phe Arg Glu Asn
                        340                 345                 350

Ala Lys Ala Lys Thr Asp His Gly Ala Glu Ile Val Tyr Lys Ser Pro
                        355                 360                 365

Val Val Ser Gly Asp Thr Ser Pro Arg His Leu Ser Asn Val Ser Ser
                        370                 375                 380

Thr Gly Ser Ile Asp Met Val Asp Ser Pro Gln Leu Ala Thr Leu Ala
        385                 390                 395                 400

Asp Glu Val Ser Ala Ser Leu Ala Lys Gln Gly Leu
                        405                 410

<210> SEQ ID NO 104
<211> LENGTH: 410
<212> TYPE: PRT
<213> ORGANISM: Homo sapiens

<400> SEQUENCE: 104

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

-continued

```
Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
        290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
        340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 105
<211> LENGTH: 383
<212> TYPE: PRT
<213> ORGANISM: Homo sapiens

<400> SEQUENCE: 105

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240
```

-continued

```
His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
                260                 265                 270

Lys Pro Gly Gly Gly Gln Val Glu Val Lys Ser Glu Lys Leu Asp Phe
                275                 280                 285

Lys Asp Arg Val Gln Ser Lys Ile Gly Ser Leu Asp Asn Ile Thr His
                290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
                355                 360                 365

Thr Leu Ala Asp Glu Val Ser Ala Ser Leu Ala Lys Gln Gly Leu
                370                 375                 380

<210> SEQ ID NO 106
<211> LENGTH: 381
<212> TYPE: PRT
<213> ORGANISM: Homo sapiens

<400> SEQUENCE: 106

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
        130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
                180                 185                 190

Glu Pro Lys Lys Val Ala Val Val Arg Thr Pro Pro Lys Ser Pro Ser
            195                 200                 205

Ser Ala Lys Ser Arg Leu Gln Thr Ala Pro Val Pro Met Pro Asp Leu
        210                 215                 220

Lys Asn Val Lys Ser Lys Ile Gly Ser Thr Glu Asn Leu Lys His Gln
```

```
                    225                 230                 235                 240

Pro Gly Gly Gly Lys Val Gln Ile Val Tyr Lys Pro Val Asp Leu Ser
                    245                 250                 255

Lys Val Thr Ser Lys Cys Gly Ser Leu Gly Asn Ile His His Lys Pro
                    260                 265                 270

Gly Gly Gly Gln Val Glu Val Lys Ser Glu Lys Leu Asp Phe Lys Asp
                    275                 280                 285

Arg Val Gln Ser Lys Ile Gly Ser Leu Asp Asn Ile Thr His Val Pro
                    290                 295                 300

Gly Gly Gly Asn Lys Lys Ile Glu Thr His Lys Leu Thr Phe Arg Glu
    305                 310                 315                 320

Asn Ala Lys Ala Lys Thr Asp His Gly Ala Glu Ile Val Tyr Lys Ser
                    325                 330                 335

Pro Val Val Ser Gly Asp Thr Ser Pro Arg His Leu Ser Asn Val Ser
                    340                 345                 350

Ser Thr Gly Ser Ile Asp Met Val Asp Ser Pro Gln Leu Ala Thr Leu
                    355                 360                 365

Ala Asp Glu Val Ser Ala Ser Leu Ala Lys Gln Gly Leu
                    370                 375                 380

<210> SEQ ID NO 107
<211> LENGTH: 352
<212> TYPE: PRT
<213> ORGANISM: Homo sapiens

<400> SEQUENCE: 107

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Ser Ser Gly
                115                 120                 125

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
        210                 215                 220
```

```
Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
            245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
            290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Lys Asp Asn Ile Lys His Val Pro Gly Gly Gly Ser
1               5                   10

<210> SEQ ID NO 109
<211> LENGTH: 29
<212> TYPE: PRT
<213> ORGANISM: Homo sapiens

<400> SEQUENCE: 109

Asp Leu Ser Lys Val Thr Ser Lys Cys Gly Ser Leu Gly Asn Ile His
1               5                   10                  15

His Lys Pro Gly Gly Gly Gln Val Glu Val Lys Ser Glu
            20                  25

<210> SEQ ID NO 110
<211> LENGTH: 30
<212> TYPE: PRT
<213> ORGANISM: Homo sapiens

<400> SEQUENCE: 110

Ser Lys Ile Gly Ser Leu Asp Asn Ile Thr His Val Pro Gly Gly
1               5                   10                  15

Gly Asn Lys Lys Ile Glu Thr His Lys Leu Thr Phe Arg Glu Asn
            20                  25                  30

<210> SEQ ID NO 111
<211> LENGTH: 12
<212> TYPE: PRT
<213> ORGANISM: Homo sapiens

<400> SEQUENCE: 111

Leu Gly Asn Ile His His Lys Pro Gly Gly Gly Gln
1               5                   10

<210> SEQ ID NO 112
```

```
<211> LENGTH: 12
<212> TYPE: PRT
<213> ORGANISM: Homo sapiens

<400> SEQUENCE: 112

Leu Asp Asn Ile Thr His Val Pro Gly Gly Gly Asn
1               5                   10

<210> SEQ ID NO 113
<211> LENGTH: 8
<212> TYPE: PRT
<213> ORGANISM: Homo sapiens

<400> SEQUENCE: 113

Lys Val Gln Ile Ile Asn Lys Lys
1               5

<210> SEQ ID NO 114
<211> LENGTH: 29
<212> TYPE: PRT
<213> ORGANISM: Homo sapiens

<400> SEQUENCE: 114

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu
            20                  25

<210> SEQ ID NO 115
<211> LENGTH: 6
<212> TYPE: PRT
<213> ORGANISM: Homo sapiens

<400> SEQUENCE: 115

Val Gln Ile Val Tyr Lys
1               5

<210> SEQ ID NO 116
<211> LENGTH: 6
<212> TYPE: PRT
<213> ORGANISM: Homo sapiens

<400> SEQUENCE: 116

Val Gln Ile Ile Asn Lys
1               5

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Ser Leu Leu Asn Ser Arg Thr Arg Lys Asn Tyr
1               5                   10

<210> SEQ ID NO 118
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 118

Trp Ala Ser
1

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Gln Ser Phe Tyr Leu Arg Thr
1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Tyr Ile Phe Thr Asp Tyr Val Ile Ser
1               5                   10

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Phe Pro Arg Ser Gly Ser Thr
1               5

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Arg Asp Tyr Tyr Gly Thr Ser Phe Ala Met Asp Tyr
1               5                   10

<210> SEQ ID NO 123
<211> LENGTH: 13
<212> TYPE: PRT
<213> ORGANISM: Influenza A virus

<400> SEQUENCE: 123

Pro Lys Tyr Val Lys Gln Asn Thr Leu Lys Leu Ala Thr
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (3)..(3)
<223> OTHER INFORMATION: Any amino acid

<400> SEQUENCE: 124

Ala Lys Xaa Val Ala Ala Trp Thr Leu Lys Ala Ala Ala
1               5                   10

<210> SEQ ID NO 125
<211> LENGTH: 16
<212> TYPE: PRT
<213> ORGANISM: Plasmodium falciparum

<400> SEQUENCE: 125

Glu Lys Lys Ile Ala Lys Met Glu Lys Ala Ser Ser Val Phe Asn Val
1               5                   10                  15

<210> SEQ ID NO 126
<211> LENGTH: 10
<212> TYPE: PRT
<213> ORGANISM: Hepatitis B virus

<400> SEQUENCE: 126

Phe Phe Leu Leu Thr Arg Ile Leu Thr Ile
1               5                   10

<210> SEQ ID NO 127
<211> LENGTH: 19
<212> TYPE: PRT
<213> ORGANISM: Unknown
<220> FEATURE:
<223> OTHER INFORMATION: Description of Unknown: Heat Shock
      protein 65

<400> SEQUENCE: 127

Asp Gln Ser Ile Gly Asp Leu Leu Ala Glu Ala Met Asp Lys Val Gly
1               5                   10                  15

Asn Glu Gly

<210> SEQ ID NO 128
<211> LENGTH: 14
<212> TYPE: PRT
<213> ORGANISM: Mycobacterium bovis

<400> SEQUENCE: 128

Gln Val His Phe Gln Pro Leu Pro Pro Ala Val Val Lys Leu
1               5                   10

<210> SEQ ID NO 129
<211> LENGTH: 15
<212> TYPE: PRT
<213> ORGANISM: Clostridium tetani

<400> SEQUENCE: 129

Gln Tyr Ile Lys Ala Asn Ser Lys Phe Ile Gly Ile Thr Glu Leu
1               5                   10                  15

<210> SEQ ID NO 130
<211> LENGTH: 21
<212> TYPE: PRT
<213> ORGANISM: Clostridium tetani

<400> SEQUENCE: 130
```

Phe Asn Asn Phe Thr Val Ser Phe Trp Leu Arg Val Pro Lys Val Ser
1               5                   10                  15

Ala Ser His Leu Glu
            20

<210> SEQ ID NO 131
<211> LENGTH: 16
<212> TYPE: PRT
<213> ORGANISM: Human immunodeficiency virus

<400> SEQUENCE: 131

Lys Gln Ile Ile Asn Met Trp Gln Glu Val Gly Lys Ala Met Tyr Ala
1               5                   10                  15

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acattgtgat gtcacagtct ccatcctcc                                              29

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ctcctccaat tgcagcagtc tgg                                                    23

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Ile Val Met Ser Gln Ser Pro Ser Ser
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Val Gln Leu Gln Gln Ser Gly Pro Glu
1               5                   10

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ggaattcgtt gaagctcttg acaatgggtg                                         30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ggaattcaca tatgcaaggc ttacaaccac                                         30

<210> SEQ ID NO 138
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
            20                  25                  30

Val Ile Ser Trp Val Lys Gln Arg Thr Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Ser Val Thr Val Ser Ser
        115                 120

<210> SEQ ID NO 139
<211> LENGTH: 120
<212> TYPE: PRT
<213> ORGANISM: Homo sapiens

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn His Cys Tyr Tyr Tyr Gly Met Asp Val Trp Gly Gln
            100                 105                 110

Gly Thr Thr Val Thr Val Ser Ser
        115                 120

<210> SEQ ID NO 140
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Gln Ser Gly Pro Glu Val Lys Lys Pro Gly Ser
1               5                   10                  15

Ser Val Lys Val Pro Cys Lys Ala Ser Gly Tyr Ile Phe Thr Asp Tyr
                20                  25                  30

Val Ile Ser Trp Val Arg Gln Ala Thr Gly Gln Gly Leu Glu Trp Met
            35                  40                  45

Gly Glu Ile Phe Pro Arg Ser Gly Ser Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Thr Val Thr Val Ser Ser
        115                 120

<210> SEQ ID NO 141
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Tyr Leu Arg Thr Phe Gly Gly Gly Thr Lys Leu Asp Ile Lys
            100                 105                 110

<210> SEQ ID NO 142
<211> LENGTH: 112
<212> TYPE: PRT
<213> ORGANISM: Homo sapiens

<400> SEQUENCE: 142

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Leu Thr Phe Gly Gly Gly Thr Lys Val Glu Ile Lys
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Tyr Leu Arg Thr Phe Gly Gly Gly Thr Lys Val Glu Ile Lys
            100                 105                 110

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Asn Ile Lys His Val Pro Gly Gly Gly Ser
1               5                   10

<210> SEQ ID NO 145
<211> LENGTH: 120
<212> TYPE: PRT
<213> ORGANISM: Mus sp.

<400> SEQUENCE: 145

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Tyr Gly Thr Tyr Tyr Ala Met Asp Tyr Trp Gly Gln
                100                 105                 110

Gly Thr Ser Val Thr Val Ser Ser
            115                 120

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ala Ile Lys His Val Pro Gly Gly Gly Ser
1               5                   10

<210> SEQ ID NO 147
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Val Gln Leu Val Gln Ser Gly Pro Glu Val Val Lys Pro Gly Ser
1               5                   10                  15

Ser Val Lys Met Pro Cys Lys Ala Ser Gly Tyr Ile Phe Ser Asp Tyr
            20                  25                  30

Ala Ile Ser Trp Val Arg Gln Arg Thr Gly Gln Gly Leu Glu Trp Met
        35                  40                  45

Gly Glu Ile Phe Pro Arg Ser Gly Ser Thr Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Tyr Gly Met Asp Val Trp Gly Gln
                100                 105                 110

Gly Thr Thr Val Thr Val Ser Ser
            115                 120

<210> SEQ ID NO 148
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Val Gln Ser Gly Pro Glu Val Val Lys Pro Gly Ser
1               5                   10                  15

Ser Val Lys Met Pro Cys Lys Ala Ser Gly Tyr Ile Phe Ser Asp Tyr
            20                  25                  30

Ala Ile Ser Trp Val Arg Gln Arg Thr Gly Gln Gly Leu Glu Trp Met
        35                  40                  45

Gly Glu Ile Phe Pro Arg Ser Gly Ser Thr Tyr Tyr Asn Gln Lys Phe
50                  55                  60

Gln Gly Arg Val Thr Ile Thr Ala Asp Lys Ser Thr Asn Thr Ala Tyr
65                  70                  75                  80

Met Gln Leu Ser Ser Leu Thr Ser Glu Asp Thr Ala Val Tyr Tyr Cys
                85                  90                  95

Ala Arg Asp Tyr Tyr Gly Thr Ser Tyr Gly Met Asp Val Trp Gly Gln
                100                 105                 110

Gly Thr Thr Val Thr Val Ser Ser
            115                 120

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Asn Ala Lys His Val Pro Gly Gly Gly Ser
1               5                   10

<210> SEQ ID NO 150
<211> LENGTH: 112
<212> TYPE: PRT
<213> ORGANISM: Mus sp.

<400> SEQUENCE: 150

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
                100                 105                 110

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Asn Ile Ala His Val Pro Gly Gly Gly Ser
1               5                   10

<210> SEQ ID NO 152
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Arg Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Tyr Leu Arg Thr Phe Gly Gly Gly Thr Lys Val Glu Ile Lys
                100                 105                 110

<210> SEQ ID NO 153
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Val Leu Asn Ser
            20                  25                  30

Arg Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Tyr Leu Arg Thr Phe Gly Gly Gly Thr Lys Val Glu Ile Lys
                100                 105                 110

<210> SEQ ID NO 154
<211> LENGTH: 6
<212> TYPE: PRT
<213> ORGANISM: Homo sapiens

<400> SEQUENCE: 154

His Val Pro Gly Gly Gly
1               5

<210> SEQ ID NO 155
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
atattaccat ggacattgtg atgtcacag                                    29

<210> SEQ ID NO 156
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
atattattct cgagggagac ggtgactgag gt                                32

<210> SEQ ID NO 157
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
ggcggcggcg gctccggtgg tggtggttcc atgcaggtcc aattgcagca g           51

<210> SEQ ID NO 158
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
ggagccgccg ccgccagaac caccaccacc agaaccacca ccaccccgtt tgatgtccag   60
cttggtgcc                                                          69

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Asp Asn Ile Lys Ala Val Pro Gly Gly Gly Ser
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Leu Ala Trp Tyr Gln Gln Lys Pro Gly Gln Ser Pro Lys Leu Leu Ile
1               5                   10                  15

Tyr

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Asn Ile Lys His Ala Pro Gly Gly Gly Ser
1               5                   10

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Val Lys Gln Arg Thr Gly Gln Gly Leu Glu Trp Ile Gly Glu
1               5                   10                  15

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 163

His His His His His His
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 164

His Xaa Pro Gly Gly Gly
1               5

<210> SEQ ID NO 165
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
gacattgtga tgtcacagtc tccatcctcc ctggctgtgt cagcaggaga gaaggtcact    60

```
atgagctgca aatccagtca gagtctgctc aacagtagaa cccgaaagaa ctacctggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaagcaatc tttttatctt    300
cggacgttcg gtggaggcac caagctggac atcaaa                              336
```

<210> SEQ ID NO 166
<211> LENGTH: 301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
gacattgtga tgtcacagtc tccatcctcc ctggctgtgt cagcaggaga gaaggtcact    60
atgagctgca aatccagtca gagtctgctc aacagtagaa cccgaaagaa ctacctggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaagcaatc tttttatctt    300
c                                                                    301
```

<210> SEQ ID NO 167
<211> LENGTH: 301
<212> TYPE: DNA
<213> ORGANISM: Mus sp.

<400> SEQUENCE: 167

```
gacattgtga tgtcacagtc tccatcctcc ctggctgtgt cagcaggaga gaaggtcact    60
atgagctgca aatccagtca gagtctgctc aacagtagaa cccgaaagaa ctacttggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaagcaatc ttataatctt    300
c                                                                    301
```

<210> SEQ ID NO 168
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
ggacgttcgg tggaggcacc aagctggaca tcaaac                              36
```

<210> SEQ ID NO 169
<211> LENGTH: 36
<212> TYPE: DNA
<213> ORGANISM: Mus sp.

<400> SEQUENCE: 169

```
ggacgttcgg tggaggcacc aagctggaaa tcaaac                              36
```

<210> SEQ ID NO 170
<211> LENGTH: 360

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
caggtccaat tgcagcagtc tggacctgag ctggtgaagc ctgggacttc agtgaagatg    60
ccctgtaagg cttctggata catattcact gactatgtca taagctgggt gaagcagaga   120
actggacagg gccttgagtg gattggagag atttttccta gaagtggtag tacttactac   180
aatgagaagt tcaagggcaa ggccacactg actgcagaca atcctccaa cacagcctac    240 atgcagctca gcagcgtgac atctgaggac tctgcggtct atttctgtgc aagagattac   300
tacggtactt catttgctat ggactactgg ggtcaaggaa cctcagtcac cgtctcctca   360

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Asn Ile Lys His Val Pro Gly Gly Gly Ser
1               5                   10

<210> SEQ ID NO 172
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
caggtccaat tgcagcagtc tggacctgag ctggtgaagc ctgggacttc agtgaagatg    60
ccctgtaagg cttctggata catattcact gactatgtca taagctgggt gaagcagaga   120
actggacagg gccttgagtg gattggagag atttttccta gaagtggtag tacttactac   180
aatgagaagt tcaagggcaa ggccacactg actgcagaca atcctccaa cacagcctac    240 atgcagctca gcagcgtgac atctgaggac tctgcggtct atttctgtgc aaga         294

<210> SEQ ID NO 173
<211> LENGTH: 294
<212> TYPE: DNA
<213> ORGANISM: Mus sp.

<400> SEQUENCE: 173
caggttcagc tgcagcagtc tggagctgag ctggcgaggc ctggggcttc agtgaagctg    60
tcctgcaagg cttctggcta caccttcaca agctatggta taagctgggt gaagcagaga   120
actggacagg gccttgagtg gattggagag atttatccta gaagtggtaa tacttactac   180
aatgagaagt tcaagggcaa ggccacactg actgcagaca atcctccag cacagcgtac    240 atggagctcc gcagcctgac atctgaggac tctgcggtct atttctgtgc aaga         294

<210> SEQ ID NO 174
<211> LENGTH: 14
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 174
gattactacg gtac                                                           14

<210> SEQ ID NO 175
<211> LENGTH: 15
<212> TYPE: DNA
<213> ORGANISM: Mus sp.

<400> SEQUENCE: 175
gactactata ggtac                                                          15

<210> SEQ ID NO 176
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttcatttgct atggactact ggggtcaagg aacctcagtc accgtctcct cag               53

<210> SEQ ID NO 177
<211> LENGTH: 53
<212> TYPE: DNA
<213> ORGANISM: Mus sp.

<400> SEQUENCE: 177
ttactatgct atggactact ggggtcaagg aacctcagtc accgtctcct cag               53

<210> SEQ ID NO 178
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gggctgatgc tgcaccaact gtatccatct tcccaccatc cagtgagcag ttaacatctg        60
gaggtgcctc agtcgtgtgc ttcttgaaca acttctaccc caaagacatc aatgtcaggt       120
ggaagattga tggcagtgaa cgacaaaatg gcgtcctgaa cagttggact gatcaggaca       180
gcaaagacag cacctacagc atgagcagca ccctcacgtt gaccaaggac gagtatgaac       240
gacataacag ctatacctgt gaggcca                                           267

<210> SEQ ID NO 179
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
ccaaaacgac accccatct gtctatccac tggcccctgg atctgctgcc caaactaact         60
ccatggtgac cctgggatgc ctggtcaagg gctatttccc tgagccagtg acagtgacct       120
ggaactctgg atccctgtcc agcggtgtgc acaccttccc agctgtcctg cagtctgacc       180
tctacactct gagcagctca gtgactgtcc cctccagcac ctggcccagc gagaccgtca       240
```
cctgcaacgt tgcccacccg gccagcagca ccaagg         276

<210> SEQ ID NO 180
<211> LENGTH: 305
<212> TYPE: DNA
<213> ORGANISM: Homo sapiens

<400> SEQUENCE: 180
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctcc                                                              305

<210> SEQ ID NO 181
<211> LENGTH: 38
<212> TYPE: DNA
<213> ORGANISM: Homo sapiens

<400> SEQUENCE: 181
gtggacgttc ggccaaggga ccaaggtgga aatcaaac                            38

<210> SEQ ID NO 182
<211> LENGTH: 296
<212> TYPE: DNA
<213> ORGANISM: Homo sapiens

<400> SEQUENCE: 182
caggtccagc tggtgcagtc tggggctgag gtgaagaagc ctgggtcctc agtgaaggtc    60
tcctgcaagg cttctggagg caccttcagc agctatgcta tcagctgggt gcgacaggcc   120
cctggacaag gcttgagtg gatgggaggg atcatcccta tccttggtat agcaaactac   180
gcacagaagt tccagggcag agtcacgatt accgcggaca atccacgag cacagcctac   240
atggagctga gcagcctgag atctgaggac acggccgtgt attactgtgc gagaga       296

<210> SEQ ID NO 183
<211> LENGTH: 51
<212> TYPE: DNA
<213> ORGANISM: Homo sapiens

<400> SEQUENCE: 183
ctgagctgag aaccactgtg ctaactgggg acacagtgat tggcagctct a             51

<210> SEQ ID NO 184
<211> LENGTH: 8
<212> TYPE: PRT
<213> ORGANISM: Homo sapiens

<400> SEQUENCE: 184

Cys Thr His Val Pro Gly Gly Gly
1               5

<210> SEQ ID NO 185
<211> LENGTH: 50
<212> TYPE: DNA
<213> ORGANISM: Homo sapiens

<400> SEQUENCE: 185
tgatgctttt gatgtctggg gccaagggac aatggtcacc gtctcttcag    50

<210> SEQ ID NO 186
<211> LENGTH: 357
<212> TYPE: PRT
<213> ORGANISM: Homo sapiens

<400> SEQUENCE: 186

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu
        355

<210> SEQ ID NO 187
<211> LENGTH: 235
<212> TYPE: PRT
<213> ORGANISM: Homo sapiens

<400> SEQUENCE: 187

| Met | Ala | Glu | Pro | Arg | Gln | Glu | Phe | Glu | Val | Met | Glu | Asp | His | Ala | Gly |
|---|---|---|---|---|---|---|---|---|---|---|---|---|---|---|---|
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| | 50 | | | | | 55 | | | | | 60 | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Ala | Gln | Pro | His | Thr | Glu |
|---|---|---|---|---|---|---|---|---|---|---|---|---|---|---|---|
| | | | | 85 | | | | | 90 | | | | | 95 | |

| Ile | Pro | Glu | Gly | Thr | Thr | Ala | Glu | Glu | Ala | Gly | Ile | Gly | Asp | Thr | Pro |
|---|---|---|---|---|---|---|---|---|---|---|---|---|---|---|---|
| | | | 100 | | | | | 105 | | | | | 110 | | |

| Ser | Leu | Glu | Asp | Glu | Ala | Ala | Gly | His | Val | Thr | Gln | Ala | Arg | Met | Val |
|---|---|---|---|---|---|---|---|---|---|---|---|---|---|---|---|
| | | 115 | | | | | 120 | | | | | 125 | | | |

| Ser | Lys | Ser | Lys | Asp | Gly | Thr | Gly | Ser | Asp | Asp | Lys | Lys | Ala | Lys | Gly |
|---|---|---|---|---|---|---|---|---|---|---|---|---|---|---|---|
| | 130 | | | | | 135 | | | | | 140 | | | | |

| Ala | Asp | Gly | Lys | Thr | Lys | Ile | Ala | Thr | Pro | Arg | Gly | Ala | Ala | Pro | Pro |
|---|---|---|---|---|---|---|---|---|---|---|---|---|---|---|---|
| 145 | | | | | 150 | | | | | 155 | | | | | 160 |

| Gly | Gln | Lys | Gly | Gln | Ala | Asn | Ala | Thr | Arg | Ile | Pro | Ala | Lys | Thr | Pro |
|---|---|---|---|---|---|---|---|---|---|---|---|---|---|---|---|
| | | | | 165 | | | | | 170 | | | | | 175 | |

| Pro | Ala | Pro | Lys | Thr | Pro | Pro | Ser | Ser | Gly | Glu | Pro | Pro | Lys | Ser | Gly |
|---|---|---|---|---|---|---|---|---|---|---|---|---|---|---|---|
| | | | 180 | | | | | 185 | | | | | 190 | | |

| Asp | Arg | Ser | Gly | Tyr | Ser | Ser | Pro | Gly | Ser | Pro | Gly | Thr | Pro | Gly | Ser |
|---|---|---|---|---|---|---|---|---|---|---|---|---|---|---|---|
| | | 195 | | | | | 200 | | | | | 205 | | | |

| Arg | Ser | Arg | Thr | Pro | Ser | Leu | Pro | Thr | Pro | Pro | Thr | Arg | Leu | Ala | Asp |
|---|---|---|---|---|---|---|---|---|---|---|---|---|---|---|---|
| | 210 | | | | | 215 | | | | | 220 | | | | |

| Glu | Val | Ser | Ala | Ser | Leu | Ala | Lys | Gln | Gly | Leu | | | | | |
|---|---|---|---|---|---|---|---|---|---|---|---|---|---|---|---|
| 225 | | | | | 230 | | | | | 235 | | | | | |

<210> SEQ ID NO 188
<211> LENGTH: 346
<212> TYPE: PRT
<213> ORGANISM: Homo sapiens

<400> SEQUENCE: 188

| Met | Ala | Glu | Pro | Arg | Gln | Glu | Phe | Glu | Val | Met | Glu | Asp | His | Ala | Gly |
|---|---|---|---|---|---|---|---|---|---|---|---|---|---|---|---|
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| | 50 | | | | | 55 | | | | | 60 | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Ala | Gln | Pro | His | Thr | Glu |
|---|---|---|---|---|---|---|---|---|---|---|---|---|---|---|---|
| | | | | 85 | | | | | 90 | | | | | 95 | |

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Gly Asp Thr Ser Pro Arg His Leu Ser Asn Val Ser Ser Thr Gly
305                 310                 315                 320

Ser Ile Asp Met Val Asp Ser Pro Gln Leu Ala Thr Leu Ala Asp Glu
                325                 330                 335

Val Ser Ala Ser Leu Ala Lys Gln Gly Leu
            340                 345

<210> SEQ ID NO 189
<211> LENGTH: 420
<212> TYPE: PRT
<213> ORGANISM: Homo sapiens

<400> SEQUENCE: 189

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val

```
            115                 120                 125
    Ser Lys Ser Lys Asp Gly Thr Gly Ser Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                    165                 170                 175

Pro Ala Pro Lys Thr Pro Pro Ser Ser Gly Glu Pro Lys Ser Gly
                180                 185                 190

Asp Arg Ser Gly Tyr Ser Ser Pro Gly Ser Pro Gly Thr Pro Gly Ser
                    195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ala Lys
225                 230                 235                 240

Ser Arg Leu Gln Thr Ala Pro Val Pro Met Pro Asp Leu Lys Asn Val
                    245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                    325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                    405                 410                 415

Ile Asp Met Val
                420

<210> SEQ ID NO 190
<211> LENGTH: 227
<212> TYPE: PRT
<213> ORGANISM: Homo sapiens

<400> SEQUENCE: 190

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60
```

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala
225

<210> SEQ ID NO 191
<211> LENGTH: 428
<212> TYPE: PRT
<213> ORGANISM: Homo sapiens

<400> SEQUENCE: 191

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205
```

```
Arg Ser Arg Thr Pro Ser Leu Pro Thr Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Asp Leu Ser Lys
        290                 295                 300

Val Thr Ser Lys Cys Gly Ser Leu Gly Asn Ile His His Lys Pro Gly
305                 310                 315                 320

Gly Gly Gln Val Glu Val Lys Ser Glu Lys Leu Asp Phe Lys Asp Arg
            325                 330                 335

Val Gln Ser Lys Ile Gly Ser Leu Asp Asn Ile Thr His Val Pro Gly
            340                 345                 350

Gly Gly Asn Lys Lys Ile Glu Thr His Lys Leu Thr Phe Arg Glu Asn
        355                 360                 365

Ala Lys Ala Lys Thr Asp His Gly Ala Glu Ile Val Tyr Lys Ser Pro
370                 375                 380

Val Val Ser Gly Asp Thr Ser Pro Arg His Leu Ser Asn Val Ser Ser
385                 390                 395                 400

Thr Gly Ser Ile Asp Met Val Asp Ser Pro Gln Leu Ala Thr Leu Ala
            405                 410                 415

Asp Glu Val Ser Ala Ser Leu Ala Lys Gln Gly Leu
            420                 425

<210> SEQ ID NO 192
<211> LENGTH: 297
<212> TYPE: PRT
<213> ORGANISM: Homo sapiens

<400> SEQUENCE: 192

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
```

```
                    145                 150                 155                 160
        Gly Gln Lys Gly Gln Ala Asn Ala Thr Arg Ile Pro Ala Lys Thr Pro
                        165                 170                 175

Pro Ala Pro Lys Thr Pro Ser Ser Gly Glu Pro Lys Ser Gly
                        180                 185                 190

Asp Arg Ser Gly Tyr Ser Ser Pro Gly Ser Pro Gly Thr Pro Gly Ser
                        195                 200                 205

Arg Ser Arg Thr Pro Ser Leu Pro Thr Pro Thr Arg Glu Pro Lys
            210                 215                 220

Lys Val Ala Val Val Arg Thr Pro Pro Lys Ser Pro Ser Ser Ala Lys
        225                 230                 235                 240

Ser Arg Leu Gln Thr Ala Pro Val Pro Met Pro Asp Leu Lys Asn Val
                        245                 250                 255

Gly Asp Thr Ser Pro Arg His Leu Ser Asn Val Ser Ser Thr Gly Ser
                        260                 265                 270

Ile Asp Met Val Asp Ser Pro Gln Leu Ala Thr Leu Ala Asp Glu Val
                        275                 280                 285

Ser Ala Ser Leu Ala Lys Gln Gly Leu
                        290                 295

<210> SEQ ID NO 193
<211> LENGTH: 136
<212> TYPE: PRT
<213> ORGANISM: Homo sapiens

<400> SEQUENCE: 193

Met Ala Glu Pro Arg Gln Glu Phe Glu Val Met Glu Asp His Ala Gly
        1               5                   10                  15

Thr Tyr Gly Leu Gly Asp Arg Lys Asp Gln Gly Gly Tyr Thr Met His
                        20                  25                  30

Gln Asp Gln Glu Gly Asp Thr Asp Ala Gly Leu Lys Glu Ser Pro Leu
                        35                  40                  45

Gln Thr Pro Thr Glu Asp Gly Ser Glu Glu Pro Gly Ser Glu Thr Ser
                50                  55                  60

Asp Ala Lys Ser Thr Pro Thr Ala Glu Asp Val Thr Ala Pro Leu Val
        65                  70                  75                  80

Asp Glu Gly Ala Pro Gly Lys Gln Ala Ala Ala Gln Pro His Thr Glu
                        85                  90                  95

Ile Pro Glu Gly Thr Thr Ala Glu Glu Ala Gly Ile Gly Asp Thr Pro
                        100                 105                 110

Ser Leu Glu Asp Glu Ala Ala Gly His Val Thr Gln Ala Arg Met Val
                        115                 120                 125

Ser Lys Ser Lys Asp Gly Thr Gly
                        130                 135

<210> SEQ ID NO 194
<211> LENGTH: 282
<212> TYPE: PRT
<213> ORGANISM: Homo sapiens

<400> SEQUENCE: 194

Met Ala Glu Pro Arg Gln Glu Phe Glu Val Met Glu Asp His Ala Gly
        1               5                   10                  15

Thr Tyr Gly Leu Gly Asp Arg Lys Asp Gln Gly Gly Tyr Thr Met His
                        20                  25                  30

Gln Asp Gln Glu Gly Asp Thr Asp Ala Gly Leu Lys Glu Ser Pro Leu
```

```
                35                  40                  45
Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu
                275                 280

<210> SEQ ID NO 195
<211> LENGTH: 406
<212> TYPE: PRT
<213> ORGANISM: Homo sapiens

<400> SEQUENCE: 195

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
                35                  40                  45

Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125
```

Ser Lys Ser Lys Asp Thr Arg Ile Ala Lys Thr Pro Ala Pro
    130                 135                 140

Lys Thr Pro Pro Ser Ser Gly Glu Pro Lys Ser Gly Asp Arg Ser
145                 150                 155                 160

Gly Tyr Ser Ser Pro Gly Ser Pro Gly Thr Pro Gly Ser Arg Ser Arg
            165                 170                 175

Thr Pro Ser Leu Pro Thr Pro Pro Thr Arg Glu Pro Lys Lys Val Ala
            180                 185                 190

Val Val Arg Thr Pro Pro Lys Ser Pro Ser Ala Lys Ser Arg Leu
            195                 200                 205

Gln Thr Ala Pro Val Pro Met Pro Asp Leu Lys Asn Val Lys Ser Lys
    210                 215                 220

Ile Gly Ser Thr Glu Asn Leu Lys His Gln Pro Gly Gly Lys Val
225                 230                 235                 240

Gln Ile Ile Asn Lys Lys Leu Asp Leu Ser Asn Val Gln Ser Lys Cys
                245                 250                 255

Gly Ser Lys Asp Asn Ile Lys His Val Pro Gly Gly Gly Ser Val Gln
            260                 265                 270

Ile Val Tyr Lys Pro Val Asp Leu Ser Lys Val Thr Ser Lys Cys Gly
            275                 280                 285

Ser Leu Gly Asn Ile His His Lys Pro Gly Gly Gly Gln Val Glu Val
    290                 295                 300

Lys Ser Glu Lys Leu Asp Phe Lys Asp Arg Val Gln Ser Lys Ile Gly
305                 310                 315                 320

Ser Leu Asp Asn Ile Thr His Val Pro Gly Gly Gly Asn Lys Lys Ile
                325                 330                 335

Glu Thr His Lys Leu Thr Phe Arg Glu Asn Ala Lys Ala Lys Thr Asp
            340                 345                 350

His Gly Ala Glu Ile Val Tyr Lys Ser Pro Val Val Ser Gly Asp Thr
            355                 360                 365

Ser Pro Arg His Leu Ser Asn Val Ser Ser Thr Gly Ser Ile Asp Met
    370                 375                 380

Val Asp Ser Pro Gln Leu Ala Thr Leu Ala Asp Glu Val Ser Ala Ser
385                 390                 395                 400

Leu Ala Lys Gln Gly Leu
            405

<210> SEQ ID NO 196
<211> LENGTH: 222
<212> TYPE: PRT
<213> ORGANISM: Homo sapiens

<400> SEQUENCE: 196

Met Arg Glu Pro Lys Lys Val Ala Val Val Arg Thr Pro Pro Lys Ser
1               5                   10                  15

Pro Ser Ser Ala Lys Ser Arg Leu Gln Thr Ala Pro Val Pro Met Pro
                20                  25                  30

Asp Leu Lys Asn Val Lys Ser Lys Ile Gly Ser Thr Glu Asn Leu Lys
            35                  40                  45

His Gln Pro Gly Gly Gly Lys Val Gln Ile Ile Asn Lys Lys Leu Asp
        50                  55                  60

Leu Ser Asn Val Gln Ser Lys Cys Gly Ser Lys Asp Asn Ile Lys His
65                  70                  75                  80

Val Pro Gly Gly Gly Ser Val Gln Ile Val Tyr Lys Pro Val Asp Leu
                85                  90                  95

```
Ser Lys Val Thr Ser Lys Cys Gly Ser Leu Gly Asn Ile His His Lys
            100                 105                 110

Pro Gly Gly Gly Gln Val Glu Val Lys Ser Glu Lys Leu Asp Phe Lys
            115                 120                 125

Asp Arg Val Gln Ser Lys Ile Gly Ser Leu Asp Asn Ile Thr His Val
        130                 135                 140

Pro Gly Gly Gly Asn Lys Lys Ile Glu Thr His Lys Leu Thr Phe Arg
145                 150                 155                 160

Glu Asn Ala Lys Ala Lys Thr Asp His Gly Ala Glu Ile Val Tyr Lys
                165                 170                 175

Ser Pro Val Val Ser Gly Asp Thr Ser Pro Arg His Leu Ser Asn Val
            180                 185                 190

Ser Ser Thr Gly Ser Ile Asp Met Val Asp Ser Pro Gln Leu Ala Thr
        195                 200                 205

Leu Ala Asp Glu Val Ser Ala Ser Leu Ala Lys Gln Gly Leu
    210                 215                 220

<210> SEQ ID NO 197
<211> LENGTH: 315
<212> TYPE: PRT
<213> ORGANISM: Homo sapiens

<400> SEQUENCE: 197

Met Val Ser Lys Ser Lys Asp Gly Thr Gly Ser Asp Asp Lys Lys Ala
1               5                   10                  15

Lys Gly Ala Asp Gly Lys Thr Lys Ile Ala Thr Pro Arg Gly Ala Ala
            20                  25                  30

Pro Pro Gly Gln Lys Gly Gln Ala Asn Ala Thr Arg Ile Pro Ala Lys
        35                  40                  45

Thr Pro Pro Ala Pro Lys Thr Pro Pro Ser Ser Gly Glu Pro Pro Lys
    50                  55                  60

Ser Gly Asp Arg Ser Gly Tyr Ser Ser Pro Gly Ser Pro Gly Thr Pro
65                  70                  75                  80

Gly Ser Arg Ser Arg Thr Pro Ser Leu Pro Thr Pro Pro Thr Arg Glu
                85                  90                  95

Pro Lys Lys Val Ala Val Val Arg Thr Pro Pro Lys Ser Pro Ser Ser
            100                 105                 110

Ala Lys Ser Arg Leu Gln Thr Ala Pro Val Pro Met Pro Asp Leu Lys
        115                 120                 125

Asn Val Lys Ser Lys Ile Gly Ser Thr Glu Asn Leu Lys His Gln Pro
    130                 135                 140

Gly Gly Gly Lys Val Gln Ile Ile Asn Lys Lys Leu Asp Leu Ser Asn
145                 150                 155                 160

Val Gln Ser Lys Cys Gly Ser Lys Asp Asn Ile Lys His Val Pro Gly
                165                 170                 175

Gly Gly Ser Val Gln Ile Val Tyr Lys Pro Val Asp Leu Ser Lys Val
            180                 185                 190

Thr Ser Lys Cys Gly Ser Leu Gly Asn Ile His His Lys Pro Gly Gly
        195                 200                 205

Gly Gln Val Glu Val Lys Ser Glu Lys Leu Asp Phe Lys Asp Arg Val
    210                 215                 220

Gln Ser Lys Ile Gly Ser Leu Asp Asn Ile Thr His Val Pro Gly Gly
225                 230                 235                 240

Gly Asn Lys Lys Ile Glu Thr His Lys Leu Thr Phe Arg Glu Asn Ala
```

```
            245                 250                 255
Lys Ala Lys Thr Asp His Gly Ala Glu Ile Val Tyr Lys Ser Pro Val
            260                 265                 270

Val Ser Gly Asp Thr Ser Pro Arg His Leu Ser Asn Val Ser Ser Thr
            275                 280                 285

Gly Ser Ile Asp Met Val Asp Ser Pro Gln Leu Ala Thr Leu Ala Asp
            290                 295                 300

Glu Val Ser Ala Ser Leu Ala Lys Gln Gly Leu
305                 310                 315

<210> SEQ ID NO 198
<211> LENGTH: 96
<212> TYPE: PRT
<213> ORGANISM: Homo sapiens

<400> SEQUENCE: 198

Met Ile Lys His Val Pro Gly Gly Ser Val Gln Ile Val Tyr Lys
1               5                   10                  15

Pro Val Asp Leu Ser Lys Val Thr Ser Lys Cys Gly Ser Leu Gly Asn
                20                  25                  30

Ile His His Lys Pro Gly Gly Gly Gln Val Glu Val Lys Ser Glu Lys
            35                  40                  45

Leu Asp Phe Lys Asp Arg Val Gln Ser Lys Ile Gly Ser Leu Asp Asn
    50                  55                  60

Ile Thr His Val Pro Gly Gly Gly Asn Lys Lys Ile Glu Thr His Lys
65                  70                  75                  80

Leu Thr Phe Arg Glu Asn Ala Lys Ala Lys Thr Asp His Gly Ala Glu
                85                  90                  95

<210> SEQ ID NO 199
<211> LENGTH: 242
<212> TYPE: PRT
<213> ORGANISM: Homo sapiens

<400> SEQUENCE: 199

Met Ile Ala Thr Pro Arg Gly Ala Ala Pro Gly Gln Lys Gly Gln
1               5                   10                  15

Ala Asn Ala Thr Arg Ile Pro Ala Lys Thr Pro Pro Ala Pro Lys Thr
                20                  25                  30

Pro Pro Ser Ser Gly Glu Pro Pro Lys Ser Gly Asp Arg Ser Gly Tyr
            35                  40                  45

Ser Ser Pro Gly Ser Pro Gly Thr Pro Gly Ser Arg Ser Arg Thr Pro
    50                  55                  60

Ser Leu Pro Thr Pro Pro Thr Arg Glu Pro Lys Lys Val Ala Val Val
65                  70                  75                  80

Arg Thr Pro Pro Lys Ser Pro Ser Ser Ala Lys Ser Arg Leu Gln Thr
                85                  90                  95

Ala Pro Val Pro Met Pro Asp Leu Lys Asn Val Lys Ser Lys Ile Gly
            100                 105                 110

Ser Thr Glu Asn Leu Lys His Gln Pro Gly Gly Gly Lys Val Gln Ile
        115                 120                 125

Ile Asn Lys Lys Leu Asp Leu Ser Asn Val Gln Ser Lys Cys Gly Ser
    130                 135                 140

Lys Asp Asn Ile Lys His Val Pro Gly Gly Gly Ser Val Gln Ile Val
145                 150                 155                 160

Tyr Lys Pro Val Asp Leu Ser Lys Val Thr Ser Lys Cys Gly Ser Leu
```

-continued

```
                165                 170                 175
Gly Asn Ile His His Lys Pro Gly Gly Gly Gln Val Glu Val Lys Ser
            180                 185                 190
Glu Lys Leu Asp Phe Lys Asp Arg Val Gln Ser Lys Ile Gly Ser Leu
        195                 200                 205
Asp Asn Ile Thr His Val Pro Gly Gly Gly Asn Lys Lys Ile Glu Thr
    210                 215                 220
His Lys Leu Thr Phe Arg Glu Asn Ala Lys Ala Lys Thr Asp His Gly
225                 230                 235                 240
Ala Glu

<210> SEQ ID NO 200
<211> LENGTH: 10
<212> TYPE: PRT
<213> ORGANISM: Homo sapiens

<400> SEQUENCE: 200

Asn Ile Lys Ala Val Pro Gly Gly Gly Ser
1               5                   10

<210> SEQ ID NO 201
<211> LENGTH: 10
<212> TYPE: PRT
<213> ORGANISM: Homo sapiens

<400> SEQUENCE: 201

Asn Ile Lys His Val Pro Gly Gly Gly Ser
1               5                   10

<210> SEQ ID NO 202
<211> LENGTH: 9
<212> TYPE: PRT
<213> ORGANISM: Homo sapiens

<400> SEQUENCE: 202

Ile Lys His Val Pro Gly Gly Gly Ser
1               5

<210> SEQ ID NO 203
<211> LENGTH: 9
<212> TYPE: PRT
<213> ORGANISM: Homo sapiens

<400> SEQUENCE: 203

Lys His Val Pro Gly Gly Gly Ser Val
1               5

<210> SEQ ID NO 204
<211> LENGTH: 9
<212> TYPE: PRT
<213> ORGANISM: Homo sapiens

<400> SEQUENCE: 204

His Val Pro Gly Gly Gly Ser Val Gln
1               5

<210> SEQ ID NO 205
<211> LENGTH: 8
<212> TYPE: PRT
<213> ORGANISM: Homo sapiens

<400> SEQUENCE: 205
```

Val Pro Gly Gly Gly Ser Val Gln
1               5

<210> SEQ ID NO 206
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Lys Ser Arg Leu Gln Thr Ala Pro Val Pro Met Pro Asp Leu Lys Asn
1               5                   10                  15

Val Lys Ser Lys Ile Gly Ser Thr Glu Asn Leu Lys His Gln Pro
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Val Lys Ser Lys Ile Gly Ser Thr Glu Asn Leu Lys His Gln Pro Gly
1               5                   10                  15

Gly Gly Lys Val Gln Ile Val Tyr Lys Pro Val Asp Leu Ser
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: phospho-Ser

<400> SEQUENCE: 208

Val Lys Ser Lys Ile Gly Ser Thr Glu Asn Leu Lys His Gln Pro Gly
1               5                   10                  15

Gly Gly Lys Val Gln Ile Val Tyr Lys Pro Val Asp Leu Ser
            20                  25                  30

<210> SEQ ID NO 209
<211> LENGTH: 31
<212> TYPE: PRT
<213> ORGANISM: Homo sapiens

<400> SEQUENCE: 209

Cys Val Lys Ser Lys Ile Gly Ser Thr Glu Asn Leu Lys His Gln Pro
1               5                   10                  15

Gly Gly Gly Lys Val Gln Ile Ile Asn Lys Lys Leu Asp Leu Ser
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<221> NAME/KEY: MOD_RES
<222> LOCATION: (7)..(7)
<223> OTHER INFORMATION: phospho-Ser

<400> SEQUENCE: 210

Val Lys Ser Lys Ile Gly Ser Thr Glu Asn Leu Lys His Gln Pro Gly
1               5                   10                  15

Gly Gly Lys Val Gln Ile Ile Asn Lys Lys Leu Asp Leu Ser
            20                  25                  30

<210> SEQ ID NO 211
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Lys Ile Gly Ser Thr Glu Asn Leu Lys His Gln Pro Gly Gly Gly Lys
1               5                   10                  15

Val Gln Ile Val Tyr Lys Pro Val Asp Leu Ser Lys Val Thr
            20                  25                  30

<210> SEQ ID NO 212
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: phospho-Ser

<400> SEQUENCE: 212

Lys Ile Gly Ser Thr Glu Asn Leu Lys His Gln Pro Gly Gly Gly Lys
1               5                   10                  15

Val Gln Ile Val Tyr Lys Pro Val Asp Leu Ser Lys Val Thr
            20                  25                  30

<210> SEQ ID NO 213
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Cys Val Gln Ile Ile Asn Lys Lys Leu Asp Leu Ser Asn Val Gln Ser
1               5                   10                  15

Lys Cys Gly Ser Lys Asp Asn Ile Lys His Val Pro Gly Gly Gly
            20                  25                  30

<210> SEQ ID NO 214
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (4)..(4)
<223> OTHER INFORMATION: phospho-Ser

<400> SEQUENCE: 214

Lys Ile Gly Ser Thr Glu Asn Leu Lys His Gln Pro Gly Gly Gly Lys
1               5                   10                  15

Val Gln Ile Ile Asn Lys Lys Leu Asp Leu Ser Asn Val Gln
            20                  25                  30

<210> SEQ ID NO 215
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Pro Gly Gly Gly Lys Val Gln Ile Ile Asn Lys Lys Leu Asp Leu Ser
1               5                   10                  15

Asn Val Gln Ser Lys Cys Gly Ser Lys Asp Asn Ile Lys His Val
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Cys Thr Pro Pro Ser Ser Gly Glu Pro Pro Lys Ser Gly Asp Arg Ser
1               5                   10                  15

Gly Tyr Ser Ser Pro Gly Ser Pro Gly Thr Pro Gly Ser Arg Ser
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Asn Leu Lys His Gln Pro Gly Gly Gly Lys Val Gln Ile Val Tyr
1               5                   10                  15

Lys Pro Val Asp Leu Ser Lys Val Thr Ser Lys Cys Gly Ser
            20                  25                  30

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Cys Lys Asp Asn Ile Lys His Val Pro Gly Gly Gly Ser
1               5                   10

<210> SEQ ID NO 219
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Leu Asp Leu Ser Asn Val Gln Ser Lys Cys Gly Ser Lys Asp Asn
1               5                   10                  15

Ile Lys His Val Pro Gly Gly Gly Ser
            20                  25

<210> SEQ ID NO 220
<211> LENGTH: 8
<212> TYPE: PRT
<213> ORGANISM: Homo sapiens

<400> SEQUENCE: 220

Cys His His Lys Pro Gly Gly Gly
1               5

<210> SEQ ID NO 221
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Cys Gly Ser Lys Asp Asn Ile Lys His Val Pro Gly Gly Gly Ser Val
1               5                   10                  15

Gln Ile Val Tyr Lys Pro Val Asp Leu Ser Lys Val Thr Ser
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Pro Gly Gly Gly Ser Val Gln Ile Val Tyr Lys Pro Val Asp Leu Ser
1               5                   10                  15

Lys Val Thr Ser Lys Cys Gly Ser Leu Gly Asn Ile His His
            20                  25                  30

<210> SEQ ID NO 223
<211> LENGTH: 6
<212> TYPE: PRT
<213> ORGANISM: Homo sapiens

<400> SEQUENCE: 223

His Gln Pro Gly Gly Gly
1               5

<210> SEQ ID NO 224
<211> LENGTH: 6
<212> TYPE: PRT
<213> ORGANISM: Homo sapiens

<400> SEQUENCE: 224

His Lys Pro Gly Gly Gly
```

```
1               5
```

<210> SEQ ID NO 225
<211> LENGTH: 104
<212> TYPE: PRT
<213> ORGANISM: Homo sapiens

<400> SEQUENCE: 225

```
Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100
```

<210> SEQ ID NO 226
<211> LENGTH: 104
<212> TYPE: PRT
<213> ORGANISM: Pan sp.

<400> SEQUENCE: 226

```
Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100
```

<210> SEQ ID NO 227
<211> LENGTH: 104
<212> TYPE: PRT
<213> ORGANISM: Macaca sp.

<400> SEQUENCE: 227

```
Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60
```

His His Lys Pro Gly Gly Gly Gln Val Glu Val Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Ser
            100

<210> SEQ ID NO 228
<211> LENGTH: 104
<212> TYPE: PRT
<213> ORGANISM: Unknown
<220> FEATURE:
<223> OTHER INFORMATION: Description of Unknown: Gibbon
      tau polypeptide

<400> SEQUENCE: 228

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
                20                  25                  30

Ile Lys His Val Pro Gly Gly Gly Ser Val Gln Ile Val Tyr Lys Pro
            35                  40                  45

Val Asp Leu Ser Lys Val Thr Ser Lys Cys Gly Ser Leu Gly Asn Ile
        50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 229
<211> LENGTH: 104
<212> TYPE: PRT
<213> ORGANISM: Pongo sp.

<400> SEQUENCE: 229

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
                20                  25                  30

Ile Lys His Val Pro Gly Gly Gly Ser Val Gln Ile Val Tyr Lys Pro
            35                  40                  45

Val Asp Leu Ser Lys Val Thr Ser Lys Cys Gly Ser Leu Gly Asn Ile
        50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly His
            100

<210> SEQ ID NO 230
<211> LENGTH: 104
<212> TYPE: PRT
<213> ORGANISM: Ailuropoda melanoleuca

<400> SEQUENCE: 230

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 231
<211> LENGTH: 104
<212> TYPE: PRT
<213> ORGANISM: Sus sp.

<400> SEQUENCE: 231

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 232
<211> LENGTH: 104
<212> TYPE: PRT
<213> ORGANISM: Equus sp.

<400> SEQUENCE: 232

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly His
            100

<210> SEQ ID NO 233
<211> LENGTH: 104
<212> TYPE: PRT
<213> ORGANISM: Canis lupus

<400> SEQUENCE: 233

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 234
<211> LENGTH: 104
<212> TYPE: PRT
<213> ORGANISM: Unknown
<220> FEATURE:
<223> OTHER INFORMATION: Description of Unknown: Rabbit
      tau polypeptide

<400> SEQUENCE: 234

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 235
<211> LENGTH: 104
<212> TYPE: PRT
<213> ORGANISM: Rattus sp.

<400> SEQUENCE: 235

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile

```
                    50                  55                  60
His His Lys Pro Gly Gly Gly Gln Val Glu Val Lys Ser Glu Lys Leu
 65                  70                  75                  80

Asp Phe Lys Asp Arg Val Gln Ser Lys Ile Gly Ser Leu Asp Asn Ile
                 85                  90                  95

Thr His Val Pro Gly Gly Gly Asn
            100

<210> SEQ ID NO 236
<211> LENGTH: 104
<212> TYPE: PRT
<213> ORGANISM: Unknown
<220> FEATURE:
<223> OTHER INFORMATION: Description of Unknown: Vole
      tau polypeptide

<400> SEQUENCE: 236

Asn Leu Lys His Gln Pro Gly Gly Gly Lys Val Gln Ile Ile Asn Lys
 1               5                  10                  15

Lys Leu Asp Leu Ser Asn Val Gln Ser Lys Cys Gly Ser Lys Asp Asn
                20                  25                  30

Ile Lys His Val Pro Gly Gly Gly Ser Val Gln Ile Val Tyr Lys Pro
            35                  40                  45

Val Asp Leu Ser Lys Val Thr Ser Lys Cys Gly Ser Leu Gly Asn Ile
 50                  55                  60

His His Lys Pro Gly Gly Gly Gln Val Glu Val Lys Ser Glu Lys Leu
 65                  70                  75                  80

Asp Phe Lys Asp Arg Val Gln Ser Lys Ile Gly Ser Leu Asp Asn Ile
                 85                  90                  95

Thr His Val Pro Gly Gly Gly Asn
            100

<210> SEQ ID NO 237
<211> LENGTH: 104
<212> TYPE: PRT
<213> ORGANISM: Mus sp.

<400> SEQUENCE: 237

Asn Leu Lys His Gln Pro Gly Gly Gly Lys Val Gln Ile Ile Asn Lys
 1               5                  10                  15

Lys Leu Asp Leu Ser Asn Val Gln Ser Lys Cys Gly Ser Lys Asp Asn
                20                  25                  30

Ile Lys His Val Pro Gly Gly Gly Ser Val Gln Ile Val Tyr Lys Pro
            35                  40                  45

Val Asp Leu Ser Lys Val Thr Ser Lys Cys Gly Ser Leu Gly Asn Ile
 50                  55                  60

His His Lys Pro Gly Gly Gly Gln Val Glu Val Lys Ser Glu Lys Leu
 65                  70                  75                  80

Asp Phe Lys Asp Arg Val Gln Ser Lys Ile Gly Ser Leu Asp Asn Ile
                 85                  90                  95

Thr His Val Pro Gly Gly Gly Asn
            100

<210> SEQ ID NO 238
<211> LENGTH: 104
<212> TYPE: PRT
<213> ORGANISM: Unknown
<220> FEATURE:
<223> OTHER INFORMATION: Description of Unknown: Ground
``` squirrel tau polypeptide

<400> SEQUENCE: 238

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 239
<211> LENGTH: 104
<212> TYPE: PRT
<213> ORGANISM: Bos sp.

<400> SEQUENCE: 239

Asn Leu Lys His Gln Pro Gly Gly Gly Lys Val Gln Ile Ile Asn Lys
1               5                   10                  15

Lys Leu Asp Leu Ser Asn Val Gln Ser Lys Cys Gly Ser Lys Asp Asn
            20                  25                  30

Ile Lys His Val Pro Gly Gly Gly Ser Val Gln Ile Val Tyr Lys Pro
        35                  40                  45

Val Asp Leu Ser Lys Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

Asp Phe Lys Asp Arg Val Gln Ser Lys Ile Gly Ser Leu Asp Asn Ile
                85                  90                  95

Thr His Val Pro Gly Gly Gly Asn
            100

<210> SEQ ID NO 240
<211> LENGTH: 104
<212> TYPE: PRT
<213> ORGANISM: Unknown
<220> FEATURE:
<223> OTHER INFORMATION: Description of Unknown: Fowl
      tau polypeptide

<400> SEQUENCE: 240

Asn Leu Lys His Gln Pro Gly Gly Gly Lys Val Gln Ile Ile Asn Lys
1               5                   10                  15

Lys Leu Asp Phe Ser Ser Val Gln Ser Lys Cys Gly Ser Lys Asp Asn
            20                  25                  30

Ile Lys His Ile Pro Gly Gly Gly Ser Val Gln Ile Val Tyr Lys Pro
        35                  40                  45

Val Asp Leu Ser His Val Thr Ser Lys Cys Gly Ser Leu Gly Asn Ile
    50                  55                  60

His His Lys Pro Gly Gly Gly Gln Val Glu Val Lys Ser Glu Lys Leu
65                  70                  75                  80

```
Asp Phe Lys Asp Lys Val Gln Ser Lys Ile Gly Ser Leu Asp Asn Ile
                85                  90                  95

Ser His Val Pro Gly Gly Gly Asn
            100
```

<210> SEQ ID NO 241
<211> LENGTH: 104
<212> TYPE: PRT
<213> ORGANISM: Unknown
<220> FEATURE:
<223> OTHER INFORMATION: Description of Unknown: Finch
      tau polypeptide

<400> SEQUENCE: 241

```
Asn Leu Lys His Gln Pro Gly Gly Gly Lys Val Gln Ile Ile Asn Lys
1               5                   10                  15

Lys Leu Asp Phe Ser Ser Val Gln Ser Lys Cys Gly Ser Lys Asp Asn
                20                  25                  30

Ile Lys His Ile Pro Gly Gly Gly Ser Val Gln Ile Val Tyr Lys Pro
            35                  40                  45

Val Asp Leu Ser His Val Thr Ser Lys Cys Gly Ser Leu Gly Asn Ile
50                  55                  60

His His Lys Pro Gly Gly Gly Gln Val Glu Val Lys Ser Glu Lys Leu
65                  70                  75                  80

Asp Phe Lys Asp Lys Val Gln Ser Lys Ile Gly Ser Leu Asp Asn Ile
                85                  90                  95

Ser His Val Pro Gly Gly Gly Asn
            100
```

<210> SEQ ID NO 242
<211> LENGTH: 102
<212> TYPE: PRT
<213> ORGANISM: Danio rerio

<400> SEQUENCE: 242

```
Asn Ile Lys His Ala Pro Gly Gly Gly Asn Val Gln Ile Leu Asp Gln
1               5                   10                  15

Lys Leu Asp Leu Thr Asn Val Gln Ala Arg Cys Gly Ser Lys Asp Asn
                20                  25                  30

Leu Lys His Val Pro Gly Gly Gly Lys Val Gln Ile Leu His Lys Lys
            35                  40                  45

Ile Asp Leu Ser Asn Val Gln Ser Lys Cys Gly Ser Lys Asp Asn Leu
50                  55                  60

Arg His Lys Pro Gly Gly Gly Asn Ile Glu Ile Arg Ser Glu Lys Leu
65                  70                  75                  80

Asp Phe Lys Ala Gln Ser Lys Ile Gly Ser Met Asp Asn Ile Lys His
                85                  90                  95

Thr Pro Gly Gly Gly Asn
            100
```

<210> SEQ ID NO 243
<211> LENGTH: 103
<212> TYPE: PRT
<213> ORGANISM: Xenopus laevis

<400> SEQUENCE: 243

```
Asn Ile Arg His Gln Pro Gly Gly Gly Lys Val Gln Ile Val His Lys
1               5                   10                  15
```

```
Lys Val Asp Leu Gly Asn Val Gln Ser Lys Cys Gly Ser Asp Asn
            20                  25                  30

Leu Lys His Val Pro Gly Gly Gly Ala Ile Gln Ile Thr His Lys Pro
        35                  40                  45

Ile Asp Leu Thr Arg Val Thr Ser Lys Cys Gly Ser Phe Val Asn Ile
 50                  55                  60

His His Lys Pro Gly Gly Gly Asn Val Glu Leu Lys Ser Glu Lys Leu
65                  70                  75                  80

Glu Phe Asp Lys Ile Gln Ser Lys Ile Gly Ser Leu Asp Asn Val Thr
                85                  90                  95

His Val Pro Gly Gly Gly Ala
            100

<210> SEQ ID NO 244
<211> LENGTH: 101
<212> TYPE: PRT
<213> ORGANISM: Drosophila sp.

<400> SEQUENCE: 244

Asn Ala Thr Tyr Lys Pro Gly Gly Gly His Val Lys Ile Glu Ser Lys
1               5                   10                  15

Lys Ile Asp Ile Lys Ala Ala Pro Arg Ile Glu Ala Lys Asn Asp Lys
            20                  25                  30

Tyr Met Pro Lys Gly Gly Glu Lys Lys Ile Val Thr Thr Lys Leu Gln
        35                  40                  45

Trp Asn Ala Lys Ser Lys Ile Gly Ser Leu Glu Asn Ala Ala His Lys
 50                  55                  60

Pro Gly Gly Gly Asp Lys Lys Ile Glu Thr Leu Lys Met Asp Phe Lys
65                  70                  75                  80

Asp Lys Ala Lys Pro Lys Val Gly Ser Thr Ala Asn Val Lys His Gln
                85                  90                  95

Pro Gly Gly Gly Asp
            100

<210> SEQ ID NO 245
<211> LENGTH: 97
<212> TYPE: PRT
<213> ORGANISM: Unknown
<220> FEATURE:
<223> OTHER INFORMATION: Description of Unknown: Roundworm
      tau polypeptide

<400> SEQUENCE: 245

Asn His Lys Ala Gly Gly Gly Asn Val Glu Ile Phe Ser Glu Lys Arg
1               5                   10                  15

Leu Tyr Asn Ala Gln Ser Lys Val Gly Ser Leu Lys Asn Ala Thr His
            20                  25                  30

Val Ala Gly Gly Gly Asn Val Gln Ile Glu Asn Arg Lys Leu Asp Phe
        35                  40                  45

Ser Ala Ala Ser Pro Lys Val Gly Ser Lys Thr Asn Tyr Gln Pro Ala
 50                  55                  60

Lys Ser Asp Val Lys Ile Val Ser Glu Lys Leu Thr Trp Gln Ala Lys
65                  70                  75                  80

Ser Lys Val Gly Ser Met Asp Asn Ala Ala His Lys Pro Ala Gly Gly
                85                  90                  95

Asn
```

```
<210> SEQ ID NO 246
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gly Ser Thr Glu Asn Leu Lys His Gln Pro Gly Gly Lys Val Gln
1               5                   10                  15

Ile Ile Asn Lys Lys Leu Asp Leu Ser Asn Val Gln Ser Lys Cys Gly
                20                  25                  30

Ser Lys Asp Asn Ile Lys His Val Pro Gly Gly Ser Val Gln Ile
            35                  40                  45

Val Tyr Lys Pro Val Asp Leu Ser Lys Val Thr Ser Lys Cys Gly Ser
    50                  55                  60

Leu Gly Asn Ile His His Val Pro Gly Gly Gln Val Glu Val Lys
65                  70                  75                  80

Ser Glu Lys Leu Asp Phe Lys Asp Arg Val Gln Ser Lys Ile Gly Ser
                85                  90                  95

Leu Asp Asn Ile Thr His Val Pro Gly Gly Gly Asn Lys Lys Ile Glu
            100                 105                 110

Thr

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gln Ser Leu Leu Ala Ser Arg Thr Arg Lys Asn Tyr
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Ser Leu Leu Asn Ser Ala Thr Arg Lys Asn Tyr
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Ser Leu Leu Asn Ser Arg Thr Arg Lys Asn Ala
1               5                   10

<210> SEQ ID NO 250
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 250

Gly Trp Ser Ile His Ser Pro Gly Gly Gly Ser Cys
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Val Phe Gln His Leu Pro Gly Gly Gly Ser Cys
1               5                   10

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Leu Ala Trp Tyr Gln Gln Lys Pro Gly Gln Ser Pro Lys Leu Leu Ile
1               5                   10                  15

Ala

<210> SEQ ID NO 253
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Ala Ser
1

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Gln Ser Phe Tyr Leu Arg Thr
1               5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255
```

```
Lys Ala Ser Phe Tyr Leu Arg Thr
1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Lys Gln Ala Phe Tyr Leu Arg Thr
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Lys Gln Ser Ala Tyr Leu Arg Thr
1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Lys Gln Ser Phe Ala Leu Arg Thr
1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Lys Gln Ser Phe Tyr Ala Arg Thr
1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Lys Gln Ser Phe Tyr Leu Ala Thr
1               5

<210> SEQ ID NO 261
<211> LENGTH: 10
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 261

Gly Tyr Ile Phe Thr Asp Ala Val Ile Ser
1               5                   10

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Tyr Ile Phe Thr Asp Tyr Ala Ile Ser
1               5                   10

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Trp Val Lys Gln Arg Thr Gly Gln Gly Leu Glu Trp Ile Gly Ala
1               5                   10                  15

<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ile Ala Pro Arg Ser Gly Ser Thr
1               5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ile Phe Pro Arg Ser Gly Ala Thr
1               5

<210> SEQ ID NO 266
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Arg Ala Tyr Tyr Gly Thr Ser Phe Ala Met Asp Tyr
1               5                   10

```
<210> SEQ ID NO 267
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Arg Asp Ala Tyr Gly Thr Ser Phe Ala Met Asp Tyr
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Arg Asp Tyr Ala Gly Thr Ser Phe Ala Met Asp Tyr
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ala Arg Asp Tyr Tyr Ala Thr Ser Phe Ala Met Asp Tyr
1               5                   10

<210> SEQ ID NO 270
<211> LENGTH: 12
<212> TYPE: PRT
<213> ORGANISM: Homo sapiens

<400> SEQUENCE: 270

Thr Glu Asn Leu Lys His Gln Pro Gly Gly Gly Lys
1               5                   10

<210> SEQ ID NO 271
<211> LENGTH: 7
<212> TYPE: PRT
<213> ORGANISM: Homo sapiens

<400> SEQUENCE: 271

Lys His Gln Pro Gly Gly Gly
1               5

<210> SEQ ID NO 272
<211> LENGTH: 6
<212> TYPE: PRT
<213> ORGANISM: Homo sapiens

<400> SEQUENCE: 272

His Gln Pro Gly Gly Gly
1               5

<210> SEQ ID NO 273
<211> LENGTH: 5
<212> TYPE: PRT
<213> ORGANISM: Homo sapiens
```

```
<400> SEQUENCE: 273

His Gln Pro Gly Gly
1               5

<210> SEQ ID NO 274
<211> LENGTH: 5
<212> TYPE: PRT
<213> ORGANISM: Homo sapiens

<400> SEQUENCE: 274

Gln Pro Gly Gly Gly
1               5

<210> SEQ ID NO 275
<211> LENGTH: 42
<212> TYPE: PRT
<213> ORGANISM: Homo sapiens

<400> SEQUENCE: 275

Glu Asn Leu Lys His Gln Pro Gly Gly Gly Lys Val Gln Ile Ile Asn
1               5                   10                  15

Lys Lys Leu Asp Leu Ser Asn Val Gln Ser Lys Cys Gly Ser Lys Asp
            20                  25                  30

Asn Ile Lys His Val Pro Gly Gly Gly Ser
        35                  40

<210> SEQ ID NO 276
<211> LENGTH: 7
<212> TYPE: PRT
<213> ORGANISM: Homo sapiens

<400> SEQUENCE: 276

Lys His Val Pro Gly Gly Gly
1               5

<210> SEQ ID NO 277
<211> LENGTH: 6
<212> TYPE: PRT
<213> ORGANISM: Homo sapiens

<400> SEQUENCE: 277

His Val Pro Gly Gly Gly
1               5

<210> SEQ ID NO 278
<211> LENGTH: 5
<212> TYPE: PRT
<213> ORGANISM: Homo sapiens

<400> SEQUENCE: 278

His Val Pro Gly Gly
1               5

<210> SEQ ID NO 279
<211> LENGTH: 5
<212> TYPE: PRT
<213> ORGANISM: Homo sapiens

<400> SEQUENCE: 279

Val Pro Gly Gly Gly
1               5
```

```
<210> SEQ ID NO 280
<211> LENGTH: 19
<212> TYPE: PRT
<213> ORGANISM: Homo sapiens

<400> SEQUENCE: 280

Asp Asn Ile Lys His Val Pro Gly Gly Gly Ser Val Gln Ile Val Tyr
1               5                   10                  15

Lys Pro Val

<210> SEQ ID NO 281
<211> LENGTH: 7
<212> TYPE: PRT
<213> ORGANISM: Homo sapiens

<400> SEQUENCE: 281

His His Lys Pro Gly Gly Gly
1               5

<210> SEQ ID NO 282
<211> LENGTH: 6
<212> TYPE: PRT
<213> ORGANISM: Homo sapiens

<400> SEQUENCE: 282

His Lys Pro Gly Gly Gly
1               5

<210> SEQ ID NO 283
<211> LENGTH: 7
<212> TYPE: PRT
<213> ORGANISM: Homo sapiens

<400> SEQUENCE: 283

Thr His Val Pro Gly Gly Gly
1               5
```